(12) United States Patent
Skaaksrud et al.

(10) Patent No.: US 11,491,643 B2
(45) Date of Patent: Nov. 8, 2022

(54) METHODS OF PERFORMING A DISPATCHED CONSUMER-TO-STORE LOGISTICS OPERATION RELATED TO AN ITEM BEING REPLACED USING A MODULAR AUTONOMOUS BOT APPARATUS ASSEMBLY AND A DISPATCH SERVER

(71) Applicant: FEDEX CORPORATE SERVICES, INC., Collierville, TN (US)

(72) Inventors: Ole-Petter Skaaksrud, Germantown, TN (US); Frank Mayfield, Collierville, TN (US); Daniel Gates, Memphis, TN (US)

(73) Assignee: FEDEX CORPORATE SERVICES, INC., Collierville, TN (US)

( * ) Notice: Subject to any disclaimer, the term of this patent is extended or adjusted under 35 U.S.C. 154(b) by 746 days.

(21) Appl. No.: 16/351,587

(22) Filed: Mar. 13, 2019

(65) Prior Publication Data

US 2019/0287063 A1 Sep. 19, 2019

Related U.S. Application Data

(60) Provisional application No. 62/642,732, filed on Mar. 14, 2018.

(51) Int. Cl.
*B25J 9/08* (2006.01)
*G06Q 10/08* (2012.01)
(Continued)

(52) U.S. Cl.
CPC ............ *B25J 9/08* (2013.01); *B25J 5/007* (2013.01); *B25J 9/162* (2013.01); *B25J 9/163* (2013.01);
(Continued)

(58) Field of Classification Search
None
See application file for complete search history.

(56) References Cited

U.S. PATENT DOCUMENTS 6,484,083 B1 11/2002 Hayward et al.
8,370,990 B2 2/2013 Yu et al.
(Continued)

FOREIGN PATENT DOCUMENTS

EP 2651787 B1 5/2016
JP 2017200846 A 11/2017
(Continued)

OTHER PUBLICATIONS

Grob et al., "Object Transport by Modular Robots that Self-assemble", May 2006, IEEE International Conference, pp. 2558-2564.
(Continued)

*Primary Examiner* — Curtis J King
(74) *Attorney, Agent, or Firm* — Withers & Keys, LLC

(57) ABSTRACT

Methods are described that perform a dispatched consumer-to-store return or swap logistics operation for an item being replaced using a modular autonomous bot apparatus assembly and a dispatch server. The method begins with receiving a return operation dispatch command that includes identifier information, transport parameters, and designated pickup information for the item being replaced/returned, along with authentication information related to an authorized supplier of the item being replaced. Modular components of the bot apparatus are verified to be compatible with the dispatched logistics operation. The MAM then autonomously causes the bot apparatus to move to the designated pickup location, notifies the authorized supplier of an approaching pickup, receives supplier authorization input to permissively allow access to a payload area within the bot apparatus, monitors loading as the item being replaced is received along with
(Continued)

return documentation, and then autonomously causes movement of the bot apparatus back to the origin location.

112 Claims, 112 Drawing Sheets

(51) Int. Cl.

| | |
|---|---|
| *B25J 5/00* | (2006.01) |
| *B25J 19/02* | (2006.01) |
| *G05D 1/02* | (2020.01) |
| *G08G 1/00* | (2006.01) |
| *G05D 1/00* | (2006.01) |
| *B60Q 5/00* | (2006.01) |
| *B60W 10/04* | (2006.01) |
| *B60W 10/20* | (2006.01) |
| *B60W 30/09* | (2012.01) |
| *H04B 1/3822* | (2015.01) |
| *B25J 9/16* | (2006.01) |
| *B65G 1/137* | (2006.01) |
| *G06F 21/32* | (2013.01) |
| *G06Q 30/06* | (2012.01) |
| *B60P 3/00* | (2006.01) |
| *B65G 67/24* | (2006.01) |
| *H02J 9/00* | (2006.01) |
| *B65D 88/52* | (2006.01) |
| *B65D 90/02* | (2019.01) |
| *B65D 90/08* | (2006.01) |
| *B65D 90/18* | (2006.01) |
| *B60G 17/015* | (2006.01) |
| *G01C 21/34* | (2006.01) |
| *H04W 52/32* | (2009.01) |
| *B60C 5/00* | (2006.01) |
| *G07C 9/37* | (2020.01) |
| *G07C 9/00* | (2020.01) |
| *G07C 9/27* | (2020.01) |
| *G06Q 50/28* | (2012.01) |
| *H04W 84/20* | (2009.01) |

(52) U.S. Cl.
CPC ........... *B25J 9/1666* (2013.01); *B25J 9/1679* (2013.01); *B25J 19/02* (2013.01); *B60C 5/005* (2013.01); *B60G 17/0152* (2013.01); *B60P 3/007* (2013.01); *B60Q 5/005* (2013.01); *B60W 10/04* (2013.01); *B60W 10/20* (2013.01); *B60W 30/09* (2013.01); *B65D 88/524* (2013.01); *B65D 90/023* (2013.01); *B65D 90/08* (2013.01); *B65D 90/18* (2013.01); *B65G 1/1373* (2013.01); *B65G 67/24* (2013.01); *G01C 21/3438* (2013.01); *G05D 1/0011* (2013.01); *G05D 1/0022* (2013.01); *G05D 1/0088* (2013.01); *G05D 1/021* (2013.01); *G05D 1/027* (2013.01); *G05D 1/0214* (2013.01); *G05D 1/0223* (2013.01); *G05D 1/0225* (2013.01); *G05D 1/0274* (2013.01); *G05D 1/0276* (2013.01); *G05D 1/0287* (2013.01); *G05D 1/0295* (2013.01); *G06F 21/32* (2013.01); *G06Q 10/083* (2013.01); *G06Q 10/0832* (2013.01); *G06Q 10/0833* (2013.01); *G06Q 10/0836* (2013.01); *G06Q 10/0837* (2013.01); *G06Q 10/0838* (2013.01); *G06Q 10/0875* (2013.01); *G06Q 30/0633* (2013.01); *G07C 9/00182* (2013.01); *G07C 9/00563* (2013.01); *G07C 9/00571* (2013.01); *G07C 9/00857* (2013.01); *G07C 9/27* (2020.01); *G07C 9/37* (2020.01); *G08G 1/202* (2013.01); *H02J 9/00* (2013.01); *H04B 1/3822* (2013.01); *H04W 52/322* (2013.01); *B60W 2554/00* (2020.02); *G05B 2219/39172* (2013.01); *G05B 2219/50391* (2013.01); *G05D 2201/0206* (2013.01); *G05D 2201/0216* (2013.01); *G06Q 50/28* (2013.01); *G07C 2009/0092* (2013.01); *H04W 84/20* (2013.01)

(56) References Cited

U.S. PATENT DOCUMENTS

| | | | |
|---|---|---|---|
| 8,626,383 | B2 | 1/2014 | PrudHomme-Lacroix et al. |
| 8,757,309 | B2 | 6/2014 | Schmitt et al. |
| 9,120,622 | B1 | 9/2015 | Elazary et al. |
| 9,244,147 | B1 | 1/2016 | Soundararajan et al. |
| 9,256,852 | B1 | 2/2016 | Myllymaki |
| 9,403,566 | B2 | 8/2016 | Jacobsen et al. |
| 9,527,605 | B1 | 12/2016 | Gentry et al. |
| 9,598,237 | B2 | 3/2017 | Cyrulik et al. |
| 9,741,010 | B1 | 8/2017 | Heinla |
| 9,770,825 | B2 | 9/2017 | Goldenberg et al. |
| 9,796,529 | B1 | 10/2017 | Hoareau et al. |
| 10,022,867 | B2 | 7/2018 | Saboo et al. |
| 10,207,403 | B1 | 2/2019 | Wiley |
| 10,265,871 | B2 | 4/2019 | Hance et al. |
| 10,286,558 | B1 | 5/2019 | Asada et al. |
| 10,421,326 | B2 | 9/2019 | Wiley et al. |
| 10,438,162 | B2 | 10/2019 | Sharma et al. |
| 10,538,190 | B1 | 1/2020 | Metellus et al. |
| 10,545,509 | B1 | 1/2020 | Jessen et al. |
| 10,549,915 | B1* | 2/2020 | Theobald ................ B25J 13/06 |
| 10,556,334 | B1* | 2/2020 | Theobald ................ B25J 9/1679 |
| 10,678,242 | B2 | 6/2020 | Wiley |
| 10,807,715 | B2 | 10/2020 | Shannon |
| 10,874,240 | B2 | 12/2020 | Lewis et al. |
| 10,875,174 | B2 | 12/2020 | Skaaksrud et al. |
| 11,027,419 | B2 | 6/2021 | Skaaksrud et al. |
| 11,027,420 | B2 | 6/2021 | Skaaksrud et al. |
| 11,077,551 | B2 | 8/2021 | Skaaksrud et al. |
| 11,090,802 | B2 | 8/2021 | Skaaksrud et al. |
| 11,117,255 | B2 | 8/2021 | Skaaksrud et al. |
| 11,135,717 | B2 | 10/2021 | Skaaksrud et al. |
| 11,224,969 | B2 | 1/2022 | Skaaksrud et al. |
| 11,227,299 | B2 | 1/2022 | Baalke et al. |
| 11,235,457 | B2 | 2/2022 | Skaaksrud et al. |
| 11,331,790 | B2 | 5/2022 | Skaaksrud et al. |
| 2001/0032147 | A1* | 10/2001 | Siegel .................. G06Q 20/10 |
| | | | 705/26.1 |
| 2001/0052680 | A1 | 12/2001 | Bennington |
| 2005/0098556 | A1 | 5/2005 | Kellerer |
| 2007/0219666 | A1 | 9/2007 | Filippov et al. |
| 2008/0294287 | A1 | 11/2008 | Kawano et al. |
| 2009/0044655 | A1 | 2/2009 | DeLouis et al. |
| 2010/0263948 | A1 | 10/2010 | Couture et al. |
| 2011/0238205 | A1 | 9/2011 | Kemp et al. |
| 2012/0235791 | A1 | 9/2012 | Donlan et al. |
| 2013/0011234 | A1* | 1/2013 | Pretlove .................. B25J 5/005 |
| | | | 701/2 |
| 2013/0033381 | A1 | 2/2013 | Breed |
| 2013/0298652 | A1 | 11/2013 | Gillette, II |
| 2014/0032034 | A1 | 1/2014 | Raptopoulos et al. |
| 2014/0042199 | A1 | 2/2014 | Gegory, Jr. |
| 2014/0054361 | A1 | 2/2014 | Derby et al. |
| 2015/0006005 | A1 | 1/2015 | Yu et al. |
| 2015/0083509 | A1* | 3/2015 | Borroni-Bird ........ B60W 10/08 |
| | | | 180/204 |
| 2015/0153175 | A1 | 6/2015 | Skaaksrud |
| 2015/0186840 | A1 | 7/2015 | Torres et al. |
| 2015/0347959 | A1 | 12/2015 | Skaaksrud |
| 2016/0140315 | A1 | 5/2016 | Diaz et al. |
| 2016/0167724 | A1* | 6/2016 | Kilibarda ............ B62D 65/022 |
| | | | 29/401.1 |
| 2016/0194195 | A1* | 7/2016 | Kabre .................. G06Q 20/18 |
| | | | 705/23 |
| 2016/0207418 | A1 | 7/2016 | Bergstrom et al. |

(56) References Cited

U.S. PATENT DOCUMENTS

| | | |
|---|---|---|
| 2016/0235236 A1 | 8/2016 | Byers et al. |
| 2016/0353239 A1 | 12/2016 | Kjellsson et al. |
| 2017/0012830 A1 | 1/2017 | Skaaksrud et al. |
| 2017/0091710 A1 | 3/2017 | Van Dyke |
| 2017/0124789 A1 | 5/2017 | Rephlo |
| 2017/0225336 A1 | 8/2017 | Deyle et al. |
| 2017/0259811 A1 | 9/2017 | Couture et al. |
| 2018/0013211 A1 | 1/2018 | Ricci |
| 2018/0014988 A1 | 1/2018 | Diaz-Flores et al. |
| 2018/0022405 A1 | 1/2018 | Gecchelin et al. |
| 2018/0024554 A1 | 1/2018 | Brady et al. |
| 2018/0056985 A1 | 3/2018 | Couture et al. |
| 2018/0070753 A1 | 3/2018 | Eveloff et al. |
| 2018/0127211 A1* | 5/2018 | Jarvis ................. B65G 1/1373 |
| 2018/0127212 A1* | 5/2018 | Jarvis ..................... B60P 1/02 |
| 2018/0130017 A1 | 5/2018 | Gupte |
| 2018/0139152 A1 | 5/2018 | Shaw et al. |
| 2018/0169685 A1 | 6/2018 | Taylor et al. |
| 2018/0229843 A1 | 8/2018 | Costanzo et al. |
| 2018/0326886 A1 | 11/2018 | Sibley |
| 2018/0330319 A1 | 11/2018 | Liang et al. |
| 2018/0365635 A1 | 12/2018 | Lucrecia et al. |
| 2019/0028904 A1 | 1/2019 | Carpenter et al. |
| 2019/0033883 A1 | 1/2019 | Ferguson et al. |
| 2019/0034967 A1 | 1/2019 | Ferguson et al. |
| 2019/0043370 A1 | 2/2019 | Mulhall et al. |
| 2019/0047460 A1 | 2/2019 | Goldberg et al. |
| 2019/0057342 A1 | 2/2019 | Ferguson et al. |
| 2019/0113935 A1 | 4/2019 | Kuo et al. |
| 2019/0121368 A1 | 4/2019 | Bussetti et al. |
| 2019/0200510 A1 | 7/2019 | Chrysanthakopoulos et al. |
| 2019/0200519 A1 | 7/2019 | Chrysanthakopoulos et al. |
| 2019/0232504 A1 | 8/2019 | Radetzki et al. |
| 2019/0241079 A1 | 8/2019 | Huo |
| 2019/0283239 A1 | 9/2019 | Skaaksrud et al. |
| 2019/0283240 A1 | 9/2019 | Skaaksrud et al. |
| 2019/0283252 A1 | 9/2019 | Skaaksrud et al. |
| 2019/0283648 A1 | 9/2019 | Skaaksrud et al. |
| 2019/0283962 A1 | 9/2019 | Skaaksrud et al. |
| 2019/0286138 A1 | 9/2019 | Skaaksrud et al. |
| 2019/0286139 A1 | 9/2019 | Skaaksrud et al. |
| 2019/0286152 A1 | 9/2019 | Skaaksrud et al. |
| 2019/0286164 A1 | 9/2019 | Skaaksrud et al. |
| 2019/0287046 A1 | 9/2019 | Skaaksrud et al. |
| 2019/0287047 A1 | 9/2019 | Skaaksrud et al. |
| 2019/0287059 A1 | 9/2019 | Skaaksrud et al. |
| 2019/0287062 A1 | 9/2019 | Skaaksrud et al. |
| 2019/0287063 A1* | 9/2019 | Skaaksrud ............ B65G 67/24 |
| 2020/0102147 A1* | 4/2020 | Sullivan .................. B66F 9/065 |
| 2020/0103882 A1* | 4/2020 | Sullivan ............... G06Q 10/087 |
| 2020/0349786 A1 | 11/2020 | Ho et al. |
| 2021/0072751 A1 | 3/2021 | Gillett |
| 2021/0132625 A1* | 5/2021 | Gillett ...................... B64D 1/22 |
| 2021/0213604 A1* | 7/2021 | Lee ........................... B25J 9/08 |
| 2021/0308860 A1* | 10/2021 | Skaaksrud .......... G07C 9/00857 |
| 2021/0354287 A1* | 11/2021 | Skaaksrud ............... B25J 5/007 |
| 2021/0395011 A1 | 12/2021 | Crawford, Jr. et al. |
| 2022/0076326 A1* | 3/2022 | Mahajan .............. G06N 3/0454 |

FOREIGN PATENT DOCUMENTS

| | | |
|---|---|---|
| WO | 2015099890 A2 | 7/2015 |
| WO | 2017064202 A1 | 4/2017 |
| WO | 2018040541 A1 | 3/2018 |

OTHER PUBLICATIONS

Herbrechtsmeier et al., "AMiRo: A Modular & Customizable Open-Source Mini Robot Platform", 2016, IEEE, pp. 687-692.

Lisowski et al., "Specifications of a small electric vehicle: modular and distributed approach", 1987, IEEE, pp. 919-924.

Taher et al., "Multi-domain Autonomous Mobile Network for Sensing", 2016, IEEE, 6 pages.

Wilcox, "ATHLETE: A Mobility and Manipulation System for the Moon", 2007, IEEE, pp. 1-10.

Grob et al., "Autonomous Self-Assembly in Swarm-Bots", IEEE Transactions on Robotics, Dec. 2006, pp. 1115-1130, vol. 22, No. 6.

Lembke et al., "RoboMote: Mobile Autonomous Aardware Platform for Wireless Ad-hoc Sensor Networks", 2011, IEEE, p. 940-944.

Szabo et al., "Control System Architecture for a Remotely Operated Unmanned Land Vehicle", 1990, IEEE, pp. 876-882.

Wang et al., "MASmote—A Mobility Node for MAS-net (Mobile Actuator Sensor Networks)", 2004, IEEE, p. 816-821.

PCT Application No. PCT/US2019/021963 International Preliminary Report on Patentability, dated Sep. 15, 2020.

PCT Application No. PCT/US2019/021963 International Search Report and Written Opinion, dated Jul. 2, 2019.

Bouloubasis et al., "Cooperative Transport of Extended Payloads", IEEE, 2005, pp. 882-887.

Paulos et al., "Automated Self-Assembly of Large Maritime Structures by a Team of Robotic Boats", IEEE Transactions on Automaiton Science and Engineering, Jul. 2015, pp. 958-968, vol. 12, No. 3.

Sahin, "GroundScouts: Architecture for a Modular Micro Robotic Platform for Swarm Intelligence and Cooperative Robotics", 2004 IEEE International Conference on Systems, Man and Cybernetics, pp. 929-934.

International Application No. PCT/US22/15552 International Search Report and Written Opinion dated Jun. 21, 2022.

* cited by examiner

- Locations of Master Nodes M1, M2, and M3 are known
- Location of ID Nodes A and B are determined through triangulation across Master Nodes M1, M2 and M3

- Location of ID Node C determined through triangulation across ID Node B and Master Nodes M1 and M2

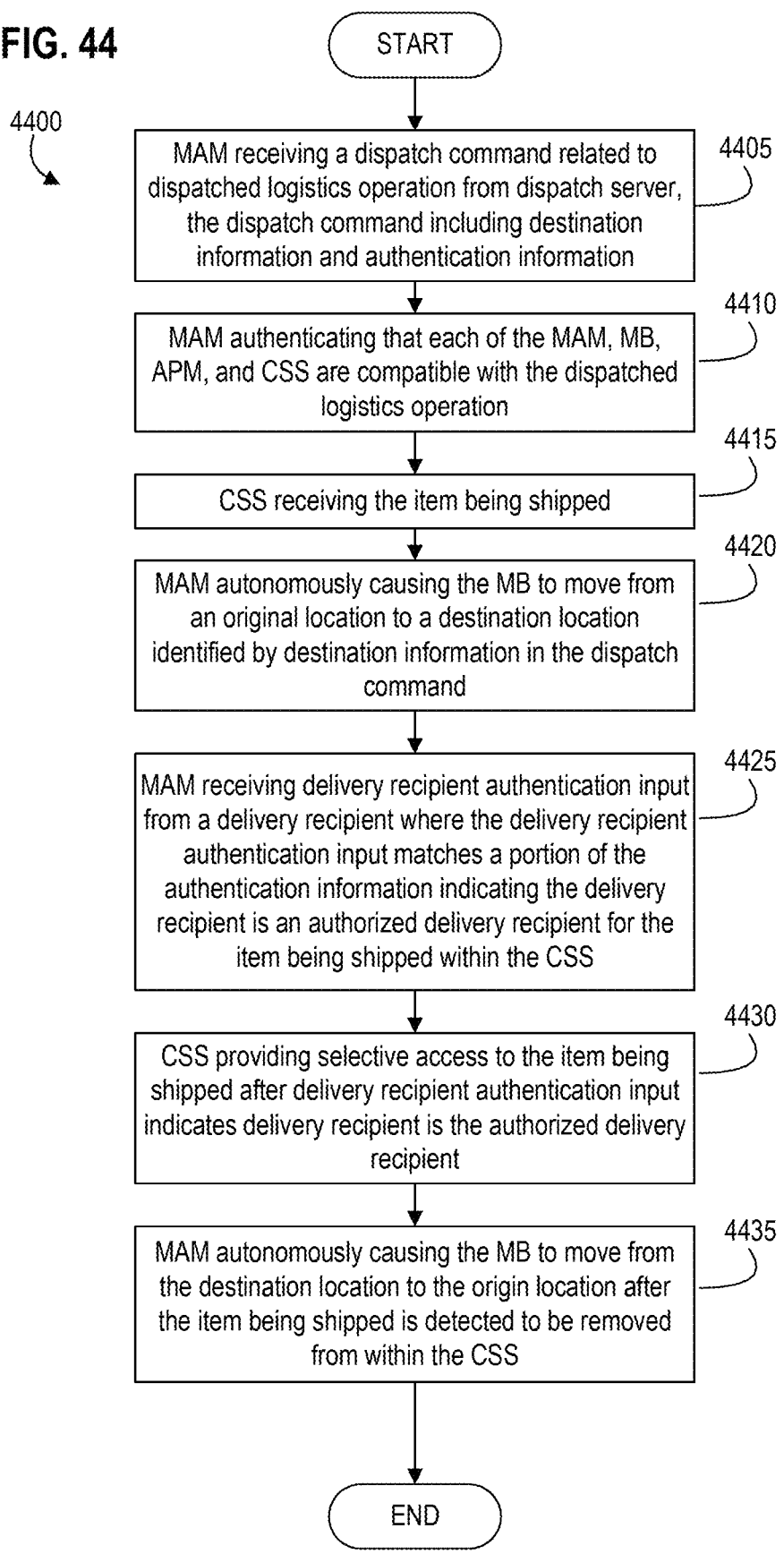

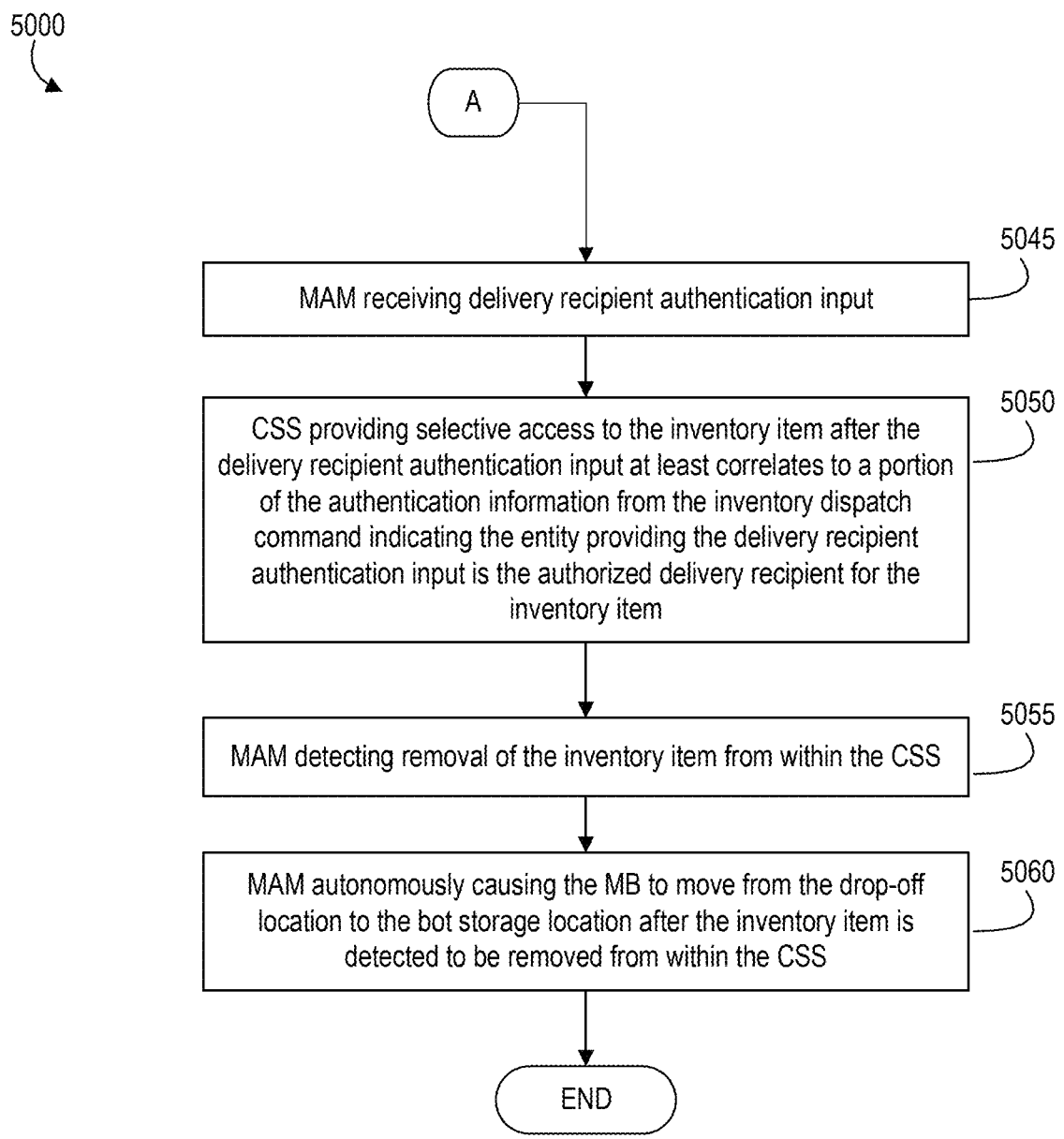

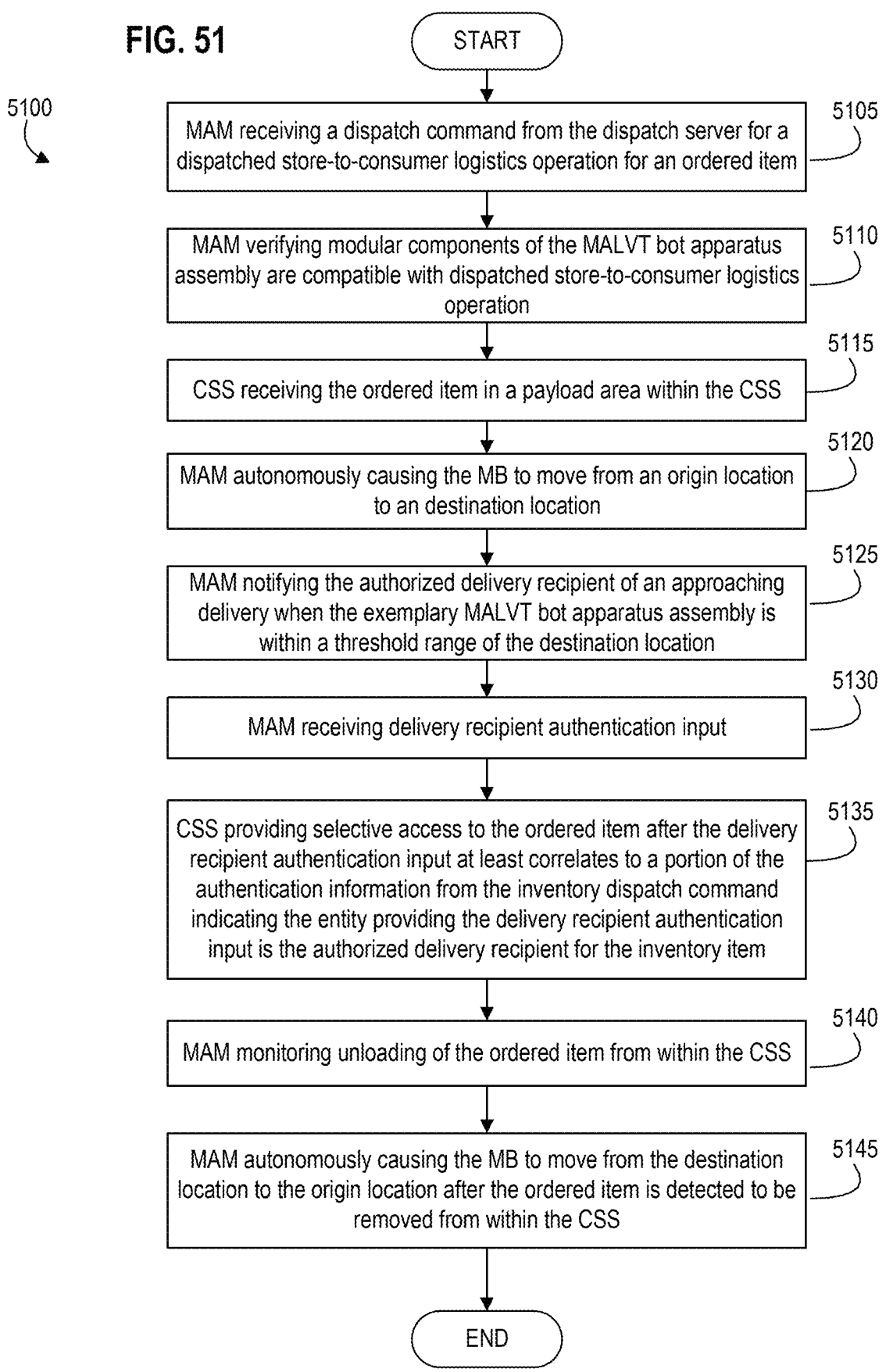

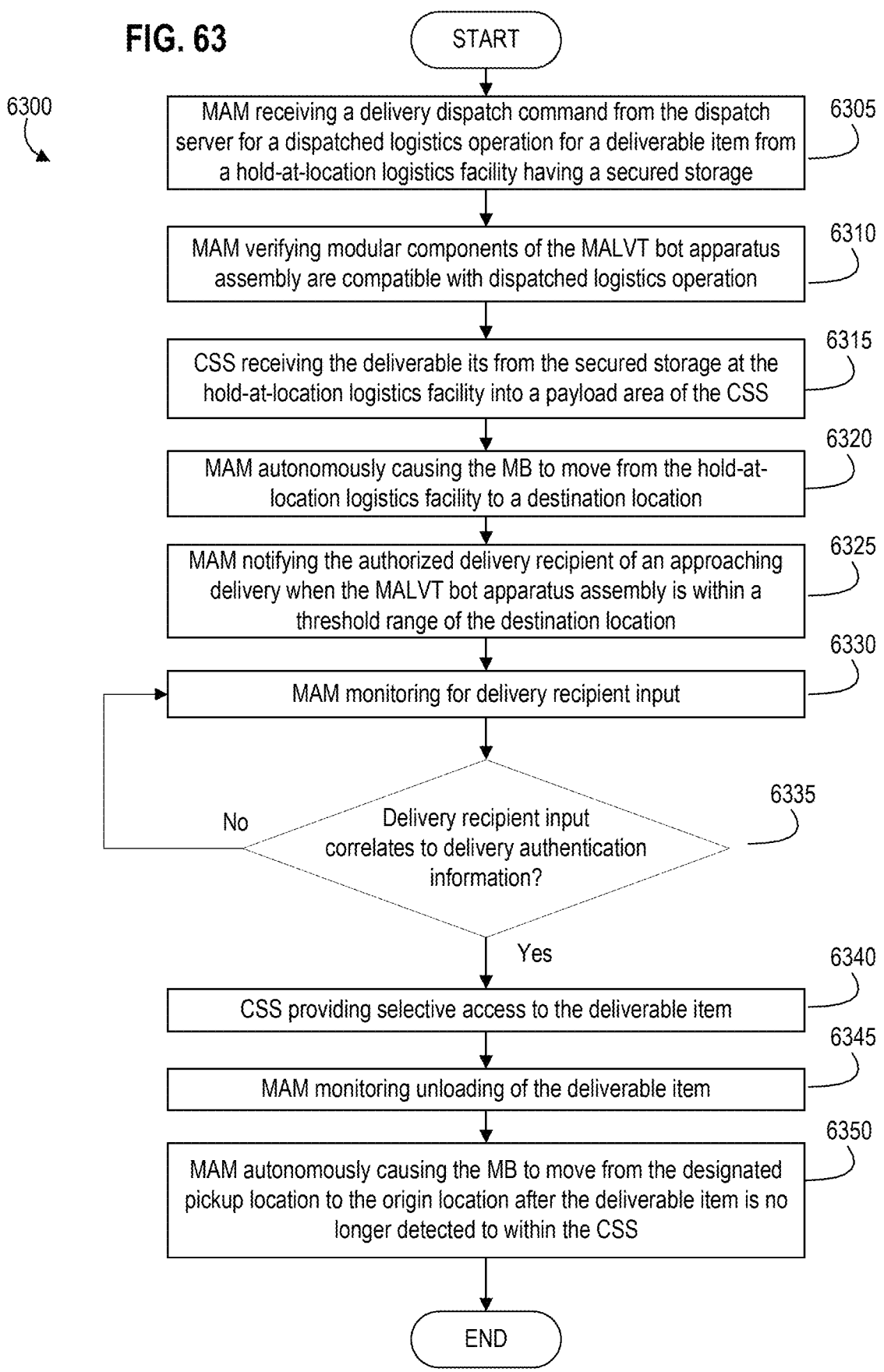

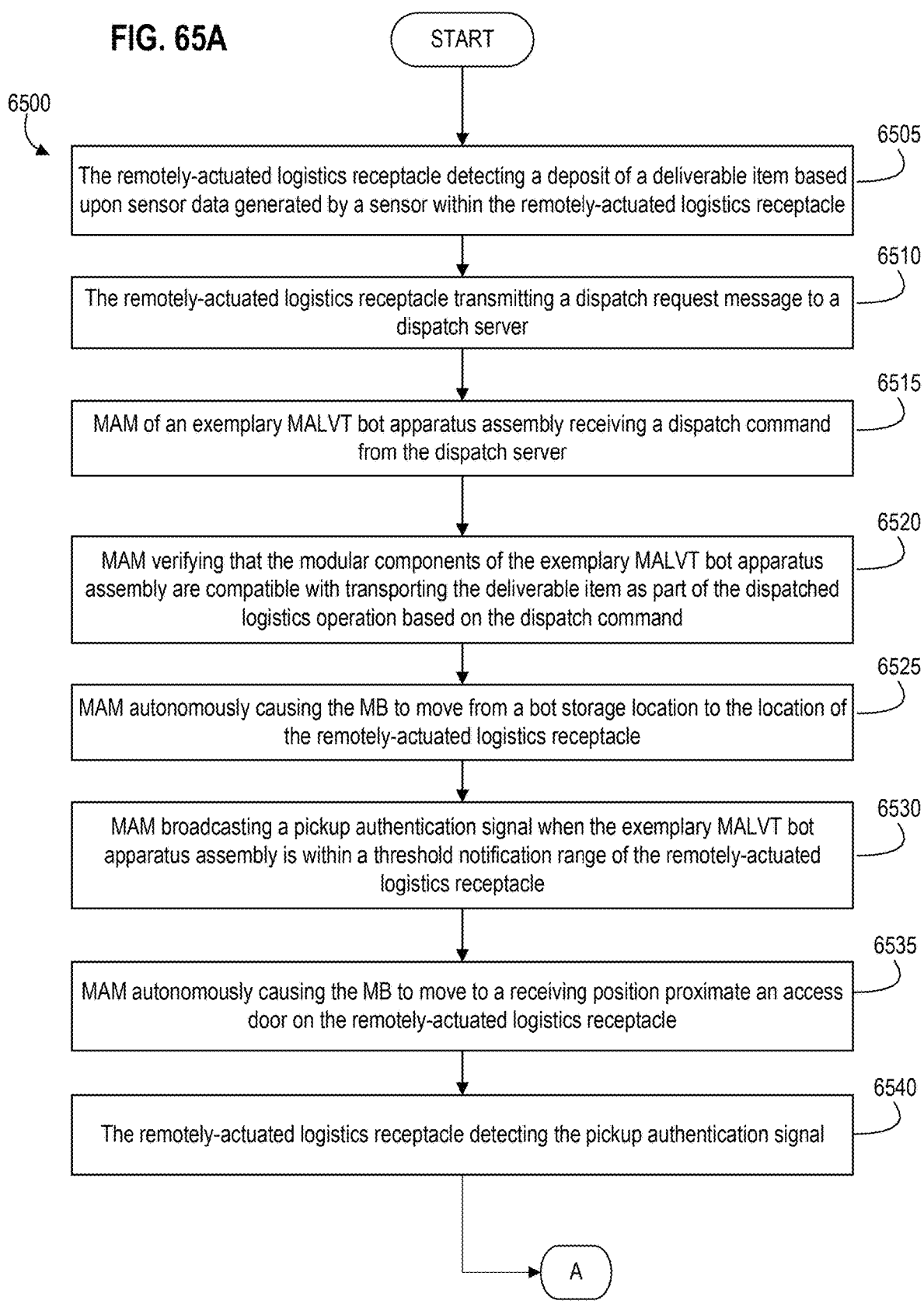

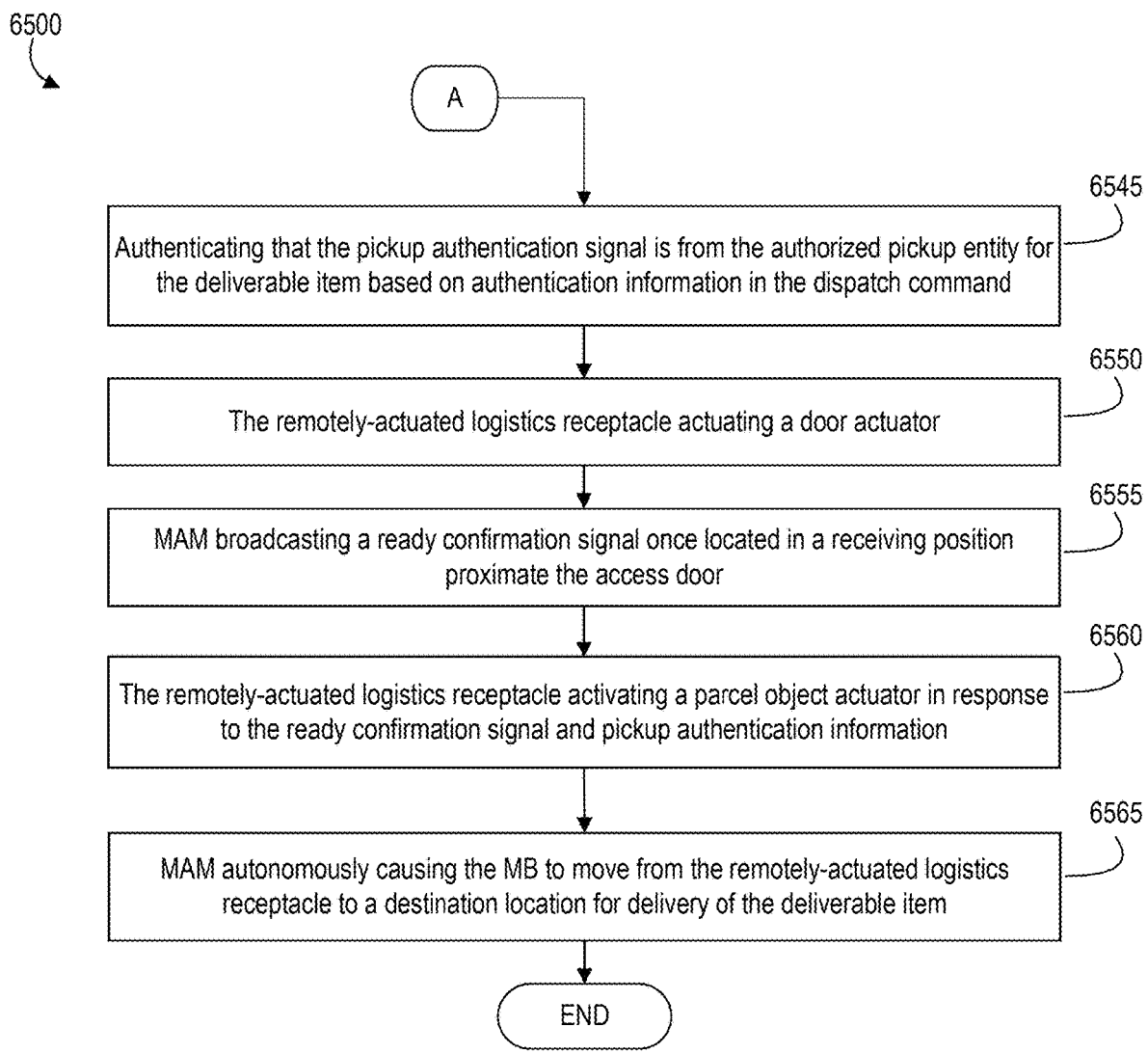

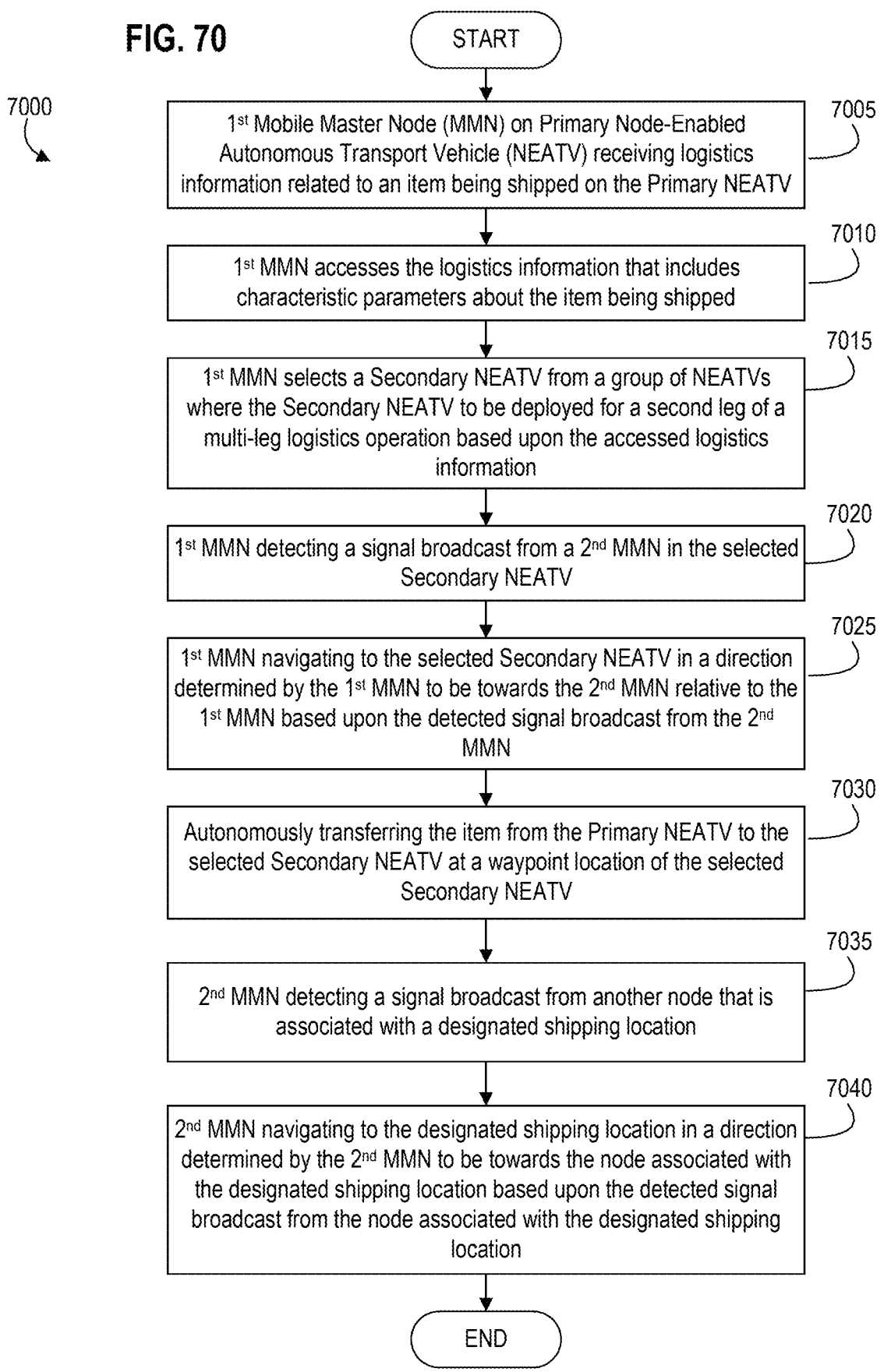

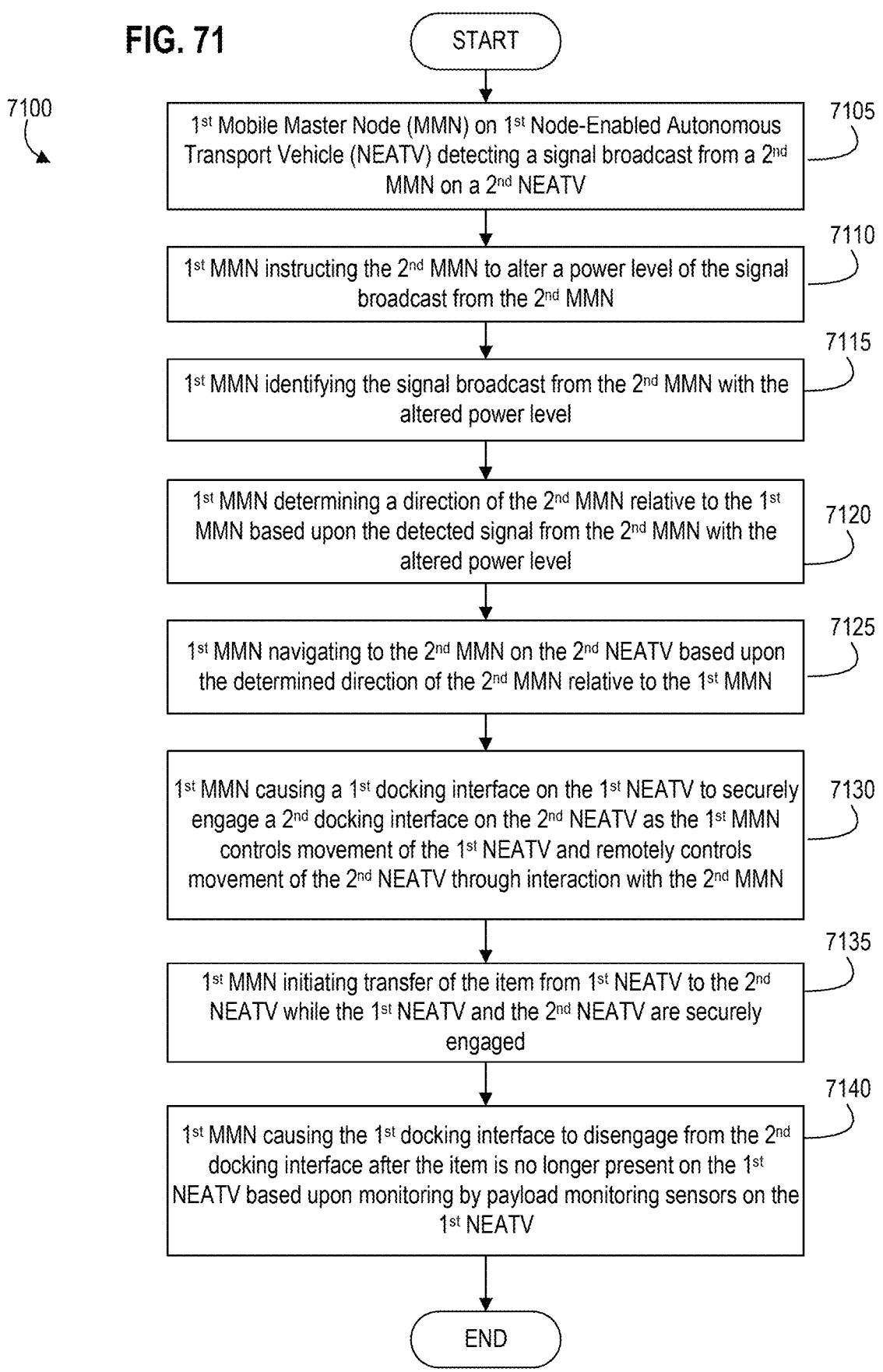

METHODS OF PERFORMING A DISPATCHED CONSUMER-TO-STORE LOGISTICS OPERATION RELATED TO AN ITEM BEING REPLACED USING A MODULAR AUTONOMOUS BOT APPARATUS ASSEMBLY AND A DISPATCH SERVER

PRIORITY AND RELATED APPLICATIONS

The present application hereby claims the benefit of priority to related Provisional Patent Application No. 62/642,732 filed on Mar. 14, 2018 and entitled "Enhanced Apparatus, Assemblies, and Systems Involving a Modular Autonomous Logistics Vehicle Transport and Methods of Operating the Same."

The present application is also related in subject matter to the following concurrently filed non-provisional patent applications where each also claims the benefit of priority to the same above-referenced provisional patent application: (1) Non-Provisional patent application Ser. No. 16/351,566 entitled "A Modular Mobility Base for a Modular Autonomous Logistics Vehicle Transport Apparatus"; (2) Non-Provisional patent application Ser. No. 16/351,576 entitled "A Modular Multiple Mobility Base Assembly Apparatus for Transporting an Item Being Shipped"; (3) Non-Provisional patent application Ser. No. 16/351,584 entitled "A Modular Auxiliary Power Module for a Modular Autonomous Bot Apparatus that Transports an Item Being Shipped"; (4) Non-Provisional patent application Ser. No. 16/351,590 entitled "A Modular Cargo Storage Apparatus for use on a Base Platform of a Modular Autonomous Bot Apparatus that Transports an Item Being Shipped"; (5) Non-Provisional patent application Ser. No. 16/351,634 entitled "A Detachable Modular Mobile Autonomy Control Module for a Modular Autonomous Bot Apparatus that Transports an Item Being Shipped"; (6) Non-Provisional patent application Ser. No. 16/351,642 entitled "A Modular Autonomous Bot Apparatus that Transports an Item Being Shipped"; (7) Non-Provisional patent application Ser. No. 16/351,683 entitled "Methods of Performing a Dispatched Logistics Operation Related to an Item Being Shipped and Using a Modular Autonomous Bot Apparatus Assembly and a Dispatch Server"; (8) Non-Provisional patent application Ser. No. 16/351,573 entitled "Methods of Performing an Inventory Management Related Dispatched Logistics Operation for an Inventory Item and Using a Modular Autonomous Bot Apparatus Assembly and a Dispatch Server"; (9) Non-Provisional patent application Ser. No. 16/351,579 entitled "Methods of Performing a Dispatched Store-to-Consumer Logistics Operation Related to an Ordered Item and Using a Modular Autonomous Bot Apparatus Assembly and a Dispatch Server"; (10) Non-Provisional patent application Ser. No. 16/351,598 entitled "Methods of Performing a Dispatched Medical Logistics Operation Related to a Diagnosis Kit for Treating a Patient and Using a Modular Autonomous Bot Apparatus Assembly and a Dispatch Server"; (11) Non-Provisional patent application Ser. No. 16/351,604 entitled "Apparatus and Systems of a Modular Autonomous Cart Apparatus Assembly for Transporting an Item Being Shipped"; (12) Non-Provisional patent application Ser. No. 16/351,619 entitled "Apparatus, Systems, and Methods for Performing a Dispatched Logistics Operation for a Deliverable Item from a Hold-at-Location Logistics Facility Using a Modular Autonomous Bot Apparatus Assembly, a Dispatch Server and an Enhanced Remotely Actuated Logistics Receptacle Apparatus"; and (13) Non-Provisional patent application Ser. No. 16/351,681 entitled "Methods and Systems for Navigating to a Designated Shipping Location as Part of a Multi-Leg Logistics Operations using a Wireless Node Network and Multiple Node-Enabled Autonomous Transport Vehicles in the Network."

FIELD OF THE DISCLOSURE

The present disclosure generally relates to systems, apparatus, assemblies, and methods in the field of logistics and, more particularly, to various aspects of enhanced systems, apparatus, assemblies, and methods related to deployment and use of a highly autonomous transport system that may include and leverage uses of elements of a multi-purpose type of modular autonomous logistics vehicle transport (MALVT) or node-enabled autonomous transport vehicle (AV), an assembly of such a multi-purpose type of modular autonomous logistics vehicle transport (MALVT) or node-enabled autonomous transport vehicle (AV), and systems that involve a multi-purpose type of modular autonomous logistics vehicle transport (MALVT) or node-enabled autonomous transport vehicle (AV).

BACKGROUND

In the technical field of logistics involving delivery and pickup of items and objects for transport between locations, existing systems have deployed delivery vans and courier personnel that manage and implement dispatched logistics operations to deliver and pickup of such items and objects from businesses and residential locations. However, deploying manually controlled logistics delivery vehicles and systems may incur In general, autonomous and semi-autonomous vehicles that can move and maneuver from an origin location to a different location exist, but are not without problems in the field of logistics. For example, common autonomous or semi-autonomous logistics systems are less adaptive than needed. A particular autonomous logistics delivery vehicle may lack compatibility for specifically tasked logistics operations or the ability to efficiently handle a wide variety of different sized items/objects. Furthermore, known autonomous logistics delivery solutions may incur undesired waste involved with dispatching oversized delivery vehicles for a given logistics operation. The lack of interoperability with a location's facilities and pathway obstacles are also problems that face common logistics delivery vehicles that are autonomously controlled.

To address these requirements and present further enhanced and improved devices, assemblies, systems, and methods for autonomous delivery or pickup of items/objects being shipped, there remains a need for improved systems that may provide more extensive, robust, adaptive, and interactive autonomous logistics vehicles that address such problems with a modular autonomous logistics bot apparatus as individual modular components of an assembly, as a particular assembly of such components, and systems of modular autonomous logistics vehicles that do so in a cost effective, dynamic, innovative solution that addresses such problems in practical applications that leverage such modular components and modular autonomous logistics vehicles using such components.

SUMMARY

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

In the following description, certain aspects and embodiments will become evident. It should be understood that the aspects and embodiments, in their broadest sense, could be practiced without having one or more features of these aspects and embodiments. It should be understood that these aspects and embodiments are merely exemplary.

In one aspect of the disclosure, a method is described for performing a dispatched consumer-to-store return logistics operation related to an item being replaced and using a modular autonomous bot apparatus assembly and a dispatch server. In this first aspect, the modular autonomous bot apparatus assembly used in the method has at least a modular mobility base propelling the modular autonomous bot apparatus assembly, a modular auxiliary power module providing power for the modular autonomous bot apparatus assembly, a modular cargo storage system operative to at least temporarily maintain the item being replaced within the modular autonomous bot apparatus assembly, and a modular mobile autonomy control module that autonomously controls operation of the modular autonomous bot apparatus assembly during the dispatched consumer-to-store return logistics operation. The method begins with the modular mobile autonomy control module receiving a return operation dispatch command from the dispatch server. Such a return operation dispatch command has at least identifier information on the item being replaced, transport parameters on the item being replaced, designated pickup information related to pickup of the item being replaced, and pickup authentication information related to an authorized supplier of the item being replaced. The method then has the modular mobile autonomy control module verifying that each of the modular mobile autonomy control module, the modular mobility base, the modular auxiliary power module, and the modular cargo storage system are compatible with the dispatched consumer-to-store return logistics operation based upon the dispatch command. Thereafter, the method has the modular mobile autonomy control module autonomously causing the modular mobility base to move from an origin location on a route to a designated pickup location identified by the designated pickup information. On the way, the modular mobile autonomy control module notifies the authorized supplier of the item being replaced of an approaching pickup for the item being replaced once the modular autonomous bot apparatus assembly is within a threshold notification range of the designated pickup location identified by the designated pickup information. At the designated pickup location, the method continues by receiving supplier authentication input by the modular mobile autonomy control module from a return entity disposed external to the modular autonomous bot apparatus assembly. The method has the modular cargo storage system providing selective access to a payload area within the modular cargo storage system only when the supplier authentication input received correlates to the pickup authentication information indicating that the return entity providing the supplier authentication input is the authorized supplier of the item being replaced. The method has the modular mobile autonomy control module monitoring loading of the item being replaced into the payload area of the modular cargo storage system using one or more sensors on at least one of the modular mobile autonomy control module and the modular cargo storage system, and then receiving, by the modular cargo storage system, the item being replaced and its return documentation in the payload area within the modular cargo storage system. The method concludes with the modular mobile autonomy control module autonomously causing the modular mobility base to move from the designated pickup location on a return route to the origin location after the item being replaced is detected to be within the modular cargo storage system based upon monitoring the loading of the item being replaced and the return documentation is loaded within the modular cargo storage system with the item being replaced.

In another aspect of the disclosure, a method is described for performing a dispatched swap logistics operation related to an item being replaced being swapped for a replacement item and using a modular autonomous bot apparatus assembly and a dispatch server. In this additional aspect, the modular autonomous bot apparatus assembly used as part of this method has at least a modular mobility base propelling the modular autonomous bot apparatus assembly, a modular auxiliary power module providing power for the modular autonomous bot apparatus assembly, a modular cargo storage system configured to at least maintain the item being replaced within the modular autonomous bot apparatus assembly, and a modular mobile autonomy control module that autonomously controls operation of the modular autonomous bot apparatus assembly during the dispatched swap logistics operation. The method beings with the modular mobile autonomy control module receiving a swap operation dispatch command from the dispatch server. The swap operation dispatch command has at least identifier information on the item being replaced and identifier information on the replacement item, transport parameters on the item being replaced and the replacement item, designated pickup information related to swapping the item being replaced for the replacement item, and pickup authentication information related to an authorized delivery recipient of replacement item. The method proceeds with the modular mobile autonomy control module verifying that each of the modular mobile autonomy control module, the modular mobility base, the modular auxiliary power module, and the modular cargo storage system are compatible with the dispatched swap logistics operation based upon the swap operation dispatch command. The method then has the modular cargo storage system receiving the replacement item in a payload area within the modular cargo storage system before the modular mobile autonomy control module autonomously causes the modular mobility base to move from an origin location on a route to a designated swap location identified by the designated pickup information. On the way, the modular mobile autonomy control module notifies the authorized delivery recipient of the replacement item of an approaching pickup for the item being replaced and delivery of the replacement item once the modular autonomous bot apparatus assembly is within a threshold notification range of the designated swap location identified by the designated pickup information. At the designated swap location, the method continues by receiving delivery recipient authentication input by the modular mobile autonomy control module from a delivery recipient disposed external to the modular autonomous bot apparatus assembly. The method then has the modular cargo storage system providing selective access to the payload area within the modular cargo storage system only when the delivery recipient authentication input received correlates to the pickup authentication information indicating that the delivery recipient providing the delivery recipient authentication input is the authorized delivery recipient of the replacement item. The modular mobile autonomy control module then monitors an exchange of the replacement item from the payload area of the modular cargo storage system with the item being replaced using one or more sensors on at least one of the modular mobile autonomy control module and the modular cargo storage system. Thereafter, the method has the modular mobile autonomy control module autonomously causing the modular mobility base to move from the designated swap location on a return route to the origin location after the item being replaced is detected to be within the modular cargo storage system based upon the monitored loading of the item being replaced.

Each of these aspects and features of such aspects respectively effect improvements to the technology of autonomous logistics vehicles. Additional advantages of this and other aspects of the disclosed embodiments and examples will be set forth in part in the description which follows, and in part will be obvious from the description, or may be learned by practice of the invention. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments according to one or more principles of the invention and together with the description, serve to explain one or more principles of the invention. In the drawings.

FIG. 44 is a flow diagram of an exemplary method for performing a dispatched logistics operation involving delivery of an item being shipped using a modular autonomous bot apparatus assembly (MALVT bot apparatus assembly) and a dispatch server in accordance with an embodiment of the invention;

FIGS. 50A-50B are parts of a flow diagram of an alternative embodiment of an exemplary method for performing an inventory management related dispatched logistics operation involving an inventory item using a modular autonomous bot apparatus assembly (MALVT bot apparatus assembly) and an inventory management server in accordance with an embodiment of the invention;

FIG. 51 is a flow diagram of an embodiment of an exemplary method for performing a dispatched store-toconsumer logistics operation related to an ordered item and using a modular autonomous bot apparatus assembly (MALVT bot apparatus assembly) and a dispatch server in accordance with an embodiment of the invention;

FIG. 63 is a flow diagram of an embodiment of an exemplary method for performing a dispatched logistics operation for a deliverable item from a hold-at-location logistics facility having a secured storage and using a modular autonomous bot apparatus assembly (MALVT bot apparatus assembly) and a dispatch server in accordance with an embodiment of the invention;

FIGS. 65A-65B are a flow diagram of an embodiment of an exemplary method for performing a dispatched logistics operation for a deliverable item maintained within a remotely-actuated logistics receptacle and using a modular autonomous bot apparatus assembly (MALVT bot apparatus assembly) and a dispatch server in accordance with an embodiment of the invention;

FIG. 70 is a flow diagram of an embodiment of an exemplary method for navigating to a designated shipping location as part of a multi-leg logistics operation using multiple nodes in a wireless node network, a server in the network, a first node-enabled autonomous transport vehicle in the network, and a selected one of a group of other node-enabled autonomous transport vehicles in accordance with an embodiment of the invention; and FIG. 71 is a flow diagram of an embodiment of another exemplary method for navigating to a designated shipping location as part of a multi-leg logistics operation using multiple nodes in a wireless node network, a server in the network, and multiple node-enabled autonomous transport vehicles in the network where one of the node-enabled autonomous transport vehicles operates as master to control at least docking and transferring operations as part of the multi-leg logistics operation in accordance with an embodiment of the invention.

DESCRIPTION OF THE EMBODIMENTS

Figure 1:
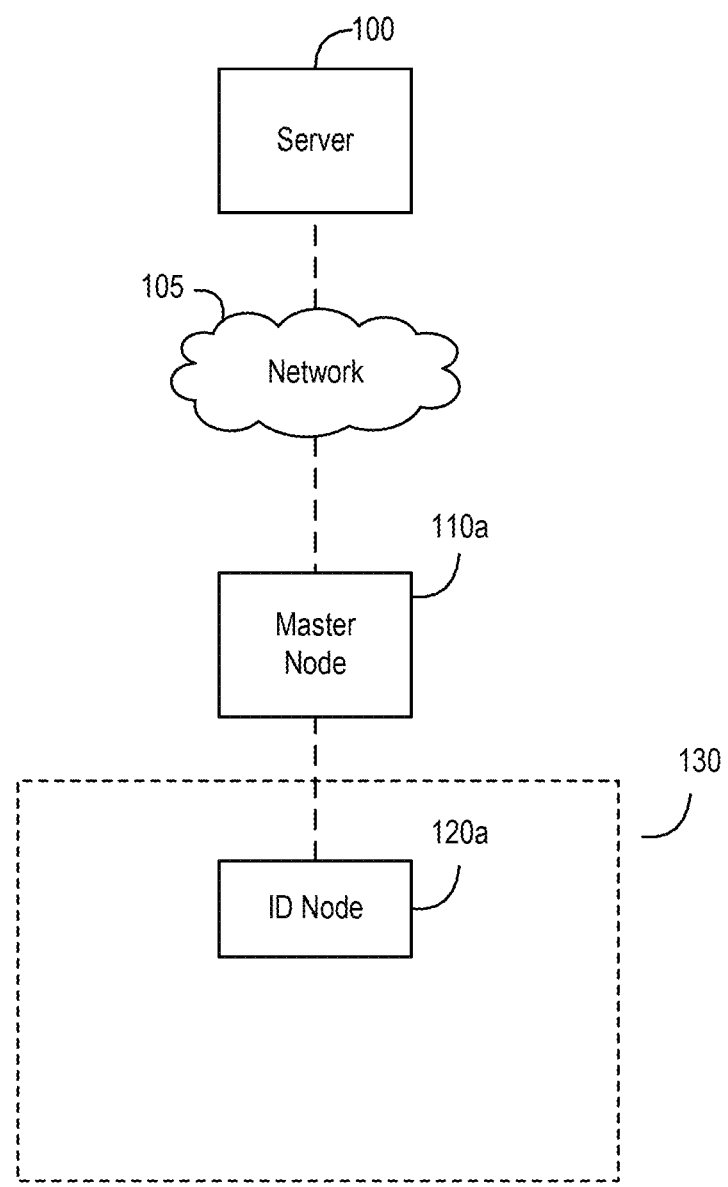
FIG. 1 is a diagram of an exemplary wireless node network as known in the art.

Reference will now be made in detail to exemplary embodiments. Wherever possible, the same reference numbers are used in the drawings and the description to refer to the same or like parts. However, those skilled in the art will appreciate that different embodiments may implement a particular part in different ways according to the needs of the intended deployment and operating environment for the respective embodiments.

Reference will also be made throughout this description to wireless node-based network devices (e.g., ID nodes, master nodes, container nodes, and servers that operate in a wireless node network), exemplary techniques that use such node-based devices, and interactions with such devices in the logistics delivery field as explained in more detail within U.S. application Ser. No. 14/445,523 (now issued as U.S. Pat. No. 8,989,053), U.S. application Ser. No. 14/979,685 (published as U.S. Patent Application Publication No. US 2016/01232481), and U.S. application Ser. No. 15/433,023 (published as U.S. Patent Application Publication No. US 2017/0279892), which are each hereby incorporated by reference. The information disclosed in U.S. application Ser. No. 14/445,523 (now issued as U.S. Pat. No. 8,989,053), U.S. application Ser. No. 14/979,685 (published as U.S. Patent Application Publication No. US 2016/01232481), and U.S. application Ser. No. 15/433,023 (published as U.S. Patent Application Publication No. US 2017/0279892) is collectively referred to as TRON Network Reference Information or more generally referenced as TRON technology within the present description. In particular, those skilled in the art will appreciate that the description of such node-based devices, how they interact and communicate, how they associate with other nodes to establish secure communications and information sharing, and how they use various node locating techniques to determine the location of a particular node in the network provides a foundational teaching of building block elements that may be used as control elements that may interact with each other in embodiments of exemplary modular autonomous logistics transport vehicle apparatus (MALVT bot apparatus) and components thereof as described in more detail below.

In general, the following description begins with a broad overview of the TRON technology referenced above that may be used in implementations of different embodiments involving modular autonomous logistics bots, assemblies, components, vehicles, and systems. Embodiments of an exemplary MALVT bot apparatus are presented and explained as respective modular components of such an apparatus and as a modular assembly of compatible components that may be assembled to form an exemplary MALVT bot apparatus for use in a logistics operation (e.g., delivery of an item/object, pickup of an item/object). Further embodiments are described about different practical use applications that involve the use of one or more components and/or one or more exemplary MALVT bot apparatus assemblies deployed in varying types of logistics operations. Finally, embodiments are presented that involve multiple autonomous logistics vehicle transports that may be deployed for different legs of a single multi-leg logistics operation.

Overview of TRON Wireless Node Network Technology

In more detail, the following description along with FIGS. 1-16 provide a background overview of a known type of wireless node network with one or more lower level devices or nodes (e.g., an ID node) that rely on shorter-range communication with a higher level device or node (e.g., a master node), which is operative to communicate with a server over a different communication interface while the lower level node is unable to communicate directly with the server. Those skilled in the art will appreciate that such a hierarchy of different functional communicating network components (generally referred to as network devices) may be characterized as a network of nodes. Those skilled in the art will appreciate that in some embodiments, the wireless node network may include the server as well as different wireless nodes despite the fact that the server may not be a dedicated wireless component. In other embodiments, the network may include similar types of wireless nodes or different types of wireless nodes.

Those skilled in the art will understand through the following detailed description that the nodes may be associated with items (e.g., an object, a package, a person, a piece of equipment) and may be used to identify and locate the items while being dynamically programmed during operation of the network and while the items move along an anticipated path (e.g., a transit path from an origin point to a destination point). Those skilled in the art will further understand through the following detailed description that these known type of nodes may be deployed as control systems, control electronics, controllers, processors, control modules, or other control elements that may wirelessly communicate with other nodes (e.g., a controller in a modular mobility base component and an autonomous control system in a modular mobile autonomous control module), receive input from sensors, generate output messaging and display information as well as generate control signals that manage and control an autonomous delivery vehicle.

Again, FIGS. 1-16 provide background information on such known types of wireless nodes that may be programmed to interact to detect other nodes, associate with other nodes, receive and respond to sensor data, generate control signals, manage other nodes, and locate other nodes in a hierarchical manner. FIG. 1 illustrates a basic diagram of an exemplary wireless node network. The exemplary network shown in FIG. 1 comprises a server 100 connected to a network 105, which is also operatively connected to different network components, such as a master node 110a and indirectly to an ID node 120a through master node 110a. Master node 110a is typically connected to an ID node 120a via short-range wireless communications (e.g., Bluetooth® formatted communications). Master node 110a is typically connected to server 100 through network 105 via longer-range wireless communication (e.g., cellular) and/or medium range wireless communication (e.g., wireless local area data networks or Wi-Fi). ID node 120a is typically a low cost device that may be easily placed into a package, be integrated as part of packaging, or otherwise associated with an item to be tracked and located, such as package 130, a person, or object (e.g., vehicle, etc.). Generally, an ID node is capable of communicating directly with a master node but incapable of communicating directly with the server, while a master node is capable of communicating directly with the server and separately and directly communicating with other nodes (such as an ID node or another master node). The ability to deploy a hierarchy of nodes within an exemplary wireless node network to distribute tasks and functions at the different levels in an efficient and economical manner helps to facilitate a wide variety of adaptive locating, tracking, managing, and reporting applications using such a network of nodes as discussed in more detail below.

In general, the lower cost, lower complexity ID node 120a is managed by the higher complexity master node 110a and server 100 as part of keeping track of the location of ID node 120a (and the associated item), thereby providing intelligent, robust, and broad visibility about the location and status of ID node 120a. In a typical deployment example, ID node 120a is first associated with an item (e.g., package 130, a person, or object). As ID node 120a moves with the item, the ID node 120a becomes associated with the master node 110a, and the server 100 is updated with such information. Further movement of the ID node 120a and item may cause the ID node 120a to disassociate with master node 110a and be handed off to become associated another master node (not shown), after which the server 100 is again updated. As such, the server 100 generally operates to coordinate and manage information related to the ID node 120*a* as the item physically moves from one location to another. Further details of the architecture and functionality of an exemplary ID node and master node as described below in more detail with respect to FIGS. 3 and 4, while exemplary server 100 is described below in more detail with respect to FIG. 5.

While server 100 is shown connecting through network 105, those skilled in the art will appreciate that server 100 may have a more direct or dedicated connections to other components illustrated in FIG. 1, such as master node 110*a*, depending upon implementation details and desired communication paths. Furthermore, those skilled in the art will appreciate that an exemplary server may contain a collection of information in a database (not shown in FIG. 1), while multiple databases maintained on multiple server platforms or network storage servers may be used in other embodiments to maintain such a collection of information. Furthermore, those skilled in the art will appreciate that a database may be implemented with cloud technology that essentially provides networked storage of collections of information that may be directly accessible to devices, such as master node 110*a*.

Network 105 may be a general data communication network involving a variety of communication networks or paths. Those skilled in the art will appreciate that such exemplary networks or paths may be implemented with hard wired structures (e.g., LAN, WAN, telecommunication lines, telecommunication support structures and telecommunication processing equipment, etc.), wireless structures (e.g., antennas, receivers, modems, routers, repeaters, etc.) and/or a combination of both depending upon the desired implementation of a network that interconnects server 100 and other components shown in FIG. 1 in an embodiment of the present invention.

Master node 110*a* and ID node 120*a* are types of nodes. A node is generally an apparatus or device used to perform one or more tasks as part of a network of components. An embodiment of a node may have a unique identifier, such as a Media Access Control (MAC) address or an address assigned to a hardware radio like an Internet Protocol 6 (IPv6) identifier. In some embodiments, the node's unique identifier may be correlated to a shipment identifier (e.g., a shipment tracking number in one example), or may itself be a shipment's tracking reference.

An ID node, such as ID node 120*a*, is generally a low cost active wireless device. In one embodiment, an exemplary ID node is a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. For example, the physical implementation of an exemplary ID node may be small, and, thus, amenable to integration into a package, label, container, or other type of object. In some implementations of an ID node, the node is rechargeable while other implementations do not permit recharging the power source for the ID node. In other implementations, the ID node is environmentally self-contained or sealed so as to enable robust and reliable operations in a variety of environmentally harsh conditions.

A master node, such as master node 110*a*, generally serves as an intelligent bridge between the ID node 120*a* and the server 100. Accordingly, a master node is generally more sophisticated than an ID node. In one example, an exemplary master node is a device having a processing or logic unit, a short-range radio (with may have variable RF characteristics) used for communicating with other nodes (ID nodes and other master nodes), a medium and/or long-range radio for communication with the server 100, memory accessible by the processing unit, a timer operatively coupled to the processing unit, and a power source (e.g., a battery or a wired power supply connection) that provides power for the circuitry of the master node. The exemplary master node, such as master node 110*a*, may be positioned in a known fixed location or, alternatively, be a mobile unit having dedicated location positioning circuitry (e.g., GPS circuitry) to allow the master node to determine its location by itself.

While the example illustrated in FIG. 1 shows only a single master node and a single ID node, those skilled in the art will appreciate that a wireless network may include a wide array of similar or different master nodes that each communicate with the server 100 and/or other master nodes, and a wide variety of similar or different ID nodes. Thus, the exemplary network shown in FIG. 1 is a basic example, while the exemplary network shown in FIG. 2 is a more detailed exemplary wireless node network.

Figure 2:
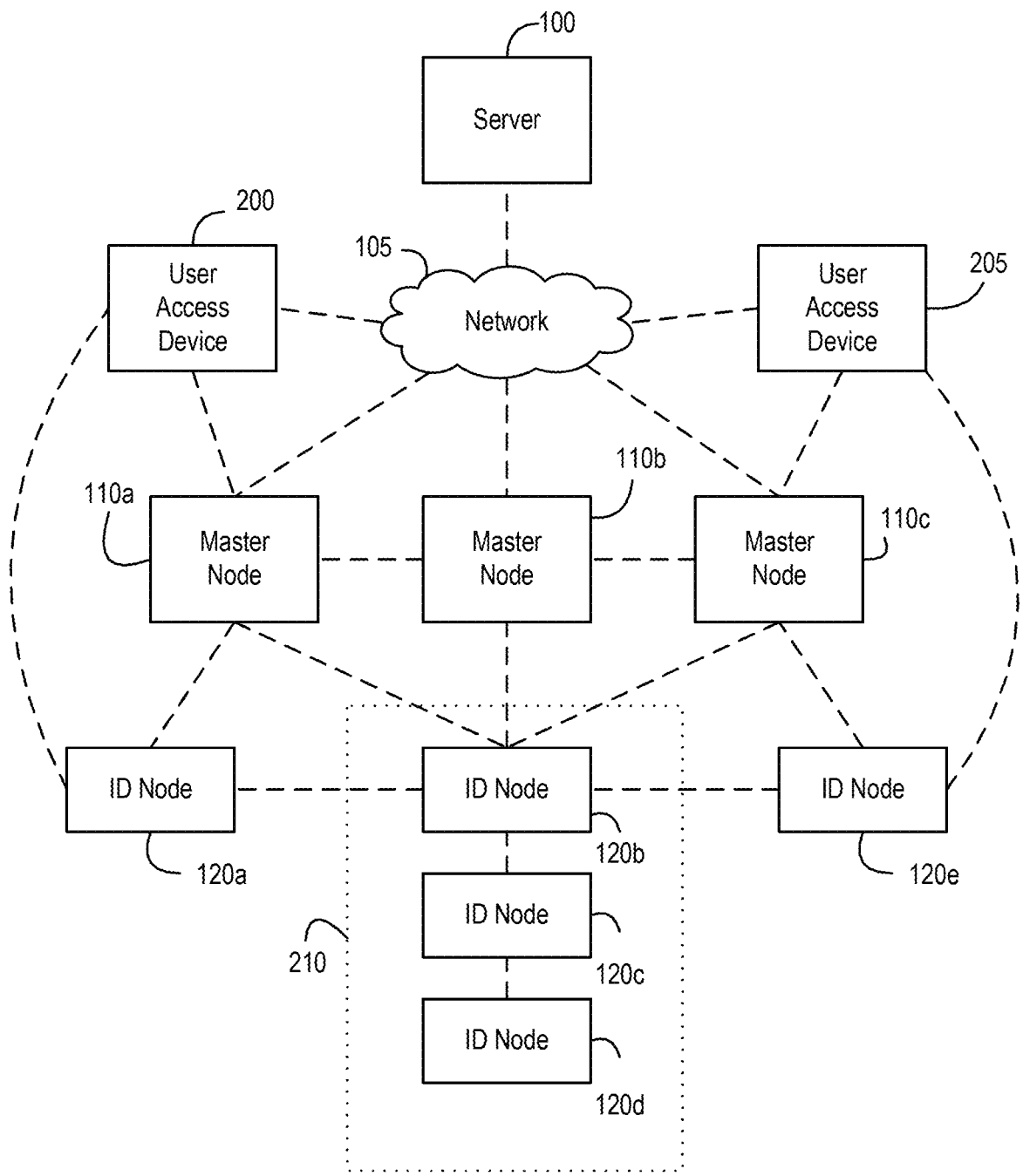
FIG. 2 is a more detailed diagram of an exemplary wireless node network as known in the art.

Referring now to FIG. 2, another exemplary wireless node network is shown including server 100 and network 105. Here, master nodes 110*a*, 110*b*, 110*c* are deployed and connected to network 105 (and by virtue of those respective connections, to server 100) as well as to each other. ID nodes 120*a*, 120*b*, 120*e* are shown as connectable or operative to communicate via different paths to various master nodes. However, ID nodes 120*c* and 120*d* are shown in FIG. 2 connected to ID node 120*b* but not to any of the master nodes. This may be the case if, for example, ID nodes 120*b*, 120*c*, 120*d* are associated with different items (e.g., packages) within a larger container 210 (or grouped together on a pallet). In such an example, only ID node 120*b* may remain within the wireless communication range of any master node. This may, for example, be because of the positions of the different ID nodes within the container relative to the closest master node, adverse RF shielding caused by the container, adverse RF shielding caused by packaging of the item, or adverse RF shielding caused by other proximate material that interferes with radio transmissions (e.g., several packages of metal items between the ID node and any master node outside the container). Thus, in the illustrated configuration of the exemplary network shown in FIG. 2, ID nodes 120*c* and 120*d* may be out of range from the master nodes, yet still have an operative communication path to a master node through ID node 120*b*.

Indeed, in one example, prior to placement within container 210, ID node 120*b* may actually be a master node but the changed RF environment when placing it in container 210 may interfere with the master node's ability to locate itself via location signals (e.g., GPS signals) and cause the master node to temporarily operate as an ID node while still providing communications and data sharing with other ID nodes in container 210.

User access devices 200, 205 are also illustrated in FIG. 2 as being able to connect to network 105, master nodes, and ID nodes. Generally, user access devices 200 and 205 are types of external wireless nodes that allow a user to interact with one or more components of a wireless node network. In various examples, user access devices 200, 205, may be implemented using a desktop computer, a laptop computer, a tablet (such as an Apple iPad® touchscreen tablet), a personal area network device (such as a Bluetooth® device), a smartphone (such as an Apple iPhone®), a smart wearable device (such as a Samsung Galaxy Gear™ smartwatch device, or a Google Glass™ wearable smart optics) or other such devices capable of communicating over network 105 with server 100, over a wired or wireless communication path to master node and ID nodes.

As shown in FIG. 2, user access devices 200, 205 are coupled and in communication with network 105, but each of them may also be in communication with each other or other network components in a more direct manner (e.g., via near field communication (NFC), over a Bluetooth® wireless connection, over a Wi-Fi network, dedicated wired connection, or other communication path).

In one example, a user access device, such as device 200 or 205, may facilitate associating an ID node (such as ID node 120a) with the tracking number of a package at the start of a shipment process, coordinating with the server 100 to check on the status and/or location of the package and associated ID node during transit, and possibly retrieving data from a master node or ID node related to the shipped package. Thus, those skilled in the art will appreciate that a user access device, such as devices 200, 205, are essentially interactive communication platforms by which a user may initiate shipment of an item, track an item, determine the status and location of an item, retrieve information about an item, as well as initiate dispatch of a logistics operation or interact with other nodes as part of a dispatched operation.

An example user access device, such as device 200 or 205, may include sufficient hardware and code (e.g., an app or other program code section or sections) to operate as a master node or an ID node in various embodiments as discussed in more detail below. For example, device 200 may be implemented as a mobile smartphone and functionally may operate as an exemplary ID node that broadcasts advertising packet messages to other ID nodes or master nodes for association and sharing data with such nodes. In another example, device 200 is implemented as a mobile smartphone and may operate as an exemplary master node that communicates and associates with ID nodes and other master nodes, as described herein, and communicates with the server 100. Thus, those skilled in the art will appreciate an exemplary ID node in FIG. 3 and an exemplary master node in FIG. 4, and their respective parts, code and program modules, may be implemented with an appropriately programmed user access device, such as device 200 or 205. Thus, the following description of an exemplary ID node in FIG. 3 and an exemplary master node in FIG. 4 will be applicable to a user access device operating as an ID node or a master node, respectively.

ID Node

Figure 3:
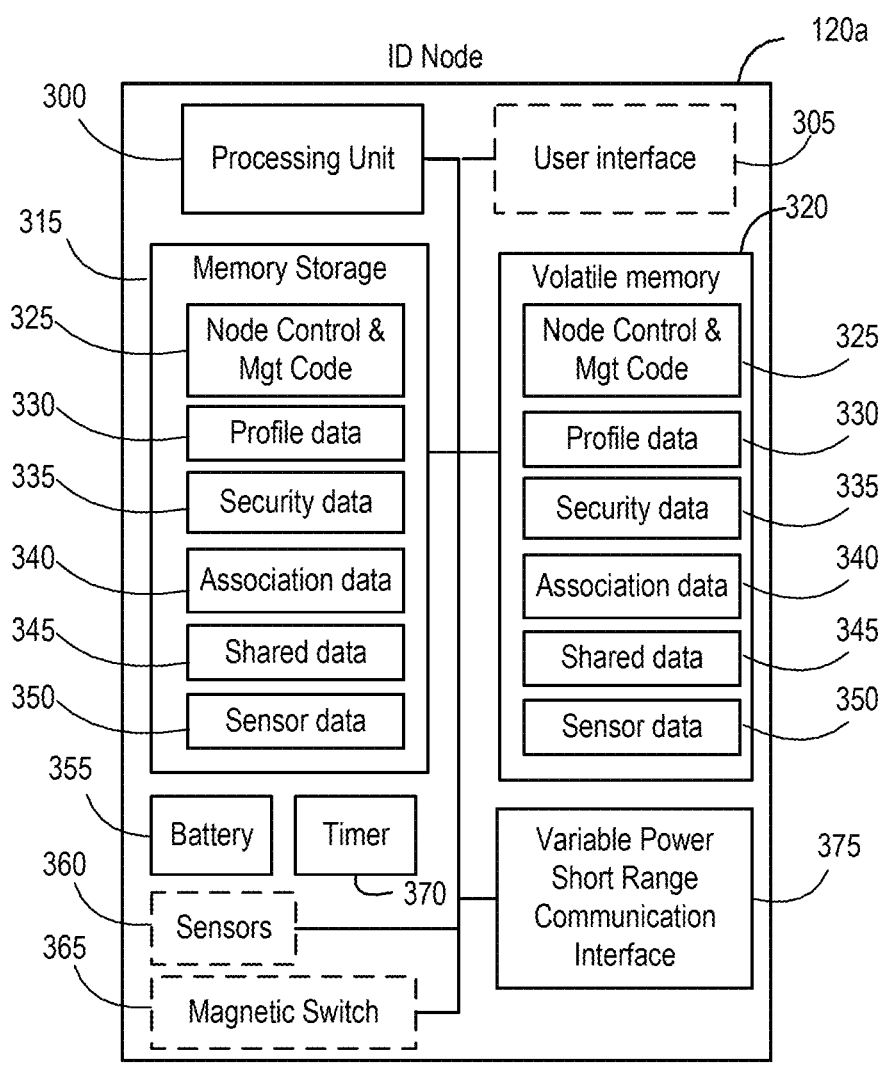
FIG. 3 is a more detailed diagram of an exemplary ID node device as known in the art.

FIG. 3 is a more detailed diagram of an exemplary ID node device. As previously described, one example of an ID node includes a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node. Referring now to the more detailed embodiment of FIG. 3, exemplary ID node 120a is shown to comprise a processing or logic unit 300 coupled to a variable power short-range communication interface 375, memory storage 315, volatile memory 320, timer 370, and battery 355. Those skilled in the art will appreciate that processing unit 300 is logic, such as a low power consumption microcontroller, that generally performs computations on data and executes operational and application program code and other program modules or sections thereof within the ID node 120a. As such, exemplary processing unit 300 operates as a transceiver-based processing core of ID node 120a.

Those skilled in the art will also appreciate that exemplary ID node 120a is a hardware-based component that may be implemented with a single processor or logic unit, such as unit 300. In one embodiment, processing unit 300 may be implemented with an Intel® 8051 CPU Core and associated peripheral circuitry as dictated by the needs of the particular application. Less complex microcontrollers or discrete circuitry may be used to implement processing unit 300 as well as more complex and sophisticated microprocessors. Additionally, exemplary processing unit 300 may be integrated into a single chip transceiver used as a core of ID node 120a.

The variable power short-range communication interface 375 of ID node 120a is generally a programmable radio and an omni-directional antenna coupled to the processing unit 300. In other embodiments, interface 375 may use an antenna with a different antenna profile when directionality may be desired. Examples of variable power short-range communication interface 375 may include other interfacing hardware (not shown) for operatively coupling the device to a specific short-range communication path (e.g., a Bluetooth® Low Energy (BLE) connection path communicating at 2.4 GHz).

In one example, various RF characteristics of the radio's transceiver, such as the RF output power and/or the RF receiver sensitivity may be dynamically and programmatically varied under control of processing unit 300. In other examples, further RF characteristics of the radio's transceiver may be programmatically varied, such as frequency, duty cycle, timing, modulation schemes, spread spectrum frequency hopping aspects, etc., as needed to flexibly adjust the RF output signal depending upon a desired implementation and anticipated use of ID node 120a. As will be explained in more detail below, some embodiments may use Broadcast Profile having parameters that may be programmatically altered or adjusted. In other words, embodiments of ID node 120a (or any other ID node) may have programmatically adjustable RF characteristics (such as an adjustable RF output signal power, an adjustable RF receiver sensitivity, the ability to switch to a different frequency or frequency band, etc.).

The battery 355 for ID node 120a is a type of power source that generally powers the circuitry implementing ID node 120a. In one embodiment, battery 355 may be a rechargeable power source. In other embodiments, battery 355 may be a non-rechargeable power source intended to be disposed of after use. In some examples of an ID node, the power source may involve alternative energy generation, such as a solar cell.

The timer 370 for ID node 120a generally provides one or more timing circuits used in, for example, time delay, pulse generation, and oscillator applications. In an example where ID node 120a conserves power by entering a sleep or dormant state for a predetermined time period as part of overall power conservation techniques, timer 370 assists processing unit 300 in managing timing operations. Additionally, an example may allow an ID node to share data to synchronize different nodes with respect to timer 370 and a common timing reference between nodes and the server.

An example may implement ID node 120a to optionally include a basic user interface (UI) 305 indicating status and allowing basic interaction like start/stop. In one embodiment, the UI 305 may be implemented with status lights, such as multi-mode LEDs. Different colors of the lights may indicate a different status or mode for the ID node 120a (e.g., an advertising mode (broadcasting), a scanning mode (listening), a current power status, a battery level status, an association status, an error, as sensed condition (e.g., exceeding a temperature threshold, exceeding a moisture threshold, and the like)). Other examples of an ID node may implement UI 305 in a more sophisticated manner with a graphics display or the like where such status or mode information may be displayed as well as one or more prompts.

In a further example, an exemplary status light used as part of the UI 305 of an ID node may also indicate a shipment state. In more detail, an exemplary shipment state may include a status of the shipped item or a status of the item's current shipment journey from an origin to a destination.

An example may also implement ID node 120a to optionally include one or more sensors 360. In some examples, an ID node implemented with one or more sensors 360 may be referred to as a sensor node. Examples of sensor 360 may include one or more environmental sensors (e.g., pressure, movement, light, temperature, humidity, magnetic field, altitude, attitude, orientation, acceleration, etc.) and dedicated location sensors (e.g., GPS sensor, IR sensor, proximity sensor, etc.). Those skilled in the art will understand that additional types of sensors that measure other characteristics are contemplated for use as sensor 360. Additionally, those skilled in the art will understand that a sensor node may include additional program features to manage the collection, storage, sharing, and publication of the captured sensor data.

An example may further implement ID node 120a to optionally include one or more magnetic switches 365. A magnetic switch 365, such as a reed switch, generally operates to close or open an electrical path or connection in response to an applied magnetic field. In other words, magnetic switch 365 is actuated by the presence of a magnetic field or the removal of a magnetic field. Various applications, as discussed in other examples described in more detail below, may involve the operation of ID node 120a having magnetic switch 365.

Consistent with the example shown in FIG. 3, exemplary ID node 120a may be implemented based upon a Texas Instruments CC2540 Bluetooth® Low Energy (BLE) System-on-Chip, which includes various peripherals (e.g., timer circuitry, USB, USART, general-purpose I/O pins, IR interface circuitry, DMA circuitry) to operate as an ID node and, if necessary, to interface with different possible sensors and other circuitry (e.g., additional logic chips, relays, magnetic switches) that make up the ID node.

In additional examples, one skilled in the art will appreciate that similar functionality in an ID node may be implemented in other types of hardware. For example, ID node 120a may be implemented with specially optimized hardware (e.g., a particular application specific integrated circuit (ASIC) having the same operational control and functionality as node control and management code, as described below, discrete logic, or a combination of hardware and firmware depending upon requirements of the ID node, such as power, processing speed, level of adjustability for the RF characteristics, number of memory storage units coupled to the processor(s), cost, space, etc.

As noted above, ID node 120a includes memory accessible by the processing unit 300. Memory storage 315 and volatile memory 320 are each operatively coupled to processing unit 300. Both memory components provide programming and data elements used by processing unit 300. In the embodiment shown in FIG. 3, memory storage 315 maintains a variety of program code (e.g., node control and management code 325) and other data elements (e.g., profile data 330, security data 335, association data 340, shared data 345, sensor data 350, and the like). Memory storage 315 is a tangible, non-transient computer readable medium on which information (e.g., executable code/modules, node data, sensor measurements, etc.) may be kept in a non-volatile and non-transitory manner. Examples of such memory storage 315 may include a hard disk drive, ROM, flash memory, or other media structure that allows long term, non-volatile storage of information. In contrast, volatile memory 320 is typically a random access memory (RAM) structure used by processing unit 300 during operation of the ID node 120a. Upon power up of ID node 120a, volatile memory 320 may be populated with an operational program (such as node control and management code 325) or specific program modules that help facilitate particular operations of ID node 120a. And during operation of ID node 120a, volatile memory 320 may also include certain data (e.g., profile data 330, security data 335, association data 340, shared data 345, sensor data 350, and the like) generated as the ID node 120a executes instructions as programmed or loaded from memory storage 315. However, those skilled in the art will appreciate that not all data elements illustrated in FIG. 3 must appear in memory storage 315 and volatile memory 320 at the same time.

Node Control & Management Code

Generally, an example of node control and management code 325 is a collection of software features implemented as programmatic functions or program modules that generally control the behavior of a node, such as ID node 120a. In an example, the functionality of code 325 may be generally similar as implemented in different types of nodes, such as a master node, an ID node, and a sensor node. However, those skilled in the art will appreciate that while some principles of operation are similar between such nodes, other examples may implement the functionality with some degree of specialization or in a different manner depending on the desired application and use of the node.

In a general example, exemplary node control and management code 325 may generally comprise several programmatic functions or program modules including (1) a node advertise and query (scan) logic manager (also referred to herein as a node communications manager), which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; and (4) an association manager focusing on how the node associates with other nodes. What follows is description of various examples of these basic program modules used by nodes.

Node Communications Manager—Advertising & Scanning

In an example, the node advertise and query (scan) logic manager for a node governs how and when the node should advertise (transmit) its address or query (scan) for the address of neighboring nodes. Advertising is generally done with a message, which may have different information in various parts (e.g., headers, fields, flags, etc.). The message may be a single or multiple packets.

In the example, the "advertise" mode (as opposed to "query" or "scan" mode) is a default mode for an ID Node and has the node broadcasting or transmitting a message with its address and related metadata regarding the node. For example, exemplary metadata may include information such as the RF output power level, a reference number, a status flag, a battery level, and a manufacturer name for the node.

Figure 6:
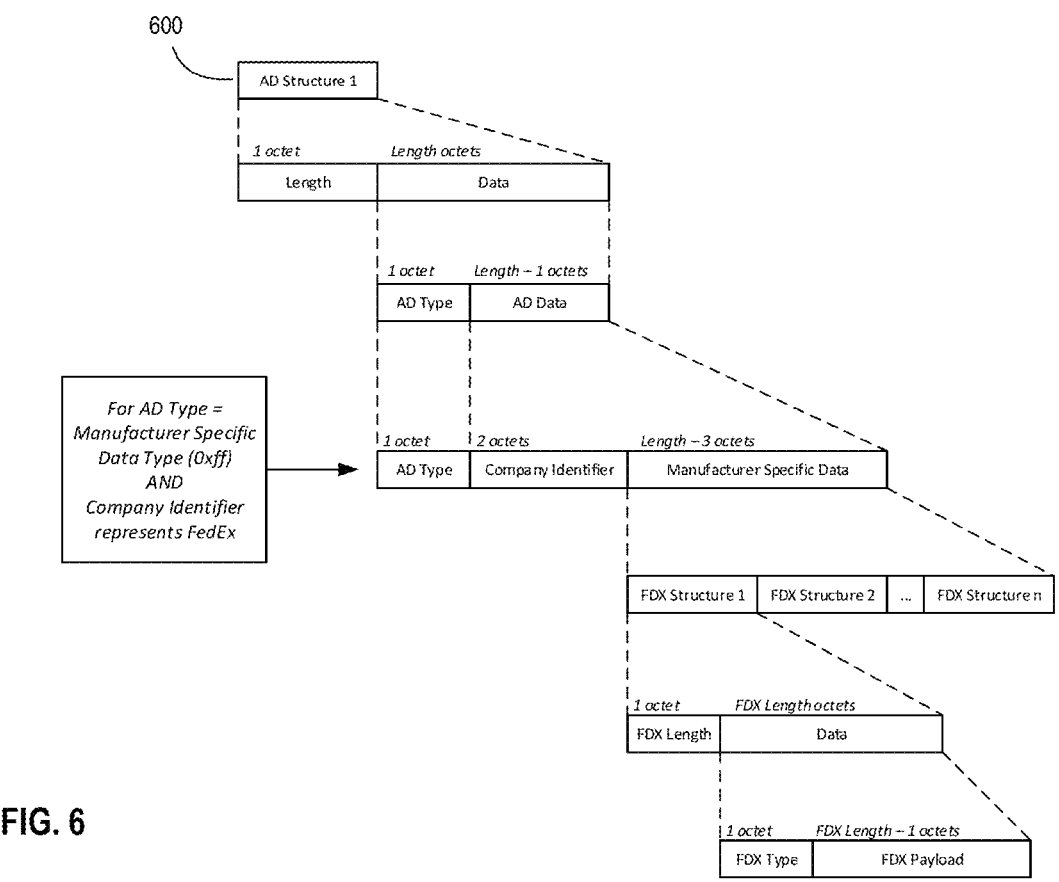
FIG. 6 is a diagram illustrating the structure or format of an exemplary advertisement data packet as known in the art.

FIG. 6 is a diagram illustrating the structure or format of an exemplary advertisement data packet. Referring now to FIG. 6, the structure of an exemplary advertisement data packet 600 broadcast as a signal or message from an ID node, such as ID node 120a, is shown. Packet 600 appears with an increasing level of detail showing exemplary metadata and a format that separately maintains distinct types of metadata in different parts of the packet. Different examples may include different types of metadata depending on the deployed application of the ID node.

Figure 7:
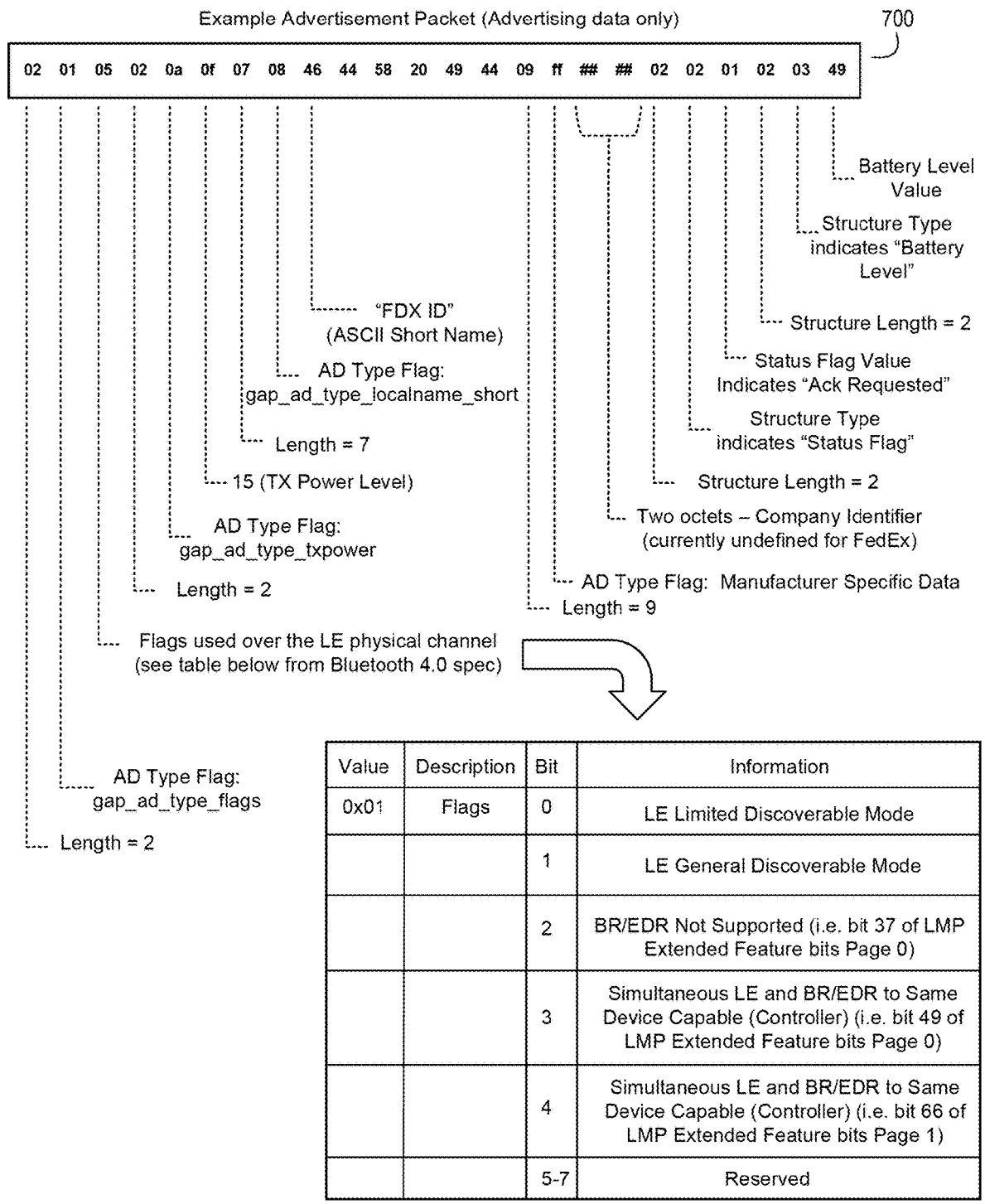
FIG. 7 is a diagram illustrating sample content for an exemplary advertisement data packet as known in the art.

FIG. 7 is a diagram illustrating sample content for an exemplary advertisement data packet. Referring now to FIG. 7, an exemplary advertisement data packet 700 is illustrated with exemplary metadata including showing sample information such as the RF Output Power level (e.g., "TX Power Level"), a reference number (e.g., "'FDX ID' (ASCII Short Name)", a status flag (e.g., "Status Flag Value (indicates 'Ack Requested')"), a battery level (e.g., "Battery Level Value (Indicates 73% charge)", and a manufacturer name for the node (e.g., "Company Identifier (currently undefined for FedEx)"). In one example, those skilled in the art will appreciate that the reference number may be omitted or obfuscated for security purposes.

In one example, an exemplary advertising data packet may include the RF Output power level, as noted above in FIG. 7, to enable one way to help identify the type of node doing the broadcasting and the location of the broadcasting node. However, if the broadcast RF output power level is fixed and known by the node type, only the node type need be identifiable from an exemplary advertising data packet, such as packet 700.

Regarding how a node communicates, an exemplary node may be in one of several different communication modes. A node in an advertising (or transmit or broadcast) mode is visible to any other node set in a query (or scan or listen) mode. In an example, the frequency and length of advertising may be application and power dependent. For example, in normal operations, an exemplary node will generally advertise in a periodic manner and expect to make an active connection to another node at certain intervals, which may be dictated by conditions set by server 100. In an example, such conditions may be set individually for a node by the server or a higher level node in the network.

If an exemplary node has not received acknowledgement for an advertising packet within a particular period, it may enter one or more alert stages. For example, if an exemplary node has not received acknowledgement from another node for an advertising packet broadcast by the exemplary node within a particular time period (also generally referred to as an Alert Interval), the exemplary node will enter an Alert Stage 1 status. This prompts the exemplary node to issue a follow-up advertising packet having one or more parts of it altered to indicate the Alert Stage 1 status. In more detail, this exemplary follow-up advertising packet may have a different advertising alert header instructing nearby nodes to send a SCAN_REQ message upon receiving an advertisement packet.

If an exemplary node has not received acknowledgement from a master node for an advertising packet broadcast by the exemplary node within another time period (e.g., a request from the master node to actively connect and a success connection made), it will enter another alert stage, such as an Alert Stage 2 status. This prompts the exemplary node to issue a follow-up advertising packet having one or more parts of it altered to indicate the Alert Stage 2 status.

In more detail, this exemplary follow-up advertising packet may have a different advertising alert header instructing nearby master nodes to send a SCAN_REQ message upon receiving an advertisement packet.

If an exemplary node has data to upload to the backend, it may also enter another type of alert stage. In one example, for example, if an exemplary node has sensor data collected by the exemplary node (or received from one or more other nodes that have communicated with the exemplary node), and the data needs to be uploaded to server 100, the exemplary node may enter an update alert stage, such as an Alert Stage 3. This prompts the exemplary node to issue a follow-up advertising packet having one or more parts of it altered to indicate the Alert Stage 3 status. In more detail, this exemplary follow-up advertising packet may have a different advertising alert header instructing nearby master nodes to make a connection with the exemplary node so that the data (e.g., sensor data 350) may be transmitted from the exemplary node (e.g., ID node 120a) to a nearby master node (e.g., master node 110a). The transmitted data may then be stored by the nearby master node as sensor data 450 in either or both of the master node's volatile memory 420 and memory storage 415. Subsequent to that storage operation, the nearby master node will transfer the data (e.g., sensor data 450) to server 100.

As illustrated in FIG. 7 and explained in the above description of alert level stages, a status flag in a header of an exemplary advertising data packet is a field used in the association logic in one or more examples. For example, in one example, the existence of a status flag in the advertising data packet allows a first node to communicate its status to a second node, and for the second node to report that status to the backend server, such as server 100, without an active direct connection from the first node to the server. In other words, the status flag helps facilitate passive interactions between nodes (such as passive associations).

In a more detailed example, several exemplary status types are established with respect to communications with other nodes. For example, the exemplary status types may comprise the following:

Alert Level 0—no issue, operating normal;
Alert Level 1—The advertising node is requesting that any available node acknowledge the receipt of its advertisement packet;
Alert Level 2—The advertising node is requesting that any available master node acknowledge the receipt of its advertisement packet;
Alert Level 3—Data for Upload—node has captured data available for upload through a master node; and
Synchronize—The advertising node requests to connect with a device or sensor that can synchronize data (such as timer or location information).

By broadcasting the status via, for example, a portion of a header in an advertising data packet, one or more nodes within range of the broadcasting node can determine the node's status and initiate active connections if requested in the status message.

A request for more information from the advertising node may, in some examples, come in the form of a SCAN_REQ message. In general, an exemplary SCAN_REQ is a message sent from a scanning (listening) master node to an advertising node requesting additional information from the advertising node. In this example, the alert status bit may indicate to the scanning master node, for example, at an application layer, whether the advertising node is in a mode that will or will not accept a SCAN_REQ. In one example, the non-connectable and discoverable modes of node advertising are in compliance with Bluetooth® Low Energy (BLE) standards.

In another example, a node may have further different modes of operation while scanning or listening for other nodes. For example, a node's query or scanning mode may be active or passive. When a node is scanning while passive, the node will receive advertising data packets, but will not acknowledge and send SCAN_REQ. However, when a node is scanning while active, the node will receive advertising data packets, and will acknowledge receipt by sending a SCAN_REQ. A more detailed example may provide the passive and active modes of scanning or inquiry in compliance with Bluetooth® Low Energy (BLE) standards.

In an example, an exemplary node is scanning as it listens for other wireless nodes broadcasting on the short-range radio. An exemplary scanning node may capture, for example, a MAC address of the advertising node, a signal strength of the RF output signal transmitted from the advertising node, and any other metadata published by the advertising node (e.g., other information in the advertising data packet). Those skilled in the art will appreciate that the scope of "listening" when a node is scanning may vary. For example, the query may be limited. In other words, the scope of what a node is particularly interested in and for which it is listening may be focused or otherwise limited. In such a case, for example, the information collected may be limited to particular information from a targeted population of short-range wireless nodes advertising; but the information collection may be considered "open" where information from any advertising device is collected.

When nodes are advertising or scanning, an example may make further use of status flags and additional modes when advertising or scanning as part of how nodes communicate and may be managed. In one example, when a scanning (listening) node receives an advertising data packet with the status flag indicating an Alert Level 1 or 2 status, and the scanning node is in "Passive" scanning mode, the node will switch to "Active" scanning mode for some interval. However, when the scanning node in this situation is already in an "Active" scanning mode, the node will send the SCAN_REQ message and receive a SCAN_RSP from the advertising node (e.g., a message providing the additional information requested from the advertising node). The scanning node will then switch back to a "Passive" scanning mode.

In another example, when an advertising (broadcasting) node receives a SCAN_REQ from a scanning node, the advertising node will consider that its advertising data packet has been acknowledged. Further, the advertising node will reset its "Alert" status flag back to an Alert Level 0 status. This allows the advertising node to effectively receive an acknowledgement to its advertisement without ever making a connection to the scanning node, which advantageously and significantly saves on power consumption.

In yet another example, when a scanning node receives an advertising data packet with an Alert Level 3 status flag set, the scanning node will attempt to make a connection with the advertising device. Once the connection is made, the advertising device will attempt to upload its data to the connected device Thus, an example of the node advertise and query (scan) logic manager of code 325 may rely upon one or more status flags, advertising modes, scanning modes, as nodes communicate with each other in various advantageous manners.

Node Information Control & Exchange Manager

In an example, the information control and exchange manager part of node control and management code 325 determines whether and how information may be exchanged between nodes. In the example, the information control and exchange manager establishes different node operational states where information may be changed according to a desired paradigm for the state. In more detail, an example of information control and exchange manager may establish different levels of information exchange between nodes with a "non-connectable advertising" state or mode of operation, a "discoverable advertising" state or mode, and a "general advertising" state or mode operation. When a node is in the "non-connectable advertising" mode, the node information exchange is limited. For example, the advertising node may broadcast information that is captured by one or more querying (scanning) nodes, but no two-way exchange of information happens.

When a node is in the "discoverable advertising" mode and a scanning node is in "Active" mode, the node information exchange in enabled both ways. For example, the advertising node sends the advertising packet, and in response the scanning node sends the SCAN_REQ packet. After the advertising node receives the SCAN_REQ requesting additional information, the advertising node sends the SCAN_RSP with the requested information. Thus, in the "discoverable advertising" mode there is a two-way exchange of information, but no active connection is made between the two nodes exchanging information.

Finally, for advanced two-way information exchange, an active connection may be used between nodes and information may be exchanged both ways to and from different nodes. In a more detailed example, at this level of two-way information exchange, nodes are first identified and then authenticated as part of establishing the active connection. Once authenticated and thereafter actively connected to each other, the nodes may securely share information back and forth. In one example, a sensor node uploading previously captured environmental information to a master node may be in this mode or state. In another example, an ID node uploading the stored results of a node scanning operation to a master node may be in this mode or state. In yet another example, a master node sharing a timer and/or location information with corresponding nodes may be in this mode or state.

Node Power Manager

In an example, the node power manager part of node control and management code 325 focuses on managing power consumption and the advantageous use of power (e.g., an adjustable level of RF output signal power) in a node. In general, nodes are either powered by a battery (such as battery 355 in an ID node), or by an interface (such as battery/power interface 470 in a master node) to an external power source. Examples of an external power source may include, in some examples, power supplied from an outlet or power connection within a facility, or power generated onboard a conveyance (e.g., automobile, truck, train, aircraft, ship, etc.). Those skilled in the art will appreciate that an interface to an external power source will be generally referred to as a "wired" power connection, and that node power manager may be informed whether a node is wired or powered off a battery, such as battery 355. Further examples may implement an interface to an external power source with wireless power transmission, such as via inductive coils.

In one example, a node may manage power used when performing tasks. For example, a node may manage power when determining which node should perform a particular task. In more detail, the collective power consumption of a group of devices may be managed by electing to employ wired nodes, when feasible or desired, to accomplish a particular task, and saving the battery-powered nodes for other less energy burdensome or taxing tasks. In another example, historic data may inform the system of the power needed to accomplish a particular task, and the system may make a determination of which node should accomplish the particular task based upon such historic data. In other examples, profile data may also be used to inform the system of the power needed to accomplish a particular task (e.g., a sensor profile that describes power requirements for operation of a sensor node that gathers sensor data over a certain period of time and under certain conditions). The system may also make a determination of which node should accomplish the particular task based upon such profile data.

In another example, the exemplary node power manager may manage power when determining how to best to use and adjust power to more accurately accomplish a particular task. In one example, an RF signal output from a node (such as a short-range RF output signal from an ID node) may periodically move through a range of output power or simply switch between two or more settings that differ in a detectable manner. As disclosed in more detail below, the variability and dynamic adjustment of RF output signal power may allow other nodes (such as one or more master nodes) to see each node at the upper range of the RF output signal power, and only see nodes physically close to the advertising node at the lower range of signal power.

In another example, the exemplary node power manager may cause a change to a characteristic of its RF output signal power when the node has been associated to a physical place or another node by virtue of context data (such as context data 560 and association logic that utilizes that type of information). In one example, the node may be instructed to change how often the node communicates and/or a characteristic of its RF output power to preserve power.

In yet another example, all advertising nodes may have their respective node power managers periodically cause each respective node to broadcast at a maximum RF output signal power level to ensure they still are within range of a scanning ID Node or Master Node. Doing so may increase the chance of being in communication range and allows the individual nodes to be properly located and managed within the network. The broadcast duration may be set or dynamically changed to allow pairing to occur if needed.

Rather than adjust the RF output signal power level, the exemplary node power manager may, in some examples, adjust the RF receiver sensitivity of a node. This allows for an adjustable range of reception (as opposed to merely an adjustable range of broadcast), which may similarly be used to manage power and enhance location determinations as discussed herein.

In yet another example, a combination approach may be used in which the node power manager may concurrently and independently adjust more than one RF characteristic of a node. For example, an exemplary node power manager may adjust an RF output signal power level and also adjust the RF receiver sensitivity of a node as the node is located and associated with other nodes. Those skilled in the art will realize that this may be especially useful in an area with an unusually dense concentration of nodes, and a combination of changing RF output signal power levels.

An example of the exemplary node manager may refer to a power profile (e.g., an exemplary type of profile data 330, 430) when adjusting a node's power characteristics (e.g., consumption of power, use of power, output signal frequency, duty cycle of the output put signal, timing, power levels, etc.).

Node Association Manager

In an exemplary example, the node association manager part of node control and management code 325 focuses on how the nodes associate with other nodes in conjunction and consistent with the server-side association manager in code 525, as discussed in more detail below. Thus, exemplary node association manager, when executing in a node, directs how the node associates (e.g., enters an active connection mode) with one or more other nodes with input from the server.

The exemplary node association manager for a node may indicate through a Status Flag if the node requires an acknowledgement or connection, or if it has information available for upload to the backend. Thus, while a node may not be associated or actively connected yet to another node, a status of the node may be inferred from, for example, the status information in the node's broadcast header.

Regarding connections between nodes, there are generally secure connections and unsecure connections. While an example may allow unsecure connections between one or more sets of nodes, other examples rely upon secure connections or authenticate pairings of nodes. In one example, for a node to pair with another node, the exemplary node association manager first identifies the nodes to be associated and transmits an association request to the server. The request may include a specific request to pair the nodes and ask for the corresponding pairing credentials from the server, such as server 100. The server 100 may have staged pairing credentials on particular nodes based on information indicating the nodes would be within wireless proximity and future pairing may occur. Visibility to the node relationship may have been determined through scan-advertising, or $3^{rd}$ party data such as barcode scan information indicating the nodes to be within proximity currently or at a future state.

When connecting or not connecting to exchange information under the exemplary node information exchange modes described above, nodes generally operate in a number of states, which make up an exemplary advertise cycle for an exemplary ID node. Such an exemplary advertise cycle for a node is further explained below with reference to FIG. 8 and in conjunction and consistent with the server-side association manager in code 525, as discussed in more detail below.

Airborne Mode Program Module

In one example, node control and management code 325 may also include an airborne mode program module (not shown). In another example, the airborne mode program module may be implemented as a part of the node power manager program module of code 325. An exemplary airborne mode program module generally operates to manage the output power of the ID node's variable power short-range communication interface 375 when the ID node is operating in an aircraft. Operating a wireless device within an aircraft may, in some circumstances, have an unintentional impact on other electronic systems on the aircraft. In more detail, an example of the airborne mode program module may operate to transition the ID node from different states or modes depending upon particular operations and/or operational conditions of the aircraft. For example, an exemplary airborne mode program module may operate to transition the ID node from one state or mode (e.g., a normal mode prior to takeoff, a disabled mode during takeoff, an airborne mode while aloft, a disabled mode during descent, and a normal mode after landing) based upon detected environmental conditions (e.g., pressure, altitude) and/or flight detail information associated with the aircraft. In this way, an ID node may be allowed to normally operate when onboard an aircraft, be disabled from operating at all in some circumstances, and be able to operate in an airplane mode that allows sensing and sensor data capture, but that may limit transmission of an RF output signal to avoid interference with the aircraft's onboard electronics. Further information related to a method of managing a wireless device (such as an ID node) in an aircraft is disclosed in greater detail in U.S. patent application Ser. No. 12/761,963 entitled "System and Method for Management of Wireless Devices Aboard an Aircraft," which is hereby incorporated by reference.

Node Data

As previously noted, volatile memory 320 may also include certain data (e.g., profile data 330, security data 335, association data 340, shared data 345, sensor data, and the like) generated as the ID node 120a executes instructions as programmed or loaded from memory storage 315. In general, data used on a node, such as an ID node, may be received from other nodes or generated by the node during operations.

In one example, profile data 330 is a type of data that defines a general type of behavior for an ID node, such as a Broadcast Profile (discussed in more detail below). In another example where ID node 120a is a BLE device, profile data 330 may include a Bluetooth® compatible profile related to battery service (exposing the state of a battery within a device), proximity between BLE devices, or messaging between BLE devices. Thus, exemplary profile data 330 may exist in volatile memory 320 and/or memory storage 315 as a type of data that defines parameters of node behavior.

In one example, it may be desired to allow secured pairings of nodes. As will be explained in more detail below, as part of secure pairing of nodes, a request for pairing credentials is generated and sent to server 100. Thus, exemplary security data 335 (e.g., PIN data, security certificates, keys, etc.) may exist in volatile memory 320 and/or memory storage 315 as a type of data associated with providing secured relationships between nodes, such as the requested security credentials.

Association data, such as association data 340, generally identifies a connected relationship between nodes. For example, ID node 120a may become associated with the master node 110a as the ID node 120a moves within range of the master node 110a and after the server directs the two nodes to associate (with authorization). As a result, information identifying the relationship between ID node 120a and master node 110a may be generated and provided to server 100 and may be provided, as some point, to each of ID node 120a and master node 110a. Thus, exemplary association data 340 may exist in volatile memory 320 and/or memory storage 315 as a type of data identifying associations between nodes and may be generated locally as part of associating between nodes.

Shared data 345 may exist in volatile memory 320 and/or memory storage 315 as a type of data exchanged between nodes. For example, context data (such as environmental data or historic data) may be a type of shared data 345.

Sensor data 350 may also exist in volatile memory 320 and/or memory storage 315 as a type of data recorded and collected from an onboard sensor or from another node. For example, sensor data 350 may include temperature readings from a temperature sensor onboard an ID node and/or humidity readings from a humidity sensor in another ID node (e.g., from another of the ID nodes within container 210 as shown in FIG. 2).

Thus, an ID node (such as node 120a shown in FIG. 3) is a lower cost wireless node that communicates with other ID nodes and master nodes via a short-range radio with variable RF characteristics, can be associated with other nodes, can broadcast to and scan for other nodes, associated with other nodes, and store/exchange information with other nodes.

Master Node

Figure 4:
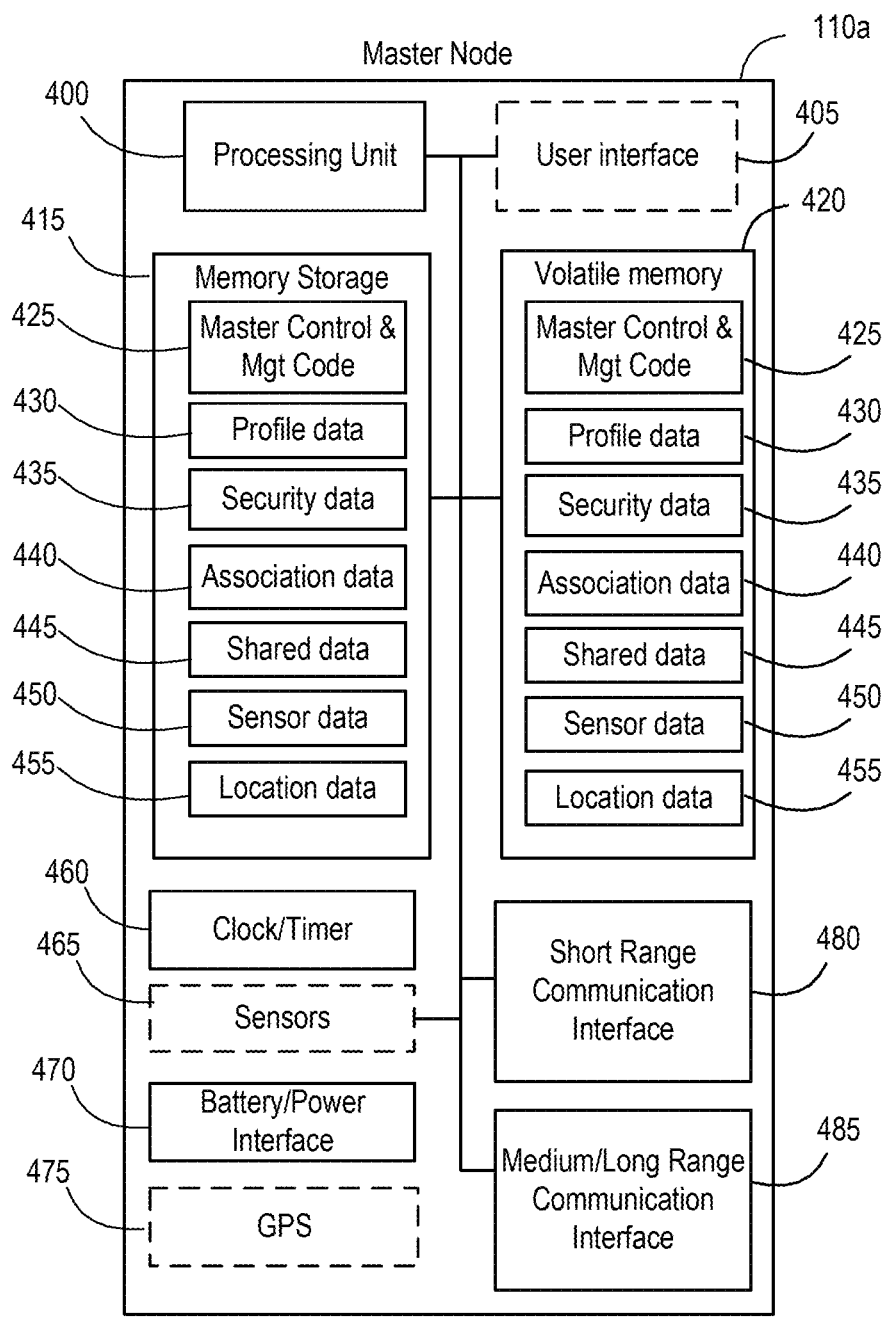
FIG. 4 is a more detailed diagram of an exemplary master node device as known in the art.

A master node, such as master node 110a shown in more detail in FIG. 4, shares many ID node features but generally expands upon them in order to function as a bridge to the server 100. In general, while an ID node is a type of lower level node in an exemplary wireless node network, a master node is a type of higher level node. An exemplary master node may be in a fixed location or otherwise stationary, while other example master nodes may be implemented as movable and mobile devices.

Referring now to FIG. 4, exemplary master node 110a comprises a processing or logic unit 400 coupled to a short-range communication interface 485, memory storage 415, volatile memory 420, clock/timer 460, and battery/power interface 470. In some examples, the short-range communication interface 485 may have variable power characteristics, such as receiver sensitivity and RF output power level. Those skilled in the art will appreciate that processing unit 400 is logic, such as a microprocessor or microcontroller, which generally performs computations on data and executes operational and application program code and other program modules within the master node 110a.

In general, those skilled in the art will appreciate that the description of hardware with respect to master node 110a in FIG. 4 applies to the similar hardware and software features appearing in each type of node, including a master node. Those skilled in the art will appreciate that exemplary master node 110a is a hardware-based component that may implement processor 400 with a single processor or logic unit, a more powerful multi-core processor, or multiple processors depending upon the desired implementation. In one example, processing unit 400 may be implemented with a low power microprocessor and associated peripheral circuitry. Less complex microcontrollers or discrete circuitry may be used to implement processing unit 400 as well as more complex and sophisticated general purpose or dedicated purpose processors.

In yet another example, exemplary processing unit 400 may be implemented by a low power ARM1176JZ-F application processor used as part of a single-board computer, such as the Raspberry Pi Computer Model B-Rev-2. The ARM application processor is embedded within a Broadcom® BCM2835 system-on-chip (SoC) deployed in the Raspberry Pi Computer. In this example, the Raspberry Pi Computer device operates as a core of exemplary master node 110a and includes a Secure Digital memory card slot and flash memory card operating as memory storage 415, a 512 Mbyte RAM memory storage operating as volatile memory 420, an operating system (such as Linux) stored on memory storage 415 and running in volatile memory 420, and peripherals that implement clock/timer 460, and a power supply operating as a power interface 470.

Like short-range interface 375 in ID node 120a, exemplary master node 110a includes a short-range communication interface 480 as a programmable radio and an omni-directional antenna coupled to the processing unit 400. In some examples, the short-range communication interface 480 may have variable RF power characteristics, such as receiver sensitivity and/or RF output signal power level. In some examples, interface 480 may use an antenna with a different antenna profile when directionality may be desired. Examples of short-range communication interface 480 may include other hardware (not shown) for operatively coupling the device to a specific short-range communication path (e.g., a Bluetooth® Low Energy (BLE) connection path communicating at 2.4 GHz). While BLE is used in one example to enable a short-range communication protocol, variable power short-range interface 480 may be implemented with other low power, short-range communication protocols, such as ultra-low power communication protocols used with ultra-wideband impulse radio communications, ZigBee protocols, IEEE 802.15.4 standard communication protocols, and the like.

In one example, various RF characteristics of the radio's transceiver, such as the RF output power and the RF receiver sensitivity may be dynamically and programmatically varied under control of processing unit 400. In other examples, further RF characteristics of the radio's transceiver may be programmatically varied, such as frequency, duty cycle, timing, modulation schemes, spread spectrum frequency hopping aspects, etc., as needed to flexibly adjust the RF output signal as needed depending upon a desired implementation and anticipated use of exemplary master node 110a. In other words, examples of master node 110a (or any other master node) may have programmatically adjustable RF characteristics (such as an adjustable RF output signal power, an adjustable RF receiver sensitivity, the ability to switch to a different frequency or frequency band, etc.).

In addition to the short-range communication interface 480, exemplary master node 110a includes a medium and/or long-range communication interface 485 to provide a communication path to server 100 via network 105. In one example, communication interface 485 may be implemented with a medium range radio in the form of an IEEE 802.11g compliant Wi-Fi transceiver. In another example, communication interface 485 may be implemented with a longer range radio in the form of a cellular radio. In yet another example, both a Wi-Fi transceiver and a cellular radio may be used when best available or according to a priority (e.g., first attempt to use the Wi-Fi transceiver if available due to possible lower costs; and if not, then rely on the cellular radio). In other words, an example may rely upon the longer range cellular radio part of interface 485 as an alternative to the medium range Wi-Fi transceiver radio, or when the medium range radio is out of reach from a connecting infrastructure radio within network 105. In still another example, the short-range communication interface 480 and/or the medium/long-range communication interface 485 may be implemented with a wireless radio transceiver (e.g., a hardware radio, a wireless transceiver implemented with a combination of hardware and software, or a software defined radio (SDR) implementation of a wireless radio transceiver capable of providing the functionality of both interface 480 and 485).

Thus, in these examples, medium and/or long-range communication interface 485 may be used to communicate captured node information (e.g., profile data 430, association data 440, shared data 445, sensor data 450, and location data 455) to server 100.

The battery/power interface 470 for master node 110a generally powers the circuitry implementing master node 110a. In one example, battery/power interface 470 may be a rechargeable power source. For example, a master node may have a rechargeable power source along with a solar panel that charges the power source in order to help facilitate deployment of the master in a remote location. In another example, battery/power interface 470 may be a non-rechargeable power source intended to be disposed of after use. In yet another example, battery/power interface 470 may be a power interface connector (such as a power cord and internal power supply on master node 110a). Thus, when an exemplary master node is in a fixed or stationary configuration, it may be powered by a power cord connected to an electrical outlet, which is coupled to an external power source. However, other mobile master nodes may use an internal power source, such as a battery.

The clock/timer 460 for master node 110a generally provides one or more timing circuits used in, for example, time delay, pulse generation, and oscillator applications. In an example where master node 110a conserves power by entering a sleep or dormant state for a predetermined time period as part of overall power conservation techniques, clock/timer 460 assists processing unit 400 in managing timing operations.

Optionally, an example may also implement master node 110a as including one or more sensors 465 (similar to sensors deployed on ID node based Sensor nodes and described above with respect to FIG. 3). Additionally, an example of master node 110a may also provide a user interface 405 to indicate status and allow basic interaction for review of captured node data and interaction with nodes and server 100. In one example, user interface 405 may provide a display, interactive buttons or soft keys, and a pointing device to facilitate interaction with the display. In a further example, a data entry device may also be used as part of the user interface 405. In other examples, user interface 405 may take the form of one or more lights (e.g., status lights), audible input and output devices (e.g., a microphone and speaker), or touchscreen.

As previously noted, an exemplary master node, such as master node 110a, may be positioned in a known fixed location or, alternatively, includes dedicated location positioning circuitry 475 (e.g., GPS circuitry) to allow the master node self-determine its location or to determine its location by itself. In other examples, alternative circuitry and techniques may be relied upon for location circuitry 475 (rather than GPS), such as location circuitry compatible with other satellite-based systems (e.g., the European Galileo system, the Russian GLONASS system, the Chinese Compass system), terrestrial radio-based positioning systems (e.g., cell phone tower-based or Wi-Fi-based systems), infrared positioning systems, visible light based positioning systems, and ultrasound-based positioning systems).

Regarding memory storage 415 and volatile memory 420, both are operatively coupled to processing unit 400 in exemplary master node 110a. Both memory components provide program elements used by processing unit 400 and maintain and store data elements accessible to processing unit 400 (similar to the possible data elements stored in memory storage 315 and volatile memory 320 for exemplary ID node 120a).

In the example shown in FIG. 4, memory storage 415 maintains a variety of executable program code (e.g., master control and management code 425), data similar to that kept in an ID node's memory storage 315 (e.g., profile data 430, security data 435, association data 440, shared data 445, sensor data 450, and the like) as well as other data more specific to the operation of master node 110a (e.g., location data 455 that is related to the location of a particular node). Like memory storage 315, memory storage 415 is a tangible, non-transient computer readable medium on which information (e.g., executable code/modules, node data, sensor measurements, etc.) may be kept in a non-volatile and non-transitory manner.

Like volatile memory 320 in ID node 120*a*, volatile memory 420 is typically a random access memory (RAM) structure used by processing unit 400 during operation of the master node 110*a*. Upon power up of master node 110*a*, volatile memory 120 may be populated with an operational program (such as master control and management code 425) or specific program modules that help facilitate particular operations of master node 110*a*. And during operation of master 110*a*, volatile memory 420 may also include certain data (e.g., profile data 430, security data 435, association data 440, shared data 445, sensor data 450, and the like) generated as the master node 110*a* executes instructions as programmed or loaded from memory storage 415.

Master Control & Management Code

Generally, an example of master control and management code 425 is a collection of software features implemented as programmatic functions or program modules that generally control the behavior of a master node, such as master node 110*a*. In one example, master control and management code 425 generally comprises several programmatic functions or program modules including (1) a node advertise and query (scan) logic manager, which manages how and when a node communicates; (2) an information control and exchange manager, which manages whether and how information may be exchanged between nodes; (3) a node power manager, which manages power consumption and aspects of RF output signal power and/or receiver sensitivity for variable short-range communications; (4) an association manager focusing on how the node associates with other nodes; and (5) a location aware/capture module to determine node location.

Master Node Program Modules and ID Node Modules

In an exemplary example, program modules (1)-(4) of master node control and management code 425 generally align with the functionality of similarly named program modules (1)-(4) of node control and management code 325 as described above with respect to FIG. 3. Additionally, as node control and management code 325 may also comprise an airborne mode program module, those skilled in the art will appreciate and understand that master node control and management code 425 may also comprise a similar functionality airborne mode program module in order to allow advantageous operations of a master node while airborne. However, and consistent with examples set forth below, such modules may have some differences when in a master node compared with those controlling an ID node.

Location Aware/Capture Module

In addition to exemplary program modules (1)-(4) of code 425, an exemplary example of master node control and management code 425 will further comprise an exemplary location aware/capture module related to node location (more generally referred to as a location manager module for a master node). In general, the exemplary location aware/capture module deployed in an exemplary master node may determine its own location and, in some examples, the location of a connected node. Examples of the exemplary location aware/capture module may work in conjunction with location manager program code residing and operating in a server (e.g., as part of server control and management code 525) when determining node locations of other nodes, as discussed in more detail herein.

In one example, a master node may be positioned in a known, fixed location. In such an example, the exemplary location aware/capture module may be aware that the master node location is a known, fixed location, which may be defined in a fixed, preset, or preprogrammed part of memory storage 415 (e.g., information in the location data 455 maintained in memory storage 415). Examples of such location information may include conventional location coordinates or other descriptive specifics that identify the location of the master node. In another example where the master node may not be inherently known or a fixed location at all times (e.g., for a mobile master node), the exemplary location aware/capture module may communicate with location circuitry, such as GPS circuitry 475 on a master node, to determine the current location of the master node.

In an example, the location of the master node may be communicated to the server, which may use this location information as part of managing and tracking nodes in the wireless node network. For example, if an exemplary master node is mobile and has determined a new current location using location circuitry 475, the master node may provide that new current location for the master node to the server. Additionally, when the master node's exemplary location aware/capture module determines the location of a node associated with the master node, the master node may also provide the location of that node associated with the master node to the server.

Server

Figure 5:
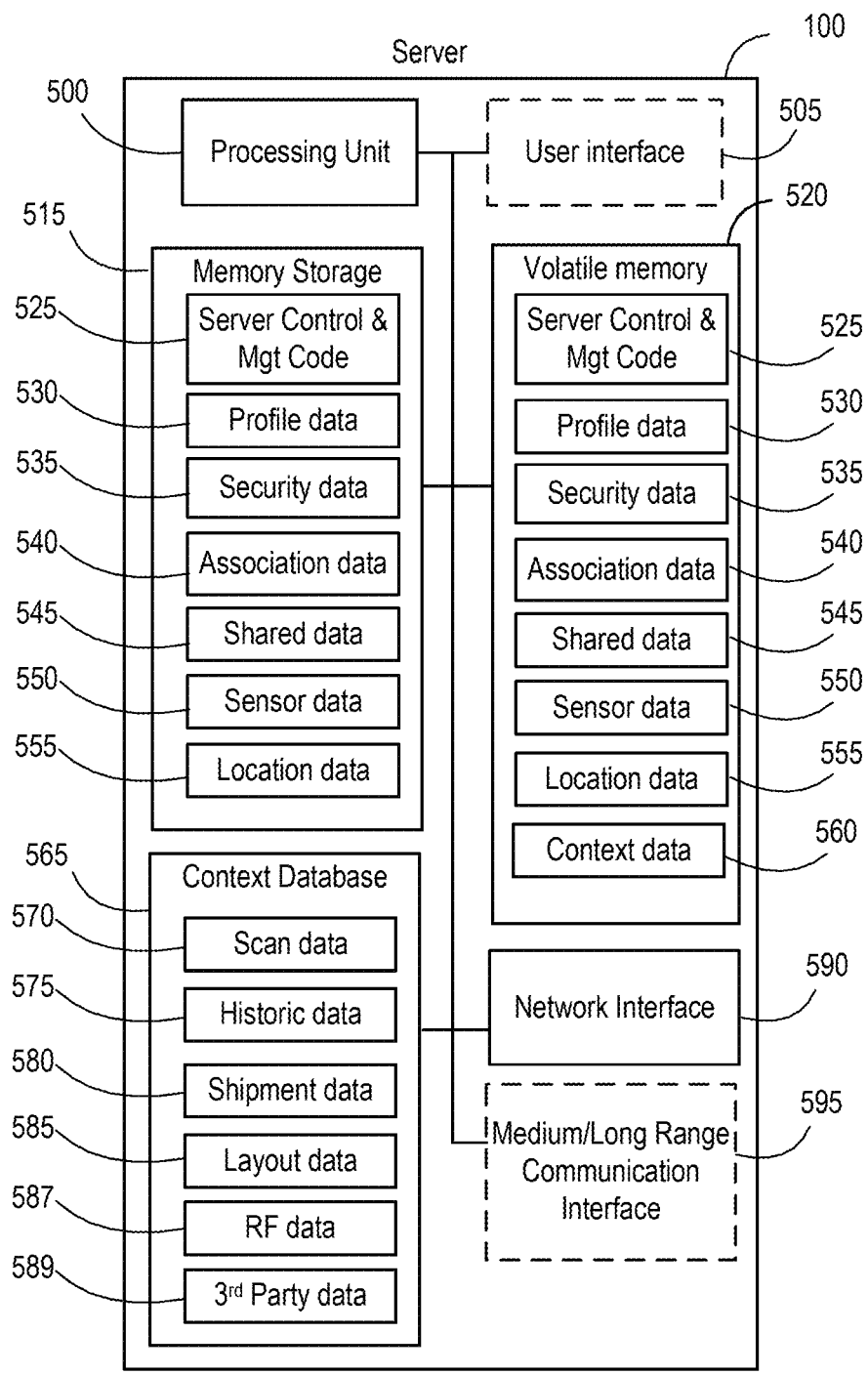
FIG. 5 is a more detailed diagram of an exemplary server as known in the art.

While FIGS. 3 and 4 illustrate details of hardware and software aspects of an exemplary ID node and exemplary master node, respectively, FIG. 5 provides a more detailed diagram of an exemplary server that may operate as part of an exemplary wireless node network. In an exemplary example, server 100 may be referred to as an Association and Data Management Server (ADMS) that manages the nodes, collects information from the nodes, stores the collected information from the nodes, maintains or has access to context data related to the environment in which the nodes are operating, and may provide information about the nodes (e.g., status, sensor information, etc.) to requesting entities. Further details on various examples that take advantage of this functionality are explained below. Those skilled in the art will appreciate that node density, geographic installation characterization, and network connectively are all types of examples of factors that may impact a final architecture desired for an example of a wireless node network. Additionally, in embodiments described in more detail below, a server that may interact with master nodes and ID nodes as described here may be implemented and deployed as a dispatch server that is responsive to dispatch requests and transmits dispatch commands to different nodes (such as a master node operating as an autonomous controller within a modular mobile autonomous control module (also referred to as an exemplar MAM component).

Referring now to FIG. 5, exemplary server 100 is shown as a networked computing platform capable of connecting to and interacting with at least the wireless master nodes. In other examples, exemplary server 100 is also capable of connecting to and interacting with one or more user access devices. Those skilled in the art will appreciate that exemplary server 100 is a hardware-based component that may be implemented in a wide variety of ways. For example, server 100 may use a single processor or may be implemented as one or more part of a multi-processor component that communicates with devices (such as user access devices 200, 205) and wireless nodes (such as master node 110*a*).

In general, those skilled in the art will further appreciate that server 100 may be implemented as a single computing system, a distributed server (e.g., separate servers for separate server related tasks), a hierarchical server (e.g., a server implemented with multiple levels where information may be maintained at different levels and tasks performed at different levels depending on implementation), or a server farm that logically allows multiple distinct components to function as one server computing platform device from the perspective of a client device (e.g., devices 200, 205 or master node 110*a*). In some regional deployments, an exemplary server may include servers dedicated for specific geographic regions as information collected within different regions may include and be subject to different regulatory controls and requirements implemented on respective regional servers.

Likewise, while the example shown in FIG. 5 illustrates a single memory storage 515, exemplary server 100 may deploy more than one memory storage media. And memory storage media may be in differing non-transitory forms (e.g., conventional hard disk drives, solid state memory such as flash memory, optical drives, RAID systems, cloud storage configured memory, network storage appliances, etc.).

At its core, exemplary server 100 shown in FIG. 5 comprises a processing or logic unit 500 coupled to a network interface 590, which facilitates and enables operative connections and communications through network 105 with one or more master nodes as well as, in some examples, user access devices, such as devices 200, 205. In one example, server 100 may include a medium and/or long-range communication interface 595 with which to more directly communicate with one or more master nodes. Using these communication paths as well as program code or program modules (such as server control and management code 525), the server 100 generally operates to coordinate and manage information related to an ID node as an item associated with the ID node physically moves from one location to another.

As a computing platform, the processing unit 500 of exemplary server 100 is operatively coupled to memory storage 515 and volatile memory 520, which collectively store and provide a variety of executable program code (e.g., server control and management code 525), data similar to that kept in a master or ID node's respective memory storage (e.g., profile data 530, security data 535, association data 540, shared data 545, sensor data 550, location data 555) and context data 560 related to the environment in which the nodes are operating (e.g., information generated from within the wireless node network and information created external to the wireless node network).

Like memory storage 315 and storage 415, memory storage 515 is a tangible, non-transient computer readable medium on which information (e.g., executable code/modules (e.g., server control and management code 525), node-related data (e.g., profile data 530, security data 535, association data 540, location data 555, etc.), measurement information (e.g., a type of shared data 545, sensor data 550, etc.), and information on the contextual environment for the nodes (e.g., context data 560) may be kept in a non-volatile and non-transitory manner.

Those skilled in the art will appreciate that the above identification of particular program code and data are not exhaustive and that examples may include further executable program code or modules as well as other data relevant to operations of a processing-based device, such as an ID node, a master node, and a server.

Context Data

As noted above, server 100 may access context data 560 as part of managing nodes in the wireless node network. The exemplary server 100 may contain a collection of such context data 560 in a context database 565 according to an example. As illustrated in FIG. 5, exemplary context database 565 is a single database accessible by processing unit 500 internal to server 100. Those skilled in the art will readily understand that other configurations that provide an accessible collection of context data 560 are possible and contemplated within the scope and principles of examples of the invention. For example, context database 565 may be an externally accessible database (or multiple databases), such as an accessible storage maintained outside the server 100 via a dedicated interface or a network storage device (or network attached storage (NAS) unit). In yet another example, the context database may be separately maintained by an external database server (not shown) that is distinct from server 100, but accessible through a communication path from server 100 to a separate database server (e.g., via network 105). Furthermore, those skilled in the art will appreciate that context database 565 may be implemented with cloud technology that essentially provides a distributed networked storage of collections of information (such as context data 560, sensor data 550, shared data 545, etc.) accessible to server 100.

Within context database 565, an exemplary example of the collection of context data 560 may be maintained that generally relates to an environment in which the nodes are operating or anticipated to be operating. In more detail, the context data 560 may generally relate to what a similar node has experienced in a similar environment to what a given node is presently experiencing or is anticipated to experience as the given node moves.

In a general example, an environment in which a node may be actually or anticipated to be operating may include different types of environments—for example, an electronic communication environment (e.g., an RF environment that may be cluttered with signals or include materials or structure that may impede or otherwise shield RF communications), a physical environment of an anticipated path along with the identified node moves (e.g., temperature, humidity, security, and other physical characteristics), a conveyance environment related to how a node may move or be anticipated to be moving (e.g., speed and other parameters of a truck, airplane, conveyor system), and a density environment related to the density of nodes within an area near a particular node (e.g., how many nodes are anticipated to occupy a corridor or a storage facility through which a particular ID node is anticipated to transit on its shipping path).

In light of these different aspects of a node's operating environment, exemplary context data 560 may provide information related to different structures and conditions related to movement of an item (e.g., a particular type of courier device, vehicle, facility, transportation container, etc.). Such information may be generated by an entity operating the wireless node network, such as a shipping company. Additionally, exemplary context data 560 may include third party data generated external to the wireless node network. Thus, context data, such as data 560, may include a wide variety of data that generally relates to the environment in which the nodes are operating and may be used to advantageously provide enhanced node management capabilities.

In general, FIG. 5 illustrates exemplary types of context data 560 being maintained in database 565 and in volatile memory 520. Those skilled in the art will appreciate that context data 560 may also be maintained in other data structures, in addition to or instead of maintaining such information in a database. As illustrated in FIG. 5, exemplary types of context data 560 may include but are not limited to scan data 570, historic data 575, shipment data 580, layout data 585, RF data 587, and 3$^{rd}$ party data.

Scan data 570 is generally data collected for a particular item related to an event. For example, when an item is placed in a package (such as package 130), a label may be generated and placed on the exterior of the package. The label may include a visual identifier that, when scanned by an appropriate scanning device capable of capturing, identifies the package. The information generated in response to scanning the identifier (a type of event), may be considered a type of scan data. Other scan data 570 may include, for example, general inventory data generated upon manual entry of information related to the package; captured package custodial control data; and bar code scan data.

Historic data 575 is generally data previously collected and/or analyzed related to a common characteristic. Historic data 575 embodies operational knowledge and know-how for a particular characteristic relevant to operations of the wireless node network. For example, the common characteristic may be a particular event (e.g., movement of an item from an open air environment to within a particular closed environment, such as a building), a type of item (e.g., a type of package, a type of content being shipped, a location, a shipment path, etc.), a success rate with a particular item (e.g., successful shipment), and the like. Another example of historic data 575 may include processing information associated with how an item has been historically processed as it is moved from one location to another (e.g., when moving within a particular facility, processing information may indicate the item is on a particular conveyor and may include information about the conveyor (such as speed and how long it is anticipated the item will be on the conveyor)).

Shipment data 580 is generally data related to an item being moved from one location to another location. In one example, shipment data 580 may comprise a tracking number, content information for an item being shipped, address information related to an origin and destination locations, and other characteristics of the item being moved. Shipment data may further comprise authentication related information for an item (e.g., identifier information on an authorized delivery recipient for the item).

Layout data 585 is generally data related to the physical area of one or more parts of an anticipated path. For example, an example of layout data 585 may include building schematics and physical dimensions of portions of a building in which a node may be transiting. An example may further include density information associated with physical areas to be transited and anticipated numbers of potential nodes in those areas as types of layout data. In another example, an example of layout data may include a configuration of how a group of packages may be assembled on a pallet, placed into a shipping container (e.g., a unit load device (ULD)) that helps move a collection of items on various forms with single mode or intermodal transport.

RF data 587 is generally signal degradation information about a signal path environment for a particular type of node and may relate to particular adverse RF conditions that may cause signal fluctuations, interference, or other degradation from the otherwise optimal signal path environment for that type of node. For example, RF data may include shielding effects when using a particular packaging or location, shielding effects when the package is within a particular type of container or assembled as part of a palletized shipment, shielding effects when particular content is shipped, and other physical and electronic interference factors.

Third party data 589 is an additional type of context data 560 that generally includes data generated outside the network. For example, third party data may include weather information associated with particular areas to be transited as the item is moved along an anticipated path from one location to another. Those skilled in the art will appreciate other types of third party data that relate to physical and environmental conditions to be faced by an item being moved from one location to another may also be considered context data 560.

The use of context data, such as context data 560 described above, advantageously helps server 100 (and other nodes) better manage movement of items, provide better location determination, enhance intelligent operation and management of different levels of the wireless node network, and provide enhanced visibility to the current location and status of the item during operation of the wireless node network. In one example, server control and management code 525 may provide such functionality that enables the wireless node network to be contextually aware and responsive.

Server Control & Management Code

Generally, server control and management code 525 controls operations of exemplary server 100. In an example, server control and management code 525 is a collection of software features implemented as programmatic functions in code or separate program modules that generally control the behavior of server 100. Thus, exemplary server control and management code 525 may be implemented with several programmatic functions or program modules including, but not limited to, (1) a server-side association manager, which provides a framework for more robust and intelligent management of nodes in the wireless node network; (2) a context-based node manager, which enhances management of nodes in the wireless node network based upon context data; (3) a security manager, which manages secure pairing aspects of node management; (4) a node update manager, which provides updated or different programming for a particular node and shares information with nodes; (5) a location manager for determining and tracking the location of nodes in the network; and (6) an information update manager, which services requests for information related to the current status of a node or generally providing information about a node or collected from a node Server-Side Association Manager The server-side association manager (also referred to as a server-side association management function) is generally a program module in exemplary code 525 that is responsible for intelligently managing the nodes in the wireless node network using a secure information framework. In an example, this framework may be implemented to be a context-driven, learning sensor platform. The framework may also enable a way for information (such as RF scan, location, date/time, and sensor data) to be securely shared across nodes, a way to change the behavior of a node, and for a node to know it is considered "missing." The framework established during operation of the server-side association manager allows the network of nodes to be managed as a system with enhanced and optimized accuracy of determining the physical location of each ID Node. Further information regarding particular examples of such an association management framework and methods are explained below in more detail Context-Based Association Manager The context-based node manager is generally a program module in exemplary code 525 that is responsible for incorporating context data as part of management operations to provide an enhanced data foundation upon which visibility of the nodes may be provided. In some examples, the context-based node manager may be implemented as part of the server-side association manager while other examples may implement the context-based node manager as a separate program module.

In one example, the enhanced data foundation relies upon context data, such as context data 560 (e.g., scan data 570, historic data 575, shipment data 580, layout data 585, and other third party contextual data providing information regarding the conditions and environment surrounding an item and ID node moving from one location to another). Such context data (e.g., the network know-how, building layouts, and operational knowledge of nodes and shipping paths used with the wireless node network) may provide the enhanced building blocks that allow the server 100 to manage tracking and locating of nodes in a robustly enriched contextual environment. In an example, context-based management provides visibility to the system through data analysis for when and how associations should be expected as the nodes travel through the wireless node network. In other examples, it may provide the foundation for better understanding RF signal degradation, which can be caused by the operating environment, packaging, package content, and/or other packages related to an item and its ID node Security Manager The security manager module, which may be implemented separately or as part of the association manager module in exemplary server control and management code 525, helps with associating two nodes in the wireless node network by managing aspects of secure pairing of the nodes. In one example, security manager module provides the appropriate pairing credentials to allow a node to securely connect to another node. Thus, when a node desires to connect to another node, an example requires appropriate pairing credentials be generated by the server, provided to the nodes, and observed within the nodes to allow for a successful connection or association of nodes.

In operation, a node (such as master node 110*a*) identifies the address of the node (such as ID node 120*a*) to whom it desires to connect. With this address, the node prepares a pairing request and sends the request to the server 100. The server 100 operates under the control of the security manager module of the association manager, and determines whether the requesting node should be connected or otherwise associated with the other node. If not, the server does not issue the requested security credentials. If so and in accordance with the desired association management paradigm set by the association manager of code 525, server provides the requested credentials necessary for a successful wireless pairing and the establishment of secure communications between the associated nodes.

Node Update Manager

The exemplary server control and management code 525 may include a node update manager module that provides updated programming information to nodes within the wireless node network and collects information from such nodes (e.g., shared data 545, sensor data 550). The node update module may be implemented separately or as part of the association manager module in exemplary server control and management code 525.

Providing an update to a node's programming may facilitate and enable distribution of node functions to save power and better manage the nodes as a system. For example, one example may alter the functional responsibility of different nodes depending on the context or association situation by temporarily offloading responsibility for a particular function from one node to another node. Typically, the server directs other nodes to change functional responsibility. However, in some examples, a master node may direct other nodes to alter functional responsibility.

Sharing information between nodes and with server (e.g., via an exemplary node update manager) facilitates collecting information from a node and sharing information with other nodes as part of an association management function of server 100. For example, one example may collect and share RF scan data (a type of shared data 545), information about a node's location (a type of location data 555), system information about date/time (another type of shared data 545), and sensor measurements collected from sensor nodes (a type of sensor data 550)

Location Manager

The exemplary server control and management code 525 may include a location manager module that helps determine and track node locations. In a general example, the location of a node may be determined by the node itself (e.g., a master node's ability to determine its own location via location circuitry 475), by a node associated with that node (e.g., where a master node may determine the location of an ID node), by the server itself (e.g., using location information determined by one or more techniques implemented as part of code 525), and by a combined effort of a master node and the server.

In general, an exemplary ID node may be directly or indirectly dependent on a master node to determine its actual physical location. Examples may use one or more methodologies to determine node location. For example and as more specifically described below, possible methods for determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. Further information and examples of how an exemplary location manager module may determine a node's location in accordance with such exemplary techniques are provided in more detail below.

Additionally, those skilled in the art will appreciate that it may also be possible to determine what constitutes an actionable location versus actual location based upon contextual information about the item being tracked. For example, a larger item may require relatively less location accuracy than a small item such that operational decisions and status updates may be easier implemented with knowledge of context. If the size of the item is known, the location accuracy can be tuned accordingly. Thus, if a larger item is to be tracked, or if the system's contextual awareness of it is such that lower location accuracy can be used, a stronger signal and thus wider area of scanning may be employed, which may help in situations where RF interference or shielding is an issue.

Information Update Manager

The exemplary server control and management code 525 may include an information update manager module that provides information related to operations of the wireless node network and status of nodes. Such information may be provided in response to a request from a device outside the wireless node network (such as user access device 200). For example, someone shipping an item may inquire about the current status of the item via their laptop or smartphone (types of user access devices), which would connect to server 100 and request such information. In response, the information update manager module may service such a request by determining which node is associated with the item, gathering status information related to the item (e.g., location data, etc.), and provide the requested information in a form that is targeted, timely, and useful to the inquiring entity.

In another example, a user access device may connect to server 100 and request particular sensor data from a particular node. In response, information update manager may coordinate with node update manager, and provide the gathered sensor data 545 as requested to the user access device.

Node Filtering Manager

An example of exemplary server control and management code 525 may optionally comprise a node filtering manager, which helps manage the traffic of nodes with a multi-level filtering mechanism. The filtering essentially sets up rules that limit potential associations and communications. An example of such a node filtering management may define different levels or modes of filtering for a master node (e.g., which ID nodes can be managed by a master node as a way of limiting the communication and management burdens on a master node).

In one example, a "local" mode may be defined where the ID node only communicates and is managed by the assigned master node at the location where the last wireless node contact back to server 100 and/or where third party data indicates the assigned master node and ID node are in physical and wireless proximity. Thus, for the "local" mode of traffic filtering, only the assigned master node communicates and processes information from a proximately close and assigned ID node.

Moving up to a less restrictive filtering mode, a "regional" mode of filtering may be defined where the ID node may communicate and be managed by any master node at the location last reported back to server 100 and/or where third party data indicates the ID node is located. Thus, for the "regional" mode of traffic filtering, any master node near the ID node may communicate and process information from that ID node. This may be useful, for example, when desiring to implement a limit on associations and pairings to within a particular facility.

At the least restrictive filtering mode, a "global" mode of filtering may be defined as essentially system-wide communication where the ID node may be allowed to communicate and be managed by any master node. In other words, the "global" mode of traffic filtering allows any ID node within the wireless node network to communicate information through a particular master node near the ID node may communicate and process information from that ID node.

Thus, with such exemplary filtering modes, an ID node in a certain condition (e.g., distress, adverse environmental conditions, adverse conditions of the node, etc.) may signal the need to bypass any filtering mechanism in place that helps manage communications and association by using the "Alert" Status Flag. In such an example, this would operate to override any filtering rules set at the Master Node level in order to allow an ID node to be "found" and connect to another node.

Thus, exemplary server 100 is operative, when executing code 525 and having access to the types of data described above, to manage the nodes, collect information from the nodes, store the collected information from the nodes, maintain or have access to context data related to the environment in which the nodes are operating, and provide information about the nodes (e.g., status, sensor information, etc.) to a requesting entity.

Node Communication & Association Examples

To better illustrate how exemplary management and communication principles may be implemented within an exemplary wireless node network, FIGS. 8-12 provide several examples of how exemplary components of the wireless node network may generally communicate (advertising & scanning), associate, and exchange information during different types of operations in various embodiments.

Node Advertising Cycle Example

As generally explained above, a node may have several different types of advertising states in which the node may be connectable with other nodes and may communicate with other nodes (such as when a master node implementing an autonomous controller within an exemplary MALVT bot apparatus detects other nodes (e.g., an ID node implemented with an elevator or actuated door) and wants to connect to such other nodes and securely communicate with such other nodes). And as a node moves within a wireless node network, the node's state of advertising and connection may change as the node disassociates with a previously connected node, associates with a new node, or finds itself not associated with other nodes. In some situations, a node may be fine and in normal operation not be connected or associated with another node. However, in other situations, a node may raise an issue with potentially being lost if it has not connected with any other node in a very long period of time. As such, a node may go through different types of advertising states in these different operational situations.

Generally, a node may be in a state where it is not connectable with other nodes for a certain period of time (also referred to as a non-connectable interval). But later, in another state, the node may want to be connected and advertises as such for a defined connectable period (also referred to as a connectable interval). As the node advertises to be connected, the node may expect to be connected at some point. In other words, there may be a selectable time period within which a node expects to be connected to another node. However, if the node is not connected to another node within that period of time (referred to as an Alert Interval), the node may need to take specific or urgent action depending upon the circumstances. For example, if a node has not been connected to another node for 30 minutes (e.g., an example alert interval), the node may change operation internally to look "harder" for other nodes with which to connect. More specifically, the node may change its status flag from an Alert Level 0 (no issue, operating normal) to Alert Level 2 in order to request that any available master node acknowledge receipt of the advertisement packet broadcasted by the node seeking a connection.

Figure 8:
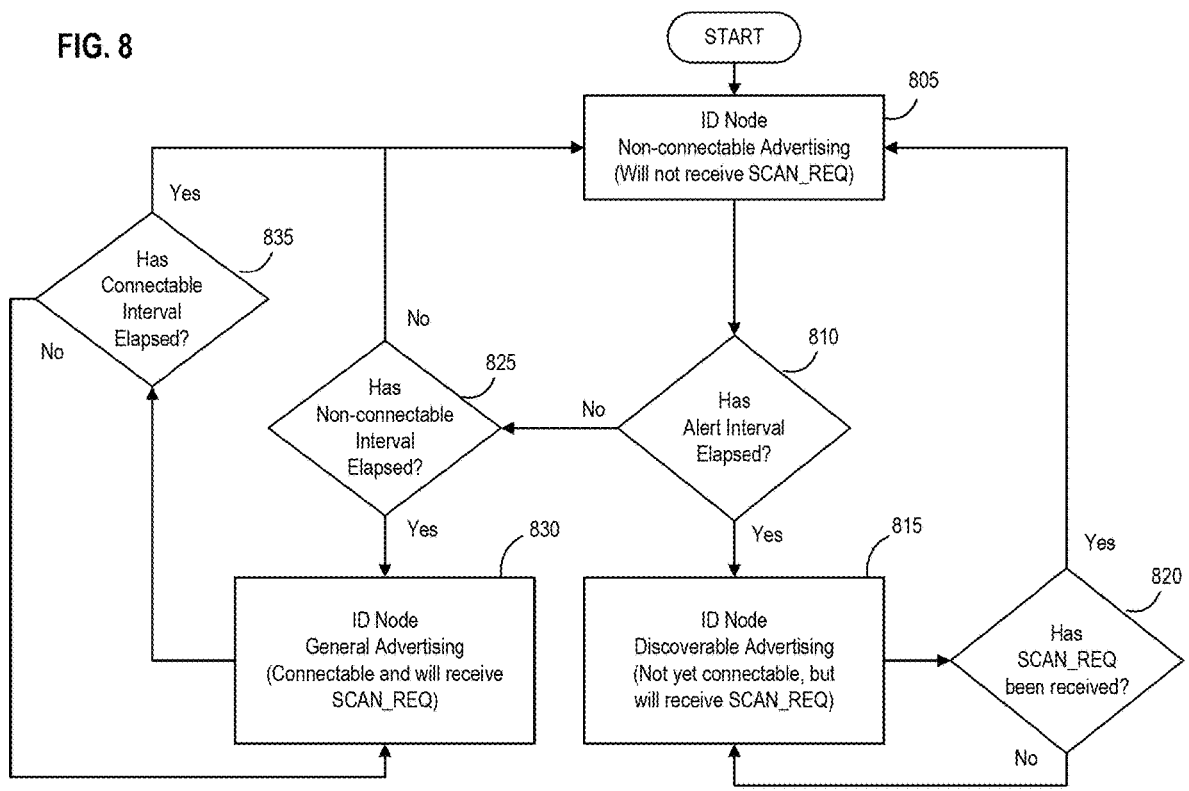
FIG. 8 is a state diagram illustrating exemplary states and transitions between the states as part of operations by an exemplary node as known in the art.

FIG. 8 is a diagram illustrating exemplary advertising states (or information exchange and node connectability states) and factors involved in transitions between the states by an exemplary ID node in a wireless node network. Referring now to FIG. 8, three exemplary states for a node are illustrated as part of an exemplary advertising cycle for the node—namely, an ID Node Non-Connectable Advertising state 805, an ID Node Discoverable Advertising state 815, and an ID Node General Advertising state 830. Transitions between these states will depend on factors related to expirations of the types of intervals described above. In an example, the duration of each of these intervals will depend upon the system implementation and the contextual environment within which the ID node is operating. Such time intervals may, for example, be set by server 100 as part of data (e.g., profile data, association data, context data) provided to the node when updating the node and managing operations of the node.

Referring to the example illustrated in FIG. 8, an exemplary ID node may have an alert interval set at, for example, 30 minutes, and be in ID Node Non-Connectable Advertising state 805 with a non-connectable interval set at 5 minutes. In state 805, the ID node may broadcast or advertise, but is not connectable and will not receive a SCAN_REQ message (a type of request for more information sent to the advertising node from another node). Thus, the ID node in state 805 in this example may advertise in a non-connectable manner for at least 5 minutes but expects to be connected within 30 minutes.

If the alert interval has not yet elapsed (factor 810) and the non-connectable interval is still running (factor 825), the ID node simply stays in state 805. However, if the alert interval has not elapsed (factor 810) and the non-connectable interval elapses (factor 825), the ID node will enter a mode where it wants to try to connect to another node for a period of time (e.g., a 1 minute connectable interval) and will move to the ID Node General Advertising state 830 in the exemplary advertising cycle of FIG. 8. In state 830, as long as the connectable interval is running, the ID node will stay in this state where it is connectable to another node and will receive SCAN_REQ types of requests from other nodes in response to the advertising packets the ID node is broadcasting. However, when the connectable interval (e.g., the 1 min period) elapses or expires (factor 835), the ID node returns back to the Non-connectable Advertising state 805 for either the next time the non-connectable interval elapses (and the ID node again tries to connect in state 830) or the alert interval finally elapses (and the ID node finds itself in a situation where it has not connected to another node despite its efforts to connect in state 830).

When the alert interval finally elapses (factor 810), the ID node moves to the ID Node Discoverable Advertising state 815. Here, the ID node is not yet connectable but will receive a SCAN_REQ type of request from other nodes in response to advertising packets the ID node is broadcasting. In this state 815, the exemplary ID node may alter its status flag to indicate and reflect that its alert interval has expired and that the node is now no longer in normal operation. In other words, the ID node may change the status flag to a type of alert status being broadcasted to indicate the ID node urgently needs to connect with another node. For example, the status flag of the advertising packet broadcast by the ID node may be changed to one of the higher Alert Levels depending on whether the node needs to upload data (e.g., Alert Level 3 status) or synchronize timer or other data with another node (e.g., Synchronize status). With this change in status flag, and the ID node in state 815 broadcasting, the ID node awaits to receive a request from another node that has received the broadcast and requested more information via a SCAN_REQ message (factor 820) sent to the ID node from that other node. Once a SCAN_REQ message has been received by the ID node (factor 820), the ID node that went into the alert mode because it had not connected with another node within the alert interval can connect with that other node, upload or share data as needed, and then shift back to state 805 and restart the alert interval and non-connectable intervals.

Master Node to ID Node Association Example

Advertising (broadcasting) and scanning (listening) are ways nodes may communicate during association operations. FIGS. 9-12 provide examples of how network elements of a wireless node network (e.g., ID nodes, master nodes, and a server) may communicate and operate when connecting and associating as part of several exemplary wireless node network operations.

Figure 9:
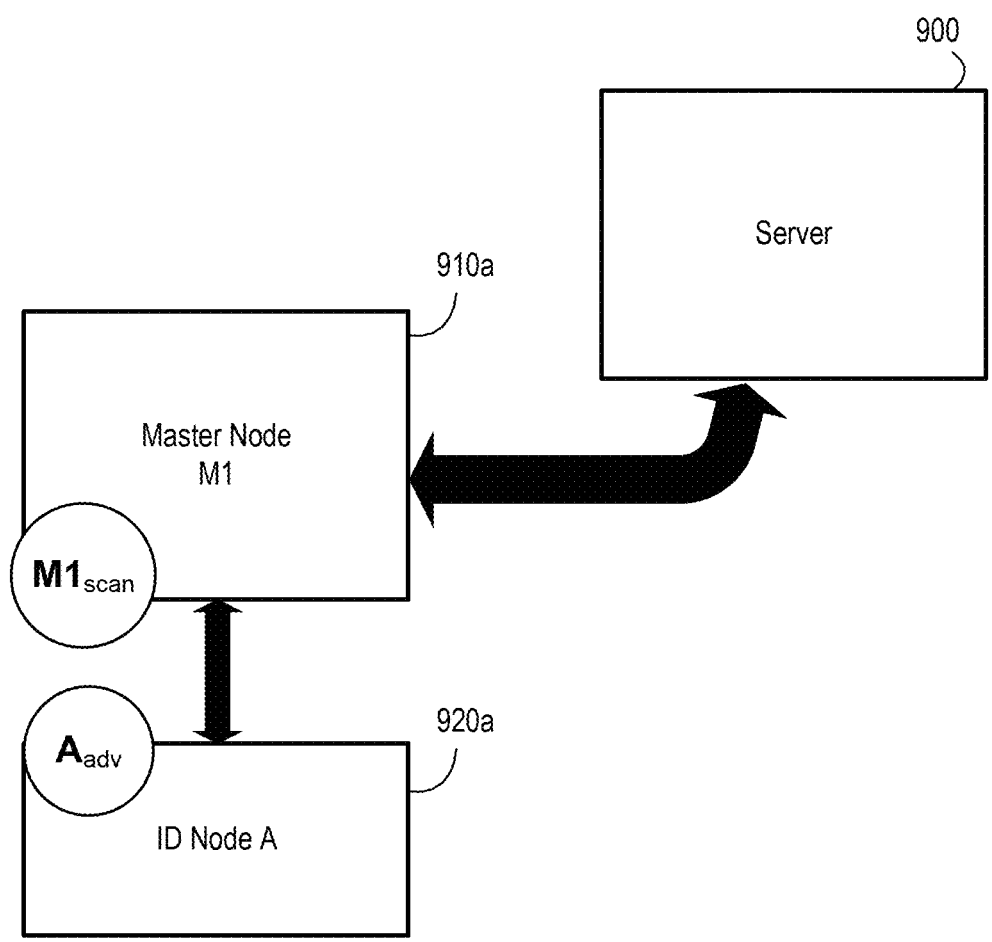
FIG. 9 is a diagram illustrating exemplary components of a wireless node network during an exemplary master-to-ID node association as known in the art.

FIG. 9 is a diagram illustrating exemplary components of a wireless node network during an exemplary master-to-ID node association. Referring now to FIG. 9, exemplary master node M1 910a is illustrated within communication range of exemplary ID node A 920a. Master node M1 910a also has a communication path back to server 900. As shown, master node M1 910a is in a scanning or listening mode (e.g., indicated by the "$M1_{scan}$" label) while ID node A 920a is in an advertising or broadcasting mode (e.g., indicated by the "$A_{adv}$" label). In this example, M1 master node 910a has captured the address of ID node A 920a through A's advertising of at least one advertising data packet, and has reported it to the server 900. In this manner, the capturing and reporting operations effectively create a "passive" association between the nodes and proximity-based custodial control. Such an association may be recorded in the server, such as server 900, as part of association data, such as association data 540.

In another example, passive association between a master node and ID node may be extended to an "active" association or connection. For example, with reference to the example shown in FIG. 9, server 900 may instruct master node M1 910a to associate, connect, or otherwise pair with ID node A 920a, and forwards the required security information (e.g., PIN credentials, security certificates, keys) to master node M1 910a. Depending on the advertising state of ID node A 920a, ID node A 910a may only be visible (discoverable) but not connectable. In such a situation, the master node M1 910a must wait until ID node A 920a is in a connectable state (e.g., the ID Node General Advertising state) and can be paired. As discussed above with reference to FIG. 8, each ID node has a certain time window during each time period where it can be paired or connected.

In this example, when the ID node A 920a is successfully paired with master node M1 910a, ID node A 920a may no longer advertise its address. By default, only an unassociated device will advertise its address. A paired or associated node will only advertise its address if instructed to do so.

ID Node to ID Node Association Example

Figure 10:
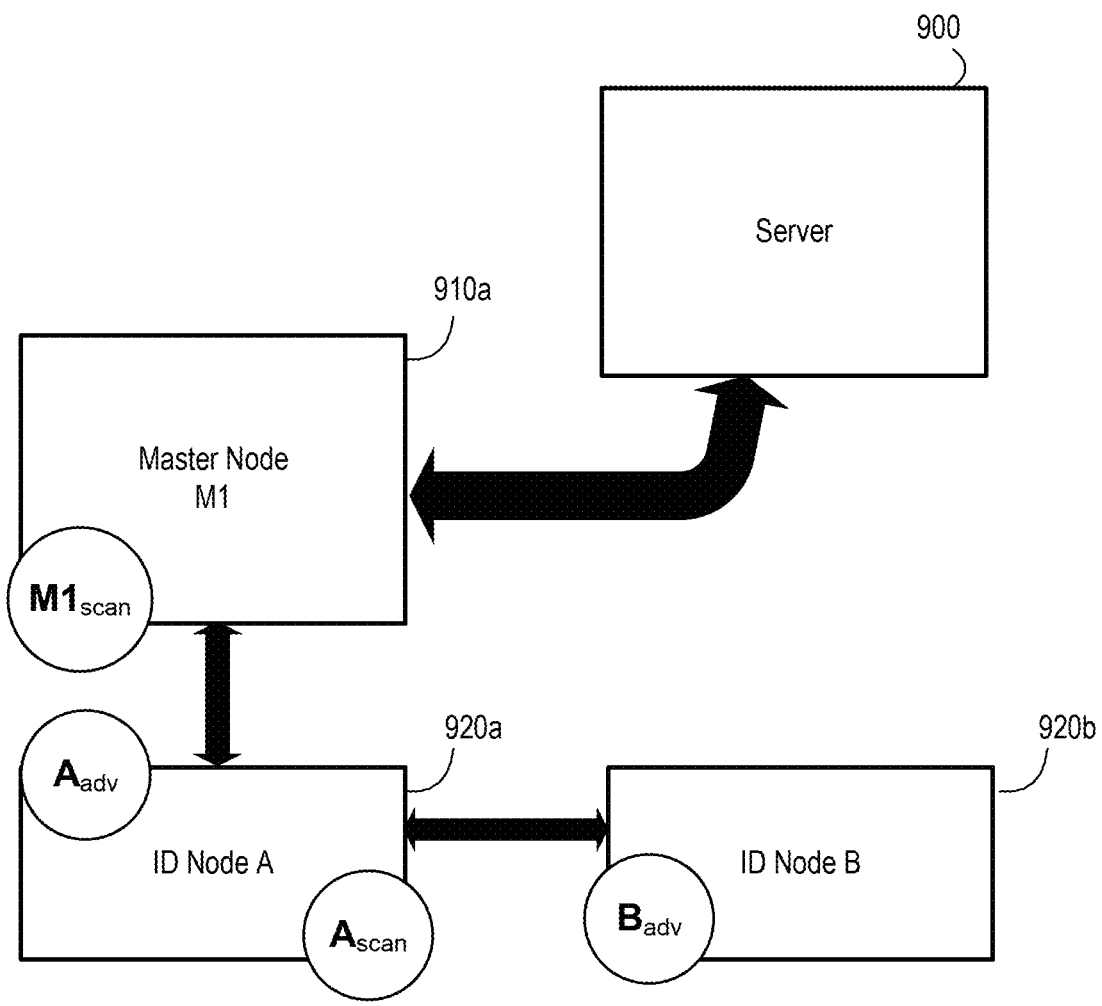
FIG. 10 is a diagram illustrating exemplary components of a wireless node network during an exemplary ID-to-ID node association as known in the art.

In various examples, an ID node may associate with or connect to other ID nodes. FIG. 10 is a diagram illustrating exemplary components of a wireless node network during an exemplary ID-to-ID node association. Referring now to FIG. 10, exemplary master node M1 910a, ID node A 920a, and server 900 are similarly disposed as shown in FIG. 9, but with the addition of ID node B 920b, which is within communication range of ID node A 920a. In this example, ID node A 920a is running in query (scan) mode (e.g., $A_{scan}$) listening for ID node B 920b. When ID node A 910a detects ID node B 920b advertising (e.g., $B_{adv}$) with one or more advertising data packets as part of an advertised message from ID node B 920b, ID node A 920a identifies a status flag from the message indicating ID node B 920b has, for example, data (e.g., sensor data 350) for upload. As a result, ID node A 920a logs the scan result (e.g., as a type of association data 340) and, when next connected to master node M1 910a, ID node A 920a uploads the captured scan log information to the server 900. In this manner, the ID node scanning, capturing, and reporting operations effectively create a "passive" association between the different ID nodes. Such a passive association may be recorded in the server 900 as part of association data 540.

In another example, passive association between two ID nodes may be extended to an "active" association or connection. For example, with reference to the example shown in FIG. 10, based upon the captured status flag and uploaded information about ID node B 920b under that mode, the server 900 may issue a request to ID node A 920a through master node M1 910a to actively connect or pair with ID node B 920b for the purpose of downloading information from ID node B 920b. In one example, security credentials that authorize the active connection between ID node A 920a and ID node B 920b are downloaded to ID node A 920a from master node M1 910a, which received them from server 900. In another example, the requisite security credentials may have been pre-staged at ID node A 920a. And rather than rely upon an ID node to ID node connection, master node M1 may have connected directly with ID node B 920b if M1 was within communication range of ID node B 920b.

Information Query ID Node to Master Node Example

Figure 11:
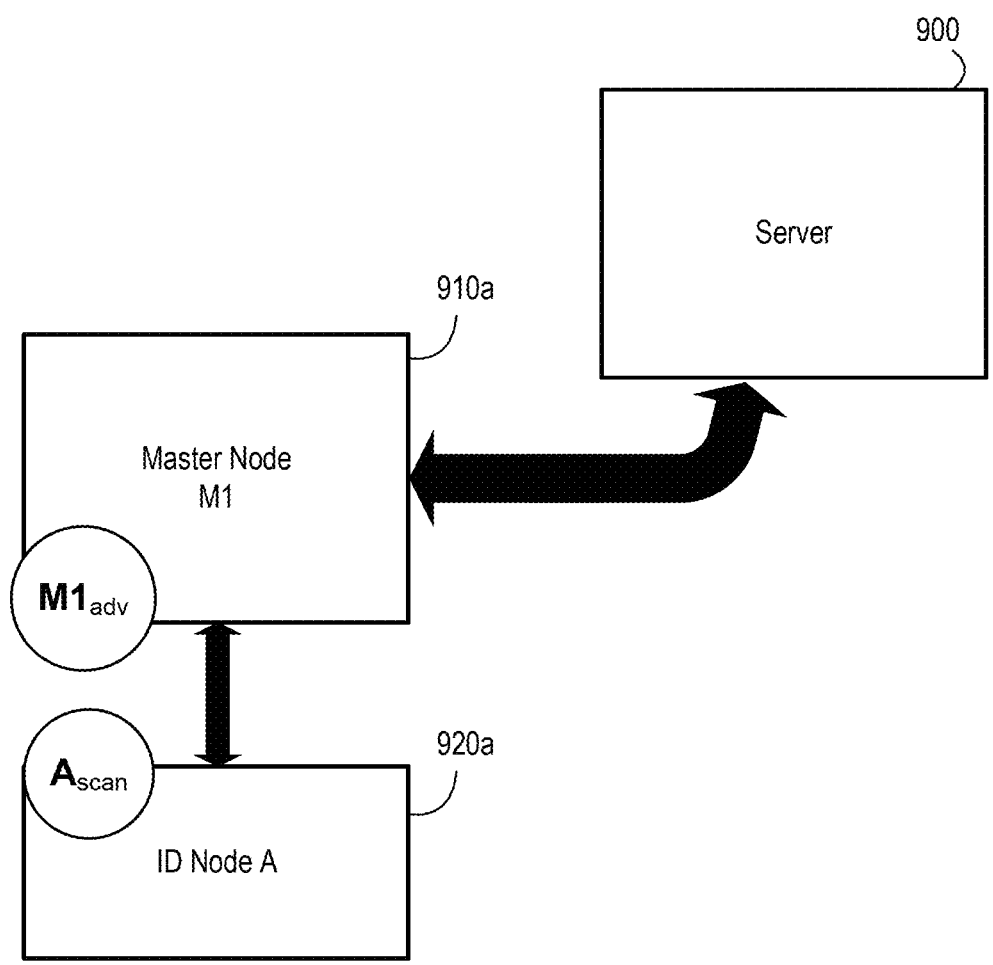
FIG. 11 is a diagram illustrating exemplary components of a wireless node network during an exemplary ID-to-master node query as known in the art.

An exemplary ID Node may also issue queries to other nodes, both master nodes and ID nodes. FIG. 11 is a diagram illustrating exemplary components of a wireless node network during an exemplary ID-to-master node query. Referring now to FIG. 11, a similar group of nodes as shown in FIG. 9 appears, except that exemplary master node M1 910a is in an advertising or broadcasting mode (e.g., $M1_{adv}$) while ID node A 920a is in a scanning mode (e.g., $A_{scan}$). In this configuration, ID node A 920a may query master node M1 910a for information. In one example, the query may be initiated through the ID node setting its status flag. The requested information may be information to be shared, such as a current time, location, or environmental information held by the master node M1 910a.

In a passive association example, ID node A 920a in $A_{scan}$ mode may have captured the address of master node M1 910a. However, since an ID node cannot directly connect to the server 900 to request pairing security credentials (e.g., security pin information that authorizes an active connection between ID node A 920a and master node M1 910a), a passive association and corresponding pairing will have been initiated from the master node. In another example, it may be possible for ID node A 920a to have the pairing credentials stored as security data 335 from a previous connection. This would allow ID node A 920a then to initiate the active association with master node M1 910a after a passive association.

Alert Level Advertising Example

Figure 12:
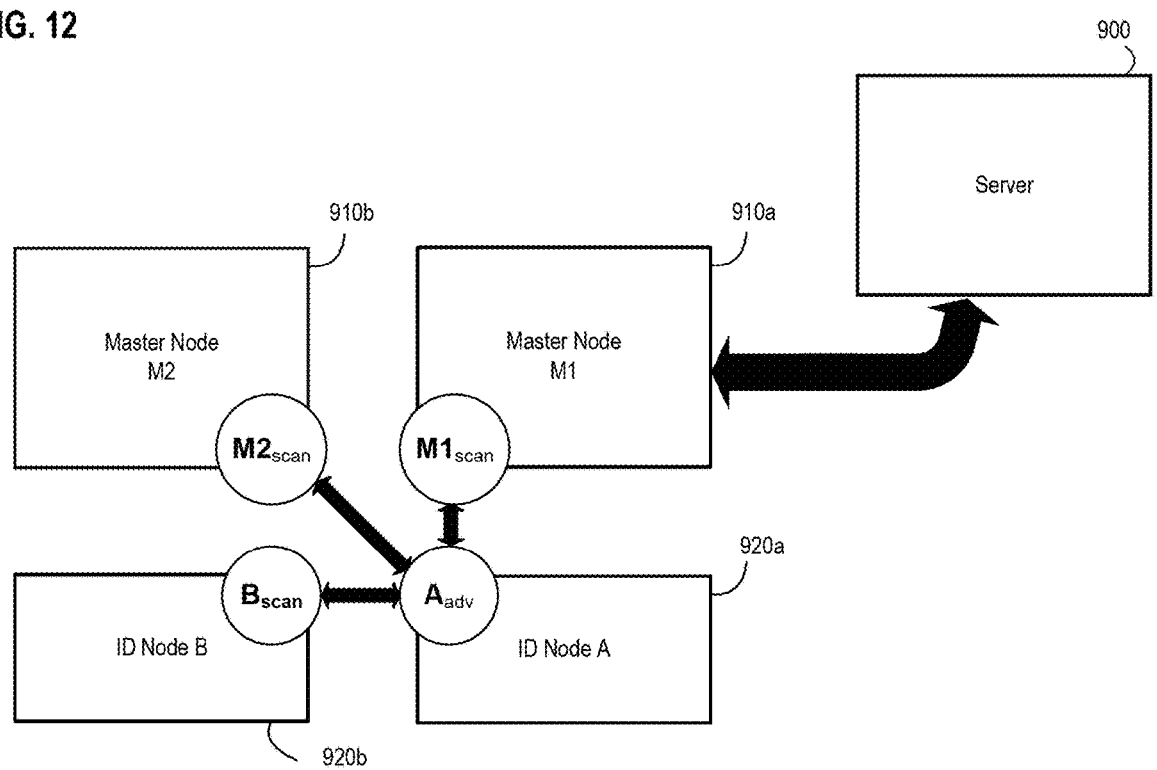
FIG. 12 is a diagram illustrating exemplary components of a wireless node network during an exemplary alert advertising mode as known in the art.

As previously noted, a node may enter an alert stage or level in one or more examples. For example, if a node has not received an acknowledgement from a master node for an advertising packet within a set period (e.g., an Alert Interval as described in some examples), the node will enter a particular alert stage for more specialized advertising so that it may be "found" or pass along information. FIG. 12 is a diagram illustrating exemplary components of a wireless node network during an exemplary alert advertising mode. Referring now to FIG. 12, a similar group of nodes as shown in FIG. 9 appears, with the addition of another master node (master node M2 910b) and another ID node (ID node B 920b). Exemplary ID node A 920a is in an advertising or broadcasting mode (e.g., $A_{adv}$) while nodes M1, M2, and B are each in scanning mode (e.g., $M1_{scan}$, $M2_{scan}$, and $B_{scan}$). In this example and configuration as shown in FIG. 12, the status flag in an advertising message from ID node A 920a has been set to a particular alert level (e.g., Alert Level 2) in the header of the message, requesting any nearby master node to acknowledge it. In one example, this mode may be entered if ID node A 920a has not connected with another node for a set period or time. In another example, ID node A 920a may enter this specialized advertising mode upon received instructions (e.g., from server 900 or another nearby node) or a triggered condition (other than time), such as when a sensor input (such as light) is detected or otherwise registered and the node issues continuous updates of its address as a security feature. The ID node A 920a set at this alert level and in this specialized advertising mode is thus set in an active pairing mode, waiting for pairing credentials.

From a passive association perspective, any node in scanning mode can passively associate with such an advertising node (e.g., ID node A 920a in this alert mode). Thus, in an example, the Alert Level 2 status flag in the advertising header broadcast by ID node A 920a indicates that urgent and active intervention is requested, rather than merely passively associate without an active connection.

From an active association perspective, any node that uploads the special advertising header of ID node A 920a may be forwarded the security credentials from the server 900. This would allow for the node receiving such credentials to actively associate or pair with ID node A 920a.

Node Location Determination Methodologies

As part of managing and operating a wireless node network in accordance with one or more examples of the invention, a node may determine its own location or the location of another node. FIGS. 13-16 provide some exemplary diagrams illustrating some methods in which a node's location may be determined. Some nodes, as noted above, include location circuitry and can self-locate using, for example, GPS positioning, Wi-Fi triangulation, and the like. And as explained above, an exemplary ID node may be directly or indirectly dependent on a master node (which can self-locate) to determine its location. In the examples discussed and described herein, a location of a node may generally encompass a current or past location. For example, an example that determines a node's location may be a current location if the node is not moving, but may necessarily determine the location as a past location should the node be in a state of motion.

Likewise, the term location alone may include a position with varying degrees of precision. For example, a location may encompass an actual position with defined coordinates in three-dimensional space, but use of the term location may also include merely a relative position. Thus, the term location is intended to have a general meaning unless otherwise expressly limited to a more specific type of location.

Determining node location may done by a master node alone, the server alone, or the master node working together with the server. And on such devices, examples may use one or more methodologies to determine a node's location and further refine the location. Such example methodologies may include, but are not limited to, determining node location may relate to controlling an RF characteristic of a node (e.g., an RF output signal level and/or RF receiver sensitivity level), determining relative proximity, considering association information, considering location adjustments for context information and an RF environment, chaining triangulation, as well as hierarchical and adaptive methods that combine various location methodologies. A more detailed description of these exemplary node location determination techniques is provided below.

Location Through Proximity

In one example, a signal strength measurement between two or more nodes may be used to determine the proximity of the nodes. If neither node's actual location is known, one example may infer a location relationship of the two nodes through proximity.

Proximity when Varying Power Characteristics

For example, an exemplary method of determining a node's location in a wireless node network of nodes may involve varying a node's power characteristic, such as the output power of one of the nodes. Generally and as explained with reference to FIG. 13, the power characteristic may be varied to identify closer ones of the nodes to the node broadcasting. The node broadcasting may transmit one or a series of signals while other nodes may report receiving one or more of the signals. Those other nodes that receive at least one signal broadcast from the transmitting node may be deemed part of a close group of nodes. And as the power characteristic is varied (increased or decreased or both), a closest group of nodes (or single node) may be identified as the smallest group of nodes of those that receive at least one signal from the broadcasting node. Accordingly, while not absolute, a type of location for the broadcasting node may be determined based on the closest one or group of nodes. This may be repeated for neighboring nodes to yield a set of closest node information for each of the nodes. In more detail, an exemplary set of closest node information for each of the nodes may include which nodes are closest (via the lowest power characteristic) and more robustly supplement this information with which other nodes are incrementally further away (via increasingly larger power characteristics). Thus, the set of closest node information provides the basis for a determination of how close the nodes in the network are to each other, which provides a type of location determination for each node.

Additionally, context data may be referenced in certain examples to further enhance determining how close the nodes are to each other. For example, combining the set of closest node information with context data, such as scan information that registers when an item changes custodial control in a delivery system, may further refine how to determine the location of the nodes. Scan and other context information will help determine if one or more of the nodes, for example, are known to be in the same container, vehicle or moving on a belt together. Thus, this type of context data may be integrated into a further step of refining how close the nodes are to each other based upon the context data.

In general, a location of a node based upon proximity may be determined when a power characteristic of nodes is changed or varied in a wireless node network. An exemplary method of doing so may being with instructing a first of the nodes to vary the power characteristic for one or more signals broadcast by the first node. In a more detailed example, such an instruction may cause the first node, for example, to incrementally decrease or incrementally increase the power characteristic (such as an output power level) between values.

Next, the method continues by identifying a first group of other nodes in the wireless node network that are near the first node based upon those of the other nodes that received at least one of the signals broadcast by the first node as the first node varies the power characteristic. In a further example, this step may incrementally identifying which of the first group of other nodes are receiving at least one of the broadcast signals as the first node incrementally varies the output power level of the signals broadcast. The incrementally identified nodes may be deemed a set of increasingly close nodes to the first node.

The method then continues by identifying a closest one or more of the other nodes as a smallest group of the other nodes that received at least one of the one or more signals broadcast by the first node as the first node varies the power characteristic.

The method then concludes by determining a location of the first node based upon the closest one or more of the other nodes. Thus, as the power characteristic is varied, the group of nodes that have received at least one of the signals broadcast by the first node may change and the smallest such group being a closest group of nodes (even if just one node) to the first node. In a more detailed example, the final step may comprise determining the location of the first node based upon the closest one or more of the other nodes and the set of increasingly close nodes to the first node as the set of increasingly close nodes provides more detailed proximity information for a refined location determination.

Figure 14:
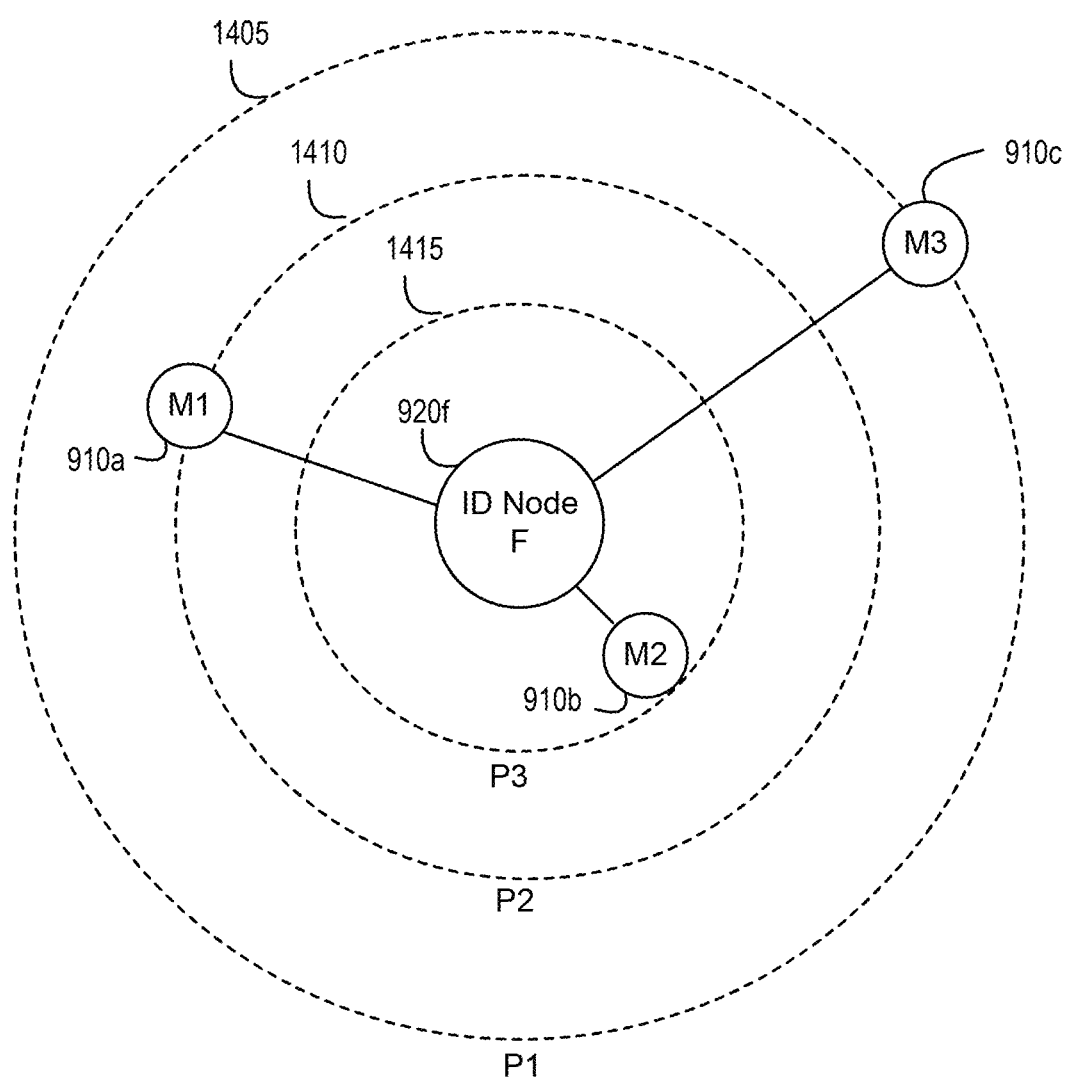
FIG. 14 is a diagram illustrating an exemplary location determination using ID node advertise as known in the art.

For example, referring to FIG. 14, the set of increasingly close nodes to the ID node F 920f may include node M3 as being farthest away and M1 being closer than M3. When the power characteristic of ID node F incrementally decreases, and its output power level changes from P1 to P2, M3 can no longer receive the signal, but M1 and M2 still do. And as the power characteristic of ID node F continues to incrementally decrease, and its output power level is changed from P2 to P3, M1 can no longer receive the signal, but only M2 does as the last of the nodes closest to ID node F. Thus, in this example, determining the location of ID node F may be based upon the fact that M2 is the closest node and the set of increasingly close nodes include M1 and M3 with M1 being closer than M3.

In another example, one or more further refinements to the first nodes location may be performed. In one example, the method's steps may be repeated where a second of the nodes is instructed to vary the power characteristic for one or more signals broadcast by the second node, and then the method may further refine the location of the first node based upon a location of the second node. In a more detailed example, the method's steps may be repeated where a second of the nodes is instructed to vary the power characteristic for one or more signals broadcast by the second node, and then the method may further the location of the first node based upon a location of the second node and a set of increasingly close nodes to the second node. With this increasingly cross-related information on what nodes are closer to other nodes and to what degree, which may be further repeated for additional nodes, examples may further refine the location of the first node within the network.

This method may further include determining context data related to the first node, and refining the location of the first node based upon the context data. In an example where the power characteristic is output power level, the incremental changes in the output power level of the broadcast signal may be set according to the context data.

This method may also determine the context data to be related to the closest node to the first node, and refine the location of the first node based upon the context data. In still another example, this method may determine the context data to be related to the incrementally identified nodes in the set of increasingly close nodes to the first node, and refining the location of the first node based upon the context data. For example, the closest node and the set of increasingly close nodes may have scan data that indicate they are within the same container. This exemplary context data may be used to further refine the location of the node being located, which may help efficiently determine that node is near the container. As such, those skilled in the will appreciate that context data for the node being located as well as nodes identified to be close to that node may provide relevant input to advantageously help further refine the location of the node.

Those skilled in the art will appreciate that such a location method as disclosed and explained above in various examples may be implemented on a server apparatus, such as server 100 illustrated in FIG. 5, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above and variations of that method.

An example of such a server apparatus may include a server (such as server 100) operative to communicate with a plurality of nodes in the wireless node network. As explained with respect to FIG. 5, the server generally includes a server processing unit, a server volatile memory, a server memory storage, and at least one communication interface. In this example, the volatile memory, memory storage, and communication interface are each coupled to the processing unit. The memory storage maintains at least a program code section and location data related to a location of one or more of the nodes. The communication interface provides a communication path operatively coupling the server with the nodes.

The server processing unit, as mentioned above, is operative when running the program code section, to perform the steps and operations as described above relative to this method and variations of that method described above.

Proximity when Observing Signal Patterns and Strengths Over a Time Period

In another example, an improved method for determining a node's location through proximity may include analyzing the signal patterns and strengths between an advertising node and a listening node. In one example, a threshold may be set for association based on an observed message count and/or recorded signal strength within a specific time period may improve the ability to locate a node (e.g., an ID node) to that of another node (e.g., a master node). In some examples, the observed message count may be implemented as an averaged count over a repeated time periods. Further still, other examples may filter outlying observations in the observation data set to help improve the quality of data relied upon for setting a threshold for association and, as a result, determine a node's location.

In a more detailed example, an improved method for determining a node's location through proximity may show captured advertising message counts as a component for a node's location and determining a node's direction of travel. In this example, two exemplary master nodes (e.g., master node M1 910*a* and M2 910*b*) may capture advertising messages from one ID node (e.g., ID node A 920*a*). Master node M1 may observe and capture (e.g., record information related to the observation) 60 messages from ID node A within a 2 minute period, while master node M2 only observes and captures 7 advertising messages from ID node A within that same period. Based upon the difference in how often messages are observed from ID node A by master node M1 compared to those observed by master node M2, the system is able to determine that ID node A would more proximate to master node M1, and it's known location.

In a further example, comparing the average time stamp of the captured records may allow the system can make a more accurate determination of location. For example, if the average captured message found on master node M2 is increasingly growing larger (e.g., taking longer for messages to go from ID node A to master node M2), this indicates ID node A is moving away from master node M2. If the average captured message found on master node M2 is growing increasingly larger while the average captured message found on master node M1 is increasingly growing smaller, this indicates ID node A is moving away from master node M2 and toward master node M1. Thus, over a number of observed time periods, the change in message timing (transmission to reception) may also be relied upon to enhance or refine a node's location.

In yet another example, the observed signal strength may be a component in location determination and estimating direction of travel and may allow the system can make a more accurate determination of location. For example, two master nodes (M1 910*a* and M2 920*b*) may be capturing advertising messages from a node (ID node A 920*a*). M1 captures 60 messages from ID node A within 2 minutes, while M2 captures only 7 messages. The average signal strength observed for signals from ID node A by master node M1 is higher compared to the average signal strength observed by master node M2. Based upon this observed signal strength information, the system would determine that ID node A to be at M1, but a predicted path may indicate ID node A is heading towards M2. As the master nodes M1 and M2 continue to capture records, the system (e.g., management code 524 operating on server 900, which is in communication with M1 and M2) processes the continued feed of capture records from M1 and M2. With this observed signal strength information, the server 900 would expect that the count and average signal strength of messages from ID node A over the time period observed (2 minutes) to increase for observations at M2 and to decrease for observations at M1 when ID node A is physically moving closer to M2 and away from M1. Thus, the change in observed powers levels and in how often messages are observed may indicate actual node movement in an example.

Basing node proximity location and node directional determinations on observed signal patterns and characteristic strengths over a period of time has the advantage of reducing the likelihood of unwanted and spurious signal anomalies causing an ID node's location to be incorrectly determined. And the above exemplary methods for determining movement characteristics of a node (e.g., moving closer to one node, moving closer to one but away from another, etc.) as part of refining the node location may be applied in combination with the various examples for determining node location described herein.

In an example, such an improved method based on node proximity location and node directional determinations on observed signal patterns and characteristic strengths over a period of time may begin by instructing a first and a second other nodes to detect any message broadcast from the one node over a period of time. The period of time may be set based upon a variety of factors, such as context data. In more detail, the period of time may be dynamically changed based upon context data as the one node moves into different contextual environments.

The method has the server receiving a first indication from the first other node and receiving a second indication from the second other node. Finally, the method determines a location of the one node based upon a difference in the first indication and the second indication. The first indication is related to a characteristic of messages broadcast from the one node that are detected by the first other node during the period of time. Likewise, the second indication is related to the characteristic of messages broadcast from the one node that are detected by the second other node during the period of time. These indications may include, for example, a count of messages received by the respective other nodes, a transit time factor (e.g., an average transit time for a message to be detected after broadcast), and an average signal strength.

In one example, the first indication may be a first count of messages broadcast from the one node that are detected by the first other node during the period of time, and the second indication may be a second count of messages broadcast from the one node that are detected by the second other node during the period of time. As such, determining the location of the one node may be the location that is closer to the first other node than the second other node when the first count is greater than the second count. Additionally, the method may further include determining an actual node movement direction for the one node based upon comparing the first count and the second count over a plurality of time periods. For example, the method may repeat observations over several of these time periods and track the first count and second count over time to determine which is increasing, which is decreasing, and determine movement of the one node based upon these measurements over time.

In another detailed example, the first indication may be a first time factor of messages broadcast from the one node that are detected by the first other node during the predetermined time period, and the second indication may be a second time factor of messages broadcast from the one node that are detected by the second other node during the period of time. And an actual node movement direction for the one node may be based upon comparing the first time factor and the second time factor. In a more detailed example, the first time factor may be an average transit time for a message detected at the first other node to go from the one node to the first other node, and the second time factor is an average transit time for a message detected at the second other node to go from the one node to the second other node. As such, determining the location of the one node may be that the location is closer to the first other node than the second other node when the first time factor is less than the second time factor.

In yet another example, the first indication may be a first average signal strength of messages broadcast from the one node that are detected by the first other node during the period of time, and the second indication may be a second average signal strength of messages broadcast from the one node that are detected by the second other node during the period of time. As such, determining the location of the one node may be that the location is closer to the first other node than the second other node when the first average signal strength is greater than the second average signal strength.

The improved method described above may also include, in an example, observing a degree of change in the first average signal strength and a degree of change in the second average signal strength over repeated time periods, and determining an actual node movement direction for the one node based upon comparing the degree of change in the first average signal strength and the degree of change in the second average signal strength.

In another example, the method may also refine the determined location of the one node. In this example, the method may further comprise refining the location of the one node based upon at least one of a first updated location received from the first other node and a second updated location received from the second other node. For example, when first other node is a mobile master node and it is the closer of the two nodes to the one node being located, the example can take advantage of the location signaling onboard the first other node that provides the current location of the first other node. That current location data may be transmitted by the first other node to the server to update the server in its calculation of the location for the one node.

In still another example, the improved method may layer context data with the determined location to refine the location of the node. Context data related to the one node may be determined by the server, and so the location of the one node may be refined based upon that context data. In another example, context data related to the closer of the first other node and the second other node when compared to the location of the one node. For example, the server may be aware that a particular master node is closer to the one node compared to a second master node, and that the particular master node is within a container. With this additional context data related to the particular master node, the server may refine the location of the one node based upon the context data. Other exemplary types of relevant context data may be relied upon when refining the location of the one node, such as context data of a particular shielding associated with the environment near the particular master node (e.g., a particular type of ULD having known RF shielding characteristics, etc.).

Additionally, the method may involve looking to see if the one node is behaving as expected. More specifically, a further example of the method may further compare the location of the one node to a predicted path of the one node to determine if the one node is located outside the predicted path. This may allow the server to use learned, historic data when creating a predicted path, and keep track of the one node relative to being within an acceptable range associated with this predicted path. The method may also generate a notification if the one node is outside the predicted path. In this manner, actionable tasks can then be taken to locate the one node—e.g., changing filter mode options for nodes in that general area, etc.

Those skilled in the art will appreciate that such an improved node locating method as disclosed and explained above in various examples may be implemented on a server, such as server 100 illustrated in FIG. 5, running one or more parts of server control and management code 525 (e.g., the location manager). Such code may be stored on a non-transitory computer-readable medium such as memory storage 515 on server 100. Thus, when executing code 525, the server's processing unit 500 may be operative to perform operations or steps from the exemplary methods disclosed above and variations of that method.

Association Driven Locating with Variable RF Characteristics

As noted above, a signal strength measurement between two or more nodes may be used to determine relative distance between nodes. If one of the nodes has a known location (such as master node M1 910*a*), a relative location of one or more nodes within a range of the known location node is generally a function of how accurate the system may determine a distance between the node with known location and associated nodes. In other words, an example may identify a relative location of an item and its related node by relying upon association-driven variable low-power RF output signals to determine a distance the node is from a known location.

Location Determination Through Master Node Advertise

Figure 13:
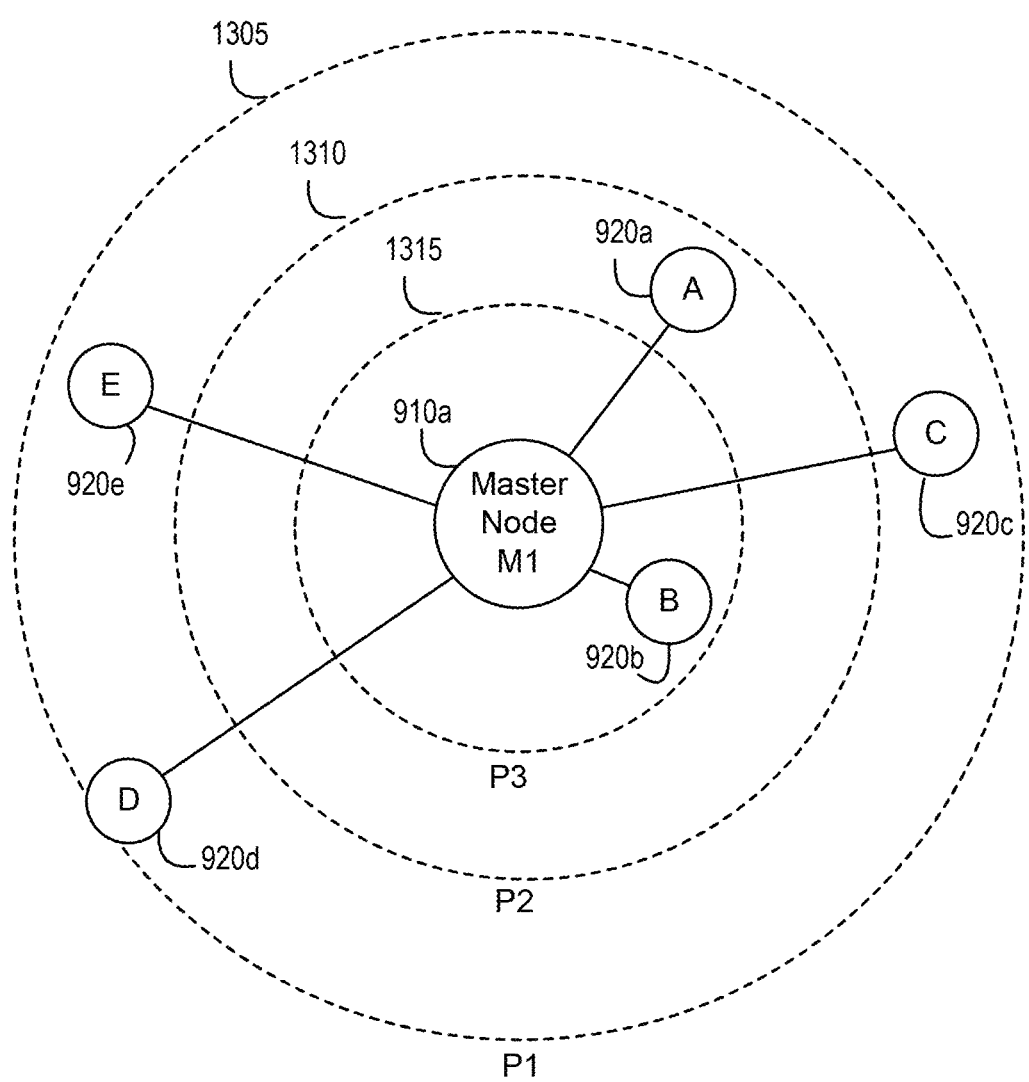
FIG. 13 is a diagram illustrating an exemplary location determination using master node advertise as known in the art.

As generally mentioned above, determining node location may relate to controlling an RF characteristic of a node (e.g., an RF output signal level and/or RF receiver sensitivity level) and, more specifically, may involve aspects of controlling master node advertising. FIG. 13 is a diagram illustrating an exemplary location determination using master node advertise. In the illustrated example shown in FIG. 13, a master node, such as master node M1 910*a*, with a known location is broadcasting an advertising message at varying RF output power levels. FIG. 13 illustrates the exemplary different RF output power levels as concentric ranges 1305-1315 about master node M1 910*a*. Thus, master node M1 910*a* may broadcast at a maximum power P1, related to range 1305, but may control the RF output power level and dynamically change the RF output power level to P2 and broadcast at a smaller range 1310, or to P3 and broadcast to an even smaller range 1315.

In the illustrated example, receiving ID nodes A-E 920*a*-920*e* are in query (scan) mode and can each use the received signal at different levels to determine how far away from the transmitting M1 they are located. Those skilled in the art will appreciate that while the illustrated example shown in FIG. 13 has the receiving nodes all as ID nodes, other examples may have receiving nodes be either master or ID nodes or a mixture.

In the exemplary example of FIG. 13, the location for nodes A-E may be determined based upon the known location of master node M1 910*a*. That location, plus a range measurement when each of respective receiving nodes A-E last receives a signal from node M1, and factoring in a confidence factor of the range measurement, provides a location determination for the nodes according to variable RF signal power. Depending on a quality of the range measurement, the individual receiving nodes may or may not have an individually calculated location. In yet another example, if third party or context data, such as scan information, is available, a refined location may be determined using such data as an additional confidence factor. As the communication range of M1 is limited from P1 to P3, the accuracy of location by association goes up.

In the illustrated example of FIG. 13, an exemplary method of determining a node's location may be described that uses master node advertising. First, when the master node M1's variable power short range communication interface 480 is set to P1, its maximum output, master node M1 910*a* is seen by each of ID nodes A-E 920*a*-920*e*. Based upon analytics or historic measurements, the open air performance (optimal range) of the radio in M1's variable power short range communication interface 480 at P1 power level may have been previously been found to be approximately 30 feet. Thus, without the need to examine RSSI levels from the individual ID nodes A-E 920*a*-920*e* and without the need for active calibration phases, the system may know that ID nodes A-E are within 30 feet of master node M1 910*a*.

Next, when the master node M1's variable power short range communication interface 480 is set to P2, a medium output level in this example, master node M1 is seen by nodes A and B. From previous analytics or historic measurements, it was determined the open air performance (optimal range) of the master node M1's variable power short range communication interface 480 running at P2 power level is approximately 15 feet. Thus, without the need to examine RSSI levels from the individual nodes, we know ID nodes A 920*a* and B 920*b* are within 15 feet of master node M1. Furthermore, we know the ID nodes no longer receiving the broadcasted RF signal from master node M1 910*a* (e.g., ID nodes C 920*c*, D 920*d*, and E 920*e*) are somewhere within 30 feet of master node M1 910*a*, but probably more than 15 feet away from M1.

And when the master node M1's variable power short range communication interface 480 is set to P3, its minimum output level in this example, it is seen by ID node B 920*b*. From previous analytics or historic measurements, it was determined the open air performance (optimal range) of the master node M1's variable power short range communication interface 480 running at P3 power level is approximately 5 feet. Thus, without the need to examine RSSI levels from the individual ID nodes, we know the location of ID node B 920*b* is within 5 feet of the known location of master node M1 910*a*.

The ranging steps, as discussed in the example above, may then be repeated for any of the identified nodes in order to build a more accurate picture of the relative location of each node. The granularity of RF characteristic settings (e.g., the RF output signal power level setting) will provide more granularity of location differentiation when performing the ranging steps. In one example, the ranging steps may be performed over a set of gross RF characteristics settings (e.g., few settings over a wide range), and similar steps may then be performed over more select ranges for the RF characteristics settings.

An example of such a method for location determination using one or more associations of nodes in a wireless node network is described below. This method begins where a first of the nodes broadcasts one or more first messages at a first anticipated or predicted range distance. In one example, the first anticipated range distance is an optimal range for the first node. For example, the first node's radio in its communication interface may have a maximum setting to allow the node to broadcast at maximized range assuming a clear environment. Such a setting provides a known anticipated range distance. In the example of FIG. 13, master node M1 910*a* may be broadcasting at a maximum power level P1 that reaches a first range distance from node M1. However, if node M1 is known to be within an adverse RF shielding environment, the first anticipated range distance may be a distance adjusted to account for the contextual environment of such shielding (e.g., a type of context data). Anticipated range distances may be adjusted depending upon one or more types of relevant context (e.g., one or more types of context data related to how an RF output signal from the node may be impeded).

Next, the method identifies which of the nodes associated with the first node received at least one of the first messages. In one example, the first node may be able to access and review association data in its onboard memory storage as part of identifying which are the nodes associated with it. In one example, the associations with the first node may be passive associations (e.g., not actively paired and securely connected) or active associations (e.g., actively paired and able to securely connect and share data), or a combination of both types of associations.

Next, the first node broadcasts one or more second messages at a second anticipated range distance, which is incrementally smaller than the first anticipated range distance. In the example of FIG. 13, master node M1 910*a* may be the first node and now is broadcasting at a medium power level P2 that reaches a second anticipated range distance from node M1. By incrementally changing the RF power level in this manner, master node M1 910*a* now no longer can reach nodes C-E as shown in FIG. 13.

The method then concludes by determining a location of one or more of the identified associated nodes that did not receive any of the second messages but received at least one of the first messages, where the location is between the first and second anticipated range distances from the first node. Again, in the example of FIG. 13, master node M1 910*a* may determine the location of nodes C-E (given they did not receive the message sent out the second anticipated range distance at RF power level P2) to between the first anticipated range distance (when master node M1 was broadcasting at power level P1) and the second anticipated range distance (when master node M1 was broadcasting at power level P2) from the known location of master node M1.

In one example, the method may also have the first node broadcasting one or more third messages at a third anticipated range distance (incrementally smaller range than the second anticipated range distance), and determining a location of one or more of the identified associated nodes that did not receive any of the third messages but received at least one of the second messages, where the location is approximately near the second anticipated range distance from the first node. Again, in the example of FIG. 13, by incrementally changing the power level down to P1 and broadcasting a third message at an anticipated range distance for that P1 level, the master node M1 can determine the location of node A (as node A received the second message but did not receive the third message) to be approximately near the anticipated range distance for P2 from the location of master node M1.

Additional examples of the method may also refine such determined locations by updating the location of the first node. In one example, the first node may be a mobile node. As such, refining may involve determining a current mobile location of the first node, and refining the location of the one or more of the identified associated nodes that did not receive any of the second messages but received at least one of the first messages based upon the current mobile location of the first node. Thus, as the first node moves and updates its own location (e.g., via GPS signals received by location circuitry 475 on a master node), the first node is able to leverage its own updated location and advantageously refine the location of nodes associated with it.

And, in some examples, the refined location of associated nodes may be transmitted to a server. This provides an update to the server, and aids in tracking and managing the location of nodes in the network. Again, referring back to the example of FIG. 13, master node M1 910a may take advantage of such a method for locating associated nodes, such as the locations of ID nodes A-E 920a-920e, and update server 100 with this new location data related to the current location of node M1 and any of the nodes associated with node M1.

Those skilled in the art will appreciate that this exemplary method as disclosed and explained above in various examples may be implemented on a node (e.g., master node 110a in FIG. 4, master node M1 910a in FIG. 13) running one or more parts of master control and management code 425 (e.g., the location aware/capture module). Such code may be stored on a non-transitory computer-readable medium, such as memory storage 415 on master node 110a. Thus, when executing code 425, the master node's processing unit 400 may be operative to perform operations or steps from the exemplary methods disclosed above and variations of that method.

In another example, a node apparatus is described in a wireless node network that uses location determination by association as described with reference to the steps related to the above-described method. As mentioned above, such as node apparatus may be implemented with a master node having a node processing unit, a node volatile memory, a node memory storage, and a first and second communication interface. Each of the memories and communication interfaces are coupled to the node processing unit. Further, the node memory storage maintains at least a program code section, association data, and location data and, at times, shipping information. The first communication interface provides a first communication path operatively coupling the node with a plurality of other nodes in the network, while the second communication interface provides a second communication path operatively and separately coupling the node with a server in the network.

In this example, the node processing unit is operative to transmit one or more first messages via the first communication interface at a first anticipated range distance, and identify which of the others nodes that are associated with the first node received at least one of the first messages. In one example, the node processing unit may be operative to access the association data in the node memory storage when identifying which of the nodes associated (e.g., passive, active, or both types of associations) with the first node received at least one of the first messages.

The first anticipated range distance may be an optimal transmission range for the first communication interface and, in a more detailed example, may be adjusted based upon context data (e.g., RF shielding inherent from the surrounding environment of the node). In yet another example, the first anticipated range distance and the second anticipated range distance may be adjusted based upon one or more types of context data related to how an RF output signal transmit from the first communication interface may be impeded by an environment of the node.

The node processing unit is also operative to transmit one or more second messages via the first communication interface at a second anticipate range distance (incrementally smaller than the first anticipated range distance) and determine a location of one or more of the identified associated nodes that did not receive any of the second messages but received at least one of the first messages. That location is between the first anticipate range distance from a known location of the node and the second anticipated range distance from the known location of the node. In a further example, the node processing unit may be operative to store the determined location in the node memory storage as part of the location data.

The node processing unit may also be operative to transmit one or more third messages via the first communication interface at a third anticipated range distance (incrementally smaller range than the second anticipated range distance) and determine a location of one or more of the identified associated nodes that did not receive any of the third messages but received at least one of the second messages, where the location is between the second anticipated range distance from the known location of the node and the third anticipated range distance from the known location of the node.

In another example, the node may be mobile and the node processing unit may be further operative to refine the location of the one or more of the identified associated nodes that did not receive the second message but received the first message by updating a location of the first node. In more detail, the node processing unit may be operative to determine a current mobile location of the first node (e.g., check with location circuitry onboard the node for valid GPS signals and a location lock based on such signals), and refine the location of the one or more of the identified associated nodes that did not receive any of the second messages but received at least one of the first messages based upon the current mobile location of the first node. The node processing unit may also be operative to transmit the refined location to the server over the second communication interface.

Location Determination Through ID Node Advertise

While FIG. 13 provides an example of location determination through master node advertising, FIG. 14 focuses on location determination through ID node advertising. In particular, FIG. 14 is a diagram illustrating an exemplary location determination using ID node advertise. In the illustrated example shown in FIG. 14, exemplary ID node F 920*f* is in an advertising mode but is without a known location. As with FIG. 13, FIG. 14 illustrates the exemplary different RF output power levels from ID node F 920*f* as concentric ranges 1405-1415 about ID node F 920*f*. Thus, ID node F 920*f* may broadcast at a maximum power P1, related to range 1405, but may control the RF output power level and dynamically change the RF output power level to P2 and broadcast at a smaller range 1410, or to P3 and broadcast to an even smaller range 1415. Master nodes M1-M3 910*a*-910*c* are disposed in various known locations relatively near ID node F 920*f*, which has an unknown location. As such, ID node F 920*f* may take advantage of the ability to adjust an RF characteristic, such as RF output signal power level, of its own short-range communication interface as part of how the system may determine location of ID node F through ID node advertising.

In the illustrated example, an RF output signal power level of ID node F 920*f* may be varied or dynamically adjusted via programmable settings (such as profile settings or parameters) related to operations of variable power short range communication interface 375. Additionally, while an actual communication range may vary with the surrounding environment, a maximum anticipated communication range of the ID node's transmitter at each power level is known assuming an optimal operating environment or no substantial RF shielding or interference. Thus, a particular power level setting for a broadcasting node is inherently associated with a corresponding anticipated range distance.

In an exemplary method of determining a nodes location using ID node advertising, the RF output signal power level may be varied across multiple power levels to improve location through master node association. In more detail, when the ID node F's variable power short range communication interface 375 is set to P1, its maximum output, ID node F 920*f* is seen by each of master nodes M1-3 910*a*-910*c*. The anticipated open air performance or range distance (optimal range, or range based upon analytics or historic measurements) of the radio in ID node F's variable power short range communication interface 375 at P1 power level may have been previously been found to be approximately 30 feet. Thus, without any examination of RSSI levels from the individual master nodes, the system knows ID Node F is within 30 feet of master nodes M1-M3.

Next, when the ID node F's variable power short range communication interface 375 is set to P2, a medium output level in this example, ID node F 920*f* is seen by master nodes M1 910*a* and M2 910*b*. The anticipated open air performance or range distance (optimal range, or range based upon analytics or historic measurements) of the radio in ID node F's variable power short range communication interface 375 at running at P2 power level is approximately 15 feet. Thus, without any examination of RSSI levels from the individual nodes, we know master nodes M1 910*a* and M2 910*b* are within 15 feet of ID node F 920*f* in this example. Furthermore, we know the master node no longer receiving the broadcasted RF signal from ID node F 920*f* (e.g., master node M3 910*c*) is somewhere within 30 feet of ID node F 920*f*, but probably more than 15 feet away from node F in this example.

And when ID node F's variable power short range communication interface 375 is set to P3, its minimum output level in this example, ID node F 920*f* is seen by only master node M2 910*b*. The anticipated open air performance or range distance (optimal range, or range based upon analytics or historic measurements) of the radio in ID node F's variable power short range communication interface 375 at P3 power level is approximately 5 feet. Thus, without any examination of RSSI levels from the master nodes, we know the location of ID node F 920*f* is within 5 feet of the known location of master node M2 910*b* in this example.

The ranging steps with respect to the changed RF characteristics of an advertising ID node, as discussed in the example above, may then be repeated for any of the identified nodes in order to building a more complete picture of the relative location of each node.

Furthermore, the timing between such ranging steps may vary dynamically depending upon whether the node is moving. Those skilled in the art will appreciate that when moving, a quicker flow through such ranging steps will help to provide better accuracy given the movement of nodes. Thus, the time interval between instructing a node to broadcast one or more messages at a particular power level and then instructing that node to broadcast one or more messages at a different power level may be desired to be shorter when the node is moving, which can be determined based upon context data. For example, the context data may indicate the node is within a node package an on a moving conveyor system. As such, the node is moving relative to fixed master nodes that may be positioned along the conveyor system. Thus, server may have the first node perform the ranging steps where power is varied in relative quick succession compared to a situation where the context data indicates the node is not moving or is substantially stationary.

An example of such a method for location determination using one or more associations of nodes in a wireless node network is described as follows, and explains a particular way to locate a node using associations and master node one or more master node advertising techniques. The example method begins by instructing a first of the nodes to broadcast one or more first messages at a first power level, the first power level being related to a first anticipated range distance. In one example, the first anticipated range distance may be an optimal range for the first of the nodes (e.g., a transmission range that assumes there are no obstructions and a clear signal path between nodes). In another example, the first anticipated range distance may be an optimal range for the first node adjusted based upon context data (e.g., data related to the surrounding RF environment of the first node).

Next, the method identifies which of the nodes associated with the first node have known locations. For example, this type of identification may be accomplished by reviewing association data that indicates which of the nodes are associated with the first node (e.g., via passive association, via active association, or via a combination of both), determining which of the nodes are associated with the first node based upon the reviewed association data, and identifying which of those associated nodes have known locations.

The method continues by determining which of the identified associated nodes received at least one of the first messages. Next, the method instructs the first node to broadcast one or more second messages at a second power level, where the second power level is related to a second anticipated range distance and the second power level incrementally smaller than the first power level. In a further example, the first anticipated range distance and the second anticipated range distance may be adjusted based upon one or more types of context data related to how an RF output signal from the first node may be impeded.

The method then determines which of the identified associated nodes received at least one of the second messages. The method concludes by determining a location of the first node to be at or between the first anticipated range distance and the second anticipated range distance from each of the identified associated nodes that did not receive at least one of the second messages but received at least one of the first messages.

As mentioned above, determining the node's location may be improved when accounting for movement. As such, an example of this method may instruct the first node to broadcast the one or more second messages within a time interval after instructing the first node to broadcast the one or more first messages. The time interval may be predetermined in some implementations, but also may be a dynamically set parameter in other implementations based upon context data related to the first node. In more detail, the time interval may be reduced from a prior value when the context data related to the first node indicates the first node is moving, but may be increased from a prior value when the context data related to the first node indicates the first node is substantially stationary.

In another example, the method may further include instructing the first node to broadcast one or more third messages at a third power level. Such a third power level is related to a third anticipated range distance and incrementally smaller range than the second anticipated range distance. Thereafter, the method may determining the location of the first node to be at or between the second anticipated range distance and the third anticipated range distance from each of the identified associated nodes that did not receive any of the third messages but received at least one of the second messages.

In another example, the method may comprise refining the location of the first node with an updated location of one or more of the identified associated nodes that did not receive at least one of the second messages but received at least one of the first messages. For example, if the first node is associated with a mobile master node, the location of the first node may be refined with an updated location of the mobile master node (which may be closer to the first node than previously determined).

In a further example, the first node in the operation of the method described above may not be self-aware of its own location. In another example, the first node may have been previously self-aware of the location of the first node but may no longer be self-aware of the location of the first node prior to broadcasting the one or more first messages. In more detail, the first node may no longer be self-aware of the location of the first node prior to broadcasting the first message because of a change in the environment surrounding the first node. Such a change in the environment may be, for example, when the first node has moved inside a structure (e.g., building, vehicle, aircraft, container, hallway, tunnel, etc.) that blocks location signals from being received by the first node.

Those skilled in the art will appreciate that such a method as disclosed and explained above in various examples may be implemented on a node (e.g., master node 110*a* in FIG. 4) running one or more parts of master control and management code 425 (e.g., the location aware/capture module) to control operations of an ID node (such as ID node F in FIG. 14) as part of location determination via ID node advertising. Such code may be stored on a non-transitory computer-readable medium, such as memory storage 415 on master node 110*a*. Thus, when executing code 425, the master node's processing unit 400 may be operative to perform operations or steps from the exemplary methods disclosed above and variations of that method.

From an apparatus perspective, an exemplary node apparatus in a wireless node network that uses location determination by association may comprises a node processing unit, node memory coupled to and used by the node processing unit (e.g., a node volatile memory and a node memory storage). The node memory storage maintains at least a program code section, association data, and location data. The node apparatus further includes a first communication interface that provides a first communication path coupled to the node processing unit and operatively coupling the node with a plurality of other nodes in the network. For example, the master node 110*a* illustrated in FIG. 4 includes such types of operational structure.

The node processing unit (e.g., processing unit 400 of master node 110*a*), when executing at least the program code section resident in the node volatile memory, is operative to perform specific functions or steps. In particular, the node processing unit is operative to communicate an instruction to a first of the other nodes (e.g., an ID node or master node temporarily operating as an ID node) via the first communication interface to cause the first other node to broadcast one or more first messages at a first power level, where the first power level is related to a first anticipated range distance.

The first anticipated range distance may be an optimal range for the first of the nodes and, in more detail, an optimal range for the first of the nodes adjusted based upon context data. In even more detail, the first anticipated range distance and the second anticipated range distance may be adjusted based upon one or more types of context data related to how an RF output signal broadcast from the first node may be impeded.

The node processing unit is also operative to identify which of the nodes associated with the first node have known locations. To do this, the node processing unit may access and review association data stored on the node memory storage (e.g., data indicating what nodes are passively or actively associated with the first other node), may determine which of the remaining other nodes are associated with the first other node based upon the reviewed association data, and may identify which of the remaining other nodes determined to be associated with the first other node have known locations.

The node processing unit is also operative to determine which of the identified associated nodes received at least one of the first messages, and to communicate another instruction via the first communication interface to the first node to cause the first node to broadcast one or more second messages at a second power level, where the second power level being is to a second anticipated range distance and incrementally smaller than the first power level.

Finally, the node processing unit is operative to determine which of the identified associated nodes received at least one of the second messages, and then determine a location of the first node to be at or between the first anticipated range distance and the second anticipated range distance from each of the identified associated nodes that did not receive at least one of the second messages but received at least one of the first messages.

In a further example, the node processing unit may be operative to communicate a third instruction via the first communication interface to the first node to cause the first node to broadcast one or more third messages at a third power level. The third power level is related to a third anticipated range distance and incrementally smaller range than the second anticipated range distance. Additionally, the node processing unit may then be operative to determine the location of the first node to be at or between the second anticipated range distance and the third anticipated range distance from each of the identified associated nodes that did not receive any of the third messages but received at least one of the second messages.

In still another example, the node processing unit is able to account for movement of the first node with a time interval between instructions sent to the first node. In particular, the node processing unit may be further operative to communicate another instruction via the first communication interface to the first node to broadcast the second messages within a time interval after instructing the first node to broadcast the first messages. In a more detailed example, the time interval may be dynamically set based upon context data related to the first node. In even more detail, the time interval may be programmatically reduced from a prior value when the context data related to the first node indicates the first node is moving (e.g., the first node is on a moving conveyor system) and/or the time value of the interval may be increased from a prior value when the context data related to the first node indicates the first node is substantially stationary (e.g., the node is within a node package recently placed in a storage area).

The node processing unit, in a further example, may be operative to refine the location of the first other node with an updated location of one or more of the identified associated nodes that did not receive at least one of the second messages but received at least one of the first messages, and cause a second communication interface (e.g., medium/long range communication interface 485 coupled to processing unit 400) to transmit the refined location to the server.

From a server perspective, another exemplary method for location determination using one or more associations of nodes in a wireless node network is explained as follows. Those skilled in the art will appreciate that while a server may operate to implement the steps as laid out in the method discussed above, this additional method provides more details as to how a server processing unit (such as processing unit 500 running server code 525) may implement such a method at that level of the network. In this more detailed example, the server is communicating directly with a master node (e.g., a first node) to direct and control how the master node interacts with and causes operations to be undertaken on the ID node (e.g., a second node). Thus, this method more precisely calls for communicating with a first node via a communication interface to cause a second node in the network to broadcast one or more first messages at a first power level at the request of the first node, where the first power level is related to and corresponds with a first anticipated range distance. Likewise, this method more precisely calls for communicating with the first node via the communication interface to cause the second node to broadcast one or more second messages at a second power level at the request of the first node, the second power level being related to a second anticipated range distance and incrementally smaller than the first power level. The other steps from the additional method are similar to those explained above relative to the previously-described method, and that the similar principles will apply to this additional method.

Those skilled in the art will appreciate that this additional method as disclosed and explained above in various examples may be implemented on a server (e.g., server 100 in FIG. 5) running one or more parts of server control and management code 525 to direct a master node to control operations of an ID node (such as ID node F in FIG. 14) as part of location determination via ID node advertising. Such code may be stored on a non-transitory computer-readable medium, such as memory storage 515 on server 100. Thus, when executing code 525, the server's processing unit 500 may be operative to perform operations or steps from the exemplary methods disclosed above, and variations of that method.

And similar to the node apparatus described above, one example includes an exemplary server apparatus in a wireless node network that uses location determination by association. The exemplary server apparatus generally comprises a server processing unit, server memory coupled to and used by the server processing unit (e.g., a server volatile memory and a server memory storage). The server memory storage maintains at least a program code section, association data, and location data. The server apparatus further includes a communication interface coupled to the server processing unit and that provides access to a communication path operatively coupling the server with at least a first node in the network.

The exemplary server processing unit, when executing at least the program code section resident in the server volatile memory, is operative to perform specific functions or steps. In particular, the server processing unit is operative to communicate with the first node via the communication interface to cause a second node in the network to broadcast one or more first messages at a first power level at the request of the first node, where the first power level is related to a first anticipated range distance; identify which of the remaining nodes in the network associated with the second node have known locations; determine which of the identified associated nodes received at least one of the first messages; communicate with the first node via the communication interface to cause the second node to broadcast one or more second messages at a second power level at the request of the first node, where the second power level is related to a second anticipated range distance and incrementally smaller than the first power level; determine which of the identified associated nodes received at least one of the second messages; and determine a location of the second node to be at or between the first anticipated range distance and the second anticipated range distance from each of the identified associated nodes that did not receive any of the second messages but received at least one of the first messages. And in a further example, the server apparatus' processing unit may be further operative to store the determined location in the server memory storage as part of the location data.

In another example, the server apparatus' processing unit may be operative to communicate with the first node via the communication interface to cause the second node to broadcast the one or more second messages within a time interval after communicating with the first node to cause the second node to broadcast the one or more first messages. As previously mentioned, this type of time interval may dynamically set based upon context data related to the second node. Context data may also be used as set forth above with respect to the node apparatus but applied here to the second node—such was where the first anticipated range distance is the optimal range for the second node adjusted based upon context data.

Master Node Location Determination Through Advertise

In another example, a master node typically is self-locating with its own location circuitry but may no longer know its location under the current environmental conditions. For example, such a situation may occur when a master node determines its current location via GPS location circuitry 475, but the master node finds itself without access to an adequate number of GPS signals (e.g., it cannot determine a location due to the lack of a sufficient number of GPS signals from diverse GPS satellites). Such a situation may happen when the master node moves indoors is proximate to a structure that interferes with the location signals.

In an exemplary example where a master node attempts to determine its own location via advertising techniques, the master node may detect a loss of location confidence (e.g., upon a loss of detected GPS signals; upon detecting a separate signal to processing unit 400 indicating the master node's location is unknown; when processing unit 400 senses movement (e.g., via accelerometers (not shown) or the like) but cannot confirm that the location circuitry 475 is providing updated location information for the node, etc.). In other words, the master node becomes aware that it no longer has a known location.

Next, the master node responds by beginning to broadcast one or more advertising messages in a similar way as ID node F 920f is described as doing with respect to FIG. 14. This is done so that the master node having an unknown location can advantageously leverage off the known locations of nearby other nodes. As such, an example may allow a type of leveraged chaining effect whereby known locations of particular types of nodes may be used to extend location information to other nodes that do not know their locations (e.g., ID nodes) or nodes that have detected a loss of location confidence (e.g., master nodes). Thus, such an example may be used to determine an indoor location of a master node (including equipment equipped with master node functionality) in cases where signals for the conventional onboard location circuitry 475 are not available.

In the exemplary method, the method may be such that the first node is not self-aware of the location of the first node. This may happen when the first node (e.g., an ID node) is actually a master node that was previously self-aware of its own location (e.g., via received GPS signals) but is no longer self-aware of its location (e.g., when the GPS signals can no longer be received), which has the master node changing operation to operate as an ID node prior to broadcasting the first message. In other words, the master node may no longer be self-aware of its location and begin operating as an ID node for purposes of location determination prior to broadcasting the first message because of a change in the environment surrounding the master node, such as when the master node has moved inside a structure that blocks location signals from being received by the master node. Thus, an example may advantageously allow a node to adaptively alter operations when moving from a clear outdoor environment to an indoor environment. And a server may interact with such a master node while that master node is operating, for location purposes, as an ID node, temporarily.

Location with Improved RSSI Measurements

In another example, a signal strength measurement between two or more nodes may be used to determine the proximity of the nodes by using one or more improvements to conventional RSSI measurements. In conventional RSSI measurements, such as with Bluetooth 4.0, those skilled in the art will appreciate that adaptive frequency hopping as part of spread spectrum techniques may cause undesirably cause the signal strength to fluctuate. In other words, the advantage of using frequency hopping and spread spectrum for security and avoidance of interference may have a negative impact on using such signals for stable proximity-based location determinations. Thus, it may be desired to emphasize stability of a signal and limits to fluctuation for purposes of location determination.

In one example, a type of improvement for RSSI measurements may include reducing the number of channels and/or a corresponding frequency range in use during advertising from nodes. For example, a node may have processing unit 300/400 adaptively control variable power short range communication interface 375/480 to reduce the number of channels and/or the frequency range used during node advertising. Such a dynamic change may be implemented, in some examples, by altering the content of a particular type of profile data 330/430, such as an RF profile data that effectively defines RF characteristics of a node (e.g., frequency, power level, duty cycle, channel numbers, channel spacing, alternative fluctuation modes, etc.). In one further example, a first fluctuation mode may be defined that provides a default or more standard communication protocol, such as the conventional frequency hopping, spread spectrum, and channel allocations for Bluetooth® communications. Other alternative modes (one or more) may be defined that alter one or more RF characteristics to provide increasingly more stable and less fluctuations of the RF output signal from a node. Thus, a node may be dynamically placed into one or more modes regarding such RF characteristics that increasingly emphasize stability of the node's RF output signal and limits fluctuation for purposes of enhanced location determination using RSSI measurements.

In another example, a type of improvement for RSSI measurements may include ensuring visibility to and advantageously managing automatic gain control (AGC) circuitry (not shown) that may cause the RF output signal to vary for a node. For example, a node may include a type of AGC circuitry as part of variable power short range communication interface 375/480. This type of AGC circuitry may allow node processing unit 300/400 or other logic circuitry that is part of variable power short range communication interface 375/480 to limit fluctuations under certain conditions (e.g., when attempting to use RSSI location determination techniques). In this example, different AGC circuitry settings may be defined in exemplary RF profile data that effectively defines RF characteristics of a node (e.g., frequency, power level, duty cycle, channel numbers, channel spacing, alternative fluctuation modes, etc.). This is yet another example of how a node may be dynamically placed into one or more modes regarding such RF characteristics (including AGC circuitry settings) that increasingly emphasize stability of the node's RF output signal and limits fluctuation for purposes of enhanced location determination using RSSI measurements.

Location with Adjustments for Environmental Factors in RF Signal Quality

In general, those skilled in the art will appreciate that environmental factors may cause a communication signal, such as an RF signal, to fluctuate or be transmitted and received in a manner that undesirably varies depending upon a signal path environment. Passive physical interference factors (e.g., forms of electronic signal shielding) may be substantially close and cause drops in signal strength across the output ranges of the nodes. Additionally, active radio interference factors may vary across the RF output ranges of the nodes depending upon other active devices in the reception vicinity. Thus, the proximate environment of a node may have a multitude of adverse factors that impact communications and, as a result, the ability to locate the node.

In one example, making location determinations may be enhanced by a data analytics type of approach that may adjust and account for different RF environmental factors for a similar type of node in a similar type of situation. For example, the quality of the RF output signal of a particular type of node and the corresponding physical range of that signal to a receiver of known sensitivity may be determined for a given environment. In this example, the system defines a maximum range of that signal based on a predetermined condition, such as open-air connectivity. This may assume an environment with no signal degradation due to interference or physical shielding. However, both interference and physical shielding may diminish the range of the RF output signal of a node. In a dynamically adaptive and learning manner, the system may collect information on how a particular type of node may operate in a particular environment under certain settings (e.g., reported signal strengths and corresponding settings for RF output signal power levels). This analysis of a similar environment may be repeated. In other words, through such data analytics of an anticipated environment to be faced by a similar node, signal loss information can be generated and applied as a type of context data (i.e., RF data) for a node in a similar environment to refine location determination. Thus, an exemplary example may refine location determinations with adaptive signal loss characteristics based on a contextual appreciation of an anticipated environment (e.g., physical shielding such as packaging, package contents, proximate package, proximate package contents, and physical infrastructure causing signal variance) without requiring a calibration phase.

And advantageously combining those data points with $3^{rd}$ party data describing the physical environment, in which the node was located in at that time, may refine location even further. Such information may be used as RF data (a type of context data) in future efforts to manage and locate a similar type of node anticipated to be in a similar environment.

In more detail, in an example that refines a location determination based upon context and data analytics to adjust for known RF impediments, the maximum physical range of a node's RF output signal relative to a receiver of known RF sensitivity is determined. In one example, this first range value may be referred to as a theoretical or nominal open-air range of a similar type transmitter-receiver node pair in a similar environment but with substantially no physical shielding or signal interference negatively impacting the signal range. A second range value, which may be considered an actual RF range value, may be the observed range of the signal in a similar environment but where there are contextual factors reducing the communication range, including physical shielding due to factors like packaging, package contents, proximate package, proximate package contents, physical infrastructure, interference from other radio sources, or shipper specific information such as vehicle or facility layout information. Through access to prior data analysis of the differing range values and with knowledge of the operational environment of the transmitting node was in (e.g., a similar environment to the proximate environment of the node), a refined location may be determined using an approximation of an actual RF output range that intelligently adjusts what may be anticipated to be the RF environment of the node. In other words, by knowing the appropriate contextual environment related to a node (such as signal degradation information on how a similar node operates in a similar environment), an improved location determination may be made to make intelligent yet efficient adjustments (such as communication distance adjustments) that provide a refined location of the node.

In one example, such as the example shown in FIG. 2, master node 110b is outside of a container (such as a Uniform Load Device (ULD) container 210 known to be used for transporting groups of items on aircraft) that has an ID node inside the container. A first or theoretical range value between master node 110b and ID node 120b may be determined to be 10 feet at a specific RF output power level when the package (and related ID node) may be known to be less than 10 feet away from the scanning node (e.g., master node 110b). A second range value at similar distances with similar types of nodes, but with incident RF signal loss as a result of communicating through the wall of the container 210, may be between 4 and 5 feet. If context data, such as $3^{rd}$ party information or scan data, indicates the transmitting node is within the ULD container 210, the system would expect the transmission range to be limited according to the data analytics associated with this known RF impediment (e.g., characteristics for transmitting through ULD container 210), thus reducing the possible scanning nodes that may see the broadcasting node within the ULD container, or require the transmitting node to increase its RF output power to be heard.

Related to such a technique, an exemplary method for location determination of a first node in a wireless node network based on context data is described as follows. Such a method begins with a network device (such as a master node or server) accessing a first type of the context data related to a proximate environment of the first node. The first type of context data comprises signal degradation information on how a second node would operate in a similar environment to the proximate environment of the first node when the second node is a similar type as the first node. Thus, rather than calibrating with an actual measurement relative to the current proximate environment of the first node, the signal degradation information provides compensation information on what may be generally anticipated in a more general proximate environment based on how a similar type of node may operate in a similar environment. As the similar environment of the similar node is generally an approximation for what is anticipated to be the proximate environment of the first node, this advantageously avoids the need for an actual calibration of the proximate environment.

In one example, the signal degradation information may be based upon a difference in how the second node communicates when exposed to an adverse communication environment (such as a similar environment to the proximate environment of the first node) compared to how the second node would communicates when exposed to a nominal communication environment (such as an environment that is unencumbered by shielding and interference factors). Those skilled in the art will appreciate that a nominal communication environment need not be perfectly clear of all influences that shield or interfere with communications. The types and aspects of signal degradation information may vary depending on a wide variety of factors. In one example, the signal degradation information may be related to at least one of shielding and interference. Thus, signal degradation information may include both passive and active factors that impact the communication environment.

In another example, the signal degradation environment may be based upon a degraded operation of the second node when the similar environment is an adverse communication environment. In more detail, the signal degradation information may be based upon a difference in how the second node communicates when exposed to the adverse communication environment compared to how the second node communicates when exposed to a substantially normal communication environment, such as an open air environment.

In still another example, signal degradation information may relate to at least shipment data for one or more items being shipped (e.g., currently shipped or shipped in the past) and located in the proximate environment of the first node.

For instance, a package near the first node may include metallic materials that may impede or block RF signals and the signal degradation information may relate to such information about close packages being shipped near the first node. In another example, the signal degradation information may relate to at least layout data for one or more physical structures in the proximate environment of the first node. In more detail, the layout data may be for one or more physical structures (e.g., walls, machinery, enclosures, and conveyances) in the proximate environment of the node near a predicted path for the first node. In yet another example, the signal degradation information relates to at least historic data on one or more analyzed prior operations of the second node.

Next, the network device, such as a master node or server, may adjust an anticipated communication distance related to the first node based upon on the first type of the context data. In one example, the anticipated communication distance may be a theoretical broadcast distance based upon parameters of the device's radio. Such an anticipated communication distance is known as it is an estimate of the radio's range. In one example, the adjusted communication distance comprises an anticipated reduced range distance for a transmission from the first node. In another example, the adjusted communication distance comprises an anticipated reduced receiver sensitivity distance for the first node.

In yet another example, adjusting the communication distance may be accomplished by adaptively adjusting, by the network device, the communication distance based upon the signal degradation information and a second type of the context data. In other words, the communication distance may be adjusted based upon signal degradation information considered along with other types of context data, such as how the first node is being moved (such as an anticipated movement of the first node along a predicted transit path for the first node) or a density of other nodes near the first node.

Next, the network device determines the location of the first node based upon the adjusted communication distance. In a further example, the method may also update the adjusted communication distance by the network device based upon movement of the first node, and may refine the location of the first node with an updated adjusted communication distance. This may happen with the first node is a mobile master node capable of self-determining its own location.

Those skilled in the art will appreciate that such a method as disclosed and explained above in various examples may be implemented on a network device (e.g., exemplary master node 110a in FIG. 4 or server 100 in FIG. 5) running one or more parts of their respective control and management code to perform steps of method 3200 as described above. Such code may be stored on a non-transitory computer-readable medium, such as memory storage 415 on master node 110a or memory storage 515 on server 100. Thus, when executing such code, the respective network device's processing unit may be operative to perform operations or steps from the exemplary methods disclosed above and variations of that method.

In more detail, an exemplary network device apparatus for determining a location of a first node in a wireless node network based on context data, the exemplary network device may include a processing unit, a volatile memory coupled to the processing unit, and a memory storage coupled to the processing unit. The exemplary network device further includes a communication interface coupled to the processing unit and that provides a communication path operatively coupling the network device with the first node in the network.

The memory storage for the device maintains at least a program code section and context data having at least signal degradation information. Such signal degradation information, as a type of context data, is information on how a second node would operate in a similar environment to a proximate environment of the first node when the second node is a similar type as the first node. Examples of signal degradation information may include those discussed above.

When executing at least the program code section when resident in the volatile memory, the processing unit of the network device is operative to perform the method steps noted and described above. In more detail, the processing unit is operative to at least connect with the memory storage to access the signal degradation information, adjust a communication distance (if needed) related to the first node based upon on the signal degradation information, determine the location of the first node based upon the adjusted communication distance, and store the determined location of the first node as location data on the memory storage.

Adjusting the communication distance by the processing unit may be accomplished as described above. And as mentioned above, the processing unit may be further operative to adaptively adjust the communication distance where other types of context data are also considered, such as movement and anticipated node movement as detailed out above.

In a further example, the network device may be a mobile master node that includes location circuitry (such as GPS circuitry 475 of exemplary master node 110a shown in FIG. 4). In this example, the processing of the network device may be further operative to determine a location of the network device based upon an output signal from the location circuitry received by the processing unit, and determine the location of the first node based upon the adjusted communication distance and the location of the network device. As such, the first type of the context data related to the proximate environment of the first node is based upon the determined location of the first node.

Those skilled in the art will also appreciate that in some operational environments, the signal degradation information may not require any adjustment to the communication distance in an example. However, in other environments (e.g., adverse RF environments), the signal degradation information may provide a basis for adjusting the communication distance in the example, even if not performed every time. Thus, an adjustment to the communication distance may not be needed in all proximate environments of the first node but may be performed, if needed, based on the proximate environment of the first node. It is the ability of an example to adjust this communication distance when needed and if needed that advantageously allows for locating the first node with more accuracy.

Location Through Triangulation

Figure 15:
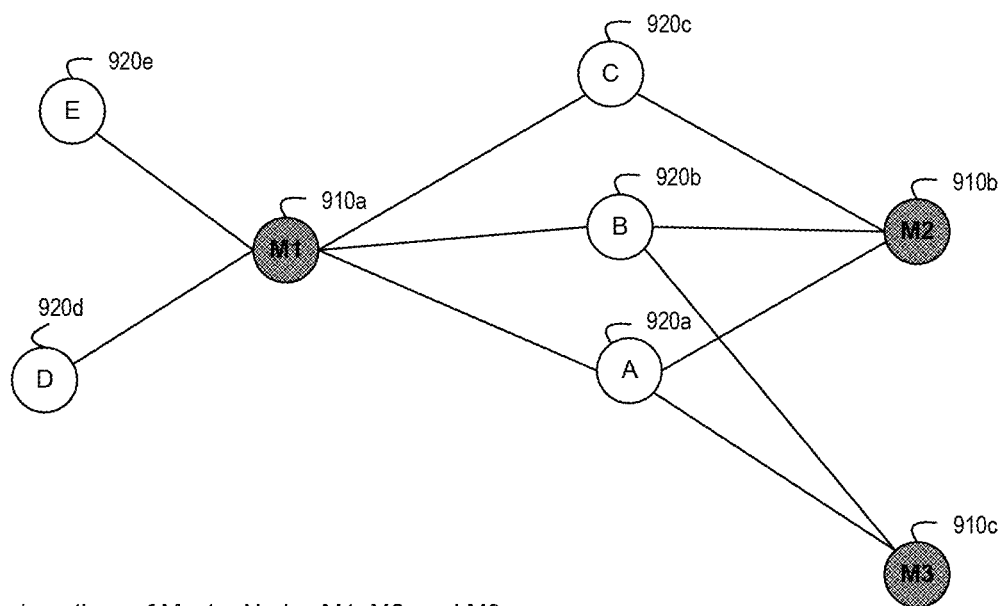
FIG. 15 is a diagram illustrating an exemplary location determination through triangulation as known in the art.

In some examples, various methods for determining a node's location may rely upon, at least in part, triangulation techniques. In other words, as the wireless node network collects data on receiver-transmitter pairs, other methods for determining location of the individual nodes that utilize triangulation, at least in part, may become possible. FIG. 15 is a diagram illustrating an exemplary location determination through triangulation within a wireless node network. Referring now to the illustrated example of FIG. 15, three exemplary master nodes M1-M3 910a-910c are shown with each master node having a known location. Exemplary ID nodes A-E 920a-920e are also shown where they are at least in communication range of one or more of exemplary master nodes MA-M3 910a-910c.

In this illustrated example, the master nodes M1-M3 may detect and collect advertising messages from ID nodes A-E at varying and known power levels. The captured information is forwarded by the master nodes M1-M3 to the backend server 100, where location determinations may be made. For example, factors like RSSI and visibility of each node at each power level may be used to determine, with a higher degree of accuracy, the location of nodes where sufficient information is available.

For an exemplary system to triangulate a node, three nodes with known locations must have seen the broadcasting node. In this example, two advertising ID nodes, A 920a and B 920b, were seen by the three nodes having known locations (master nodes M1-M3 910a-910c). Based upon the captured information, the locations of ID node A 920a and ID node B 920b are calculated.

Chaining Triangulation

Figure 16:
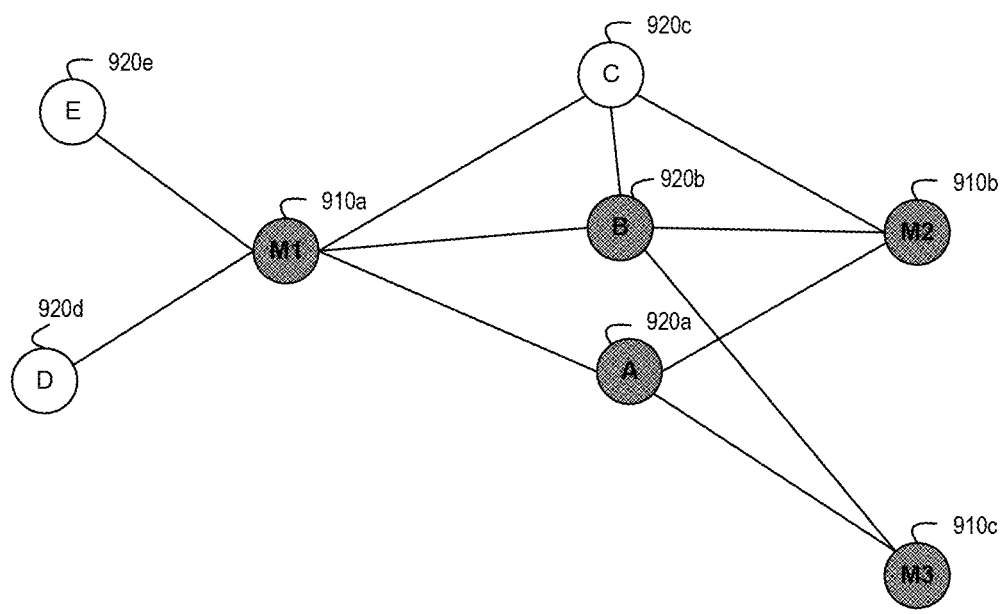
FIG. 16 is a diagram illustrating an exemplary location determination through chaining triangulation as known in the art.

In another example, a node with an inferred location may be used with triangulation techniques to determine a location of another node in a wireless node network. FIG. 16 is a diagram illustrating an exemplary location determination through chaining triangulation. The locations of ID nodes A 920a and B 920c have been determined by triangulating across master nodes M1-M3, as illustrated in the exemplary example shown in FIG. 15. However, as illustrated in FIG. 16, the location of ID node C 920c may also be determined according to an example.

For example, an exemplary method of determining a node's location through chaining triangulation begins with determining the calculated location of ID node B 920b (as explained with reference to FIG. 15). Next, a node closer to ID node B 920b may be used to get the missing third signal point needed for triangulation. This may be accomplished by placing ID node B 920b in a query (scan) mode such that it listens for a message from ID node C 902c. ID node C is instructed to advertise, thus providing a signal that may be captured by ID node B. After capturing the signal profile of C, ID node B may communicate or share the captured information and forward it along to the backend server 100 through either of the master nodes M1 or M2. The resulting location determination of ID node C 920c may have a higher level of position error due to it being partially based on a calculated reference (e.g., the location of ID node B), but the leveraged location determination of ID node C 920c may be sufficiently accurate (or be an actionable location) that useful information may be gleaned about ID node C 920c. For example, a leveraged or chained location determination of ID node C may indicate, with the help of context data, that nodes M1, M2, and ID node B are all close enough to ID node C that ID node C is determined to be within the same container nodes M1, M2, and ID node B.

Location Through Proximity to Triangulation (LP2T)

In an example where chaining triangulation may determine location through proximity to triangulation (LP2T), a starting point may be determining the relative location of an ID node to a master node based on the proximity method, as explained above. However, when the relative location of the ID node has been determined, a more accurate or refined location of the ID node may be determined based upon the location of all master nodes that can capture the RF output signal broadcast from the ID node, and then triangulating based on observed signal strength of the ID node. In this example, the proximity-based location is used as an input in the triangulation calculation to estimate likely signal deterioration historically observed between a node at the proximity-determined location and scanning master nodes. In a further example, by taking into account historic data on patterns of signal deterioration, a more accurate triangulation may be possible, leading to a more accurate location determination.

Related to this additional node location technique, an exemplary method for determining a node location using chaining triangulation for one of a plurality of nodes in a wireless node network having a server is described as follows. Such an exemplary node location need not be precise or exacting, but can be sufficiently accurate without absolutes. Such an exemplary method begins with the server receiving a location of a first of the nodes from the first node. Next, the server receives a location of a second of the nodes from the second node. For example, with reference to the example shown in FIG. 16, master nodes M1 910a and M2 910b may transmit their respective location coordinates from their respective onboard location circuitry to the server so that the server has the current locations of these two master nodes.

Next, the server infers a location of a third of the nodes. For instance, in the example illustrated in FIG. 16, the server may infer the location of ID node B 920b. In one example, inferring may comprise having the server determine a proximate-based location of the third node relative to another of the nodes having a known location, such that the proximate-based location operates as the inferred location of the third node.

In another example, inferring the location of the third node may comprise having the server determine a relative location of the third node to the first node (as the node having a known location) or to the second node (as another node having a known location). The method may also, in another example, include having the server adjust the inferred location of the third node to determine a refined location of the third node based upon third node context data related to the inferred location of the third node.

Next, the method concludes with the server triangulating the location of the one node based upon determined distances to each of the first and second nodes, and a determined distance of the one node to the inferred location of the third nodes.

In a more detailed example, the method may triangulate the location of the one node by accessing first node context data related to a contextual environment near the first node and second node context data related a contextual environment near the second node. Such contextual environments may include an environment of being on a conveyor system, or within a particular facility, or next to materials that may degrade or shield signals being received by the one node. Next, the more detailed triangulating may have the server adjust the determined distance of the one node to the location of the first node based upon the first node context data to provide a refined distance of the one node to the location of the of the first node. Then, the server may triangulate the location of the one node based upon the adjusted determined distance of the one node to the location of the first node, the adjusted determined distance of the one node to the location of second node, and a determined distance of the one node to the refined location of the third node.

In a further example, this method may also have the server transmitting an instruction so as to cause the server to transmit an instruction to cause the one node to broadcast a plurality of advertising signals over a period of time. In such an example, the determined distance of the one node to the location of the first node may be based upon captured signals from the one node by the first node over the period of time and reported to the server by the first node. In another example, the determined distance of the one node to the location of the second node may be based upon captured signals from the one node by the second node and reported to the server by the second node.

In still another example, the server may transmit an instruction to cause the one node to broadcast a plurality of advertising signals at different power levels. In such an example, the determined distance of the one node to the location of the first node may be based upon captured signals from the one node by the first node and reported to the server by the first node. In another example, the determined distance of the one node to the location of the second node may be based upon captured signals from the one node by the second node and reported to the server by the second node.

In yet another example, this method may also have the server transmitting the location information out to a requesting entity (e.g., another node, a user access device, etc.) upon receipt of a request for a location of the one node from that entity.

Those skilled in the art will appreciate that this method as disclosed and explained above in various examples may be implemented on a server (such as exemplary server 100 as illustrated in FIG. 5) running one or more parts of a control and management code (such as an code 525) to implement any of the above described functionality. Such code may be stored on a non-transitory computer-readable medium (such as memory storage 515 in an exemplary server). Thus, when executing such code, a processing unit of the server (such as unit 500) may be operative to perform operations or steps from the exemplary methods disclosed above, including variations of that method.

A server apparatus is also described in an example for determining a location using chaining triangulation for one of a plurality of nodes in a wireless node network. The server apparatus generally comprises a server processing unit, a server volatile memory, a server memory storage, and a communication interface. The server volatile memory, server memory storage, and communication interface are each configured in the apparatus as coupled to the server processing unit. The server memory storage maintains at least a program code section and location data related to nodes in the network. In some examples, the server memory storage may also maintain context data, such as first node context data and second node context data. The communication interface provides a communication path operatively coupling the server with nodes in the network, such as a first and second node.

The server processing unit, when executing at least the program code section resident in the server volatile memory, is operative to perform various functions, such as the functions described in the steps above related to method 3300. In particular, the server processing unit is operative to receive a request over the communication interface for the location of the one node. Based on the request, the server processing unit is then operative to receive the respective locations of the first and second nodes, and store the locations as part of the location data kept on the server memory storage. The server processing unit is further operative to infer a location of a third of the nodes, and store the inferred location of the third node as part of the location data kept on the server memory storage. The server processing unit then is operative to triangulate the location of the one node based upon a determined distance of the one node to the location of the first node, a determined distance of the one node to the location of second node, and a determined distance of the one node to the inferred location of the third node. And finally, the server processing unit is operative to transmit the location information to the requesting entity over the communication interface in response to the request.

In one example, the server processing unit may be further operative to infer the location of the third of the nodes by being operative to determine a proximate-based location of the third node relative to another of the nodes having a known location, where the proximate-based location operates as the inferred location of the third node.

In another example, the server processing unit may be further operative to transmit an instruction over the communication interface to cause the one node to broadcast a plurality of advertising signals over a period of time. In this example, the determined distance of the one node to the location of the first node may be based upon captured signals from the one node by the first node over the period of time and reported to the server by the first node. Alternatively, the determined distance of the one node to the location of the second node may be based upon captured signals from the one node by the second node and reported to the server by the second node.

In another example, the server processing unit may be further operative to transmit an instruction over the communication interface to cause the one node to broadcast a plurality of advertising signals at different power levels. In such an example, the determined distance of the one node to the location of the first node may be based upon captured signals from the one node by the first node and reported to the server by the first node. Alternatively, the determined distance of the one node to the location of the second node may be based upon captured signals from the one node by the second node and reported to the server by the second node.

In yet another example, the server processing unit may be further operative to infer the location of the third node by being operative to determine a relative location of the third node to the first node or, alternatively, to the second node.

In still another example, context data may be relied upon to refine locations. More specifically, the server processing unit may be further operative to adjust the inferred location of the third node to determine a refined location of the third node based upon third node context data related to the inferred location of the third node.

In a more detailed example, the server memory storage may further maintains context data, and the server processing unit may be further operative to triangulate by being operative to access first node context data as part of the context data maintained on the server memory storage, where the first node context data is related to a contextual environment near the first node. Likewise, the server processing unit may be further operative to access second node context data as part of the context data maintained on the server memory storage, where the second node context data is related a contextual environment near the second node. The server processing unit may then be operative to adjust the determined distance of the one node to the location of the first node based upon the first node context data to provide a refined distance of the one node to the location of the of the first node. As such, the server processing unit may be operative to triangulate the location of the one node based upon the adjusted determined distance of the one node to the location of the first node, the adjusted determined distance of the one node to the location of second node, and a determined distance of the one node to the refined location of the third node.

Combined Methods for Determining Node Location

In light of the examples explained above for locating a node (such as a node-based control element deployed in a modular component of an exemplary MALVT bot apparatus or a node-based mobile wireless device or a node-based control element for actuating a door, elevator, object articulation system, and the like), one skilled in the art will appreciate that a further example expressly contemplates using more than one of the above-described location determination techniques when determining a refined location of a node in a wireless node network. For example, such combination examples may apply an ordered or prioritized approach whereby a first location technique is applied to generate first location information regarding the location of a node in the wireless network. Thereafter, a second location technique may be selected from a hierarchy or prioritized set of techniques (some of which may work better in certain circumstances and be chosen or dynamically prioritized based upon the contextual environment), and applied to generate second location information regarding the location of the node or refining the location of the node. Other examples may apply additional location techniques to generate further refined location information.

In an example, the information in the exemplary hierarchy generally identifies which technique may be preferred to be used initially as well as a ranked grouping or listing of when to apply other location techniques. Such information in the exemplary hierarchy may be fixed (based upon successful historic data and experience) or be dynamically altered over time as nodes may move relative to each other and, for example, based upon context data that provides more information relative to the a current or anticipated contextual environment.

MALVT Apparatus, Components & Systems

In light of the above-described wireless node technology that may be used as building blocks for control elements within implementations of different embodiments involving modular autonomous logistics bots, assemblies, components, vehicles, and systems described herein, the following provides further details on embodiments of an exemplary MALVT bot apparatus including respective modular components of such an apparatus and including embodiments of a modular assembly of such compatible components that may be assembled to form an exemplary MALVT bot apparatus for use in one or more particular logistics operations (e.g., delivery of an item/object, pickup of an item/object).

In general, those skilled in the art will appreciate that an exemplary MALVT bot apparatus is a type of transport vehicle that may be implemented to operate on multiple types of terrain, such as on and off roadways, navigating different types of pathways, corridors, and transit conduits indoors as well as outdoors and operating within and outside of different types of delivery vehicles. The high-level modular design of an exemplary MALVT bot apparatus, as an individual component as wells as part of an assembled system (whether pre-assembled for immediate dispatch or whether assembled on demand in response to a dispatch command), will facilitate interoperability for different exemplary use case scenarios (e.g., such as last-mile delivery) and allow for more efficient storage and deployment of fleets of exemplary MALVT bot apparatus devices as explained in more detail below. Using novel modular architecture principles in various embodiments also allows for taking advantage of rapid hardware and software developments in the foundational technologies used in such a process, an apparatus or a system, including but not limited to self-driving technology, long/short range wireless communications, Artificial Intelligence (AI), high-resolution mapping, context & location sensors, and electric vehicle technology.

In more detail, some exemplary novel, innovative, and advantageous aspects and features of an enhanced and improved autonomous transport system and methods that use elements of the same include, for example, the following:

Modular design and interoperability of components, including a smart Mobile Autonomy Module (MAM) or "Hat" to provide sensing and control for the exemplary MALTV bot apparatus. Such modularity and use of inter-module locking mechanisms may enhance and improve how to minimize risk of injury as well.

Ability of an exemplary MALTV bot apparatus to provide "stand-up" and "tilting" functionality, which could support unassisted object delivery. Such an object may generally be referred to an item being shipped, but may be a package, a group of packages, a palletized group of packages, an unwrapped item, and the like.

Ability to utilize different components of an exemplary MALTV bot apparatus independently, such as the Mobility Base (MB), to provide robotic assistance solutions to existing couriers for dense metropolitan delivery areas. Additionally, MBs may be grouped using a larger connecting platform for transporting larger shipments.

Ability to utilize and interface with a hierarchical Internet-of-Things (IoT) type of wireless node network (see TRON Network Reference Information), such as a TRON network including ID nodes, ULD nodes and the AI engine. Interfacing with TRON technology devices and systems may provide contextual awareness of an object in shipment, provide granular navigation, and manage authentication of various wireless devices that interoperate for robotic object delivery.

End-to-end integration with other existing systems, including fleet management systems, dispatch and operations, and human monitoring and decision support systems for different exemplary MALTV bot apparatus while engaged and deployed in the operational environments (i.e., when does an exemplary MALTV bot apparatus need to be deployed instead of a human courier?).

The description that follows includes a general glossary section of terms and acronyms used within the description as well as descriptions of different embodiment of exemplary MALVT bot apparatus and its related components, practical applications of such parts of and assemblies of one or more MALVT bot apparatus devices deployed in different embodiments, as well as an embodiment where a single logistics operation may be implemented with multiple node-enabled autonomous logistics vehicle transports (also referenced as a node-enabled AV or autonomous transport vehicle), such as multiple different MALVT bot apparatus.

As noted above, what follows are general meanings for terms and acronyms that may be used in different embodiments of this disclosure. Such meanings are intended to be exemplary, and not limiting, as considered by those skilled in the art.

TRON: As explained in more detail above, this is an exemplary hierarchical Internet of things (IoT) network using different types of wireless nodes that enables device to device communication and connectivity for location, authentication, and association across multiple platforms.

Authentication (AuthN): An exemplary cybersecurity validation process that is concerned with authenticating an entity is "who they say they are". AuthN schemes are numerous, including login/password, etc.

Authorization (AuthZ): An exemplary cybersecurity process that identifies the permissions that an authenticated user is entitled to, such as read-only access to a database, etc.

Central Processing Unit (CPU): A conventional processing unit utilized in personal computers, laptops, and other computing devices and historically has been built and used to process executable instructions. Due to a high speed of operation (clock rate), those skilled in the art will appreciate that a CPU is a general purpose processing unit, with a large degree of flexibility.

Dedicated Short Range Communication (DSRC): A two-way, low-latency, short-to-medium-range wireless system developed to transmit data between vehicles (V2V) and the transportation infrastructure (V2I), used for operations related to traffic flow improvement, traffic safety, and other intelligent transportation service applications.

Department of Transportation (DOT): An agency of the Executive Branch of the US Government, and is run by the Office of the Secretary (OST). The DOT has multiple administrations to deal with different modes of transportation, including the National Highway Traffic Safety Administration, Federal Aviation Administration, and Federal Railroad Administration, among others.

Graphics Processing Unit (GPU): A family of specialty processors that have been optimized for highly intensive and massively parallel processing required for graphics rendering at a high refresh rates. These processors have been optimized to process multi-dimensional arrays and floating point operations. As GPUs have been found to be useful for other tasks, such as deep learning, AI, bitcoin mining, etc., the term General Purpose GPU, or GPGPU has emerged to generally refer to a GPU.

Human-to-Machine Interface (H2M, or HMI): A user interface that connects an operator to the controller of an industrial machine, robot, or computer. Examples of such an interface may include a keyboard, switch, display, touch interface, and the like. This interface can include electronic components for signaling and controlling autonomous systems.

Inertial Measurement Unit (IMU): An electronic device that generally measures and reports movement and, more particularly, may measure and report an object's acceleration, rotation, and sometimes the magnetic field surrounding the object. These measurements are collected by a combination of accelerometers, gyrometers, and magnetometers. Usually used in conjunction with Global Positioning Sensors (GPS) and LIDAR.

Light Detection and Ranging (LIDAR): A remote sensing device that uses pulsed laser light to measure distances and create "point maps" of the surrounding environment. These point maps can be used with Artificial Intelligence platforms to detect and classify different types of objects in the environment: trees, cars, pedestrians, bikers, etc.

Light Emitting Diode (LED): A low power, solid state (semiconductor) light source. LEDs can be made into a display that can show text & video or a user interface.

Machine-to-Machine Interface (M2M): Communication protocols (typically over wireless communication channels, but can be wired) that enable networked devices to exchange information directly and perform actions without human intervention.

National Highway Traffic Safety Administration (NHTSA): This is a US government agency, part of the DOT that is responsible for keeping people safe on America's roadways. NHTSA is dedicated to achieving the highest standards of excellence in motor vehicle and highway safety.

Organic LED (OLED): A new generation LED technology developed with a thin emissive electroluminescent layer, based on organic compounds. OLED technologies may be used in modern displays found in televisions, smart phones, tablets, etc. Next-generation OLED technologies are being created in the form of flexible displays for wearable technologies.

Radio Detection and Ranging (RADAR): A remote sensing system/device that utilizes radio waves to determine the range, angle and velocity of objects in the surrounding environment.

MALVT Apparatus, Components & Systems: Overview of Components

An exemplary MALVT bot system is implemented as being modular, with multiple level component areas with each component being modular and able to be changed out from the assembled bot system. These components (also generally referenced as units) may be assembled to form an exemplary MALVT bot apparatus (also generally referenced as an assembly of one or more such components). Such assembly may be performed to order (e.g., in response to the need for transporting an object) or may be performed ahead of time. Such assembly may be performed based on the particular needs for a given order as well (e.g., based on characteristics of the object being shipped or transported, such as weight, size, environmental condition needs, and the like).

In one embodiment, such components may include a Mobility Base (MB), an Auxiliary Power Unit (APM) or Base Adapter Plate Module (BAPM), a Cargo Storage Unit (CSS), and a Mobile Autonomy Module (MAM). These components are highly modular so that they can be managed at scale separately, while allowing quick assembly into a working exemplary MALTV bot apparatus within a short period of time. As use cases for the exemplary MALTV bot apparatus are implemented, multiple versions of components may be deployed and built to support these use cases. For example, various sizes of the CSS may be built to support multiple delivery options.

In further embodiments, the component modules of an exemplary MALVT bot apparatus may involve authentication as a verified unit and/or when assembling the components to make an exemplary MALVT bot apparatus for a particular use or deployment purpose. Such authentication may be performed component-to-component, or by one component (e.g., a MAM component) once assembled with that one component interrogating the other components to ensure authentic and proper components have been used in the exemplary MALVT bot apparatus assembly.

The use of such authentication may, for example, be for security purposes—e.g., to ensure that only particular components are used for an assembly or to ensure that non-authorized components are not used as part of an assembly or for certain purposes (such as using a particular MB component that has a weight limit that is less than required by a certain deployment or a CSS component that does not have the storage capacity for a certain deployment). Such authentication may be used when assembling or deploying an assembled exemplary MALVT bot apparatus for regulatory and/or contractual compliance. For example, if a customer is not allowed to use a certain sized CSS (or box size that requires a particular sized CSS component), the authentication feature may not allow the assembled exemplary MALVT bot apparatus using such a CSS to operate with or for such a customer. Such regulatory/contractual compliance may have a basis in safety (e.g., not allowing overweight assemblies), logistical requirements (e.g., passageways in a particular facility not allowing widths over a prescribed amount, elevators having weight limits, etc.), and the like.

The modularity aspect of such an embodiment of components that make up an exemplary MALVT bot apparatus may help reduce or otherwise minimize impacts and/or risk of injury through use of inter-component locking mechanisms. For example, if an impact is unavoidable or during an impact, the locking mechanisms between components may be set to disengage (e.g., based upon a setting, based upon a threshold impact sensed by an impact sensor on the exemplary MALVT bot apparatus). That may allow the different components to easily be separated to minimize the force of the impact on a person, vehicle, and/or structure.

Figure 17:
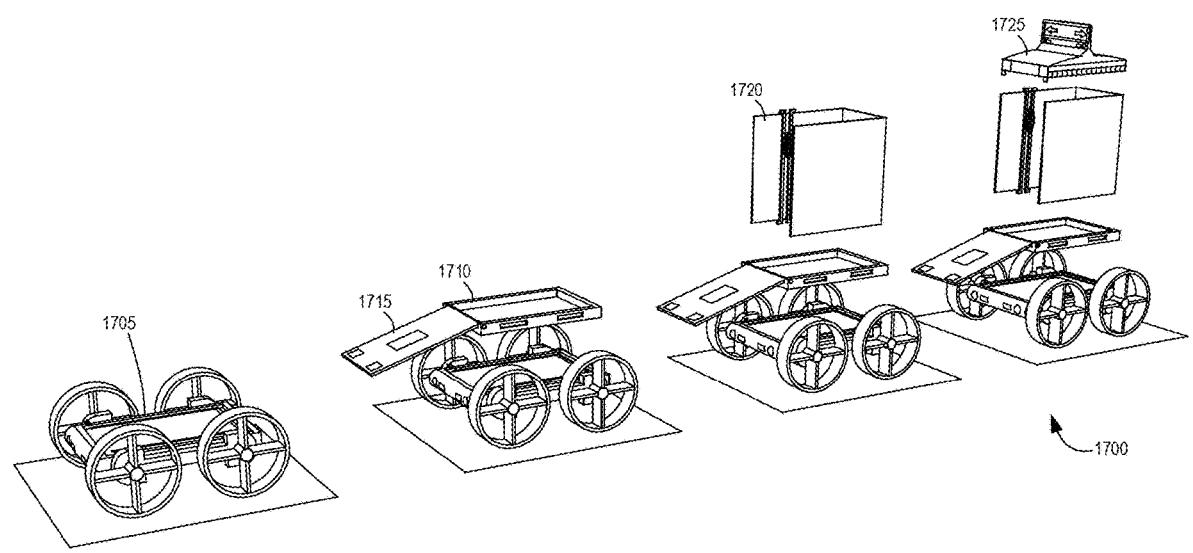
FIG. 17 is a diagram of an exemplary assembly of different exemplary modular autonomous logistics transport vehicle apparatus (MALVT bot apparatus) and components thereof in accordance with an embodiment of the invention.

FIG. 17 is a diagram of an exemplary assembly of different exemplary modular autonomous logistics transport vehicle apparatus (MALVT bot apparatus) 1700 and components thereof in accordance with an embodiment of the invention. Referring now to FIG. 17, the diagram shows a sequence of exemplary MALTV bot apparatus components, including exemplary MB 1705, APM or BAPM 1710, CSS 1720, and MAM 1725. This sequence is a logical progression of assembly starting with the MB 1705, on which the APM or BAPM 1710 are attached (having a cargo door 1715), and on which the CSS 1720 is unfolded and attached to the APM/BAPM 1725. The MAM 1725 is then mounted to and fastened to the CSS 1720 and its interfacing bus and connections as explained in more detail below.

Modular Mobility Base (MB) Component

Figure 18A:
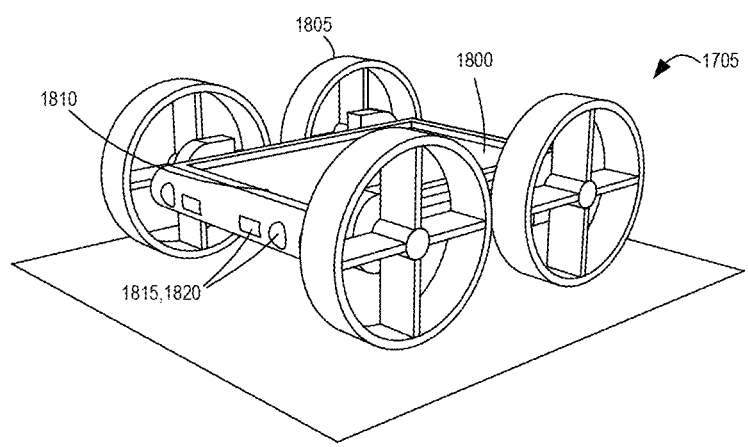
FIG. 18A is a diagram of an exemplary modular mobility base (MB) unit component of an exemplary MALVT bot apparatus in accordance with an embodiment of the invention.
Figure 18B:
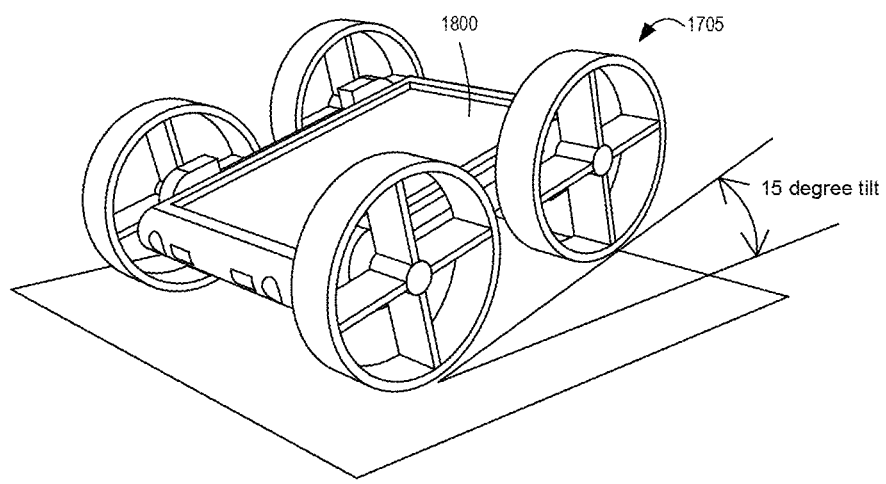
FIG. 18B is an additional diagram of the exemplary modular mobility base unit component of FIG. 18A shown in a tilted configuration in accordance with an embodiment of the invention.
Figure 18C:
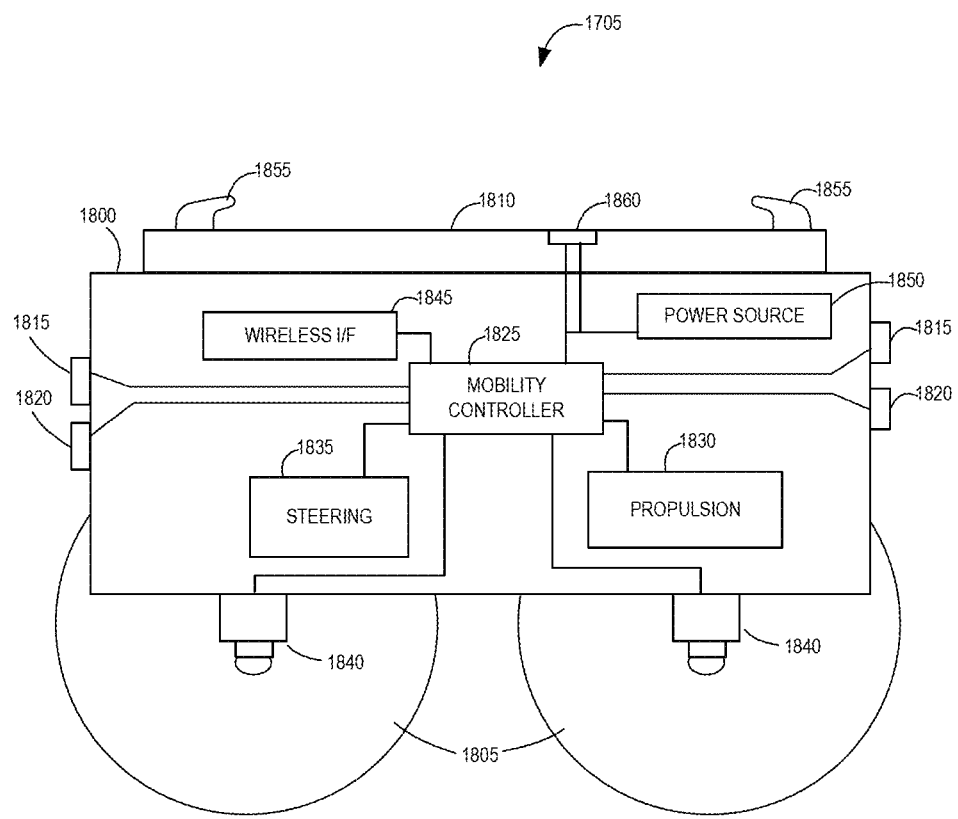
FIG. 18C is a block diagram showing further details of an exemplary modular mobility base unit component in accordance with an embodiment of the invention.

In general, FIGS. 18A-18C relate to details about the modular mobility base component. In more detail, FIG. 18A is a diagram of an exemplary modular mobility base (MB) unit or component 1705 of an exemplary MALVT bot apparatus 1700 in accordance with an embodiment of the invention. Referring now to FIG. 18A, the Mobility Base (MB) 1705 is shown having a base 1800 (e.g., a mobile base platform) and wheels 1805 that generally provides a "unit" of autonomous propulsion to an exemplary MALVT bot apparatus 1700. In one embodiment and shown in more detail in FIG. 18C, the base 1800 of exemplary MB 1705 may include integral control electronics (e.g., a controller or processor (also referenced as a mobility controller) with interface circuitry to sensors and actuators) that controls steering, propulsion (e.g., via an electric motor powered by an onboard or off-board power source, such as a battery and the like), braking, and other actuated movement of MB 1705. Such integral control electronics may be implemented in processing-based control logic and processing systems within the base 1800 of the MB 1705. Other embodiments of an MB 1705 may rely upon control for steering and propulsion systems within the MB 1705 but have such control being provided by the MAM component 1725 of the exemplary MALVT bot apparatus 1700.

Aside from propulsion and steering, an exemplary MB 1705 may include one or more sensors 1815 (e.g., front AV sensors, such as cameras, proximity sensors, IR sensors, LiDAR sensors, environmental sensors, light sensors, motion detectors, tilt sensors, impact sensors, and the like) and lights 1820 used to allow for autonomous detection of nearby objects and obstacles. As shown in FIG. 18A, the exemplary MB 1705 may also deploy an alignment channel 1810, which may be used for keeping additional components attached to or loaded onto the MB 1705 in a controlled position when moving.

Those skilled in the art will also appreciate that the exemplary MB 1705 may be implemented in a variety of sizes with a variety of propulsion options (e.g., wheeled, tracked, etc.) that may depend upon, for example, the types of objects to be transported in its CSS 1720, the environment in which the MB 1705 will be running (e.g., inside, outdoors), the accuracy required in movement (e.g., width for operations, turn around spacing, etc.), and the anticipated payload and articulating loading and unloading mechanisms to help load and unload the CSS 1720 supported on the MB 1705.

An exemplary MB 1705 may also provide power to additional components of the MALVT bot apparatus 1700. Such power may be provided with power connections or bus interfaces location on base 1800 (or as part of the alignment channel 1810 of base 1800) as the additional components are attached to the MB 1705. As described in more detail below, some embodiments of an MALVT bot apparatus 1700 may deploy an auxiliary power module (APM) 1710 to serve as an additional source of power or, in some instances, a main source of power for the MALVT bot apparatus 1700 (including power for the MB 1705) that can be easily swapped in and out as a line replaceable unit for repairs and hot swapping for recharging purposes.

The ability for an exemplary MB 1705 to raise and tilt at various angles enables novel and unique object transfer solutions to humans and other intermediate storage devices. FIG. 18B is the exemplary mobility base unit component 1705 of FIG. 18A, but shown in a tilted configuration in accordance with an embodiment of the invention. Referring now to FIG. 18B, a sample tilting operation is shown where the base portion 1800 is articulated to a different orientation relative to the ground contacts (e.g., the wheelbase supporting wheels 1805) so as to place the contents held normally on the MB 1705 in a tilted configuration by lifting one end of the MB 1705 relative to the other end. In other embodiments, different lifting/tilting actuators disposed within base 1800 (e.g., one or more actuators connected to different axles or motors for wheels 1805 or part of an adjustable suspension system for base 1800) may be deployed in different parts of the MB 1705 (e.g., different sides, different corners) so as to allow for selective and articulable lifting and/or tilting of the MB 1705 under control of the control electronics integral within base 1800 (or at the control of the MAM 1725 or other component in communication with the MB's control electronics) in custom orientations. In other words, such actuators that implement such tilting action may be responsively controlled with the integral control logic systems onboard the MB 1705 or, alternatively, in the MAM component 1725. Further embodiments may deploy alternative lifting mechanisms for the base 1800, such as a "scissor-lift" type actuated mechanism, which may be used alone or in conjunction with the previously described tilting actuator mechanisms.

As noted above, self-sensing (such as vehicle tilt, proximity, environmental sensing) via sensors 1815 deployed on and focused around the exemplary MB 1705 may be incorporated into the exemplary MB 1705 to provide a safe baseline autonomous operation level for use cases that may not involve other components (e.g., powered dolly, "follow-me" luggage cart, etc.) as described in more detail below. Any required or desired illumination for proper sensor operation may be included, for example, at one or more points along the edges of the MB 1705 via lights 1820. Such illumination via lights 1820 may be with visual light or other wavelengths that correspond with sensors used on the MB 1705 (e.g., infrared, etc.).

While FIGS. 18A and 18B illustrate an exemplary MB 1705 in perspective view, FIG. 18C is a block diagram showing some of the external as well as internal details of exemplary modular mobility base unit component 1705 in accordance with an embodiment of the invention and consistent with the description above relative to exemplary MB 1705. Referring now to FIG. 18C, an exemplary modular mobility base for a modular autonomous bot apparatus that transports an item being shipped is illustrated as exemplary MB 1705 having at least a mobile base platform 1800, a modular component alignment interface 1810, a mobility controller 1825, a propulsion system 1830 that causes movement of one or more wheels 1805 (which may include all wheels 1805 for more robust propulsion), a steering system 1835 that can responsively alter the direction of at least some of wheels 1805 (which may include altering the direction of all wheels 1805 for refined movement), sensors 1815, and lights 1820.

The exemplary mobile base platform 1800 essentially provides a moving support platform on which other components of a modular autonomous bot apparatus may be assembled. In more detail, exemplary mobile base platform 1800 may be implemented with a support base and wheels 1805, where the support base of platform 1800 has a top support surface on which the modular alignment interface 1810 is disposed and peripheral edges on which the sensors 1815 are disposed. Wheels 1805 are effectively coupled to the support base.

The exemplary modular component alignment interface (an example of which being the alignment channel 1810 of base 1800 shown in FIG. 18A) is shown in FIG. 18C as being disposed on the mobile base platform 1800. Consistent with the embodiment shown in FIG. 18A, the exemplary modular alignment interface 1810 provides at least one channel (such as the raised alignment channel 1810 shown in FIG. 18A) into which another modular component of the modular autonomous bot apparatus can be placed and secured on the mobile base platform 1800. As placed, interface 1810 may interlock with a corresponding interface (such as a latch or other registration channel) on an APM 1710.

The exemplary mobility controller 1825 is a processor-based control element disposed as part of the mobile base platform 1800 and may be implemented with an ID node type of controller and programming to interface with other circuitry onboard the modular mobility base as well as with other modular components within a modular autonomous bot apparatus assembly of such components. In more detail, mobility controller 1825 is operative to generate a propulsion control signal for controlling speed of the modular mobility base 1705 and a steering control signal for controlling navigation of the modular mobility base 1705. Those skilled in the art will appreciate that the propulsion control signal that impacts and controls speed of the propulsion system 1830 may also control braking (e.g., via an active reduction in speed of wheels 1805 and/or with the propulsion control signal actuating one or more brakes (not shown) on the modular mobility base 1705).

The exemplary propulsion system 1830 is connected to the mobile base platform 1800 in that the propulsion system 1830 is effectively coupled to the mobile base platform 1800 and operative to provide propulsive power to wheels 1805, which causes the modular mobility base 1705 to move. Propulsion system 1830 may, for example, be implemented using one or more motors disposed on the mobile base platform 1800 responsive to the propulsion control signals from mobility controller 1825 where the motor(s) effectively couple the motor's output to wheels 1805 to alter rotation of one or more of the wheels 1805. In another example, propulsion system 1830 may be implemented by one or more motors integrated with one or more of wheels 1805 (e.g., including motors for each of wheels 1805 that may be independently controlled). Propulsion system 1830 is responsive to the propulsion control signal provided by mobility controller 1825, which may include different signals provided to each motor to implement independent control of the collective set of motors under control of the propulsion control signal. In response to the propulsion control signal, propulsion system 1830 is operative to move the modular mobility base 1705 from a stationary position, and cause changes to the speed of the modular mobility base 1705 (e.g., actively increasing the speed or decreasing the speed of the modular mobility base 1705). While exemplary modular mobility base 1705 is shown to ride on wheels 1805, further embodiments may implement wheels 1805 as, for example, tracks, moving legs, hybrid wheel/track systems, maglev locomotive elements that allow for movement of the modular mobility base 1705, and the like.

The exemplary steering system 1835 is also connected to the mobile base platform in that the steering system 1835 is effectively coupled to the mobile base platform 1800 and operative to steer the modular mobility base 1705 via, for example, actuated changes to one or more of wheels 1805, which causes the modular mobility base 1705 to change directional movement in response to the steering control signal from mobility controller 1825. In more detail, an embodiment may have some wheels 1805 being coupled to the propulsion system 1830 (e.g., those of wheels 1805 that are powered by one or more motors) and other wheels 1805 being coupled to the steering system 1835. In still another embodiment, all wheels 1805 may be power driven by one or more motors while less than all of the wheels 1805 may be coupled to the steering system 1835. In yet another embodiment, some or all wheels 1805 may be power driven by one or more motors while all of the wheels 1805 may be coupled to the steering system 1835 for independent and selective steering that provides enhanced and robust steering and propulsion of the modular mobility base 1705.

The exemplary sensors 1815 are disposed on the modular mobility base 1705 (e.g., on parts of the mobile base platform 1800) and each are coupled to the mobility controller 1825. As noted above, sensors 1815 allow for autonomous detection of nearby objects and pathway obstacles and do so by being operative to autonomously generate and provide feedback sensor data to the mobility controller 1825 about a condition of the modular mobility base (e.g., conditions surrounding the modular mobility base, conditions in a movement path of the modular mobility base, and the like). In an embodiment, different ones of exemplary sensors 1815 may be operative to detect a tilt characteristic of the mobile base platform 1800 (e.g., a level status for the platform), to detect an environmental characteristic next to the mobile base platform 1800 (e.g., a temperature outside the platform 1800), and to detect a proximity characteristic about what is next to the mobile base platform 1800 (e.g., a distance to pathway obstacle in front of the platform 1800). As such, an embodiment may have at least one of the sensors 1815 being a proximity sensor operative to autonomously detect an object in a movement path of the modular mobility base 1705 and provide proximity sensor data to the mobility controller 1825 on the detected object as the feedback sensor data. The mobility controller 1825 may receive the feedback sensor data from the proximity sensor(s) of sensors 1815 and responsively generate a change to at least one of the propulsion control signal and the steering control signal so as to avoid collisions and autonomously navigate along the movement path.

And as noted above with FIG. 18A, exemplary lights 1820 may be disposed on the modular mobility base 1705 (e.g., on parts of the mobile base platform 1800) and may be activated by the mobility controller 1825 to provide pathway illumination so to assist with autonomous detections of nearby objects and pathway obstacles. Lights 1820 may be disposed on platform 1800 in a configuration to focus the light generated by lights 1820 externally from the mobile base platform 1800 to facilitate sensor detection via one or more of sensors 1815. In one example, one or more of the lights 1820 may be implemented as a multi-spectral light providing multi-spectral visibility to facilitate sensor detection by at least one of the sensors 1815 (e.g., infra-red light so as to enhance night vision, and the like).

An embodiment of the modular mobility base 1705 may deploy wheels 1805 in a configuration fixed relative to the mobile base platform 1800 that allows for movement of wheels 1805 to effect movement of modular mobility base 1705, but another embodiment may have the modular mobility base 1705 having the mobile base platform 1800 including a selectively adjustable suspension system 1840 that essentially couples the wheels 1805 to the support base 1800 in a selectively configuration. Such a selectively adjustable suspension system 1840 may include electronically and/or hydraulically adjustable coils, springs, shocks, or other actuators that selectively couple wheels 1805 and mobile base platform 1800 in an articulated and adjustable manner.

In more detail, an exemplary selectively adjustable suspension system 1840 may include actuators that may be activated to change an oriented configuration of the support base 1800 relative to the set of wheels 1805 from a first orientation state to a second orientation state in response to a support base orientation control signal from the mobility controller 1825. For example, mobility controller 1825 may receive sensor data from one or more of sensors 1815 indicating a detected level status of the mobile base platform 1800. In response to such sensor data from sensors 1815, mobility controller 1825 may operate in a feedback control manner to generate a support base orientation control signal that adjusts the level orientation of the mobile base platform 1800 to a desired orientation—whether that be level (e.g., so as to keep items being shipped in a level orientation) or to lift and/or tilt the mobile base platform 1800 into the desired position and orientation. In this way, the support base orientation control signal(s) may activate one or more actuators in the adjustable suspension system to change the oriented configuration to a lifted attitude orientation, a tilted attitude orientation, or a combination lift and tilt attitude orientation.

In a further embodiment, the mobility controller 1825 may be programmatically configured to generate one or more support base orientation control signals to cause the selectively adjustable suspension system 1840 to activate and change the oriented configuration of the support base 1800 relative to the set of wheels 1805 from the first orientation state to the second orientation state based upon and in response to a control command from another modular component of the modular autonomous bot apparatus (such as an exemplary MAM 1725). As explained in more detail below, the ability of the modular mobility base 1705 to change its orientation in response to control signals directly from its mobility controller 1825 or control commands from a controller in exemplary MAM 1725 (which may cause the mobility controller 1825 to active and change the oriented configuration of support base 1800) enabled a type of articulated object manipulation for an item/object supported within the modular autonomous bot apparatus assembly having the MB 1705. The change in oriented configuration of support base 1800 may cause the item/object supported by exemplary MB 1705 to move or slide in a controlled and desired manner to facilitate delivery or removal of the item/object from within the modular autonomous bot apparatus assembly having the MB 1705.

In a further embodiment, exemplary modular mobility base 1705 may also include a wireless transceiver 1845 operatively coupled to the mobility controller 1825. The wireless transceiver 1845 may be implemented as a hardware radio, a wireless transceiver implemented with a combination of hardware and software, or a software defined radio (SDR) implementation of a wireless radio transceiver similar to that described above with respect to an ID node. Such a wireless transceiver 1845 provides a bi-directional wireless data path between the mobility controller 1825 and other modular components equipped with similar wireless transceivers as well as external wireless nodes disposed external to the modular autonomous bot apparatus. As such, exemplary wireless transceiver 1845 on exemplary modular mobility base 1705 may facilitate remote wireless control of the modular mobility base 1705 via the bi-directional wireless data path by another modular component or an external wireless node disposed external to the modular mobility base 1705. For example, exemplary mobility controller 1825 may generate the support base orientation control signal to cause the selectively adjustable suspension system 1840 to activate and change the oriented configuration of the support base 1800 relative to the set of wheels 1805 from the first orientation state to the second orientation state based upon and in response to control command from a MAM 1725 or a wireless control command from such an external wireless node disposed external to the modular mobility base 1705 (e.g., from a handheld mobile user access device similar to devices 200, 205 described above, and the like).

The exemplary modular component alignment interface noted above on exemplary modular mobility base 1705 may be implemented with a variety of features. For example and as already discussed above, the modular component alignment interface may be implemented with alignment channel 1810 on support base 1800 shown in FIGS. 18A and 18C. A further embodiment of such a modular component alignment interface may be implemented with a registration interface and a coupling receiver. In this example, the registration interface (such as channel 1810) is disposed on the top support surface of the mobile base platform 1800 as a type of securing and alignment interface into which another modular component of the modular autonomous bot apparatus can be placed and secured on the mobile base platform 1800. More specifically, the registration interface may be implemented as raised alignment channels (as shown in FIG. 18A) but also as recessed alignment channels into which mated alignment structure from another modular component may fit and cause a mutual alignment between the corresponding proximate modular components. A further example may have the registration interface being implemented as multiple alignment channels where each of the alignment channels are disposed proximate one of the peripheral edges of the support base 1800. The coupling receiver part of the modular component alignment interface in this example may be disposed on the top support surface of the mobile base platform 1800 and provide a secure receiving latch element 1855 (e.g., an interlocking latch) for a corresponding mated coupling latch element on another modular component of the modular autonomous bot apparatus. As such, the secure receiving latch 1855 may fit into and temporarily attach to the mated coupling latch element on the proximate modular component attaching to the exemplary modular mobility base 1725.

As will be described in more detail below, exemplary modular components of an exemplary MALVT modular autonomous bot apparatus 1700 may communicate with each other through wireless communication as well as through a common modular component electronics interface that provides a conduit for power sharing and data/control communications between the different modular components making up the exemplary MALVT modular autonomous bot apparatus 1700. As such, an exemplary modular mobility base 1705 may also include an exemplary modular component electronics interface 1860 disposed on the top support surface of the mobile base platform 1800. Exemplary modular component electronics interface 1860 provides a bus-like conduit or a power and data mated interface to at least the another modular component of the modular autonomous bot apparatus so that actively powered devices and circuitry may be coupled to a power part of interface 1860, while electronic devices that communicate with others onboard or outside of exemplary MB 1705 may be operatively coupled to a data/control communications part of interface 1860. For example, mobility controller 1825 may be coupled to interface 1860 so that mobility controller 1825 may have a wired connection to electronic components in other modular components of an exemplary MALVT modular autonomous bot apparatus 1700 (e.g., an autonomous controller that is operating in an exemplary MAM 1725 and coupled to mobility controller 1825 through interface 1860). In more detail, data/control communications part of interface 1860 may be implemented with a modular mated bus interface connection for at least relaying feedback sensor data from the sensors 1815 coupled to the mobility controller 1825 to at least another modular component of the modular autonomous bot apparatus and for receiving control commands from other modular components of the modular autonomous bot apparatus that responsively causes the mobility controller 1825 to generate the propulsion control signal and the steering control signal.

While exemplary modular mobility base 1705 may be powered by another modular component (e.g., exemplary APM 1710), an embodiment of exemplary modular mobility base 1705 may include an onboard power source 1850 that supplies electrical power to onboard active electronics, such as the mobility controller 1825, the propulsion system 1830, the steering system 1835, and the sensors 1815 and lights 1820. In more detail, the onboard power source 1850 may be connected to the power and data mated interface 1860, which may also include a power output connection that provides electrical power from the onboard power source 1850 to the another modular component.

In a further embodiment, the exemplary modular mobility base 1705 may include an onboard power controller (not shown as a separate device, but may be implemented as a power switch on power source 1850 or a power switch integrated as part of mobility controller 1825) that selectively applies electrical power from an external power source (via a power input connection on interface 1860) and/or the onboard power source 1850 to at least the mobility controller 1825, the propulsion system 1830, the steering system 1835, the sensors 185, and lights 1820.

Those skilled in the art will appreciate that an exemplary embodiment of a modular mobility base 1705 may have at least its mobility controller 1825, wireless transceiver 1845, and sensors 1815 implemented by an ID node or a master node as explained above.

Multiple Modular Mobility Unit Assembly

Figure 19:
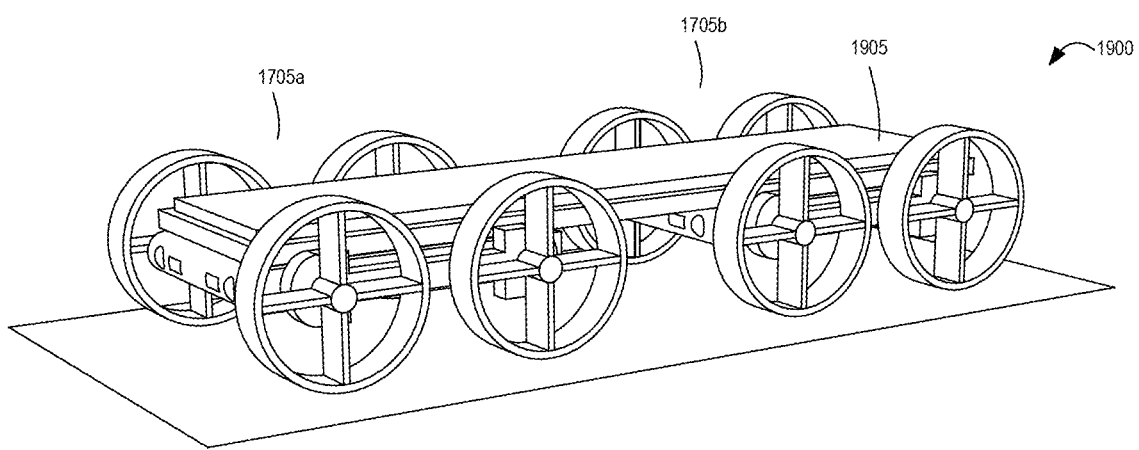
FIG. 19 is a diagram of an exemplary assembly of multiple modular mobility base unit components paired with an exemplary base adapter plate module (BAPM) in accordance with an embodiment of the invention.

With an embodiment of this modular design, a system of exemplary MB units 1705 may be operated in a "collaboration mode" to achieve higher operational throughput, such as enhanced functionality for on-road use or higher payload for freight operations in station. FIG. 19 is a diagram of an exemplary assembly 1900 of multiple modular mobility base components 1705a, 1705b paired with an exemplary extended base adapter plate module (BAPM) 1905 in accordance with an embodiment of the invention.

Referring now to FIG. 19, paired or grouped types of specially configured MALVT bot apparatus devices (e.g., wirelessly paired MB units 1705a, 1705b) may act cooperatively with one collective platform (e.g., extended BAPM 1905 supported by both MB units 100a, 100b) for larger or heavier to handle items. In this configuration, the MB (e.g., each of MB units 1705a, 1705b) uses a Machine-to-Machine interface (M2M) to enable inter-component communication between the MB 1705a and other components (such as the other MB 1705b supporting the rest of the BAPM 1905). An exemplary M2M interface may, for example, be implemented as a wireless communication interface (e.g., Bluetooth, Wi-Fi, cellular, NFC, ZigBee, or other wireless communication formatted interfaces) that allows the bot component to securely connect with (e.g, via secure or authorized associations between bot components using TRON node association techniques) so that bot components communicate and interact in a cooperative manner. In addition, M2M communications may be used by the exemplary MALVT bot apparatus 1700 to communicate with other smart, connected devices, both stationary and mobile (e.g., ID nodes and mobile master nodes separate from the MALVT bot apparatus 1700 as described in the TRON Network Reference Information incorporated by reference as noted above) using wireless communications (e.g., Bluetooth, cellular, and the like). Those skilled in the art will appreciate that M2M communications may be implemented as a standard protocol utilizing Application Programming Interfaces (APIs) to support modular software development, and may utilize wired/wireless technologies as applicable for a particular application and embodiment. As such, the M2M communication deployed in an exemplary MB 1705 may allow for multiple MALVT bot apparatus assemblies to pair together and cooperate in order to carry larger loads acting as a single unit. For example, this may involve coordinated propulsion and steering of each MB 1705a, 1705b in the paired assembly 400 as shown in FIG. 19 with one of the MBs 100a operating as a master autonomous unit and the other MB 1705b accepting input and operating as a type of slave autonomous unit (i.e., MB 1705b operating in a semi-autonomous manner at the control of MB 1705a, but operating autonomous as a collective assembly 1900). As such, the exemplary embodiment of such a paired assembly 1900 collectively operates as a single unit larger MALVT bot system that may be deployed and used for such larger loads.

With reference to FIG. 19 as well as the details explained above regarding exemplary modular mobility base 1705 as shown in FIG. 18C, an embodiment of an exemplary modular multiple mobility base assembly apparatus 1900 may include a base adapter plate (such as plate 1905) and two different modular mobility bases (such as MBs 1705a, 1705b). The base adapter plate 1905 has a top side and a bottom side, where the top side provides a transport area for supporting the item being shipped. As explained above and shown in FIG. 19, exemplary base adapter plate 1905 spans long enough to be supported on either end by the two MBs 1705a, 1705b. As will be explained in more detail below, the two MBs 1705a and 1705b operate in a cooperative manner to function as part of the assembled apparatus 1900. As such, one of the MBs 1705a is configured to operate as a master while the other MB 1705b is configured to work with the master, but operate as a slave device.

In more detail, the first modular mobility base (e.g., MB 1705a) in this exemplary modular multiple mobility base assembly apparatus 1900 operating as a master autonomous mobile vehicle is coupled to the bottom side on one end of the base adapter plate 1905. The first modular mobility base 1705a has a first mobile base platform, a first mobility controller, a first propulsion system, a first steering system, a first wireless transceiver, and a first group of sensors similar to that explained with reference to exemplary MB 1705. In more detail, the first mobility controller is disposed as part of the first mobile base platform on MB 1705a. The first mobility controller (similar to mobility controller 1825) is programmatically configured to be operative to generate a master propulsion control signal for controlling speed of the first modular mobility base and a master steering control signal for controlling navigation of the first modular mobility base. The first propulsion system is connected to the first mobile base platform, and is responsive to the master propulsion control signal from the first mobility controller and operative to cause changes to the speed of the first modular mobility base. The first steering system connected is also to the mobile base platform and coupled to the first propulsion system (at least some of the wheels or tracks that may be part of the first propulsion system). The first steering system is responsive to the master steering control signal from the first mobility controller and operative to cause changes to directional movement of the first modular mobility base. The first wireless transceiver on MB 1705a is operatively coupled to the first mobility controller, and provides a first bi-directional wireless data and command interface for the first mobility controller. The sensors on MB 1705a are coupled to the first mobility controller, disposed on the first mobile base platform, and operative to autonomously generate and provide first feedback sensor data to the first mobility controller about a condition of the first modular mobility base.

The second modular mobility base, MB 1705b as shown in FIG. 19, of assembly apparatus 1900 is coupled to the bottom side on the other end of the base adapter plate 1905. While using similar components as MB 1705a, the second modular mobility base is wirelessly paired to the first modular mobility base and operating as a slave autonomous mobile vehicle under control of the first modular mobility base. In other words, the second modular mobility base 1705b generally operates as an autonomous mobile vehicle. But when configured as the slave modular mobility base component of modular multiple mobility base assembly apparatus 1900, the second modular mobility base 1705b takes navigational movement direction from the master modular mobility base 1705a (i.e., the mobility controller within MB 1705a) and provides the master modular mobility base 1705a with sensor data detected by the second modular mobility base 1705b.

In this configuration, the second modular mobility base MB 1705b has a second mobile base platform, a second mobility controller, a second propulsion system, a second steering system, a second wireless transceiver, and a second group of sensors similar to that explained with reference to exemplary MB 1705. The second mobility controller disposed as part of the second mobile base platform is programmatically configured to be operative to generate a responsive propulsion control signal for controlling speed of the second modular mobility base and generate a responsive steering control signal for controlling navigation of the second modular mobility base. However, the responsive propulsion control signal and the responsive steering control signal are generated by the second mobility controller based upon master control input received from the first modular mobility base as part of the cooperation between the two modular mobility bases that make up the modular multiple mobility base assembly apparatus 1900. Likewise, some of the other components of the second modular mobility base are configured and operate differently to operate as the slave autonomous mobile vehicle under control of the first modular mobility base.

For example, the second propulsion system is connected to the second mobile base platform, and responds to the responsive propulsion control signal from the second mobility controller so as to cause changes to the speed of the second modular mobility base. Likewise, the second steering system is connected to the second mobile base platform and coupled to the second propulsion system (at least some of the wheels or tracks that may be part of the second propulsion system), is responsive to the responsive steering control signal from the second mobility controller, and operative to cause changes to directional movement of the second modular mobility base.

The second wireless transceiver on the second modular mobility base is operatively coupled to the second mobility controller, provides a second bi-directional wireless data and command interface for the second mobility controller, and is operative to communicate with at least the first mobility controller and receive the master control input over a secure paired wireless connection between the first bi-directional wireless data and command interface for the first mobility controller and the second bi-directional wireless data and command interface for the second mobility controller.

The sensors on the second modular mobility base are coupled to the second mobility controller, wherein each of these second sensors are disposed on the second mobile base platform, and being operative to autonomously generate and provide second feedback sensor data to the second mobility controller about a condition of the second modular mobility base.

As shown in FIG. 19, each of the first modular mobility base 1705a and the second modular mobility base 1705b support the base adapter plate 1905 from below. An embodiment of modular multiple mobility base assembly apparatus 1900 may deploy modular alignment structures on the bottom of base adapter plate 1905 and on top of each of the MBs 1701a, 1705b to assist with connections and ensure a proper alignment for the assembled components. In more detail, an embodiment may have the first mobile base platform on the first modular mobility base use a first support plate alignment channel disposed on a top of the first mobile base platform (similar to the alignment channels described relative to exemplary MB 1705 above). Likewise, the second mobile base platform on the second modular mobility base may use a similar support plate alignment channel disposed on a top of the second mobile base platform. Such support plate alignment channels may be raised to protrude from the respective mobile base platform, or may be recessed into the respective mobile base platform.

To mate to such support plate alignment channel structures on the respective MBs, an embodiment of base adapter plate 1905 may use a first support plate alignment seat and a second support plate alignment seat disposed on the bottom side of the base adapter plate 1905. Such support plate alignment seats provide a mated interface to the respective support plate alignment channels on the different MBs 1705a, 1705b. Such support plate alignment seats may be raised to protrude from the respective mobile base platform, or may be recessed into the respective mobile base platform. Additionally, an embodiment may have the respective modular mobility bases 1705a, 1705b of exemplary modular multiple mobility base assembly apparatus 1900 secured to the bottom side of the base adapter plate 1905 using one or more detachable couplings that allow the respective modular mobility base to be latched and locked to the bottom side of the base adapter plate 1905. In more detail, such exemplary detachable couplings on respective modular mobility bases 1705a, 1705b may be implemented as interlocking latches that detachably mate with the bottom side of the base adapter plate 1905.

As noted above, the respective modular mobility bases 1705a, 1705b of exemplary modular multiple mobility base assembly apparatus 1900 are paired and collaborate during operation via communication between the mobility controllers within the respective modular mobility bases 1705a, 1705b. For example, an embodiment may have the mobility controller on one of the modular mobility bases in the assembly 1900 (e.g., MB 1705b) broadcast a pairing request. The mobility controller from the other modular mobility base (e.g., MB 1705a) may detect the pairing request using the wireless transceiver on MB 1705a. In response to the pairing request, the mobility controller on MB 1705a establishes the secure paired wireless connection with the mobility controller on MB 1705b, so as to allow for secure control commands and sensor data to flow between the respective modular mobility bases 1705a, 1705b of exemplary modular multiple mobility base assembly apparatus 1900. In more detail, the mobility controller from MB 1705a may establish an authorized association with the mobility controller in MB 1705b in response to the detected pairing request and based upon a security credential sent to the mobility controller in MB 1705a from the mobility controller in MB 1705b. This established authorization allows the mobility controller in MB 1705a to generate and provide the mobility controller in MB 1705b with the master control input over the secure paired wireless connection and for the mobility controller in MB 1705b to receive and respond to the master control input as a way of implementing collaborative operations between the respective modular mobility bases 1705a, 1705b as part of apparatus 1900. In like manner, the established authorization allows the mobility controller in MB 1705b to provide the mobility controller in MB 1705a with the feedback sensor data about the condition of MB 1705b over the secure paired wireless connection and for the mobility controller in MB 1705b to receive and respond to the feedback sensor data about the condition of MB 1705b as a way of implementing collaborative operations between the respective modular mobility bases 1705a, 1705b as part of apparatus 1900. Such shared feedback sensor data further allows the mobility controller in MB 1705a to generate updated master control input based upon the received feedback sensor data and provide the mobility controller in MB 1705b with the updated master control input over the secure paired wireless connection and for the mobility controller in MB 1705b to receive and respond to the updated master control input (e.g., via updated responsive propulsion control signals and updated steering control signals).

In further embodiments, collaboration may not be limited to coordinated steering and propulsion types of movement for the respective modular mobility bases 1705a, 1705b of exemplary modular multiple mobility base assembly apparatus 1900. Collaboration may involve selective lifting of the base adapter plate 1905 by coordinated actions of the respective modular mobility bases 1705a, 1705b. For example, an embodiment of the exemplary modular multiple mobility base assembly apparatus 1900 may have each of the respective mobile base platforms in MB 1705a, 1705b having a support base, a set of wheels, and a selectively adjustable first suspension system that couples the support base to the set of wheels similar to that explained above relative to exemplary MB 1705 shown in FIG. 18C. Each of the respective mobile base platforms in MB 1705a, 1705b may also have their respective adjustable suspension system (with their own respective controllable actuators) being operative to change an oriented configuration of its respective support base relative to the wheels from a first orientation state to a second orientation state in response to respective support base orientation control signals from the respective mobility controller in the MB 1705a, 1705b. More specifically, the support base orientation control signal generated by the mobility controller in MB 1705b (i.e., the MB operating as the slave autonomous mobile vehicle under control of MB 1705a) may be in response to a coordinated support base orientation control signal from the mobility controller in MB 1705a. In such a situation, the mobility controller in MB 1705a may be operative to maintain a desired orientation configuration of the base adapter plate 1905 (e.g., a desired tilted attitude configuration of the base adapter plate, desired tilted attitude configuration of the base adapter plate, or a desired combination lift and tilt attitude configuration of the base adapter plate) by periodically generating an update for the support base orientation control signal provided to the adjustable suspension system on MB 1705a and generating an update for the coordinated support base orientation control signal provided to the mobility controller in MB 1705b for the adjustable suspension system on MB 1705b.

When configured with such respective adjustable suspension systems having their own actuators to control and adjust the desired orientation of the base adapter plate 1905, support base actuator control signals from the mobility controller in MB 1705a may cause the support base actuators in its suspension system to raise the support base in MB 1705a relative to its wheels, and support base actuator control signals based upon the coordinated support base orientation control signal from the mobility controller in MB 1705a cause the support base actuators in the suspension system of MB 1705b to lower the support base in MB 1705b relative to the wheels of MB 1705b.

Further embodiments may have the mobility controller in the master MB 1705a coordinating adjustment of the desired orientation of the base adapter plate 1905 based on sensor data from of MB 1705a and MP 1705b. For example, an embodiment may have the mobility controller in MB 1705a being operative to responsively generate an update to the support base orientation control signal for the suspension on MB 1705a and the coordinated support base orientation control signal for the suspension on MB 1705b based upon a combination of feedback sensor data from sensors on master MB 1705a and feedback sensor data from sensors on slave MB 1705b as provided by the mobility controller on salve MB 1705b to the mobility controller on master MB 1705a.

Still of the embodiments may adjust the desired orientation of the base adapter plate 1905 based on a remote wireless command received by the apparatus 1900. For example, the mobility controller on MB 1705*a* may be operative to responsively generate an update to the support base orientation control signal for the suspension on MB 1705*a* and the coordinated support base orientation control signal for the suspension on MB 1705*b* based upon and in response to a control command received by the mobility controller on MB 1705*a* over the wireless transceiver on MB 1705*a*. This would allow, for example, a courier using an external wireless node to remotely actuate and control the desired orientation of the apparatus 1900 with commands sent to the mobility controller on the master one of the modular mobility bases of apparatus 1900, which then coordinates the changes to the different suspension systems to maintain the desired orientation—whether the apparatus 1900 is stationary or if the apparatus 1900 is moving where the level status of the apparatus 1900 may be dynamically changing causing further updated to alter and adapt the relative orientation of the base adapter plate 1905 as part of maintaining the desired orientation.

In a further embodiment, exemplary base adapter plate 1905 may include a power source that may be coupled to each of the respective MBs 1705*a*, 1705*b* through output power connections on the bottom side of the base adapter plate 1905. Such a power source as part of base adapter plate 1905 may be configured similar to onboard power source 1850 on an individual modular mobility base, and may operate with respect to a particular modular mobility source as an external power source operative to provide power to that MB through power and data mated interface 1860 as connected to one of the output power connections on the bottom side of the base adapter plate 1905.

Those skilled in the art will appreciate that exemplary embodiments of each of the respective MBs 1705*a*, 1705*b* may have their respective mobility controllers, wireless transceivers, and sensors as explained above implemented by an ID node or a master node.

Auxiliary Power Module (APM) & Base Adapter Plate Module (BAPM) Components

In an embodiment and as generally noted above, exemplary APM 1710 as shown in FIG. 17 may serve to provide a primary or additional source of power for components of the exemplary MALVT bot apparatus 1700, and also work as an adapter plate that the walls of a cargo container (such as an exemplary CSS 1720) will fit within (and may be secured to). Embodiments of this same exemplary modular APM 1710 may be deployed with a bottom-hinged door plate 120 and contain actuated components (e.g., such as door actuator that may use powered joints (using, for example, a hinge) on the APM's door 1715, one or more screw drive linear actuators that actuate the cargo door 1715 relative to the base adapter platform of the AMP, a hydraulic piston actuator attached to the APM's door 1715 and the APM 1710 to move the cargo door 1715, and the like) that are fixed to the APM 1710 and the door plate 1715 so as to allow that door 1715 to be controlled for actuated or self-closure and locking. In general, the cargo door 1715 hinged or otherwise joined to the base of the APM 1710 may enable the exemplary MALVT bot apparatus 1700 to carefully dispense an object without a human in the loop. In one embodiment, such an adapter plate may be configured as part of the APM 1710. In another embodiment, such an adapter plate may be configured as part of an exemplary modular BAPM (Base Adapter Plate Module—e.g., configured as an APM but providing no additional power, while providing a base adapter plate along with an articulated and actuated cargo door only). In still another embodiment, such a cargo door 1715 may be implemented as part of the CSS component 1720 rather than part of the APM 1710 (or BAPM) as discussed in more detail below. In still other embodiments, such a cargo door 1715 may be implemented as a closure system with an entrance door that may be raised or otherwise opened manually or articulated under control by one of the components of an exemplary MALVT bot apparatus 1700, and an extendible ramp that may be pulled out from one of the CSS 1720 or APM/BAPM units 1710 or an articulated ramp that may be actuated to extend from one of the CSS 1720 or AMP/BAPM units 1710. In still other embodiments, such a cargo door 1715 may be a standard hinged door as part of the CSS 1720.

Figure 20A:
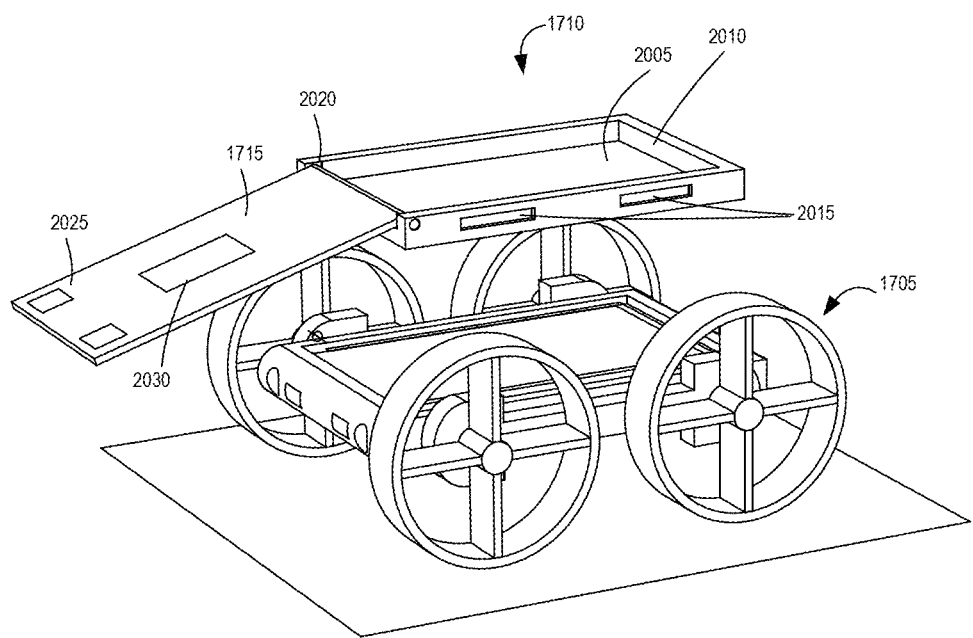
FIG. 20A is a diagram of an exemplary modular mobility base (MB) unit component paired with an exemplary modular auxiliary power module (APM) in accordance with an embodiment of the invention.

FIG. 20A is a diagram of an exemplary MB 1705 paired with an exemplary APM 1710 in accordance with an embodiment of the invention. Referring now to FIG. 20A, exemplary APM 1710 is shown with a base 2005 and an exemplary cargo door 1715 located on the front of the assembly 1700 to provide easier access. An embodiment of APM 1710 may provide mechanical fastening via, for example, a grooved or interlocking channel 2010 that aligns with and connects to an exemplary modular CSS 1720 mounted on top of base 2005, with additional electronic/mechanical latching/locking as needed for security. An embodiment of APM 1710 may provide mechanical fastening to an alignment channel via, for example, other grooved or interlocking channels or latches on the bottom of base 2005 that aligns with and connects to base 1800 of the MB 1705 shown in FIGS. 18A and 20A, with additional electronic/mechanical locking as needed for security.

In general, operation of exemplary cargo door 1715 of APM 1710 shown in FIG. 20A may be manual or may be implemented as to allow actuated opening/closing and actuated unlocking/locking via a door actuation controller (e.g., a wired or wireless receiver that responds to control input from an external wireless node or another component part of an exemplary MALVT bot apparatus). In one particular embodiment, such operation may be implemented in an autonomous mode with no user input required, or at the request of user input, after appropriate authentication. For autonomous operation, the door 1715 may be activated to open via M2M communications, such as part of an interaction between another smart wired or wirelessly connected node or device (e.g., an ID node, a master node, a smartphone, a node-enabled logistics receptacle such as a smart delivery locker, or another component part of an exemplary MALVT bot apparatus 1700 such as MAM 1725 or MB 1705) and the door actuation controller. A joint (e.g., hinge) mechanism 2020 deployed at the bottom of the cargo door 1715 may allow for minimal interaction with simple mechanical self-closing ability. Additionally, the door 1715 may contain two normally-closed electro-mechanical latching or locking mechanisms 2025: one at top, and one at bottom, to ensure the exemplary MALVT bot apparatus 1700 may be locked and secured in transit. At a delivery stop, the locks 2025 may be activated by a control element on the exemplary MALVT bot apparatus 1700 (e.g., a controller in the MAM 1725 or the integral control logic in MB 1705, such as mobility controller 1825) interacting with the door activation controller (e.g., a door actuator driver or directly with the particular actuators) to allow the door 1715 (which may be spring-loaded for self-closure) to unlock and open or close and lock. Having the downward opening door 1715 coupled with the tilting capability in an embodiment may allow a transported item/object supported on a base

2005 of the APM 1710 to slide down (e.g., slide to an intermediate storage container, such as a locker or drop box).

Figure 20B:
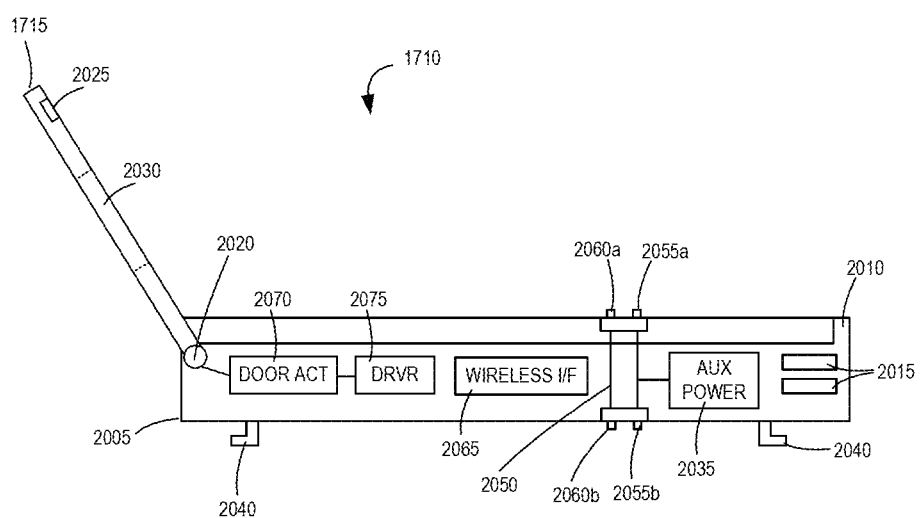
FIG. 20B is a block diagram showing further details of an exemplary modular auxiliary power module in accordance with an embodiment of the invention.

As shown in FIG. 20B, an embodiment of the APM 1710 may use a translucent panel 2030 on the cargo door 1715 as an electronic display interface that provides electronic display functionality via a micro-projection system (which may be embedded in other exemplary MALVT bot apparatus components 1700). This micro-projection system may display appropriate messages to the user by a control element (e.g., a controller in the MAM 1725 or the integral control logic in MB 1705, such as mobility controller 1825, that may drive the display panel 2030) during the delivery process. An exemplary translucent panel display 2030 may be implemented, for example, by an LED or touchscreen display that allows visibility through cargo door 1715 while also showing displayed visual information (e.g., prompted instructions related to delivery) on the cargo door via graphics, symbols, letters, and the like as controlled by a control element component of the exemplary MALVT bot apparatus (e.g., the controller or processor in the MAM unit 1725) or an external wireless node.

An embodiment of the APM 1710 may provide power to the other modules of the exemplary MALVT bot apparatus 1700 using its auxiliary power source 2035, while advantageously keeping the center of gravity low for stability of the apparatus 1700. An embodiment of the APM 1710 may also provide extended range capability for additional use cases with larger or multiple battery packs (e.g., via the use of multiple removable power packs 2015 that use batteries or other types of fuel cells). The APM battery packs 2015 may be removable and replaceable from the exemplary APM 1710 once the entire exemplary MALVT bot apparatus 1700 is assembled and without the need to disassemble the apparatus 1700 (e.g., removable battery packs 2015 being accessible on a side edge of base 2005 of APM 1710). In this manner, further types of battery/power packs that provide a different source of energy for the electricity needed to power the exemplary MALVT bot apparatus 1700 may be encapsulated within alternative battery packs for deployment in an exemplary MALVT bot apparatus 1700. Such alternative battery/power packs 2015 may involve fuel cell technology, or other energy source technologies that may have a sufficient weight to power ratio so as to be useful for an exemplary MALVT bot apparatus 1700.

If an exemplary MB 1705 were to provide sufficient power, and no additional power source may be needed for a particular configuration of apparatus 1700, a BAPM may be used as part of assembly 1700 and also provide modular mechanical connectivity from the Mobile Base unit(s) 1705 to the additional modular components of apparatus 1700 on top. A further exemplary form factor of such an exemplary BAPM may be to utilize two Mobility Bases, connected together mechanically via the BAPM—e.g., such as that shown in FIG. 19 with an extended BAPM 1905 supported by and connecting MBs 1705*a*, 1705*b*. This novel configuration (with interconnected modular MB units 1705*a*, 1705*b*) may provide additional transport capability for large objects, freight handling units, etc. And as explained above, an exemplary tandem MB configuration connected with a BAPM (such as assembly 1900 shown in FIG. 19) may provide the ability to have each MB articulate individually and/or collaboratively so as to handle terrain with obstacles (e.g., where one MB 1705*a* is actuated to move higher than the other MB 1705*b* for navigation of difficult terrain, or collectively raising up to a truck or van to receive objects while on a level surface or collaboratively adapting to an inclined or otherwise uneven ground surface). Those skilled in the art will appreciate that further embodiments may assembly such a multiple MB configuration (with an extended BAPM 1905) into an exemplary MALVT bot apparatus assembly that uses a larger sized modular CSS 1720 and larger sized modular MAM 1725 to accommodate and enclose the area above the extended BAPM 1905.

Further details explained above regarding exemplary modular auxiliary power module 1710 are explained below with reference to FIGS. 20B-20E. Referring now to the details shown in FIG. 20B, an embodiment of an exemplary modular auxiliary power module 1710 is shown with further internal details of different parts of such an exemplary APM 1715. In general, exemplary AMP 1715 is shown in an exemplary base adapter platform 2005, cargo door 1715 movably attached (e.g., via a joint, such as a hinge) to the platform 2005 and extending from the platform 2005, auxiliary power source 2035 disposed as part of the base adapter platform 2005, and an output power outlet 2055*a*, 2055*b* coupled to auxiliary power source 2035 and disposed as part of the base adapter platform 2005. The output power outlet 2055*a*, 2055*b* provides access by other components of the modular autonomous bot apparatus 1700 to power from the auxiliary power source 2035.

In more detail, exemplary base adapter platform 2005, as shown in FIGS. 20A and 20B, has a top side, a bottom side, and peripheral edges. As shown in FIG. 20A, openings for removable power packs 2015 are located along a peripheral edge and the door's hinge 2020 is disposed along another peripheral edge of the base adapter platform 2005. The top side of the base adapter platform 2005 has a cargo support area disposed between its peripheral edges, where the cargo support area (also referred to as a transport area or payload area) is configured to support an item or object being shipped.

Exemplary base adapter platform 2005 is equipped with interlocking alignment interfaces to facilitate proper alignment with proximate modular components of assembly 1700 and secure connection to such components. In more detail, the top side of the base adapter platform 2005 has a first interlocking alignment interface while the bottom side of the base adapter platform 2005 includes a second interlocking alignment interface (e.g., latches 2040). The first interlocking alignment interface may, for example, be implemented with one or more top alignment channels (e.g., channels 2010) disposed on the peripheral edges of the base adapter platform 2005 not having the cargo door as shown in FIG. 20A. In a further example, the first interlocking alignment interface may be implements with one or more latches that may be disposed on one of the top alignment channels so as to align with and securely mate another mated component of the modular autonomous bot apparatus 1700 to the top side of the base adapter platform 2005.

On the bottom of base adapter platform 2005, an embodiment of the second interlocking alignment interface may be implemented with latches 2040 configured to mate with and secure to corresponding latches (e.g., interlocking latches) on the top of an exemplary MB (e.g., MB 1705) of the modular autonomous bot apparatus 1700. Another embodiment of the second interlocking alignment interface on the bottom of base adapter platform 2005 may be implemented in at least one bottom alignment registration interface (e.g., a recessed or raised channel) configured to mate with at least one alignment registration interface on the top of an exemplary MB (e.g., MB 1705) of the modular autonomous bot apparatus interface 1700.

As shown on FIG. 20B, an embodiment of exemplary APM 1710 may have exemplary output power outlet 2055*a*, 2055*b* implemented as part of a modular component electronics interface 2050 disposed on and through the base adapter platform 2005. The modular component electronics interface 2050 is a bus-like conduit structure that provides the output power outlet 2055*a*, 2055*b* for a power bus, and a command and data communication interface 2060*a*, 2060*b* for a command and data communication bus on the base adapter platform 2005. The modular component electronics interface 2050 (with its output power outlets 2055*a*, 2055*b* and command and data communication interfaces 2060*a*, 2060*b* on the top and bottom of base adapter platform 2005) is disposed and aligned such that it can modularly connect to similar interfaces on other modular components of the modular autonomous bot apparatus 1700 when the exemplary APM 1715 is assembled as part of such an apparatus assembly 1700. Furthermore, those skilled in the art will appreciate that as a bus-like conduit structure, the modular component electronics interface 2050 allows for electronic components within APM 1715 to connect to the power and command/data conduits making up the modular component electronics interface 2050. Thus, while FIG. 20B shows auxiliary power source 2035 connected to interface 2050, those skilled in the art will appreciate that other electronic devices that are powered may be operatively coupled to the power bus related to the modular component electronics interface 2050. Likewise, those skilled in the art will appreciate that other electronic devices may be operatively coupled to the command and data communication bus related to the modular component electronics interface 2050 to communicate with other devices on other modular components through modular component electronics interface 2050. For example, exemplary translucent panel 2030 on the cargo door 1715 may be implemented as an electronic display interface providing electronic display functionality via a micro-projection system (which may be embedded in other exemplary MALVT bot apparatus components 1700), and the panel 2030 may be coupled to the command and data communication interface of the modular component electronics interface 2050 so that other devices on apparatus 1700 may communicate with and provide information to display on the panel 2030.

As noted above, exemplary cargo door 1715 may be implemented as an actuated door. This may be accomplished with, for example, actuated joint 2020 (such as an actuated hinge that may be controllable to open and close, or a self-closing joint where a spring-like element brings the door 1715 closed upon release when in an open state). In more detail, an embodiment may actuate door 1715 using wired comments from another modular component connected to the APM 1710. In such an example, an exemplary cargo door 1715 on APM 1710 may be movably attached to a peripheral edge of base adapter platform 2005 using joint 2020, and the door as an assembly may include a door actuator 2070 and a door actuator driver 2075. The door actuator 2070 may be configured as being fixed to the base adapter platform 2005 and operative to move the cargo door 1715. The door actuator driver 2075 may be coupled to the door actuator 2070 as a control element, and responsive to a cargo door control input from a control component of the modular autonomous bot apparatus 1700 received over the command and data communication interface of the modular component electronics interface 2050. As such, the door actuator driver 2075 causes the door actuator 2070 to move the cargo door 1715 relative to the base adapter platform 2005 in response to the cargo door control input.

In some embodiments, the APM 1710 may further include a wireless transceiver interface 2065 to receive control input, such as the cargo door control input, from authorized wireless control element (e.g., an external wireless node or a control element in another modular component of apparatus 1700 communicating with APM 1710 over a wireless communication path) and provide such control input to the door actuator driver 2075. However, in other embodiments, the door actuator driver 2075 may have its own integrated wireless transceiver built in. Thus, such an embodiment of door actuator driver 2075 may be coupled to the door actuator 2070 and responsive to an authorized wireless cargo door control input from a control component of the modular autonomous bot apparatus 1700 (or an authorized external wireless node disposed external to the apparatus 1700), where the authorized wireless cargo door control input is wirelessly received by the door actuator driver 2075 causing the door actuator 2070 to move the cargo door 1715 relative to the base adapter platform 2005 in response to the authorized wireless cargo door control input.

In another embodiment, the exemplary cargo door 1715 may be implemented with an actuated lock 2025 (e.g., an electro-mechanical lock with an actuated bolt or latch, an actuated latch, and a magnetic lock, and the like having integrated driver circuitry for responding to control input) for securing the door 1715 electronically by a control component of the modular autonomous bot apparatus 1700 (or an authorized external wireless node disposed external to the apparatus 1700). The electro-mechanical actuated lock 2025 may be one of several actuated locks (or latches) responsive to a door lock control input from such a control component of the modular autonomous bot apparatus 1700 (such as a controller in the MAM 1725). As such, the door lock control input may be received by the actuated lock 2025 over the command and data communication interface of the modular component electronics interface 2050 so that the actuated lock 2025 activates to open or secure the cargo door 1715 when the cargo door 1715 is in a raised/closed position in response to the door lock control input. In an example where the door lock control input is an authorized wireless control signal from a wireless transceiver working with a control component of the modular autonomous bot apparatus (e.g., a wireless transceiver working with the controller on the MAM 1725), such an authorized wireless door lock control input is wirelessly received by the actuated lock 2025, which then causes the actuated lock 2025 to activate to open or secure the cargo door 1715 when the cargo door 1715 is in a raised/closed position. In yet another example where the door lock control input is from an authorized external wireless node disposed external to the apparatus 1700 (such as a delivery recipient's smartphone operating as a mobile ID node or mobile master node), the authorized wireless door lock control input may have the same effect of controlling the opening or closing of the actuated lock 2025.

As noted above, an embodiment of APM 1710 may be implemented without door 1715 in order to be compatible with a CSS 1720 that may be implemented with its own door (which may be an actuated door controlled through the CSS 1720 and its onboard electronics and actuated devices). As such, an exemplary door-less embodiment of APM 1710 may having a base adapter platform similar to that of platform 2025, but configured without door 1715 extending from one of the peripheral edges of platform 2025. Such an exemplary door-less embodiment of APM 1710 may further include at least an auxiliary power source disposed as part of the base adapter platform (such as power source 2030) and a modular component electronics interface (similar to interface 2050 described above having an output power outlet coupled to the auxiliary power source and a command and data communication interface to at least another modular component of the modular autonomous bot apparatus).

Figure 20C:
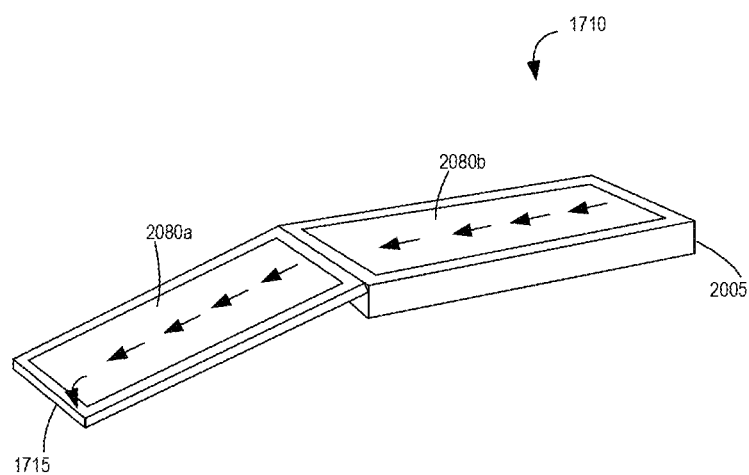
FIG. 20C is a diagram of an exemplary modular auxiliary power module having different actuated belt surfaces as a type of articulated object manipulation system that may be deployed on the exemplary modular auxiliary power module in accordance with an embodiment of the invention.
Figure 20D:
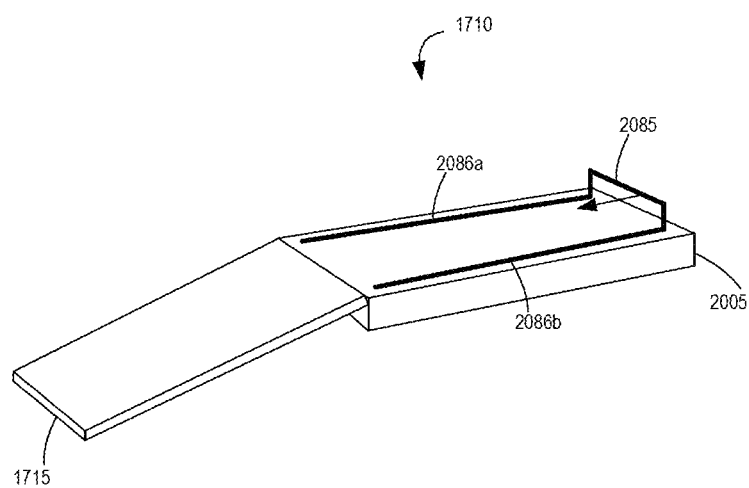
FIG. 20D is a diagram of an exemplary modular auxiliary power module having different actuated sliding arm as a type of articulated object manipulation system that may be deployed on the exemplary modular auxiliary power module in accordance with an embodiment of the invention.
Figure 20E:
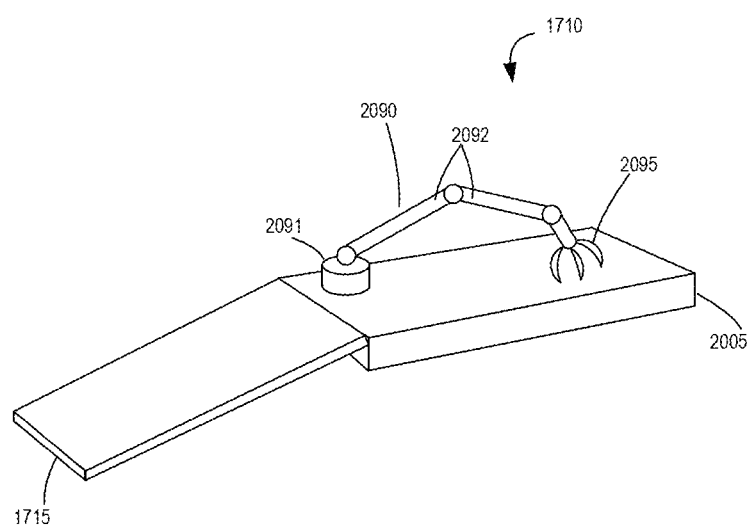
FIG. 20E is a diagram of an exemplary modular auxiliary power module having different actuated grabbing arm as a type of articulated object manipulation system that may be deployed on the exemplary modular auxiliary power module in accordance with an embodiment of the invention.

In a further embodiment, those skilled in the art will appreciate that additional articulating structure (as shown in FIGS. 20C-20E) may be deployed as part of an exemplary APM 1710 (or BAPM or CSS components 1720) to help load or unload/dispense an item/object being transported within an exemplary MALVT bot apparatus assembly 1700 in an automated manner without operator intervention. This may be helpful in an embodiment where the MB unit 1705 is not operable to tilt (at all or sufficiently) or otherwise change its level/orientation to accommodate such a loading or unloading operation.

For example and as shown in FIG. 20C, an exemplary embodiment may deploy an actuated belt surface 2080*a*, 2080*b* on the bed or base 2005 (and in some embodiments on the door 1715) of the APM 1710 such that actuation of the belt surface 2080*a*, 2080*b* moves an item/object on the APM 1710 (e.g., an object within a CSS unit 1720 being supported by the MB 1705 and APM 1710 (or BAPM)). Such an actuated belt surface 2080*a*, 2080*c* may be built into the APM/BAPM 1710 and responsive to control inputs from control/actuating electronics of the MB 1705, APM/BAPM 1710, or MAM components 115.

In more detail, an embodiment may deploy one or more actuated belt surfaces 2085 and a belt surface actuator driver coupled to and controlling the actuated belt surface 2085. In this embodiment, the actuated belt surface (such as belt surfaces 2080*a*, 2080*b*) is disposed above the top side of the base adapter platform 2005 and/or on an inner side of the cargo door 1715. The belt surface actuator driver is operatively coupled to and controls movement of the actuated belt surface by being responsive to a belt control input generated a component of the exemplary MALVT bot apparatus (e.g., the controller or processor in the MAM unit 1725) or an external wireless node. As such, the belt surface actuator driver is responsive to cause the respective actuated belt surface on the base 2005 and/or door 1715 to move the item being shipped relative to the base 2005 and/or door 1715 in response to the belt control input. In some embodiments, the belt surface actuator driver may be responsive to an authorized belt control input generated by an external wireless node disposed external to the modular autonomous bot apparatus. As such, the belt surface actuator driver may cause the respective actuated belt surface on the base 2005 and/or door 1715 to move the item being shipped relative to the base 2005 and/or door 1715 in response to the wireless authorized belt control input.

In another exemplary embodiment shown in FIG. 20D, one or more actuated sliding arms 2085 may be disposed and actuated to move on guiderails 2086*a*, 2086*b* on the APM/BAPM 1710 so as to responsively sweep the inside of the storage compartment defined by the CSS 1720 and APM/BAPM components 1710 from the back towards the front where stored items/objects may be dispensed (e.g., towards the door 1715 of the APM 1710). Such actuated sliding arms 2085 may be built into the APM/BAPM 1710 and responsive to control inputs from control/actuating electronics of the MB 1705, APM/BAPM 1710, or MAM components 1725. Such actuated sliding arms may, in some embodiments, be incorporated into the CSS unit 1720 and may be disposed at one or more different heights within the CSS 1720. In an embodiment having multiple sliding arms, internal proximity sensors may be disposed within the CSS unit 1720 and focused inward so as to detect object height so that particular ones of the sliding arms may be selected for actuation to move the item/object or items/objects stored within the CSS 1720.

In more detail, an embodiment may deploy one or more actuated sliding arms 2085 and a sliding arm actuator driver coupled to and controlling the actuated sliding arm 2085. In this embodiment, the actuated sliding arm 2085 is disposed above the top side of the base adapter platform 2005. The sliding arm actuator driver is operatively coupled to and controls movement of the actuated sliding arm 2085 by being responsive to a sliding arm control input generated a component of the exemplary MALVT bot apparatus (e.g., the controller or processor in the MAM unit 1725) or an external wireless node. As such, the sliding arm actuator driver is responsive to cause one or more of the actuated sliding arms 2090 to engage/contact the item being shipped, and slide or otherwise move the item being shipped at least towards the cargo door 1715 of the base adapter platform 2005 in response to the sliding arm control input. In some embodiments, the sliding arm actuator driver may be responsive to an authorized sliding arm control input generated by an external wireless node disposed external to the modular autonomous bot apparatus. As such, the sliding arm actuator driver may cause the actuated sliding arm 2090 to move or slide the item being shipped at least towards the cargo door 1715 of the base adapter platform 2005 in response to the wireless authorized sliding arm control input.

In a similar exemplary embodiment shown in FIG. 20E, one or more actuated movable grabbing arms 2090 (including an articulated grip head 2095) may be disposed on the APM/BAPM 1710 so as to responsively move within the inside of the storage compartment defined by the CSS 1720 and APM/BAPM components 1710 and move one or more items/objects so as to load or unload such items/objects. Such actuated movable grabbing arms 2090/2095 may have multiple degrees of freedom, be built into the APM/BAPM 1710 and responsive to control inputs from control/actuating electronics of the MB 1705, APM/BAPM 1710, or MAM components 1725. Such actuated movable grabbing arms 2090/2095 may, in some embodiments, be incorporated into the CSS unit 1720. In this embodiment, internal proximity sensors within the CSS unit 1720 may detect the relative location of such objects so that the actuated movable grabbing arms 2090/2095 are able to obtain control of the item/object or items/objects stored within the CSS 1720 and move such objects when loading or unloading/dispensing. In this manner, the item/object may be loaded into the storage compartment defined by the CSS 1720 and APM/BAPM components 1710 as well unloaded and dispensed from such a storage compartment.

In more detail, an embodiment may deploy an actuated grabbing arm 2090/2095 and a grabbing arm actuator driver coupled to and controlling the actuated grabbing arm 2090/2095. In this embodiment, the actuated grabbing arm 2090/2095 is disposed above the top side of the base adapter platform 2005, and has a stationary base 2091 coupled to the top side of the base adapter platform 2005, a movable grabbing arm 2092 coupled to the stationary base 2091 with multiple degrees of freedom of movement, and grip head 2095 disposed on the distal end of the movable grabbing arm 2092 where the grip head 2095 is articulable to grab onto the item being shipped as disposed on the top side of the base adapter platform 2005. The grabbing arm actuator driver is operatively coupled to and controls movement of the actuated grabbing arm 2090/2095 by being responsive to a grabbing arm control input generated a component of the exemplary MALVT bot apparatus (e.g., the controller or processor in the MAM unit 1725) or an external wireless node. As such, the grabbing arm actuator driver is responsive to cause the actuated grabbing arm 2090 to move towards the item being shipped, cause the grip head 2095 to grab onto the item being shipped, and cause the actuated grabbing arm 2090 to move the item being shipped as maintained within the grip head 2095 at least towards the cargo door 1715 of the base adapter platform 2005 in response to the grabbing arm control input. In some embodiments, the grabbing arm actuator driver may be responsive to an authorized grabbing arm control input generated by an external wireless node disposed external to the modular autonomous bot apparatus. As such, the grabbing arm actuator driver may cause the actuated grabbing arm 2090 to move towards the item being shipped, cause the grip head 2095 to grab onto the item being shipped, and cause the actuated grabbing arm 2090 to move the item being shipped as maintained within the grip head 2095 at least towards the cargo door 1715 of the base adapter platform 2005 in response to the wireless authorized grabbing arm control input.

To further assist with loading and/or unloading/dispensing, an embodiment of an APM/BAPM 1710 may include articulated deployment of an extendible ramp from door 1715 having its own automatically actuated belt surface (as part of the APM or BAPM 1710 and similar to the actuated belt surface 2080a shown in FIG. 20C). An exemplary extendible ramp may be implemented as part of door 1715 so as to articulate out from an opposing end of the cargo door 1715 opposite the one of the peripheral edges of the base adapter platform 2005. Such an extendible ramp, which may have an actuated belt surface similar to the actuated belt surface 2080a shown in FIG. 20C, may further allow for enhanced and improved transferring capabilities for an object to/from a user or another device external to the exemplary MALVT bot apparatus 1700 (such as a delivery vehicle or another exemplary MALVT bot apparatus). As such, an exemplary extendible ramp may be automatically extended from the APM/BAPM (or MB or CSS) under control of one of the components of the exemplary MALVT bot apparatus (e.g., the controller or processor in the MAM unit), and its surface actuated to help move an object out of or into the exemplary MALVT bot apparatus. For example, an embodiment may have such an exemplary extendible ramp being responsive to a ramp deploy control input generated by a component of the exemplary MALVT bot apparatus (e.g., the controller or processor in the MAM unit) to articulate the extendible ramp relative to the cargo door 1715. In more detail, an embodiment with such an extendible ramp may include an actuated belt surface disposed on a top side of the extendible ramp (e.g., a conveyor belt surface having an actuator motor that drives the conveyor belt as the actuated belt surface), and a belt actuator driver coupled to the actuated belt surface as a type of control circuit that activates the actuated belt surface. Such a belt actuator driver is responsive to a belt control input generated by a control component of the modular autonomous bot apparatus, and causes the actuated belt surface to move relative to the extendible ramp in response to the belt control input once the cargo door is in a deployed position. In some embodiments, the belt actuator driver may be responsive to an authorized belt control input generated by an external wireless node disposed external to the modular autonomous bot apparatus. As such, the belt actuator driver may the actuated belt surface to move relative to the extendible ramp in response to the wireless authorized belt control input once the cargo door is in a deployed position.

Those skilled in the art will appreciate that exemplary embodiments of an exemplary APM 1710 may have its wireless transceiver and actuator drivers implemented using an ID node or a master node that can provide the localized control input signal generation to provide to different actuators deployed on parts of the exemplary APM 1710.

Cargo Storage System (CSS) Component

Figure 21:
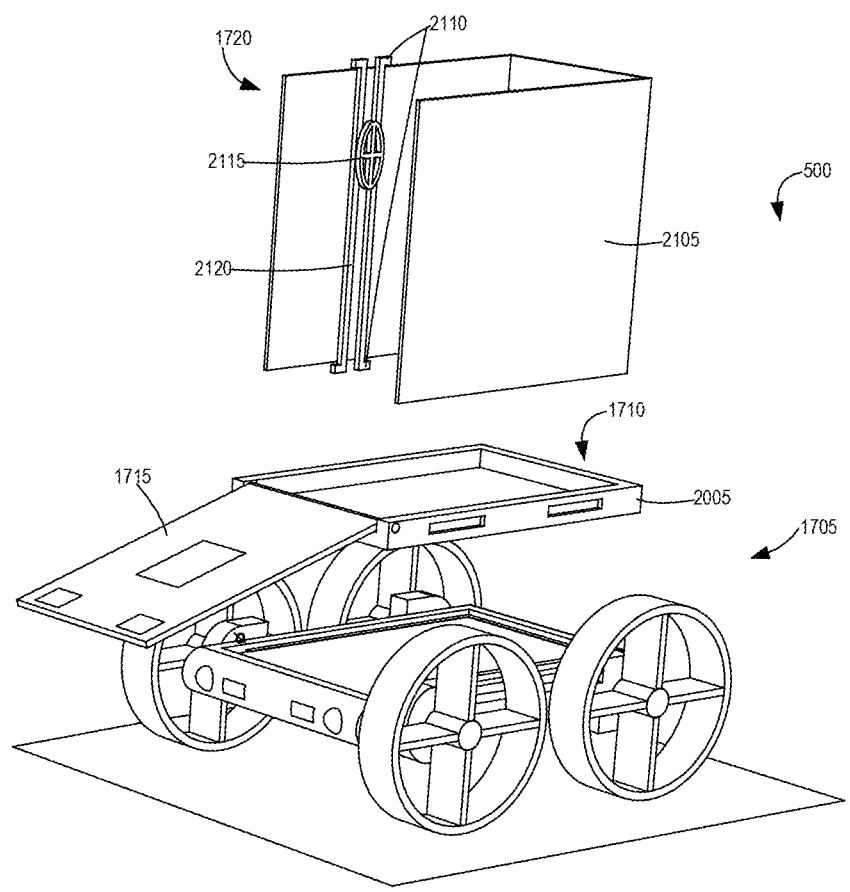
FIG. 21 is a diagram of an exemplary assembly of an exemplary mobility base (MB) unit component paired with an exemplary modular auxiliary power module (APM) and an exemplary modular cargo storage system (CSS) in accordance with an embodiment of the invention.

FIGS. 21-27C provide further details on aspects and embodiments of exemplary cargo storage system (CSS) components (such as CSS 1720) that may be used on an exemplary MALVT bot apparatus 1700. In more detail, FIG. 21 is a diagram of an exemplary assembly 2100 of an exemplary mobility base (MB) unit/component 1705 paired with an exemplary auxiliary power module (APM) component 1710 and an exemplary cargo storage component (CSS) 1720 in accordance with an embodiment of the invention. An exemplary CSS unit/component 1720, as shown in FIG. 21, is disposed on top of exemplary MB unit 1705, or exemplary APM 1710 (see, e.g., FIGS. 21, 22A). In general, embodiments of the CSS component 1720 of an exemplary MALVT bot apparatus 1700 may serve as a modular, strong, lightweight, weather-resistant container structure for cargo. An embodiment of CSS 1720 may utilize an integrated, downward opening cargo door 1715 of an exemplary APM 1710 that may also serve as an item/object (e.g., package) "slide". As noted above, an embodiment may have the object or cargo door 1715 being retractable into the base of APM 1710 for situations that would not make an outwardly folding door feasible. Further, an alternative embodiment of CSS 1720 may have its own actuated cargo door, as explained in more detail below with reference to FIG. 26.

The embodiment of exemplary CSS 1720 shown in FIGS. 21 and 22A has three jointed sides/walls 2105 and with a locking handle 2115 that operates latches 2110, which may be operated to secure and fasten the CSS component 1720 to the APM component 1710 below (as well as to the MAM component 1725 above). Jointed side/walls 2105 are collectively a set of folding structural walls configured to at least partially enclose a payload area above a base platform (e.g., base adapter platform 2005 of exemplary APM 1710) and on at least three sides above the base platform. Thus, as shown in FIGS. 21 and 22A, the jointed sides/walls 2105 form a set of vertical boundaries on the at least three sides of the payload area.

As shown in FIG. 21, the exemplary locking handle 2115 and exemplary latches 2110 of exemplary CSS 1720 include longitudinal support latches 2120 where each has a top interlocking latch and a bottom interlocking latch that, collectively, move to engage a mating set of latches (e.g., interlocking latches) on components below and above the CSS 1720 (e.g., an APM component 1710 and a MAM component 1725). In such a manner, the locking handles 2115 and latches 2110 may be disposed on one or more of the sides/walls 2105 of CSS 1720 so as to allow for secure attachment of CSS 1720 to the APM 1710 below and MAM 1725 above at one or more points of the periphery where the CSS 1720 meets with the APM 1710 and where the CSS 1720 meets with MAM 1725. As assembled where the CSS 1720 is attached to the APM 1710 and MAM 1725, those skilled in the art will appreciate that door 1715 of the APM 1710 may be raised or otherwise articulated into a closed position to close off a storage area within CSS 1720 below the attached MAM 1725.

The exemplary CSS 1720 includes a power and data conduit or transport that provides communication and power interconnections between the APM component 1710 and the MAM component 1725. In an embodiment, the positive CSS locking mechanism (e.g., via handles 2215 and latches 2110) may also integrate and provide the power and data transport conduit (e.g., a modular component power and data transport bus 2250 as shown in FIG. 22B) that may be disposed as an integral part of one of the walls 2105 and connected between the high-level modular components so that locking and latching CSS 1720 to APM 1710 engages interfaces to the power and data conduit (e.g., modular component power and data transport bus 2250) on the APM 1710. Similar locking and latching of the CSS 1720 to a MAM 1725 provide and facilitate engagement of additional power and data interfaces on the MAM 1725 so as to allow the power and data conduit of CSS 1720 to be a modular interconnection between the APM 1710 and MAM 1725 assembled with the CSS 1720 and MB 1705 as part of exemplary MALVT bot apparatus 1700.

Figure 22A:
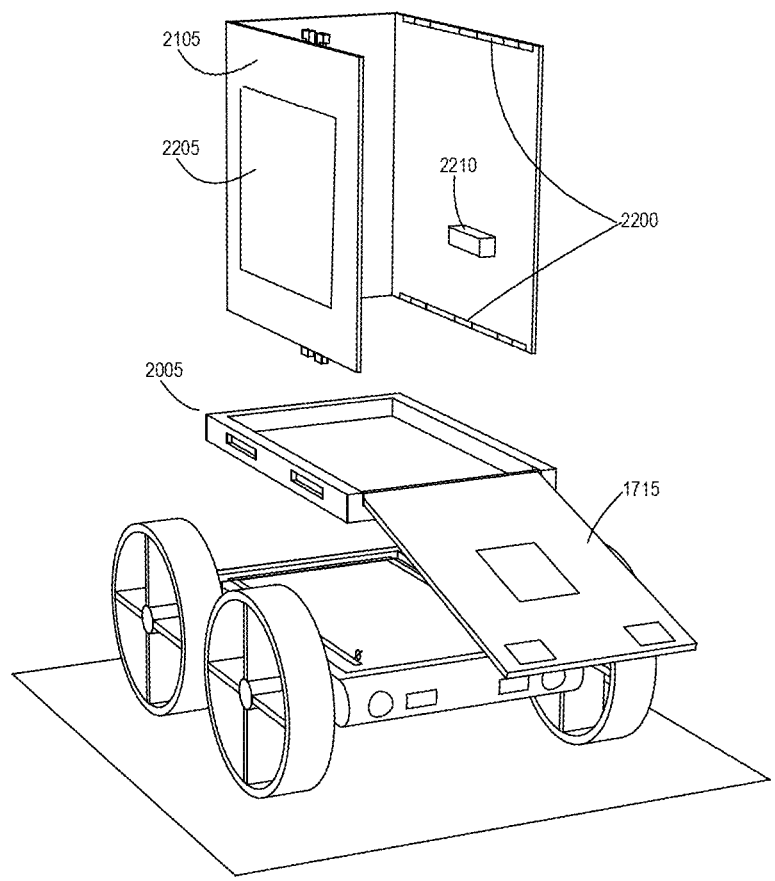
FIG. 22A is a diagram of an alternative view of the exemplary assembly of FIG. 21 having an exemplary modular mobility base (MB) unit component paired with an exemplary modular auxiliary power module (APM) and an exemplary modular cargo storage system (CSS) in accordance with an embodiment of the invention.
Figure 22B:
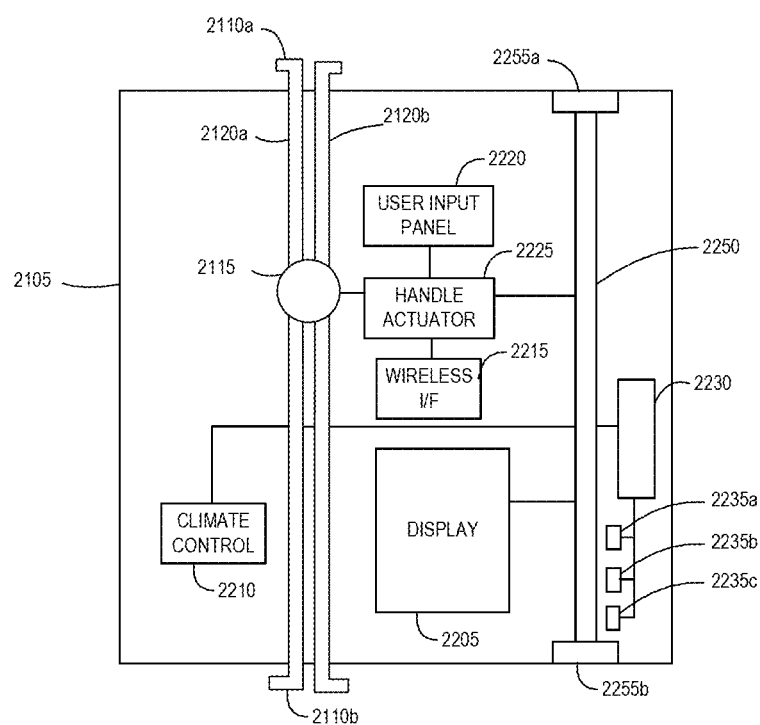
FIG. 22B is a block diagram showing further details of an exemplary modular cargo storage system component in accordance with an embodiment of the invention.

In the embodiment shown in FIG. 22A, the exemplary CSS 1720 is shown as being deployed with exemplary locking notches 2200 along its top and bottom (e.g., on the top edge and/or bottom edge of one of the sides/walls 2105). Such exemplary locking notches 2200 may be used in an embodiment of CSS 1720 to mate to corresponding interlocking structure on an APM 1710 below and/or MAM 1725 above. In this way, locking notches 2200 may provide another type of lockable connection with the APM 1710 below and the MAM 1725 above when assembled as part of an exemplary MALVT bot apparatus 1700.

Exemplary CSS component 1720 may be implemented with some or all of sides 2105 having branded graphics or with some or all sides having electronic screen displays 2205 for displayed graphics controlled by control electronics in MB 1705 or MAM 1725) depending on the operational use case with logos, identification information, warning labels and symbols, and other information useful in the logistics management and movement of what is temporarily stored and maintained with the particular CSS component 1720. An embodiment of such an electronic screen (generally referred to as an electronic display interface) on a side/wall 2105 of an exemplary CSS 1720 may be implemented as a translucent panel, similar to that described above relative to the cargo door for an APM component 1710, capable of displaying information via micro-projection or an embedded translucent LCD display grid that may be controlled or drive by a control element on assembly 1700. More specifically, display 2205 may be disposed on one of the folding structural walls 2105 as electronic display interface that is to a modular component power and data transport bus within the CSS 1720 and driven by a control element also coupled to such a bus so as to generate a visual message on the wall 2105 via the display 2205.

Figure 27A:
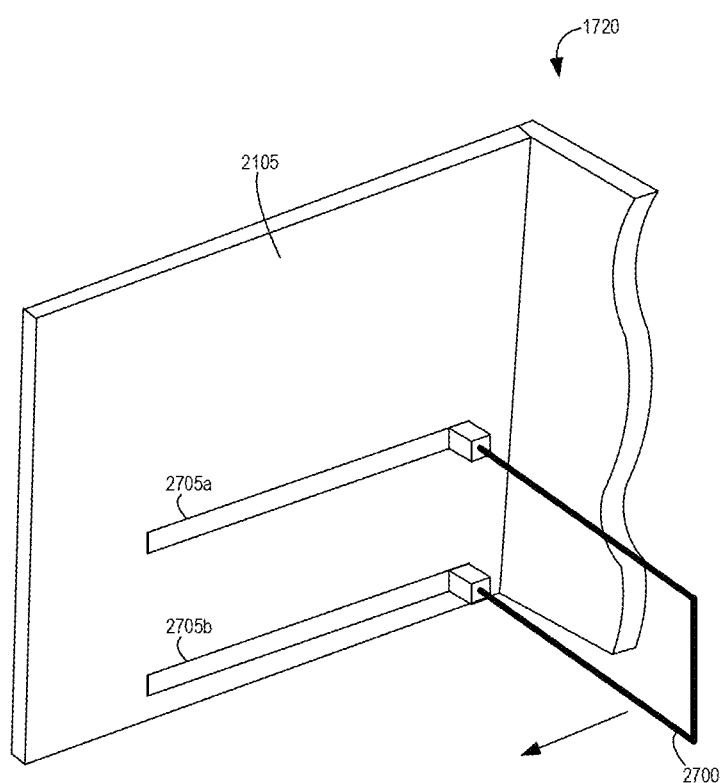
FIGS. 27A-27B are diagrams of an embodiment of an exemplary modular cargo storage system (CSS) having an exemplary actuated sliding arm disposed on one of the walls of the CSS in accordance with an embodiment of the invention.
Figure 27B:
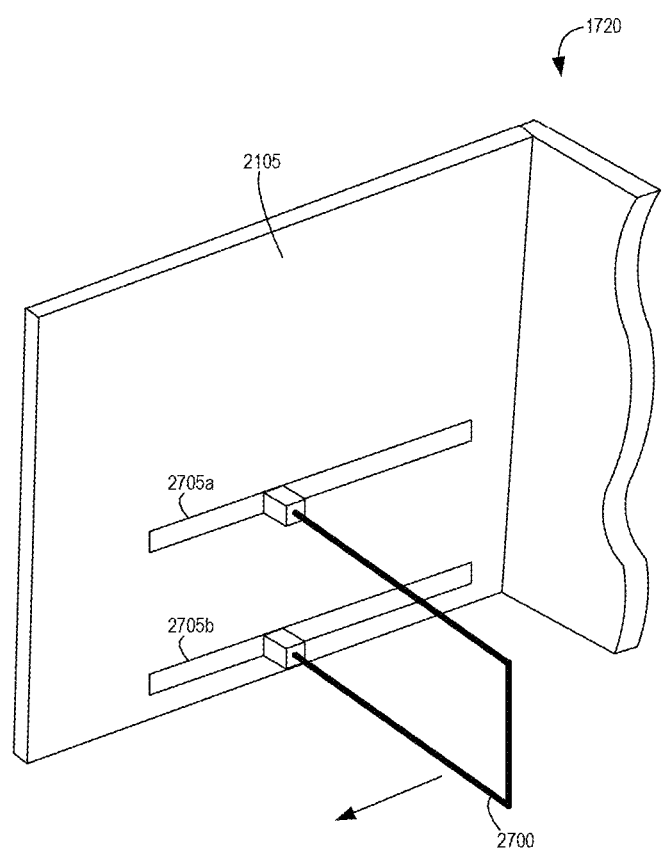
Figure 27C:
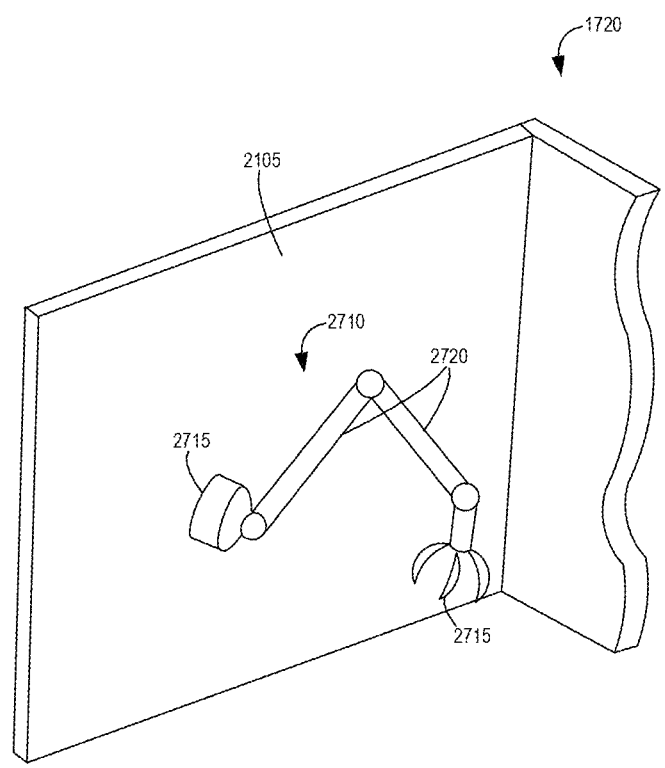
FIG. 27C is a diagram of an embodiment of an exemplary modular cargo storage system (CSS) having an exemplary actuated grabbing arm disposed on one of the walls of the CSS in accordance with an embodiment of the invention.

The exemplary CSS 1720 shown in FIG. 22A may also be deployed with physical sensing units for internal monitoring and managing of the CSS contents (e.g., one or more proximity sensors for detecting an object height of what may be moved by one or more sliding arms within the CSS) and that may communicate with the MAM 1725 attached above the CSS 1720. As will be explained in more detail below, such monitoring sensors may work in conjunction with articulating structure deployed as part of exemplary CSS 1720 (e.g., an articulating sliding arm or grabbing arm as shown in FIGS. 27A-27C) to help locate and direct movement of such articulating structure that engages and moves the item/object being shipped within the CSS 1720.

The exemplary CSS 1720 shown in FIG. 22A has a detachable modular climate control module 2210. In general, an exemplary climate control module 2210 may be a replaceable item detachably mounted to an interior side of one of the sides/walls 2105 (which may be insulated structural walls) on demand and as needed depending on the item/object to be shipped or transported. The exemplary climate control module generally has a climate control element (e.g., a heater and/or a cooling device) along with environmental sensors for the transport and monitoring of temperature sensitive items along with feedback and environmental control coupled to the climate control element. In more detail, an exemplary embodiment of detachable modular climate control module 2210 may be coupled to a modular component power and data transport bus within CSS 1720 (such as transport bus 2250), which provides access to at least power for the climate control module 2210 and, in some embodiments, control input for the climate control module 2210. As such, the climate control module 2210 can operate to heat or cool (or humidify or dehumidify) so as to alter an environment next to the climate control module 2210 (e.g., the payload area within the CSS 1720) to maintain a desired environment next to the climate control module 2210. The detachable modular climate control module 2210 may be temporarily attached to the insulated structural wall 2105, but can be removed when the set of folding insulated structural walls 2105 making up an embodiment of the CSS 1720 is configured in a folded into a stored state (such as that shown in FIGS. 23 and 24) or when removing the climate control module 2210 to replace it with another climate control module 2210 (e.g., to recharge the current climate control module, to use a different type of climate control module, and the like).

FIG. 22B is a block diagram showing further details of an exemplary modular cargo storage system component in accordance with an embodiment of the invention. Referring now to FIG. 22B, a diagram of an exemplary modular cargo storage system component 1720 as a functional block diagram of different elements that may be disposed on a side/wall 2105 (or different sides/walls 2105 that make up CSS 1720). For example, an exemplary modular component power and data transport bus 2250 is disposed on wall 2105. In this embodiment, while bus 2250 is shown disposed separate from where latches 2110a, 2110b with longitudinal support latches 2120a, 2120b run from top to bottom of the wall 2105, other embodiments may place the bus 2250 between such latches and support latches. In more detail, the exemplary modular component power and data transport bus 2250 shown in FIG. 22B has a top side modular component electronics interface 2255a and a bottom side modular component electronics interface 2255b. The top side modular component electronics interface 2255a may be disposed on a top edge of wall 2105, and the bottom side modular component electronics interface 2255b may be disposed on a bottom edge of the wall 2105. Each of the top and bottom side modular component electronics interfaces 2255a, 2255b has a power conduit outlet and a command and data communication interface. The power conduit outlet in the interface allows for power to be used by CSS 1720 and shared to other components of assembly 1700 (i.e., power may be provided through this power conduit through CSS 1720 and made available for active electronics used on and deployed with CSS 1720, such as wireless interface 2215, display 2205, actuators for the handle, locks, or other articulating structured deployed on CSS 7120).

As shown in FIG. 22B, exemplary side/wall 2105 is shown with latches 2110a, 2110b and locking handle 2115 disposed on side/wall 2105 as a type of interlocking alignment interface. The locking handle 2115, as shown in FIG.

22B (and as explained above) can be manually and/or electronically actuated to cause the set of latches 2110*a*, 2110*b* to interlock with at least the base platform on APM 1710 and with corresponding latches or notches on MAM 1725. In more detail, exemplary latches 2110*a*, 2110*b* may be implemented using a pair of longitudinal support latches 2120*a*, 2120*b* slidably attached to wall 2105 and coupled to the locking handle 2115. The longitudinal support latches 2120*a*, 2120*b* have top interlocking latches disposed above a top of the wall 2105 and a bottom interlocking latch disposed above a bottom of the wall 2105. As such, movement of the locking handle 2115 (e.g., a rotational movement of handle 2115) actuates a sliding movement of at least one of the longitudinal support latches 2120*a*, 2120*b* relative to the other in a first direction to cause the set of latches 2110*a*, 2110*b* to move and engage correlating to latching structure on the APM 1710 and MAM 1725. Moving the locking handle 2115 in the other direction actuates the sliding movement of at least one of the longitudinal support latches relative to the other of the longitudinal support latches in an opposite direction. For example, such sliding movement in response to actuation of the locking handle 2115 may move the top interlocking latches 2110*a* on each of the longitudinal support latches 2120*a*, 2120*b* towards each other above the top of the wall 2105 to engage a mating set of latches on a component of the modular autonomous bot apparatus 1700 disposed above the modular CSS 1720 (e.g., an exemplary MAM 1725). Likewise, such sliding movement of both of the longitudinal support latches 2120*a*, 2120*b* in response to actuation of the locking handle 2115 may also move the bottom interlocking latches 2110*b* on each of the longitudinal support latches 2120*a*, 2120*b* towards each other below the bottom of the wall 2105 to engage a mating set of latches on the base platform below the modular CSS 1720 (e.g., the base adapter platform 2005 of an exemplary APM 1710).

As shown in FIG. 22B, an exemplary CSS 1720 may deploy equipment that facilitates electronically actuation of the locking handle 2115 via wireless signals received through a wireless transceiver interface 2215 and passed to a handle actuator 2225, other remote control signals provided to the handle actuator 2225 from the modular component power and data transport bus 2250, and/or via input to a locally disposed user input panel (e.g., keypad, switch, button(s), touchscreen, and the like). For example, locking handle 2115 may be implemented as an actuated electro-mechanical locking handle responsive to a latch locking control input from a control component of the modular autonomous bot apparatus (e.g., a controller in exemplary MAM 1725 communicating through bus 2250). Such a latch locking control input received by the actuated electro-mechanical locking handle over the modular component power and data transport bus 2250 may actuate the set of latches 2110*a*, 2110*b* in response to the latch locking control input. In another example, such an actuated electro-mechanical locking handle may be responsive to an authorized wireless latch locking control input from a control component of the modular autonomous bot apparatus (e.g., a controller in exemplary MAM 1725 communicating through its onboard wireless transceiver). The electro-mechanical locking handle may have an integrated wireless transceiver or may be response to handle actuator 2225 via separate wireless transceiver interface 2215. The wireless latch locking control input may, as such, be wirelessly received by the actuated electro-mechanical locking handle causing the actuated electro-mechanical locking handle to actuate the set of latches 2110*a*, 2110*b* in response to the authorized wireless latch locking control input, which may be provided by an external wireless node disposed external to the modular autonomous bot apparatus 1700 authorized to unlock locking handle 2115. For example, a key code may be needed from the external wireless node to authenticate the wireless node and treat any control signal from the external wireless node as being authorized to lock or unlock the actuated locking handle 2115. In still another example, such an actuated electro-mechanical locking handle may be responsive to latch locking control input provided through user input panel 2220, which is then supplied to handle actuator 2225.

FIG. 22B also shows exemplary climate control module 2210 disposed on wall 2105. In some embodiments, exemplary climate control module 2210 may be battery powered, and/or self-regulating with a built-in environmental sensor to sense the environment next to the climate control module 2210 and a feedback thermostat integrated as part of the module using sensor data from the environmental sensor as a basis for altering the environment next to the climate control module 2210 to maintain the desired environment next to the climate control module 2210 (and within exemplary CSS 1720 when a cargo door closes the payload area within CSS 1720).

In other embodiments, exemplary climate control module 2210 may accept external power and/or remote commands/control input through modular component power and data transport bus 2250. For example, exemplary climate control module 2210 may be responsive to a climate control input from a control component of the modular autonomous bot apparatus 1700 where the climate control input is received by the climate control module 2210 the modular component power and data transport bus 2250. As such, the exemplary climate control module 2210 may alter the environment next to the climate control module 2210 to maintain the desired environment next to the climate control module 2210 (and within exemplary CSS 1720 when a cargo door closes the payload area within CSS 1720) in response to the climate control input from the control component through bus 2250. In still other embodiments, exemplary climate control module 2210 may accept wireless commands/control input from such a control component of the modular autonomous bot apparatus 1700 that is enabled with a wireless transceiver or from an authorized external wireless node disposed external to the modular autonomous bot apparatus 1700.

FIG. 22B further shows CSS 1720 may include exemplary sensors 2235*a*-2235*c* and sensor interface 2230. Exemplary sensor interface 2230 may be implemented with, for example, circuitry for buffering, processing, and/or interfacing with bus 2250. Other embodiments of sensor interface 2230 may implement a sensor wireless interface dedicated for sensor data broadcasting without the need to interface with bus 2250 or in addition to providing the sensor data on bus 2250). As noted above, an embodiment of one or more of such sensors 2235*a*-2235*c* may be implemented as one or more proximity sensors for detecting the position and/or height of an item/object that may be moved by articulating object manipulation structure deployed within the CSS (as shown in FIGS. 27A-27C). In another example, one or more of such sensors 2235*a*-2235*c* may be implemented as environmental sensors used for payload monitoring by MAM 1725 and/or climate monitoring within CSS 1720 as part of feedback for controlling climate control module 2210. Embodiments of sensors 2235*a*-2235*c* may be disposed on one or more internal sides of at least one of the folding structural walls 2105 of an exemplary CSS 1720 so that the sensors may monitor contents of the modular CSS 1720 in the payload area and/or a current environmental condition in the payload area. Sensor data from sensors 2235a-2235c may be provided through interface 2230 to bus 2250 (or directly to bus 2250), or to wireless interface 2215 through interface 2230 (or directly to wireless interface 2230) to an authorized recipient of such sensor data (e.g., an authorized control component of apparatus 1700 or an authorized external wireless node disposed external to the modular autonomous bot apparatus 1700).

Figure 23:
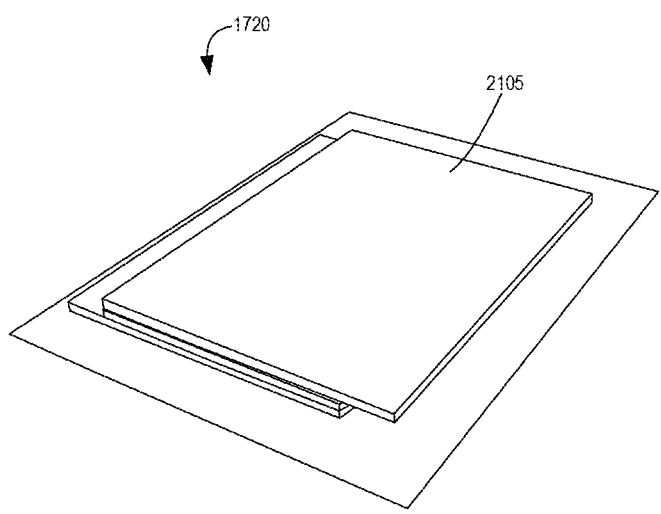
FIG. 23 is a diagram showing a folded configuration for an exemplary modular cargo storage system (CSS) in accordance with an embodiment of the invention.
Figure 24:
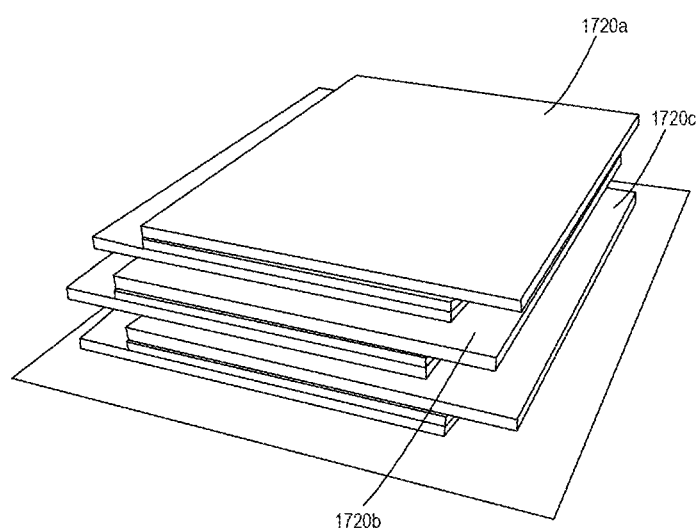
FIG. 24 is a diagram showing a folded configuration for multiple exemplary modular cargo storage system components in accordance with an embodiment of the invention.

To support storage of CSS units 1720, an embodiment of the CSS component 1720 may be implemented as a foldable component having a folding storage capability via, for example, hinged sides or walls 2105 such as shown in FIGS. 23 and 24, respectively. FIG. 23 shows a folded configuration for a single exemplary modular cargo storage system (CSS) 1720, while FIG. 24 shows multiple exemplary modular cargo storage system components 1720a-1720c in the folded configuration and stacked as they may be maintained prior to assembly at a bot storage facility or location in accordance with an embodiment of the invention. As part of the assembly of a CSS component 1720 into being part of an exemplary MALVT bot apparatus 1700, the CSS component 1720 may be unfolded from the folded configuration or stored state (as shown in FIG. 23), and aligned into channels (e.g., channels 2010 of the APM) to guide CSS 1720 into proper position with the other major components (MB 1705, APM 1710, and MAM 1725) and then secured in the proper position.

As explained above, positive locking mechanisms (e.g., locking handle 2115 and latches 2110) may be actuated electronically (such as via control signals from controllers or control processing systems within MB 1705 or MAM 1725) or, in some cases, actuated manually by handles 2115 integrated into the side 2105 of the foldable container may be employed to mechanically secure the major components (i.e., MB 1705, APM 1710, CSS 1720, and the MAM 1725). In this way, an exemplary MALVT bot apparatus 1700 may be assembled as a modular assembly, with components that may be interchanged and swapped out, and provisioned rapidly, with movement of the handle 2115 of the positive locking mechanism. The locking latches (e.g., secured by rotating the CSS locking handle 2115 shown in FIG. 21 or actuated as described above into the assembled position) may be locked via a key, a user input panel 2220 (e.g., a keypad, or touch interface) disposed on exemplary MALVT bot apparatus 1700 or secured via other types of locking systems (e.g., onboard cameras for biometric scan or facial recognition using sensors on components of the exemplary MALVT bot apparatus 1700, key code entry or electronic code interrogation using human or machine communication interfaces with the exemplary MALVT bot apparatus 1700, or node association-based unlocking based upon on authorized node-to-node associations).

Figure 25:
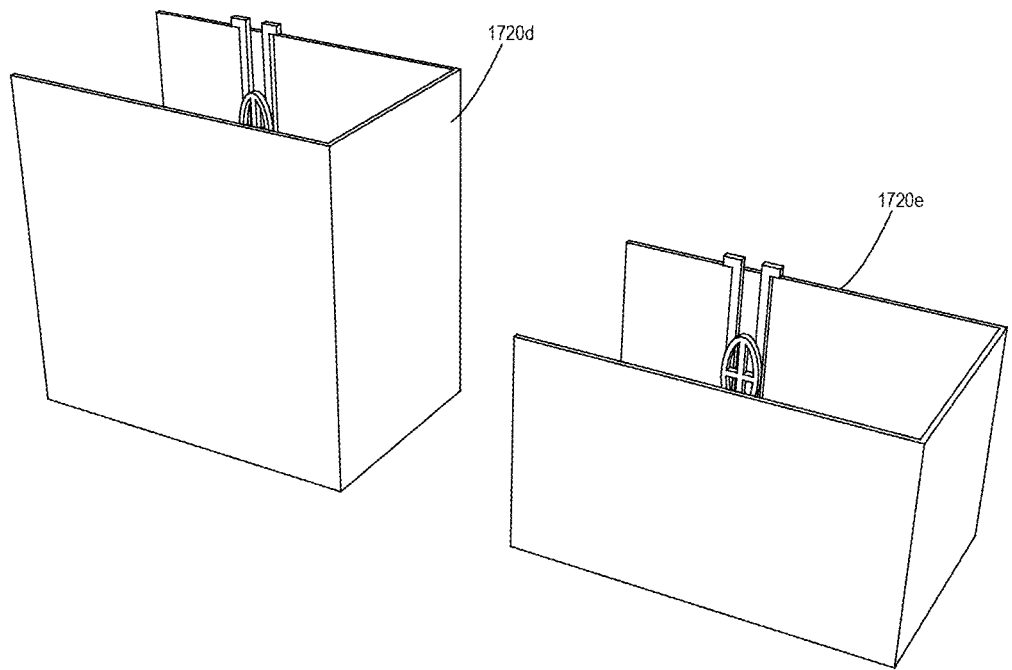
FIG. 25 is a diagram showing different exemplary form factors for different exemplary modular cargo storage system components in accordance with an embodiment of the invention.

As shown in FIG. 25, the form factor (e.g., height or other size characteristic) of an exemplary CSS 1720 may vary depending on the intended use or deployment application for the particular CSS component 1720. For example and as shown in FIG. 25, one exemplary CSS 1720d may be a taller type for use in less obstructed areas (such as in streets) while another exemplary CSS 1720e may be a shorter type for use in more limited areas (such as on sidewalks).

In still another embodiment, an alternate configuration of an exemplary CSS 1720 may be implemented as having an actuated or manually operated integrated cargo door as part of or in place of one of the sides 2105 of CSS 1720. In such an embodiment, the integrated cargo door may use a joint, such as mounted hinge, that may be operated similar to the cargo door 1715 of the APM 1710 as described above when loading and unloading cargo. A further embodiment may have an exemplary CSS 1710 configured with a cargo door in addition to the three sides/walls 2105 shown in the embodiments described above. In this further embodiment, the cargo door may slide, retract, extend out, or otherwise open relative to the other sides 2105 manually or in an actuated manner. In other words, this further embodiment has an integrated cargo door on the CSS 1720 that may be similarly implemented in how it may be articulated and configured with actuators and/or other structure to support the same characteristics of the bottom mounted door 1715 of the APM 1710, including self-closing and locking capability.

Figure 26:
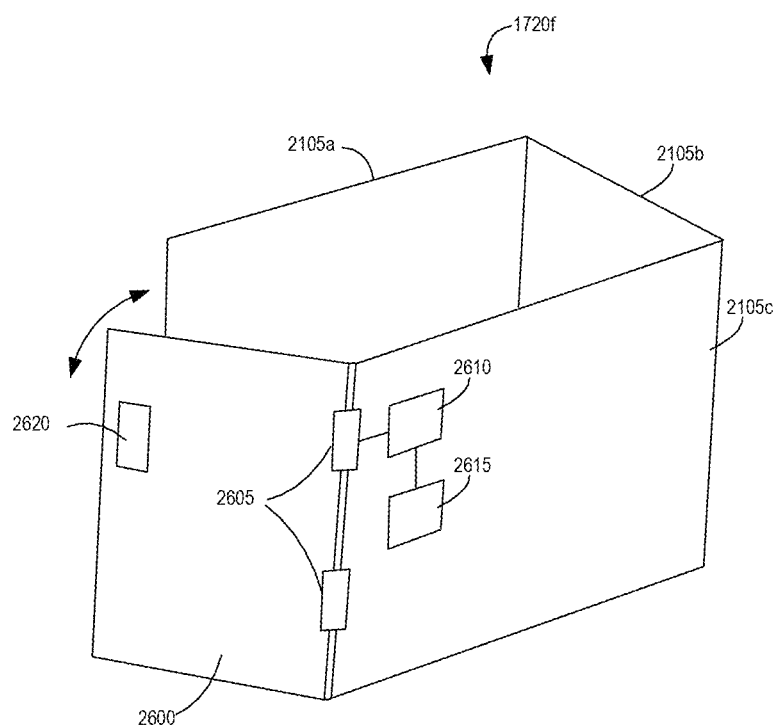
FIG. 26 is a diagram of an alternative embodiment of an exemplary modular cargo storage system (CSS) having an exemplary actuated cargo door in accordance with an embodiment of the invention.

FIG. 26 is a diagram of such an alternative embodiment of an exemplary modular cargo storage system (CSS) having an exemplary actuated cargo door in accordance with an embodiment of the invention. Referring now to FIG. 26, an embodiment of an exemplary CSS 1720f is shown having three sides/walls 2105a-2105c being jointed structural walls, and with a cargo door 2600 as a fourth type of wall, but one that opens to provide access within the payload area within CSS 1720f In more detail, exemplary CSS cargo door 2600 is configure with one or more joints 2605 that movably attach door 2600 to one of the walls 2105c so that the door may be selectively opened to provide such access within the payload area within CSS 1720f and closed to secure and vertically enclose the payload area.

Exemplary joint(s) 2605 may be implemented as a simple mechanical hinge, which in some embodiments may be spring loaded so as to actuated to self-close. In other embodiments, exemplary joint(s) 2605 may be actuated to open/close using an integrated door actuator as part of the joint itself or via a separate door actuator 2610 fixed to the cargo door 2600 and operative to selectively cause the cargo door 2600 move and provide access to within the payload area. Embodiments may also have a door actuator driver 215 coupled to the door actuator 2610 for controlling the operation of the door actuator 2610. For example, the door actuator driver 2615 may be responsive to a cargo door control input from a control component of the modular autonomous bot apparatus 1700 (e.g., a controller in the MB 1705 or MAM 1725) over bus 2250 or wirelessly transmitted from such an authorized control component within apparatus 1700 or an authorized external wireless node disposed external to the modular autonomous bot apparatus 1700. As such, the cargo door control input received by door actuator driver 2615 causes the door actuator 2610 to selectively move the cargo door in response to the cargo door control input. A further embodiment may have such a cargo door control input being generated from user input panel 2220 with input that reflects an authorized permission to have the door 2600 opened (e.g., via entry of a code). Further embodiments may use an external sensor for other m An embodiment of cargo door 2600 on CSS 1720f may include an actuated lock 2620 (e.g., an electro-mechanical lock, magnetic lock, and the like) responsive to door lock control input signals from a control component of the modular autonomous bot apparatus 1700 (e.g., a controller in the MB 1705 or MAM 1725) over bus 2250 or wirelessly transmitted from such an authorized control component within apparatus 1700 or an authorized external wireless node disposed external to the modular autonomous bot apparatus 1700. Similar to the actuated locking systems described above (e.g., related to the locking latches and locking handle), cargo door 2600 may use an actuated lock 2620 responsive to other signals or input that operate as the authorized door lock control input signal, such as input received over user input panel 2220 (e.g., key code entry via a keypad, buttons, or touch interface) disposed on exemplary MALVT bot apparatus 1700 or via a specific user input panel 2630 disposed on the cargo door 2600, input received from an externally focused sensor or camera on the CSS 1720f or other component of the apparatus 1700 (e.g., a sensor on the MAM 1725) for biometric scan or facial recognition, key code entry, or input received from electronic code interrogation using human or machine communication interfaces with the exemplary MALVT bot apparatus 1700, or node association-based unlocking based upon on authorized node-to-node associations.

A further embodiment of door 2600 on CSS 1720f may have a translucent door panel 2625 disposed on it as a type of electronic display interface where visual messages may be generated and shown with symbols and generated characters. Such a translucent panel 2625 may be implemented similar to that of translucent panel 2030 on the door 1715 on APM 1710 in that it allows visibility through the cargo door while also being operative to generate the visual message on the cargo door with generated characters (e.g., prompted instructions related to delivery of the item being shipped, electronically displayed information about the item being shipped, and the like).

FIGS. 27A-27C are diagrams of embodiments of an exemplary modular cargo storage system (CSS) having different types of exemplary actuated or articulating object manipulation systems (e.g., actuated sliding arms, actuated grabbing arms) disposed on one of the walls of the CSS in accordance with an embodiment of the invention. For example, FIG. 27A illustrates an exemplary actuated sliding arm 2700 disposed and actuated to move on guiderails 2705a, 2705b on a wall 2105 of exemplary CSS 1720. In some embodiments, the actuated sliding arm, as an assembly, is integrated with one of the walls 2015 of CSS 1720. However, other embodiments may deploy the actuated sliding arm as a detachable module that can be mounted to one of the walls 2015 of CSS 1705.

In more detail, exemplary actuated sliding arm 2700 may be disposed as an assembly (with the arm 2700 mounted to sliding bases that run within guiderails 2705a, 2705b in response to sliding arm control input). Such an actuated sliding arm assembly may be coupled to the modular component power and data transport bus 2250 so as to at least power the actuated sliding arm assembly. More specifically, the exemplary actuated sliding arm assembly may include the actuated sliding arm 2700 removably affixed to the one of the folding structural walls, and a sliding arm actuator driver coupled to the actuated sliding arm 2700 and responsive to a sliding arm control input generated by a control component of the modular autonomous bot apparatus 1700 (e.g., a controller in the MAM 1725) or to an authorized wireless sliding arm control input generated by an external wireless node disposed external to the modular autonomous bot apparatus 1700 or by a wireless transceiver in another component of the modular autonomous bot apparatus 1700. As such, the sliding arm actuator driver may the actuated sliding arm 2700 to move the item being shipped within the payload area in response to the sliding arm control input, such as that shown in FIG. 27B.

FIG. 27C is a diagram of an embodiment of an exemplary modular cargo storage system (CSS) having an exemplary actuated grabbing arm disposed on one of the walls of the CSS in accordance with an embodiment of the invention. As shown in FIG. 27C, CSS 1720 has an exemplary actuated grabbing arm assembly 2710 disposed on a wall 2105, which may be fixed or detachably disposed on the wall 2105. The assembly 2710 includes a stationary base 2715 removably attached to the wall 2105, a movable grabbing arm 2720 coupled to the stationary base 2715 with multiple degrees of freedom of movement, and grip head 2725 disposed on the distal end of the movable grabbing arm 2720 where the grip head 2725 is articulable to grab onto the item being shipped as disposed within CSS 1720. The grabbing arm actuator driver is operatively coupled to and controls movement of the actuated grabbing arm assembly 2710 by being responsive to sensor data from internal sensors (e.g., proximity sensors 2235a-2235c) indicating a location of the item) and a grabbing arm control input generated by a component of the exemplary MALVT bot apparatus 1700 (e.g., the controller or processor in the MAM unit 1725) or an external wireless node or a wireless transceiver within a component of the bot apparatus 1700. In this way, the grabbing arm actuator driver (a) detects the item being shipped using the sensor data, (b) causes the actuated grabbing arm 2720 to move towards the item being shipped, (c) causes the grip head 2725 to grab onto the item being shipped, and (d) causes the actuated grabbing arm assembly 2710 to move the item being shipped as maintained within the grip head 2725 from within the payload area to outside the payload area in response to the grabbing arm control input.

Mobile Autonomy Module (MAM) Component

Figure 32:
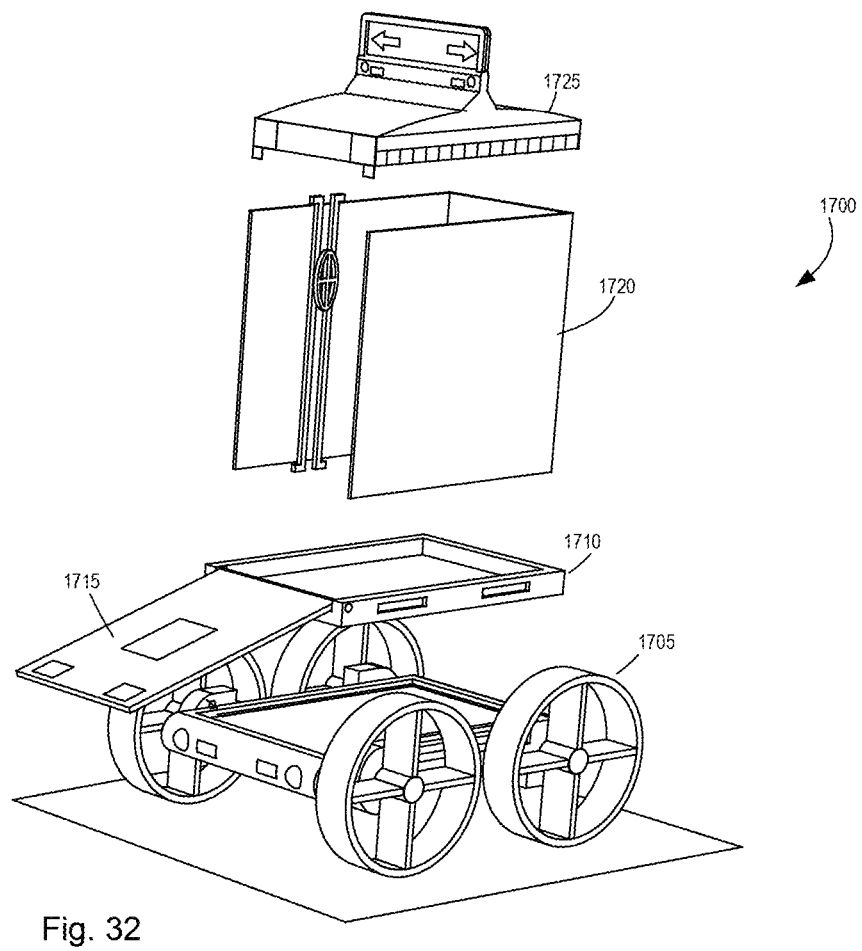
FIG. 32 is a diagram of an exemplary assembly of an exemplary modular mobility base (MB) unit component shown in conjunction with an exemplary modular auxiliary power module (APM), an exemplary modular storage system (CSS), and an exemplary modular mobile autonomy module (MAM) in accordance with an embodiment of the invention.
Figure 33:
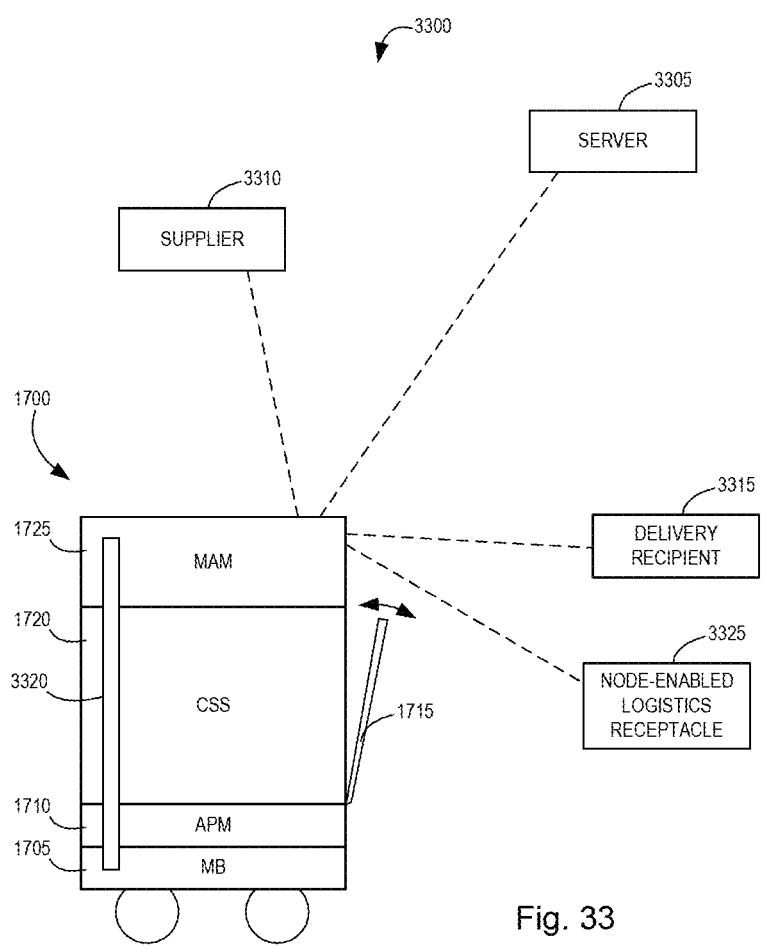
FIG. 33 is a diagram of an exemplary system having exemplary modular mobile autonomy module (MAM) within an exemplary modular autonomous bot apparatus assembly where the MAM is in communication with an exemplary server and mobile external wireless nodes in accordance with an embodiment of the invention.

As noted above, exemplary MAM 1725 is an example of a control component of apparatus 1700 deployed with sensors, lights, displays, an autonomous control system that interacts with other components of apparatus 1700 while providing a "hat" like cover for a CSS 1720 and its payload area, and payload monitoring capabilities as part of modular autonomous bot apparatus (such as exemplary MALVT bot apparatus 1700). FIGS. 28-31 provide illustrations of an exemplary Mobile Autonomy Module (MAM) 1725 as shown by itself with its components, while FIG. 32 illustrates an exemplary MAM 1725 as part of an exemplary MALVT bot apparatus 1700 in an assembled configuration and FIG. 33 illustrates an exemplary MAM 1725 operating as part of apparatus 1700 in an exemplary system where the MAM 1725 may communicate with a server and/or mobile wireless external nodes operated by a supplier and a delivery recipient.

Figure 28:
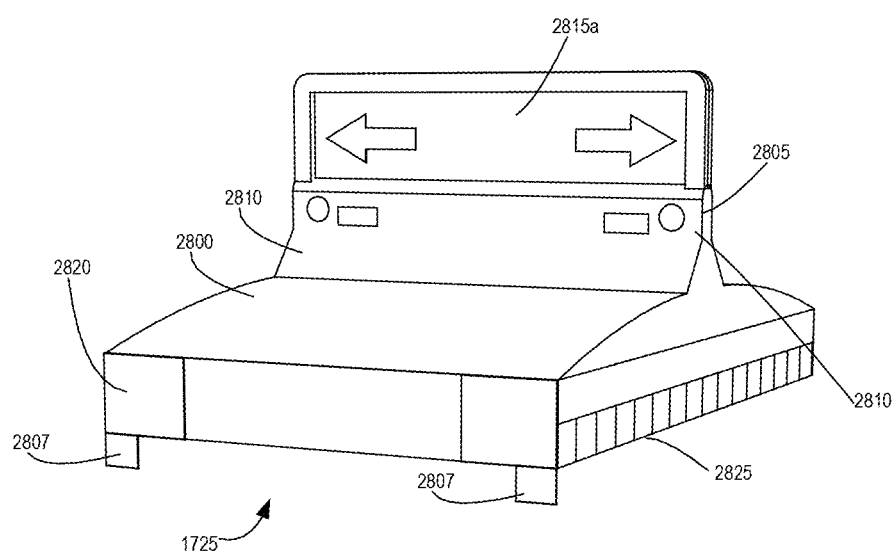
FIG. 28 is a front view of an exemplary modular mobile autonomy module (MAM) in accordance with an embodiment of the invention.
Figure 29:
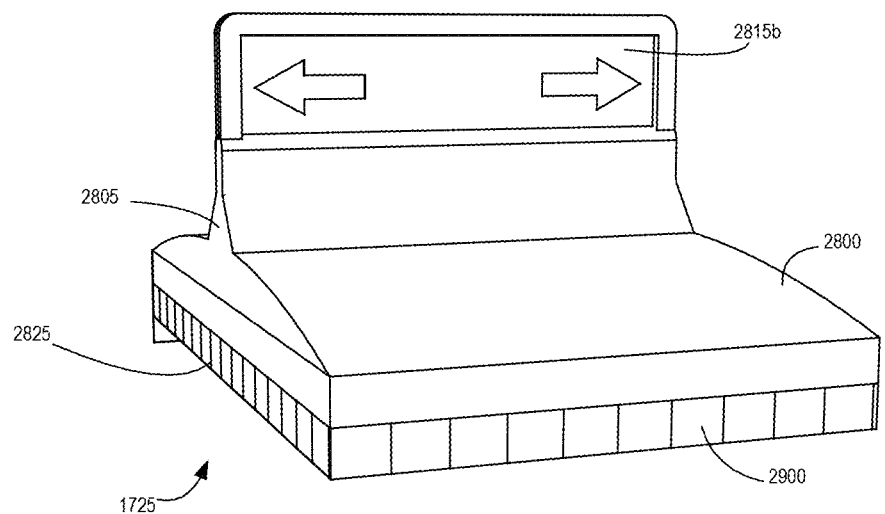
FIG. 29 is a rear view of the exemplary modular mobile autonomy module (MAM) of FIG. 28 in accordance with an embodiment of the invention.
Figure 30A:
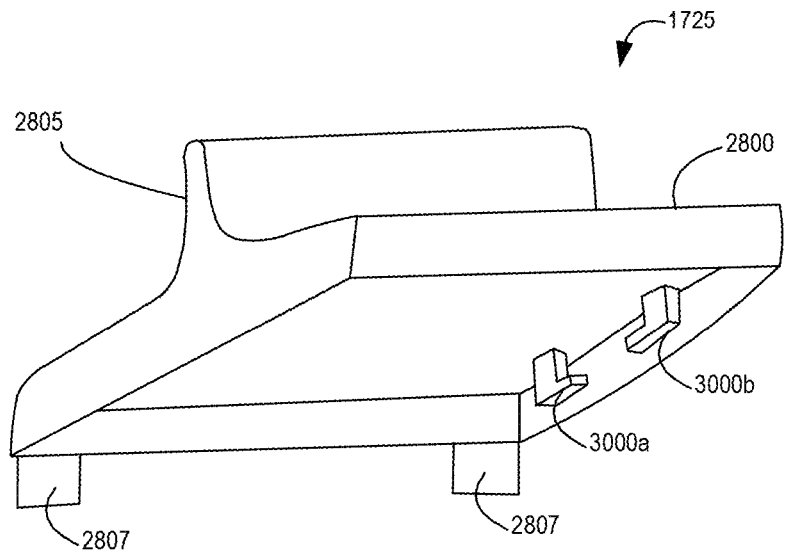
FIGS. 30A-30B are diagrams of different bottom views of the exemplary modular mobile autonomy module (MAM) of FIG. 28 in accordance with an embodiment of the invention.
Figure 30B:
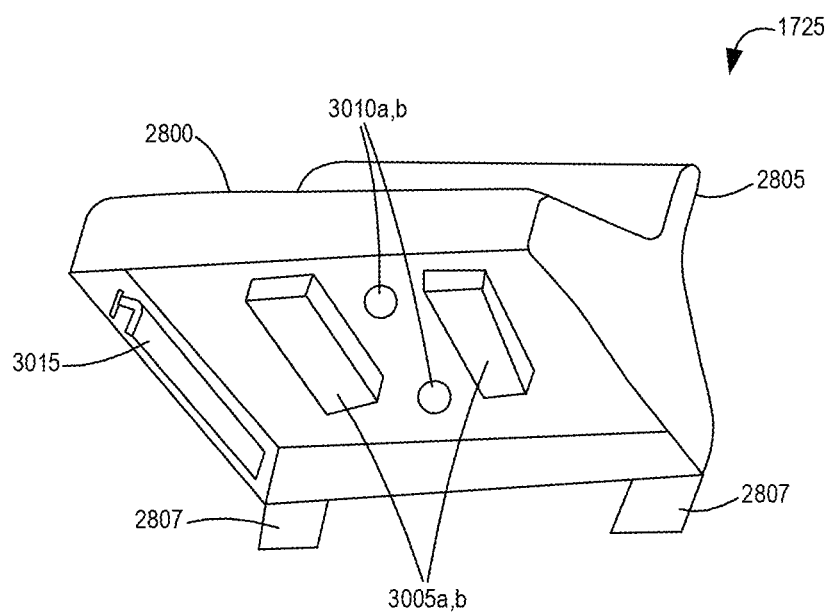

Referring now to FIG. 28, exemplary MAM 1725 is shown from its exterior as a top-level control component/device for the exemplary MALVT bot apparatus 1700. An exemplary MAM 1725, such as that shown in FIGS. 28-33, may be deployed similar to that of a master node implemented autonomous control system that communicates and controls other components of the exemplary MALVT bot apparatus 1700 in the assembled configuration, has user interfaces and location circuitry, as well as communicates with other nodes through wired connections and wireless connections. In more detail, an embodiment of MAM 1725 may be implemented, for example, with a detachable modular housing having a horizontally-oriented base cover 2800 configured to detachably cover the payload area vertically defined by walls 2105 of CSS 1720 and cargo door 1715 of APM 1705 when the MAM 1725 is attached on top of the modular CSS 1720 as part of the modular autonomous bot apparatus 1700. The base cover 2800 has a curved top side (as shown in FIGS. 28-29), a bottom side (as shown in FIGS. 30A-30B), and peripheral sides or edges upon which lights 2820 and multi-element light panels 2825, 2900 may be disposed as well as mounting tabs 2807 that help in mounting MAM 1725 onto an exemplary CSS 1720. In some embodiments, such peripheral sides/edges may also include other displays (similar to displays 2815a, 2815b) and sensors (similar to sensors 2810). In the embodiment shown in FIGS. 28-29, the detachable housing has base cover 2800 with a vertically-oriented raised display support 2805 protruding up from the top side of the base cover 2800. While the display support 2805 shown in FIGS. 28-29 is disposed across from the left side of cover 2800 to the right side of cover 2800, other embodiments of display support 2805 for an exemplary MAM 1725 may position the display support 2805 disposed on cover 2800 in other configurations—e.g., disposed from the front to the back of cover 2800, disposed diagonally on top of cover 2800, and the like.

The electronics elements used as part of MAM 1725 may be disposed in different parts of the detachable modular housing. For example, displays 2815*a*, 2815*b* may be disposed on parts of cover 2800 (e.g., on either side of vertically-oriented raised display support 2805). Sensors 2810 may be disposed on vertically-oriented raised display support 2805 (or other parts of cover 2800 in other embodiments) along with lights 2820 that are externally focused. Exemplary lights 2830 may be, for example, disposed on peripheral sides of the base cover 2800, and selectively powered by an autonomous control system within MAM 1725 to enhance processing of the sensor data from the external sensors 2810 and enhance processing of the outside sensor data from the additional sensors disposed on MB 1705 as provided to MAM 1725.

In general, further components of MAM 1725 not shown on the exterior of MAM 1725 in FIGS. 28-29 include a central controller and processing hardware similar to that of a master node that may include control electronics (e.g., one or more processors or microcontrollers as a processing system with local memory storage and volatile memory) operating as an autonomous control system or autonomous controller; location circuitry (such as a GPS chipset and antenna); wireless and wired communication interfaces for one or more hardware or software-implemented radios; program code that, when executing on the processing and controller elements, governs control of the MAM 1725 (as well as the apparatus 1700), sensor processing, autonomous movement control of the apparatus 1700 (via communication with MB 1705), navigation for the apparatus 1700 (via control provided to MB 1705), and object delivery control; and multiple command and data interfaces for display outputs (e.g., via screens, displays, LED indicators), control output (e.g., for sending control signals to control elements of MB 1705, APM 1710, and for sending control signals to control the environment within CSS 1720), and for sensor input from sensors on the MAM 1725 as well as sensors disposed in other components of apparatus 1700 (e.g., sensors within CSS 1720, sensors deployed on the MB 1705, and the like).

FIGS. 30A-30B are diagrams of different bottom views of the exemplary MAM 1725 of FIG. 28 in accordance with an embodiment of the invention. Referring now to FIG. 30A, a perspective view of exemplary MAM 1725 is illustrated showing features on the bottom side of base cover 2800, such as exemplary set of latching points 3000*a*, 3000*b*. These latching points may be incorporated on MAM 1725 as latches that work to couple the detachable modular housing to the modular CSS 1720 of the modular autonomous bot apparatus 1700. For example, latching points 3000*a*, 3000*b* may be implemented as fixed and passive latches that engage and mate (e.g., as interlocking latches) to an opposing set of moveable latches, such the movable latches 2110*a* on CSS 1720 in response to actuated movement via handle 2115. As such, the detachable modular mobile autonomy control module (e.g., exemplary MAM 1725) may be secured to the modular CSS 1720 and cover the payload area when the passive latches 3000*a*, 3000*b* are engaged with the opposing set of movable latches 2110*a* on CSS 1725.

Referring now to FIG. 30B, further elements of an exemplary MAM 1725 are shown on the bottom of the base cover 2800. For example, as shown in FIG. 30B, payload monitoring sensors are shown disposed on the bottom side of the base cover 2800 in removable payload sensor pods 3005*a*, 3005*b*. Within such removable pods or modules, the payload monitoring sensors may be deployed to generate payload sensor data, which is then sent to the control system on the MAM 1725. Such payload sensor data reflects what is going on with items in the payload area or conditions in the payload area (e.g., temperature, humidity, movement of objects/items, and the like). In more detail, with such internally focused payload monitoring sensors (shown as sensors 3130 in FIG. 31), an embodiment of MAM 1725 may also be able to sense if objects are inside the container (e.g., the storage area defined by CSS 1720 as assembled on top of APM 1710 and covered by MAM 1725), if objects have moved, and detect a condition of the object. Exemplary removable payload sensor pods 3005*a*, 3005*b* may be attached, removed, and swapped out within MAM 1725 according to a particular logistics operation tasked to the MAM 1725.

Exemplary MAM 1725 may also have interior lights 3010*a*, 3010*b* disposed on the bottom side of the base cover 2800. Such lights 3010*a*, 3010*b* may be activated by the control system in the MAM 1725, and may provide light to assist with the payload monitoring sensors (such as sensors 3130 and sensors within payload sensor pods 3005*a*, 3005*b*) and/or to assist with loading and unloading items/objects from within the CSS 1720 under the MAM 1725. In more detail, an example of exemplary interior lights 3010*a*, 3010*b* may be payload focused lights disposed on the bottom of the base cover 2800, and selectively powered by the autonomous control system 3100 to enhance processing of the payload sensor data from the payload monitoring sensors 3130 (e.g., payload sensors in payload sensor pods 3005*a*, 3005*b*) disposed on the bottom side of the base cover 2800).

Exemplary MAM 1725 may also have locking tab(s) 3015 disposed on the bottom side of the base cover 2800. Such locking tab(s) 3015 provide a corresponding interlocking structure on MAM 1725 that may interface to and secure with locking notches 2200 disposed on the top edge of wall 2105 of an exemplary CSS 1720. As such, an exemplary MAM 1725 may be aligned on one edge with a CSS 1720 by mating the locking notches 2200 of the CSS 1725 to the locking tab or tabs 3015 on the MAM 1725, and then securing the MAM 1725 to the CSS 1720 via interlocking latches 2110*a* on CSS 1720 that are moved (e.g., manually or electronically actuated) to mate with interlocking latches 3000*a*, 3000*b* on MAM 1725.

Figure 31:
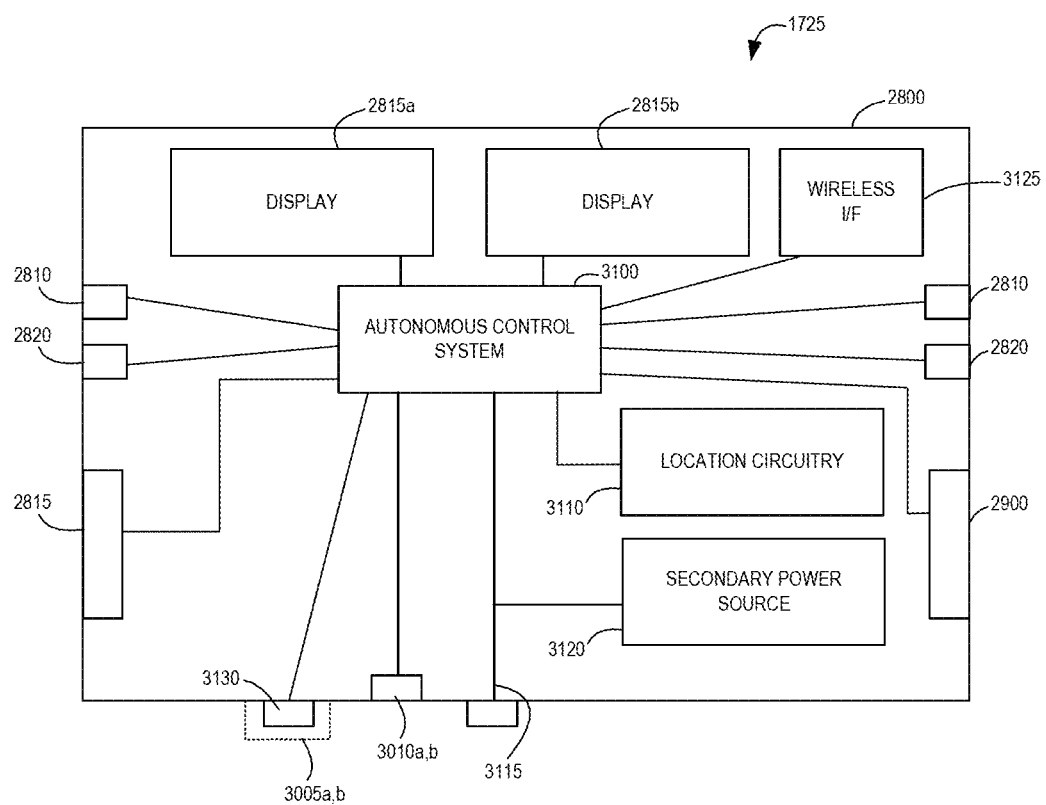
FIG. 31 is a block diagram showing further details of an exemplary modular mobile autonomy module (MAM) in accordance with an embodiment of the invention.

FIG. 31 is a block diagram showing further details of an exemplary mobile autonomy module (MAM) in accordance with an embodiment of the invention. Referring now to FIG. 31, exemplary elements of an embodiment of MAM 1725 are shown generally disposed in or on exemplary detachable modular housing (e.g., in or on base cover 2800) including autonomous control system 3100, displays 2815*a*, 2815*b*, sensors 2810, 3130, lights 2820, 3010*a*, 3010*b*, wireless radio transceiver 3125, location circuitry 3110, secondary power source 3120, as well as a modular component power and data transport bus 3115.

The exemplary autonomous control system 3100 is an implementation of at least one controller or processor that is operatively connected to the sensor array of sensors 2810, 3130 through interfacing circuitry or dedicated sensor processing circuitry that may buffer sensor data and process the sensor data. As an autonomous controller, exemplary autonomous control system 3100 has the power and self-governance in the performance of sensor processing and responsive control functions that allow the assembly 1700 to move, avoid collisions, navigate towards specified locations, and effect actuated and articulated interactions while moving or stationary as part of the logistics operations described herein. Such an exemplary autonomous control system 3100 may be implemented as an onboard processing module or system with one or more processors or controllers (such as CPUs/GPUs) and program code or software modules that execute on this platform to programmatically configure the autonomous control system 3100 to be operative to provide the autonomous capability to run an exemplary MALVT bot apparatus 1700 as discussed herein. For example, an exemplary controller/processor used as the autonomous control system 3100 in the MAM 1725 may be implemented with a central controller and processing hardware similar to that of a master node that may include control electronics (e.g., one or more processors or microcontrollers as a processing system with local memory storage and volatile memory) operating as an autonomous control system or autonomous controller that processes massive real-time data captured by the sensor array by executing program code that, when executing, governs control of the MAM 1725 (as well as the apparatus 1700), sensor processing, autonomous movement control of the apparatus 1700 (via communication with MB 1705), navigation for the apparatus 1700 (via control provided to MB 1705), and object delivery control.

An exemplary autonomous control system 3100 may also have redundant, fault-tolerant features for safety control, as well as parallel sensing and parallel processing that allows for common and/or distributed management for operations of such an exemplary autonomous control system 3100. For example, an embodiment of autonomous control system 3100 may deploy distributed management where tasks may be offloaded from a particular processor or system within autonomous control system 3100 and assigned (permanently or dynamically) to another processor or system (e.g., where a sensor may have processing of its sensor data built-in, which offloads the sensor data processing from another processor or system within an embodiment of autonomous control system 3100).

Those skilled in the art will appreciate that exemplary autonomous control system 3100 may, for example, be implemented with an NVIDIA® Jetson™ Xavier AI embedded computing module for autonomous machines that features a 512-Core Volta GPU with Tensor Cores, 8-Core ARM 64-Bit CPU, dual NVDLA deep learning accelerators, video processor for up to 2×4K 60 fps encode and decode, seven-way VLIW vision processor and 16 GB 256-Bit LPDDR4 memory. Another embodiment of such an exemplary autonomous control system 3100 may, for example, be implemented with an ARM Cortex-A76AE autonomous processor with superscalar, out-of-order processing and split-lock flexibility to allow for a split mode with highest multicore performance or split mode for advanced multicore fault-tolerance features for built-in safety and diagnostic functionality at a hardware level (e.g., fail-operational or fault-tolerant capability—where the control system detects a control system fault with memory, processing, data bus, or other control system sub-systems, reports the fault, and continues operation in a degraded mode as needed).

The exemplary location circuitry 3110 (such as a GPS chipset and antenna) is operatively coupled to the autonomous control system 3100 and generates location data on a location of the MAM 1725 and provides the location data to the autonomous control system 3100. Those skilled in the art will appreciate that location circuitry 3110 may be implemented similar to dedicated location positioning circuitry 475 (e.g., GPS circuitry) described above that allows a master node to self-determine its location or to determine its location by itself.

Exemplary external sensors 2810 are disposed on the detachable modular housing and are operatively coupled to the autonomous control system 3100. In this exemplary configuration, the external sensors 2810 generates external sensor data on an environment external to the MAM 1725 as detected by the external sensors 2810 and providing the sensor data to the autonomous control system 3100. In more detail, such external sensors 2810 may be implemented as an array of one or more sensors for detecting the outside world using one or more types of sensors. Exemplary types of sensors 2810 may include, but are not limited to, cameras, LIDAR/RADAR, Inertial Measurement Units (IMUs), location circuitry (GPS), and environmental sensors for temperature, humidity, rain, pressure, light, shock/impact, and the like. Other types of sensors 2810, depending on the application, may also include proximity sensors, chemical sensors, motion detectors, etc.

In a further embodiment, some or all of these sensors 2810 may be contained in one or more submodular "sensor domes" or sensor pods where each may be detachable or removably attached to the base cover 2800 of the MAM 1725, and may be interchanged based on use case (e.g., in-facility, on-road, etc.). As such, an exemplary replaceable sensor dome or pod may contain all sensors for the MAM 1725 or contain a subset of external sensors 2810 to be used by the MAM 1725. In a further example, different subsets of external sensors 2810 may be respectively implemented in a different interchangeable, detachable, replaceable sensor pods. Each of such sensor pods may be deployed as having a characteristic type of sensors in the subset of the external sensors 2810 (e.g., one detachable sensor pod of external sensors having night vision specific sensors, another detachable sensor pod of external sensors having proximity sensors of a particular sensing range useful for internal building deployment, another detachable sensor pod of external sensors having proximity sensors of a longer sensing range useful for exterior street deployment, and the like). Thus, like the internally focused payload monitoring sensor pods that may be detached, replaced, and used to configure and exemplary MAM 1725 for a particular targeted or dispatched logistics operation for transporting a particular item/object, the exemplary MAM 1725 may be configured with particular externally focused sensor pods that may be detached, replaced, and used for a particular targeted or dispatched logistics operation for moving assembly 1700 (including MAM 1725) through a targeted or anticipated environment when moving from an origin location (e.g., a pickup location or bot storage location) to a delivery destination location.

As shown in FIG. 28, exemplary external sensors 2810 may be placed on surfaces of the MAM 1725, such as along vertically oriented surfaces on top of the MAM 1725 on support 2805, but further embodiments may have a portion of (or all) sensors 2810 placed in other locations that focus in particular directions relative to the MAM 1725 (e.g., forward-facing sensors, side sensors, rear-facing sensors, ground-facing sensors, upward-focused sensors, and the like) or as an omni-directional sensor on the MAM 1725.

An embodiment of MAM 1725 may have the autonomous control system 3100 be programmatically adapted and configured to be operative to process at least the sensor data from the external sensors disposed on the detachable modular housing for object detection and collision avoidance as part of generating the steering and propulsion control output signals. In a further example, such sensor processing may involve sensor data that includes sensor data from external sensors 2810, sensor data from payload monitoring sensors 3010, as well as sensor data from MB 1705. In another example embodiment, autonomous control system 3100 may be implemented with dedicated sensor processing circuitry that is deployed to quickly process what may be massive amounts of sensor data (e.g., external sensor data, sensor data from internal sensors 3010$a$, 3010$b$, as well as sensor data from MB 1705) so that remaining control elements of autonomous control system 3100 (e.g., other controllers or processors) may be programmatically configured to handle other tasks of the autonomous control system 3100 without the heavy sensor data processing tasks at hand facing the MAM 1725.

Exemplary displays 2815$a$, 2815$b$ as well as side multi-element light panels 2825 on MAM 1725 provide Human-to-Machine (H2M) interfaces (also generally referenced as human-interaction interfaces on MAM 1725), such as LED/OLED displays located at the top and outside edges of the MAM component 1725 of an exemplary MALVT bot apparatus 1700. As shown in FIG. 31, exemplary displays 2815$a$, 2815$b$ are operatively coupled to and driven by autonomous control system 3100, which generates information to be shown on displays 2815$a$, 2815$b$. Similar information may be displayed on side multi-element light panels 2825 as part of an H2M interface. Such information may include, for example, transport information related to the status of the apparatus 1700 as explained below in more detail.

Exemplary displays may also be implemented as (or driven to display) navigational type indicators (e.g., headlights, turn signals, etc.). Such navigational type indicators may also be implemented by, for example, front lighting elements 2820 disposed on a leading front edge of MAM 1725, side LED multi-light panel elements 2825 (also operatively coupled to the autonomous control system 3100) that may be used as indicators or multi-element panel displays for showing other information via text or images, and other lights (such as lights 3010$a$, 3010$b$) that may be disposed on MAM 1725 to focus on select areas or regions relative to the MAM 1725 itself. The displays and indicators are disposed on different surfaces and edges of the MAM 1725 such that the controller/processor of the MAM 1725 (e.g., exemplary autonomous control system 3100) may direct information (e.g., autonomous transport information such as navigational indications, status of components and/or the assembly apparatus 1700, status of the items/objects being shipped within apparatus 1700, and the like) to present on such displays and indicators as the H2M interfaces of the MAM 1725. As such, while a customer's mobile smartphone device may operate as an interface with the exemplary MALVT bot apparatus 1700 (via M2M communications to control elements within apparatus 1700 or wireless transceivers within apparatus 1700), the H2M portion of the MAM 1725 may communicate to the outside world regarding the status of the exemplary MALVT bot apparatus 1700. For example, the H2M portion of the MAM 1725 may communicate that the system is operating properly, currently unavailable for use, requesting transition from AV (i.e., autonomous vehicle operation mode) to remote operator mode, etc. These displays 2815$a$, 2815$b$ provide information to human "neighbors" as the exemplary MALVT bot apparatus 1700 moves, senses or detects obstacles, interacts with facility systems (e.g., automatic doors, elevators, lockable storage, and the like) via node-to-node communication, association with external nodes, and secure interactions with such systems while navigating its route to the customer including turns and stops, vehicle speed, as well as any instructional information needed by the customer for object receipt.

As noted above, the side LED multi-element light panels 2825 may be deployed on the MAM 1725 on sides of base cover 2800 or other parts of MAM 1725. A similar exemplary multi-element light panel 2900 may be deployed on the back of base cover as shown in FIG. 29. Those skilled in the art will appreciate while exemplary light panels 2825 and 2900 are shown disposed on particular parts of the detachable modular housing of MAM 1725, such multi-element light panels may be disposed in other locations on the housing of MAM 1725 (e.g., along a front edge or on other surfaces of base cover 2800 or on support 2805). These multi-element light panels 2825, 2900 are shown in FIG. 31 to be operatively coupled to and driven by the autonomous control system 3100 to display relevant information, such as navigational indicators or other information via generated text, symbols, images, and the like.

Exemplary modular component power and data transport bus 3115 is disposed within the detachable modular housing of MAM 1725 as a part of a common bus that may run through the different modular components of exemplary MALVT bot apparatus 1700. As such, modular component power and data transport bus 3115 provides command and data interfaces for display outputs (e.g., via displays, LED indicators, or screens coupled to the bus 3115 on the MAM 1725 or other modular components of apparatus 1700), control output (e.g., for sending control signals to control elements of MB 1705, APM 1710, and for sending control signals to control the environment within CSS 1720), and for sensor input from sensors on the MAM 1725 as well as sensors disposed in other modular components of apparatus 1700 (e.g., sensors within CSS 1720, sensors deployed on the MB 1705, and the like). The exemplary modular component power and data transport bus 3115 has a bottom side modular component electronics interface disposed on the bottom side of the detachable modular housing's base 2800 that mates to a corresponding modular component electronics interface on the modular CSS 1720. In more detail, such a bottom side modular component electronics interface has a power conduit input interface and a command and data communication interface. The power conduit input interface is operatively coupled to active electronic devices and systems that require electrical power, such as the autonomous control system 3100, the location circuitry 3110, the displays 2815$a$, 2815$b$, and the multi-element light panels 2825, 2900. In further embodiments, additional integration aspects may involve deploying a rigid "backbone" to the exemplary MALVT bot apparatus 1700 with two components carrying both power and control commands from the MAM 1725 to the MB 1705.

In an embodiment of exemplary MAM 1725, primary power for the active electronic devices and systems on MAM 1725 may be provided from an external power source, such as the power source available on APM 1710, through such a power conduit input interface on bus 3115. However, an embodiment of exemplary MAM 1725 may be deployed with a supplemental or secondary power source 3120 onboard the MAM 1725. Such a secondary power source 3120 as shown in FIG. 31 may be disposed within the detachable modular housing, and operatively coupled to provide backup power to at least the autonomous control system 3100 (and other active electronic devices and systems on MAM 1725). Embodiments of secondary power source 3120 may be coupled to the power conduit input interface to also provide a backup supply of power to other modular components. Further embodiments of secondary power source 3120 may also have a power controller that may manage the supply of backup power from secondary power source 3120 (e.g., monitoring power being provided through the power conduit input interface and switching to the backup power available from secondary power source 3120 when needed, charging secondary power source 3120 from available power provided through the power conduit input interface, adding the backup power from secondary power source 3120 to the primary power provided available through the power conduit input interface when needed or directed by autonomous control system 3100).

The exemplary MAM 1725 may also have one or more communication interfaces implemented as wireless radio transceivers (e.g., wireless radio transceiver 3125) for near-field/mid/long-range wireless connectivity coupled to the autonomous control system 3100 as needed using one or more communication formats (e.g., Bluetooth, ZigBee, Wi-Fi, Cellular, WiLAN, and other wireless communication formats). Exemplary wireless radio transceiver 3125 may, for example, be implemented using dedicated wireless radio transceiver hardware (including antennas, receivers, transmitters, couplers, diplexers, frequency converters, modulators, and the like), a combination of hardware and software, or as a software defined radio (SDR)). As shown in FIG. 31, exemplary wireless radio transceiver 3125 is disposed within the detachable modular housing of MAM 1725 and is operatively coupled to the autonomous control system 3100 where the wireless radio transceiver 3125 is operative to communicate with other wireless devices, such as an actuated component on the modular autonomous bot apparatus 1700 having wireless capability, a wireless communication interface deployed in another modular component of the apparatus 1700 (e.g., MB 1705, APM 1710, CSS 1720), or a wireless device disposed outside of apparatus 1700 (e.g., a smartphone operated as a type of mobile ID node or mobile master node by a delivery recipient, a wireless node integrated as part of facility systems (automatic doors, elevators, lockable storage, and the like)).

In an embodiment of MAM 1725, exemplary autonomous control system 3100 is programmatically adapted and configured when executing its program code governing operation of the MAM 1725 to be operative to at least receive sensor data from the external sensors 2810 disposed on the detachable modular housing; receive outside sensor data from additional sensors disposed on the modular MB 1705 (where such outside sensor data is received over the command and data communication interface of the bus 3115 or through wireless communications via wireless radio transceiver 3125); generate steering and propulsion control output signals based on the location data from the location circuitry 3110, the sensor data from the external sensors 2810, the outside sensor data, and destination information data maintained by the autonomous control system 3100 on where the MAM 1725 has been dispatched to go; generate autonomous transport information to provide on selective ones of the multi-element light panels 2825, 2900 and/or the displays 2815a, 2815b; and generate autonomous delivery information to provide on at least one of the multi-element light panels 2825, 2900 and/or the displays 2815a, 2815b.

FIG. 32 is a diagram of an exemplary assembly 1700 of an exemplary modular mobility base (MB) unit component 1705 shown in conjunction with an exemplary modular auxiliary power module (APM) 1710, an exemplary modular cargo storage system (CSS) 1720, and an exemplary modular mobile autonomy module (MAM) 1725 in accordance with an embodiment of the invention. As shown in FIG. 32, each of the modular components of assembly 1700 are designed to be modular elements that may be pulled from a depot location or bot storage location to build an appropriate and compatible configuration of an exemplary MALVT bot assembly 1700 for a particular dispatched logistics operation and to appropriately support delivery/pickup of particular items/objects being picked up, delivered, or otherwise shipped by assembly 1700.

As a modular component itself and as part of an assembled bot assembly 1700, an exemplary MAM 1725 may communicate with various types of network devices through wireless communications. FIG. 33 is a diagram of an exemplary system 3300 having exemplary MAM 1725 within an exemplary modular autonomous bot apparatus assembly 1700 where the MAM 1725 is in communication with an exemplary server 3305 and mobile external wireless nodes 3310, 3315 in accordance with an embodiment of the invention. As part of the assembly 1700, MAM 1725 may communicate with other modular components of assembly 1700 (e.g., MB 1705, APM 1710, CSS 1720 and actuated elements therein) over a modular component power and data transport bus 3320 that extends across the different modular components of assembly 1700. And as part of assembly 1700, MAM 1725 may use its wireless radio transceiver 3125 as a wireless communication interface with which to communicate with external wireless node devices, such as backend server 3305 (whether directly through a wireless communication path or indirectly through one or more intermediary network devices), supplier mobile user access device 3310 (e.g., a type of mobile ID node or mobile master node (such as a smartphone or handheld tablet device) operated by a supplier of the item/object being shipped within CSS 1720), delivery recipient mobile user access device 3315 (e.g., a type of mobile ID node or mobile master node (such as a smartphone or handheld tablet device) operated by a intended or authorized delivery recipient for the item/object being shipped within CSS 1720); and a node-enabled logistics receptacle 3325 such as a node-enabled drop-box or parcel locker.

In such an exemplary system 3300, the MAM 1725 (through its wireless radio transceiver 3125) may be operative to receive command inputs from external wireless node devices as a remote control input or requested navigation assistance (e.g., from the delivery supplier via supplier mobile user access device 3310 or from the delivery recipient via delivery recipient mobile user access device 3315). For example, the delivery recipient may respond to a request from MAM 1725 with an updated location via a mapping location (as determined by the delivery recipient mobile user access device 3315) as a type of requested navigation assistance. Exemplary remote control input may come in the form of authorized signals that actuate cargo door 1715 on the assembly 1700 after the remote control input is verified to be from an authentic or authorized supplier or delivery recipient. In another example, the MAM 1725 (through its wireless radio transceiver 3125) may be also operative to request and receive navigation assistance from the backend server 3305 as the external wireless node, such as a changed delivery destination or remote control of the assembly 1700 via the backend server 3305 (or another external wireless node) to guide the assembly 1700 in a semi-autonomous mode.

An embodiment of exemplary MAM 1725 may also use its wireless radio transceiver 3125 to wirelessly communicate with different node-enabled packages (e.g., packages being shipped that have an ID node or master node disposed on or within the package) or items being shipped (e.g., items/objects where an ID node or master node is attached to or integrated as part of the item/object) within the interior of the CSS 1720 to capture the interior cargo status. For example, exemplary MAM 1725 through its autonomous control system 3100 and its wireless radio transceiver 3125 may operate as a master node that may detect, communicate with, and associate with different package ID nodes located within the CSS 1720 in a way to manage, track, and monitor the package or items within the CSS 1720 during transport aboard the assembly 1700.

In further embodiments, an exemplary embodiment of MAM 1725 may use its autonomous control system 3100 to generate and send various actuator control signals to different actuators deployed on an exemplary MALVT bot apparatus 1700. In particular, the autonomous control system 3100 may be programmatically adapted and configured to be operative to generate an actuator control signal as part of a logistics operation once the location data from the location circuitry 3110 indicates the MAM 1725 is at a desired logistics location (e.g., a pickup location, a delivery destination location, an origin location, and the like). In one example, such an actuator control signal may be a lock actuator control signal provided to an electro-mechanically actuated lock on the modular bot apparatus 1700 (e.g., lock 2025 on cargo door 1715) that selectively secures and unsecures access to the payload area. In another example, the actuator control signal may be a handle actuator control signal provided to an electro-mechanically actuated lock on the modular bot apparatus 1700 (e.g., handle actuator 2225) that selectively secures and unsecures access to the payload area or unlocks the CSS 1720 from its connections to other modular components of apparatus 1700). In still other examples, the actuator control signal may be a door actuator control signal provided to a door actuator on the modular bot apparatus that selectively opens and closes access to the payload area; a belt actuator control signal provided to a belt actuator on the modular bot apparatus that selectively moves the item being shipped from within the payload area; a climate control signal for a climate control module 2210 attached to the modular CSS 1720, where climate control signal selectively sets or modifies an environment within the payload area by the output of the climate control module; a sliding arm actuator control signal provided to a sliding arm actuator within the payload area that responsively moves the item being shipped in response to the sliding arm actuator control signal; a grabbing arm actuator control signal provided to a grabbing arm actuator within the payload area that responsively grasps the item being shipped and moves the item being shipped in response to the grabbing arm actuator control signal; and a support base actuator control signal provided to a selectively adjustable suspension system on the MB 1705 that responsively changes an orientation state of the modular MB 1705 in response to the support base actuator control signal.

Authentication (AuthN) of different modular components that are assembled into an exemplary MALVT bot apparatus 1700 at assemble time helps to safeguard against cybersecurity attacks, and also to ensure or verify that the respective components are compatible and ready for operational use (in general or as it relates to a specific logistics operation for a particular item/object being shipped). For example, an exemplary MAM 1725 may go through depot level calibration/alignment to ensure the sensors or particular sensor array deployed on that MAM unit 1725 is ready for operation. Likewise, an exemplary MB unit 1705 may need to ensure that it has sufficient charge before being selected for a designated route (as well as calibration/alignment of sensors 215 used on the MB). At the time of "assembly", an embodiment may deploy an encryption-based secure handshaking or authentication process (e.g., involving a challenge and response with security credentials and the like) to ensure the modular components being assembled into an exemplary MALVT bot apparatus 1700 are certified and ready for operation. In one embodiment, as assembly occurs, the autonomous control system 3100 in the MAM 1725 may perform such assembly authorization checks. In other modular components, control elements disposed in the respective modular component may be operative to perform such assembly authorization checks. For example, other components may have built-in component-to-component logic dedicated for such assembly authorization purposes where interfacing components (e.g., MB 1705 to APM 1710, APM 1710 to CSS 1720, etc.) use integral authorization/registration logic and interfaces having component identifiers and security credentials associated with the component identifiers.

Embodiments of component authentication (AuthN) and authorization (AuthZ) may also be used to enforce role-based control (RBAC) based on a number of factors that could be driven by business cases. For instance, if a component lease was determined to be expired during the process of AuthN & AuthZ as part of assembly of an exemplary MALVT bot apparatus 1700, a MAM 1725 involved in the AuthN & AuthZ may identify the relevant expired leased component and remove it from being assembled within a bot apparatus 10, but also notify a server about this so as to cause the server to initiate renewal in a fleet management system for the relevant expired leased component (or group of components).

Figure 34:
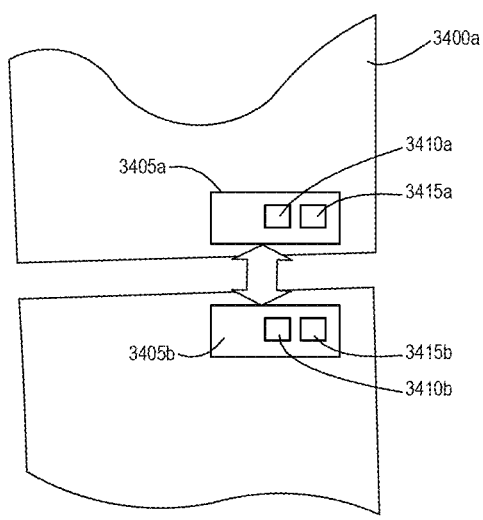
FIG. 34 is a diagram of two exemplary modular components during assembly of an exemplary modular autonomous bot apparatus assembly where authentication of the modular components is performed during assembly in accordance with an embodiment of the invention.

Consistent with the above description of an embodiment of component authentication, FIG. 34 is a diagram illustrating two exemplary modular components 3400a, 3400b as component 3400a is brought together with component 3400b during assembly. Each of exemplary components 3400a, 3400b may be representative of different ones of the exemplary modular MB 1705, exemplary modular APM 1710, exemplary modular CSS 1720, and exemplary modular MAM 1725 components that may be assembled in a component-to-component manner to assemble an exemplary MALVT bot apparatus assembly 1700. Those skilled in the art will also appreciate that exemplary components 3400a, 3400b may represent a detachable module (such as a climate control module or sensor pod) that may be added to a component of exemplary MALVT bot apparatus assembly 1700.

As shown in the embodiment illustrated in FIG. 34, exemplary components 3400a and 3400b are each respectively equipped with exemplary integral authorization/registration logic that implements an authentication interface 3405a, 3405b that carries out the encryption-based secure handshaking or authentication process (e.g., involving a challenge and response with security credentials) to ensure the modular components 3400a, 3400b are being assembled as authorized components. For example, authentication interface 3405a in modular component 3400a is operative to verify the other modular component 3400b being attached is an authenticated modular component based upon component-to-component secure handshaking with the corresponding authentication interface 3405b on the other modular component 3400b. The authentication interfaces 3405a, 3405b may interact with each other via wired connections (e.g., contacts disposed at predetermined locations of latches or edges of structure on each of the components 3400a, 3400b that come in contact during assembly) or via wireless detection and communication (e.g., via node association techniques between ID node-based authentication interfaces 3405a, 3405b; via RFID tag interrogation and response between tagged components 3400a, 3400b where each can read the other's tag as an authentication interface, and the like). As such, exemplary authentication interfaces 3405a, 3405b may implement integral authorization/registration logic in circuitry interrogates the opposing interface and assess the interrogation results (i.e., is the component being attached authenticated based on the component identifier and security credentials) via wired or wireless handshaking.

The authentication interface 3405a, 3405b of each of the components 3400a, 3400b may store and maintain a component identifier 3410a, 3410b along with security credentials 3415a, 3415b. The component identifier 3410a, 3410b at least identifies the respective component 3400a, 3400b and may include information on the component's current capabilities (e.g., charge status, etc.). The security credentials 3415a, 3415b on each component relate to the permission to use the respective component as well as a verification of compatibility of the respective components for a general or particular purpose (e.g., an assigned logistics operation for one or more items being shipped) based on rules and capabilities for the respective component. Such rules as reflected in a component's security credentials may involve regulatory rules, contractual rules, and/or safety rules particular to that component. Likewise, the capabilities of the particular component may also be reflected in the security credentials (or the component identifier) where such capabilities may involve one or more logistical constraints, size/weight limitations, readiness limitations (e.g., performance threshold(s) for the particular component in an anticipated deployment operation, and the like). For example, such logistical constraint information may include information on a determined work environment for the particular component and identified as part of a security credential maintained as part of the authentication interface on that component. The size limitations may be information as to the size of the particular component or its payload area, while the weight limitations may be information as to the weight of the particular component or the weight of what it may carry as payload.

As such, component-to-component authentication may be implemented with secure handshaking between authentication interface 3405a of component 3400a and authentication interface 3405b of component 3400b as component 3400a and 3400b are essentially brought together during assembly. Such a secure handshaking/authentication process may involve issuing a challenge by one authentication interface, to which a response with security credentials (and component identifier in many cases) will be sent by the other authentication interface. In more detail, such component-to-component secure handshaking may have one authentication interface making a comparison of the security credential response from the authentication interface on the other modular component to a security credential maintained as part of the authentication interface on the component making the comparison. The result of such a comparison indicates the authentication status (e.g., that other modular component being attached to the latching points of one component is verified to be an authenticated modular component based upon the comparison).

In general, the authentication result of an exemplary component-to-component secure handshaking between authentication interfaces may be stored by a respective component's authentication interface and may be reported to a control element (e.g., autonomous control system 3100 of MAM 1725) so that the apparatus at a system level is aware of any authentication issues (e.g., when a component has been verified to be incompatible with an assigned or dispatched operation involving the assembly using that component). Thus, a component, such as component 3400a, may record an authentication status identifier to reflect the authentication process result, and may further transmit such an authentication status identifier to a control element identifying that components 3400a and 3400a are not compatible and alerting the control element of the authentication issue.

For example, when an exemplary MAM 1725 is such a component involved in component-to-component authentication (or performs an authentication or verification check of the different components assembled as part of apparatus assembly 1700) and one or more of the components are not authenticated, the autonomous control system 3100 in MAM 1725 may be further programmatically adapted and configured to be operative to cause the wireless radio transceiver 3125 to notify a server (e.g., a dispatch server, depot server, or backend server such as server 3205) of the unauthenticated component(s)).

As such, an embodiment of exemplary MAM 1725 may provide a combination of human interface displays, sensing for the exemplary MALVT bot apparatus 1700, with built-in battery support, and serves as the "head" or "hat" control element of the exemplary MALVT bot apparatus or assembly 1700.

Integration of MALVT Components into the Bot Apparatus as an Assembly

From the main components of an exemplary MALVT bot apparatus 1700 described above, an exemplary modular assembly process or method may take place when the MB 1705, APM 1710, CSS 1720, and MAM 1725 units/components are put together and mechanically integrated into a desired an exemplary MALVT bot apparatus assembly 1700. Embodiments of such an assembly process may take place without a pre-determined dispatch operation, or may take place in an on-demand manner so that a particularly configured MALVT bot apparatus assembly is put together for a particular logistics operation for specific items being shipped.

As an assembly 1700, the different modular components described above (i.e., exemplary MB 1705, APM 1710, CSS 1720, and MAM 1725) may be combined component-by-component to have a common bus through each of the modular components. For example, as noted above, each of exemplary MB 1705, APM 1710, CSS 1720, and MAM 1725 has an interface to a common modular component power and data transport bus, where the interface providing a power conduit for each modular component and a command and data interface conduit for each modular component. Such a common modular component power and data transport bus may also provide the power conduit and command and data interface conduit to detachable modules that may be attached to modular components, such as a climate control module, removable sensor pod, and the like.

As noted above, modular components that attach to each other as part of the exemplary MALVT bot apparatus 1700 may be authenticated or verified as being authorized and/or compatible with a particular task for the exemplary MALVT bot apparatus 1700. For example, an embodiment of an exemplary MALVT bot apparatus 1700 may have its respective modular mobility base, modular auxiliary power module, modular cargo storage system, and modular mobile autonomy control module being authenticated modular components based upon a component-to-component secure handshaking between proximately attached ones of the modular mobility base, the modular auxiliary power module, the modular cargo storage system, and the modular mobile autonomy control module. The component-to-component secure handshaking, as explained above relative to FIG. 34, may be accomplished with a challenge and security credential response between proximately attached ones of the modular mobility base, the modular auxiliary power module, the modular cargo storage system, and the modular mobile autonomy control module. As such, the modular mobility base, the modular auxiliary power module, the modular cargo storage system, and the modular mobile autonomy control module may be verified as authenticated modular components for the modular autonomous bot apparatus assembly 1700 as each of the modular mobility base, the modular auxiliary power module, the modular cargo storage system, and the modular mobile autonomy control module are assembled into the modular autonomous bot apparatus assembly, as each of these modular components connect to proximate others of the modular components, and authentication interfaces that implement integral authorization/registration logic that performs encryption-based secure handshaking to ensure the different modular components are authorized components.

In more detail, the component-to-component secure handshaking may be based upon one or more regulatory rules, one or more contractual rules, and one or more safety rules as reflected in the component identifier and security credentials used in the handshaking. For example, regulatory rules may only permit certain types of modular components within certain buildings or locations. Contractual rules may limit what modular components may be retrieved and used as part of a dispatched bot apparatus 1700 (e.g., components may be leased with use and time limits on authorized use of such components). Safety rules may also limit types of modular components that may be used in particular locations or for particular dispatched tasks.

In a further embodiment, the component-to-component secure handshaking may be based upon logistical constraint information (reflected in the security credentials) on a determined work environment for the modular autonomous bot apparatus assembly. For example, such a logistical constraint information being identified as part of the security credential response provided by a challenged modular component during assembly. Exemplary logistical constraint information may, for example, identify a size limitation for the modular autonomous bot apparatus assembly (or a particular component), identify a weight limitation for the modular autonomous bot apparatus assembly (or a particular component), or identify a readiness limitation for the modular autonomous bot apparatus assembly. Such a readiness limitation may indicate or reflect performance thresholds for the modular autonomous bot apparatus assembly (or a particular component) in an anticipated deployment operation of the modular autonomous bot apparatus assembly. For example, a readiness limitation may require a threshold level of charge on a particular component or a calibration status indicating the component (or assembly) has sensors that have certified accuracy in their operation.

An embodiment of the exemplary modular autonomous bot apparatus assembly 1700 may be operative to respond in a particular manner in the face of component being within the assembly 1700 that is not authenticated or otherwise not verified compatible for use within the assembly 1700. For example, the autonomous controller of the modular mobile autonomy control module in the exemplary MAM 1725 of an exemplary MALVT bot apparatus assembly may be further programmatically adapted and configured to be operative to notify a server over its wireless radio transceiver (e.g., wireless radio transceiver 3125 that one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system. As part of or in addition to such notification, the autonomous controller of the modular mobile autonomy control module in the exemplary MAM 1725 of an exemplary MALVT bot apparatus assembly may be further programmatically adapted and configured to be operative to request a replacement component for the particular modular mobility base, modular auxiliary power module, and/or modular cargo storage system that are not authenticated modular components.

In another embodiment, a response to finding one of the modular components being not authentic or verified compatible may involve more of a local message displayed on the MAM of the apparatus 1700. For example, the autonomous controller of the modular mobile autonomy control module may be further programmatically adapted and configured to be operative to generate a component replacement request message on at least one of the human interaction interfaces disposed on the detachable modular housing (e.g., on the front display 2815*a*, the rear display 2815*b*, and/or one of the side multi-element light panels 2825) when one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system. Such a displayed component replacement request message may request a replacement component for the one or more of the modular mobility base, the modular auxiliary power module, and the modular cargo storage system that are not authenticated modular components. This may be useful to depot technicians that may be assembling a particular exemplary MALVT bot apparatus assembly 1700 in response to a particular dispatch request from a dispatch server or in a process of creating an exemplary bot apparatus assembly 1700 ready to be dispatched for a later defined task (as reflected in a later received dispatch request from the dispatch server).

As explained above relative to FIG. 34, such an authentication result of an exemplary component-to-component secure handshaking between authentication interfaces may be stored by a respective component's authentication interface and reported to a control element (e.g., autonomous control system 3100 of MAM 1725) so that the apparatus at a system level is aware of any authentication issues (e.g., when a component has been verified to be incompatible with an assigned or dispatched operation involving the assembly using that component). Thus, at the system level, a further embodiment of the autonomous controller of the modular mobile autonomy control module of the bot apparatus 1700 may be further programmatically adapted and configured to receive such an authentication result from one of the modular mobility base, the modular auxiliary power module, and the modular cargo storage system. The received authentication result indicates either that all components are authentic and verified compatible, or that at least one of the modular mobility base, the modular auxiliary power module, and the modular cargo storage system are not authenticated modular components based upon the component-to-component secure handshaking between proximate ones of the modular mobility base, the modular auxiliary power module, the modular cargo storage system, and the modular mobile autonomy control module. In response to an authentication result indicating an unauthentic component, the autonomous controller of the modular mobile autonomy control module of the bot apparatus 1700 may be further programmatically adapted and configured to notify a server over the wireless radio transceiver on the MAM that one or more of the modular mobility base, the modular auxiliary power module, and the modular cargo storage system are not authenticated modular components based upon the authentication result received, and may also generate a component replacement request message on at least one of the human interaction interfaces disposed on the detachable modular housing based upon the authentication result received.

While the authentication process described above involves component-to-component secure handshaking of proximately disposed and connected ones of the modular components, an embodiment may have the MAM 1725 of the bot apparatus 1700 interrogate each of the different modular components of the bot apparatus 1700 itself. This may involve the MAM's own authentication interface communicating with different authentication interfaces on the different modular components of the bot apparatus 1700 where the component-to-component authentication process is now between the MAM specifically and each of the other modular components of the bot apparatus 1700. This may be accomplished with authentication interfaces being coupled to the common modular component power and data transport bus (such as bus 3115) or with authentication interfaces communicating wirelessly and performing secure handshaking via, for example, node association techniques. In this way, the authentication interactions may be conducted between the MAM 1725 and each of the other modular components of the bot apparatus assembly via a component-to-component secure handshaking between the MAM 1725 and each of the modular mobility base, the modular auxiliary power module, and the modular cargo storage system similar to that done between other proximate modular components as explained above. Thus, such a component-to-component secure handshaking may involve a challenge and security credential response between the modular mobile autonomy control module and each of the modular mobility base, the modular auxiliary power module, and the modular cargo storage system; may involve regulatory rules, contractual rules, and/or safety rules; and may be based upon logistical constraint information on a determined work environment for the modular autonomous bot apparatus assembly (or particular modular component) as explained above. The autonomous controller of the MAM may also be programmatically adapted and configured to be operative to respond with server notifications, and component replacement requests as explained above (e.g., telling the server to initiate the replacement component swap out or generate a local component replacement request message on one of the human interaction interfaces disposed on the detachable modular housing of the MAM).

Additionally, as an assembled exemplary MALVT bot apparatus 1700, different components of the apparatus may have controlled actuators consistent with the description above. For example, the modular mobility base 1705 may have a set of suspension orientation actuators (e.g., part of selectively adjustable suspension system 1840) disposed within or as part of the mobile base platform 1800, where the suspension orientation actuators can responsively alter an orientation of the mobile base platform 1800 relative to a ground surface on which the mobile base platform 1800 is supported in response to a support base orientation control command generated by the autonomous controller (e.g., autonomous control system 3100) and provided to the mobility controller over the common modular component power and data transport bus. In another example, the modular auxiliary power module may have a cargo door actuator (e.g., actuator 2070) disposed on the base adapter platform 2005, where the cargo door actuator can responsively move the articulating cargo door 1715 in response to a cargo door control command generated by the autonomous controller and provided to a door actuator driver on the base adapter platform over the common modular component power and data transport bus. In still another example, the modular auxiliary power module may have a belt actuator disposed on the base adapter platform 1800, where the belt actuator can responsively move an actuated belt surface 2080*b* disposed on the base adapter platform 2005 in response to a belt control command generated by the autonomous controller and provided to a belt actuator driver on the base adapter platform over the common modular component power and data transport bus. In yet another example, the modular auxiliary power module may have a ramp belt actuator (similar to the above-described belt actuator) disposed on the articulating cargo door 1715, where the ramp belt actuator can responsively move an actuated ramp belt surface 2080*a* disposed on the articulating cargo door 1715 in response to a ramp belt control command generated by the autonomous controller and provided to a ramp belt actuator driver on the articulating cargo door over the common modular component power and data transport bus.

Some of the controlled actuators on bot apparatus assembly 1700 involve locks, such as locks for the cargo door 1715 (whether disposed on the APM 1710 or on the CSS 1720) and the locking handle 2115 for the CSS 1720 itself. In more detail, the modular auxiliary power module further may have an actuated electro-mechanical lock that responsively secures and unsecures the articulating cargo door 1715 in response to a door lock control command generated by the autonomous controller and provided to the actuated electro-mechanical lock on the modular auxiliary power module over the common modular component power and data transport bus. Likewise, another embodiment may have the modular cargo storage system having an actuated electro-mechanical lock that responsively secures and unsecures the articulating cargo door 1715 in response to a door lock control command generated by the autonomous controller and provided to the actuated electro-mechanical lock on the modular cargo storage system over the common modular component power and data transport bus. As for the locking handle 2115 on the CSS 1720, an exemplary embodiment may have the modular cargo storage system having an actuated electro-mechanical lock that responsively actuates the set of actuated latches (e.g., latches 2110*a*, 2110*b*) in response to a latch locking control command generated by the autonomous controller and provided to the actuated electro-mechanical lock on the modular cargo storage system over the common modular component power and data transport bus.

In a further example embodiment, the modular cargo storage system may have a detachable climate control module (e.g., module 2210) disposed within the modular cargo storage system that can responsively alter an environment of the payload support area to maintain a desired environment within the payload support area in response to a climate control command generated by the autonomous controller and provided to the climate control module on the modular cargo storage system over the common modular component power and data transport bus.

In still further embodiments, the autonomous controller of the MAM 1725 may control actuation of different object or item manipulation systems, such as actuated sliding arms and/or actuated grabbing arms that may be implemented as part of the CSS 1720 or on the APM 1710 as part of the bot apparatus assembly. For example, the modular cargo storage system may have an actuated sliding arm that responsively moves the item being shipped within the payload support area in response to a sliding arm control command generated by the autonomous controller and provided to the actuated sliding arm on the modular cargo storage system over the common modular component power and data transport bus. In another example, the modular cargo storage system may have an actuated grabbing arm that responsively obtains and moves the item being shipped within the payload support area in response to a grabbing arm control command generated by the autonomous controller and provided to the actuated grabbing arm on the modular cargo storage system over the common modular component power and data transport bus.

Sensor data may also be provided across and through different modular components of the exemplary bot apparatus assembly 1700. For example, the modular mobile autonomy control module may have one or more payload monitoring sensors (e.g., sensors 3180) disposed on a bottom side of the detachable modular housing and operatively coupled to the autonomous controller. Such payload monitoring sensors generate payload sensor data on the payload support area and provide the payload sensor data to the autonomous controller so that the autonomous controller can monitor the payload sensor data and, as such, monitor what is going on in the payload area as well as monitor conditions of the item being shipped within the payload area. Such payload monitoring sensors 3180 on the MAM 1725 may be implemented in detachable sensor pods that are operatively coupled to the autonomous controller while assembling the modular autonomous bot apparatus assembly. In an embodiment, such a detachable sensor pod may include some or all of the payload monitoring sensors and be of a predetermined sensor type correlating to an assigned dispatch use profile maintained by the autonomous controller for the bot apparatus assembly 1700. Such an assigned dispatch use profile may be maintained by the MAM (e.g., the autonomous control system 3100 on MAM 1725) as a data on an assigned dispatch operation for the modular autonomous bot apparatus 1700 (which may be sent to the autonomous control system 3100 from a server, such as a dispatch server, as part of a dispatch command related to the particular assigned dispatch operation for the bot apparatus assembly 1700).

Likewise, one or more of the autonomy module sensors 2810 may be implemented in a detachable sensor pod attached to the detachable modular housing and operatively coupled to the autonomous controller while assembling the modular autonomous bot apparatus assembly. Such a detachable sensor pod may include some or all of sensors 2810 and include sensors of a predetermined sensor type correlating to the assigned dispatch use profile maintained by the autonomous controller.

An embodiment of modular autonomous bot apparatus assembly 1700 may have the autonomous controller of its MAM unit being further programmatically adapted and configured to be operative to receive such an assigned dispatch use profile for the modular autonomous bot apparatus 1700 from a server (e.g., server 3300), where the assigned dispatch use profile identifies a type of each of the modular mobility base, the modular auxiliary power module, the modular cargo storage system, and the modular mobile autonomy control module used as part of the modular autonomous bot apparatus assembly 1700. In more detail, an embodiment may have such an assigned dispatch use profile for the modular autonomous bot apparatus 1700 providing authentication information used for verifying an authentication status for each of the modular mobility base, the modular auxiliary power module, the modular cargo storage system, and the modular mobile autonomy control module used as part of the modular autonomous bot apparatus assembly. In other words, such authentication information may include security credentials and/or component identifier information used when verifying an authentication status for each of the modular mobility base, the modular auxiliary power module, the modular cargo storage system, and the modular mobile autonomy control module used as part of the modular autonomous bot apparatus assembly.

As assembled into an exemplary modular autonomous bot apparatus assembly 1700, the autonomous controller of the MAM (e.g., autonomous control system 3100 of MAM 1725) may be further programmatically adapted and configured to be operative to wirelessly receive a remote command input for the modular autonomous bot apparatus 1700 from an external wireless node through the wireless radio transceiver interface (e.g., wireless radio transceiver 3125 on MAM 1725). For example and as shown in FIG. 33, such a remote command input may be a remote control input from a delivery supplier (e.g., remote control wireless signals sent from supplier mobile user access device 3310) or may be a remote control input from a delivery recipient (e.g., remote control wireless signals sent from delivery recipient mobile user access device 3315).

And as assembled into an exemplary modular autonomous bot apparatus assembly 1700, the autonomous controller of the MAM (e.g., autonomous control system 3100 of MAM 1725) may be further programmatically adapted and configured to be operative to wirelessly request and receive navigation assistance from a backend server (e.g., server 3300) as a type of remote control input. This may come in the form of updated routing information, for example, but may also come in the form of remotely supplied control signals for controlling the propulsion and steering systems on the MB of the assembly 1700, or control signals described above that initiate any of the actuators disposed on the assembly 1700 (e.g., actuating the cargo door 1715 to unlock and open, actuating the suspension system on the MB to tilt and initiate movement of the item being shipped out of the CSS, actuating any of the object manipulation systems, and the like). In like manner, the autonomous controller may also be further programmatically adapted and configured to be operative to wirelessly request and receive navigation assistance and authorized remote control input from an authorized handheld wireless user access device as the external wireless node (e.g., from a bot depot technician operating a smartphone to initiate unlocking and opening of the cargo door 1715, etc.).

In a further embodiment, the assembled modular autonomous bot apparatus assembly 1700 may be configured and operative for enhanced remote operation for last leg delivery options using the assembly 1700. For example, the autonomous controller of the MAM (e.g., autonomous control system 3100 of MAM 1725) may be further programmatically adapted and configured to receive location information from location circuitry 3110; detect when a current location of the modular autonomous bot apparatus 1700 is within a threshold distance from a destination point according to an assigned dispatch use profile for the modular autonomous bot apparatus 1700. Once within the threshold distance, the autonomous controller is then operative in this embodiment to transmit a remote control request over the wireless radio transceiver interface to the external wireless node (e.g., a courier mobile external wireless node similar to node 3310 shown in FIG. 33); receive a series of remote control command inputs from the external wireless node through the wireless radio transceiver 3125 on the MAM 1725; generate responsive steering control commands and responsive propulsion control command based upon the series of remote control command inputs; and transmit the responsive steering control commands and the responsive propulsion control commands to the mobility controller 1825 on MB 1705 through the common modular component power and data transport bus 3115 for receipt by the mobility controller 1825, which allows the external wireless node to control navigation of the modular autonomous bot apparatus assembly 1700 during a final segment of a deployment operation of the modular autonomous bot apparatus assembly 1700 as the modular autonomous bot apparatus assembly 1700 moves to the destination point.

A further enhancement may have an embodiment capturing and forwarding sensor data gathered during this last leg or final segment of the deployment operation. For example, the autonomous controller (e.g., autonomous control system 3100 in MAM 1725) may be further programmatically adapted and configured to be operative to receive base feedback sensor data from the MB 1705 during the final segment of the deployment operation of the modular autonomous bot apparatus assembly 1700 as the modular autonomous bot apparatus assembly 1700 moves to the destination point; receive onboard sensor data from the autonomy module sensors 2810 during the final segment of the deployment operation of the modular autonomous bot apparatus assembly as the modular autonomous bot apparatus assembly moves to the destination point; and transmit at least a subset of the received base feedback sensor data and the received onboard sensor data to the external wireless node as remote navigation feedback information.

In still another enhanced embodiment, the captured sensor data may be used to update onboard routing information with higher definition mapping information to maintain locally on the assembled apparatus 1700. For example, the autonomous controller (e.g., autonomous control system 3100 in MAM 1725) may be further programmatically adapted and configured to be operative to update onboard routing information on the autonomous controller with at least a portion of the received base feedback sensor data and the received onboard sensor data. Such onboard routing information may be maintained by the autonomous controller in a database of mapping information. As such, the portion of the received base feedback sensor data and the received onboard sensor data that update the database of mapping information may provide higher definition information than exists within the database of mapping information for the final segment of the deployment operation.

Figure 35:
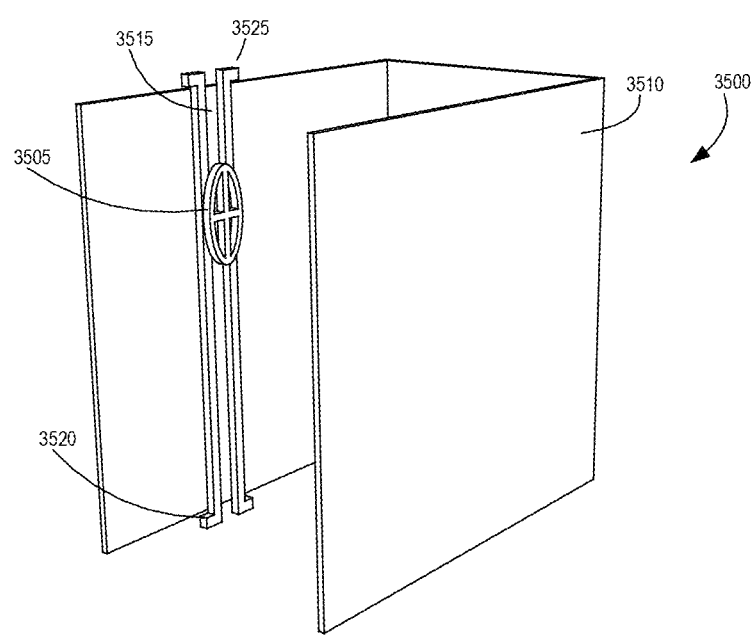
FIG. 35 is a diagram illustrating an exemplary smart latching and interface configuration used with another embodiment of an exemplary cargo storage system (CSS) in accordance with an embodiment of the invention.
Figure 36:
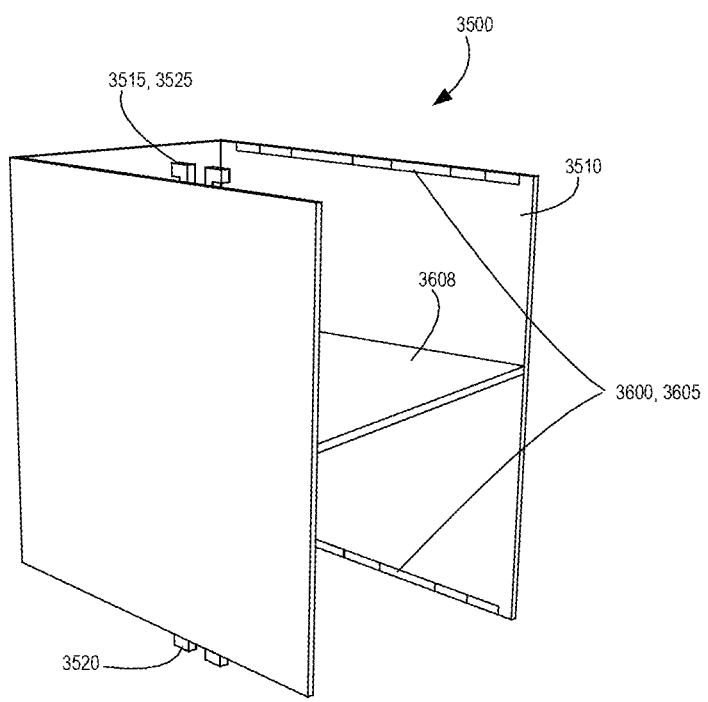
FIG. 36 is a diagram illustrating an exemplary fastening configuration used with an exemplary cargo storage unit (CSS) in accordance with an embodiment of the invention.

Further embodiments may deploy and use additional features as part of the modular components that make up the exemplary MALVT bot apparatus 1700. For example, an embodiment may use an exemplary novel latching mechanism to ensure that components are aligned and coupled for proper operation. FIG. 35 is a diagram illustrating further details of an exemplary latching and interface configuration used with another embodiment of an exemplary cargo storage system component (CSS) in accordance with an embodiment of the invention. Referring now to FIG. 35, exemplary CSS 3500 (similar to exemplary CSS 1720) is shown in more detail having side walls 3510, latching system 3505, and latch engagements 3520, 3525 extending from a top and bottom of exemplary CSS 3500. In this embodiment of exemplary CSS 3500, an embodiment of exemplary latching system 3505 may serve a dual purpose as a "bus" 3515 for transmission and protection of system power and data (e.g., integrating a modular component power and data transport bus 2250 as shown in FIG. 22B as part of latching system 3505), providing electrical connectivity between the main components of the exemplary MALVT bot apparatus 1700. In one embodiment, the latch 3505 may be built into the side wall 3510 of the CSS cargo unit 3500, and secured with a key once final assembly is completed, as shown in FIG. 35. An embodiment may implement such a "smart latch" 3505 as being streamlined and integrated with the wall 3510 of CSS 3500 as much as possible to facilitate compact folding of the collective walls 3510 that form and make up CSS 3500 so that CSS 3500 may be more easily stowed while avoiding having the structure of the latch 3505 protruding to obstruct or otherwise impede the change from an assembled state to the folded storage state. On the interior wall opposite the smart latch 3505, a series of locking tabs 3600, 3605 (as shown in FIG. 36) may be built into the top and bottom of the interior of CSS 3500. These locking tabs 3600, 3605 are coupling elements that enables and allows the MAM 1725 and APM 1710 to be mechanically and removably fastened and secured on the side opposite the smart latch 3505 (as well as latch engagements 3520, 3525), providing tension once the latch 3505 is secured.

In another embodiment, the "smart latch" 3505 shown in FIG. 35 (which may be implemented using exemplary locking handle 2115 shown in FIG. 22B) may be activated via human control when the lock mechanism of latch 3505 (handle 2115) is rotated. In a further embodiment, the latch 3505 may be electronically activated via M2M communication with an actuator that may be part of latch 3505 (e.g., via handle actuator 2225 as shown in FIG. 22B) and under the control of MB 1705 or MAM 1725. An enhanced use in an embodiment of the exemplary MALVT bot apparatus 1700 may have such a smart latch automatically react and activate under certain detected circumstances. For example, the exemplary MALVT bot apparatus 1700 may sense and adverse operation and enter into a failsafe mode (e.g., due to impending crash, power failure, upon sending a request for intervention or human assistance, etc.), the smart latch 3505 may be automatically activated into an unlock mode to facilitate this failsafe operation. However, in other embodiments, conditions may be detected by MAM 1725 where the smart latch 3505 may be automatically activated to keep latch 3505 in a locked state to prevent unauthorized access to and/or removal of CSS 3500 (and any contents within CSS 3500).

In more detail, such an automatic failsafe mode using an exemplary smart latching feature may have the autonomous controller (e.g., autonomous control system 3100 in MAM 1725) being further programmatically adapted and configured to be operative to receive base feedback sensor data from the mobility controller 1825 (e.g., from sensors 1825 on MA 1705 as relayed to autonomous control system 3100 on MAM 1725 through the common modular component power and data transport bus 3320 shown in FIG. 33 for the assembly 1700); receive the onboard sensor data from the autonomy module sensors 2810; detect an adverse approaching impact based upon the base feedback sensor data and the onboard sensor data; generate a failsafe mode unlock signal for the actuated electro-mechanical lock disposed on the modular cargo storage system in response to the detected adverse approaching impact; and transmit the failsafe mode unlock signal to the actuated electro-mechanical lock on the modular cargo storage system over the common modular component power and data transport bus 3320 to cause the actuated electro-mechanical lock to unlock the set of actuated set of latches 2110*a*, 2110*b* in response to the detected adverse approaching impact.

In another example where the adverse operation relates to apparatus power levels, the autonomous controller may be further programmatically adapted and configured to be operative to detect an adverse power level of the auxiliary power source below a failure threshold power level; generate a failsafe mode unlock signal for the actuated electro-mechanical lock disposed on the modular cargo storage system in response to the detected adverse power level of the auxiliary power source 2035 (and/or secondary power source 3120); and transmit the failsafe mode unlock signal to the actuated electro-mechanical lock on the modular cargo storage system over the common modular component power and data transport bus to cause the actuated electro-mechanical lock to unlock the set of actuated set of latches 2110*a*, 2110*b* in response to the detected adverse power level of the auxiliary power source.

In still another example where the adverse operation is related to a situation where assistance has been requested, the autonomous controller may be further programmatically adapted and configured to be operative to generate a failsafe mode unlock signal for the actuated electro-mechanical lock disposed on the modular cargo storage system after transmitting a request for assistance to a server (e.g., server 3300) or to an external wireless node (e.g., supplier mobile user access device 3310 or delivery recipient mobile user access device 3315); and transmit the failsafe mode unlock signal to the actuated electro-mechanical lock on the modular cargo storage system over the common modular component power and data transport bus to cause the actuated electro-mechanical lock to unlock the set of actuated set of latches 2110*a*, 2110*b* in response to the detected adverse power level of the auxiliary power source.

Further embodiments of an exemplary MALVT bot apparatus 1700 may be assembled, dispatched, and/or deployed with additional features that allow for transporting multiple different items/objects and where some may require different environmental environments than others. For example, the CSS unit component 3500 (or CSS 1720) used as part of such an exemplary MALVT bot apparatus 1700 may be deployed with one or more detachable organized separator/supports, such as shelving separators 3608, that partitions the interior cargo space within the CSS unit into compartments. As shown in FIG. 36, exemplary shelving separator 3608 partitions the payload area within CSS 3500 into different compartments where each may be serviced by different climate control modules (such as exemplary climate control module 2210). In such an embodiment, the shelving may take advantage of the power and data bus on the CSS interior (e.g., bus 2250) as needed, for example, interior lighting, separate power connections for climate control systems (e.g., multiple exemplary detachable climate control modules 2210 deployed in different partitioned compartments of the payload area for separate objects destined for different recipients, for objects requiring different environments for transport, and the like). Such climate control systems may be detachably fixed to the walls of the CSS or to shelving separators 3608 within the payload area.

Figure 37:
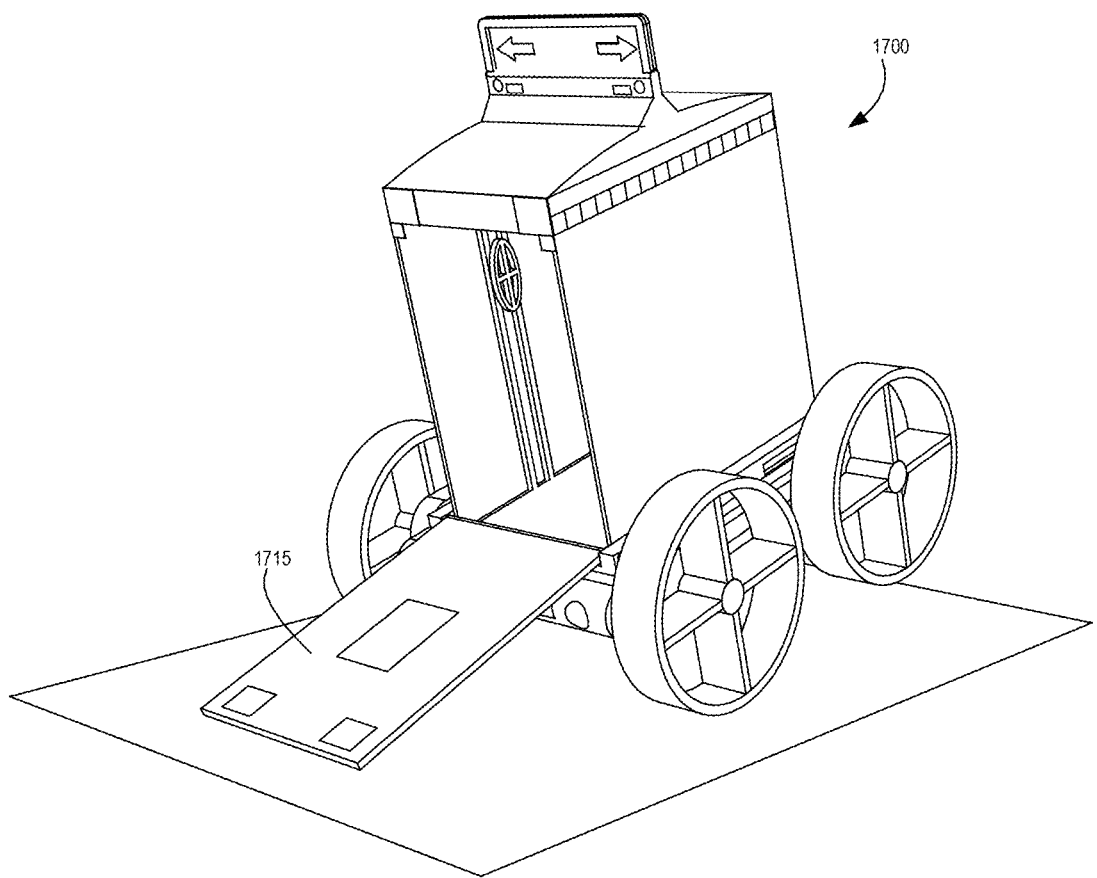
FIG. 37 is a diagram of an exemplary modular autonomous logistics transport vehicle apparatus (MALVT bot apparatus) in a configuration having a cargo door extended and in a forward tilted orientation in accordance with an embodiment of the invention.
Figure 38:
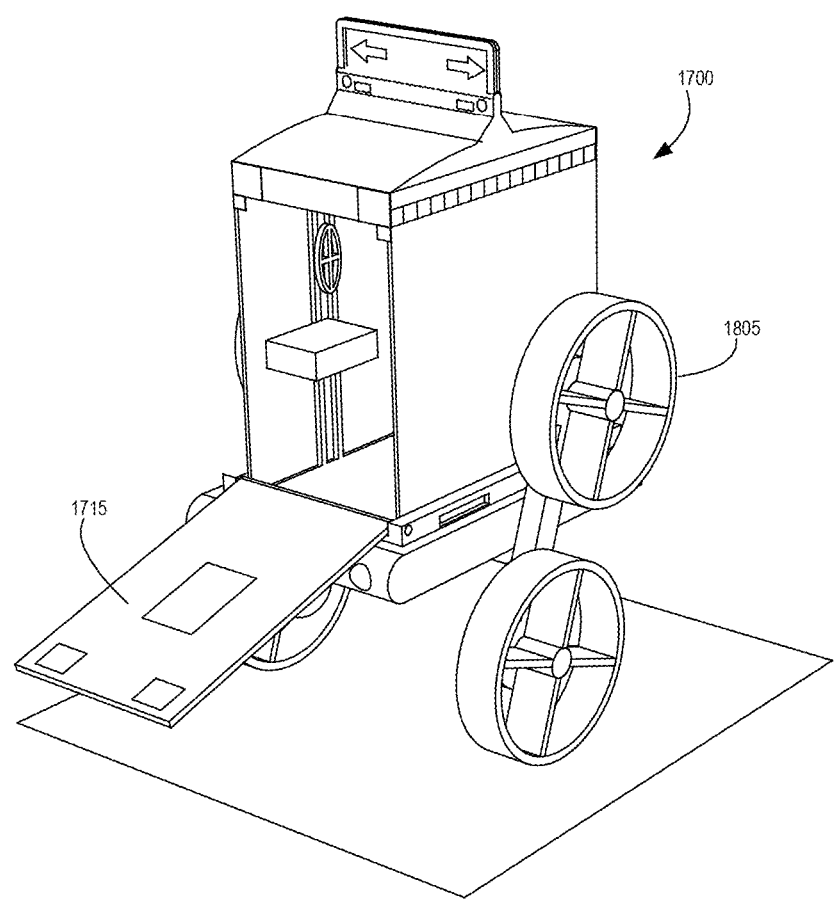
FIG. 38 is a diagram of an exemplary modular autonomous logistics transport vehicle apparatus (MALVT bot apparatus) in a configuration having a cargo door extended and in a "standup" mode orientation in accordance with an embodiment of the invention.

In a further assembly embodiment, the standing and tilting functionalities of an exemplary MALVT bot apparatus 1700 may be utilized in delivery scenarios where the exemplary MALVT bot apparatus 1700 is delivering to a drop box, parcel locker, or apartment drop-off location. FIG. 37 is a diagram of an exemplary MALVT bot apparatus 1700 in a configuration having a cargo door 1715 extended and in a forward tilted orientation in accordance with an embodiment of the invention (e.g., by activating an exemplary selectively adjustable suspension system 1840 with actuators to achieve a desired tilt configuration), while FIG. 38 is a diagram of the MALVT bot apparatus 1700 in a configuration having a cargo door 1715 extended and in a "standup" mode orientation in accordance with an embodiment of the invention (by activating an exemplary selectively adjustable suspension system 1840 with actuators to achieve a desired lift configuration). As shown in FIGS. 37 and 38, embodiments of exemplary MALVT bot apparatus 1700 may deploy articulated movements of the MB 1705 (and the assembled other components of the exemplary MALVT bot apparatus) using tilting/lifting modes and configurations (as activated with particular actuators within MB 1705 as discussed above).

Figure 39:
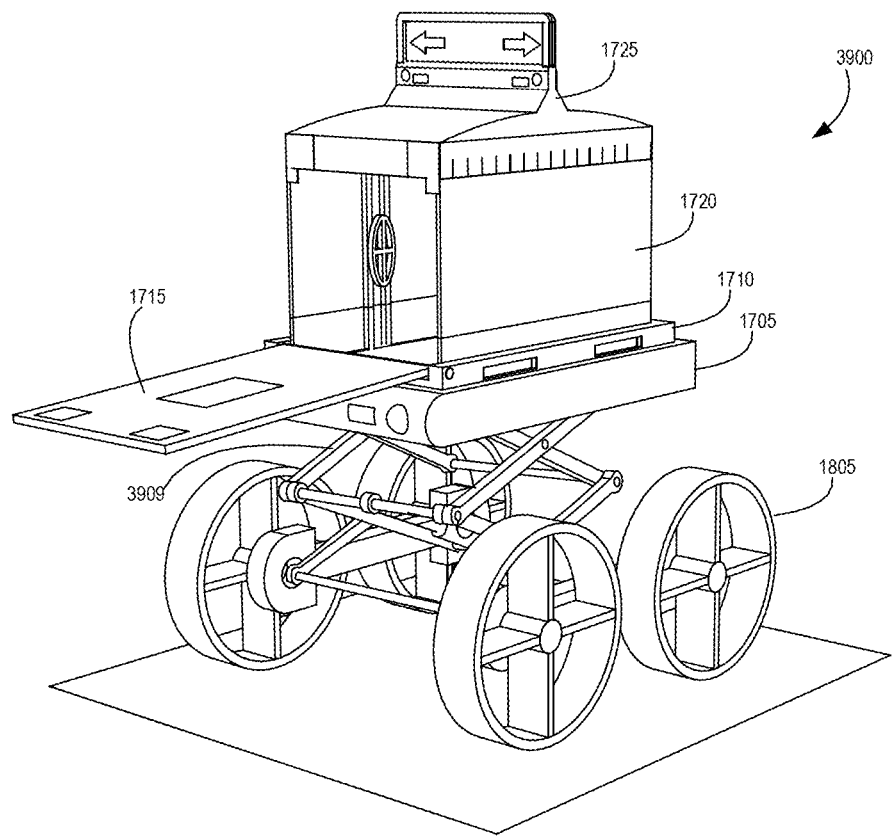
FIG. 39 is a front view diagram of an exemplary modular autonomous logistics transport vehicle apparatus (MALVT bot apparatus) in a configuration having a cargo door extended and in a lifted orientation in accordance with an embodiment of the invention.
Figure 40:
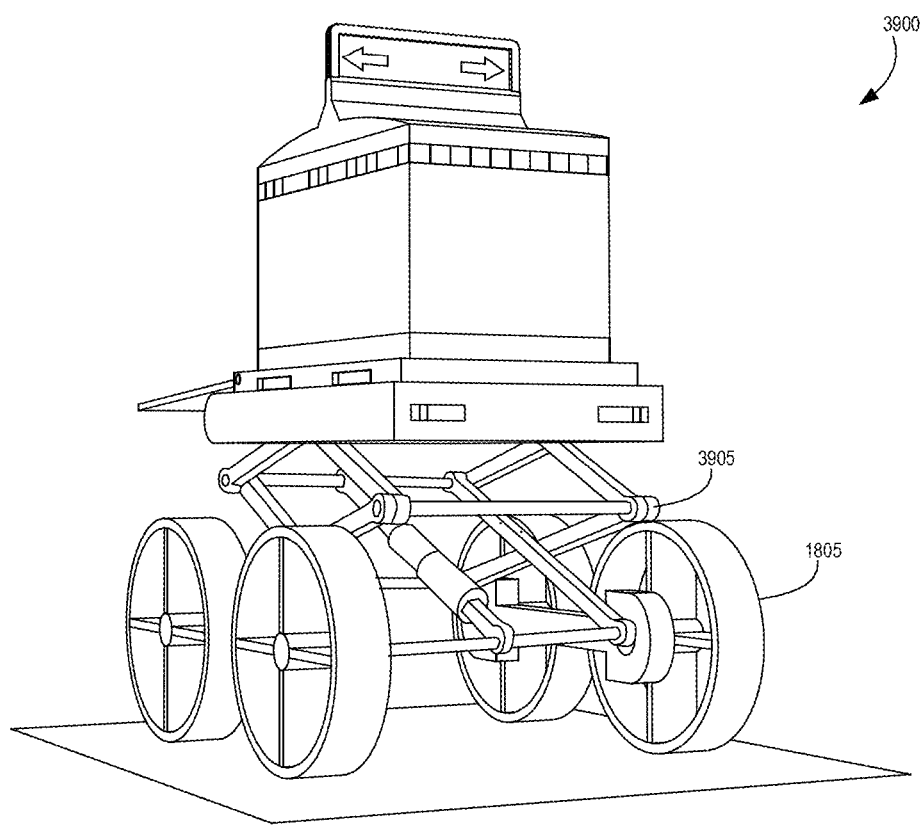
FIG. 40 is a rear view diagram of an exemplary modular autonomous logistics transport vehicle apparatus (MALVT bot apparatus) in a configuration having a cargo door extended and in a lifted orientation in accordance with an embodiment of the invention.

In a further embodiment, alternate lifting mechanisms may be used as part of an exemplary MALVT bot apparatus (e.g., part of selectively adjustable suspension system 1840), such as a "scissor-lift" type mechanism mentioned previously. FIG. 39 is a front view diagram of an exemplary MALVT bot apparatus 3900 (similar to apparatus 1700) in a configuration having a cargo door 1715 extended and in a lifted orientation using articulating scissor-lift 3905 that responsively lifts and lowers the base of MB 1705 (separate from the wheels 1805 and their wheelbase). FIG. 40 shows the same exemplary MALVT bot apparatus 3900 but from a rear view perspective. An apparatus 3900 using such a scissor-lift 3905 may provide a higher lift capability, such as might be needed for use cases where the exemplary MALVT bot apparatus 3900 is interfacing with other vehicles, building access doors, steps, platforms, etc.

MALVT Bot Apparatus Storage & Assembly Process

In further embodiments, the process of assembling an exemplary MALVT bot apparatus from storage may be implemented in a variety of ways. In some embodiments, some of all of the respective modular components that make up an exemplary MALVT bot apparatus assembly 1700 stored in a bot storage location or depot where modular components may be selected for inclusion within an exemplary MALVT bot apparatus assembly 1700.

An embodiment may deploy a pre-assembly process for checkout/certification before going on-road ("Health Checks") as part of an assembled exemplary MALVT bot apparatus (e.g., activation of predetermined features on the component prior to and once assembled and integrated as part of the bot apparatus), management systems for handling processes when dealing with large scale fleets; and the definition of particular calibration/periodic maintenance required for particular components. For example, an exemplary MB 1705 may have its sensors 1815 certified to be calibrated and indicative of a level of readiness for a particular assigned logistics operation (e.g., a logistics operation associated with dispatch command and an assigned dispatch use profile used by a bot assembly built for or compatible with that logistics operation). Other sensors deployed on different components of an exemplary MALVT bot apparatus assembly 1700 make likewise be certified as calibrated in order to meet a readiness limitation for the assembly 1700 (or component itself). In another example, an exemplary APM 1710 may have its power source charged to a threshold level in order to be certified as ready for deployment (i.e., indicative of a level of readiness for a particular assigned logistics operation).

Another embodiment may have modular components or detachable modules/pods that may be used as authorized parts of an exemplary MALVT bot apparatus assembly 1700 (e.g., different sized CSS units 1720, different types of detachable climate control modules 2210, removable sensor pods 3005*a* with different numbers of sensors and/or types of sensors in the pod, different sized deployable separators 3608 to use within a CSS 1720, and the like) dispensed from a vending unit, machine or other type of modular bot component depot when assembling an exemplary MALVT bot apparatus. Such dispensing may be manually initiated by a depot technician involved in assembling the exemplary MALVT bot apparatus or, in some embodiments, dispensing from the vending machine or depot system may be initiated by an assembly server that has received a request for the assembly of the particular exemplary MALVT bot apparatus and coordinated with both the depot technician via M2H messaging as well as M2M communication with the vending machine. For example, such a vending machine may manage and store different types of modular components and detachable modules/pods in secure compartments of a larger storage locker system that may be manually or automatically unlocked so that the relevant modular component, detachable module, pod, or separator may be dispensed from its storage location and used when assembling the exemplary MALVT bot apparatus assembly 1700. The process of assembling the dispensed components into an exemplary MALVT bot apparatus 1700, including AuthN and AuthZ for proper authorized and secure operation may also involve removal of particular modular bot components from a fleet/ inventory usage (e.g., for repairs, calibration, charging (e.g., when stored in the vending unit), and the like). Likewise, particular modular bot components that may be leased for use as part of a fleet may be removed from the fleet/ inventory (e.g., from within storage in the bot storage facility or within a vending machine) when the lease expires for that component, which may prompt notification to renew such a lease and enable continued use of the component without incurring the disruptive interruption of physical removal of the component from the inventor.

Figure 42:
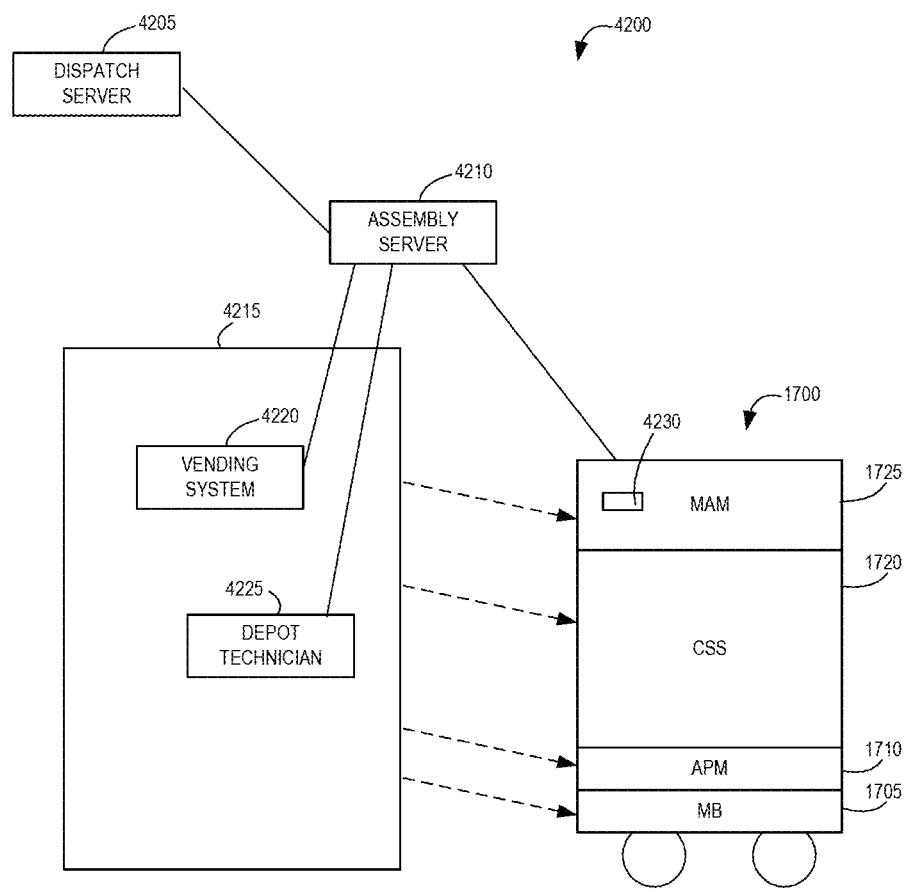
FIG. 42 is a diagram of an exemplary system involved in assembling an modular autonomous logistics transport vehicle apparatus (MALVT bot apparatus) in accordance with an embodiment of the invention.

In some assembly embodiments, assembly of the bot apparatus may be proactive (i.e., building an exemplary MALVT bot apparatus assembly from different modular components ahead of time prior to the bot apparatus assembly being assigned to a particular logistics operation). Other embodiments may implement more of an "on-demand" or reactive assembly of an exemplary MALVT bot apparatus assembly 1700 in a manner that achieves an authenticated and verified compatible bot apparatus assembly 1700 for a particular logistics operation consistent with an assigned dispatch use profile for the bot apparatus assembly 1700. FIG. 42 is a diagram of an exemplary system involved in assembling an exemplary modular autonomous logistics transport vehicle apparatus (MALVT bot apparatus) in accordance with an embodiment of the invention. Referring now to FIG. 42, exemplary system 4200 is shown with a dispatch server 4205, an assembly server 4210, a vending system 4220 located at a bot storage depot location 4215 and serviced by a depot technician operating a mobile wireless node 4225. In general, exemplary dispatch server 4205 (which may be implemented as a networked server or a wireless node that is operated by a third party or dispatching entity to assign a particular assembly 1700 for a particular logistics operation) may receive a dispatch request related to a particular dispatch logistics operation requiring an exemplary MALVT bot apparatus assembly 1700 to facilitate pickup and/or delivery of one or more items/objects. In this example, exemplary dispatch server 4205 may initiate building of the exemplary MALVT bot apparatus assembly 1700 for the logistics operation with an assembly request sent to exemplary assembly server 4210, which may manage inventory and direct one or both of vending system 4220 and the depot technician operating a mobile wireless node 4225 as part of assembling the exemplary MALVT bot apparatus assembly 1700 for the logistics operation. Those skilled in the art will appreciate that embodiments of system 4200 may implement dispatch server 4205 and assembly server 4210 with a common server system supporting dispatch requests and coordinating the assembly operation that produces a particular exemplary MALVT bot apparatus assembly 1700 for a specific logistics operation (or type of logistics operation).

Figure 41:
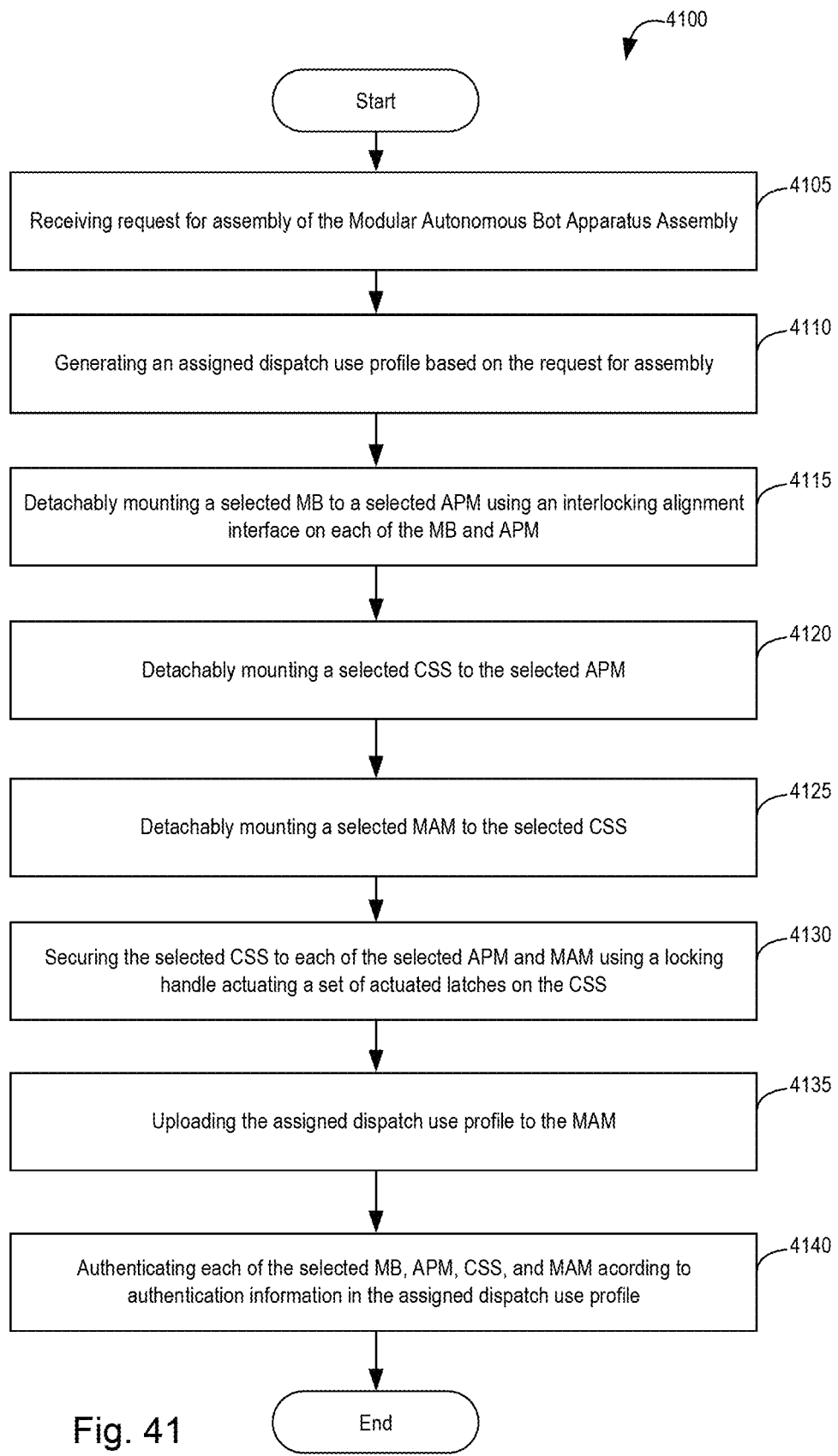
FIG. 41 is a flow diagram of an exemplary method for on-demand building of a modular autonomous bot apparatus assembly that transports an item being shipped in accordance with an embodiment of the invention.

FIG. 41 is a flow diagram of an exemplary method on-demand building of a modular autonomous bot apparatus assembly that transports an item being shipped in accordance with an embodiment of the invention. Referring now to FIG. 41 and the exemplary assembly environment of system 4200 shown in FIG. 42, exemplary method 4100 begins at step 4105 by receiving a request for assembly of the modular autonomous bot apparatus assembly by an assembly server (such as assembly server 4210). At step 4110, method 4100 proceeds with the assembly server generating an assigned dispatch use profile that identifies a type of each of a modular mobility base, a modular auxiliary power module, a modular cargo storage system, and a modular mobile autonomy control module to be used as authorized parts of the modular autonomous bot apparatus assembly based on the request for assembly. An exemplary embodiment of an assigned dispatch use profile 4230 may be implemented as a data structure maintaining data on such a profile of information about the dispatched logistics operation for the desired bot apparatus assembly, what will be transported, the types of modular components needed in the bot apparatus assembly for the logistics operation, and authentication information about such modular components for use in verifying compatibility of the components/assembly with the logistics operation and authenticating the components/assembly may be used for the logistics operation from a permission standpoint.

Steps 4115-4125 have exemplary method 4100 gathering selected modular components for assembly into the modular autonomous bot apparatus assembly. This may involve, for example, the assembly server causing each of the selected modular mobility base, the selected modular auxiliary power module, the selected modular cargo storage system, and the selected modular mobile autonomy control module to be pulled from a modular bot component storage (such as component storage areas within bot storage depot location 4215 or from vending system 4220 at the bot storage depot location 4215) as according to the assigned dispatch use profile (or a desired logistics operation identified in the assigned dispatch use profile). For example, such an action may involve communications between assembly server 4210 and the mobile wireless node 4225 operated by the depot technician assigned to the build of exemplary MALVT bot apparatus assembly 1700 shown in FIG. 42. As such, the depot technician operating the mobile wireless node 4225 may gather an exemplary CSS component selected based upon a cargo size characteristic for the desired logistics operation (e.g., the logistics operation requires transport of a relatively large object that requires a larger sized CSS modular component), or based upon an organized storage characteristic for the desired logistics operation (e.g., the logistics operation requires transport of multiple items that need to be physically separated during transport or need to separately climate controlled with different desired environments for the different items being shipped).

Selection of the different modular components, as indicated in the assigned dispatch use profile, may be based upon a variety of characteristics of the particular module and the particular logistics operation desired for the bot assembly 1700. For example, the selected modular cargo storage system from the modular bot component storage may be selected based upon an environmental storage characteristic for the desired logistics operation. In another example, the selected modular mobility base from the modular bot component storage may be selected based upon an anticipated path for the desired logistics operation, or based upon a base sensor requirement for the desired logistics operation. In still another example, the selected modular auxiliary power module from the modular bot component storage may be selected based upon a power requirement for the desired logistics operation, or based upon an articulated delivery assistance requirement for the desired logistics operation. And in yet another example, the selected modular mobile autonomy control module from the modular bot component storage may be selected based upon an autonomy module sensor requirement for the desired logistics operation, display capacity for H2M communications, and the like.

Thus, method 4100 proceeds at step 4115 by detachably mounting a selected modular mobility base to a selected modular auxiliary power module using an interlocking alignment interface disposed on each of the selected modular mobility base (e.g., interlocking alignment interface 1810 on MB 1705) and the selected modular auxiliary power module (e.g., an alignment channel or latches on APM 1710). At step 4120, method 4100 proceeds by detachably mounting a selected modular cargo storage system to a top of the selected modular auxiliary power module, and then at step 4125, method 4100 proceeds by detachably mounting a selected modular mobile autonomy control module to a top of the selected modular cargo storage system. Then at step 4130, method 4100 secures the selected modular cargo storage system to each of the selected modular auxiliary power module and the selected modular mobile autonomy control module using a locking handle (e.g., handle 2115) actuating at least one set of actuated latches (e.g., latches 2110) disposed on the selected modular cargo storage system.

At step 4135, method 4100 proceeds with the assembly server downloading or otherwise transmitting the assigned dispatch use profile for the modular autonomous bot apparatus assembly to the selected modular mobile autonomy control module. For example, as shown in FIG. 42, exemplary assembly server 4210 may establish communication with the autonomous controller (e.g., autonomous control system 3100) within MAM 1725 and download exemplary assigned dispatch use profile 4230 to the autonomous controller. Using authentication information contained in the assigned dispatch use profile, method 4100 proceeds at step 4140 by authenticating each of the selected modular mobility base, the selected modular auxiliary power module, the selected modular cargo storage system according to authentication information in the assigned dispatch use profile.

Such an authenticating step provides, for example, a verification of compatibility for each of the selected modular mobility base, the selected modular auxiliary power module, the selected modular cargo storage system, and the selected modular mobile autonomy control module. In more detail, the authenticating step may be implemented with component-to-component secure handshaking between proximately attached ones of the selected modular mobility base, the selected modular auxiliary power module, the selected modular cargo storage system, and the selected modular mobile autonomy control module. For example, the component-to-component secure handshaking may be implemented with a challenge and security credential response between proximately attached ones of the selected modular mobility base, the selected modular auxiliary power module, the selected modular cargo storage system, and the selected modular mobile autonomy control module similar to that explained with reference to FIG. 34.

In some embodiments of method 4100, step 4140 may have the selected modular mobile autonomy control module, as a control element, authenticating each of the selected modular mobility base, the selected modular auxiliary power module, and the selected modular cargo storage system according to the authentication information in the assigned dispatch use profile. This may be accomplished, for example, with a component-to-component secure handshaking between the selected modular mobile autonomy control module and each of the selected modular mobility base, the selected modular auxiliary power module, and the selected modular cargo storage system according to the authentication information in the assigned dispatch use profile where the component-to-component secure handshaking involves a challenge and security credential response between the selected modular mobile autonomy control module and each of the selected modular mobility base, the selected modular auxiliary power module, and the selected modular cargo storage system according to the authentication information in the assigned dispatch use profile.

A further embodiment of method 4100 may also include responsive actions taken when one of the modular components is not authenticated. For example, an embodiment of method 4100 may further include the step of transmitting a replacement component request message to the assembly server 4210 by the selected modular mobile autonomy control module (e.g., exemplary MAM 1725 shown in FIG. 42). In this embodiment, the replacement component request message indicates that one or more of the selected modular mobility base, the selected modular auxiliary power module, and the selected modular cargo storage system are not authenticated modular components based upon the component-to-component secure handshaking between the selected modular mobile autonomy control module and each of the selected modular mobility base, the selected modular auxiliary power module, and the selected modular cargo storage system. Receipt of the replacement component request message by the assembly server may, for example, cause the assembly server to initiate replacement of the selected modular mobility base, the selected modular auxiliary power module, and the selected modular cargo storage system indicated as being not authenticated modular components for the modular autonomous bot apparatus assembly according to the authentication information in the assigned dispatch use profile.

In still another embodiment of method 4100 where the operating environment may be a fleet logistics environment where multiple MALVT bot apparatus assemblies are maintained and deployed on various logistics operations, method 4100 may further include the assembly server causing each of the selected modular mobility base, the selected modular auxiliary power module, the selected modular cargo storage system, and the selected modular mobile autonomy control module to be pulled from a fleet modular bot component storage (e.g., via assembly server communications with a fleet depot technician operating a mobile wireless node and/or a fleet vending system similar to that of system 4220). However, in this embodiment, the assembly server causes the particular selected modular components to be pulled from the fleet modular bot component storage according to one of multiple licensed fleet use profiles. Such a licensed fleet use profile may indicate an operational permission status relative to a particular modular component (e.g., the leased status of a particular MB or CSS for use in the fleet operations). Thus, the licensed fleet use profile may include the assigned dispatch use profile with the addition of such relevant fleet usage information, such as permissive status.

Still further embodiments of method 4100 may involve dispensing from vending machines (e.g., exemplary vending system 4220) as part of the assembly process. For example, an embodiment of method 4100 may further include the step of dispensing at least one of the modular mobility base, the modular auxiliary power module, the modular cargo storage system, and the modular mobile autonomy control module from a vending machine. This may involve, in particular, dispensing the modular cargo storage system to be used as one of the authorized parts of the modular autonomous bot apparatus assembly from a vending machine maintaining a multiple different sized modular cargo storage systems.

In even more detail, such dispensing may involve receiving, by the vending machine, a selection of at least one of the modular mobility base, the modular auxiliary power module, the modular cargo storage system, and the modular mobile autonomy control module. Such a selection being received from the assembly server is in response to the request for assembly of the modular autonomous bot apparatus assembly, and is being consistent with the assigned dispatch use profile identifying the type of each of the modular mobility base, the modular auxiliary power module, the modular cargo storage system, and the modular mobile autonomy control module to be used as the authorized parts of the modular autonomous bot apparatus assembly based on the request for assembly. With the received selection, the vending machine (e.g., vending system 4220 as shown in FIG. 42) may dispense the selected one of the modular mobility base, the modular auxiliary power module, the modular cargo storage system, and the modular mobile autonomy control module from the vending machine.

Such vending systems may also be used during assembly of an exemplary MALVT bot apparatus assembly to dispense other detachable parts used on the bot apparatus assembly. For example, a further embodiment of method 4100 may further include the step of dispensing a detachable module from a vending machine, where the detachable module is deployed within the modular cargo storage system. Such a detachable module may be a detachable climate control module (e.g., exemplary detachable modular climate control module 2210), a detachable sensor pod (e.g., exemplary removable payload sensor pod 3005a), and a detachable separator that may be deployed to partition and organize space within a CSS into different compartments (e.g., separator 3608). Thus, an exemplary vending machine used in this embodiment of method 4100 may have different types of detachable climate control modules available for dispensing from the vending machine, where each of the different types of detachable climate control modules has a different environmental control range; different types of detachable sensor pods available for dispensing from the vending machine, where each of the different types of detachable sensor pods having a different characteristic type of sensor; and different types of separators where each type may partition the payload area into different numbers of compartments, may provide different structural support for items loaded into any partitioned compartments, may provide different insulation between such compartments, and the like.

Integration of Exemplary MALVT Bot Apparatus with Other Systems

As noted earlier, an exemplary MALVT bot apparatus or system using such apparatus may be integrated with existing backend server or IT systems for improved and enhanced operations that use and deploy one or more specially configured exemplary MALVT bot apparatus. These type of systems may include servers for dispatch and operational systems for planning and daily routing and fleet management; pricing and revenue systems for collection of fees, surcharges, and taxes; mobile integration to business or IT systems to ensure smart phones are part of the customer experience; and enterprise foundational services, including logistics services in the address, shipment, and geospatial domains.

Embodiments that integrate an exemplary MALVT bot apparatus and/or systems of such devices may be scaled up for large scale applications as well as diverse concurrent deployments for different applications. Embodiments that deploy such an integrated approach are designed to be compliant with information security rules and policies (e.g., those rules and policies for existing business or IT systems) and incorporate procedures to protect customer data.

As noted above, embodiments may utilize and interface with a hierarchical Internet-of-Things (IoT) type of wireless node network (such as the TRON technology described and referenced above) that is an example of such a business or IT system. Additionally, embodiments may use node and server devices from such a wireless node network as part of implementing applications involving an exemplary MALVT bot apparatus and systems of such devices. For example, as explained above, exemplary node and server devices from such a TRON wireless node network may include ID nodes on a lower level of the network, master nodes and/or ULD container nodes at a middle level of the network, and one or more servers at a higher level of the network. Those skilled in the art will appreciate that the control logic (e.g., processor, controller, CPU, GPU, and the like) deployed in different component units of an exemplary MALVT bot apparatus may be considered an ID node, master node, or container node based upon such TRON technology.

Consistent with the above overview of TRON wireless network technology, an exemplary TRON wireless node network may include specially configured processing systems and wireless nodes (as opposed to generic computers), such as a server connected to a network. The server is also operatively connected to different network components, such as a master node and indirectly to an ID node through the master node. In contrast to a generic computer, the master node is wireless node device typically connected to a wireless ID node via short-range wireless communications (e.g., Bluetooth® formatted communications) and includes self-location circuitry (such as a GPS receiver and antenna). The master node is typically connected to the server through the network via longer-range wireless communication (e.g., cellular) and/or medium range wireless communication (e.g., wireless local area data networks or Wi-Fi) where both short-range and medium-range and longer-range wireless communications may be implemented in hardware (e.g., transceivers and antennas), a combination of hardware and software, and/or via one or more software defined radios (SDR). And in contrast to a generic computer, the wireless ID node is typically a low cost wireless node device that may be easily placed into an package, be integrated as part of packaging (or a component of an exemplary MALVT bot apparatus), or otherwise associated with an item to be shipped, tracked and located, such as a package, a person, object (e.g., vehicle, etc.), or component of an exemplary MALVT bot apparatus. Generally, an ID node is capable of communicating directly with a master node but incapable of communicating directly with the server, while a master node is capable of communicating directly with the server and separately and directly communicating with other nodes (such as an ID node or another master node). The ability to deploy a hierarchy of wireless nodes within an exemplary wireless node network to distribute tasks and functions at the different levels in an efficient and economical manner helps to facilitate a wide variety of adaptive locating, tracking, managing, and reporting applications using such a network of nodes, and can be extended for use with different components of an exemplary MALVT bot apparatus (such as exemplary MALVT bot apparatus 1700) or systems that use one or more of such exemplary MALVT bot apparatus.

An exemplary wireless ID node is a transceiver-based processing or logic unit having a short-range radio with variable RF characteristics (e.g., programmable RF output power range, programmable receiver sensitivity), memory accessible by the processing unit, a timer operatively coupled to the processing unit, and a power source (e.g., a battery) that provides power for the circuitry of the ID node.

An exemplary master node generally serves as an intelligent bridge between an ID node and the server. Accordingly, an exemplary master node is generally more sophisticated than an ID node. In one example embodiment, an exemplary master node is a device having a processing or logic unit (such as a microprocessor, microcontroller, CPU, or GPU), a short-range transceiver (that may have variable RF characteristics) used for communicating with other nodes (ID nodes and other master nodes), a medium and/or long-range transceiver for communication with the server, memory accessible by the processing unit, a timer operatively coupled to the processing unit, and a power source (e.g., a battery or a wired power supply connection) that provides power for the circuitry of the master node. The exemplary master node may be positioned in a known fixed location or, alternatively, be used as a mobile wireless node (such as the controller/processor used within a MAM component 1725 of an exemplary MALVT bot apparatus) having dedicated location positioning circuitry (e.g., GPS circuitry) to allow the master node to determine its location by itself.

In addition to an ID node and a master node, which are elements of an exemplary TRON wireless node network, a further embodiment of an enhanced exemplary wireless node network may include a specific type of node element integrated with, attached to, or otherwise associated with a type of logistics container (such as a ULD used when transporting items on an aircraft, a trailer capable of being moved by a truck, a train car capable of being moved on a railway system by a locomotive, an intermodal shipping container capable of being moved on at least two different types of transportation modalities, and the like). This further type of node element is generally referred to as a container node, and is explained in more detail within U.S. Patent Application Publication No. US 2016/01232481, which is incorporated by reference. Further embodiments may deploy such a container node as part of an exemplary TRON network application to facilitate enhanced system scanning capabilities that leverage off using this type of container node in addition to fixed facility nodes, along with localized scanning, and more intelligent and efficient use of the hierarchy of network elements to accomplish scanning for ID nodes in order to better handle the congestion issues anticipated.

An exemplary server from a TRON network application may be considered a specially configured networked computing platform capable of connecting to and interacting with at least the wireless master nodes and/or container nodes, and may be used as part of an application involving one or more exemplary MALVT bot apparatus (such as exemplary MALVT bot apparatus 1700 described above) or a system using one or more exemplary MALVT bot apparatus. As explained in more detail in U.S. Pat. No. 8,989,053, a TRON server may be considered to use a programmatically configured single processor or may be implemented as one or more part of a specially programmed multi-processor component that communicates with devices (such as user access devices like smart phones, laptops, or other handheld wireless processing based devices) and wireless nodes (such as a master node or a container node). Such a server may be implemented as a single computing system, a distributed server (e.g., separate servers for separate server related tasks), a hierarchical server (e.g., a server implemented with multiple levels where information may be maintained at different levels and tasks performed at different levels depending on implementation), or a server farm that logically allows multiple distinct components to function as one server computing platform device from the perspective of a client. In some regional deployments, an exemplary server may include servers dedicated for specific geographic regions as information collected within different regions may include and be subject to different regulatory controls and requirements implemented on respective regional servers.

An exemplary TRON server that may be used with an exemplary MALVT bot apparatus may deploy more than one memory storage media. The memory storage media may be in differing non-transitory forms (e.g., conventional hard disk drives, solid state memory such as flash memory, optical drives, RAID systems, cloud storage configured memory, network storage appliances, etc.). Such an exemplary server may be implemented, at its core, with a processing or logic unit coupled to a network interface, which facilitates and enables operative connections and communications through the network with one or more master nodes, container nodes, as well as, in some embodiments, user access devices. The exemplary server may include a medium and/or long-range communication interface with which to more directly communicate with one or more master nodes, container nodes, and/or user access devices. Using these communication paths as well as program code or program modules stored on the server and executed by the server, the server generally operates to coordinate and manage information related to an ID node as an item associated with the ID node physically moves from one location to another. This same type of coordination and management may be applicable to coordinating and managing information related to an exemplary MALVT bot apparatus, components or such an exemplary MALVT bot apparatus, and the contents carried by an exemplary MALVT bot apparatus (whether node-enabled packages/items or non-node-enabled packages/items as objects within a CSS unit).

As a computing platform, the processing unit of an exemplary server is operatively coupled to a memory storage and volatile memory, which collectively store and provide a variety of executable program code (e.g., server control and management code as well as artificial intelligence (AI) systems for learning about managing network devices, context related to such devices, and anticipated environments related to the same), data similar to that kept in a master/container/ID node's respective memory storage (e.g., profile data, security data, association data, shared data, sensor data, location data) and context data related to the environment in which the nodes are operating (e.g., information generated from within the wireless node network and information created external to the wireless node network). As such, an exemplary server used as part of an embodiment is specially programmed and configured to interact with the wireless nodes beyond that of being a generic computer.

In embodiments involving an exemplary MALVT bot apparatus (such as exemplary MALVT bot apparatus 1700), an exemplary MB 1705 may be implemented using a wireless ID node as the mobility controller or processor that performs control for steering and propulsion or interfaces with separate control logic for steering and propulsion. The wireless ID node may have wired control signals to such steering and propulsion systems or interfaces or may send control signals via wireless M2M communications to such systems or interfaces. Thus, an ID node implementation within an MB 1705 may also have and take advantage of wired and wireless communication with other devices, such as that explained in more detail in the TRON Network Reference Information incorporated by reference.

Likewise, in embodiments involving an exemplary MALVT bot apparatus (such as exemplary MALVT bot apparatus 1700), an exemplary APM or BAPM component 1710 may be implemented using a wireless ID node as a processing and control device that interfaces with the MB 1705 and the MAM 1725. In a further embodiment, an exemplary APM or BAPM 1710 may be implemented using a wireless master node or container node at a higher level of the wireless node network as its processing and control device, where such a master/container node interfaces with the MB 1705, may interface with node-enabled objects being transported within a CSS 1720 by the APM or BAPM 1710, and further may interface with the MAM 1725 and/or server disposed external to the exemplary MALVT bot apparatus.

Further, in embodiments involving an exemplary MALVT bot apparatus (such as exemplary MALVT bot apparatus 1700), an exemplary MAM component 1725 may be implemented using a wireless master node or container node as its autonomous controller or autonomous control system (i.e., a type of processing and control device), where such a wireless master/container node may interface with the MB 1720 (e.g., implemented as a wireless ID node), may interface with node-enabled items/objects being transported within a CSS component 1720 (e.g., where such items/objects may be packaged or unpackaged items that are wireless ID node or master node enabled), may interface with the APM or BAPM 1710 supporting the CSS component 1720 (e.g., where the APM or BAPM 1710 may be implemented using wireless ID nodes, master nodes, or container nodes), and further interface with the server.

Furthermore, embodiments may involve or implement an exemplary MALVT bot apparatus (such as exemplary MALVT bot apparatus 1700) with a wireless master node or container node as its processing and control device in order to provide TRON infrastructure support. For example, an exemplary embodiment may involve operations in a warehouse where no or limited TRON technology based infrastructure support exists for a hierarchical network of wireless ID nodes, wireless master nodes/container nodes, and specially programmed and configured backend support servers that can enhanced logistics management of items being shipped. In such an embodiment, one or more exemplary MALVT bot apparatus may be deployed to help assist with and/or help with navigation of another exemplary MALVT bot apparatus transporting an item/object being shipped. For example, one bot apparatus may collaboratively map the operating area of the warehouse to facilitate movement and navigation by the other exemplary MALVT bot apparatus transporting an item/object being shipped. This may have one bot apparatus deployed with more acute and higher accuracy sensors (e.g., LiDAR, RADAR) while allowing for lower sensing requirements (e.g., proximity sensing, GPS locating, etc.) of the other exemplary MALVT bot apparatus transporting an item/object being shipped.

In this manner, interfacing TRON-based technology devices and systems with an exemplary MALVT bot apparatus and/or systems using such an exemplary MALVT bot apparatus (such as exemplary MALVT bot apparatus 1700) may provide contextual awareness of an object/package in shipment (e.g., an object temporarily stored within a CSS unit 1720 of such an assembled bot apparatus 10), provide granular navigation, and manage authentication of various wireless devices that interoperate for robotic object/package delivery. The contextual awareness may, for example, involve situational awareness for the environment of the exemplary MALVT bot apparatus, such as the operational environment of the apparatus, the anticipated operational environment of the apparatus (e.g., environmental, electronic density, physical layout), and regulatory compliance for the apparatus based on current and anticipated location.

Further Operational Considerations

For embodiments that use an exemplary MALVT bot apparatus (such as exemplary MALVT bot apparatus 1700 described above), the particular implementation of such an exemplary apparatus (or system that uses one or more of such an exemplary apparatus or components that make up such and exemplary apparatus) may include one or more of the below listed different features/characteristics for function, use parameters, interoperability factors, and otherwise operational aspects:

Functional/Physical Specifications

Overall Dimensions—The dimensions of exemplary MALVT bot apparatus (e.g., min/max height, width, length) may be impacted by weight and speed desired/needed as well as operating environment and regulatory requirements for the particular practical application where the exemplary MALVT bot apparatus has been programmed and is operative for use.

Power for MB 1705, APM 1710—The built-in connections in an embodiment may support multiple batteries that can be plugged into the component, and will not protrude into the cargo unit (e.g., CSS 1720). An electrical conduit (such as conduit or bus 2050, 2250) with appropriate plugs may support power transfer from batteries in the MB 1705 (or APM 1710) to the MAM 1725, depending on the power needs of the bot apparatus assembly 1700.

Batteries—Batteries as power sources may be interchangeable, chargeable as a standalone battery, or while in MB 1705, APU 1710, if appropriate power connectors are deployed in the embodiment.

Internal Power—MAM 1725 may be implemented to have an internal power component (e.g., secondary power source 3120) that may provide minimal power, rechargeable when the unit is in storage. Embodiments of MAM 1725 may receive operating power from the MB 1705 or APM 1710 under normal operating conditions via bus 3115, but allow for switchable power source operations when power from the MB 1705 and/or APM 1710 cease (e.g., with power monitoring and switching logic as described above relative to secondary power source 3120).

Locking Mechanisms—System assembly can be performed via mechanical locking (e.g., via a keypad, traditional key lock, and the like). Embodiments of MB 1705, APM 1710, CSS 1720, and MAM 1725 can be mechanically assembled and fastened during bot provision/assembly at a bot storage depot. For customer access to the cargo area (e.g., via cargo door 1715), an embodiment may utilize a powered or actuated lock within the CSS 1720 consistent with the description above where such a lock may be electronically actuated (rather than just manually). An exemplary electronic lock may allow for local use only (e.g., activation between open/closed states using an electromechanical keypad, actuation via Bluetooth Low Energy (BLE), Fingerprint, facial scan or other biometric input, voice input through a microphone (pass-phrase), and the like) or may allow for both local and remote interaction (e.g., activation between open/closed states using a transmission of a predetermined unlock sequence from another bot component or outside the bot apparatus by a remote operator/user operating a connected user access device, such as a smartphone or tablet). An embodiment of such an electronic lock on CSS 1720 (may receive power via the electrical conduit (e.g., conduit 2250). The Cargo Door (e.g., door 1715) may have a mechanical fastening system (e.g., lock 2025) to secure the door while in transit, but may not require a locking mechanism in other embodiments (e.g., in-station use cases).

Machine to Machine Interaction—An exemplary MALVT bot apparatus at delivery locations may interface and interact with devices and systems outside the bot apparatus on a physical level as well. As such, the mechanical design of embodiments of an exemplary MALVT bot apparatus 1700 may facilitate interaction with an object receptacle (package deposit receptacle). For example, an exemplary MALVT bot apparatus may utilize a retractable front door (such as door 1715) that opens when exemplary MALVT bot apparatus approaches a particular delivery receptacle (e.g., when the bot apparatus detects a current location to be within a threshold distance of the delivery receptacle, which responsively triggers unlocking the CSS 1720 and engaging delivery structure, such as doors, articulating arms, or the like, to initiate removal of the object from the bot apparatus and placement of the object with the delivery receptacle). In another example, use the above-described "stand up" and tilt functionality to facilitate a gravity delivery of an object (object weight may be a factor) may be accomplished with the mechanical design that allows for such selective actuation of the orientation, angle, tilt, and movement of the bot apparatus and its delivery components (e.g., door 1715, moving ramps, conveyors, and the like).

Ground clearance of exemplary MALVT bot apparatus—The adaptive mechanical ground clearance design of embodiments of an exemplary MALVT bot apparatus with, for example, the wheels and suspension system of its MB 1705, all the bot apparatus to maneuver through and navigate broken/buckled sidewalks, tree roots, standing water, and grassy sloped terrain. Wheels or other propulsion tracks may be selected for enhanced traction via tread materials and patterns, and suspensions on the MB 1705 may be autonomously and selectively articulable to adaptively handle such environments.

Visual Navigation Indicators—Embodiments of the exemplary MALVT bot apparatus may generate displays that indicate turn signals, braking, vehicle speed, etc. as part of visual displays disposed on the MB 1705, CSS 1720, as well as the MAM 1725 components as described above. Embodiments may deploy lighting for dusk/nighttime operation as described above as well.

Alerts & Sensors—Embodiments of the exemplary MALVT bot apparatus may deploy proximity sensors to assist with locating itself and collision avoidance, as well as visual and audio alerts through its displays and speakers through which such alerts may be broadcast while the exemplary MALVT bot apparatus is en route. Embodiments of the exemplary MALVT bot apparatus 1700 may deploy environmental sensing (e.g., on one or more of the MB 1705, APM 1710, CSS 1720, and/or MAM 1725 components) to monitor sound, ambient temperature external and/or internal to the bot apparatus, used to adjust runtime parameters (e.g., speed) to ensure adequate battery for route, and used to adjust the route to avoid adverse environmental conditions (e.g., avoid the rain outside if an indoor path is available while en route to a destination).

Collaboration of Multiple MALVT Bot Apparatus—Embodiments may deploy a group of MALVT bot apparatus assemblies, which may be specially dispatched and programmed to interact with each other in an advantageous practical application to collaborate to carry a single larger item. For example, this may involve embodiments of a collaboration mode of multiple MB units, such as that shown in FIG. 19 where both MB units 1705a, 1705b are physically connected with one base adapter plate 1905 (e.g., implemented with a large or extended sized BAPM 405 to provide a larger support base) capable of handling and supporting a larger item/object or group of items/objects being shipped. In another example, different exemplar MALVT bot apparatus assemblies may collaborate as an impromptu sort belt with bots and truck.

Cargo Door Closure Mechanisms—Embodiments of the exemplary MALVT bot apparatus may use a cargo door (e.g., door 1715) that is self-closing. For example, the cargo door may be equipped with a delayed spring activated closing (closing after a period of time), a motion sensor actuated closing (closing once a sensor on the bot apparatus (e.g., APM 1710, CSS 1720, or MAM 1725) detect there is no movement relative to the area surrounding the cargo door and electronically causing a responsive closure of the cargo door via actuators on the door hinge or the door itself). Such an embodiment may be useful if a customer does not close the door after object retrieval, and helps avoid theft of other objects still within the CSS 1720 of the bot apparatus.

Operating Specifications: Operational Design Domain (ODD)

Embodiments of the exemplary MALVT bot apparatus may deploy its MAM 1725 (or MB 1720 in certain embodiments) to have and use specific types of operational specification data or parameters that may be used as a type of context data on environment and anticipated environment where the bot apparatus 1700 is or will be (or is anticipated to be operating based upon a planned, predicted or otherwise determined route). Such operations specifications that may be included in a dispatch command for an operation (i.e., data that is also referred to collectively as a contextual operations design domain (ODD)) may include, for example, data structures that maintain information on the following:

Geographic area (e.g., city, rural, mountain desert, etc.);
Speed (e.g., max, normal operational speed based on mode);
Range (may vary due to environmental conditions, temperature, terrain, slope);
Payload;
Roadway types (e.g., street/sidewalk/bike lane, etc.);
Terrain (e.g., types of terrain, such as uneven ground, broken/heaved sidewalk, tree roots, storm drains, curbs, stairs, rough paved surfaces (gravel/mud), sloped terrain, maximum slope traversal without excessive battery drain on various surface types);
Operation through standing water (how deep);
Temperature/Humidity operational ranges (e.g., including quantification range/battery as a function of operational ranges);
Weather conditions (e.g., rain intensity/duration, snow/sleet);
Weather Ratings for Components (e.g., IP Code specifications, such as IP67, as it relates to bot component weather resistance capabilities, such as water resistance, water proof, dust resistance, and the like).

DOT, NHTSE, Other Regulatory Requirements for Autonomous Ops

Embodiments of the exemplary MALVT bot apparatus 1700 may be deployed in practical use applications where particular regulatory requirements impart guidelines or requirements for operation of the bot apparatus as an autonomous vehicle (AV) in operation. Such regulatory requirements may, for example, include:

Object and Event Detection and Response (OEDR);
Normal Driving—behavioral competencies;
Crash Avoidance Capability;
Fallback (minimal risk condition); and
Account for State and local regulations that will apply testing and operation ADA Consideration of Human-Bot Interactions Embodiments of the exemplary MALVT bot apparatus may be deployed in practical use applications where standard for accessible design under the Americans with Disabilities Act (ADA) or other standards impart guidelines or requirements on how the exemplary MALVT bot apparatus may accommodate customer interaction with special needs customers (e.g., proximity sensing for strollers, wheelchair uses).

Infrastructure & Lifestyle Management for MALVT Bot Apparatus Components

Storage of components—The components that are assembled into an exemplary MALVT bot apparatus 1700 (including detachable sensor pods, replaceable power sources, and the like) may include features and aspects that relate to when those components are not yet assembled and are stored prior to assembly into such a bot apparatus. For example, an exemplary MAM 1725 (or other battery equipped component) may fit into a storage unit (dock) to charge the battery component, download data & check for maintenance needs. When in a storage configuration, an exemplary CSS 1720 may be collapsible (as noted above and shown in FIGS. 23 and 24). An exemplary MB unit 1705 may charge when in a "vending unit", and interact with a backend server of a Fleet Management System, which collectively allows and enables a type of "First in Last out" usage for MB units charging in the vending unit to ensure uniform operation throughout the fleet.

Asset Tracking/Data Management

Embodiments of the exemplary MALVT bot apparatus may implement data communications requirements during "off-duty" periods (e.g., on a nightly cycle, when recharging particular components, and the like), upload of battery & system metrics, and operational (pickup & delivery) metrics. Embodiments of the exemplary MALVT bot apparatus may also communicate with backend fleet management systems (e.g., specially configured and programmed servers that support one or more exemplary MALVT bot apparatus 1700 in the below described practical use applications) for remote real-time operator assist, normal route tracking/mapping, and pickup scheduling.

Evolution of Technology Enablers

Use Cases for 5G Technologies

Embodiments of the exemplary MALVT bot apparatus and system of multiple such bot apparatus may integrate with or deploy massive Internet of Things (IoT) devices at the core of different components primarily for M2M communications. As such, the use of such high speed IoT devices integrated as part of different components may be used for practical applications where high-speed throughput, with low latency, is desired to enable real-time control at high speeds (e.g., up to 500 km/hr) of the bot apparatus. Such high speed IoT devices may also provide enhanced mobile broadband for faster service and better coverage for fixed and moving user access devices (e.g., smartphones, laptops, and the like) as well as for support of extended visualization on such remote devices via 3D video, augmented reality, and virtual reality displays on the remote devices.

Dedicated Short Range Communications

Embodiments of the exemplary MALVT bot apparatus and system of multiple such bot apparatus may also provide low latency, high bandwidth connectivity for short to medium range 2-way wireless communications. This may take the form of Vehicle to Vehicle Connectivity (V2V) and/or Vehicle to Infrastructure Connectivity (V2I).

Smart Cities Integration

Embodiments of the exemplary MALVT bot apparatus 1700 and system of multiple such bot apparatus may further provide interoperability with exemplary Smart City infrastructure frameworks and platforms. Typical components of such an exemplary framework may include:

Signal phase and timing message systems, which provides two-way communication between a traffic signal controller and a mobile device;
Telematics systems, which collect and transmit vehicle data information real-time to an organization; and
Dynamic traffic management systems for autonomous vehicles, based on real-time traffic data being collected from connected vehicles Practical Applications with MALVT Bot Apparatus/Systems In general, embodiments of an exemplary MALVT bot apparatus/system for the customer as described below may involve an app on a user access device (e.g., a smart phone, laptop, tablet, or other computing device (such as a wireless mobile node)) leveraging wireless, mobile location, GPS, and/or in facility TRON network location. Aspects and features of wireless node network TRON elements described above that may be used in embodiments to implement some components of the exemplary MALVT bot apparatus may be deployed so as to enable the relevant bot apparatus component (e.g., an exemplary MAM 1725) to provide location, association, and authentication for customer-to-machine, machine-to-machine, and location assistance relative to the exemplary MALVT bot apparatus. What follows are different embodiments of practical use applications that deploy and use one or more specially programmed MALVT bot apparatus assemblies as a particular device (or components thereof) or as a system in use with other exemplary MALVT bot apparatus and/or other systems (such as a backend server specially programmed to support the exemplary MALVT bot apparatus, a logistics receptacle that may interface with the exemplary MALVT bot apparatus, or a user access that may interface with the exemplary MALVT bot apparatus).

Figure 43A:
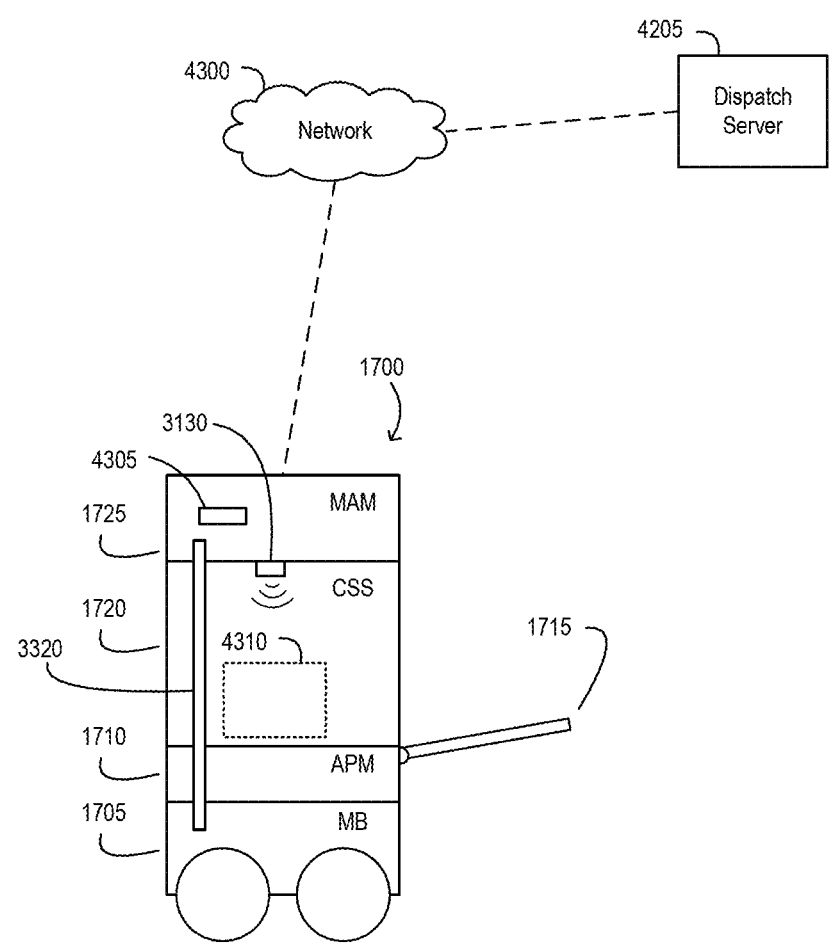
FIGS. 43A-43F are diagrams of an exemplary modular autonomous logistics transport vehicle apparatus (MALVT bot apparatus) in various stages of an exemplary dispatched logistics operation in accordance with an embodiment of the invention.

FIGS. 43A-43F are diagrams of an exemplary modular autonomous logistics transport vehicle apparatus (MALVT bot apparatus) assembly 1700 as it is involved in various stages of an exemplary dispatched logistics operation in accordance with an embodiment of the invention. Referring now to FIG. 43A, exemplary MALVT bot apparatus assembly 1700 is shown in an assembled configuration (e.g., after assembly according to exemplary method 4100) with a dispatch server 4205. In this general example, exemplary dispatch server 4205 transmits a dispatch command 4305 through network 4300 (e.g., via a wireless communication path) for receipt by the exemplary MAM 1725 in exemplary MALVT bot apparatus assembly 1700. As part of the exemplary dispatched logistics operation related to the dispatch command 4305, an item or object 4310 may be loaded into exemplary CSS 1720 after cargo door 1715 is opened. Detection of the loaded item may be accomplished using internal sensor(s) 3130 that monitor the payload area in CSS 1720 and under MAM 1725. Once the exemplary CSS 1720 has received item 4310 being shipped or otherwise transported on exemplary MALVT bot apparatus assembly 1700, exemplary MALVT bot apparatus assembly 1700 may have the autonomous controller in MAM 1725 direct and control movement of exemplary MB 1705 to move exemplary MALVT bot apparatus assembly 1700 from one location to another.

Figure 43B:
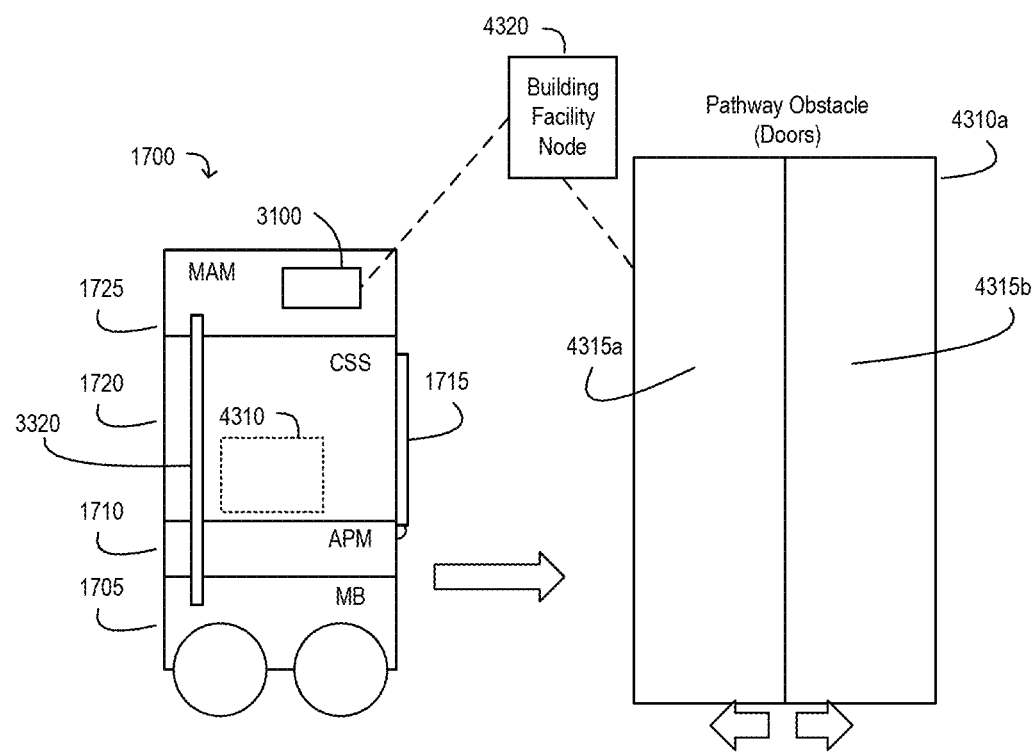

As shown in FIG. 43B, exemplary MALVT bot apparatus assembly 1700 is generally illustrated in transit and moving towards a destination location for the exemplary dispatched logistics operation identified as part of the dispatch command 4305. Along the transit route to the destination location, exemplary MALVT bot apparatus assembly 1700 may uses its location circuitry (e.g., location circuitry 3110 on exemplary MAM 1725) and sensors deployed on the MAM 1725 and MB 1705 to which it navigates to the destination location, and encounter pathway obstacles 4310 along the transit route. And as shown in FIG. 43B, exemplary MALVT bot apparatus assembly 1700 may encounter a pathway obstacle 4310a (e.g., a door, elevator, lock, and the like) that may be an actuated type of pathway obstacle where a facility node 4320 operatively coupled to the pathway obstacle 4310a controls actuation to clear such an obstacle for exemplary MALVT bot apparatus assembly 1700 and allow further movement past the obstacle. For example, exemplary MALVT bot apparatus assembly 1700 may move towards an actuated set of doors 4315a, 4315b as exemplary pathway obstacle 4310a, which is controlled by building facility node 4320 (e.g., an ID node or master node) capable of wireless communication with at least exemplary MAM 1725 (e.g., with autonomous control system 3100 through wireless radio transceiver 3125) on exemplary MALVT bot apparatus assembly 1700. As such, exemplary MALVT bot apparatus assembly 1700 may coordinate wirelessly with building facility node 4320 to initiate opening of the doors 4315a, 4315b—e.g., through node-to-node association that permissively establishes a secure connection between autonomous control system 3100 (operating as a mobile master node) in exemplary MALVT bot apparatus assembly 1700 and the building facility node 4320, or other handshaking communication that has exemplary MALVT bot apparatus assembly 1700 transmitting a control signal to cause the building facility node 4320 to actuate the pathway obstacle (i.e., the doors 4315a, 4315b). A similar interaction between exemplary MALVT bot apparatus assembly 1700 and other building facility nodes may occur with other pathway obstacles that may be wirelessly actuated to allow exemplary MALVT bot apparatus assembly 1700 to pass (e.g., node-enabled elevator, a node-enabled moving walkway, a node-enabled lift at a loading dock, and the like).

Figure 43C:
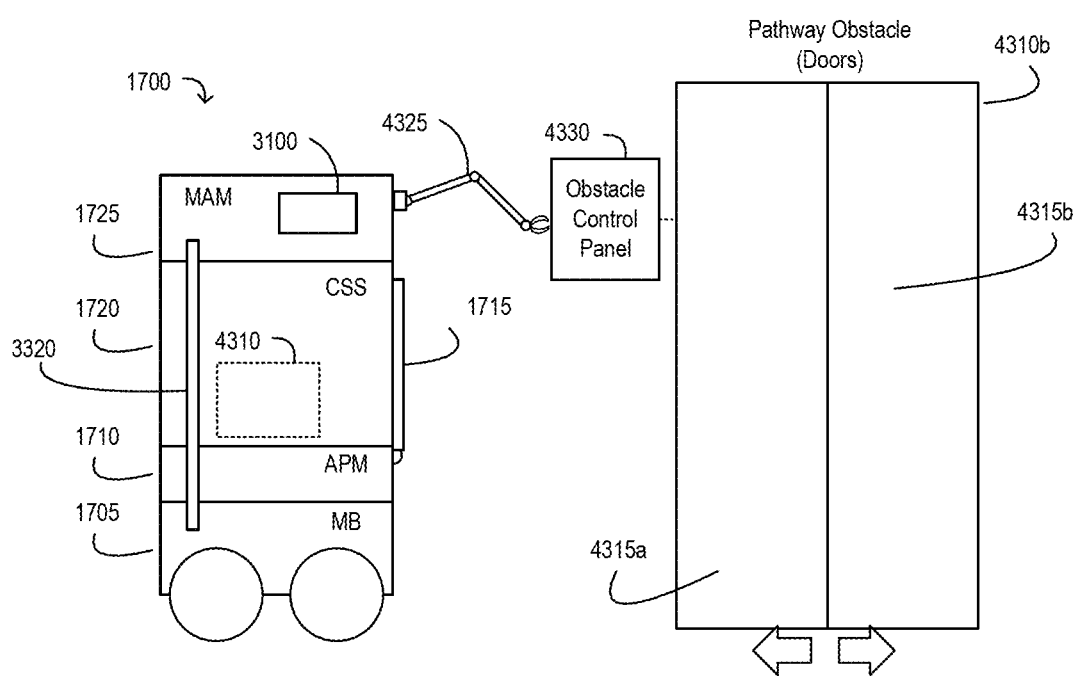

In some situations, pathway obstacles may appear in the transit route for exemplary MALVT bot apparatus assembly 1700 where such pathway obstacles are not capable of wireless interaction to initiate clearing of the obstacle. For example, as shown in FIG. 43C, exemplary MALVT bot apparatus assembly 1700 is faced with an exemplary door pathway obstacle 4310b that is manually actuated. In more detail and as shown in FIG. 43C, exemplary door pathway obstacle 4310b is shown with doors 4315a, 4315b similar to door 4310a in FIG. 43B, but exemplary door pathway obstacle 4310b is actuated via an exemplary obstacle control panel 4330. Control panel 4330 may have, for example, buttons, switches, levers, and the like that may be physically contacted to initiate actuation of doors 4315a, 4315b. As such, exemplary MALVT bot apparatus assembly 1700 may be deployed with an exemplary articulating arm 4325 disposed on the assembly 1700. In this embodiment, exemplary articulating arm 4325 is shown attached to MAM 1725 and is operatively coupled to autonomous control system 3100 so as to be responsive to control signals that move the arm 4325 while sensors on MAM 1725, MB 1705, and/or deployed on the arm 4325 may generate sensor data (e.g., proximity data, machine vision data, and the like) that allows autonomous control system 3100 to guide the arm 4325 to a desired control input area or selector (e.g., a particular button, switch, and the like) that actuates doors 4315a, 4315b. Control system 3100 is operative to use the sensor data to recognize the desired control input area or selector, and move arm 3425 accordingly to manually contact and initiate actuation of the pathway obstacle (e.g., manually actuated door 4310b). Those skilled in the art will appreciate that an embodiment of articulating arm 4325 may be incorporated into other modular components of exemplary MALVT bot apparatus assembly 1700 and be operatively controlled by autonomous control system 3100 with control input to and sensor output from arm 4325 going through bus 3320. Embodiments of articular arm 4325 may recess into a storage channel or chamber on one of the modular components of exemplary MALVT bot apparatus assembly 1700 when not in use, and may further assist with loading and unloading of the item 4310 during an exemplary dispatched logistics operation. Further, those skilled in the art will also appreciate that other manually actuated pathway obstacles (e.g., exemplary locks, elevator buttons, door handles, and the like) may be interacted with in a similar manner with one or more articulating arms 4325 disposed on exemplary MALVT bot apparatus assembly 1700

Figure 43D:
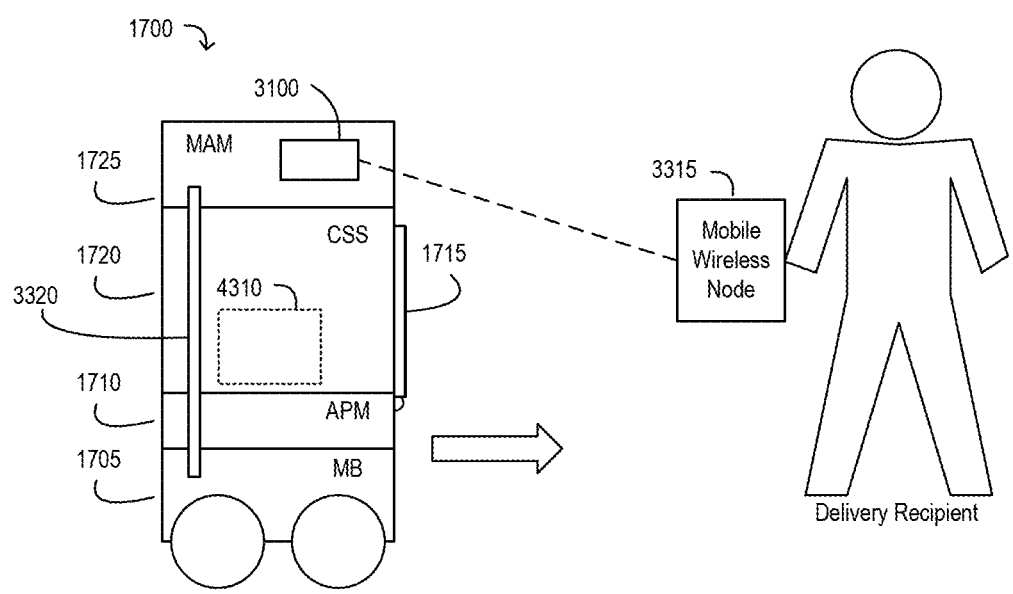
Figure 43E:
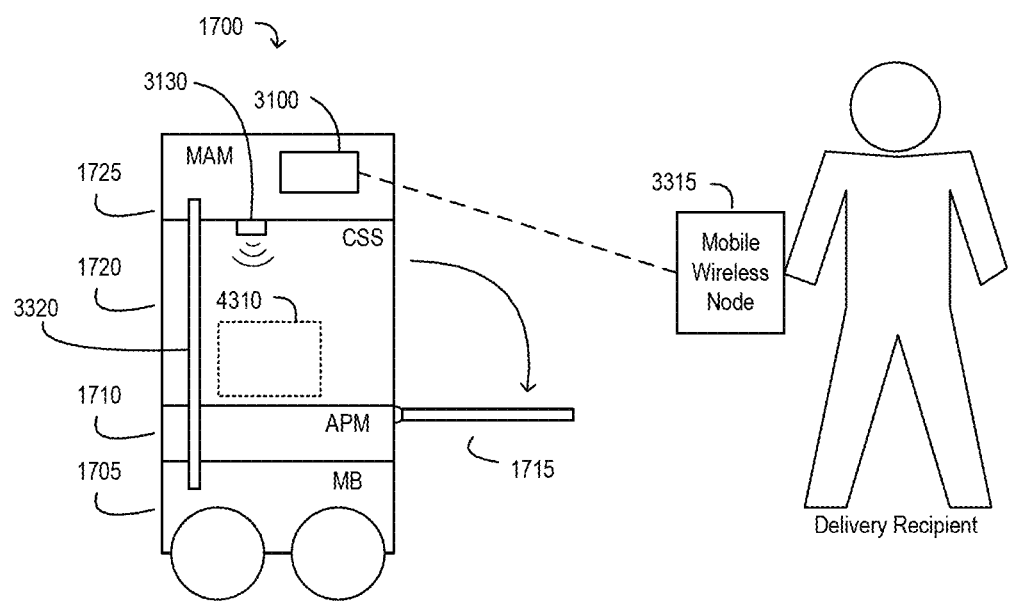
Figure 43F:
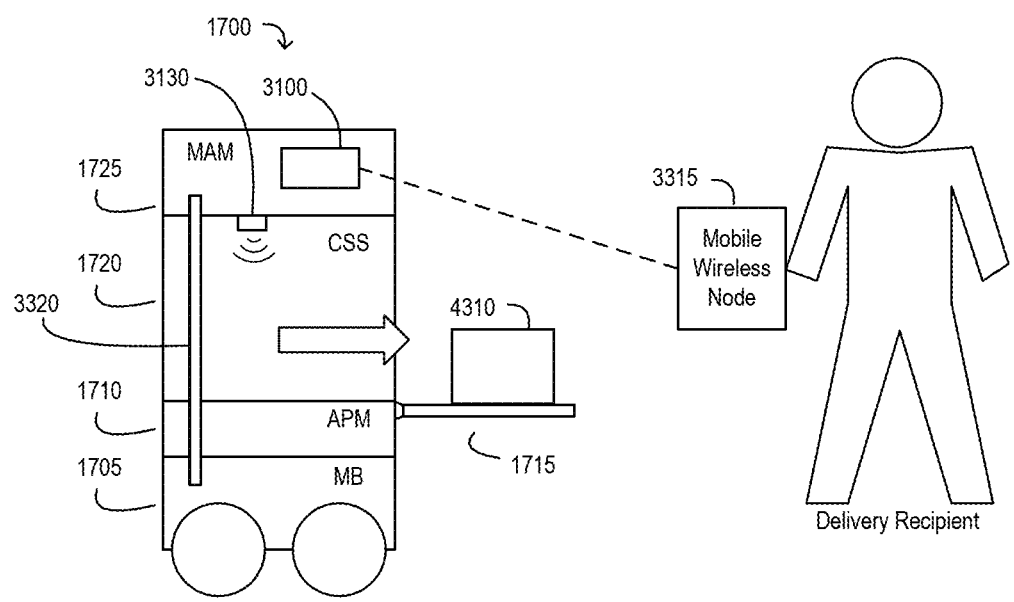

As exemplary MALVT bot apparatus assembly 1700 continues on its transit route towards the destination location in this example, exemplary MALVT bot apparatus assembly 1700 may communicate with a delivery recipient as shown in FIG. 43D. Referring now to FIG. 43D, exemplary MALVT bot apparatus assembly 1700 may, for example, send notifications to the delivery recipient through wireless communications with a wireless node 3315 (e.g., a smartphone, tablet, mobile/fixed ID node or mobile/fixed master node) operated by the delivery recipient. Further, exemplary MALVT bot apparatus assembly 1700 may receive authentication input from the delivery recipient wireless node 3315 so as to perform authentication checks to verify that the delivery recipient is the authorized delivery recipient for the item 4310 being transported for delivery within exemplary MALVT bot apparatus assembly 1700. If the delivery recipient is authenticated to be the authorized delivery recipient for item 4310, cargo door 1715 may be actuated to open by the MAM 1725 (i.e., the autonomous control system 3100). Internal sensors that monitor the payload within exemplary MALVT bot apparatus assembly 1700 (e.g., exemplary payload monitoring sensors 3130) may detect what is in the payload area of the CSS 1720 and may detect when item 4310 is removed. Such removal may be enhanced with object manipulation systems (e.g., moving belt surfaces, actuated sweeping arms, actuated grabbing arms, and the like as described above) and/or causing the exemplary MALVT bot apparatus assembly 1700 to tilt so as to help slide the item 4310 towards the cargo door 1715 or, in some instances, out onto the extended surface of door 1715 as shown in FIG. 43F. Directions for removal may be communicated by exemplary MALVT bot apparatus assembly 1700 to delivery recipient wireless node 3315 and/or may be displayed on H2M interfaces on exemplary MALVT bot apparatus assembly 1700 and/or via audio directions played through one or more speakers on exemplary MALVT bot apparatus assembly 1700.

Further details of particular embodiments are presented below for dispatched delivery, pickup, and other specialized applications of exemplary MALVT bot apparatus assembly 1700 in other types of dispatched logistics operations. FIG. 44 is a flow diagram of an exemplary method for performing a dispatched logistics operation involving delivery of an item being shipped using a modular autonomous bot apparatus assembly (MALVT bot apparatus assembly) and a dispatch server in accordance with an embodiment of the invention. Exemplary method 4400 makes use, for example, of exemplary MALVT bot apparatus assembly 1700 and exemplary dispatch server 4205. Exemplary MALVT bot apparatus assembly 1700, as part of method 4400, is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 4400.

Referring now to FIG. 44, exemplary method 4400 begins at step 4405 with the modular mobile autonomy control module receiving a dispatch command from the dispatch server, where the dispatch command includes at least destination information and authentication information related to a dispatched logistics operation. For example, as shown in FIG. 43A, MAM 1725 is part of exemplary MALVT bot apparatus assembly 1700 and receives an exemplary dispatch command 4305 from dispatch server 4205. This may happen during assembly of exemplary MALVT bot apparatus assembly 1700 (e.g., before MAM 1725 is connected with all components of exemplary MALVT bot apparatus assembly 1700) or once all of the modular components of exemplary MALVT bot apparatus assembly 1700 are gathered, connected, and authenticated as authorized modular components to use in assembly 1700.

At step 4410, method 4400 proceeds with the modular mobile autonomy control module authenticating that each of the modular mobile autonomy control module, the modular mobility base, the modular auxiliary power module, and the modular cargo storage system are compatible with the dispatched logistics operation. In more detail, at step 4110, the authentication performed may, for example, verify that the different components of exemplary MALVT bot apparatus assembly 1700 are compatible with the particular aspects required to carry out the dispatched logistics operation. For example, the authentication information related to the dispatched logistics operation that is included in the dispatch command may include logistical constraint information on the dispatched logistics operation (e.g., information on a determined work environment for a particular component of exemplary MALVT bot apparatus assembly 1700 or the assembly 1700 as a combined unit), size/weight limitations, and readiness limitations (e.g., performance threshold(s) for the particular component/assembly in the dispatched logistics operation). As such, the step of authenticating, by the modular mobile autonomy control module, that each of the modular mobility base, the modular auxiliary power module, and the modular cargo storage system are compatible with the dispatched logistics operation may be based at least upon a comparison of each of the modular mobility base, the modular auxiliary power module, and the modular cargo storage system to the logistical constraint information on the dispatched logistics operation.

At step 4415, method 4400 proceeds with the modular cargo storage system receiving the item being shipped. For example, as shown in FIG. 43A, item 4310 may be received and then maintained within a payload area of CSS 1720, on a base adapter platform of APM 1710, and below the MAM 1725. In more detail, step 4415 may receive the item being shipped with the modular mobile autonomy control module (e.g., MAM 1725) actuating an actuated cargo door (e.g., door 1715) disposed on the modular auxiliary power module to an open position. As shown in FIG. 43A and explained in more detail above, actuated cargo door 1715 provides a seal to a payload area within the modular CSS 1720 when the actuated cargo door 1715 is in a closed position and the actuated cargo door 1715 provides access to the payload area within the modular CSS 1720 when the actuated cargo door 1715 is in the open position. Such an actuated cargo door 1715 may be actuated by the modular mobile autonomy control module using an actuated joint 2020 on the actuated cargo door 1715 to cause the actuated cargo door 1715 to move from the closed position to the open position. A further embodiment may have the MAM 1725 actuating the cargo door by actuating an electro-mechanical lock 2025 on the door 1715 to cause the actuated cargo door 1715 to unlock before moving from the closed position to the open position as part of step 4415.

Further embodiments of method 4400 may have step 4415 actuating object manipulation systems deployed on exemplary MALVT bot apparatus assembly 1700. For example, step 4415 may involve the modular mobile autonomy control module actuating an actuated sliding arm disposed on the modular cargo storage system to move the item being shipped into a payload area within the modular cargo storage system, or actuating an actuated grabbing arm disposed on the modular cargo storage system to grab and move the item being shipped into a payload area within the modular cargo storage system as part of receiving the item being shipped.

In another example, step 4415 may involve the modular mobile autonomy control module actuating an actuated belt surface (e.g., moving belt surface 2080a, 2080b) disposed on the modular auxiliary power module as a movable support surface exposed within a payload area inside the modular cargo storage system. As part of step 4415, the actuated belt surface, when actuated, causes the item as placed on the actuated belt surface to move within the payload area as part of receiving the item being shipped.

At step 4420, method 4400 proceeds with the modular mobile autonomy control module autonomously causing the modular mobility base to move from an origin location on a route to a destination location identified by the destination information. This may, for example, have MAM 1725 autonomously causing modular MB 1705 to move from the origin location to the destination location while avoiding a collision with an obstacle in a transit path on the route to the destination location using sensors disposed on at least one of the modular mobility base and the modular mobile autonomy control module.

In general, the embodiments described herein may have the modular mobile autonomy control module (e.g., exemplary MAM 1725) autonomously causing the modular mobility base (e.g., exemplary MB 1705) to move between locations by providing control signals to systems (e.g., mobility controller 1825 for indirect control of propulsion system 1830 and steering system 1835, or signals that may directly control propulsion system 1830 and steering system 1835) based upon feedback the control module receives about its environment (e.g., location data from location circuitry 3110, sensor data from externally focused sensors deployed on the assembly, such as mobility base sensors 1815, autonomy module sensors 2810, and the like)

Relative to method 4400 and in more detail, step 4420 may involve wirelessly interacting with facility nodes (e.g., ID nodes, master nodes, and the like) that may control different pathway obstacles, such as elevators, doors, lifts, walkways, locks, and other controlled pathway obstacles that may be cleared through control by such wireless-enabled facility nodes. For example, the step of autonomously causing the modular mobility base to move from the origin location on the route to the destination location identified by the destination information may have the modular mobile autonomy control module autonomously causing the modular mobility base to move from the origin location to the destination location while interacting with a wireless building facility node (e.g., exemplary building facility node 4320) to actuate a pathway obstacle disposed in a path on the route to the destination location. Such a pathway obstacle may be an actuated door (e.g., actuated doors 4310a) controlled by the wireless building facility node, an actuated elevator controlled by the wireless building facility node, or an actuated lock controlled by the wireless building facility node.

For example, interacting with the wireless building facility node to actuate the pathway obstacle may involve establishing an authorized association pairing between the modular mobile autonomy control module and the wireless building facility node based upon the authentication information related to the dispatched logistics operation, and causing the wireless building facility node to actuate the pathway obstacle after establishing the authorized association pairing between the modular mobile autonomy control module and the wireless building facility node. In this way, a prerequisite authorized association pairing of the two wireless nodes (e.g., autonomous controller operating as a master node in MAM 1725 and the building facility node 4320 operating as an ID/master node) establishes a foundational secure communication path between the nodes and facilitates movement of assembly 1700 while maintaining a sense of secure access to the building facility node. For example, as shown in FIG. 43B, autonomous control system 3100 of MAM 1725 and building facility node 4320 may permissively establish a trackable and authorized association (e.g., based on security credentials, and involving the generation of association data representing the associative link between the two nodes), which then allows the autonomous control system 3100 to request building facility node 4320 to actuate doors 4310a.

In other embodiments, step 4420 may involve exemplary MALVT bot apparatus assembly 1700 physically interacting with and engaging a pathway obstacle while moving on its transit path to, for example, the destination location. In more detail, an embodiment of step 4420 may have the modular mobile autonomy control module autonomously causing the modular mobility base to move from the original location to the destination location while engaging a pathway obstacle disposed in a path on the route to the destination location using an articulating arm disposed on the modular autonomous bot apparatus assembly and using sensors (e.g., proximity sensors, cameras, vision systems, etc.) on at least one of the modular mobility base and the modular mobile autonomy control module. For example, as shown in FIG. 43C, exemplary articulating arm 4325 may be controlled by MAM 1725 so as to engage a control panel 4330 of door 4310b as part of actuating the doors 4310b to open and allow assembly 1700 to move through the doors 4310b. Examples of engaging the pathway obstacle using such an articulating arm may include engaging such a control panel with buttons, switches, or other control elements such as a handle. Such pathway obstacles may include, for example, a manually actuated door, a manually actuated elevator, or a manually actuated lock (having a handle or knob that can open/close the lock). In more detail, an embodiment may involve engaging the pathway obstacle using the articulating arm and sensors with the modular mobile autonomy control module guiding the articulating arm to a control element (e.g., control panel, button, switch, handle, and the like) of the pathway obstacle using one or more of the sensors on at least one of the modular mobility base and the modular mobile autonomy control module, and then having the modular mobile autonomy control module actuating the pathway obstacle once the articulating arm engages the control element of the pathway obstacle.

At step 4425, method 4400 proceeds by receiving delivery recipient authentication input by the modular mobile autonomy control module from a delivery recipient disposed external to the modular autonomous bot apparatus assembly. The delivery recipient authentication input may be provided to the modular mobile autonomy control module in various ways—e.g., wirelessly (such as that shown in the example of FIG. 43D), through input on a user input panel, through biometrics, and the like. If the delivery recipient authentication input matches or otherwise correlates to at least a portion of the authentication information related to the dispatched logistics operation indicating the delivery recipient providing the delivery recipient authentication input is the authorized delivery recipient for the item being shipped within assembly 1700, the entity providing the delivery recipient authentication input is determined to be the authorized delivery recipient and the exemplary MALVT bot apparatus 1700 is assured of a proper delivery to an authorized entity according to the dispatched logistics operation.

At step 4430, method 4400 continues with the modular cargo storage system providing selective access to the item being shipped within the modular cargo storage system after the delivery recipient authentication input received correlates (or otherwise matches) to the portion of the authentication information indicating the delivery recipient providing the delivery recipient authentication input is the authorized delivery recipient. Selective access, for example, may involve actuating door 1715 to an open position providing the authenticated and authorized delivery recipient with access to item 4310 as shown in FIG. 43E. In more detail, providing selective access as part of step 4430 may, for example, involve actuating a joint 2020 joint on the actuated cargo door 1715 to cause the actuated cargo door 1715 to move from the closed position to the open position; actuating electro-mechanical lock 2025 on the actuated cargo door 1715 to cause the actuated cargo door 1715 to unlock before moving from the closed position to the open position.

In other examples, providing selective access as part of step 4430 may also have the modular mobile autonomy control module controlling and actuating an actuated sliding arm (e.g., arm 2085 shown in FIG. 20D) disposed on the modular cargo storage system to move the item being shipped out from a payload area within the modular cargo storage system; controlling and actuating an actuated grabbing arm (e.g., arm 2090 shown in FIG. 20E) disposed on the modular cargo storage system to grab and move the item being shipped 4310 out from a payload area within the modular cargo storage system, such as to the position shown in FIG. 43F. Further still, providing selective access as part of step 4430 may also have the modular mobile autonomy control module controlling and actuating an actuated belt surface (e.g., surfaces 2080a, 2080b shown in FIG. 20C) disposed on the modular auxiliary power module as a movable support surface exposed within a payload area inside the modular cargo storage system. In this example, the actuated belt surface, when actuated, causes the item being shipped 4310 as placed on the actuated belt surface to move out from within the payload area, such as to the position shown in FIG. 43F.

At step 4435, method 4400 then proceeds with the modular mobile autonomy control module autonomously causing the modular mobility base to move from the destination location on a return route to the origin location after the item being shipped is detected to be removed from within the modular cargo storage system. For example, as shown in FIGS. 43E and 43F, exemplary MAM 1725 may be deployed with internal sensors (e.g., exemplary payload monitoring sensor 3130) integrated as part of MAM 1725 or in a detachable sensor pod (e.g., 3005a). Using such an internal sensor or multiple internal sensors, MAM 1725 may monitor what is currently disposed in the payload area of CSS 1720 below the MAM 1725, and detect when the item 4310 has been removed from CSS 1720. Removal may have the MAM 1725 further identifying the particular item being removed to ensure the correct item is removes (e.g., via visual scanning of the item 4310 using one or more of the internal sensors and/or tracking movement of node-enabled items where the location of the particular node with item 4310 may be detected as being moved). In this way, MAM 1725 may detect when the appropriate item is removed at the destination location and, in some cases, provide responsive feedback to the delivery recipient when an incorrect item is mistakenly removed from CSS 1720 (e.g., through H2M feedback via visual information generated on displays 2815a, 2815b, panels 2815, 2900; via audio notification with messaging delivered through a speaker disposed on the MAM 1725 (or other component of assembly 1700); and/or via M2M electronic notification to the delivery recipient mobile wireless node 3315.

Further embodiments of method 4400 may authenticate that the entity providing the delivery recipient authentication input is actually the authorized delivery recipient in more detailed ways. For example, as part of step 4425, an embodiment may have the delivery recipient authentication input received through a user input panel (e.g., user input panel 2220) disposed on the modular autonomous bot apparatus and coupled to the modular mobile autonomy control module. In more detail, such delivery recipient authentication input received by the modular mobile autonomy control module may be an access code provided by the delivery recipient through the user input panel disposed on the modular cargo storage system and operatively coupled to the modular mobile autonomy control module. In another example, the user input panel may scan and accept biometric input (e.g., fingerprint, facial scan, retinal scan and the like), and the delivery recipient authentication input may be such biometric input provided by the delivery recipient through the user input panel disposed on the modular cargo storage system and operatively coupled to the modular mobile autonomy control module.

In further examples, the delivery recipient authentication input received by the modular mobile autonomy control module may be provided through an external wireless node (e.g., delivery recipient mobile wireless node 3315) disposed external to the modular autonomous bot apparatus assembly. In such an embodiment, the delivery recipient authentication input received may be a wireless message or signal that includes, for example, an access code provided by the delivery recipient through the external wireless node disposed external to the modular autonomous bot apparatus assembly or biometric input provided by the delivery recipient through the external wireless node disposed external to the modular autonomous bot apparatus assembly.

In more detail, the authentication information related to the dispatched logistics operation may include an identifier of the authorized delivery recipient for the item being shipped as part of the dispatched logistics operation (e.g., a name, an identification code number, an address, reference biometric data for the authorized delivery recipient, identifier information on a wireless node device (e.g., smartphone, etc.), and the like). As such, a further embodiment may have step of receiving the delivery recipient authentication input in step 4425 implemented with the modular mobile autonomy control module first detecting an advertising signal as the delivery recipient authentication input from an external wireless node (e.g., delivery recipient mobile wireless node 3315) within a predetermined range of the modular autonomous bot apparatus assembly once the modular autonomous bot apparatus assembly has arrived at the destination location identified by the destination information; and then having the modular mobile autonomy control module authenticating that the external wireless node is associated with the authorized delivery recipient based upon the identifier of the authorized delivery recipient (e.g., delivery recipient's name) and identifier information within the detected advertising signal broadcast from the external wireless node (e.g., phone number of the smartphone operating as the delivery recipient mobile wireless node 3315).

In another example, the step of receiving the delivery recipient authentication input in step 4425 may have the modular mobile autonomy control module first detecting an unprompted advertising signal from an external wireless node within a predetermined range of the modular autonomous bot apparatus assembly once the modular autonomous bot apparatus assembly has arrived at the destination location identified by the destination information (e.g., detecting such an unprompted signal without first transmitting an interrogation signal to cause the signal to be sent from the external wireless node). Once the advertising signal is detected by the modular mobile autonomy control module, this embodiment of step 4425 proceeds with establishing a secure association between the external node and the modular mobile autonomy control module. The secure association between the external node and the modular mobile autonomy control module is reflected in association data generated locally on one or both of the external node and the modular mobile autonomy control module, and allows secure sharing of information between the external node and the modular mobile autonomy control module as being pre-authorized by the dispatch server and as it relates to the dispatched logistics operation.

Further embodiments may have the delivery recipient authentication input implemented using multi-factor authentication input. For example, the process of receiving the delivery recipient authentication input may involve multiple steps where each step has the delivery recipient providing different types of authentication input (where each may be verified against the authentication information from the dispatched logistics operation) and where the different types of authentication input may be provided in different ways, such as a first step having first authentication input from the delivery recipient being a pass code provided on a user input panel on the apparatus 1700, and a second step having biometric input from the delivery recipient provided through a camera sensor disposed on the apparatus 1700. Further embodiments may use other modes of providing different types of authentication input that may be used collectively as the delivery recipient authentication input (e.g., wireless input with a text code or other message, audio input for voice recognition and matching, RFID tag interrogation by an RFID reader disposed on the apparatus 1700 (such as part of the wireless interface on MAM 1725), and the like).

As shown in FIGS. 43A, 43E, and 43F, monitoring of the payload area in CSS 1720 may be accomplished with one or more internal payload monitoring sensors 3130. In some embodiments, such sensors 3130 (as well as other sensors deployed on exemplary MALVT bot apparatus assembly 1700) may scan and identify the item being shipped (in addition to or instead of receiving confirmation via human input that the right item has been loaded or unloaded). For example, the step of receiving the item being shipped in step 4415 of method 4400 may, in a further embodiment, involve confirming that the item received corresponds to the dispatched logistics operation based upon a readable identification on the item received; and receiving, by the modular mobile autonomy control module, a confirmation input acknowledging that the item received corresponds to the dispatched logistics operation based upon the readable identification on the item received. Such a readable identification may be a human readable identification disposed on the item received (e.g., a printed or attached label on the item) and/or a machine readable identification disposed on the item received (e.g., a scannable label, barcode, or other symbol(s) identifying the item). In more detail, the confirmation input may be input received on a user input panel 2220 disposed on the modular cargo storage system and operatively coupled to the modular mobile autonomy control module.

In a further example, step 4415 of receiving the item being shipped may be implemented in a further embodiment of method 4400 with a payload monitoring sensor 3130 on the modular mobile autonomy control module monitoring a payload area within the modular cargo storage system; detecting, by modular mobile autonomy control module, the item being shipped within the payload area based upon scan data generated by the payload monitoring sensor; and confirming that the item detected within the payload area corresponds to the dispatched logistics operation based upon a machine readable identification on the item received as indicated by the scan data generated by the payload monitoring sensor.

In light of the exemplary method 4400 and its variations of embodiments described above, further embodiments are described in more detail below relative to specific practical application or use cases may deploy an exemplary MALVT bot apparatus 1700 in various types of dispatched logistics operations.

High Rise Building—Internal Deliveries

An exemplary MALVT bot apparatus assembly 1700 may be dispatched for different types of logistics operations in buildings. For example, an embodiment may have one or more exemplary MALVT bot apparatus 1700 stored on the ground level of commercial office buildings (e.g., a type of origin location), and be dispatched in order to complete a delivery related dispatched logistics operation. The item being shipped (e.g., item 4310) may be food or object deliveries from outside vendors, which may be loaded into the exemplary MALVT bot apparatus at the building's lobby by attendants or other persons. The exemplary MALVT bot apparatus 1700 then completes delivery without need for third party employees walking through the building.

In general, an embodiment may perform exemplary method 4400 with the exemplary MALVT bot apparatus 1700 where the apparatus 1700 travels to a recipient in the building as part of the dispatched logistics operation and alerts the recipient of delivery. The recipient (e.g., the authorized delivery recipient) authenticates delivery via an app running on a node device (e.g., delivery recipient mobile wireless node 3315) that interacts with the exemplary MALVT bot apparatus 1700, via a TRON node-to-node association implemented as part of the exemplary MALVT bot apparatus 1700, or via a display screen (e.g., displays 2815a, 2815b) on the exemplary MALVT bot apparatus. The recipient may then receive delivery, and the exemplary MALVT bot apparatus 1700 may then return to its origin location (such as a base in the lobby or another bot storage location). Those skilled in the art will appreciate that wireless node elements, such as TRON ID nodes and master node, may be used to implement the exemplary MALVT bot apparatus 1700 (e.g., control elements on the apparatus, such as the autonomous control system 3100 on MAM 1725) is this particular embodiment and can be leveraged for location, door & lock operation, elevator operation, and authentication as described above. Those skilled in the art will appreciate that embodiments may involve on-demand building of an exemplary MALVT bot apparatus assembly for such building-related deployments (e.g., consistent with the process explained above relative to FIG. 41, exemplary method 4100, and its variations), as well as embodiments that may responsively dispatch an exemplary MALVT bot apparatus assembly on a building-related dispatched logistics operation (e.g., consistent with the process explained above relative to FIG. 44, exemplary method 4400, and its variations).

For example, in such an embodiment, a further embodiment of exemplary method 4400 may further have the exemplary MALVT bot apparatus 1700 notifying the delivery recipient of delivery arrival prior to authenticating input from the recipient that allow access to the item being shipped. For example, method 4400 may include the step of generating a display alert for the authorized delivery recipient on a display (e.g., 2815a, 2815b) on the modular mobile autonomy control module once the modular autonomous bot apparatus assembly is within a threshold notification range of the destination location identified by the destination information. This allows for autonomous pre-delivery notification for the delivery recipient, and advantageously allows for delivery preparations to commence by the delivery recipient without having to require the delivery recipient to leave and go to a different location to pick the delivered item. In another example, method 4400 may implement such notification by generating an audio notification for the authorized delivery recipient on a speaker on the modular mobile autonomy control module once the modular autonomous bot apparatus assembly is within a threshold notification range of the destination location identified by the destination information. In still another embodiment, method 4400 may further have the exemplary MALVT bot apparatus assembly transmitting a delivery notification message to an external wireless node identified to be related to the delivery recipient (e.g., delivery recipient mobile wireless node 3315 shown in FIG. 43E) once the modular autonomous bot apparatus assembly is within a threshold notification range of the destination location identified by the destination information.

In another embodiment where exemplary method 4400 may be performed, one or more exemplary MALVT bot apparatus may be leased to a company with a multi-floor presence in a high rise building (commercial banks, large law-firms, etc.). In this particular embodiment and as part of exemplary method 4400, an exemplary MALVT bot apparatus may be hailed or dispatched by an employee (e.g., via coordination with dispatch server 4205) to receive an item to be delivered to another location within the building. The sender confirms a location for delivery via coordinates, office mapping, or TRON enablement of the exemplary MALVT bot apparatus for locating the apparatus (e.g., a wireless node of the delivery recipient that may be located using node location techniques described above). The delivery item is then placed inside the exemplary MALVT bot apparatus, which then travels through the office space and arrives at the recipient who authenticates delivery with delivery authentication input (e.g., via input on a user input panel prompted using a display screen, wireless input via an app on the recipient's wireless mobile node, TRON node-to-node association), and receives item. The exemplary MALVT bot apparatus may then return to storage (e.g., a type of origin location). As noted above, such an exemplary MALVT bot apparatus may be equipped with the capability to operate elevators and potentially open doors using actuated articulating arms and vision systems or via electronic integration with a building's automated systems for elevators and door openers.

In another embodiment, exemplary method 4400 may be implemented with the exemplary MALVT bot apparatus 1700 where the exemplary MALVT bot apparatus 1700 may act as an internal courier ferrying paperwork as the item 4310 to different floors or across the office. The exemplary MALVT bot apparatus may also be used by delivery company or courier service outside the office. The exemplary MALVT bot apparatus 1700 may be stored in a leased space and complete deliveries in vertical space with the lobby of the building acting as a hold at location (HAL) type of logistics receptacle enhanced with a mobile automated delivery to the final recipient within the building. The exemplary MALVT bot apparatus in this embodiment will have the capability to operate elevators and potentially open doors using actuated articulating arms and vision systems or via electronic integration with a building's automated systems for elevators and door openers.

Accordingly, in such an embodiment, a further embodiment of exemplary method 4400 involving a multi-floor use case with storage on one floor and dispatch to other floors may have the origin location being a storage location on a predetermined floor of a multi-level facility where the modular autonomous bot apparatus assembly 1700 is maintained until dispatched for the dispatched logistics operation, and where the destination location is located on another floor of the multi-level facility. In a further embodiment of exemplary method 4400, the origin location may be a multi-component storage location on a predetermined floor of such a multi-level facility where each of the modular mobility base, the modular auxiliary power module, the modular cargo storage system, and the modular mobile autonomy control module used as part of the modular autonomous bot apparatus assembly is maintained in an unassembled form until on-demand assembly of the modular autonomous bot apparatus assembly occurs (e.g., per exemplary method 4100) in response to the dispatch command from the dispatch server, and where the destination location is located on another floor of the multi-level facility. In yet another embodiment of exemplary method 4400, the origin location comprises a multi-component storage location on a predetermined floor of a multi-level facility where each of the modular mobility base, the modular auxiliary power module, the modular cargo storage system, and the modular mobile autonomy control module are leased components used as part of the modular autonomous bot apparatus assembly and where each of the leased components is maintained until dispatched as part of the modular autonomous bot apparatus assembly for the dispatched logistics operation; and where the destination location is located on another floor of the multi-level facility.

Thus, while embodiments of method 4400 may have the exemplary MALVT bot apparatus assembly receive the item being shipped at an origin location, other embodiments of method 4400 may have the CSS component of the exemplary MALVT bot apparatus assembly receive the item at a separate intermediate loading location for pickup, delivery, or as part of a return operation. Accordingly, a further embodiment of exemplary method 4400 may have the origin location for the dispatched logistics operation being a bot storage location where the modular autonomous bot apparatus assembly is initially maintained and wherein the destination information defines an intermediate loading location defined as part of the destination information (e.g., location coordinates, an identified location relative to an office mapping, a location of an external wireless node disposed outside of the modular autonomous bot apparatus assembly and related to a sender of the item being shipped, a location of a master node disposed as part of a facility, a lobby location of a multi-floor facility, and the like). In some example embodiments, the modular autonomous bot apparatus assembly may be temporarily disposed at the lobby of the multi-floor facility (as the intermediate loading location) as a hold-at-location logistics receptacle to receive the item being shipped before autonomously moving to the destination location with the item being shipped.

Movement to the intermediate loading location may, in some cases, begin after receipt of a confirmation message from the dispatch server, where such a confirmation message verifies the intermediate loading location as provided by a sender of the item being shipped.

In such an example embodiment involving an intermediate loading location, step 4415 of receiving the item being shipped may have the modular mobile autonomy control module autonomously causing the modular mobility base to move from the bot storage location to the intermediate loading location, and receiving, by the modular cargo storage system, the item being shipped at the intermediate loading location. Additionally, in this example embodiment, step 4420 of autonomously causing the modular mobility base to move from the origin location on the route to the destination location identified by the destination information may have the modular mobile autonomy control module causing the modular mobility base to move from the intermediate loading location on an intermediate delivery route to the destination location identified by the destination information. As such, in this example embodiment, step 4435 may then be revised to have to the modular mobile autonomy control module cause the modular mobility base to move from the destination location on the return route to the bot storage location after the item being shipped is detected to be removed from within the modular cargo storage system.

In further embodiments related to operations within a hotel environment, exemplary method 4400 may be implemented with the exemplary MALVT bot apparatus 1700 where the exemplary MALVT bot apparatus may be stationed in a hotel lobby. In general and as part of this hotel embodiment, when a customer needs an item delivered to their room (e.g., toiletries, food, etc.), the requested items may be loaded into the exemplary MALVT bot apparatus and the exemplary MALVT bot apparatus is dispatched to the customers room, another room designated by the customer, or the customers location leveraging TRON node locating techniques involving the customer's wireless node (e.g., a smartphone operating as a type of ID or master node). The exemplary MALVT bot apparatus arrives at customer's room (or other identified delivery location) and alerts customer that it is there (e.g., via display prompt, audio notification, electronic notification to the customer's user access device, or machine-to-machine notification via association using TRON elements operating as the customer's user access device and the controller in the MAM unit of the exemplary MALVT bot apparatus). The customer authenticates delivery and retrieves the items from the CSS component. The exemplary MALVT bot apparatus ensures all items have been removed and returns to the lobby.

Accordingly, in such a further embodiment of exemplary method 4400 involving a separate intermediate loading location and hotel environment, the dispatch command from the dispatch server may be initiated by a hotel customer request received by the dispatch server for delivery of the item being shipped (e.g., the requested toiletries, room service items, cleaning supplies, pillows, blankets, and the like) and the bot storage location may be a storage facility within a hotel building (e.g., a storage room near the hotel's retail services, housekeeping facilities, and the like). Likewise, the intermediate loading location may be defined (as part of the destination information for the modular autonomous bot apparatus assembly) to be a location within the hotel designated by the delivery recipient sending the hotel customer request. Such a location within the hotel may, for example, be a designated hotel room within the hotel building, a designated services area within the hotel building, a designated conference room within the hotel building, or a location of an external mobile wireless node related to the delivery recipient (such as the location of delivery recipient mobile wireless node 3315). And in this further embodiment, method 4400 may also include notifying the delivery recipient of an approaching delivery once the modular autonomous bot apparatus assembly is within a threshold notification range of the destination location within the hotel identified by the destination information.

Further embodiments related to operations within a hotel environment may relate to luggage being picked up and delivered. In general and as part of this hotel embodiment involving luggage, exemplary method 4400 may be implemented with the exemplary MALVT bot apparatus 1700 where the hotel customer may hail an exemplary MALVT bot apparatus for help with luggage when checking out. The exemplary MALVT bot apparatus may be dispatched to the room and the customer loads luggage onto the CSS component of the responding exemplary MALVT bot apparatus. The exemplary MALVT bot apparatus may then follow the customer out to a vehicle, or proceed to a particular holding area near the hotel lobby (e.g., a loading zone) and await further interaction with the customer's user access device to proceed to the customer's vehicle. The exemplary MALVT bot apparatus then may return to a base or other holding location (e.g., back to its origin or other bot storage location) once the customer has removed luggage from the CSS unit.

Accordingly, in such a further embodiment of exemplary method 4400 involving a hotel environment and luggage as the item being shipped, the origin location for the dispatched logistics operation may be a bot storage location within a hotel building where the modular autonomous bot apparatus is initially maintained (e.g., in the hotel lobby, in a hotel storage room, and the like). The destination information identified in the dispatch commend may be an intermediate loading location (e.g., the hotel customer's hotel room) and a drop-off location (e.g., the hotel lobby). As such, receiving the item being shipped at step 4415 may be implemented with the modular mobile autonomy control module autonomously causing the modular mobility base to move from the bot storage location to the intermediate loading location, notifying the delivery recipient of an approaching pickup once the modular autonomous bot apparatus assembly is within a threshold notification range of the intermediate loading location identified by the destination information, and having the modular cargo storage system receiving the item being shipped (e.g., the customer's luggage) at the intermediate locating location (e.g., the customer's room). Thereafter, this embodiment of method 4400 may autonomously cause the modular mobility base to move from the origin location on the route to the destination location identified by the destination information as part of step 4420 by having the modular mobile autonomy control module causing the modular mobility base to move from the intermediate loading location on an intermediate delivery route to the drop-off location identified by the destination information as the destination location (e.g., the hotel lobby). And, this embodiment of method 4400 may autonomously cause the modular mobility base to move from the destination location on the return route to the origin location after the item being shipped is detected to be removed as part of step 4435 by having the modular mobile autonomy control module autonomously causing the modular mobility base to move from the drop-off location on the return route to the bot storage location after the item being shipped is detected to be removed from within the modular cargo storage system.

In a further embodiment, there may a holding location and a secondary drop-off location involved, such as a hotel lobby luggage storage location and a second drop-off at a loading zone or at the customer's vehicle. As such, exemplary method 4400 may have the modular mobile autonomy control module autonomously causing the modular mobility base to move from the intermediate loading location on the intermediate delivery route to the drop-off location being implemented by first having the modular mobile autonomy control module autonomously causing the modular mobility base to move from the intermediate loading location on the intermediate delivery route to the drop-off location and holding at the drop-off location as a first holding location identified as part of the destination information (e.g., the hotel luggage storage location or room), and then autonomously causing the modular mobility base to move from the first holding location to a secondary drop-off location identified as the location of an external mobile wireless node related to the delivery recipient. This last step may use node locating techniques as well as node-to-node association as described above, and be implemented with the modular mobile autonomy control module detecting an advertising signal from the external mobile wireless node related to the delivery recipient; establishing, by the modular mobile autonomy control module, an authorized secure association between the modular mobile autonomy control module and the external mobile wireless node based upon the authentication information related to the dispatched logistics operation; and autonomously causing, by the modular mobile autonomy control module, the modular mobility base to move from the first holding location to the secondary drop-off location after establishing the authorized secure association. In another example, the modular mobile autonomy control module may autonomously cause the modular mobility base to move from the secondary drop-off location to the bot storage location after the item being shipped is detected to be removed from within the modular cargo storage system at the secondary drop-off location.

In further embodiments related to operations within a hotel environment and where the hotel customer requests pickup of an item/object, such as their luggage, according to an embodiment of method 4400, the exemplary MALVT bot apparatus assembly involved in such a dispatched operation may operate in manner that follows the customer after pickup of the item at the intermediate loading location (e.g., pickup of the customer's luggage at the customer's hotel room as the intermediate loading location). Accordingly, an embodiment of method 4400 may have the origin location for the dispatched logistics operation being a bot storage location within a hotel building where the modular autonomous bot apparatus is initially maintained, and may have the destination information in the dispatch command being an intermediate loading location (e.g., the customer's hotel room) and a drop-off location (e.g., the hotel lobby, a loading zone, or the customer's vehicle). As such, the step of receiving the item being shipped in step 4415 may be implemented with the modular mobile autonomy control module autonomously causing the modular mobility base to move from the bot storage location to the intermediate loading location; detecting an advertising signal from an external mobile wireless node related to the delivery recipient (e.g., mobile wireless node 3315); establishing an authorized secure association between the modular mobile autonomy control module and the external mobile wireless node based upon the authentication information related to the dispatched logistics operation, the established authorized secure association authenticating the delivery recipient related to the external mobile wireless node; and transmitting, by the modular mobile autonomy control module, an impending pickup message to the external mobile wireless node about an approaching pickup of the item being shipped once the modular autonomous bot apparatus assembly has established the authorized secure association between the modular mobile autonomy control module and the external mobile wireless node; and receiving, by the modular cargo storage system, the item being shipped at the intermediate locating location.

Additionally as part of this particular embodiment, step 4420 may be implemented with the modular mobile autonomy control module causing the modular mobility base move from the intermediate loading location towards the external mobile wireless node in a following mode as the external mobile wireless node moves towards the drop-off location; and where step 4435 may be implemented as autonomously causing, by the modular mobile autonomy control module, the modular mobility base to move from the drop-off location to the bot storage location after the item being shipped is detected to be removed from within the modular cargo storage system at the drop-off location.

As part of this particular embodiment of exemplary method 4400, the bot apparatus 1700 may be an enhanced version where the modular mobility base may have a master mobility base, a slave mobility base, and an extended base adapter plate coupled to each of the master mobility base and the slave mobility base to support the item being shipped, and where each of the master and slave mobility bases being responsive to control input from the modular mobile autonomy control module to cause coordinated movement of the modular mobility base. Such an enhanced version of the exemplary MALVT bot apparatus used in this embodiment of method 4400 may allow for greater transport loads to be handled by the bot apparatus (e.g., a larger amount of luggage to be picked up from a customer's hotel room and brought to a drop-off location).

Further embodiments may deploy multiple exemplary MALVT bot apparatus 1700, which may cooperate in order to move heavy hard to handle items through (e.g., furniture) through an office, building, hotel, or other facility. In such embodiments, a pair of exemplary bot apparatus assemblies may cooperate via TRON technology, with one acting as a master and providing coordinated steering and propulsion input to the other sale and collectively use one larger platform able to carry heavier encumbering loads with relative ease compared to office moving and utility services. Coupled exemplary MALVT bot apparatus may also follow movers via TRON location enablement (e.g., node locating techniques and node-to-node association as described above) similar to how an exemplary MALVT bot apparatus may follow a hotel customer after pickup of an item (e.g., luggage).

In still another embodiment, multiple exemplary MALVT bot apparatus may cooperate in order to move heavy or hard to handle items in a residential environment for residents when moving in or unloading large cargo/purchases (e.g., televisions, furniture). For example, an embodiment may use a base pair (e.g., a pair of MBs such as that shown in FIG. 19) as such exemplary bot apparatus that cooperate via TRON technology acting as one larger platform (e.g., one MB controlling the other MB, a common MAM controlling the two MBs using master node and ID node TRON device management technology, or one MAM controlling the other MAM and MB in another bot) to facilitate carrying heavier or encumbering loads than a single person can carry on their own. Coupled exemplary MALVT bot apparatus may also follow a moving resident via TRON location enablement (e.g., node locating techniques and node-to-node association as described above) similar to how an exemplary MALVT bot apparatus may follow a hotel customer after pickup of an item (e.g., luggage).

Further embodiments in a high-rise delivery/pickup logistics operation environment may implement exemplary method 4400 with an exemplary MALVT bot apparatus 1700 from a group of one or more exemplary MALVT bot apparatus (e.g., a pool of exemplary MALVT bot apparatus assemblies that may be dispatched) for building maintenance part delivery, shred box removal, garbage removal, or office supply delivery within the facility. Those skilled in the art will appreciate that the above aspects of TRON technology may be incorporated into control elements in components of the exemplary MALVT bot apparatus and leveraged for location, door & lock operation, elevator operation, and authentication using the various nodes (e.g., different nodes embedded in or in responsive communication with an actuated door, lock, or elevator) and node locating techniques described above.

Additional embodiments where an exemplary MALVT bot apparatus may be dispatched according to a dispatch comment may have objects being delivered to a delivery, package, or shipped object room (generally referred to herein as a facility's object room) and held for final delivery until authorized by the end recipient. In general, a delivery recipient may receive a notification of delivery and arrange for an exemplary MALVT bot apparatus to complete delivery from the object room to a housing unit in the facility. The exemplary MALVT bot apparatus may be dispatched with the object to the door of the final recipient who authorizes object delivery and receives the objects. The exemplary MALVT bot apparatus may then return to storage, moves on to the next delivery, or returns to an object room to pick up another delivery.

Figure 46:
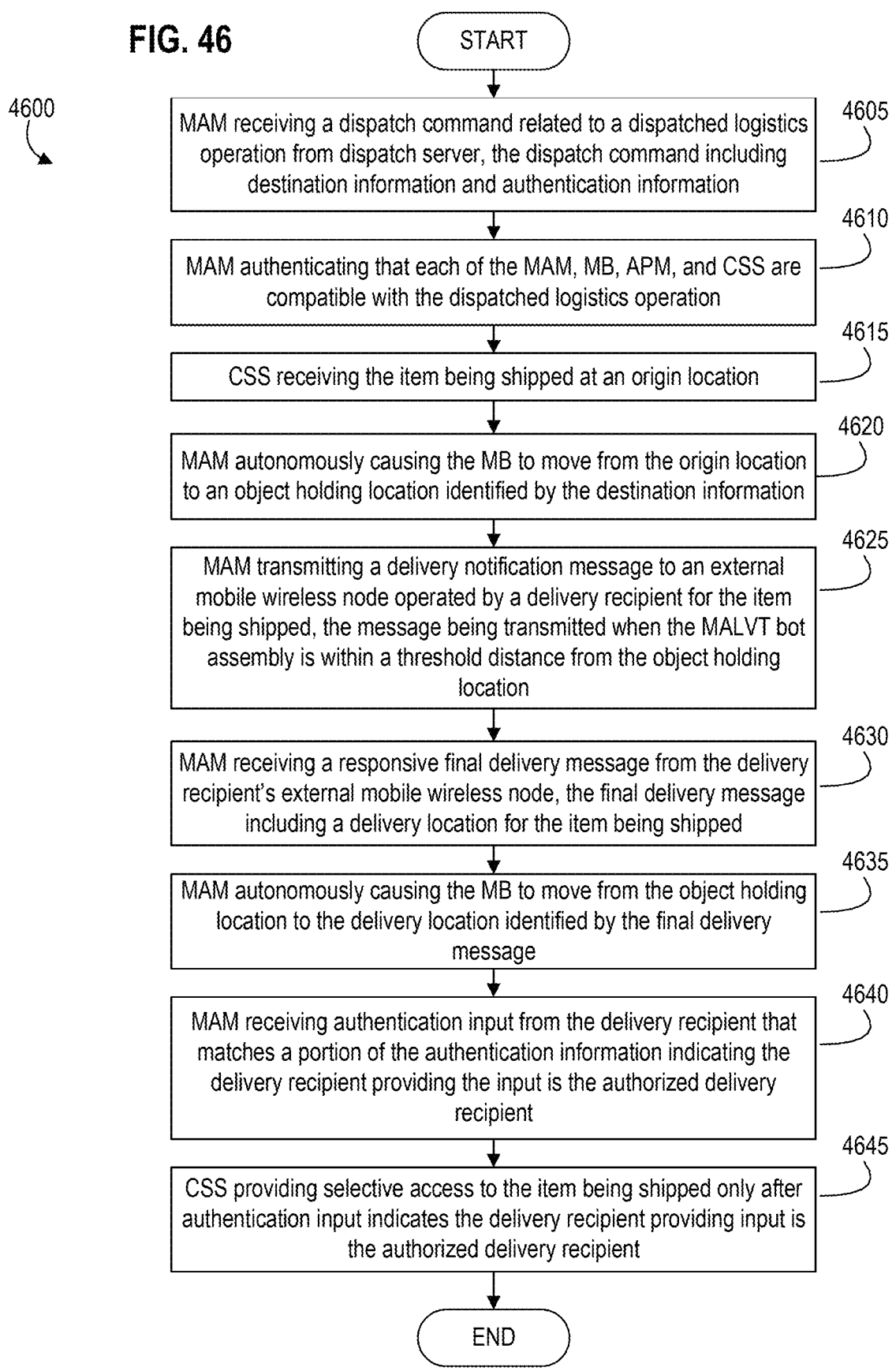
FIG. 46 is a flow diagram of another embodiment of an exemplary method for performing a dispatched logistics operation involving pickup, holding at an object holding location, and delivery of an item being shipped using a modular autonomous bot apparatus assembly (MALVT bot apparatus assembly) and a dispatch server in accordance with an embodiment of the invention.

For example, FIG. 46 is a flow diagram of such embodiment of an exemplary method for performing a dispatched logistics operation involving pickup, holding at an object holding location, and delivery of an item being shipped using a modular autonomous bot apparatus assembly (MALVT bot apparatus assembly) and a dispatch server in accordance with an embodiment of the invention. Like that of method 4400, exemplary method 4600 makes use, for example, of exemplary MALVT bot apparatus assembly 1700 and exemplary dispatch server 4205. Exemplary MALVT bot apparatus assembly 1700, as part of method 4600, is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 4600.

Referring now to FIG. 46, exemplary method 4600 begins at step 4605 with the modular mobile autonomy control module receiving a dispatch command from the dispatch server, where the dispatch command includes at least destination information and authentication information related to the dispatched logistics operation. At step 4610, method 4600 proceeds with the modular mobile autonomy control module authenticating that each of the modular mobility base, the modular auxiliary power module, and the modular cargo storage system are compatible with the dispatched logistics operation (similar to step 4410 and its variations as described above relative to method 4400). Then, at step 4615, method 4600 proceeds with the modular cargo storage system receiving the item being shipped at an origin location (similar to step 4415 and its variations as described above relative to method 4400).

At step 4620, method 4600 has the modular mobile autonomy control module autonomously causing the modular mobility base to move from the origin location on a route to an object holding location identified by the destination information. At the object holding location, step 4625 of method 4600 has the modular mobile autonomy control module transmitting a delivery notification message to an external mobile wireless node operated by a delivery recipient for the item being shipped (e.g., delivery recipient mobile wireless node 3315) when the modular autonomous bot apparatus assembly is within a threshold distance from the object holding location. At step 4630, the modular mobile autonomy control module receives a responsive final delivery message from the external mobile wireless node, where the responsive final delivery message includes at least a delivery location for the item being shipped.

At step 4635, method 4600 has the modular mobile autonomy control module autonomously causing the modular mobility base to move from the object holding location to the delivery location identified by the responsive final delivery message. At the delivery location, method 4600 proceeds to step 4640 with receiving authentication input by the modular mobile autonomy control module from the delivery recipient. If the authentication input correlates to at least a portion of the authentication information related to the dispatched logistics operation, the delivery recipient that provided the authentication input is determined to be the authorized delivery recipient for the item being shipped within the module cargo storage system. Thereafter, at step 4645, method 4600 proceeds with the modular cargo storage system providing selective access to the item being shipped within the modular cargo storage system after the authentication input received correlates to the portion of the authentication information indicating the delivery recipient providing the authentication input is the authorized delivery recipient.

A further embodiment of method 4600 may also include the step of autonomously causing, by the modular mobile autonomy control module, the modular mobility base to move from the delivery location to the origin location after the item being shipped is detected to be removed from within the modular cargo storage system. For example, as shown in FIG. 43F, when item 4310 is no longer detected by sensor 3130 to be within the CSS 1720, MAM 1725 may autonomously and responsively send steering and propulsion control signals to the MB 1703, which causes the MB to move on a route back to the origin location.

In still another embodiment, method 4600 may cause movement from the delivery location back to the object holding location. In more detail, this may involve having the modular mobile autonomy control module autonomously causing the modular mobility base to move from the delivery location to the object holding location after the item being shipped is detected to be removed from within the modular cargo storage system. Further still, method 4600 may also have the modular mobile autonomy control module transmitting a second delivery notification message to a second external mobile wireless node operated by a second delivery recipient for an additional item maintained within the modular cargo storage system when the modular autonomous bot apparatus assembly is within the threshold distance from the object holding location. In this way, the exemplary MALVT bot apparatus assembly performing method 4600 may return to the object holding location and wait to deliver the additional item to the second delivery recipient. As such, the modular mobile autonomy control module may then receive a second responsive final delivery message from the second external mobile wireless node (where the second responsive final delivery message includes at least a second delivery location for the additional item maintained within the modular cargo system) and then cause the modular mobility base to move from the object holding location to the second delivery location identified by the second responsive final delivery message from the external mobile wireless node.

In still another embodiment of method 4600, the exemplary MALVT bot apparatus assembly may move back to the object holding location to pickup an additional item for delivery from that location (rather than returning for delivery of an item already and still within the CSS payload area). In more detail, such a further embodiment of method 4600 may have the modular mobile autonomy control module receiving a second dispatch command from the dispatch server, where the second dispatch command includes at least second destination information and second authentication information related to a second dispatched logistics operation (e.g., delivery of a second item to be picked up at the object holding location). The modular mobile autonomy control module proceeds in this further embodiment of method 4600 with autonomously causing the modular mobility base to move from the delivery location to the object holding location after the item being shipped is detected to be removed from within the modular cargo storage system; receiving, by the modular cargo storage system, the second item being shipped at the object holding location; transmitting, by the modular mobile autonomy control module, a second delivery notification message to a second external mobile wireless node operated by a second delivery recipient for the second item; and receiving, by the modular mobile autonomy control module, a second responsive final delivery message from the second external mobile wireless node, where the second responsive final delivery message included at least a second delivery location for the second item. Based upon this second responsive final delivery message, method 4600 continues with the modular mobile autonomy control module autonomously causing the modular mobility base to move from the object holding location to the second delivery location identified by the second responsive final delivery message from the second external mobile wireless node.

In another embodiment, an exemplary MALVT bot apparatus may be stored in lobby of residential building and dispatched for food deliveries according to either exemplary embodiments of method 4400 or method 4600. In general, when a food delivery arrives, the exemplary MALVT bot apparatus may be activated to receive the delivery from a delivery person (similar to picking up an item in an object holding location, such as the lobby), and complete the delivery within the building. Once delivery is completed, the exemplary MALVT bot apparatus assembly returns to storage. As with the other embodiments, bot interactions using TRON technology may be incorporated and leveraged for location, door & lock operation, elevator operation, and authentication using the various nodes (e.g., different nodes embedded in or in responsive communication with an actuated door, lock, or elevator) and node locating techniques described above. The CSS component of the exemplary MALVT bot apparatus assembly may be compartmentalized or partitioned using separators (such as exemplary separator 3608), climate controlled using exemplary detachable climate control modules 2210, and/or insulated so as to accommodate the intended food to be delivered.

Parts Delivery

Within an environment of a large private corporate facility, an exemplary MALVT bot apparatus may be dispatched and deployed to act as a shuttle for parts, tools, components, or other needs for mechanics or repairmen in an embodiment. In general, such an exemplary MALVT bot apparatus (e.g., exemplary MALVT bot apparatus assembly 1700) may be initially disposed in a centralized warehouse and be dispatched with the appropriate item upon a request by an authorized maintenance person. TRON capabilities enable the exemplary MALVT bot apparatus (operating as a master node through its autonomous controller in MAM 1725) to locate the repair person (via the person's user access device operating as an ID node) and make a delivery directly to the recipient without the need for addresses or mapping which may not be readily available. The recipient may then authenticate delivery via an app operating on the recipient's user access device, via TRON node interactions for association-based authenticated delivery, or via interaction with the display screen on the MAM component. TRON enabled coupled exemplary MALVT bot apparatus devices may be leveraged for movement of heavy and hard to handle equipment (e.g., using a BAPM and multiple MBs, an enlarged CSS, and a suitably sized MAM). Those skilled in the art will appreciate that embodiments may involve on-demand building of an exemplary MALVT bot apparatus assembly for such parts delivery-related deployments (e.g., consistent with the process explained above relative to FIG. 41, exemplary method 4100, and its variations), as well as embodiments that may responsively dispatch an exemplary MALVT bot apparatus assembly on a parts delivery related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 where the exemplary MALVT bot apparatus may be specially dispatched as a shuttle for such items, the origin location for the dispatched logistics operation may be a centralized bot storage location within a warehouse where the modular autonomous bot apparatus is initially maintained (e.g., assembled proactively into assembly 1700 for such types of shuttle dispatch operation or in components for on-demand assembly into a particular exemplary MALVT bot apparatus assembly 1700). The dispatch command sent by the dispatch server may be initiated based upon a dispatch request received by the dispatch server, where the dispatch request is sent from an authorized maintenance person related to the dispatched logistics operation. Such a dispatch command includes identifier information of an external mobile wireless node operated by the authorized maintenance person, and the destination information from the dispatch command is a mobile node location of the external mobile wireless node operated by the authorized maintenance person.

In step 4425 in this further embodiment of method 4400, the step of receiving deliver recipient authentication input may be through a user input panel on the exemplary MALVT bot apparatus assembly (e.g., input from the delivery recipient in the form of an access code and/or biometric input), or through wireless authentication based on the identifier information. In more detail, an embodiment may have step 4425 detecting, by the modular mobile autonomy control module, an advertising signal from the external mobile wireless node as the delivery recipient authentication input as the modular autonomous bot apparatus assembly approaches the mobile node location of the external mobile wireless node. Upson such a detection, the modular mobile autonomy control module then authenticates that the external mobile wireless node is associated with the authorized delivery recipient for the item being shipped within the modular cargo storage system (e.g., the parts being shuttled) based upon (a) the identifier information of the external mobile wireless node from the dispatch command and (b) identifier information within the detected advertising signal broadcast from the external mobile wireless node.

In such a further embodiment of method 4400, the exemplary MALVT bot apparatus assembly may be implemented with a specially configured assembly using a pair of MB units and an extended base adapter plate to handle heavier loads. In more detail, as part of a further embodiment of method 4400, the modular mobility base compatible with the dispatched logistics operation may be implemented using a master mobility base, a slave mobility base, and an extended base adapter plate coupled to each of the master mobility base and the slave mobility base to support the item being shipped (such as that shown in FIG. 19). As such, each of the master mobility base and the slave mobility base are responsive to control input from the modular mobile autonomy control module to cause coordinated movement of the modular mobility bases. Further, the modular cargo storage system compatible with the dispatched logistics operation in such a further embodiment may be one of multiple different sized modular cargo storage systems, where the compatible sized modular cargo storage system is one compatible with a size parameter for the item being shipped as part of the dispatched logistics operation. Likewise, the modular mobile autonomy control module compatible with the dispatched logistics operation in such a further embodiment may be one of multiple different sized modular mobile autonomy control modules, where the compatible sized modular mobile autonomy control module is one compatible with the size parameter for the item being shipped as part of the dispatched logistics operation. For example, with the exemplary master MB 1705*a* and slave MB 1705*b* and extended base adapter plate 1905 shown in FIG. 19, a compatible CSS 1720 that may mount to plate 1905 is larger than with another sized CSS 1720 that would mount to plate 2005, and a similarly sized MAM 1725 would be one compatible with the larger sized CSS that fits on plate 1905.

Hospital Assistant

In another embodiment, an exemplary MALVT bot apparatus may configured and used to serve as a transportation unit for various items throughout a hospital. In general, prescription drugs, for example, may be ferried from a pharmacy within the hospital to the patient's room using the exemplary MALVT bot apparatus (e.g., exemplary MALVT bot apparatus assembly 1700). Such an exemplary MALVT bot apparatus assembly may use TRON node elements (such as ID nodes and/or master nodes as discussed above for control elements) and use such node elements as part of an exemplary MALVT bot apparatus to identify and locate the correct nurse (e.g., one that is operating a mobile wireless node, such as node 3315) for delivery and authentication ensuring proper chain of custody of drugs. An exemplary MALVT bot apparatus in such an embodiment may carry needed medical supplies to rooms when requested by hospital staff. Such an exemplary MALVT bot apparatus assembly may be configured to deliver meals to patients confined to people in rooms, including patients who have been quarantined due to infectious dieses without fear of contamination of hospital staff. An appropriately insulated, organized, and/or climate controlled CSS unit as described above may be used. An exemplary MALVT bot apparatus assembly may safely and securely pickup and remove biohazard storage boxes as part of a dispatched logistics operation to a proper disposal facility, which has the advantage of helping to lower the risk of potential infection as well as carry samples to test areas (or different sites in the case of campus hospitals). In such embodiments, the exemplary MALVT bot apparatus assembly may be connected to an internal hospital alarm system (e.g., via wireless monitoring of the alarm system or simply receiving a signal from the alarm system—audible, electronic, and the like) and automatically and responsively move against a wall and out of the way when a "code" event (e.g., patient alarm requiring additional doctors or nurses to a patient's room ASAP) occurs. Those skilled in the art will appreciate that in these hospital related deployments, configurations of such an exemplary MALVT bot apparatus assembly, which may use TRON nodes as control elements, may be leveraged for movement of heavy and hard to handle equipment (e.g., using a BAPM and multiple MBs, an enlarged CSS, and a suitably sized MAM). Additionally, the display elements (e.g., screens 2815*a*, 2815*b*, and other light panels) on the MAM 1725 on such an assembly may present warnings of hazardous contents (e.g., generated warning information related to the item being shipped), relay information for medication administration (e.g., generated medical administration information, such as product warnings on the medication being shipped within the bot apparatus assembly), or act as an authentication measure to present prompted messages that request authentication input so that the item being shipped may be released and delivered.

Those skilled in the art will appreciate that embodiments may involve on-demand building of an exemplary MALVT bot apparatus assembly for such hospital-related deployments (e.g., consistent with the process explained above relative to FIG. 41, exemplary method 4100, and its variations), as well as embodiments that may responsively dispatch an exemplary MALVT bot apparatus assembly on a hospital related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 in such a hospital environment with an intermediate loading location, the bot storage location for the dispatched logistics operation may be a centralized bot storage location within a hospital where the modular autonomous bot apparatus is initially maintained while the intermediate loading location is a medical supply storage (e.g., a pharmaceutical supply storage where the item being shipped may be a prescribed medicine according to the dispatched logistics operation). The dispatch command sent by the dispatch server is initiated based upon a dispatch request received by the dispatch server. The dispatch request is sent from an authorized hospital staff related to the dispatched logistics operation, and the responsive the dispatch command from the dispatch server includes identifier information of an external mobile wireless node operated by the authorized hospital staff. In more detail, the destination location in this further embodiment of exemplary method 4400 may be a predetermined location within the hospital for a patient currently located within the hospital (e.g., a patient's room, a pre-op area within the hospital, and the like) or the mobile node location of the external mobile wireless node operated by the authorized hospital staff sending the request (or the mobile node location of another designated mobile wireless node).

In more detail, such a further embodiment of the exemplary method 4400 may also have the modular mobile autonomy control module storing the delivery recipient authentication input as chain of custody information for the item being shipped (e.g., medication, medical supplies, and the like). Such chain of custody information may be further transmitted to a server (e.g., a hospital-based server that tracks and accounts for medical supplies being billed to a patient for their care and treatment while in the hospital).

In another example of such a further embodiment of exemplary method 4400 operating in a hospital environment, the exemplary MALVT bot apparatus assembly may be dispatched on a logistics operation involving meal pickup and delivery to patients within the hospital. In more detail and for example, as part of an embodiment of method 4400, the bot storage location for the dispatched logistics operation may be a centralized bot storage location within a hospital where the modular autonomous bot apparatus is initially maintained. The dispatch command sent by the dispatch server is initiated based upon a dispatch request received by the dispatch server and sent from an authorized hospital staff related to the dispatched logistics operation. In this embodiment, the intermediate loading location is a hospital meal supply location, and the modular cargo storage system used in this embodiment of method 4400 has a segmented and insulated payload area (e.g., using exemplary separators 3608 that are insulated) for transporting meals as the item being shipped, and a detachable climate control module (e.g., exemplary climate control module 2210) responsive to climate control input from the modular mobile autonomy control module to maintain a desired environment within the modular cargo storage system.

In another example of such a further embodiment of exemplary method 4400 operating in a hospital environment, the exemplary MALVT bot apparatus assembly may be dispatched on a logistics operation involving biohazard material as the item being shipped. In more detail and for example, as part of an embodiment of method 4400, the bot storage location for the dispatched logistics operation may be a centralized bot storage location within a hospital where the modular autonomous bot apparatus is initially maintained. The dispatch command sent by the dispatch server is initiated based upon a dispatch request received by the dispatch server, and sent from an authorized hospital staff related to the biohazard-related dispatched logistics operation. As part of this further embodiment of exemplary method 4400, the intermediate loading location is a biohazard material repository location, and the destination location is a biohazard material disposal location. As part of exemplary method 4400 in this particular embodiment, further steps may have modular components of the exemplary MALVT bot apparatus being disconnected and sanitized after the biohazard-related logistics operation.

In another example of such a further embodiment of exemplary method 4400 operating in a hospital environment, the exemplary MALVT bot apparatus assembly may be dispatched on a logistics operation where there is responsive integration and/or actions of the exemplary MALVT bot apparatus assembly to a hospital alarm system. In one example, as part of an embodiment of method 4400, method 4400 may further have the modular mobile autonomy control module receiving a wireless hospital alarm signal during the dispatched logistics operation; and autonomously causing the modular mobility base to interrupt movement and position the modular mobility base in a predetermined unobstructive position within a current environment of the modular autonomous bot apparatus assembly. Such a predetermined unobstructive position may, for example, be a position against a wall within the current environment of the modular autonomous bot apparatus assembly as sensed by one or more sensors on the modular autonomous bot apparatus assembly, or a position within the current environment of the modular autonomous bot apparatus assembly and sensed by the modular mobile autonomy control module to be unoccupied relative to movement sensed within the current environment of the modular autonomous bot apparatus assembly. Further embodiments may detect the hospital alarm with the modular mobile autonomy control module monitoring, using a microphone, for a hospital alarm tone or series of tones that may be recognized by the modular mobile autonomy control module as representing the hospital alarm, which then causes the modular mobility base to interrupt movement and position the modular mobility base in a predetermined unobstructive position within a current environment of the modular autonomous bot apparatus assembly.

In still another example of such a further embodiment of exemplary method 4400 operating in a hospital environment, the exemplary MALVT bot apparatus assembly be deployed and configured with a BAPM and two modular mobility base units to handle larger items to move within the hospital. For example, as part of an embodiment of method 4400, the modular mobility base compatible with the dispatched logistics operation in method 4400 may include a master mobility base, a slave mobility base, and an extended base adapter plate coupled to each of the master mobility base and the slave mobility base to support the item being shipped, where each of the master mobility base and the slave mobility base is responsive to control input from the modular mobile autonomy control module to cause coordinated movement of the modular mobility base as required in steps of method 4400.

Likewise, particular types and sizes of modular components of exemplary MALVT bot apparatus assembly may be specifically selected as needed for specific the hospital-related dispatched logistics operation involved in such an embodiment of method 4400. For example, the modular cargo storage system compatible with the dispatched logistics operation within the hospital may be one of several different sized modular cargo storage systems, where the selected one of the different sized modular cargo storage systems is compatible with a size parameter for the item being shipped as part of the dispatched logistics operation within the hospital. As such, an appropriate CSS 1720 may be used on top of the extended base adapter plate described above in an embodiment where such a configured bot apparatus is deployed on a dispatched logistics operation to pick up and deliver a greater number of items or simply larger items. Those skilled in the art will further appreciate that in such an example, the modular mobile autonomy control module compatible with the dispatched logistics operation within the hospital may also be one of several of different sized modular mobile autonomy control modules. And like the modular cargo storage system component, the particular mobile autonomy control module used for the bot apparatus may be one that is compatible with the size parameter for the item being shipped as part of the dispatched logistics operation within the hospital.

Document Delivery

In further embodiments, an exemplary MALVT bot apparatus may be used as a secure courier between office buildings for a variety of companies that currently leverage internal staff or foot couriers. For example, law firms, finance firms, government work may be transported securely and transparently from one office to the other using an exemplary MALVT bot apparatus and its security features. In general, an exemplary embodiment may have the sender hailing a secure delivery exemplary MALVT bot apparatus using, for example, wireless node interactions between the sender's user access device and the MAM (e.g., having a controller operating as a master node where the sender's user access devices is operating as an ID node). The requested exemplary MALVT bot apparatus responds and arrives to receive the documents. The security and authentication needs for the delivery may be selectively deployed depending on the type of documents, the sender, and the recipient. The sender may leverage TRON technology in such a secure courier type of dispatched logistics operation embodiment, which may involve wireless communications with user access devices (e.g., supplier mobile user access device 3310 (e.g., a type of mobile ID node or mobile master node) such as a smartphone or handheld tablet device) and a node-enabled component of the exemplary MALVT bot apparatus (e.g., the autonomous controller 3100 on exemplary MAM 1725)) or enter a physical location to cause the exemplary MALVT bot apparatus to be dispatched, which may alert the recipient of departure as well as provide an estimated arrival time by the exemplary MALVT bot apparatus. In this general example involving secure courier type of logistics operations, the exemplary MALVT bot apparatus may arrive at location and alert the recipient of delivery. The recipient may receive delivery of the documents within the CSS component with the selected level of security/authentication/authorization via display screen, app, or TRON implemented interactive based secure delivery features (e.g., biometrics, key code, two factor authentication, TRON node-to-node association, etc.). After delivery, the exemplary MALVT bot apparatus may return to the original storage location, and/or return signed or updated documents to the sender or third party if needed. Those skilled in the art will appreciate that such secure courier related embodiments may involve on-demand building of an exemplary MALVT bot apparatus assembly for such secure document delivery-related deployments (e.g., consistent with the process explained above relative to FIG. 41, exemplary method 4100, and its variations), as well as embodiments that may responsively dispatch an exemplary MALVT bot apparatus assembly on a document delivery-related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in further embodiment of exemplary method 4400 involving secure document delivery logistics operations, the dispatch command sent by the dispatch server may be initiated based upon a dispatch request received by the dispatch server and where the request is sent from a sending entity related to the dispatched logistics operation. The dispatch command includes sender identifier information of an external mobile wireless node operated by the sending entity and delivery recipient identifier information related to a delivery recipient for the item being shipped. Further, as part of this embodiment of method 4400, the origin location for the dispatched logistics operation is a bot storage location where the modular autonomous bot apparatus is initially maintained and the destination information defines an intermediate loading location defined as part of the destination information. As part of this embodiment of exemplary method 4400, the step of receiving the item being shipped at step 4415 has the modular mobile autonomy control module autonomously causing the modular mobility base to move from the bot storage location to the intermediate loading location (e.g., a mobile node location of the external mobile wireless node operated by the sending entity); receiving sending entity authentication input by the modular mobile autonomy control module from the sending entity, where the sending entity authentication input correlates to a portion of the authentication information related to the dispatched logistics operation indicating the sending entity providing that sending entity authentication input is an authorized provider for the item being shipped within the module cargo storage system as part of the dispatched logistics operation; having the modular cargo storage system providing selective access to within the modular cargo storage system after the sending entity authentication input is confirmed to be from the authorized provider for the item (i.e., the received sending entity authentication input correlates to the portion of the authentication information indicating the sending entity providing the sending entity authentication input is the authorized provider for the item being shipped); receiving, by the modular cargo storage system, the item being shipped (e.g., one or more documents to be transported within the modular cargo storage system) at the intermediate locating location; and securing, by the modular mobile autonomy control module, the item being shipped within the modular cargo storage system. Additionally, as part of this embodiment of exemplary method 4400, step 4420 may be implemented as causing, by the modular mobile autonomy control module, the modular mobility base to move from the intermediate loading location on an intermediate delivery route to the destination location identified by the destination information (e.g., a mobile node location of an external mobile wireless node operated by the delivery recipient), and step 4435 may be implemented as autonomously causing, by the modular mobile autonomy control module, the modular mobility base to move from the destination location on the return route to the bot storage location after the item being shipped is detected to be removed from within the modular cargo storage system.

In more detail and as part of this further embodiment of method 4400, the step of receiving the sending entity authentication input may be further implemented with wireless input, input through a user input panel (or other sensor) on the exemplary MALVT bot apparatus involved in the operation, or recognized voice input through a microphone on the exemplary MALVT bot apparatus. For example, the modular mobile autonomy control module may first detect an advertising signal from the sending entity's mobile wireless node as the sending entity authentication input as the modular autonomous bot apparatus assembly (e.g., exemplary MALVT bot apparatus assembly 1700) approaches the mobile node location of the sending entity's external mobile wireless node, and then authenticate that the external mobile wireless node operated by the sending entity is associated with the sending entity for the item being shipped within the modular cargo storage system based upon (a) the identifier information of the external mobile wireless node operated by the sending entity from the dispatch command and (b) identifier information within the detected advertising signal.

In another example in such an embodiment of method 4400, the sending entity authentication input received by the modular mobile autonomy control module may be provided as an access code through a user input panel disposed on the modular autonomous bot apparatus coupled to the modular mobile autonomy control module (e.g., exemplary user input panel 2220), biometric input provided the user input panel disposed or via a sensor disposed on the exemplary MALVT bot apparatus assembly, or wireless input from an external mobile wireless node, or a combination of such input in a multi-factor form of authentication input.

In more detail and as part of this further embodiment of method 4400, the step of receiving the delivery recipient authentication input may be similarly implemented with wireless input, input through a user input panel (or other sensor) on the exemplary MALVT bot apparatus involved in the operation, or recognized voice input through a microphone on the exemplary MALVT bot apparatus. For example, the modular mobile autonomy control module may first detect an advertising signal from the delivery recipient's mobile wireless node as the delivery recipient authentication input as the modular autonomous bot apparatus assembly (e.g., exemplary MALVT bot apparatus assembly 1700) approaches the mobile node location of the delivery recipient's external mobile wireless node, and then authenticate that the external mobile wireless node operated by the delivery recipient is associated with the authorized delivery recipient for the item being shipped within the modular cargo storage system based upon (a) the delivery recipient identifier information from the dispatch command and (b) identifier information of the external mobile wireless node operated by the delivery recipient within the detected advertising signal.

In still another example in such an embodiment of method 4400, the delivery recipient authentication input received by the modular mobile autonomy control module may be provided as an access code through a user input panel disposed on the modular autonomous bot apparatus coupled to the modular mobile autonomy control module (e.g., exemplary user input panel 2220), biometric input provided the user input panel disposed or via a sensor disposed on the exemplary MALVT bot apparatus assembly, or wireless input from an external mobile wireless node, or a combination of such input in a multi-factor form of authentication input.

In yet another example in such an embodiment of method 4400 involving secure delivery of documents, method 4400 may further include the step of transmitting, by the modular mobile autonomy control module, a pickup notification to the sending entity of an approaching pickup as part of the dispatched logistics operation once the modular autonomous bot apparatus assembly is within a threshold notification range of the intermediate loading location identified by the destination information. Thereafter, method 4400 may also include the step of transmitting, by the modular mobile autonomy control module, a departure notification to the delivery recipient of an estimated drop-off as part of the dispatched logistics operation once the modular autonomous bot apparatus assembly moves a threshold departure distance from the intermediate loading location. Such a departure notification may include an estimated time of arrival for the modular autonomous bot apparatus assembly to arrive at the destination location from a current location of the modular autonomous bot apparatus assembly. An embodiment of method 4400 involving secure delivery of documents may also include the step of transmitting, by the modular mobile autonomy control module, a drop-off notification to the delivery recipient of an approaching drop-off as part of the dispatched logistics operation once the modular autonomous bot apparatus assembly is within a threshold notification range of the destination location identified by the destination information.

Upon delivery of the item being shipped (e.g., documents and the like), the exemplary MALVT bot apparatus may, as part of this embodiment of method 4400, return to the sending entity with an additional item within the CSS 1720 (e.g., modified or signed documents), or proceed to another location with such an additional item. For example, step 4435 may be implemented by autonomously causing, by the modular mobile autonomy control module, the modular mobility base to move from the destination location back to the intermediate loading location after the item being shipped is detected to be removed from within the modular cargo storage system at the destination location and an additional item is detected to be placed within the modular cargo storage system at the destination location; and then autonomously causing, by the modular mobile autonomy control module, the modular mobility base to move from the intermediate loading location to the bot storage location after the additional item is detected to be removed from within the modular cargo storage system at the intermediate loading location.

This may also include steps of receiving secondary sending entity authentication input by the modular mobile autonomy control module from the sending entity while at the intermediate loading location after the modular mobility base returns to the intermediate loading location, where the secondary sending entity authentication input at least correlates to (e.g., matches all or at least a threshold amount of) the portion of the authentication information related to the dispatched logistics operation indicating the sending entity that provided the secondary sending entity authentication input is the authorized provider for the item being shipped within the module cargo storage system as part of the dispatched logistics operation. The modular cargo storage system may then provide selective access to within the modular cargo storage system for removal of the additional item after the secondary sending entity authentication input received correlates to the portion of the authentication information indicating the sending entity providing the secondary sending entity authentication input is the authorized provider for the item being shipped.

As noted above, upon delivery of the item being shipped (e.g., documents and the like), the exemplary MALVT bot apparatus may, as part of this embodiment of method 4400, proceed to another location with the additional item. For example, step 4435 may be implemented by autonomously causing, by the modular mobile autonomy control module, the modular mobility base to move from the destination location to a secondary delivery location after the item being shipped is detected to be removed from within the modular cargo storage system at the destination location and after an additional item is detected within the modular cargo storage system while at the destination location, the secondary delivery location being identified as part of the destination information related to the dispatched logistics operation. The modular mobile autonomy control module then may autonomously cause the modular mobility base to move from the secondary delivery location to the bot storage location after the additional item is detected to be removed from within the modular cargo storage system at the secondary delivery location. In addition, method 4400 in this particular embodiment may also proceed by receiving third party entity authentication input by the modular mobile autonomy control module from a third party entity while at the secondary delivery location after the modular mobility base arrives at the secondary delivery location. The third party entity authentication input correlates to a portion of the authentication information related to the dispatched logistics operation indicating the third party entity that provided the third party entity authentication input is an authorized third party recipient for the additional item within the module cargo storage system as part of the dispatched logistics operation. Thereafter, the modular cargo storage system may provide selective access to within the modular cargo storage system for removal of the additional item after the third party entity authentication input received correlates to the portion of the authentication information indicating the third party entity providing the third party entity authentication input is the authorized third party recipient for the additional item.

Medical Device Kit

A further embodiment may involve medical kits of supplies used for medical procedures. For example, a surgical implant company, such as Smith & Nephew, may send hospitals one or more "kits" of components needed for a surgery or other medical procedure with a variety of sizes and instruments that may be used for the procedure, but with some components from the kit never being used and remaining in pristine condition for use in another procedure. In general, a dispatched exemplary MALVT bot apparatus assembly in such an environment may have equipment or components of a medical kit that remains unused after a medical procedure be loaded into a waiting exemplary MALVT bot apparatus stored at the hospital with a centralized return location as the delivery address mapped (e.g., via TRON node locating techniques or via GPS location circuitry onboard the exemplary MALVT bot apparatus). Once the unused equipment is secured within the CSS 1720 of the exemplary MALVT bot apparatus assembly 1700, the exemplary MALVT bot apparatus assembly 1700 may autonomously depart and proceed to deliver the unused equipment from the medical kit. The receiving center at the centralized return location (or elsewhere as defined in the relevant dispatch command for the dispatched logistics operation) will receive an update that the exemplary MALVT bot apparatus is on the way with an estimated time of arrival. The recipient at the receiving center authenticates delivery with techniques described above (e.g., via app input, input via a secure TRON node-to-node association, or input prompted through a display screen, such as voice input, or biometric input via sensors on the exemplary MALVT bot apparatus). If a new kit is needed to replenish inventory it is loaded into the exemplary MALVT bot apparatus and the exemplary MALVT bot apparatus returns to the hospital.

Those skilled in the art will appreciate that embodiments may involve on-demand building of an exemplary MALVT bot apparatus assembly for such medical kit-related deployments (e.g., consistent with the process explained above relative to FIG. 41, exemplary method 4100, and its variations), as well as embodiments that may responsively dispatch an exemplary MALVT bot apparatus assembly on a medical kit-related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 involving a hospital environment with an intermediate loading location, the item being shipped may include at least one of multiple components of a medical kit used for a medical procedure. The component of the medical kit to be shipped is unused as part of the medical procedure and in condition for use in a second medical procedure (e.g., still sterile, in packaging, and the like). In this further embodiment, the origin location for the medical kit-related dispatched logistics operation may be a bot storage location where the modular autonomous bot apparatus is initially maintained, while the destination information defines an intermediate return loading location (e.g., a room relative to an office mapping, a set of coordinates, or a mobile node location of an external mobile wireless node operated by the returning entity medical personnel) and a destination location for the dispatched logistics operation as a centralized return location for the component(s) being returned via this dispatched logistics operation.

Additionally, as part of this further embodiment of method 4400, step 4415 in this embodiment may be implemented with the modular mobile autonomy control module autonomously causing the modular mobility base to move from the bot storage location to the intermediate return loading location; receiving returning entity medical personnel authentication input by the modular mobile autonomy control module from returning entity medical personnel related to the dispatched logistics operation (where the returning entity medical personnel authentication input correlates to a portion of the authentication information indicating the personnel providing the returning entity medical personnel authentication input is an authorized return supplier for the item being shipped); providing, by the modular cargo storage system, selective access to within the modular cargo storage system after the returning entity medical personnel authentication input indicates the returning entity medical personnel is the authorized return supplier for the item (due to the correlation with the authentication information). The modular cargo storage system may then receive the item being shipped at the intermediate locating location, and have the modular mobile autonomy control module securing the item being shipped within the modular cargo storage system (e.g., by closing the cargo door and/or locking the cargo storage system with the item within it).

Additionally, step 4420 in this embodiment may, as a result be implemented with the modular mobile autonomy control module autonomously causing the modular mobility base to move from the intermediate loading location (where it has been loaded with the unused part of the medical kit) on an intermediate delivery route to the destination location identified by the destination information. Thereafter, step 4435 in this embodiment may be implemented by the modular mobile autonomy control module autonomously causing the modular mobility base to move from the destination location on the return route to the bot storage location after the item being shipped (e.g., the unused part of the medical kit) is detected to be removed from within the modular cargo storage system using, for example, internal sensor 3130 on MAM 1725 that monitors the payload area of CSS 1720.

In a further example, the step of receiving the returning entity medical personnel authentication input may have the modular mobile autonomy control module detecting an advertising signal from the external mobile wireless node operated by the returning entity medical personnel as the returning entity medical personnel authentication input when the modular autonomous bot apparatus assembly approaches the mobile node location of the external mobile wireless node operated by the returning entity medical personnel; and the modular mobile autonomy control module authenticating that the external mobile wireless node operated by the returning entity medical personnel is associated with the returning entity medical personnel for the item being shipped within the modular cargo storage system based upon (a) the identifier information of the external mobile wireless node operated by the returning entity medical personnel from the dispatch command and (b) identifier information within the detected advertising signal. Other ways of authenticating the pickup may be accomplished by, for example, receiving the returning entity medical personnel authentication input through a user input panel disposed on the modular autonomous bot apparatus coupled to the modular mobile autonomy control module (via access code or biometric input), or through another sensor on the modular autonomous bot apparatus (e.g., a microphone).

Similar ways of authenticating the delivery may be employed with delivery receipt authentication input being received in different forms and using different input mechanisms (e.g., wireless, user input panel, other sensors). For example, the step of receiving the delivery recipient authentication input may be implemented in this embodiment with the modular mobile autonomy control module detecting an advertising signal from an external mobile wireless node operated by a centralized return location recipient as the delivery recipient authentication input as the modular autonomous bot apparatus assembly approaches the mobile node location of the external mobile wireless node operated by the centralized return location recipient; and then authenticating that the mobile wireless node providing such input is associated with the centralized return location recipient for the item being shipped within the modular cargo storage system based upon (a) the delivery recipient identifier information from the dispatch command and (b) identifier information of the external mobile wireless node operated by the centralized return location recipient within the detected advertising signal.

Further still, as part of this medical kit related embodiment of method 4400, method 4400 may generate notifications to arrival and departures of the exemplary MALVT bot apparatus assembly. For example, the medical kit related embodiment of method 4400 described above may include the step of transmitting, by the modular mobile autonomy control module, a pickup notification to the returning entity medical personnel of an approaching pickup as part of the dispatched logistics operation once the modular autonomous bot apparatus assembly is within a threshold notification range of the intermediate loading location identified by the destination information. In another example, method 4400 may also include the step of transmitting, by the modular mobile autonomy control module, a departure notification (which may have an estimated time of arrival) to the centralized return location recipient of an estimated drop-off as part of the dispatched logistics operation once the modular autonomous bot apparatus assembly moves a threshold departure distance from the intermediate loading location. The departure notification may, in some embodiments, include an estimated time of arrival for the modular autonomous bot apparatus assembly to arrive at the destination location from a current location of the modular autonomous bot apparatus assembly. Further still, another example of method 4400 may have the modular mobile autonomy control module transmitting a drop-off notification to the centralized return location recipient of an approaching drop-off as part of the dispatched logistics operation once the modular autonomous bot apparatus assembly is within a threshold notification range of the destination location identified by the destination information.

In this further embodiment of method 4400 involving a medical kit, there may be an option to return with a replacement for the unused part or a different kit. For example, step 4435 may be implemented by the modular mobile autonomy control module autonomously causing the modular mobility base to move from the destination location back to the intermediate loading location after the item being shipped is detected to be removed from the CSS at the destination location and an additional item (e.g., a replacement medical kit or a medical kit for a different type of medical procedure) is detected to be placed within the CSS at the destination location; and autonomously causing the modular mobility base to move from the intermediate loading location to the bot storage location after the additional item is detected to be removed from within the modular cargo storage system at the intermediate loading location.

Office Document Shredding

Further embodiments may involve logistics operations involving shredding containers and documents to be shredded that need transport. For example, one or more exemplary MALVT bot apparatus may be leased by a commercial document shredding company to take strong box shredding containers (e.g., shred bins) to a singular location in a building to be picked up, or deliver the shredding containers to a centralized location receiving deliveries from multiple buildings overnight. Traditionally, the document shredding company may employ trucks and personnel to empty shred bins in commercial offices. However, an exemplary MALVT bot apparatus may be deployed as part of a dispatched logistics operation to go office-to-office or between certain locations within an office to remove shred bins and take the shredding documents (e.g., within the bins or as documents themselves loaded into an exemplary CSS that can handle a desired volume of such documents) to a centralized facility, which will drastically cut down on logistic & fleet management costs. The exemplary MALVT bot apparatus in this embodiment may operate elevators, doors, and interact with shred bins using actuated articulating arms and vision systems or via electronic integration with a building's automated systems for elevators and door openers. Aspects of TRON wireless node technology may be incorporated and leveraged for location, door & lock operation, elevator operation, machine-to-machine interaction (e.g., node to node wireless communication) and authentication using the various nodes (e.g., different nodes embedded in or in responsive communication with an actuated door, lock, or elevator) and node locating techniques as described above.

Those skilled in the art will appreciate that embodiments may involve on-demand building of an exemplary MALVT bot apparatus assembly for such office shredding-related deployments (e.g., consistent with the process explained above relative to FIG. 41, exemplary method 4100, and its variations), as well as embodiments that may responsively dispatch an exemplary MALVT bot apparatus assembly on an office shredding-related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 involving the collection of documents for shredding and used of an intermediate loading location (where the documents are picked up), the item being shipped by the exemplary MALVT bot apparatus assembly is documents collected for secure shredding and, in some cases, may also include a container that securely maintains such documents to be shredded. The destination location in this further embodiment is a centralized shred pickup facility, and the intermediate loading location is a location of a container maintaining the documents collected for secure shredding (e.g., an identified location relative to an office mapping of the container maintaining the documents collected for secure shredding, a location of an external wireless node built into or as a part of the shredding document container maintaining the documents collected for secure shredding, or a mobile location of the container's wireless node). As such, this particular embodiment of method 4400 may implement step 4415 by first receiving pickup authentication input by the modular mobile autonomy control module from a document supplier through a user input panel disposed on the modular autonomous bot apparatus coupled to the modular mobile autonomy control module; and then having the modular cargo storage system provide selective access to within the modular cargo storage system for loading of the item being shipped after the pickup authentication input received correlates to a portion of the authentication information related to an authorized document supplier.

The pickup recipient authentication input received in this particular embodiment of method 4400 may come in several forms. For example, the pickup recipient authentication input received by the modular mobile autonomy control module may be an access code provided by the document supplier through the user input panel disposed on the modular cargo storage system and operatively coupled to the modular mobile autonomy control module or a biometric input provided by the document supplier through the user input panel (which may have a biometric input sensor or scanner).

In another example, receiving the pickup recipient authentication input may, in more detail, involve receiving pickup authentication input by the modular mobile autonomy control module by detecting an advertising signal from the external wireless node that is part of the container maintaining the documents collected for secure shredding and verifying the detected advertising signal includes identifier information that correlates to a portion of the authentication information related to an authorized document supplier for the container. Thereafter, the modular cargo storage system may then provide selective access to within the modular cargo storage system for loading of the item being shipped after the pickup authentication input received correlates to the portion of the authentication information related to the authorized document supplier.

In this particular embodiment of method 4400 involving documents for shredding, the delivery recipient authentication input received may also come in various forms. For example, the delivery receipt authentication input may be information received through a user input panel disposed on the modular autonomous bot apparatus coupled to the modular mobile autonomy control module, such as an access code provided by the delivery recipient through the user input panel or biometric input provided by the delivery recipient through the user input panel (which has a biometric sensor or scanner) or another sensor that may receive such biometric input from the delivery recipient.

In a further example where delivery may be authenticated via wireless authentication, the authentication information related to the dispatched logistics operation may include an identifier of the authorized delivery recipient for the item being shipped as part of the dispatched logistics operation.

Furthermore, the step of receiving the delivery recipient authentication input at step 4425 may be implemented with the modular mobile autonomy control module detecting an advertising signal as the delivery recipient authentication input from an external wireless node related to the destination location within a predetermined range of the modular autonomous bot apparatus assembly once the modular autonomous bot apparatus assembly has arrived at the destination location identified by the destination information; and having the modular mobile autonomy control module authenticate that the external wireless node related to the destination location is associated with the authorized delivery recipient for the item being shipped within the modular cargo storage system based upon the identifier of the authorized delivery recipient and identifier information within the detected advertising signal broadcast from the external wireless node related to the destination location.

In this particular embodiment of method 4400 involving documents for shredding that may be picked up in a particular shred bin/container, step 4415 may be implemented by deploying an articulating arm (e.g., exemplary arm 4325, 2090) disposed on the modular autonomous bot apparatus assembly and using proximity and vision sensors disposed on at least one of the modular mobility base and the modular mobile autonomy control module to engage the item being shipped (e.g., the shred bin container) and placing the item within the modular cargo storage system. In more detail, receiving the item being shipped in this particular embodiment may be implemented with the modular mobile autonomy control module guiding the articulating arm to the item being shipped using proximity and vision sensors disposed on at least one of the modular mobility base and the modular mobile autonomy control module; engaging, by the articulating arm, the item being shipped; and moving, by the articulating arm, the item being shipped to a position within the modular cargo storage system.

In a further embodiment, the articulating arm may be used to open a closable access point on the shred bin container and transfer the documents to be shredded into the CSS payload area for transport on the exemplary MALVT bot apparatus assembly. For example, the step of receiving the item being shipped at step 4415 may be implemented with the modular mobile autonomy control module guiding the articulating arm to a closable access point on the container using one or more of the proximity and vision sensors disposed on at least one of the modular mobility base and the modular mobile autonomy control module; engaging, by the articulating arm, the closable access point on the container to enabled access to within the container (e.g., opening the container using the articulating arm to manipulate the closeable access point); engaging, by the articulating arm, the documents collected for secure shredding; and moving, by the articulating arm, the documents collected for secure shredding to a position within the modular cargo storage system.

In yet a further embodiment, the articulating arm may be used to obtain the shred bin container itself and place it within the CSS payload area for transport on the exemplary MALVT bot apparatus assembly. For example, the step of receiving the item being shipped at step 4415 may be implemented by deploying an articulating arm disposed on the modular autonomous bot apparatus assembly and using a plurality of proximity and vision sensors disposed on at least one of the modular mobility base and the modular mobile autonomy control module to engage the container and place the container within the modular cargo storage system. In some embodiments, this may be accomplished with a single articulating arm, but in other embodiments, the exemplary MALVT bot apparatus assembly may deploy multiple articulating arms to use when engaging, manipulating, and moving an item being shipped, such as a shred bin container filled with documents for shredding.

In still another embodiment of method 4400, the dispatch command may have the exemplary MALVT bot apparatus assembly being dispatched to pickup documents for shredding from multiple locations before dropping them all off at a document shredding facility (e.g., a fixed building or a mobile facility deployed outside of an office building in which the exemplary MALVT bot apparatus is conducting the pickup operations). For example, an embodiment of method 4400 may have the item being shipped being a plurality of documents collected for secure shredding; the destination location being a centralized shred pickup facility; the origin location for the dispatched logistics operation being a bot storage location where the modular autonomous bot apparatus is initially maintained; and where the destination information defines multiple intermediate loading locations as part of the dispatched logistics operation. As such, step 4415 involving receiving the item being shipped may be implemented with the modular mobile autonomy control module autonomously causing the modular mobility base to move from the bot storage location to a first of the intermediate loading locations; receiving, by the modular cargo storage system, a first portion of the item being shipped at first of the intermediate locating locations (e.g., a first group of documents to be shredded); autonomously causing, by the modular mobile autonomy control module, the modular mobility base to move from the first intermediate loading location to a second of the intermediate loading locations; and receiving, by the modular cargo storage system, a second portion of the item being shipped at first of the intermediate locating locations (e.g., a second group of documents to be shredded). Step 4420 in this embodiment of method 4400 may be implemented with the modular mobile autonomy control module autonomously causing the modular mobility base to move from the second of the intermediate loading locations to the destination location identified by the destination information; and step 4435 may be implemented with the modular mobile autonomy control module autonomously causing the modular mobility base to move from the destination location on the return route to the bot storage location after each of at least the first portion of the item being shipped and the second portion of the item being shipped are detected to be removed from within the modular cargo storage system.

Pharmaceutical Fulfilment

In another embodiment, an exemplary MALVT bot apparatus may be deployed as part of a dispatched logistics operation involving fulfillment of pharmaceutical orders. In an exemplary embodiment, a third shift pharmacist at a 24-hour location may prepare overnight prescriptions for non 24-hour affiliated pharmacies in a micro trade area around the 24-hour location, which may allow the collective pharmacy business to utilize off-peak labor. In such a situation, an embodiment of the invention may have one or more exemplary MALVT bot apparatus for each non 24-hour affiliated pharmacy loaded in after the overnight fulfillment of prescriptions at the 24-hour location, and dispatched to the non-24-hour affiliated pharmacies in time with the opening of the non-24-hour affiliated pharmacy store locations. Pharmaceutical technicians at such non 24-hour affiliated pharmacy locations may then authenticate delivery via an app operating on the technician's user access device, via TRON node interactions for association-based authenticated delivery, or via interaction with the display screen, user input panel, and/or sensors on the MAM component. As the technician unloads the exemplary MALVT bot apparatus, the exemplary MALVT bot apparatus may monitor the unload (e.g., making sure what is unloaded from the CSS is supposed to be at the new location), ensure that all contents have been removed, and then the bot apparatus may return to the base 24-hour location. The exemplary MALVT bot apparatus in this embodiment may run on a particular and reliable schedule in order to ensure the technicians are anticipating arrival of such exemplary MALVT bot apparatus with fulfilled ordered. Multi-factor authentication may be implemented to enhance security, and the exemplary MALVT bot apparatus may generate and provide chain of custody information related to the transported pharmaceutical orders being fulfilled. Aspects of TRON wireless node technology may be incorporated and leveraged as control elements within components of the exemplary MALVT bot apparatus and with other nodes for location, door & lock operation, elevator operation, and authentication using the various nodes (e.g., different nodes embedded in or in responsive communication with an actuated door, lock, or elevator) and node locating techniques described above. Those skilled in the art will appreciate that embodiments may involve on-demand building of an exemplary MALVT bot apparatus assembly for such pharmaceutical fulfillment-related deployments (e.g., consistent with the process explained above relative to FIG. 41, exemplary method 4100, and its variations), as well as embodiments that may responsively dispatch an exemplary MALVT bot apparatus assembly on a pharmaceutical fulfillment-related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 involving pharmaceutical fulfillment orders, the origin location may be an extended hour centralized base depot for pharmaceutical prescription supplies where the modular autonomous bot apparatus is initially maintained. The dispatch command sent by the dispatch server may be initiated based upon a dispatch request received by the dispatch server and sent from an authorized pharmaceutical personnel at a remote pharmaceutical outlet served by the extended hour (e.g., 24-hours) centralized base depot for pharmaceutical prescription supplies. The dispatch command is related to the dispatched logistics operation and includes at least identifier information of an external mobile wireless node operated by the authorized pharmaceutical personnel. The destination location identified by the destination information in the dispatch command includes a location of the remote pharmaceutical outlet and may also include a mobile node location of an external mobile wireless node operated by the authorized pharmaceutical person.

Related to chain of custody features, this particular embodiment of exemplary method 4400 may further include the step of generating, by the modular mobile autonomy control module, a first inventory data structure corresponding to the item being shipped upon receiving the item being shipped. The first inventory data structure includes a first chain of custody entry reflecting departure from the extended hour centralized base depot for pharmaceutical prescription supplies for the item being shipped in the custody of the modular autonomous bot apparatus assembly. Method 4400 may also include generating a second chain of custody entry within the first inventory data structure after arrival at the remote pharmaceutical outlet, where the second chain of custody reflects arrival from the extended hour centralized base depot for pharmaceutical prescription supplies for the item being shipped to the remote pharmaceutical outlet in the custody of the modular autonomous bot apparatus assembly. Additionally, method 4400 may also include generating, by the modular mobile autonomy control module, a third chain of custody entry within the first inventory data structure after arrival at the remote pharmaceutical outlet and after detecting the item being shipped has been removed from within the modular cargo storage system, the third chain of custody reflecting the item being shipped changing custody to the remote pharmaceutical outlet from the modular autonomous bot apparatus assembly.

In more detail, this particular embodiment of exemplary method 4400 may autonomously cause the modular mobility base to move from the destination location on a return route to the origin location after the item being shipped is detected to be removed from within the modular cargo storage system by having the modular mobile autonomy control module monitoring an unloading status of the modular cargo storage system using at least one sensor on at least one of the modular mobile autonomy control module and the modular cargo storage system; detecting when the item being shipped is removed from within the modular cargo storage system based upon sensor data from such a sensor; and generating the third chain of custody entry within the first inventory data structure when the sensor data reflects the item being shipped is no longer within the modular cargo storage system.

In this particular embodiment of method 4400, the dispatch command sent by the dispatch server may be one of multiple dispatch commands for different dispatched logistics operations from the extended hour centralized base depot for pharmaceutical prescription supplies to the remote pharmaceutical outlet, where the dispatch commands may be sent on a predetermined schedule for the remote pharmaceutical outlet. In another example, such different dispatch commands may be for different dispatched logistics operations from the extended hour centralized base depot for pharmaceutical prescription supplies to a multiple different serviced remote pharmaceutical outlets, where the remote pharmaceutical outlet is one of the serviced remote pharmaceutical outlets by the extended hour centralized base depot for pharmaceutical prescription supplies.

As noted above, the use of multi-factor or multi-level authentication may be deployed with authenticating delivery or pickup as part of embodiments of method 4400. For example, an embodiment of method 4400 may have the authentication information related to the dispatched logistics operation implemented with multi-level authentication information, such as at least (a) passcode authentication information and (b) identifier information of an external mobile wireless node operated by the authorized delivery recipient. In another example, the multi-level authentication information may be implemented using distinct communication paths for authentication input, such as (a) a first passcode authentication information related to a first communication path with the delivery recipient (e.g., an access code submitted to the exemplary MALVT bot apparatus assembly via its user input panel) and (b) a second passcode authentication information related to a second communication path with the delivery recipient (e.g., another access code or device signature for a wireless mobile node submitted to the exemplary MALVT bot apparatus assembly via its wireless communications with the wireless mobile node).

Further still, such multi-level authentication information may be implemented using, for example, at least two of passcode authentication information, biometric scanning authentication information, device signature authentication information, and voice authentication information.

Fleet Augmentation

In an embodiment, one or more exemplary MALVT bot apparatus may be staged as a vehicle type at a business location doing multiple duty with, for example, print delivery, inventory rebalancing, hold-at-location (HAL) delivery, as part of providing multiple types of delivery services. In general, as orders come in, a dispatch system (e.g., a dedicated dispatch server 4205, a server that performs dispatching as well as other business tasks, or a dispatch program module running on another business server system) may determine if the origin and destination, time commitment, and payload are physically and economically conducive to dispatching exemplary MALVT bot apparatus for pickup/transit/delivery for a particular time period, such as during the current day. An exemplary MALVT bot apparatus may receive a dispatch order from the dispatch system and embark on the dispatched logistics job covered by the order. The exemplary MALVT bot apparatus may go to pick up a delivery from retailer, customer, or other entity, etc. as part of an exemplary logistics operation in this embodiment. A fulfiller may receive an alert that the exemplary MALVT bot apparatus is in-route with an estimated time of arrival. The display screen on the exemplary MALVT bot apparatus may offer instructions or information on the order, a fulfillment associate (or system) may load the exemplary MALVT bot apparatus and confirm that it can continue the dispatched logistics job covered by the order. The end customer then may receive an alert from the exemplary MALVT bot apparatus along with an estimated time of arrival such that the end customer may interact with the exemplary MALVT bot apparatus change the window for delivery. If the window for delivery is significantly changed, the exemplary MALVT bot apparatus may temporarily return to a holding location at the business location (rather than wait at the end customer's location). If not, the exemplary MALVT bot apparatus continues to the end customer and makes the delivery with authentication procedures. As the end customer unloads the exemplary MALVT bot apparatus, the exemplary MALVT bot apparatus may monitor unloading (e.g., making sure what is unloaded from the CSS is supposed to be at the new location) and ensure that all contents have been removed, and then the bot apparatus may return to the base location. Aspects of TRON technology may be incorporated and leveraged for location, door & lock operation, elevator operation, and authentication using the various nodes (e.g., different nodes embedded in or in responsive communication with an actuated door, lock, or elevator) and node locating techniques described above. Those skilled in the art will appreciate that embodiments may involve on-demand building of an exemplary MALVT bot apparatus assembly for such fleet augmentation-related deployments (e.g., consistent with the process explained above relative to FIG. 41, exemplary method 4100, and its variations), as well as embodiments that may responsively dispatch an exemplary MALVT bot apparatus assembly on a fleet augmentation-related dispatched logistics operation (e.g., consistent with the process explained above relative to FIG. 44, exemplary method 4400, and its variations; as well as consistent with the process explained above relative to FIG. 44, exemplary method 4600, and its variations).

Accordingly, in such a further embodiment of exemplary method 4400 involving a fleet augmentation environment with an intermediate loading location, the origin location may be a location of a business entity for delivery services where the modular autonomous bot apparatus is initially maintained, and the dispatch command sent by the dispatch server is initiated based upon a dispatch request received by the dispatch server and sent from the delivery recipient. In this further embodiment, method 4400 may, before the authenticating step 4410, include the step of determining, by the dispatch server, if the dispatched logistics operation related to the dispatch request is a fulfillable type of dispatch logistics operation for the business entity for delivery services based upon fulfillment requirements for the dispatched logistics operation related to the dispatch request, where the determining step is performed prior to the authenticating step. At least one of the fulfillment requirements may, for example, be a location parameter (e.g., including the origin location and the destination location); a timing parameter for conducting the dispatched logistics operation relate to the dispatch request; and a payload parameter for transporting the item being shipped as part of the dispatched logistics operation relate to the dispatch request.

Then, this further embodiment of method 4400 proceeds to step 4410 where the modular mobile autonomy control module authenticates that each of the modular mobile autonomy control module, the modular mobility base, the modular auxiliary power module, and the modular cargo storage system are compatible with the dispatched logistics operation by verifying whether each of the modular mobile autonomy control module, the modular mobility base, the modular auxiliary power module, and the modular cargo storage system are compatible with the fulfillment requirements for the dispatched logistics operation related to the dispatch request prior to moving from the origin location.

Additionally, this further embodiment of method 4400 related to fleet augmentation may also include notifying, by the modular mobile autonomy control module, a supplier of the item being shipped of (a) an approaching pickup at the intermediate loading location and (b) an estimated time of arrival at the intermediate loading location before arriving at the intermediate loading location; receiving supplier authentication input by the modular mobile autonomy control module from the supplier disposed external to the modular autonomous bot apparatus assembly at the intermediate loading location before receiving the item being shipped, where the supplier authentication input correlates to a portion of the authentication information related to the dispatched logistics operation indicating the supplier that provided the supplier authentication input is an authorized supplier for the item being shipped related to the dispatched logistics operation; and notifying, by the modular mobile autonomy control module, the delivery recipient of an approaching delivery after receiving the item being shipped at the intermediate loading location and notifying the delivery recipient of an estimated time of arrival at the destination location. Furthermore, in this embodiment, the modular autonomous bot apparatus assembly may be one of multiple leased modular autonomous bot apparatus assemblies to the business entity at the origin location or a modular assembly of different leased modular autonomous bot apparatus components under lease by the business entity at the origin location.

Additionally, this further embodiment of method 4400 related to fleet augmentation may also include generating instructions or information on the order to assist with loading. For example, the step of receiving the item being shipped at the intermediate loading location may be implemented with the modular mobile autonomy control module generating a loading assistance prompt message on a display disposed on the modular mobile autonomy control module (e.g., display 2815a, 2815b). Such a loading assistance prompt message may provide information on the item being shipped to be provided by the supplier and instructions for placing the item being shipped within the modular cargo storage system as part of the dispatched logistics operation.

Additionally, this further embodiment of method 4400 related to fleet augmentation may also include notifying the delivery recipient before the leaving the pickup/loading location. For example, the step of notifying, by the modular mobile autonomy control module, the delivery recipient of an approaching delivery after receiving the item being shipped at the intermediate loading location and notifying the delivery recipient of an estimated time of arrival at the destination location may be performed after receiving the item being shipped at the intermediate loading location and before the modular mobility based moves from the intermediate loading location. In another example, the step of notifying, by the modular mobile autonomy control module, the delivery recipient of an approaching delivery after receiving the item being shipped at the intermediate loading location and notifying the delivery recipient of an estimated time of arrival at the destination location may be performed once the modular autonomous bot apparatus assembly is within a threshold notification range of the destination location identified by the destination information.

This further embodiment of method 4400 related to fleet augmentation may also allow for changing delivery details once item is picked up and the delivery recipient is notified. For example, this further embodiment of method 4400 may also include the steps of receiving, by the modular mobile autonomy control module, a delivery change notification in response to notifying the delivery recipient of the approaching delivery at the destination location; and altering, by the modular mobile autonomy control module, the intermediate delivery route according to the delivery change notification. Such an altered intermediate delivery route results in a modified delivery (e.g., an altered delivery time or delivery location) for the item being shipped according to the delivery change notification. In more detail, such a modified delivery may be implemented with the modular mobile autonomy control module causing the modular mobility base to move on a modified return route to a holding location (e.g., the intermediate holding location) before moving to an altered destination location for delivery of the item being shipped at an altered time for delivery at the altered destination location.

This further embodiment of method 4400 related to fleet augmentation may also have monitored unloading to make sure the correct item is unloaded from within the modular cargo storage system of the exemplary MALVT bot apparatus system. For example, this further embodiment of method 4400 may also include verifying, by the modular mobile autonomy control module, an unload status of the item being shipped using one or more sensors (e.g, sensors 3130) on the modular mobile autonomy control module that monitors a payload area of the modular cargo storage system. Such an unload status may reflect an identifier of the item being shipped that has been removed from within the modular cargo storage system.

In another example, this further embodiment of method 4400 may include the step of verifying, by the modular mobile autonomy control module, that an object removed from within the payload area of the modular cargo storage system using the one or more sensors is the item being shipped and authorized to be removed at the destination location according to the dispatched logistics operation. Method 4400 may then also include transmitting a warning message by the modular mobile autonomy control module to the dispatch server when the object removed from within the payload area of the modular cargo storage system using the one or more sensors is not the item being shipped and authorized to be removed at the destination location according to the dispatched logistics operation, where the warning message indicates an unauthorized unloading of the modular cargo storage system and includes sensor data from the payload monitoring sensors. Method 4400 may also include generating an audio warning message by the modular mobile autonomy control module when the object removed from within the payload area of the modular cargo storage system using the one or more sensors is not the item authorized to be removed at the destination location according to the dispatched logistics operation. Such an audio warning message may indicate an unauthorized unloading of the modular cargo storage system and requesting replacement of the object removed.

Express Pickup

In another embodiment, a customer may request an express pickup of an item or object for delivery elsewhere via, for example, an online or retailer assisted order where the customer inputs dimension sizes and weight for the item to be picked up. If such information on size and weight allows, a customer may be offered a pick up option by an exemplary MALVT bot apparatus with available pickup windows. In general, an embodiment may dispatch the exemplary MALVT bot apparatus assembly to meet the customer at a particular address input by the customer or at the customer's location (e.g., a location determined by GPS, input, TRON, etc.). The customer may then authenticate pickup via an app operating on the recipient's user access device, via TRON node interactions for association-based authenticated delivery, or via interaction with the display screen, sensors, or user input panel on the MAM component. Once authenticated, the exemplary MALVT bot apparatus selectively opens to receive the object being picked up. The customer then places the item/object in the CSS component of the exemplary MALVT bot apparatus, and closes door (or interacts with the MAM component to have the door of the CSS component closed). The exemplary MALVT bot apparatus may scan or communicate with the item/object to ensure that the object is inside. Thereafter, the exemplary MALVT bot apparatus assembly with the item/object loaded inside returns to drop off the item/object with the retailer, business, or next courier involved with transporting the item/object.

Figure 45:
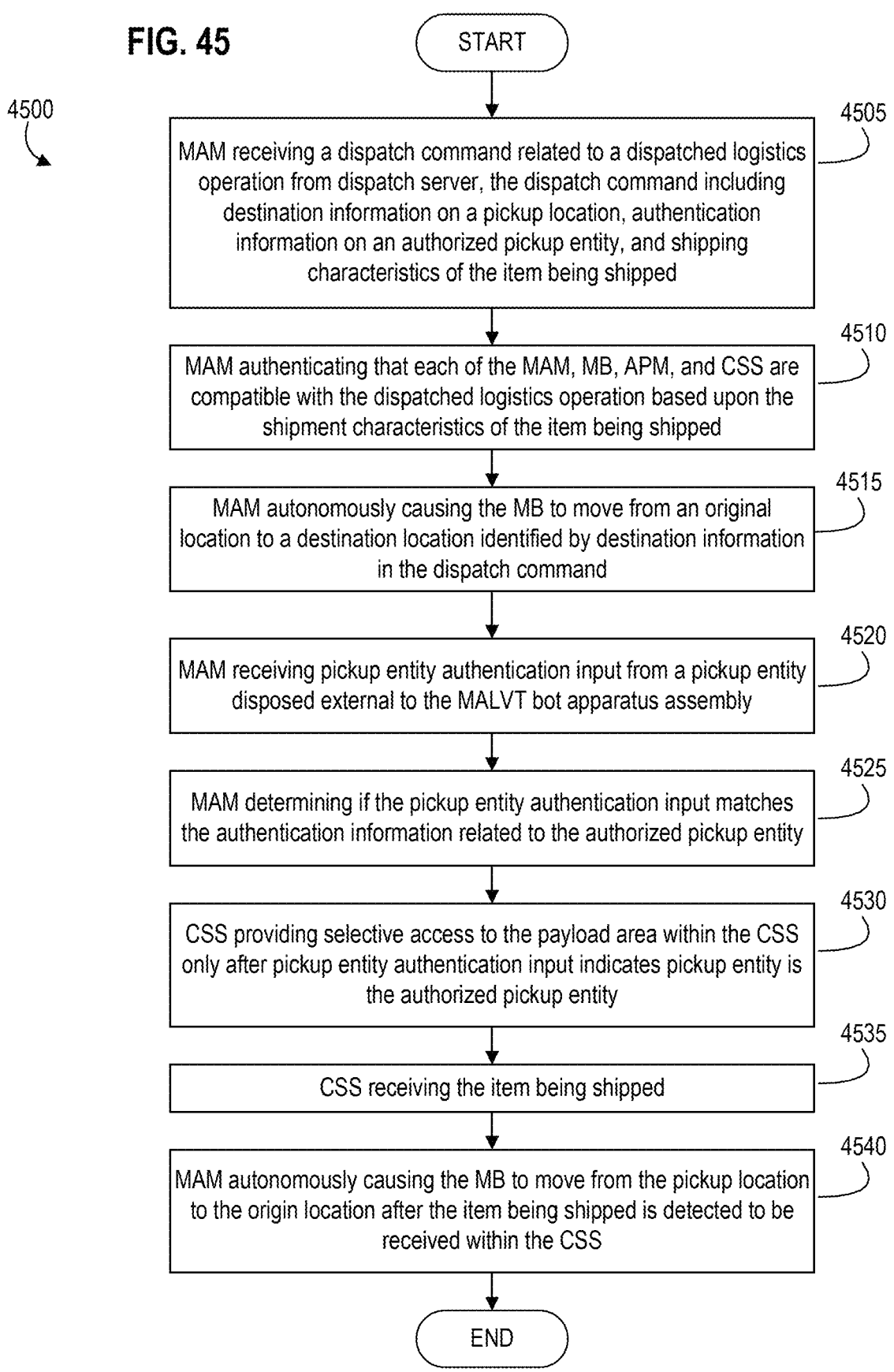
FIG. 45 is a flow diagram of another embodiment of an exemplary method for performing a dispatched logistics operation involving pickup of an item being shipped using a modular autonomous bot apparatus assembly (MALVT bot apparatus assembly) and a dispatch server in accordance with an embodiment of the invention.

FIG. 45 is a flow diagram of another embodiment of an exemplary method 4500 for performing a dispatched logistics operation involving pickup of an item being shipped using a modular autonomous bot apparatus assembly (MALVT bot apparatus assembly) and a dispatch server in accordance with an embodiment of the invention. Like that of method 4400, exemplary method 4500 makes use, for example, of exemplary MALVT bot apparatus assembly 1700 and exemplary dispatch server 4205. Exemplary MALVT bot apparatus assembly 1700, as part of method 4500, is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 4500.

Referring now to FIG. 45, exemplary method 4500 begins at step 4505 with the modular mobile autonomy control module receiving a dispatch command related to the dispatched logistics operation from the dispatch server. The dispatch command received includes at least destination information related to a pickup location (e.g., a mobile location of an external mobile wireless node operated by the authorized pickup entity), authentication information related to an authorized pickup entity, and shipment characteristics of the item being shipped and may also include identifier information of the external mobile wireless node operated by the authorized pickup entity as part of the authentication information. In more detail, the dispatch command sent by the dispatch server may be initiated based upon a dispatch request received by the dispatch server. Such a dispatch request may be sent by the pickup entity related to the dispatched logistics operation.

At step 4510, method 4500 proceeds with the modular mobile autonomy control module authenticating that each of the modular mobile autonomy control module, the modular mobility base, the modular auxiliary power module, and the modular cargo storage system are compatible with the dispatched logistics operation based upon the shipment characteristics of the item being shipped as indicated in the dispatch command. Exemplary ways of authenticating that each of the components of the exemplary MALVT bot apparatus assembly in step 4510 are authenticated may be accomplished as described above, for example as described relative to step 4410 or 4610 and their respective variations.

At step 4515, method 4500 has the modular mobile autonomy control module autonomously causing the modular mobility base to move from an origin location on a route to the pickup location identified by the destination information.

At step 4520, method 4500 proceeds with receiving pickup entity authentication input by the modular mobile autonomy control module from a pickup entity disposed external to the modular autonomous bot apparatus assembly. Exemplary ways of receiving authentication input from an entity external to the exemplary MALVT bot apparatus assembly used in method 4500 in step 4520 may be accomplished with similar manners of receiving authentication input as described above (e.g., ways of receiving delivery recipient authentication input as described relative to step 4425 and its variations).

At step 4525, method 4500 proceeds with determining if the pickup entity authentication input correlates to the authentication information related to the authorized pickup entity according to the dispatch command. For example, exemplary MAM 1725 of exemplary MALVT bot apparatus assembly 1700 may receive the pickup entity authentication input (e.g., via user input panel, sensors, wireless communications with a wireless node external to the assembly 1700) and compare the pickup entity authentication input to the authentication information provided in the dispatch command sent to MAM 1725. If the received pickup entity authentication input matches or otherwise correlates to the authentication information in the dispatch command, MAM 1725 determines that the entity providing the pickup entity authentication input is the authorized pickup entity.

At step 4530, method 4500 proceeds with the modular cargo storage system providing selective access to a payload area within the modular cargo storage system only after the pickup entity authentication input received correlates to the authentication information related to the authorized pickup entity according to the dispatch command, thus ensuring a level of secured access to and use of the exemplary MALVT bot apparatus when deployed for pickup as part of method 4500.

With access to the payload area of the modular cargo storage system achieved, method 4500 proceeds at step 4535 with receiving the item being shipped. In more detail, step 4535 may receive the item by, for example, having the modular mobile autonomy control module monitoring a payload area within the modular cargo storage system using at least one sensor on at least one of the modular mobile autonomy control module and the modular cargo storage system, and detecting when the item is received within the modular cargo storage system based upon sensor data from the sensor. For example, exemplary MAM 1725 may use its payload monitoring sensors (e.g., sensors 3130) to detect when the item is received within the CSS 1720. In another example, an exemplary CSS 1720 may have its own payload monitoring sensors operatively coupled to autonomous control system 3100 in MAM 1725 through bus 2250, and such CSS sensors may detect when the item is received within the CSS 1720. A further example may have the CSS 1720 partitioned with separators 3608 into different compartments, where each compartment may have dedicated payload monitoring sensors that monitor what is in the respective compartment within CSS 1720 so that those different compartmental payload monitoring sensors may provide sensor data to MAM 1725 through bus 2250 for monitoring when an item is received within a particular compartment of CSS 1720.

In a further implementation of step 4535, the step of receiving the item being shipped may be implemented with the modular mobile autonomy control module monitoring the payload area within the modular cargo storage system for a wireless node associated with the item being shipped, and detecting when the item being shipped is received within the modular cargo storage system when the wireless node associated with the item being shipped is determined to be located within the payload area within the modular cargo storage system based upon one or more detected signals broadcast by the wireless node associated with the item being shipped. The detected signal may involve or initiate a node-to-node association of the wireless node associated with the item and the autonomous controller on the modular mobile autonomy control module (e.g., autonomous control system 3100 on MAM 1725), or may be used to locate the wireless node associated with the item and determine the item is within the CSS. For example, the detected signal from the item's wireless node (e.g., an ID node) may be sensed by the controller of the MAM 1725 using TRON node-locating techniques as described herein so as to allow MAM 1725 to detect the location of a item's wireless nose and, as a result, detect when the item is received within the CSS 1720 for transport within the exemplary MALVT bot apparatus assembly 1700.

Receiving the item at the pickup location as part of step 4535 may involve personnel at the pickup location, who may be prompted via displays, sounds, or messages to their wireless nodes to place the item into the modular cargo storage system of the exemplary MALVT bot apparatus assembly 1700. However, step 4535 may be implemented without personnel present at the pickup location via use of articulating arms (e.g., arm 4325) or other object manipulation systems described above that may be deployed by exemplary modular components of the assembly (e.g., moving belt surfaces 2080*a*, 2080*b*, sweeping arms 2085, 2700, grabbing arms 2090, 2710) as part of receiving the item being picked up. Additionally, exemplary MALVT bot apparatus assembly 1700 may interact with a logistics receptacle (such as a drop box or parcel locker, similar to how assembly 1700 may engage and remove documents for shredding from a shred bin container), via manual manipulation of handles, keypads, or other access points of the logistics receptacle as a type of pathway obstacle to be cleared by the exemplary MALVT bot apparatus assembly 1700 so that the item may be received into the CSS 1720 of the exemplary MALVT bot apparatus assembly 1700. As such, step 4535 of method 4500 may involve clearing this type of pathway obstacle (e.g., a logistics receptacle, such as a drop-box or parcel locker) to gain unrestricted access to such a logistics receptacle without help from personnel at the pickup location. In more detail, step 4535 may be implemented by deploying an articulating arm disposed on the modular autonomous bot apparatus assembly (e.g., arm 4325) and sensors (e.g., proximity and vision sensors) disposed on at least one of the modular mobility base and the modular mobile autonomy control module to engage the item being shipped and place the item being shipped within the modular cargo storage system. More particularly, an embodiment of step 4535 may involve deploying an articulating arm disposed on the modular autonomous bot apparatus assembly and using proximity and vision sensors disposed on at least one of the modular mobility base and the modular mobile autonomy control module to engage a logistics receptacle currently maintaining the item being shipped; guiding, by the modular mobile autonomy control module, the articulating arm to a closable access point (e.g., a door, lid, access opening, and the like) on the logistics receptacle using one or more of the proximity and vision sensors disposed on at least one of the modular mobility base and the modular mobile autonomy control module; engaging, by the articulating arm, the closable access point on the container to enabled access to within the logistics receptacle; engaging, by the articulating arm, the item being shipped while maintained within the logistics receptacle; and moving, by the articulating arm, the item being shipped from within the logistics receptacle to a position within the modular cargo storage system.

At step 4540, method 4500 proceeds with the modular mobile autonomy control module autonomously causing the modular mobility base to move from the pickup location on a return route to the origin location after the item being shipped is detected to be received within the modular cargo storage system. In a more detailed embodiment, step 4540 may be implemented with the modular mobile autonomy control module autonomously causing the modular mobility base to move from the pickup location to a secondary pickup location for an additional item being shipped according to a secondary dispatched logistics operation identified in a subsequent dispatch commend received by the modular mobile autonomy control module and from the dispatch server. The additional item may be received by the modular cargo storage system, and then the modular mobile autonomy control module may responsively and autonomously cause the modular mobility base to move from the secondary pickup location to the origin location after the additional item being shipped is detected to be received within the modular cargo storage system.

Inventory Management

In another embodiment, a business establishment may have multiple locations within a trade area that is small enough to fit within the range of an exemplary MALVT bot apparatus. Such an embodiment may have the business establishment sending an exemplary MALVT bot apparatus between locations to pick up and drop off inventory in order to balance inventory or to eliminate a temporary stock outage. For example, an embodiment may use an inventory "hub" location" as a way of avoiding vendor charges for small order penalties and/or to avoid over ordering/overstocking. The inventory hub location of the business establishment's location may order a quantity of product (generally referred to as an inventory item) above a minimum order penalty and for a maximum discount/buying power. Upon receipt of the order, the hub location would have the business establishment split the received order into smaller orders (which may include one or more of the inventory items), dispatch an exemplary MALVT bot apparatus to each "spoke" store location leveraging TRON, GPS, or mapping for directions with their small quantity for stocking. The recipient at the remote business location may then authenticate delivery via an app operating on the recipient's user access device, via TRON node interactions for association-based authenticated delivery, or via interaction with the display screen on the MAM component. The exemplary MALVT bot apparatus would then return to base at the hub location or be placed, for example, into a ready for dispatch group at the spoke location. Real-time small batch restocking can help business establishments operate on a Just-In-Time inventory system. The display screen on the exemplary MALVT bot apparatus' MAM component may also be leveraged as informational or advertising space for customers.

Figure 47A:
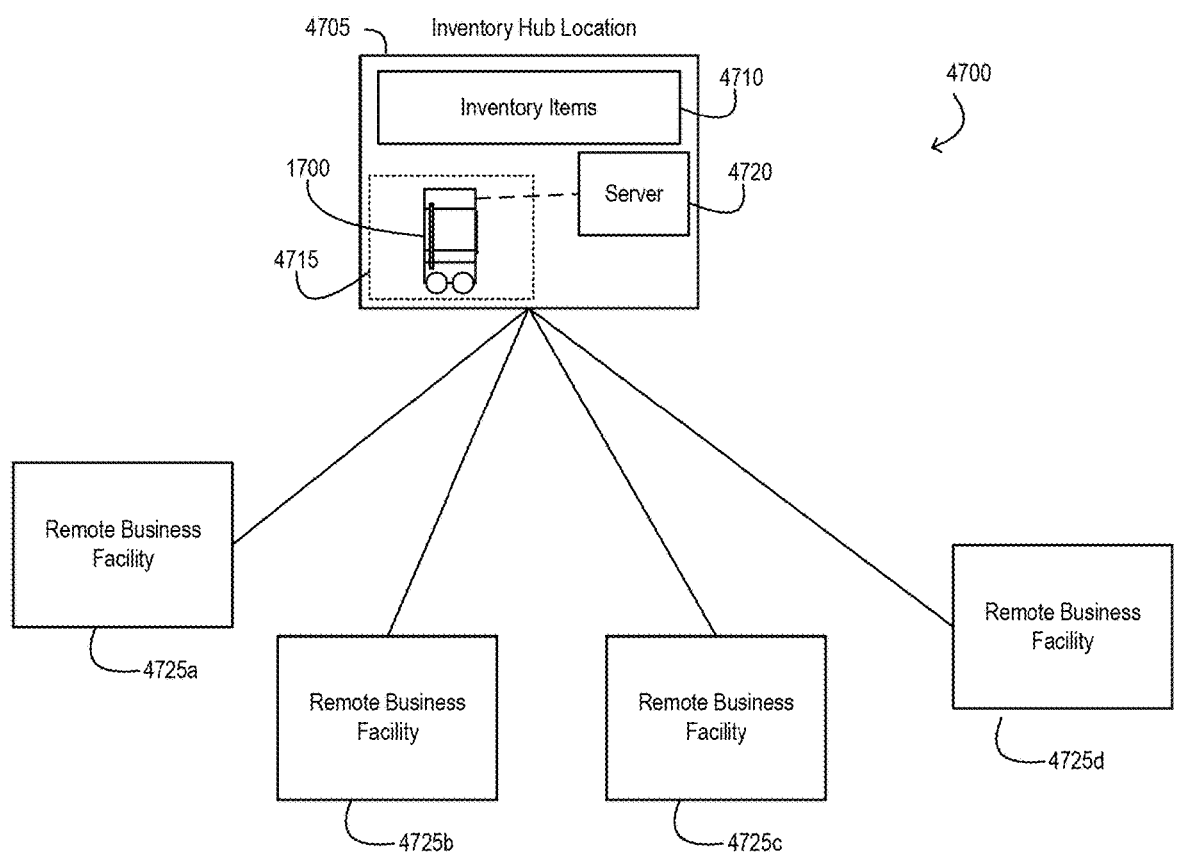
FIG. 47A-47B are diagrams of an exemplary system involving an exemplary modular autonomous logistics transport vehicle apparatus (MALVT bot apparatus) the performs an inventory management related dispatched logistics operation related to an inventory item at an inventory hub location and one of multiple remote business locations in accordance with an embodiment of the invention.

FIGS. 47A-50B describe different embodiments related to inventory items that may be transported as part of a dispatched logistics operation on an exemplary MALVT bot apparatus assembly. In more detail, FIG. 47A-47B are diagrams of an exemplary system involving an exemplary modular autonomous logistics transport vehicle apparatus (MALVT bot apparatus) the performs an inventory management related dispatched logistics operation related to an inventory item at an inventory hub location and one of multiple remote business locations in accordance with an embodiment of the invention. Referring now to FIG. 47B, an exemplary group of business locations 4700 are shown and include exemplary inventory hub location 4705 along with remote business facilities 4725a-4725d. At exemplary inventory hub location 4705, a server 4720 may be operating as a dispatch server for sending dispatch commands to exemplary MALVT bot apparatus assemblies (such as assembly 1700 located in bot storage location 4715) and/or an inventory management server that is updated with inventory level reports from the different remote business facilities 4725a-4725d. Inventory hub location 4705 may also temporarily house and maintain multiple inventory items 4710 that have been ordered and that may be transported to different ones of remote business facilities 4725a. Such exemplary inventory items 4710 may be stored in one or more storage rooms at the hub location 4705, in a warehouse, on one or more shelving systems, in boxes, and the like. Exemplary MALVT bot apparatus assemblies (such as assembly 1700), the modular components that may be assembled into one or more exemplary MALVT bot apparatus assemblies, as well as dispensing systems for the same may be kept, maintained, repaired, charged, and otherwise located in parts of bot storage location 4715. Such exemplary MALVT bot apparatus assemblies may be built on-demand (e.g., in response to a dispatch request where server 4720 may operate as an assembly server) or may be maintained in a ready configuration of assembly 1700 that may be quickly dispatched by server 4720 with one or more inventory items 4710. For example, once the MAM unit in exemplary MALVT bot apparatus assembly 1700 has received an inventory dispatch command from server 4720, exemplary MALVT bot apparatus assembly 1700 may receive the particular inventory item 4710a and autonomously move from the inventory hub location 4705 to distribute the inventory item 4710a to one of the remote business locations, such as remote business facility 4725a as shown in FIG. 47B.

Figure 48A:
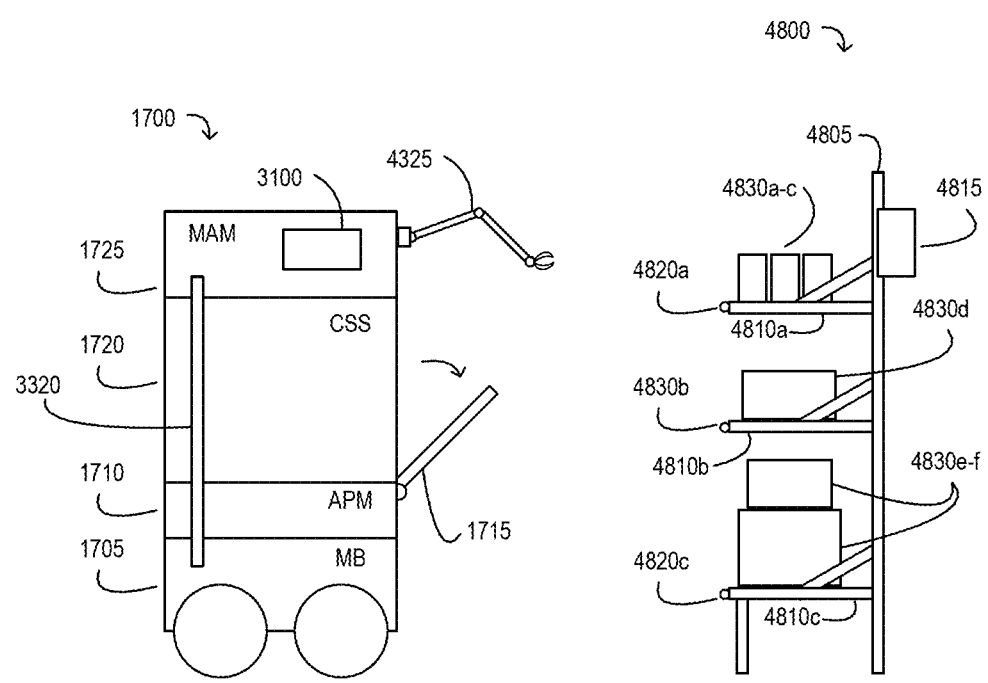
FIGS. 48A-48D are diagrams of an exemplary modular autonomous logistics transport vehicle apparatus (MALVT bot apparatus) interfacing and interacting with an exemplary node-enabled shelving system to pickup/drop-off an inventory item in accordance with an embodiment of the invention.

As part of picking up or dropping off an inventory item, one or more exemplary articulating arms 4325 may be deployed on exemplary MALVT bot apparatus assembly (or other object manipulation systems as described in more detail above) to assist with getting the inventory item from outside the bot assembly to being placed within the payload area within the CSS 1720 of exemplary MALVT bot apparatus assembly 1700. In some embodiments, the inventory items 4710 may be maintained at their respective location (e.g., at the inventory hub location 4705, at one of the remove business facilities 4725a-d) on node-enabled shelving systems that further assist with managing where a particular inventory item may be stored on a shelving system as well as facilitating enhanced pickup from and delivery of such an inventory item to an appropriate place on the node-enabled shelving system. FIG. 48A-48D are diagrams of an exemplary modular autonomous logistics transport vehicle apparatus (MALVT bot apparatus 1700) interfacing and interacting with an exemplary node-enabled shelving system 4800 to pickup/drop-off an inventory item in accordance with an embodiment of the invention. Referring now to FIG. 48A, exemplary MALVT bot apparatus assembly 1700 is shown approaching an exemplary node-enabled shelving system 4800 within an environment, for example, of the inventory hub location 4705 where exemplary inventory items 4830a-4830f (e.g., part of inventory items 4710 that may have been ordered and shipped to the inventory hub location 4705) are kept.

Figure 48B:
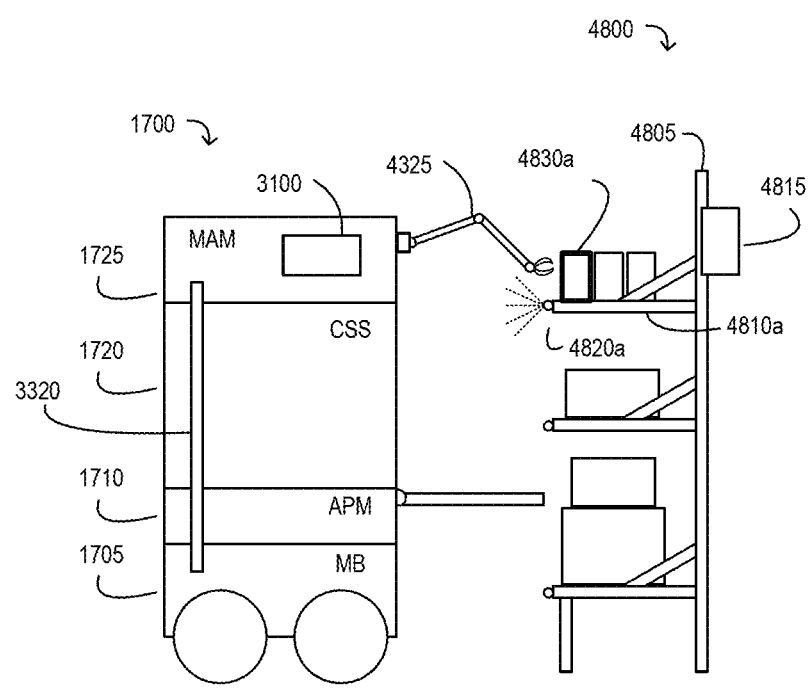
Figure 48C:
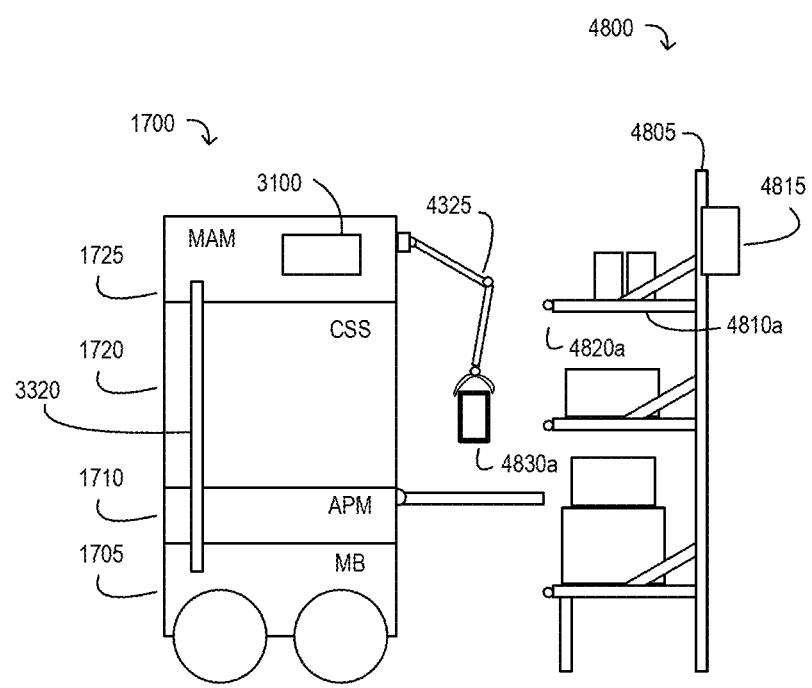
Figure 48D:
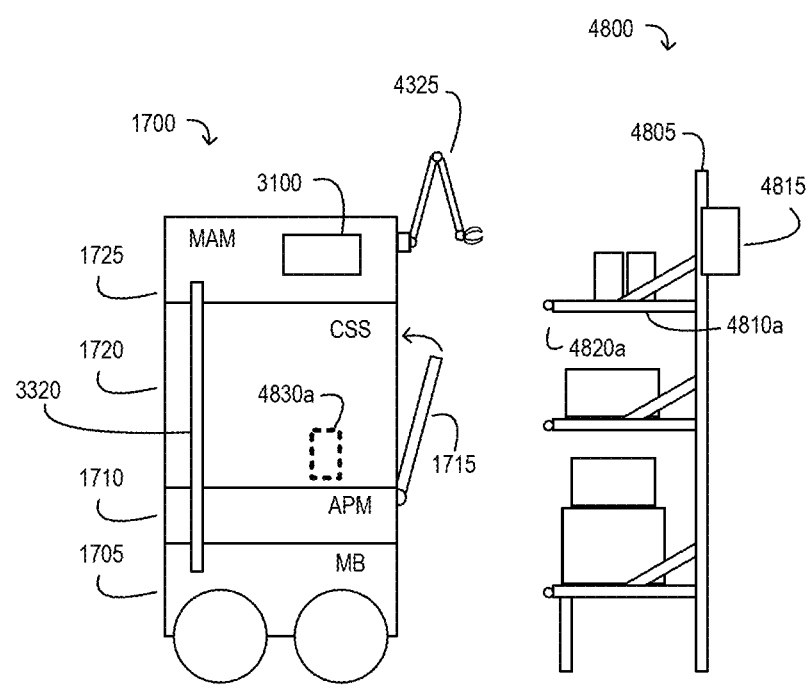

In general, an exemplary embodiment of node-enabled shelving system 4800 shown in FIGS. 48A-48D has a frame 4805 (e.g., stationary or mobile) with multiple shelves 4810a-4810c where lights 4820a-4820c are disposed at the exposed edge of the respective shelves. The lights 4820a-4820c may be activated by a shelf node 4815 (e.g., a master node or ID node assembled with the frame or otherwise attached to the system 4800). An embodiment of the shelf node 4815 communicates with at least the MAM 1725 within exemplary MALVT bot apparatus assembly 1700 and, in some examples, may also communicate with server 4720 with inventory related information. The shelf node 4815, in general, may operate to facilitate inventory management with interactive instructions via activated lighting and/or wireless communications to MAM 1725 on item placement/retrieval to and from one of the shelving system's shelves. In such a general embodiment, the shelf node 4815 may interact with the autonomous control system 3100 within a MAM 1725 on exemplary MALVT bot apparatus assembly 1700 to receive identification information related to a particular inventory item or items to be picked up (or delivered) and the shelf node 3815 may activate particular ones of the shelf edge lights 4820a-4820c to provide a visual indication of shelf location for the particular inventory item (e.g., a refined loading location) and/or where the articulated arm 4325 on exemplary MALVT bot apparatus assembly 1700 may be deployed to engage and move the particular inventory item. As shown in FIG. 48A, exemplary MALVT bot apparatus assembly 1700 may have arrived at the relevant location where the inventory item is maintained on the exemplary node-enabled shelving system 4800. Exemplary MALVT bot apparatus assembly 1700 may actuate its cargo door 1715 to open, and deploy its articulating arm 4325 and/or other object manipulation systems (e.g., as described above relative to structure that may be deployed on APM 1710 and/or CSS 1720 as well as the actuated/adjustable systems that can tilt/lift MB 1705 to facilitate sliding of an object from assembly 1700). In FIG. 48B, exemplary MALVT bot apparatus assembly 1700 has notified shelf node 4815 on exemplary node-enabled shelving system 4800 about the approaching pickup of inventory item 4830a, and has autonomously moved closer to exemplary node-enabled shelving system 4800 to pick up inventory item 4830a. Exemplary MALVT bot apparatus assembly 1700 detects light 4820a, as activated by shelf node 4815, and guides articulating arm 4325 towards inventory item 4380a on shelf 4810a associated with activated light 4820a to allow articulating arm 4325, using sensors on exemplary MALVT bot apparatus assembly 1700, to engage inventory item 4830a. As shown in FIG. 48C, articulating arm 4325 has engaged inventory item 4830a and moved it off shelf 4810a in order to place item 4830a within CSS 1720 (e.g., via direct placement of the item within the payload area of CSS 1720, via intermediate placement of the item on movable belt surfaces on cargo door 1715 or movable belt surfaces on the base adapter plate of APM 1710, or by intermediate placement that allows other object manipulation systems deployed as part of AMP 1710 and/or CSS 1720 to further move the item into the payload area of CSS 1720). In this way, the inventory item 4830a is placed within the payload area of CSS 1720 of exemplary MALVT bot apparatus assembly 1700, as shown in FIG. 48D, articulated arm 4325 may be moved to a transit/storage position, and cargo door 1715 is actuated to close so that exemplary MALVT bot apparatus assembly 1700 may move to its destination location for drop-off as indicated in the inventory dispatch command received by the autonomous control system 3100 in MAM 1725 of exemplary MALVT bot apparatus assembly 1700.

Those skilled in the art will appreciate that while FIGS. 48A-48D show an example where an exemplary inventory item 4380a is being picked up and placed within the CSS 1720 for transport within the exemplary MALVT bot apparatus assembly 1700 to another location (which may have a similar node-enabled shelving system to receive the item), similar principles may be applied to an example where the exemplary item is being removed from within the CSS using object manipulation systems described herein (including articulating arm 4325) and placed on an identified shelf (e.g., with guidance from an activated shelf light) of an exemplary node-enabled shelving system 4800 or placed on a conventional shelving system that does not provide interactive capability with the exemplary MALVT bot apparatus assembly 1700 to received pre-arrival notifications and responsively indicate where to place the transported inventory item.

Figure 49:
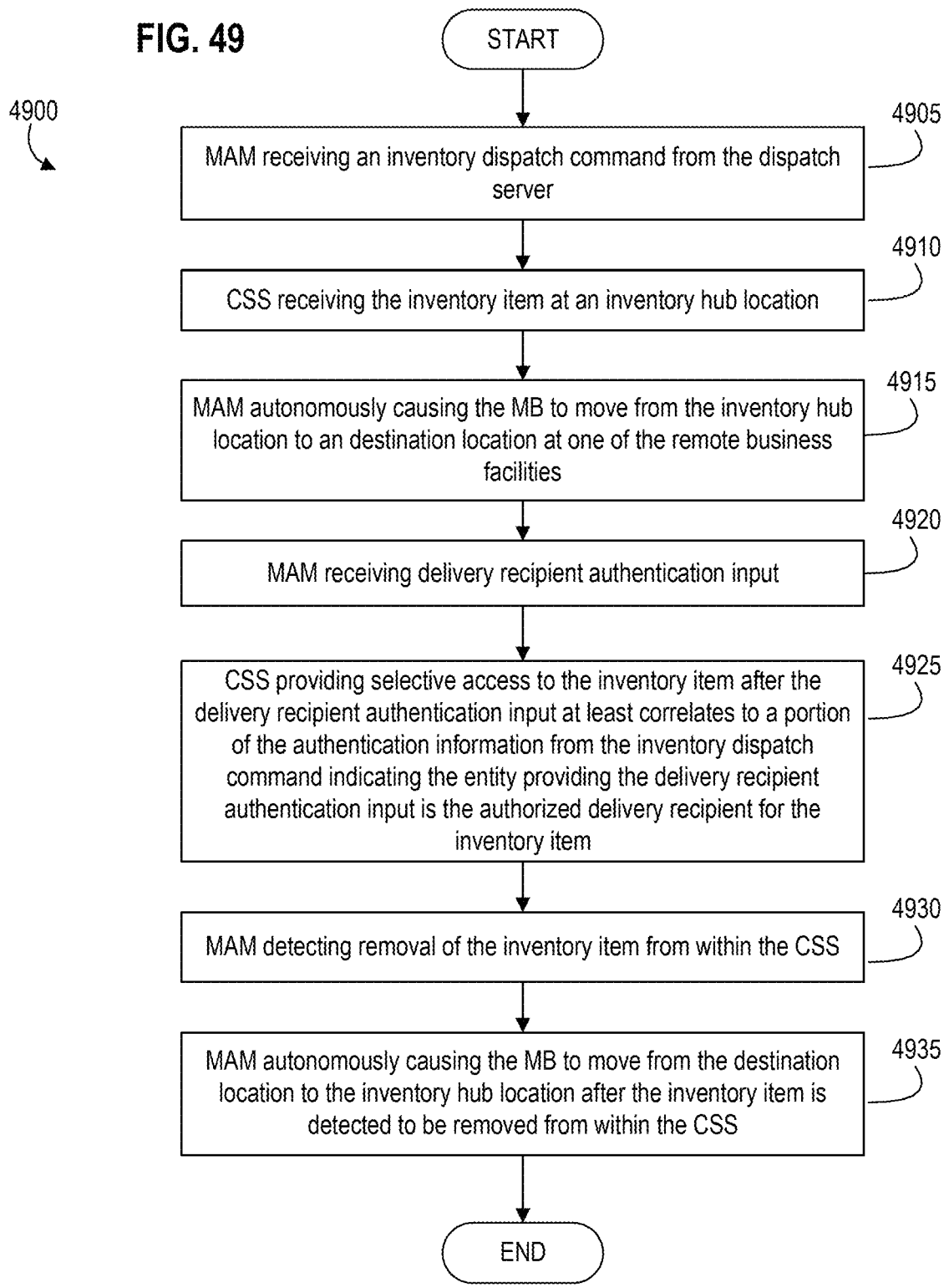
FIG. 49 is a flow diagram of an embodiment of an exemplary method for performing an inventory management related dispatched logistics operation involving an inventory item using a modular autonomous bot apparatus assembly (MALVT bot apparatus assembly) and a dispatch server in accordance with an embodiment of the invention.

FIG. 49 is a flow diagram of an embodiment of an exemplary method for performing an inventory management related dispatched logistics operation involving an inventory item using a modular autonomous bot apparatus assembly (MALVT bot apparatus assembly) and a dispatch server in accordance with an embodiment of the invention. Such a method 4900 may be used to deliver one or more inventory items (e.g., as a portion of an order received at the inventory hub location) to remote business facilities. In more detail, an embodiment of such a method 4900 may use an embodiment of exemplary MALVT bot apparatus assembly 1700 (as assembled or after an on-demand assembly) and a dispatch server (e.g., server 4720). Exemplary modular autonomous bot apparatus assembly used (e.g., assembly 1700) as part of method 4900 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 4900.

Referring now to FIG. 49, exemplary method 4900 begins at step 4905 with (a) the modular mobile autonomy control module receiving an inventory dispatch command from the dispatch server. The dispatched inventory operation involves an inventory hub location (e.g., inventory hub location 4705) and at least one of multiple remote business facilities external to the inventory hub location (e.g., remote business facilities 4725a-4725d). In more detail, the received inventory dispatch command in step (a) includes at least destination information and authentication information related to the dispatched inventory operation for the inventory item. Additionally, the inventory dispatch command assigns the inventory item for transport to the modular autonomous bot apparatus assembly from the contents of an inventory order received at the inventory hub location (e.g., out of an order for inventory items that are maintained at least as part of exemplary inventory items 4710 at inventory hub location 4705).

At step 4910, method 4900 proceeds with step (b) having the modular cargo storage system receiving the inventory item for transport at the inventory hub location.

Figure 47B:
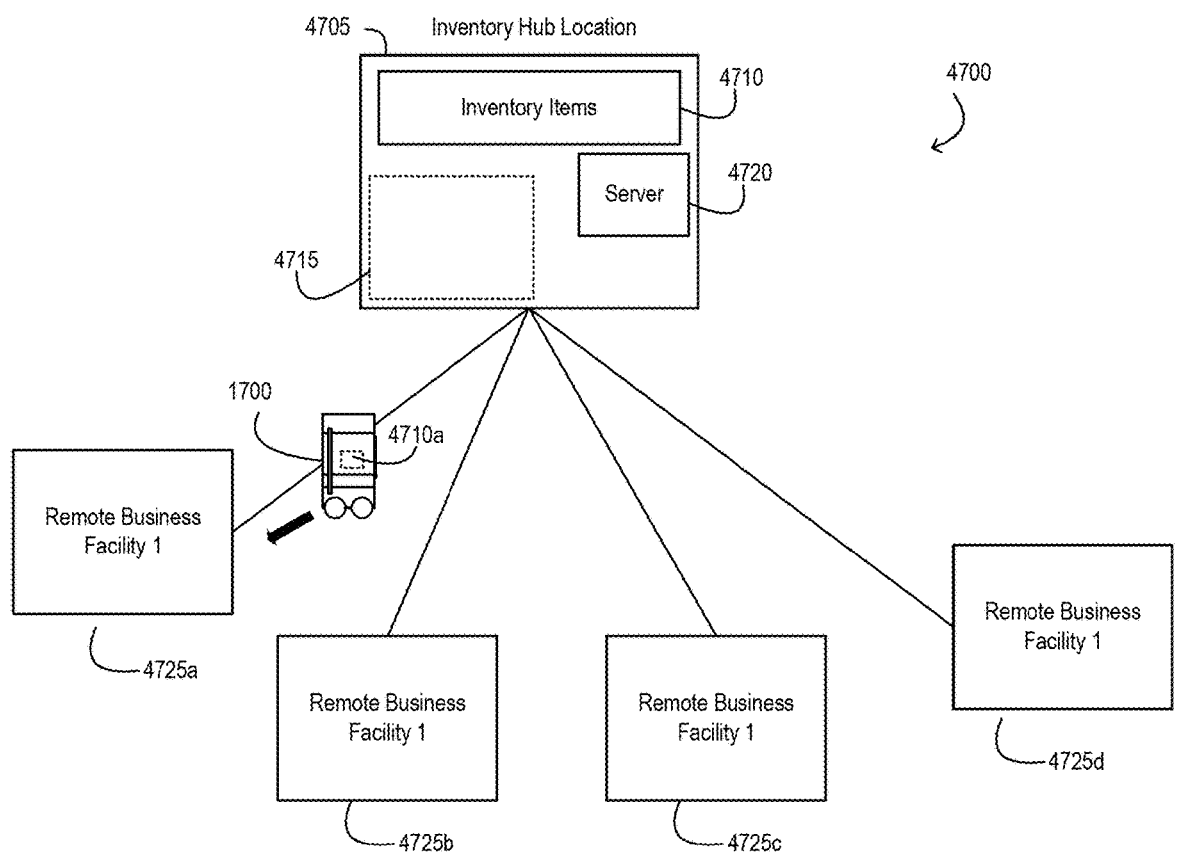

At step 4915, method 4900 proceeds with step (c) with the modular mobile autonomy control module autonomously causing the modular mobility base to move from the inventory hub location on a route outside of the inventory hub location to one of the remote business facilities as a destination location identified by the destination information for the dispatched inventory operation. For example, as shown in FIG. 47B, exemplary MALVT bot apparatus assembly 1700 moves from the inventory hub location 4705 to remote business facility 4725a.

At step 4920, method 4900 proceeds with step (d) receiving delivery recipient authentication input by the modular mobile autonomy control module from a delivery recipient disposed external to the modular autonomous bot apparatus assembly and at the destination location. If the delivery recipient providing such input is the authorized delivery recipient, the delivery recipient authentication input at least correlates to a portion of the authentication information related to the dispatched inventory operation. Method 4900 then moves to step 4925, where step (e) has the modular cargo storage system providing selective access to the inventory item for transport within the modular cargo storage system after the delivery recipient authentication input received at least correlates to the portion of the authentication information indicating the delivery recipient providing the delivery recipient authentication input is the authorized delivery recipient.

At step 4930, method 4900 proceeds with step (f) having the modular mobile autonomy control module detecting removal of the inventory item for transport from within the modular cargo storage system. For example, this may involve using payload monitoring sensors on the MAM 1725 and/or sensors disposed on interior surfaces of the CSS 1720 and monitoring by the autonomous control system 3100 in MAM 1725 during the removal process at the destination location (e.g., remote business facility 4725a). Then, at step 4935, method 4900 proceeds with step (g) having the modular mobile autonomy control module autonomously causing the modular mobility base to move from the destination location (e.g., remote business facility 4725a) on a return route to the inventory hub location after the inventory item for transport is detected to be removed from within the modular cargo storage system.

Further embodiments of exemplary method 4900 may have the MAM in the exemplary MALVT bot apparatus assembly determine if the components in the assembly are compatible with the dispatched inventory operation. For example, a further embodiment of method 4900 may include the step of authenticating, by the modular mobile autonomy control module, that each of the modular mobile autonomy control module, the modular mobility base, the modular auxiliary power module, and the modular cargo storage system are compatible with the dispatched inventory operation prior to receiving the inventory item for transport. As such, the modular cargo storage system compatible with the dispatched logistics operation may be one of different sized modular cargo storage systems, and where that one is compatible with a size parameter for the inventory item for transport as part of the dispatched inventory operation. Similarly, the modular mobile autonomy control module compatible with the dispatched logistics operation may be one of different sized modular mobile autonomy control modules, and where that one is compatible with the one of the different sized modular cargo storage systems compatible with the size parameter for the inventory item for transport as part of the dispatched inventory operation.

Further embodiments of method 4900 may also involve returning to an assembly area (e.g., a bot storage location) at the inventor hub location to change out one of the components as a result of the authentication task related to compatibility with the dispatched inventory operation. For example, method 4900 may also include the step of autonomously causing, by the modular mobile autonomy control module, the mobility base to move to an assembly area at the inventory hub location when one of the modular mobile autonomy control module, the modular mobility base, the modular auxiliary power module, or the modular cargo storage system are found to be not compatible with the dispatched inventory operation during the authenticating step. In a further example, method 4900 may also have the modular mobile autonomy control module transmitting a replacement request to the dispatch server (e.g. server 4720), which causes the dispatch server to assign another modular autonomous bot apparatus assembly to the dispatched inventory operation to operate in place of the modular autonomous bot apparatus assembly. Alternatively, method 4900 may have the modular mobile autonomy control module transmitting a module replacement request to the dispatch server. Such a module replacement request instructs the dispatch server to cause the particular one of the modular mobile autonomy control module, the modular mobility base, the modular auxiliary power module, or the modular cargo storage system found to be not compatible with the dispatched inventory operation to be replaced.

Further embodiments of method 4900 may have the inventory order including the inventory item and additional inventory items for others. For example, in method 4900, the contents of the inventory order received at the inventory hub location may include the inventory item for transport involved with this particular dispatched inventory operation and other additional inventory items to be supplied to others of the remote business facilities. In more detail, the inventory item or items transported on the bot assembly as part of method 4900 may be a restocking supply of retail item(s) sold at that remote business facility (e.g., remote business facility 4725a where item 4710a was dropped off). In other examples, the inventory item 4710a removed from within the modular cargo storage system at the destination location (e.g., remote business facility 4725a) may be dropped off as a rebalancing supply of one or more retail items sold at that remote business facility compared to a current inventory maintained in the remote business facilities (e.g., remote business facilities 4725b-4725d) and the inventory hub location.

Still further embodiments of method 4900 may have the exemplary MALVT bot apparatus assembly involved in further dispatched operations before returning to the inventory hub location. For example, the step (g) of autonomously causing, by the modular mobile autonomy control module, the modular mobility base to move from the destination location on the return route to the inventory hub location after the inventory item for transport is detected to be removed from within the modular cargo storage system may have method 4900 having the modular mobile autonomy control module first autonomously causing the modular mobility base to hold at the destination location and wait for a subsequent inventory dispatch command from the dispatch server and related to a subsequent dispatched inventory operation involving the modular autonomous bot apparatus assembly; and then having the modular mobile autonomy control module autonomously causing the modular mobility base to return to the inventory hub location after the modular autonomous bot apparatus assembly completes the subsequent dispatched inventory operation.

As part of step (d) of method 4900 and as taught above in other embodiments, delivery recipient authentication input may be received by an exemplary MALVT bot apparatus assembly in a variety of ways. For example, as part of method 4900, the delivery recipient authentication input received by the modular mobile autonomy control module may be provided by the delivery recipient through a user input panel disposed on the modular autonomous bot apparatus coupled to the modular mobile autonomy control module (e.g., with an access code provided by the delivery recipient through the user input panel, with biometric input provided by the delivery recipient through the user input panel or other sensors on the bot apparatus, and the like). The delivery recipient authentication input may also be received by the modular mobile autonomy control module as provided by the delivery recipient through an external wireless node disposed external to the modular autonomous bot apparatus assembly (e.g., where the node is running an app that interfaces with the exemplary MALVT bot apparatus assembly). Such wireless delivery recipient authentication input received by the modular mobile autonomy control module may be an access code provided by the delivery recipient through the external wireless node, or a biometric input provided by the delivery recipient through the external wireless node.

In more detail in an example where the authentication information related to the dispatched inventory operation includes an identifier of the authorized delivery recipient for the inventory item as part of the dispatched inventory operation, an embodiment of method 4900 may have step (d) of receiving the delivery recipient authentication input involving the modular mobile autonomy control module detecting an advertising signal as the delivery recipient authentication input from an external wireless node within a predetermined range of the modular autonomous bot apparatus assembly once the modular autonomous bot apparatus assembly has arrived at the destination location identified by the destination information; and then having the modular mobile autonomy control module authenticating that the external wireless node is associated with the authorized delivery recipient for the item being shipped within the modular cargo storage system based upon the identifier of the authorized delivery recipient and identifier information within the detected advertising signal broadcast from the external wireless node.

In a similar example where the authentication information related to the dispatched inventory operation includes an identifier of the authorized delivery recipient for the inventory item as part of the dispatched inventory operation, another embodiment of method 4900 may have step (d) of receiving the delivery recipient authentication input having the modular mobile autonomy control module detecting an unprompted advertising signal from an external wireless node within a predetermined range of the modular autonomous bot apparatus assembly once the modular autonomous bot apparatus assembly has arrived at the destination location identified by the destination information; and then establishing a secure association between the external node and the modular mobile autonomy control module after detecting the unprompted advertising signal from the external wireless node. The secure association between the external node and the modular mobile autonomy control module allows secure sharing of information between the external node and the modular mobile autonomy control module and being pre-authorized by the dispatch server as it relates to the dispatched inventory operation.

Still another further embodiment of method 4900 may involve delivering smaller parts of a large inventory order with multiple exemplary MALVT bot apparatus assemblies from the inventory hub location to different remote business facilities. For example, an embodiment of method 4900 may have the inventory item being a portion from multiple inventory order items in a received inventory order. As such, method 4900 may further involve repeating steps (a)-(g) for the remaining portions from the inventory order items in the received inventory order using additional modular autonomous bot apparatus assemblies to concurrently transport each of the remaining portions from the inventory order items in the received inventory order from the inventory hub location to respective others of the remote business facilities.

As described in more detail above, the exemplary MALVT bot apparatus assembly used in method 4900 may move to the destination location while wirelessly interacting with nodes that control pathway obstacles (e.g., actuated doors, elevators, locks, and the like). For example, method 4900 step (c) of autonomously causing the modular mobility base to move from the inventory hub location to the destination location may be accomplished by having the modular mobile autonomy control module autonomously cause the modular mobility base to move from the inventory hub location to the destination location while interacting with a wireless building facility node to actuate a pathway obstacle disposed in a path on the route to the destination location. Such a pathway obstacle may, for example, include an actuated door controlled by the wireless building facility node; an actuated elevator controlled by the wireless building facility node; or an actuated lock controlled by the wireless building facility node. In more detail, when interacting with the wireless building facility node to actuate the pathway obstacle, method 4900 may have the modular mobile autonomy control module (e.g., the autonomous control system 3100, which may be implemented with a mobile master node) establishing an authorized association pairing between the modular mobile autonomy control module and the wireless building facility node based upon the authentication information related to the dispatched logistics operation; and causing the wireless building facility node to actuate the pathway obstacle after establishing the authorized association pairing between the modular mobile autonomy control module and the wireless building facility node.

In other embodiments of method 4900, moving the bot apparatus assembly may involve manually interacting with various pathway obstacles. For example, an embodiment of method 4900 may have step (c) of autonomously causing the modular mobility base to move from the inventory hub location to the destination location being implemented with the modular mobile autonomy control module autonomously causing the modular mobility base to move from the inventory hub location to the destination location while engaging a pathway obstacle disposed in a path on the route to the destination location using an articulating arm disposed on the modular autonomous bot apparatus assembly (e.g., arm 4325) and using sensors disposed on at least one of the modular mobility base and the modular mobile autonomy control module. In such an example, the pathway obstacle may, for example, be a manually actuated door, a manually actuated elevator, or a manually actuated lock. Furthermore, in such an example, engaging the pathway obstacle using the articulating arm and sensors may have the modular mobile autonomy control module guiding the articulating arm to a control element of the pathway obstacle (e.g., a handle for the pathway obstacle, a button for the pathway obstacle, a switch for the pathway obstacle, and a portion of a control panel for the pathway obstacle, and the like) using one or more of the sensors disposed on at least one of the modular mobility base and the modular mobile autonomy control module; and actuating the pathway obstacle, by the modular mobile autonomy control module, once the articulating arm engages the control element of the pathway obstacle.

A further embodiment of method 4900 may implement step (b) involving receiving the inventory item with different ways to load the item as described above using actuated structure deployed on the exemplary MALVT bot apparatus assembly, such as the actuated door (e.g., via the actuated joint on the cargo door), the actuated electro-mechanical lock on the actuated cargo door, the actuated sliding arm, the actuated grabbing arm, actuated belt surfaces).

In like manner, a further embodiment of method 4900 may implement step (e) that provides access to within the modular cargo storage system and permits removal of the inventory item with different ways to unload the item as described above using actuated structure deployed on the exemplary MALVT bot apparatus assembly, such as the actuated door (e.g., via the actuated joint on the cargo door), the actuated electro-mechanical lock on the actuated cargo door, the actuated sliding arm, the actuated grabbing arm, actuated belt surfaces).

And as described with reference to FIGS. 48A-48D, further embodiments of method 4900 interface with a node-enabled shelving system (e.g., system 4800) when loading a received inventory item as part of step (b) and when unloading the inventory item once access is provided in step (e). In such embodiments, the inventory dispatch command may include a shelving system identifier corresponding to a node-enabled shelving system at the relevant pickup and/or drop-off location. In more detail, a further embodiment of method 4900 may receive the inventory item with the modular mobile autonomy control module notifying the node-enabled shelving system of an approaching pickup of the inventory item; autonomously causing the modular mobility base to move to the node-enabled shelving system as an intermediate loading location at the inventory hub location; detecting (using a vision sensor disposed on the modular autonomous bot apparatus assembly) an activated light element on the node-enabled shelving system proximate to the inventory item as maintained on the node-enabled shelving system, where the light element was activated in response to the modular mobile autonomy control module notifying the node-enabled shelving system of the approaching pickup of the inventory item; autonomously causing the modular mobility base to move to the detected activated light element on the node-enabled shelving system as a refined intermediate loading location at the first of the remote business facilities; receiving pickup authentication input by the modular mobile autonomy control module from the node-enabled shelving system at the intermediate loading location; having the modular cargo storage system providing selective access to within the modular cargo storage system when the pickup authentication input received correlates to the shelving system identifier from the inventory dispatch command; and having the modular cargo storage system receiving the inventory item for transport from the node-enabled shelving system at the intermediate loading location. In such an example, the inventory item may be received by deploying an articulating arm disposed on the modular autonomous bot apparatus assembly and using at least the vision sensor and a proximity senor disposed on at least one of the modular mobility base and the modular mobile autonomy control module to engage the inventory item as maintained on the node-enabled shelving system and place the inventory item within the modular cargo storage system. In more detail within such an example, the inventory item may be received with the modular mobile autonomy control module guiding the articulating arm to the inventory item on the node-enabled shelving system using at least the vision sensor and a proximity senor disposed on at least one of the modular mobility base and the modular mobile autonomy control module; engaging the inventory item with the articulating arm; and moving, by the articulating arm, the inventory item to a position within the modular cargo storage system.

In an example involving delivery of the inventory item into/onto a node-enabled shelving system where the inventory dispatch command includes a shelving system identifier corresponding to a node-enabled shelving system at the destination location, an embodiment of method 4900 may have steps (d) and (e) being implemented with the modular mobile autonomy control module notifying the node-enabled shelving system at the destination location of an approaching delivery of the inventory item; autonomously causing the modular mobility base to move to the node-enabled shelving system at the destination location as an intermediate unloading location at the one of the remote business facilities; detecting (using a vision sensor disposed on the modular autonomous bot apparatus assembly) an activated light element on the node-enabled shelving system proximate to the inventory item as maintained on the node-enabled shelving system, wherein the light element was activated in response to the modular mobile autonomy control module notifying the node-enabled shelving system of the approaching delivery of the inventory item; autonomously causing the modular mobility base to move to the detected activated light element on the node-enabled shelving system as a refined intermediate loading location at the first of the remote business facilities; receiving delivery authentication input by the modular mobile autonomy control module from the node-enabled shelving system at the intermediate loading location; and providing, by the modular cargo storage system, selective access to within the modular cargo storage system when the delivery authentication input received correlates to the shelving system identifier from the inventory dispatch command.

In such an example, method 4900 may have step (f) deploying an articulating arm disposed on the modular autonomous bot apparatus assembly and using at least the vision sensor and a proximity senor disposed on at least one of the modular mobility base and the modular mobile autonomy control module to engage the inventory item as maintained within the modulator cargo storage system and place the inventory item on the node-enabled shelving system. This may involve engaging, by the articulating arm, the inventory item within the modular cargo storage system; and moving, by the articulating arm, the inventory item from within the modular cargo storage system to a position within the modular cargo storage system.

Figure 50A:
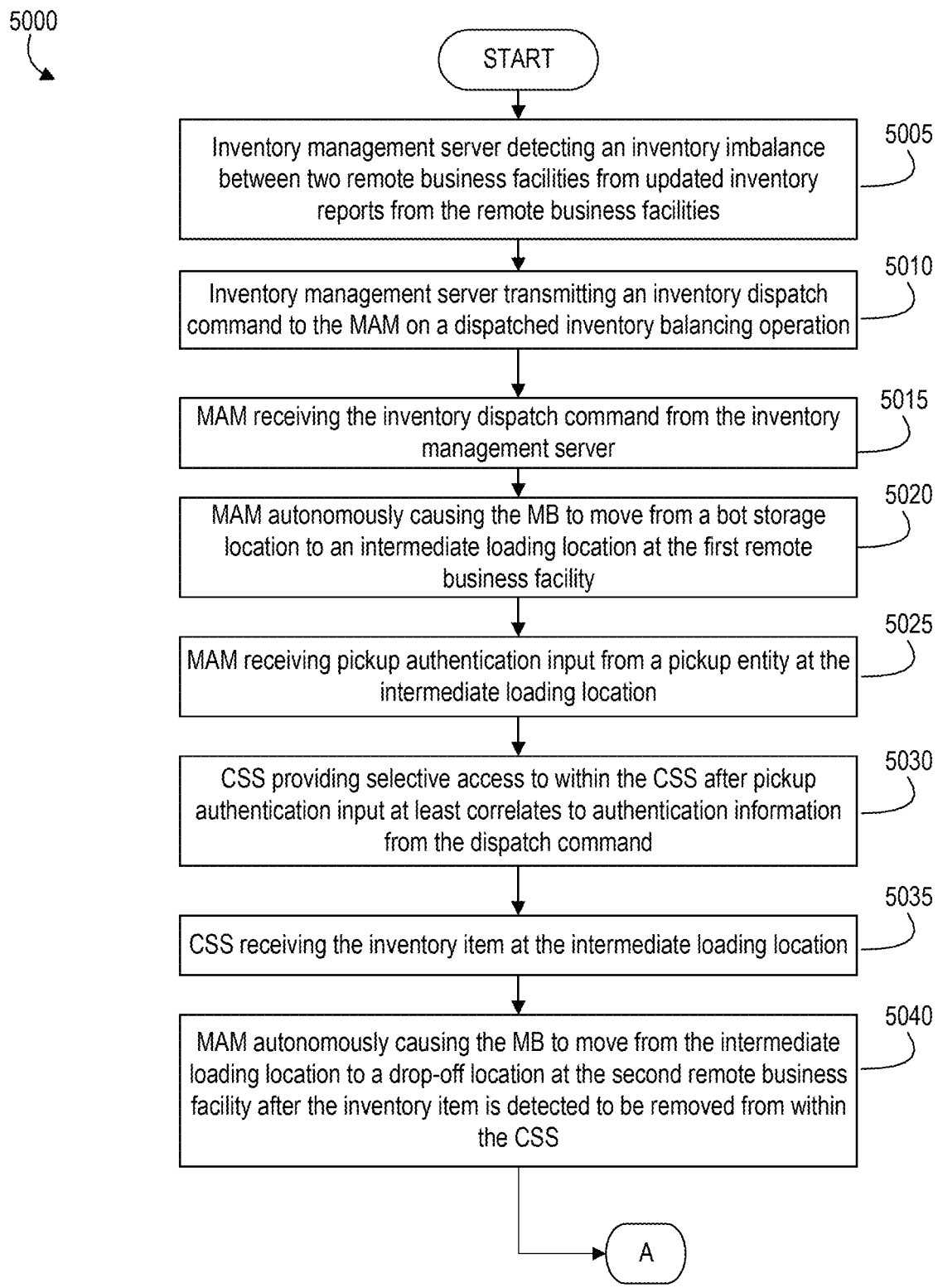

While the embodiments above described relative to FIG. 49 and exemplary method 4900 involve providing an inventory item from an inventory hub location (such as location 4705) to one of the remote retail business facilities as part of inventory management, a further embodiment may deploy an exemplary MALVT bot apparatus assembly to move inventory items between different remote business facilities. FIGS. 50A-50B are parts of a flow diagram of an alternative embodiment of an exemplary method for performing an inventory management related dispatched logistics operation between remote business facilities involving an inventory item or items and using a modular autonomous bot apparatus assembly (MALVT bot apparatus assembly) and an inventory management server in accordance with an embodiment of the invention. Such a method 5000 may be used to transfer one or more inventory items between remote business facilities as part of a dispatch inventory balancing operation as the logistics operation. In more detail, an embodiment of such a method 5000 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5000 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 5000.

Referring now to FIG. 50A, exemplary method 5000 begins at step 5005 where the inventory management server is detecting an inventory imbalance between a first of the remote business facilities and a second of the remote business facilities based upon updated inventories reported from each of the first of the remote business facilities and the second of the remote business facilities. For example, server 4720 (operating as an inventory management server) shown in FIG. 47A may detect such an inventory imbalance based upon reports sent from remote business facility 4725*a* and 4725*b*.

At step 5010, method 5000 has the inventory management server transmitting an inventory dispatch command to the modular mobile autonomy control module of an exemplary MALVT bot apparatus assembly (e.g., assembly 1700 at bot storage location 4715), where the inventory dispatch command is related to the dispatched inventory balancing operation between the first of the remote business facilities and the second of the remote business facilities.

At step 5015, method 5000 has the modular mobile autonomy control module receiving the inventory dispatch command from the inventory management server. In more detail, the inventory dispatch command includes at least destination information on an intermediate loading location at the first of the remote business facilities and a drop-off location at the second of the remote business facilities. Such an inventory dispatch command further includes authentication information related to the dispatched inventory balancing operation for the inventory item for transport.

At step 5020, method 5000 proceeds with autonomously causing, by the modular mobile autonomy control module, the modular mobility base to move from the bot storage location (e.g., location 4715) to the intermediate loading location at the first of the remote business facilities (e.g., remote business facility 4725*a*) where the inventory item may be picked up.

At step 5025, method 5000 proceeds with receiving pickup authentication input by the modular mobile autonomy control module from a pickup entity disposed external to the modular autonomous bot apparatus assembly and at the intermediate loading location. When the pickup authentication input at least correlates to a first portion of the authentication information related to the dispatched inventory balancing operation, the input indicates the pickup entity that provided the pickup authentication input is an authorized inventory item supplier for the inventory item to be transported within the module cargo storage system.

At step 5030, method 5000 has the modular cargo storage system providing selective access to within the modular cargo storage system after the pickup authentication input received correlates to the first portion of the authentication information and then, at step 5035, receiving the inventory item for transport at the intermediate loading location. Thereafter, at step 5040, method 5000 has the modular mobile autonomy control module autonomously causing the modular mobility base to move from the intermediate loading location to the drop-off location at the second of the remote business facilities.

At step 5045 as shown on FIG. 50B (which continues method 500), the exemplary MALVT bot apparatus assembly with the inventory item is at the second remote business facility for drop-off, and method 5000 proceeds by receiving delivery recipient authentication input by the modular mobile autonomy control module from a delivery recipient disposed external to the modular autonomous bot apparatus assembly and at the drop-off location. When the delivery recipient authentication input at least correlates to a portion of the authentication information related to the dispatched inventory balancing operation, the input indicates the delivery recipient that provided the delivery recipient authentication input is an authorized delivery recipient for the inventory item for transport within the module cargo storage system.

At step 5050, method 5000 proceeds with providing, by the modular cargo storage system, selective access to the inventory item for transport within the modular cargo storage system after the delivery recipient authentication input received correlates to the portion of the authentication information indicating the delivery recipient providing the delivery recipient authentication input is the authorized delivery recipient.

At step 5055, method 5000 proceeds with detecting, by the modular mobile autonomy control module, removal of the inventory item for transport from within the modular cargo storage system (using sensors as described in embodiments above), and then at step 5060, method 5000 then has the modular mobile autonomy control module autonomously causing the modular mobility base to move from the drop-off location on a return route to the bot storage location after the inventory item for transport is detected to be removed from within the modular cargo storage system. In some embodiments, step 5060 may be implemented by having the modular mobile autonomy control module autonomously causing the modular mobility base to hold at the drop-off location in a ready for dispatch mode where the exemplary MALVT bot apparatus assembly waits for a subsequent inventory dispatch command from the dispatch server where such a command is related to a subsequent dispatched inventory operation involving the modular autonomous bot apparatus assembly, and then has the modular mobile autonomy control module autonomously causing the modular mobility base to return to the inventory hub location after the modular autonomous bot apparatus assembly completes the subsequent dispatched inventory operation.

Further embodiments of method 5000 may involve the further step of authentication whether the modular components of the dispatched exemplary MALVT bot apparatus assembly is compatible with the particular dispatched inventory operation similar to that described with further embodiments of method 4900. This may involve making sure different sized modular components are the appropriate sized modular components for the dispatched inventory operation, and may involve returning to an assembly area at the bot storage location (e.g., location 4715 at the inventory hub location 4705) to change out one or more of the incompatible modular components (e.g., replace a CSS component with one of a different size, replace sensor pods on one or more of the modular components, and the like).

Further embodiments of method 5000 may involve details on authenticating delivery at the second remote business facility similar to that described above with further detailed embodiments of method 4900. For example, such delivery recipient authentication input may be received through a user input panel on the bot apparatus (e.g., with access codes, biometric input, audio input, and the like) and through wireless communications with an external wireless node operated locally at the second remote business facility where delivery recipient authentication input may be received wirelessly.

In like manner, further embodiments of method 5000 may involve details on navigating and moving to the intermediate loading location at the first remote business facility similar to that described above with further detailed embodiments of method 4900 where such moving actions by the exemplary MALVT bot apparatus assembly may involve wireless interacting with building facility nodes to actuate pathway obstacles (e.g., doors, elevators, and the like), which may involve establishing authorized association pairings between the modular mobile autonomy control module and the wireless building facility node based upon the authentication information related to the dispatched logistics operation, and causing the wireless building facility node to actuate the pathway obstacle after establishing the authorized association pairing between the modular mobile autonomy control module and the wireless building facility node. In other examples, this may involve moving to the intermediate loading location while manually interacting with pathway obstacles on the way using, for example, an articulating arm (such as arm 4325) to manipulate obstacles such as a manually actuated door, elevator, lock, door handle, and the like.

Further embodiments of method 5000 may involve details on receiving and loading the inventory item at the first remote business facility similar to that described above with further detailed embodiments of method 4900 using actuated devices and articulating object manipulation systems. Likewise, further embodiments of method 5000 may involve details on providing access to the loaded inventory item and unloading at the second remote business facility similar to that described above with further detailed embodiments of method 4900 using actuated devices and articulating object manipulation systems.

Additional embodiments of method 5000 may further involve details on interfacing with and interacting with exemplary node-enabled shelving systems (e.g., system 4800) at the first and second remote business facilities as part of receiving the inventory item for pickup and providing access to the inventory item for drop-off similar to that described above with further detailed embodiments of method 4900 using actuated devices and articulating object manipulation systems.

Store-to-Consumer Dispatched Operations

Further embodiments of an exemplary MALVT bot apparatus assembly 1700 may be deployed in particular dispatched store-to-consumer logistics operations where the exemplary MALVT bot apparatus assembly 1700 being dispatched operates to perform various types of enhanced order fulfillment tasks with one or more ordered item being responsively delivered. FIG. 51 is a flow diagram of an embodiment of an exemplary method 5100 for dispatched store-to-consumer logistics operation related to an ordered item and using a modular autonomous bot apparatus assembly (MALVT bot apparatus assembly) and a dispatch server in accordance with an embodiment of the invention. An embodiment of such a method 5100 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5100 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 5100.

Referring now to FIG. 51, exemplary method 5100 begins at step 5105 with the modular mobile autonomy control module receiving a dispatch command from the dispatch server. In step 5105, the dispatch command comprising at least identifier information on the ordered item, transport parameters on the ordered item, destination delivery information related to delivery of the ordered item, and delivery authentication information related to an authorized delivery recipient of the ordered item. In a more detailed embodiment and implementation of step 5105, the dispatch command received from the dispatch server may be a delivery order assignment message from a retail system that received a transaction order for the ordered item. As such, the retail server system that receives and processes transaction orders for customers, may have one or more parts of the retail system operate as the dispatch server (e.g., server 4205) that responsively interacts with the exemplary MALVT bot apparatus assembly (e.g., the autonomous control system 3100 within exemplary MAM 1725 of bot assembly 1700).

At step 5110, method 5100 has the modular mobile autonomy control module verifying that each of the modular mobile autonomy control module, the modular mobility base, the modular auxiliary power module, and the modular cargo storage system are compatible with the dispatched store-to-consumer logistics operation based upon the dispatch command. Verification at step 5110 may involve authenticating that the different modular components of the exemplary MALVT bot apparatus assembly involved in this dispatched store-to-consumer logistics operation is both capable of performing the operation and/or is authorized to be used in such an operation (e.g., due to logistical constraints inherent in the operation, and the like).

Thereafter, at step 5115, method 5100 has the modular cargo storage system receiving the ordered item in a payload area within the modular cargo storage system. Embodiments of method 5100 may implement step 5115 using actuated components and object manipulation systems deployed onboard the exemplary MALVT bot apparatus system as part of loading the ordered item into the modular cargo storage system. For example, an embodiment of method 5100 may have the MAM 1725 actuating an actuated cargo door (e.g., door 1715) disposed on the modular auxiliary power module (or the CSS 1720) to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position. Actuating the cargo door may involve, for example, actuating an actuated joint (e.g., joint 2020) on the actuated cargo door to cause the actuated cargo door to move from the closed position to the open position and, or actuating an electro-mechanical lock (e.g., lock 2025) on the actuated cargo door to cause the actuated cargo door to unlock before moving from the closed position to the open position. Further embodiments of method 5100 may have step 5115 actuating an actuated sliding arm disposed on the modular cargo storage system (or APM) to move the ordered item into the payload area within the modular cargo storage system and/or actuating an actuated grabbing arm disposed on the modular cargo storage system (or APM) to grab and move the ordered item into the payload area within the modular cargo storage system as part of receiving the ordered item. Likewise, further embodiments of method 5100 may implement step 5115 by actuating an actuated belt surface disposed on the modular auxiliary power module 1710 and/or door 1715 as a movable support surface exposed within the payload area that causes the ordered item, as placed on the actuated belt surface, to move within the payload area as part of receiving the ordered item.

Once the ordered item has been received within the modular cargo storage system of the exemplary MALVT bot apparatus assembly used in this operation, method 5100 continues at step 5120 with the modular mobile autonomy control module autonomously causing the modular mobility base to move from an origin location on a route to a destination location identified by the destination delivery information.

While in transit to the destination location, method 5100 has the modular mobile autonomy control module notifying the authorized delivery recipient of the ordered item of an approaching delivery once the modular autonomous bot apparatus assembly is within a threshold notification range of the destination location as part of step 5125. Such a threshold notification range may, for example, involve a specific distance from the destination location according to location coordinates generated by the MAM 1725. In other embodiments, such a threshold notification range may be keyed to passing a particular location on the route to the destination location (e.g., an actuated front door for a building, and the like). In further embodiments, this may be repeated at different notification range distances from the destination location so as to provide different notifications to the delivery recipient as the exemplary MALVT bot apparatus assembly with the ordered item continues to approach the destination location for delivery of the ordered item.

In more detail, step 5125 may have the modular mobile autonomy control module notifying the authorized delivery recipient of the ordered item of an approaching delivery with a transmitted arrival estimate at the destination location. Further implementations of step 5125 may have the MAM 1725 generating a display alert for the authorized delivery recipient on a display on the MAM once the modular autonomous bot apparatus assembly is within the threshold notification range of the destination location as part of the notification in step 5125. Additional embodiments may implement such pre-delivery notifications by, for example, generating an audio notification for the authorized delivery recipient on a speaker on the modular mobile autonomy control module; transmitting a delivery notification message to an external wireless node (e.g., an external wireless node related to a designated wireless user identified in the dispatch command, which may be a third party or the authorized delivery recipient).

At step 5130, method 5100 proceeds with receiving delivery recipient authentication input by the modular mobile autonomy control module from a delivery recipient disposed external to the modular autonomous bot apparatus assembly at the destination location.

At step 5135, method 5100 has the modular cargo storage system providing selective access to the ordered item within the modular cargo storage system only when the delivery recipient authentication input received correlates to the delivery authentication information indicating that the delivery recipient providing the delivery recipient authentication input is the authorized delivery recipient. In more detailed embodiments of method 5100, step 5135 may involve specific actions taken by the exemplary MALVT bot apparatus assembly used in method 5100 to unload the ordered item using actuated parts of the bot apparatus and exemplary object manipulation systems used as part of the exemplary bot apparatus involved in method 5100 similar to those used to load the ordered item. For example, step 5135 may have the MAM of the exemplary MALVT bot apparatus assembly used in method 5100 actuating an actuated cargo door disposed on the modular auxiliary power module (or CSS) to an open position once the delivery recipient authentication input correlates to a portion of the authentication information related to the dispatched store-to-consumer logistics operation. Such an actuated cargo door (e.g., door 1715) may be actuated via the actuated joint 2020 noted above, which may cause the actuated cargo door 1715 to move from the closed position to the open position. Similarly, the actuated cargo door (e.g., door 1715) may be actuated via an electro-mechanical lock on the actuated cargo door to cause the actuated cargo door to unlock before moving from the closed position to the open position. And consistent with the loading description above relative to step 5115, an actuated sliding arm, grabbing arm, and/or actuated belt surface may be moved under control of the MAM as part of unloading the ordered item from within the CSS.

At step 5140, method 5100 has the modular mobile autonomy control module monitoring unloading of the ordered item from within the modular cargo storage system using one or more sensors on at least one of the modular mobile autonomy control module and the modular cargo storage system. This may also involve generating a log entry in a custodial inventory data structure stored on, for example, the modular mobile autonomy control module (e.g., exemplary MAM 1725) when the ordered item is detected to be removed from within the modular cargo storage system, where the log entry indicates and reflects the removal of the ordered item from within the modular cargo storage system. In more detail, an embodiment of step 5140 may be implemented in an embodiment of method 5100 by capturing sensor data from the payload monitoring sensors on the MAM and/or CSS, and detecting when the ordered item is removed from within the CSS based upon the captured sensor data, which may be processed to transform the raw sensor data into usable data (e.g., a detected image of the ordered item using visual images of what is disposed within the modular cargo storage system).

Further examples of step 5140 may involve different types of sensors and processing of the sensor data generated by such sensors. For example, monitoring unloading of the ordered item in step 5140 may be accomplished by generating barcode scan data related to ordered item as the ordered item is removed from within the modular cargo storage system using a barcode scanner as one of the sensors, and processing the generated barcode scan data to monitor the ordered item as the ordered item is removed from within the modular cargo storage system. In another example, monitoring unloading of the ordered item in step 5140 may be accomplished by detecting advertising data related to a node with the ordered item as the ordered item is removed from within the modular cargo storage system, and processing the generated advertising data to monitor the location of the node with the ordered item as the ordered item is removed from within the modular cargo storage system. In still another example, monitoring unloading of the ordered item in step 5140 may be accomplished by generating image data related to the ordered item as the ordered item is removed from within the modular cargo storage system using a camera as one of the sensors, and processing the generated image data to monitor the ordered item as the ordered item is removed from within the modular cargo storage system. In still another example, monitoring unloading of the ordered item in step 5140 may be accomplished by generating video data related to ordered item as the ordered item is removed from within the modular cargo storage system using a video camera as one of the one or more sensors, and processing the generated video data as a type of vision system that monitors the ordered item as the ordered item is removed from within the modular cargo storage system. In yet another example, monitoring unloading of the ordered item in step 5140 may be accomplished by capturing audio data using a microphone disposed on the exemplary MALVT bot apparatus assembly as one of the sensors disposed to record sound within and proximate to the modular cargo storage system as the ordered item is removed from within the modular cargo storage system, and then processing the captured audio data to monitor the ordered item as the ordered item is removed from within the modular cargo storage system.

Further examples may have monitoring unloading of the ordered item in step 5140 be implemented by detecting movement of a wireless node associated with the ordered item as the ordered item is removed from within the modular cargo storage system based upon a signals broadcast from the wireless node associated with the ordered item. Node locating techniques disclosed herein, for example, may be used to track the location of a node-enabled ordered item and, thus, allow for monitoring of the ordered item to know when it has been removed from the modular cargo storage system (e.g., when the changed location of the node-enabled ordered item indicates the ordered item is now outside the modular cargo storage system as determined by the modular mobile autonomous control module).

At step 5145, method 5100 concludes with having the modular mobile autonomy control module autonomously causing the modular mobility base to move from the destination location on a return route to the origin location after the ordered item is detected to be removed from within the modular cargo storage system based upon monitoring the unloading of the ordered item.

More detailed embodiments of method 5100 may involve receiving and loading the ordered item after supplier authentication input has been received, and selective access to the modular cargo storage system is then permitted (e.g., via actuated and/or articulating systems onboard the exemplary MALVT bot apparatus assembly). In such an exemplary further embodiment, the dispatch command in method 5100 may also include supplier authentication information related to an authorized supplier of the ordered item. As such, step 5115 of receiving the ordered item may be implemented with receiving supplier authentication input by the modular mobile autonomy control module from a loading entity disposed external to the modular autonomous bot apparatus assembly at the origin location. The modular cargo storage system (as controlled by MAM 1725) may then provide selective access to within the modular cargo storage system only when the supplier authentication input received correlates to the supplier authentication information indicating that the loading entity providing the supplier authentication input is the authorized supplier of the ordered item.

Those skilled in the art will further appreciate that embodiments of method 5100 may have the exemplary MALVT bot apparatus assembly used in method 5100 navigating and interacting with different pathway obstacles when moving from the origin location to the destination location. For example, step 5120 of autonomously causing the modular mobility base to move from the origin location to the destination location may be implemented with the modular mobile autonomy control module autonomously causing the modular mobility base to move from the origin location to the destination location while interacting with a wireless building facility node to actuate a pathway obstacle disposed in a path on the route to the destination location (e.g., an actuated door controlled by the wireless building facility node, an actuated elevator controlled by the wireless building facility node, an actuated lock controlled by the wireless building facility node, and the like). In more detail, such interactions with the wireless building facility node to actuate the pathway obstacle may involve establishing an authorized association pairing between the modular mobile autonomy control module and the wireless building facility node based upon the authentication information related to the dispatched store-to-consumer logistics operation (e.g., a tracked an authorized logically persistent pairing as reflected by locally generated association data on the MAM), and causing the wireless building facility node to actuate the pathway obstacle after establishing the authorized association pairing.

In further embodiments where pathway obstacles may not be controlled or actuated wirelessly, embodiments of method 5100 may have moving from the origin location to the destination location involve manual interactions by the exemplary MALVT bot apparatus assembly and such pathway obstacles. For example, step 5120 of autonomously causing the modular mobility base to move from the origin location to the destination location may have the modular mobile autonomy control module autonomously causing the modular mobility base to move from the origin location to the destination location while engaging a pathway obstacle disposed in a path on the route to the destination location using an articulating arm disposed on the modular autonomous bot apparatus assembly and using sensors disposed on at least one of the modular mobility base and the modular mobile autonomy control module. Such manually manipulated pathway obstacles may include, for example, a manually actuated door, a manually actuated elevator, a manually actuated lock, or a manually actuated control panel for the pathway obstacle. In more detail, engaging the pathway obstacle using the articulating arm and sensors may involve, for example, guiding, by the modular mobile autonomy control module, the articulating arm to a control element of the pathway obstacle using one or more of the sensors; and actuating the pathway obstacle, by the modular mobile autonomy control module, once the articulating arm engages the control element of the pathway obstacle. Such a pathway obstacle control element may, for example, be a handle for the pathway obstacle, a button for the pathway obstacle, a switch for the pathway obstacle, or a portion of a control panel for the pathway obstacle.

In further detailed embodiments of method 5100, the delivery recipient authentication input received by the modular mobile autonomy control module as part of step 5130 may be provided by the delivery recipient through a user input panel (e.g., panel 2220) disposed on the modular autonomous bot apparatus coupled to the modular mobile autonomy control module. Such a user input panel may be deployed on any of the modular components of the exemplary MALVT bot apparatus, and may receive input via manual engagement of buttons or switches on the user input panel (e.g., for access codes or other manual input) or may receive input without touching the panel (e.g., with a sensor and processing system implemented on the MAM that can recognize biometric input, gestures, voice commands, and the like as authentication input which may match or at least correlate to authentication information for the particular logistics operation for the ordered item).

In other embodiments of method 5100, the delivery recipient authentication input received by the modular mobile autonomy control module in step 5130 may be provided by the delivery recipient through an external wireless node disposed external to the modular autonomous bot apparatus assembly, such as with an access code and/or biometric input provided through an app running on the external wireless node.

In still other embodiments of method 5100, the delivery authentication information for the dispatched store-to-consumer logistics operation may include an identifier of the authorized delivery recipient for the ordered item as part of the dispatched store-to-consumer logistics operation, and the delivery recipient authentication input received by the modular mobile autonomy control module in step 5130 may accomplished with the modular mobile autonomy control module detecting an advertising signal as the delivery recipient authentication input from an external wireless node within a predetermined range of the modular autonomous bot apparatus assembly once the modular autonomous bot apparatus assembly has arrived at the destination location identified by the destination information. Thereafter, the modular mobile autonomy control module may authenticate that the external wireless node is associated with the authorized delivery recipient for the ordered item based upon the identifier of the authorized delivery recipient and identifier information within the detected advertising signal broadcast from the external wireless node. For authentication input received from an external wireless node, step 5130 may also be implemented with the modular mobile autonomy control module detecting an unprompted advertising signal from such an external wireless node within a predetermined range of the modular autonomous bot apparatus assembly (i.e., without the assembly first interrogating the external wireless node) once the modular autonomous bot apparatus assembly has arrived at the destination location identified by the destination information. Once such an unprompted advertising signal is detected by the modular mobile autonomy control module, method step 5130 may involve establishing a secure association between the external node and the modular mobile autonomy control module where such a secure association between the external node and the modular mobile autonomy control module may involve generating association data identifying the logical, persistent connection between the external node and the modular mobile autonomy control module, and allows secure sharing of information between the external node and the modular mobile autonomy control module as being pre-authorized by the dispatch server as it relates to this particular dispatched store-to-consumer logistics operation.

Further embodiments of method 5100 may also involve implementing chain of custody tracking features. For example, an embodiment of method 5100 may also include the step of generating, by the modular mobile autonomy control module, a first inventory data structure maintained within memory of the control module (e.g., memory within autonomous control system 3100 in exemplary MAM 1725). Such an inventory data structure corresponds to the ordered item upon receiving the ordered item, where the first inventory data structure then includes chain of custody entries, such as an entry reflecting departure from the origin location for the ordered item while in the custody of the modular autonomous bot apparatus assembly, another entry generated after arrival at the destination location and reflecting arrival from the destination location for delivery of the ordered item from the custody of the modular autonomous bot apparatus assembly, and/or another chain of custody entry generated after arrival at the destination location and after detecting the ordered item has been removed from within the modular cargo storage system reflecting the ordered item changing custody to the authorized delivery recipient from the modular autonomous bot apparatus assembly.

In still a further embodiment of method 5100, the weight of what is to be transported as the ordered item or items may be considered and validated as prior to embarking on the dispatched store-to-consumer logistics operation involving the exemplary MALVT bot apparatus assembly or as part of the operation. For example, step 5105 of receiving the dispatch command of method 5100 may have the modular mobile autonomy control module receiving a pre-screened dispatch command from the dispatch server. This pre-screened dispatch command indicates that the dispatch server has verified the dispatched store-to-consumer logistics operation is an autonomous delivery eligible logistics operation according to a weight of the ordered item or items, and the pre-screened dispatch command has at least identifier information on the ordered item, transport parameters on the ordered item, destination delivery information related to delivery of the ordered item, and delivery authentication information related to an authorized delivery recipient of the ordered item.

In another example, such weight information may be considered when verifying in step 5110. For example, the transport parameters on the ordered item may include at least weight information about the ordered item to be transported within the modular autonomous bot apparatus assembly, and step 5110 may be implemented with the modular mobile autonomy control module verifying that each of the modular mobile autonomy control module, the modular mobility base, the modular auxiliary power module, and the modular cargo storage system are compatible with weight information about the ordered item. This may, for example, involve veifying that the modular autonomous bot apparatus assembly has a transport capacity that is compatible with the weight information about the ordered item.

In another example, the dispatch command received in step 5105 may have a delivery schedule for what is to be delivered from contents of the modular cargo storage system, and the transport parameters on the ordered item included with the dispatch command may include at least weight information about the ordered item to be transported within the modular autonomous bot apparatus assembly. As such, step 5110 may be implemented by the modular mobile autonomy control module verifying that the modular autonomous bot apparatus assembly has a transport capacity that is compatible with the weight information about the ordered item; and verifying that the delivery schedule is compatible with the weight information about the ordered item.

In more detail, an exemplary delivery schedule may have at least one pickup logistics operation to be performed as part of the dispatched store-to-consumer logistics operation, wherein the at least one pickup logistics operation anticipated to add an additional item having additional weight in the payload area with the ordered item.

Store to Home Use Cases—Pharmacy

In another store-to-consumer embodiment, an exemplary MALVT bot apparatus assembly (such as exemplary MALVT bot apparatus assembly 1700) may be involved with prescription and/or other in-store retail purchase deliveries to a home/business/mobile location. In general in such an embodiment, an exemplary order may be fulfilled by pharmacist or retail specialist, and then the address and recipient information may be transferred from the relevant pharmacy/retail sales system to exemplary MALVT bot apparatus dispatch software running on the same or on a dedicated dispatch server system (e.g., dispatch server 4205). Delivery parameters (e.g., day, desired time, recipient cell number or phone number, special instructions, etc.) may be gathered from the purchaser and selected by pharmacy/retail technician for input into the relevant pharmacy/retail sales system. Upon transfer to the dispatch system, one or more exemplary MALVT bot apparatus may be assigned and prepped for the purchase delivery. The dispatch system may provide a "drop dead" load time to the relevant purchase technician (e.g., pharmacy technician or retail specialist handling the transaction) and provides alert related to the delivery. The relevant purchase technician may then load the assigned exemplary MALVT bot apparatus no later than the drop dead time. The exemplary MALVT bot apparatus travels to the designated shipping location (e.g., the address of the recipient) leveraging GPS, mapping or TRON locating techniques, and alerts the recipient prior to arrival (e.g., via text or automated call providing authentication parameters (code, biometrics on users phone, TRON, etc.) & estimated time of arrival). The exemplary MALVT bot apparatus arrives and the recipient may then authenticate delivery via an app operating on the recipient's user access device, via TRON node interactions for association-based authenticated delivery, or via interaction with the display screen on the MAM component. The recipient may then retrieve the delivery from the CSS of the dispatched exemplary MALVT bot apparatus. As the recipient unloads the exemplary MALVT bot apparatus, the exemplary MALVT bot apparatus may monitor unloading and ensure that all contents have been removed, and then the bot apparatus may return to the pharmacy/retail location. Enhanced security, recorded transaction records (e.g., automatic video/audio recorded loading/unloading), and multi-factor authentication (e.g., two factor/biometric) may be required given the chain of custody needs.

Accordingly, in such a further embodiment of exemplary method 5100 where the ordered item is a pharmaceutical item, step 5115 of receiving the ordered item in the payload area within the modular cargo storage system may be implemented by receiving, by the modular cargo storage system, the pharmaceutical item as part of a pharmaceutical transaction between a pharmacy and the authorized delivery recipient of the pharmaceutical item. In such a further embodiment of method 5100, the destination delivery information related to the delivery of the ordered pharmaceutical item may include a requested time of day and/or requested day of the week for the modular autonomous bot apparatus assembly to arrive at the destination location for the delivery of the ordered item to the authorized delivery recipient. The destination delivery information related to the delivery of the ordered item may also include contact information for the authorized delivery recipient to use when notifying the authorized delivery recipient, and/or a special delivery instructions for delivery of the ordered item.

Related to such a pharmaceutical delivery embodiment where an authorized supplier of the ordered pharmaceutical item provides supplier authentication input during the loading process, step 5115 of method 5100 may have, prior to receiving the supplier authentication input, the dispatch server notifying a loading entity of a load time deadline for placing the ordered item within the modular cargo storage system as part of the dispatched store-to-consumer logistics operation for the ordered pharmaceutical item.

In still further pharmaceutical delivery embodiments of method 5100, multi-factor authentication may be implemented as part of receiving supplier/delivery recipient authentication input. For example, an embodiment of step 5130 of method 5100 may be implemented by receiving the delivery recipient authentication input comprises receiving multiple-factor delivery recipient authentication input from the delivery recipient, and wherein the delivery authentication information including multiple-factor authentication input answers that when collectively correlating to the multiple-factor delivery recipient authentication input from the delivery recipient indicates the delivery recipient is the authorized delivery recipient.

Store to Home Use Cases—Retail

In another store-to-consumer type of embodiment, a retailer business entity or establishment (e.g., Nordstrom, Best Buy, and Walmart) may provide a local delivery fulfilled from local stores. Customer service & inventory management may be enhanced and improved by, for example, decreased floor space needed for order pick up in an embodiment using an exemplary MALVT bot apparatus assembly (such as exemplary MALVT bot apparatus assembly 1700). In general, an exemplary customer of the retailer may order one or more items and selects a delivery timeframe. The customer may order online remotely or order locally within a store but select a deliver option. As such, the store's order fulfillment system may then transfer data related to the transaction of the items to an exemplary MALVT bot apparatus assembly. The same internal processes as an order online for pickup in store may have a retail associate pick the ordered item(s) and gather them for a localized pickup. The exemplary MALVT bot apparatus may be assigned, and then the retail associate may load the exemplary MALVT bot apparatus with inventory (e.g., with the bot apparatus monitoring the loading process), and then the exemplary MALVT bot apparatus is sent to deliver the order. The recipient (e.g., the ordering entity or a separately designated entity) receives a notification that the exemplary MALVT bot apparatus is ready and is given an estimated time of arrival. The recipient/customer can change time or accept delivery time by interacting directly with the exemplary MALVT bot apparatus (e.g., via TRON element wireless communications between a recipient/customer's user access device operating as an ID node and a component of the exemplary MALVT bot apparatus operating as a master node) or interacting indirectly with the exemplary MALVT bot apparatus via a dispatch system operated by the retailer as a type of server. Visibility and communication allows for the exemplary MALVT bot apparatus to deliver to person who authenticates may be based on store selected security protocols. The recipient may then authenticate delivery via an app operating on the recipient's user access device, via TRON node interactions for association-based authenticated delivery, or via interaction with the display screen on the MAM component. As the customer unloads the exemplary MALVT bot apparatus, the exemplary MALVT bot apparatus may monitor unloading (e.g., making sure what is unloaded from the CSS is supposed to be at the new location) and ensure that all/appropriate contents have been removed, and then the bot apparatus may return to the retail location. If the purchased item is incorrect or unsatisfactory, the customer may interact with the exemplary MALVT bot apparatus (e.g., via a display interface and human-to-machine interaction or via wireless communication between the customer's user access device and the exemplary MALVT bot apparatus) to select an option to return item to the store. The exemplary MALVT bot apparatus then either accepts the return, or ensures that it is empty and returns to the retailer. As it relates to this type of store-to-consumer logistics operation involving an exemplary MALVT bot apparatus assembly, those skilled in the art will appreciate that aspects of TRON wireless node technology as described above may be incorporated and leveraged for device/node location, door & lock operation, elevator operation, and authentication using the various nodes (e.g., different nodes embedded in or in responsive communication with an actuated door, lock, or elevator).

Accordingly, in such a further embodiment of exemplary method 5100 involving a dispatched store-to-consumer logistics operation in a retail environment, the destination delivery information received as part of the dispatch command in step 5105 may include a selected delivery timeframe for presenting the ordered item to the authorized delivery recipient. Such a selected delivery timeframe corresponds to a range of time over which the modular autonomous bot apparatus will autonomously arrive at the destination location for monitored unloading of the ordered item as part of the dispatched store-to-consumer logistics operation.

In another example of such a further embodiment of method 5100, the dispatch command received in step 5105 may include supplier authentication information related to an authorized retail personnel that obtains and provides the ordered item to the modular cargo storage system. As such, step 5115 of receiving the ordered item may be implemented by receiving supplier authentication input by the modular mobile autonomy control module from a loading retail personnel disposed external to the modular autonomous bot apparatus assembly at the origin location; and having the modular cargo storage system providing selective access to within the modular cargo storage system only when the supplier authentication input received correlates to the supplier authentication information indicating that the loading retail personnel providing the supplier authentication input is the authorized retail personnel for obtaining and providing the ordered item. In this example, the authorized retail personnel may obtain and provide the ordered item within the modular cargo storage system after the dispatch server instructs the authorized retail personnel (e.g., via messaging to a mobile wireless node based user access device operated by the authorized retail personnel) to obtain obtains and provides the ordered item to the modular cargo storage system as part of the dispatched store-to-consumer logistics operation. Furthermore, in this example, step 5115 may be implemented with the modular mobile autonomy control module monitoring loading of the ordered item from within the modular cargo storage system as the ordered item is received within the modular cargo storage system, where such monitoring may use one or more sensors on at least one of the modular mobile autonomy control module and the modular cargo storage system.

Further still, such monitored loading as part of step 5115 may also involve generating a log entry in a custodial inventory data structure (stored in memory of exemplary MAM 1725) when the ordered item is detected to be placed within the modular cargo storage system. Such a log entry reflects placement of the ordered item within the modular cargo storage system. This particular loading process in this embodiment of method 5100 for retail ordered items in step 5115 may involve capturing sensor data from sensors on at least one of the modular mobile autonomy control module and the modular cargo storage system (similar to that described above), and then detecting when the ordered item is placed within the modular cargo storage system based upon the captured sensor data (e.g., determinations based upon processing the captured sensor data, such as image data, barcode scan data, video data, audio data, movement data, as well as node location data).

In another example of such a retail focused embodiment of method 5100, a further embodiment of method 5100 may further include notifying the recipient of an anticipated delivery time with an option for the recipient to change the delivery time. In more detail, such a further embodiment of method 5100 may include the steps of having the modular mobile autonomy control module notifying the authorized delivery recipient of an anticipated delivery time of the ordered item at the destination location prior to receiving the ordered item in the modular cargo storage system, and then having the modular mobile autonomy control module receive a responsive confirmation from the authorized delivery recipient related to the anticipated delivery of the ordered item. As such, the step 5115 of receiving the ordered item within the payload area within the modular cargo storage system may depend on the responsive confirmation from the authorized delivery recipient.

In more detail in this example, step 5115 of receiving the ordered item within the payload area within the modular cargo storage system may permissively proceed upon receipt of the responsive confirmation when the responsive confirmation from the authorized delivery recipient indicates acceptance of the anticipated delivery time of the ordered item. However, in this same example, step 5115 may have receiving the ordered item within the payload area being delayed upon receipt of the responsive confirmation when the responsive confirmation from the authorized delivery recipient indicates an alternative delivery time of the ordered item.

In this same example, the step of notifying the authorized delivery recipient of the anticipated delivery time may have the modular mobile autonomy control module transmitting a wireless notification message directly to an external wireless node identified to be related to the authorized delivery recipient based upon the delivery authentication information. This wireless notification message provides the anticipated delivery time to the authorized delivery recipient. Thereafter, the step of receiving the responsive confirmation from the authorized delivery recipient may involve receiving a wireless confirmation message directly from the external wireless node identified to be related to the authorized delivery recipient, where the wireless confirmation message provides the responsive confirmation from the authorized delivery recipient.

In other embodiments of this example, notification of the delivery recipient may be implemented in a more indirect manner. For example, the step of notifying the authorized delivery recipient of the anticipated delivery time may have the modular mobile autonomy control module transmitting a notification message indirectly through the dispatch server to the authorized delivery recipient, where the notification message provides the anticipated delivery time to the authorized delivery recipient. As such, the step of receiving the responsive confirmation from the authorized delivery recipient may be accomplished by receiving a confirmation message indirectly from the authorized delivery recipient through the dispatch server, where the confirmation message provides the responsive confirmation from the authorized delivery recipient.

In further retail-related embodiments of exemplary method 5100, the delivery recipient authenticated input may be based upon predetermined store-specific authentication protocols that may be different for different stores serviced by the exemplary MALVT bot apparatus assembly. For example, an embodiment of method 5100 may implement step 5130 where the received delivery recipient authentication input must conform to a store-selected security protocol for verifying the delivery recipient authentication input is from the authorized delivery recipient so that the ordered item is provided only to the authorized delivery recipient. In more detail, such a store-selected security protocol may have the delivery recipient authentication input received by the modular mobile autonomy control module being provided by the delivery recipient through a user input panel disposed on the modular autonomous bot apparatus coupled to the modular mobile autonomy control module (e.g., with an access code, biometric input, and the like) and/or through wireless communications with an external wireless node disposed external to the modular autonomous bot apparatus assembly (e.g., with a wirelessly provide access code, biometric input, and the like).

In a further example of exemplary method 5100 involving store-selected-security protocols for verification purposes, the authentication information related to the dispatched store-to-customer logistics operation may include an identifier of the authorized delivery recipient for the ordered item as part of the dispatched store-to-consumer logistics operation. As such, step 5130 of receiving the delivery recipient authentication input using the store-selected security protocol may be further implemented with the modular mobile autonomy control module detecting an advertising signal as the delivery recipient authentication input from an external wireless node within a predetermined range of the modular autonomous bot apparatus assembly once the modular autonomous bot apparatus assembly has arrived at the destination location identified by the destination information, and then authenticating that the external wireless node is associated with the authorized delivery recipient for the ordered item within the modular cargo storage system based upon the identifier of the authorized delivery recipient and identifier information within the detected advertising signal broadcast from the external wireless node. In another example, step 5130 may be implemented with the modular mobile autonomy control module detecting an unprompted advertising signal from an external wireless node within a predetermined range of the modular autonomous bot apparatus assembly once the modular autonomous bot apparatus assembly has arrived at the destination location identified by the destination information; and establishing a secure association between the external node and the modular mobile autonomy control module after detecting the unprompted advertising signal from the external wireless node. This secure association between the external node and the modular mobile autonomy control module allows secure sharing of information between the external node and the modular mobile autonomy control module and may be pre-authorized by the dispatch server as it relates to this dispatched store-to-customer logistics operation.

In yet another example of such a further embodiment of method 5100 involving a retail environment, monitoring the unloading process as part of method 5100 may also include further responsive steps that may be initiated based upon the results of the monitoring. For example, monitoring the unloading of the ordered item as part of step 5140 in a further embodiment of method 5100 may have the modular mobile autonomy control module detecting that the ordered item has been removed from within the modular cargo storage system based upon sensor data generated by the sensors, and receiving a satisfaction indicator input by the modular mobile autonomy control module from the authorized delivery recipient after detecting that the ordered item has been removed from within the modular cargo storage system. Thereafter, the modular cargo storage system may receive the ordered item back within the modular cargo storage system if the satisfaction indicator input reflects the authorized delivery recipient is returning the ordered item. As such, step 5145 of autonomously causing the modular mobility base to move from the destination location to the origin location may be implemented as autonomously causing, by the modular mobile autonomy control module, the modular mobility base to move from the destination location on the return route to the origin location after receiving the satisfaction indicator input and transporting contents of the payload area within the modular cargo storage system depending upon the satisfaction indicator input.

Store to Home Use Cases—Food/Grocery Delivery

In another store-to-consumer type of embodiment, a restaurant may take an order from a customer in-person or online. In general, such an embodiment may have the ordered food prepared, and the ordering system transfers data to a dispatch system or software, which assigns and dispatches an exemplary MALVT bot apparatus (such as bot apparatus assembly 1700). In this general example, the exemplary MALVT bot apparatus accepts delivery and location (e.g., address, GPS, TRON determined location based on a customer's user access device operating as an ID node, etc.) and travels to the customer. The customer receives a notification that the exemplary MALVT bot apparatus has left the restaurant location with an estimate on delivery timeframe. The customer/recipient may then authenticate delivery via an app operating on the customer/recipient's user access device, via TRON node interactions for association-based authenticated delivery, or via interaction with the display screen on the MAM component. Thereafter, the customer/recipient retrieves the delivery. Visibility of the location of the exemplary MALVT bot apparatus to the customer may depend upon the restaurant. The CSS component of the exemplary MALVT bot apparatus may be implemented with organized climate control storage (e.g., a warming box cargo module, such as exemplary climate control module 2210) and/or insulated to retain a desired temp (hot or cold) and will be industry specific for the delivery food sent to the customer. Compartmental separators (such as separators 3608) may also be disposed within the CSS to separate different food orders and partition the payload area within the CSS into different climates for food items requiring different environments. Once the customer receives the delivery, the exemplary MALVT bot apparatus ensures all items have been removed (e.g., via a vision system or other onboard monitoring of the food contents via payload monitoring sensors) and returns to the origin restaurant location. The display screen on the exemplary MALVT bot apparatus can also display cautions for heat, restaurant advertisements/branding, or instructions for food preparation.

In another store-to-consumer food delivery embodiment, a customer may shop online for groceries and select delivery now (with estimated time to delivery) or delivery for a particular delivery window. The customer's purchases are prepared at location (e.g., with locations defined by a GPS, a physical address entry, TRON node location, etc.) and loaded into an exemplary MALVT bot apparatus (which may be at the purchase preparation location or be dispatched from a bot storage location to such a pickup location). The exemplary MALVT bot apparatus is then dispatched by the store's online system or a separate dispatch system (e.g., dispatch server 4205) to a specified address provided by the customer. The customer receives a notification of the departure of the exemplary MALVT bot apparatus and an estimated delivery time. The visibility of the exemplary MALVT bot apparatus to the customer may be dependent upon the food supplier. The customer may then authenticate delivery via an app operating on the recipient's user access device, via TRON node interactions for association-based authenticated delivery, or via interaction with the display screen on the MAM component. Once the customer receives the delivery, the exemplary MALVT bot apparatus ensures all items have been removed (e.g., via a vision system or other onboard monitoring of the food contents via payload monitoring sensors) and returns to the origin store location or continues to another location for another delivery (e.g., food in another partitioned food storage compartment of an exemplary multi-compartment CSS component). The CSS component of the exemplary MALVT bot apparatus may be implemented with organized climate control storage (e.g., one or more warming box cargo modules, such as exemplary climate control module 2210) and/or insulated to retain a desired temp (hot or cold) and will be industry specific for the delivery food sent to the customer. Similar to the embodiment discussed above, compartmental separators (such as separators 3608) may also be disposed within the CSS to separate different food orders and partition the payload area within the CSS into different climates for food items requiring different environments. Additionally, should the CSS component include multiple food storage compartments, a further embodiment may have individual doors (similar to cargo door 1715) where each of the compartmental doors may be actuated doors that provide an individually secure and selective opening of particular compartments based upon customer authentication for food item orders maintained within a respective compartment within CSS.

Accordingly, in such a further embodiment of exemplary method 5100 involving a dispatched store-to-consumer logistics operation in a food/grocery environment, the ordered item may be food stuffs gathered by a loading entity (restaurant worker or grocery employee), and may be multiple retail items sold by a business entity that employs the loading entity.

An embodiment of exemplary method 5100 in the food/grocery environment may include the step of transmitting, by the modular mobile autonomy control module, a dispatch command acceptance response to the dispatch server acknowledging acceptance of the dispatched store-to-consumer logistics operation based upon the dispatch command and a status of the modular autonomous bot apparatus assembly. In this way, the MAM of the exemplary MALVT bot apparatus assembly may review the details of information in the dispatch command and a status of how the bot apparatus assembly is configured and its readiness in order to provide such a dispatch command acceptance response. In more detail, this may involve having the modular mobility autonomy control module accessing context data on environmental conditions about the origin location and the destination location; generating the dispatch command acceptance response based upon the dispatch command, the status of the modular autonomous bot apparatus assembly, and the accessed context data on the environmental conditions about the origin location and the destination location; and transmitting the generated dispatch command acceptance response to the dispatch server.

And while the MAM in this example may determine it can accept the dispatched operation per the dispatch command and the status of the bot assembly, other situations may have the MAM determining it cannot accept the dispatched operation. For example, an embodiment of method 5100 may have the modular mobile autonomy control module transmitting a dispatch command decline response to the dispatch server informing the dispatch server that the modular autonomous bot apparatus assembly is unable to perform the dispatched store-to-consumer logistics operation based upon the dispatch command and the status of the modular autonomous bot apparatus assembly and that the dispatch server must send the dispatch command to another modular autonomous bot apparatus assembly at the origin location in order to complete the dispatched store-to-consumer logistics operation. In more detail, transmitting the dispatch command decline response may be accomplished in an embodiment with the modular mobility autonomy control module identifying an adverse transit condition based upon context data on environmental conditions about the origin location and the destination location (e.g., weather data, traffic data, construction information regarding these locations, building closure information, and the like); generating the dispatch command decline response based upon the dispatch command, the status of the modular autonomous bot apparatus assembly, and the adverse transit condition related to the context data on the environmental conditions about the origin location and the destination location; and transmitting the generated dispatch command decline response to the dispatch server. In still a further embodiment, method 5100 may also include having the modular mobile autonomy control module transmitting a dispatch command redirect response to the dispatch server requesting a change to the dispatched store-to-consumer logistics operation based upon context data on the environmental conditions about at least one of the origin location and the destination location.

In some examples, the context data on the environmental conditions about the origin location and the destination location may be provided by the dispatch server as part of the dispatch command received from the dispatch server. In other examples, such context data on the environmental conditions related to the origin and destination locations and routing locations in between may be requested by the MAM once having received the dispatch command. Such a request may be to the dispatch server or, in some embodiments, may be an online request where the MAM component downloads such environmental contextual information through third party weather reports, and other third party information available on a network, such as the Internet.

As noted above, a store-to-consumer food/grocery delivery embodiment may have the exemplary MALVT bot apparatus assembly used as part of method 5100 with a verified compatible modular cargo storage system having one or more climate control modules (e.g., exemplary climate control module 2210) disposed within the payload area and operative to maintain a desired environment in the payload area (or a partitioned compartment of the payload area) within the modular cargo storage system for the ordered item according to the transport parameters on the ordered item. Such a payload area may be at least a partially insulated within modular cargo storage system so as to help maintain the desired environment. Control of the climate control module in such embodiments may be accomplished with the modular mobile autonomy control module transmitting a climate control input to the climate control module to alter an environment proximate, surrounding, or otherwise next to the climate control module to maintain the desired environment in the payload area according to the transport parameters on the ordered item.

Further store-to-consumer food delivery embodiments of method 5100 may also include generating a display alert on the display on the modular mobile autonomy control module that may, for example, have a heat caution related to the ordered item, branded information on a food service entity that supplies the ordered item, instructional information related to the ordered item, and/or branded information from a food service entity that supplies the ordered item and where such branded information includes information about additional items available for order from the food service entity.

An embodiment of exemplary method 5100 in the food/grocery environment may further have the exemplary MALVT bot apparatus assembly being dispatched also having a secondary destination for an additional item within the payload area. For example, in a further food delivery related embodiment of method 5100, step 5145 of autonomously causing the modular mobility base to move on the return route to the origin location may involve having the modular mobile autonomy control module autonomously causing the modular mobility base to move from the destination location to a secondary delivery location after the ordered item is detected to be removed from within the modular cargo storage system at the destination location and after an additional item is detected within the modular cargo storage system while at the destination location. Such a secondary delivery location may be identified as part of the destination information related to the dispatched store-to-consumer logistics operation or may be separately provided to the MAM when receiving information about the additional item. Thereafter, the modular mobile autonomy control module may autonomously cause the modular mobility base to move from the secondary delivery location to the origin location after the additional item is detected as removed from within the modular cargo storage system at the secondary delivery location.

In more detail in this further embodiment, method 5100 may further have the steps of receiving third party entity authentication input by the modular mobile autonomy control module from a third party entity while at the secondary delivery location after the modular mobility base arrives at the secondary delivery location. If the third party entity authentication input correlates to a portion of the authentication information related to the dispatched store-to-consumer logistics operation, the input indicates the third party entity that provided the third party entity authentication input is an authorized third party recipient for the additional item within the module cargo storage system as part of the dispatched store-to-consumer logistics operation. Once the input indicates it is from the authorized third party recipient, the modular cargo storage system may provide selective access to within the modular cargo storage system for removal of the additional item.

Such an additional item may be kept in another compartment within the payload area of the modular cargo storage system. As such, such an embodiment of method 5100 may receive the ordered item in the payload area at step 5115 with the modular cargo storage system receiving the ordered item in a first of different separated storage compartments within the payload area within the modular cargo storage system. As such, step 5140 may have the modular mobile autonomy control module monitoring unloading of the ordered item from the first compartment within the modular cargo storage system using payload monitoring sensors on at least one of the modular mobile autonomy control module and the modular cargo storage system that monitor that first compartment. Step 5145 may then be implemented with the modular mobile autonomy control module autonomously causing the modular mobility base to move from the destination location to a secondary delivery location after the ordered item is detected to be removed from the first compartment within the modular cargo storage system at the destination location and after the additional item is detected within a second compartment of the separated storage compartments within the modular cargo storage system while at the destination location, where the secondary delivery location is identified as part of the destination information related to the dispatched store-to-consumer logistics operation. Thereafter, the modular mobile autonomy control module may autonomously cause, as part of step 5145, the modular mobility base to move from the secondary delivery location to the origin location after the additional item is detected to be removed from the second compartment within the modular cargo storage system at the secondary delivery location.

In this embodiment involving the additional item and the secondary delivery location, a further embodiment may have step 5135 providing, by the modular cargo storage system, selective access to the first compartment maintaining the ordered item within the modular cargo storage system while limiting access to others of the separated storage compartments including the second compartment. Such selective access to the first compartment may be provided only when the delivery recipient authentication input received correlates to the delivery authentication information indicating that the delivery recipient providing the delivery recipient authentication input is the authorized delivery recipient. As such, other compartments may remain inaccessible when providing the limited and selective access to the first compartment.

The different compartments within the CSS may have their respective environments controlled as noted above. For example and in this embodiment involving the different compartments for the ordered item and the additional item, a further embodiment of method 5100 may include the step of setting, by the modular mobile autonomy control module, a first detachable climate control module disposed within the first compartment of the separated storage compartments within the payload area to first desired temperature according to the transport parameters on the ordered item. For example, the ordered item in the first compartment may be frozen grocery items and so the detachable climate control module (e.g., module 2210) may be set by MAM 1725 to have an appropriate desired temperature according to a transport parameter for the frozen grocery items. Likewise, other desired temperature settings may be set for other climate control modules detachably disposed in other compartments, such as the one holding the additional item where the transport parameter on the additional item (e.g., included in the dispatch command and related to the dispatched store-to-consumer logistics operation) indicates a different desired temperature if the additional item is non-frozen perishable fruit.

Store to Home Use Cases–Retail Print/Copy Delivery

In still another store-to-consumer embodiment, a retail print/copy business establishment (RPBE) operates where a customer may come in to work on an order to be printed/copied, simply bring the order in for printing/copying, or interact with the RPBE via an online customer portal or website for such an order. In a general example embodiment, a customer may come to the RPBE for an order, and select a print/copy delivery order and transfer desired files related to the order to the RPBE (e.g., a server system at the RPBE or a remote server associated with the RPBE). Upon receipt of the order and confirmation of print/copy specifics related to the order, the RPBE (via personnel or automatically via its systems) may determine if delivery of the order is eligible to be performed by an exemplary MALVT bot apparatus. If so, the customer may be offered delivery by an exemplary MALVT bot apparatus for a decreased price and the customer selects a desired delivery timeframe. If delivery by the an exemplary MALVT bot apparatus is accepted, the ordered job will be completed and assigned to a an exemplary MALVT bot apparatus for delivery. The customer may receive a notification that the exemplary MALVT bot apparatus is ready along with an estimated time of arrival. The exemplary MALVT bot apparatus completes delivery to customer, and ensures all items have been removed and returns to appropriate RPBE location. When ordering, the customer may also have the opportunity to set up a pickup with delivery. In such an example, the customer may drop off an object (e.g., a USB thumb drive having files to be printed, documents that have been printed and packaged and are ready for shipment, and the like) back into the exemplary MALVT bot apparatus after retrieving the completed print/copy job if they have an outgoing pickup related to a further job for the RPBE. The exemplary MALVT bot apparatus may return to the RPBE location with the object picked up for sorting of the object so that the object may be shipped beyond the RPBE location. Various levels of authentication may be implemented in this embodiment via an app operating on the customer's user access device, via TRON node interactions for association-based authenticated delivery, or via interaction with the display screen on the MAM component. Visibility may be an option for the customer at time of order in order to ensure security. Aspects of TRON technology may be incorporated and leveraged for location, door & lock operation, elevator operation, and authentication using the various nodes (e.g., different nodes embedded in or in responsive communication with an actuated door, lock, or elevator) and node locating techniques described above.

Accordingly, in such a further embodiment of exemplary method 5100 involving a dispatched store-to-consumer logistics operation in a retail print/copy delivery environment, method may pre-screen the dispatched operation for eligibility for autonomous delivery. For example, step 5105 in method 5100 may be implemented with the modular mobile autonomy control module receiving a pre-screened dispatch command from the dispatch server. Such a pre-screened dispatch command indicates the dispatch server has verified the dispatched store-to-consumer logistics operation is an autonomous delivery eligible logistics operation, and where the pre-screened dispatch command includes at least identifier information on the ordered item, transport parameters on the ordered item, destination delivery information related to delivery of the ordered item, and delivery authentication information related to an authorized delivery recipient of the ordered item.

Prior to receiving the dispatch command in step 5105, an embodiment of method 5100 may have the dispatch server receiving an autonomous delivery order for the ordered item priced at an autonomous delivery option level below a non-autonomous delivery option level for the same ordered item; and then having the dispatch server transmitting the dispatch command to the modular mobile autonomy control module of the modular autonomous bot apparatus assembly.

In still another embodiment of method 5100, the exemplary MALVT bot apparatus assembly may, after delivery of the ordered item, return to the origin (e.g., the RPBE) with an additional item, such as a new print job to be processed at the RPBE. For example, step 5145 may be implemented with the modular mobile autonomy control module autonomously causing the modular mobility base to move from the destination location back to the original location after the ordered item is detected to be removed from within the modular cargo storage system at the destination location and an additional item is detected to be placed within the modular cargo storage system at the destination location, the additional item to be returned to the origin location as a new retail work order from the authorized delivery recipient. In this example, method 5100 may also include the step of autonomously causing, by the modular mobile autonomy control module, transfer of the additional item out from the payload area the modular cargo storage system at the origin location for processing of the additional item according to the new retail work order by a retail processing system located at the original location. Such an initiated transfer may, for example, involve actuated components and object manipulation systems on the exemplary MALVT bot apparatus assembly as described in more detail above (e.g., moving belt surfaces, actuated doors, grabbing arms, articulating arms, and the like).

Store to Home Use Cases—Try Before You Buy

In yet another store-to-consumer embodiment, a customer may order multiple sizes or colors of an item knowing that they will be keeping none or only some of the items and returning the other(s). In general, the customer, when ordering, may select a "try before you buy" option within a retailer's website and select a variety of sizes, colors, other options. The customer may also select a delivery window in which they can receive the delivery and try on the item. Customer location for the order is provided (e.g., via an entered address, provided or detected GPS coordinates, using TRON location techniques, etc.). A retail associate (or system) may pick and load the ordered multiple items into an exemplary MALVT bot apparatus along with preprinted return forms. The customer may confirm that the delivery window is still appropriate and receives an alert when the exemplary MALVT bot apparatus leaves with the ordered items. The exemplary MALVT bot apparatus travels to the delivery location and alerts the customer upon approaching the location and/or upon arrival at the delivery location. The recipient may then authenticate delivery via an app operating on the recipient's user access device, via TRON node interactions for association-based authenticated delivery, or via interaction with the display screen on the MAM component. The customer retrieves the items from the CSS component, tries on the items, keeps the desired items of the appropriate size, and returns the unwanted items to the exemplary MALVT bot apparatus. The exemplary MALVT bot apparatus may wait for a specified amount of time before returning to the retailer base with returned items or without any items if customer wishes. The exemplary MALVT bot apparatus alerts the retail associate (or system) upon arrival back at the retail base. The retail associate (or system) processes returns and/or purchases of items based upon what is returned within the exemplary MALVT bot apparatus. Depending upon the particular scenario and the retailer's business rules, a charge may be processed at that time, or refund may be processed at that time.

Accordingly, in such a further embodiment of exemplary method 5100 involving a dispatched store-to-consumer logistics operation in a "try before buy scenario", the ordered item may be trial items being sent to the authorized delivery recipient for satisfaction assessment before purchase. The trial items may, for example, be retail clothing of different sizes and/or different designs and/or different colors. As such, step 5140 involving monitoring of the unloading process for the ordered item (e.g., the ordered trial items being sent to the delivery recipient) may be implemented with the modular mobile autonomy control module (a) detecting that each of the trial items have been removed from within the modular cargo storage system based upon sensor data generated by the one or more sensors, (b) receiving a satisfaction indicator input from the authorized delivery recipient after detecting that the trial items have been removed from within the modular cargo storage system (where the satisfaction indicator input reflects that one or more of the trial items are to be returned after the satisfaction assessment), and (c) receiving the one or more trial items to be returned within the modular cargo storage system. Thereafter, step 5145 may be accomplished by autonomously causing, by the modular mobile autonomy control module, the modular mobility base to move from the destination location on the return route to the origin location after receiving the satisfaction indicator input and receiving those of the trial items to be returned in the payload area within the modular cargo storage system.

In some embodiments, the exemplary MALVT bot apparatus assembly may return in step 5145 with no return trial items because the recipient may be pleased with all of the trial items and want to purchase and keep all of the trial items. Thus, in such a situation, an embodiment of method 5100 may have step 5140 related to monitoring be implemented by the modular mobile autonomy control module detecting that each of the trial items have been removed from within the modular cargo storage system based upon sensor data generated by the one or more sensors, and then causing the modular mobility base to remain stationary for a predetermined period of time awaiting a satisfaction indicator input from the authorized delivery recipient after detecting that the trial items have been removed from within the modular cargo storage system. Step 5145 may, after the predetermined period of time expires without receiving the satisfaction indicator input, have the modular mobile autonomy control module autonomously cause the modular mobility base to move from the destination location on the return route to the origin location.

In a further detailed embodiment where the bot apparatus waits and then returns with some of the trial items, step 5140 of monitoring the unloading of the ordered item may be implemented with (a) the modular mobile autonomy control module detecting that each of the trial items have been removed from within the modular cargo storage system based upon sensor data generated by the one or more sensors; (b) having the modular mobile autonomy control module cause the modular mobility base to remain stationary up to a predetermined period of time awaiting a satisfaction indicator input from the authorized delivery recipient after detecting that the trial items have been removed from within the modular cargo storage system; (c) having the modular mobile autonomy control module receiving a satisfaction indicator input from the authorized delivery recipient after detecting that the trial items have been removed from within the modular cargo storage system and prior to the end of the predetermined period of time, the satisfaction indicator input reflecting one or more of the trial items are to be returned after the satisfaction assessment by the authorized delivery recipient; and (d) having the modular cargo storage system receiving the one or more trial items to be returned within the modular cargo storage system. Thereafter, step 5145 of method 5100 is implemented to have the modular mobile autonomy control module autonomously causing the modular mobility base to move from the destination location on the return route to the origin location after receiving the satisfaction indicator input and receiving the one or more of the trial items to be returned in the payload area within the modular cargo storage system.

Inventory Logistics Support

In still another embodiment, one or more exemplary MALVT bot apparatus assemblies (such as assembly 1700) may be dispatched to help to enable an inventory logistics support service to ferry inventory from a sourcing location to a customer on demand. In one example, this may involve an embodiment of exemplary method 4500 where the item being shipped as part of that method is an inventory item that is being moved as part of an inventory logistics support dispatched operation. For some inventory logistics support situations, there may be a need for time sensitive, high value parts inventory management that is robust and quick to respond to a customer's needs. For example, a customer may request an order via an existing web application on a website, and select a desired delivery time or a fastest delivery available with an estimated time of arrival. Such an order may be received at an inventory logistics support customer center and fulfilled. As part of fulfillment, an embodiment may dispatch, through a dispatch server, an exemplary MALVT bot apparatus for the order according to the principles and steps described above for exemplary method 4500 and its variations. For example, the customer (as a type of delivery recipient) may receive an update that the dispatched exemplary MALVT bot apparatus has left the stocking location (where the dispatched exemplary MALVT bot apparatus assembly has received the inventory item) along with an estimated time of arrival. The loaded exemplary MALVT bot apparatus may then autonomously move to the customer (e.g., the destination location) leveraging location techniques (e.g., via GPS, mapping, or TRON enablement with node locating techniques as described above) and alert recipient while approaching and/or upon arrival. The customer may then authenticate delivery with delivery recipient authentication input via, for example, an app operating on the recipient customer's user access device, via TRON node interactions for association-based authenticated delivery, or via interaction with the display screen on the MAM component, or via the steps described in more detail above in embodiments of method 4500. The exemplary MALVT bot apparatus assembly then returns to the stocking location (e.g., an origin location or a bot storage location at the stocking location).

In a further embodiment, warehousing locations for such an inventory logistics support service may have additional TRON implemented automation used with order fulfillment, such as ID or master node-enabled objects that may be shipped as inventory items, ID or master node-enabled shelving units (e.g., exemplary node-enabled shelving unit 4800 as shown and explained in FIGS. 48A-48D), and/or a node-enabled pick and place machine. Each of such node-enabled devices/systems can automatically interface and communicate with an exemplary MALVT bot apparatus assembly similar to communications described with exemplary node-enabled shelving system, and may respond to signals, messages, notifications, and commands from the exemplary MALVT bot apparatus assembly (e.g., notification of arrival, notification of the particular item to be picked up, and the like) so as to responsively facilitate an enhanced pick and load process for appropriate ordered items into the CSS component of an exemplary MALVT bot apparatus for delivery making the inventory logistics support service fully automated.

Figure 52A:
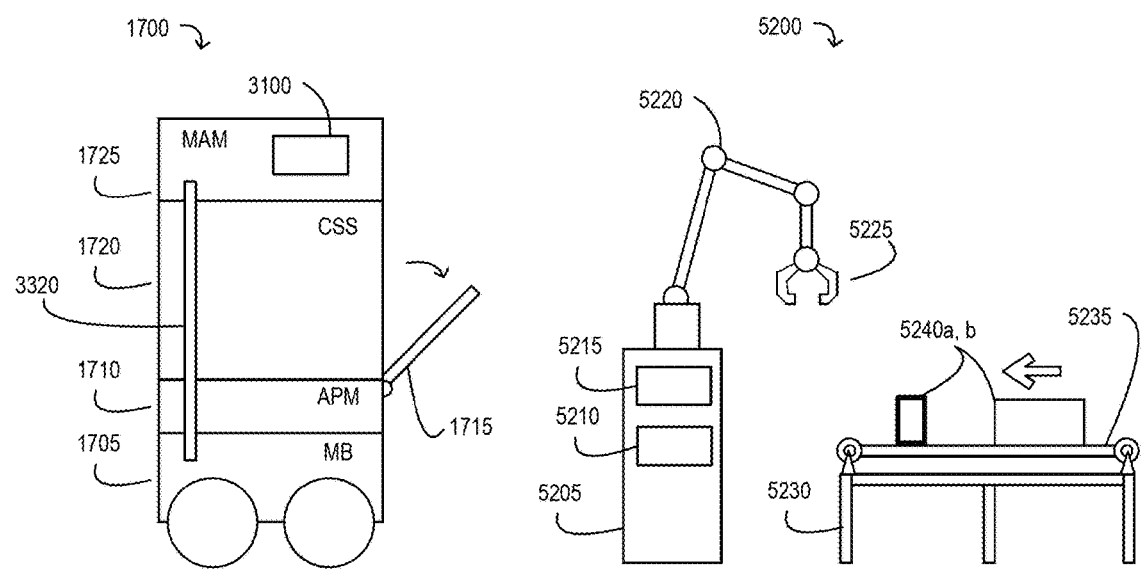
FIGS. 52A-52F are diagrams of an exemplary modular autonomous logistics transport vehicle apparatus (MALVT bot apparatus) interfacing and interacting with an exemplary node-enabled pick and place machine in a warehousing location in accordance with an embodiment of the invention.

FIG. 52A-52F are diagrams of an exemplary modular autonomous logistics transport vehicle apparatus (MALVT bot apparatus 1700) interfacing and interacting with an exemplary node-enabled pick and place machine 5200 in a warehousing location in accordance with an embodiment of the invention. Referring now to FIG. 52A, exemplary node-enabled exemplary MALVT bot apparatus assembly 1700 is shown approaching an exemplary node-enabled pick and place machine 5200 within a warehouse environment, for example, where exemplary inventory items 5240*a*, 5240*b* (e.g., part of inventory items that may have been ordered and shipped to the warehouse location and stored there for pickup and distribution). Exemplary node-enabled pick and place machine 5100, as shown FIGS. 52A-52F, has a base 5205, a wireless node 5210 (such as an ID node or master node) that interfaces with pick and place control system 5215. In some embodiments, wireless node 5210 and pick and place control system 5215 may be implemented using the same control system where an embodiment pick and place control system 5215 may operate as wireless node 5210, which communicates and interfaces with other wireless devices, such as autonomous control system 3100 in MAM 1725 of exemplary MALVT bot apparatus assembly 1700. On base 5205, system 5200 may be deployed with an articulating arm 5220 with multiple degrees of freedom and an object engaging grip head 5225 operative to be moved to engage items, such as inventory item 5240*a*, from a conveyor belt 5235 disposed on conveyor base 5230. In operation, exemplary pick and place machine 5200 may interface with inventory management systems at the warehousing location to request particular inventory items be available within reach of the pick and place machine 5200 so as to allow for automated placement of such items from the machine 5200 (e.g., conveyor belt 5235) to exemplary CSS 1720 of exemplary MALVT bot apparatus assembly 1700.

Figure 52B:
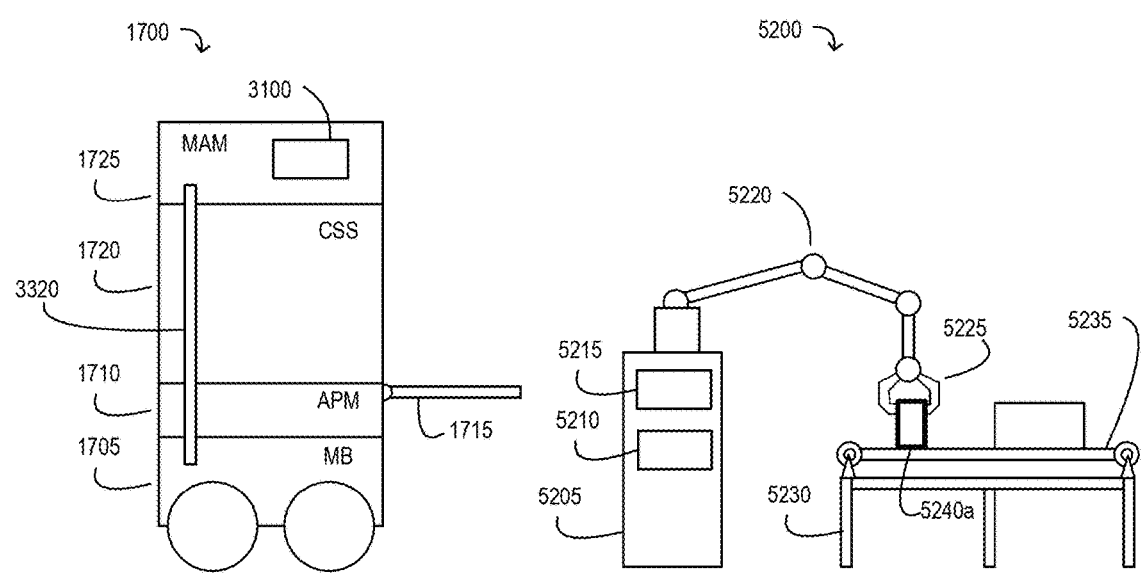
Figure 52C:
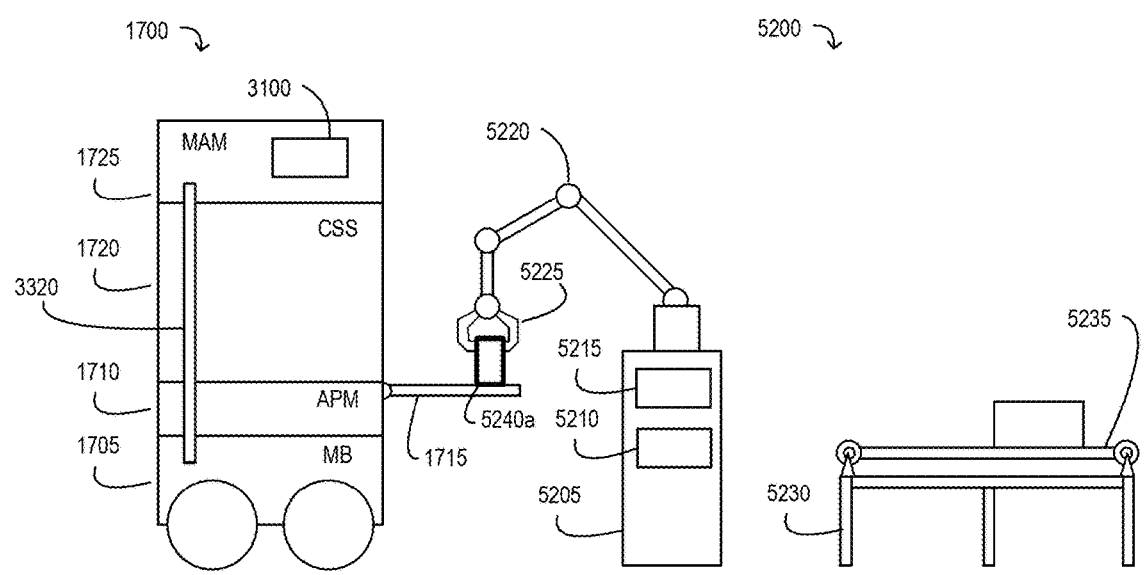
Figure 52D:
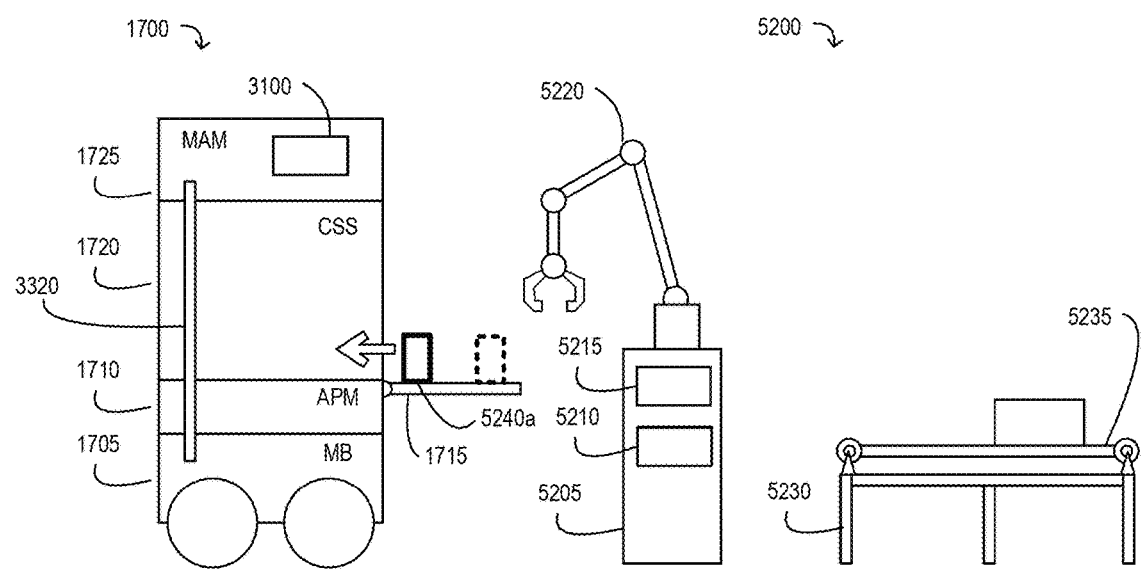
Figure 52E:
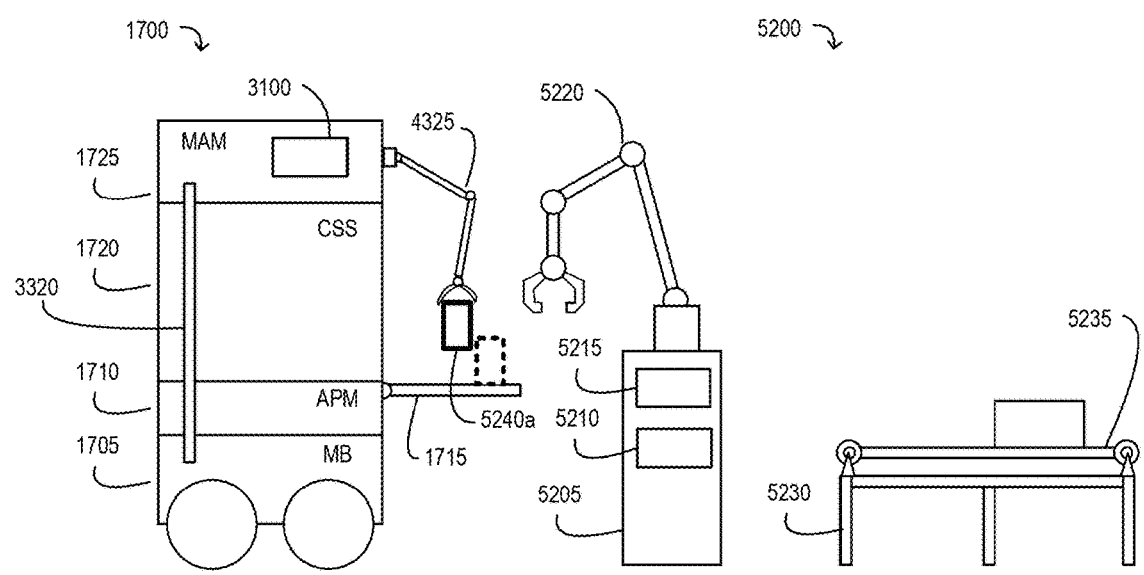
Figure 52F:
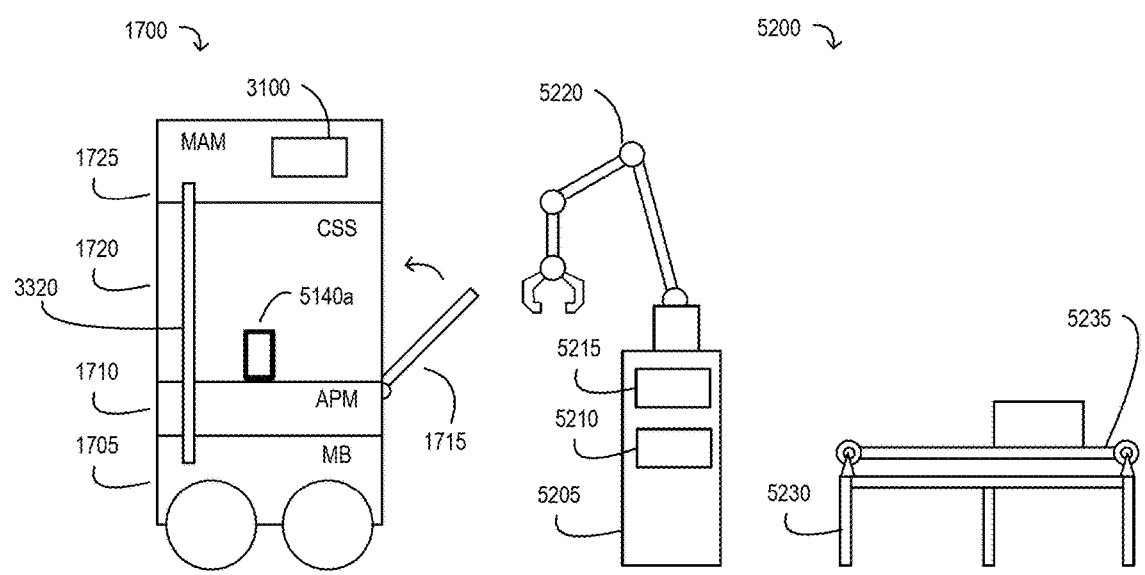

Again, in the example shown in FIG. 52A, exemplary MALVT bot apparatus assembly 1700 has approached the exemplary node-enabled pick and place machine 5200 in order to pick up an inventory item, such as inventory item 5240*a*. As exemplary MALVT bot apparatus assembly 1700 approaches the exemplary node-enabled pick and place machine 5200, exemplary MALVT bot apparatus assembly 1700 communicates with the node 5210 on the machine 5200 and opens its cargo door 1715. With the identification of the particular inventory item needed, node-enabled pick and place machine 5200 has its control system 5215 manipulate articulating arm 5220 and head 5225 to obtain custody of the inventory item 5240*a* identified by exemplary MALVT bot apparatus assembly 1700 as shown in FIG. 52B. With control of inventory item 5240*a*, the control system 5215 of machine 5200 picks the item 5240*a* from conveyor belt 5235 and places the item 5240*a* with exemplary MALVT bot apparatus assembly 1700—e.g., on the extended cargo door 1715 as shown in FIG. 52C. In FIG. 52D, node-enabled pick and place machine 5200 relinquishes control of item 5240*a* to exemplary MALVT bot apparatus assembly 1700. In one embodiment, the articulating arm 5220 and head 5225 may place the item 5240*a* within the payload area of the CSS 1720 on exemplary MALVT bot apparatus assembly 1700 before relinquishing control of item 5240*a*. However, in other embodiments, exemplary MALVT bot apparatus assembly 1700 may employ and control its own articulating arm (such as arm 4325) or other actuators and object manipulation systems (e.g., moving belts, sweeping arms, grabbing arms, and the like) to autonomously move the item 5240*a* into the payload area of CSS 1720 as shown in FIG. 52E. Once the item 5420*a* is within the payload area of CSS 1720 of exemplary MALVT bot apparatus assembly 1700, MAM 1725 actuates door 1715 to a closed position as shown in FIG. 52F to complete the example loading or pick up task involving exemplary node-enabled pick and place machine 5200.

Those skilled in the art will appreciate that other types of pick and place machines may be node-enabled so as to interface and communicate with exemplary MALVT bot apparatus assembly 1700 as part of loading such an item 5240*a* into the exemplary MALVT bot apparatus assembly 1700. Different inventory item feeder structure may be used (other than or in addition to a conveyor) and different object manipulation systems may be used (other than or in addition to an articulating arm) as part of an exemplary node-enabled pick and place machine that can be responsive to communications with exemplary MALVT bot apparatus assembly 1700 and facilitate automated loading of the exemplary MALVT bot apparatus assembly 1700 with items to be delivered.

Accordingly, in a further embodiment of exemplary method 5100 involving a dispatched store-to-consumer logistics operation where pickup of the ordered item involves interfacing and interacting with a node-enabled pick and place machine, the step of receiving the ordered item may involve further steps. For example, in such an embodiment of method 5100, the origin location may be a warehousing location for warehoused items and where the dispatch command further includes a pickup location within the warehousing location where the warehoused ordered item is to be provided by a wireless node-enabled pick and place machine (e.g., machine 5200). As such, step 5115 of receiving the ordered item in the payload area within the modular cargo storage system may have the modular mobile autonomy control module autonomously causing the modular mobility base to move from within the warehousing location to the pickup location and then have the modular mobile autonomy control module detecting an unprompted advertising signal from the wireless node-enable pick and pack machine as the modular mobility base approaches the pickup location (e.g., an advertising signal from node 5210). Once the signal is detected, step 5115 may also establish a secure association between the modular mobile autonomy control module and the wireless node-enabled pick and place machine where the secure association between the wireless node-enabled pick and place machine and the modular mobile autonomy control module allows secure sharing of information between the wireless node-enabled pick and place machine and the modular mobile autonomy control module and is pre-authorized by the dispatch server as it relates to the dispatched store-to-consumer logistics operation. With the established secure association between the wireless node-enabled pick and place machine and the modular mobile autonomy control module (which may also involve generating association data reflecting a permissive logical connection between the two devices), step 5115 may proceed with having the modular mobile autonomy control module securely sharing the identifier of the ordered item involved in the dispatched store-to-consumer logistics operation with the wireless node-enabled pick and place machine, and then receiving the ordered item in the payload area within the modular cargo storage system from the wireless node-enabled pick and place machine.

As explained above, such a node-enabled pick and place machine may place the ordered item within the payload area of the modular cargo storage system. Thus, in the example from above, step 5115 may further involve requesting, by the modular mobile autonomy control module, the wireless node-enabled pick and place machine to obtain the ordered item based upon the identifier of the ordered item securely shared with the wireless node-enabled pick and place machine; and receiving, by the modular cargo storage system, the ordered item from the wireless node-enabled pick and place machine in response to the requesting step. In this example, the ordered item received from the wireless node-enabled pick and place machine is placed by the wireless node-enabled pick and place machine within the payload area of the modular cargo storage system.

As also explained above, an embodiment of method 5100 may have such a node-enabled pick and place machine place the ordered item on an actuated belt surface as part of step 5115. For example, step 5115 may be implemented in such an embodiment with the modular mobile autonomy control module requesting the wireless node-enabled pick and place machine to obtain the ordered item based upon the identifier of the ordered item securely shared with the wireless node-enabled pick and place machine; receiving the ordered item from the wireless node-enabled pick and place machine in response to the requesting step and placed by the wireless node-enabled pick and place machine on an actuated belt surface of the modular cargo storage system; and actuating, by the modular mobile autonomy control module, the actuated belt surface to move the ordered item placed on the actuated belt surface to within the payload area of the modular cargo storage system.

Further embodiments of method 5100 may have such a node-enabled pick and place machine place the ordered item on an extended ramp (e.g., the opened cargo door, and the like) so that the exemplary MALVT bot apparatus assembly 1700 may use its own object manipulation systems to move the ordered into the payload area of the CSS. For example, step 5115 may be implements in such an embodiment with the modular mobile autonomy control module requesting the wireless node-enabled pick and place machine to obtain the ordered item based upon the identifier of the ordered item securely shared with the wireless node-enabled pick and place machine; receiving the ordered item from the wireless node-enabled pick and place machine in response to the requesting step and placed by the wireless node-enabled pick and place machine on an extended ramp of the modular cargo storage system; and actuating, by the modular mobile autonomy control module, an actuated grabbing arm disposed within the modular cargo system to move the ordered item from on the extended ramp to within the payload area of the modular cargo storage system. Alternatively or in addition, the modular mobile autonomy control module may actuate other object manipulation systems on the exemplary MALVT bot apparatus assembly (e.g., an actuated sliding arm 2085/2700 on the CSS or APM and/or an articulating arm 4325 disposed on the bot apparatus assembly) to move the ordered item into the modular cargo storage system.

Further embodiments of method 5100 may involve the transport of a node-enabled ordered item as part of a dispatched store-to-home logistics operation. In such an embodiment, the identifier information on the ordered item further may include a node identifier corresponding to a wireless node associated with the ordered item. As such, step 5115 of receiving the ordered item in the payload area within the modular cargo storage system may have the modular mobile autonomy control module detecting an unprompted advertising signal from the wireless node associated with the ordered item and then establishing a secure association between the modular mobile autonomy control module and the wireless node associated with the ordered item after detecting the unprompted advertising signal from the wireless node associated with the ordered item. Such a secure association between the wireless node associated with the ordered item and the modular mobile autonomy control module allows secure sharing of information between the wireless node associated with the ordered item and the modular mobile autonomy control module, where the secure association is pre-authorized by the dispatch server as it relates to the dispatched store-to-consumer logistics operation. Thereafter, step 5115 continues with the modular cargo storage system receiving the node-enabled ordered item in the payload area within the modular cargo storage system after establishing the secure association.

In this same embodiment, method 5100 may have step 5140 of monitoring unloading of the ordered item from within the modular cargo storage system being implemented by monitoring a location of the wireless node associated with the ordered item (operating as an ID node) by the modular mobile autonomy control module (operating as a master node); and detecting, by the modular mobile autonomy control module, when the location of the wireless node associated with the ordered item is outside the modular autonomous bot apparatus assembly.

Dispatched Logistics Operations without a Delivery Recipient Present

Beyond exemplary method 5100, some embodiments may have a dispatched store-to-consumer logistics operation involving delivery to a location where the delivery recipient may not be present for delivery authentication input from a person and/or assistance with retrieving the ordered item from within the payload of the CSS of exemplary MALVT bot apparatus assembly 1700. For example, an embodiment may be able to authenticate delivery specific to a location with delivery authentication input coming from a facility node and where articulating arms (e.g., arm 4325) or other object manipulation systems described above may be deployed by exemplary modular components of the assembly (e.g., moving belt surfaces 2080*a*, 2080*b*, sweeping arms 2085, 2700, grabbing arms 2090, 2710) as part of depositing the ordered item at its destination.

Figure 53:
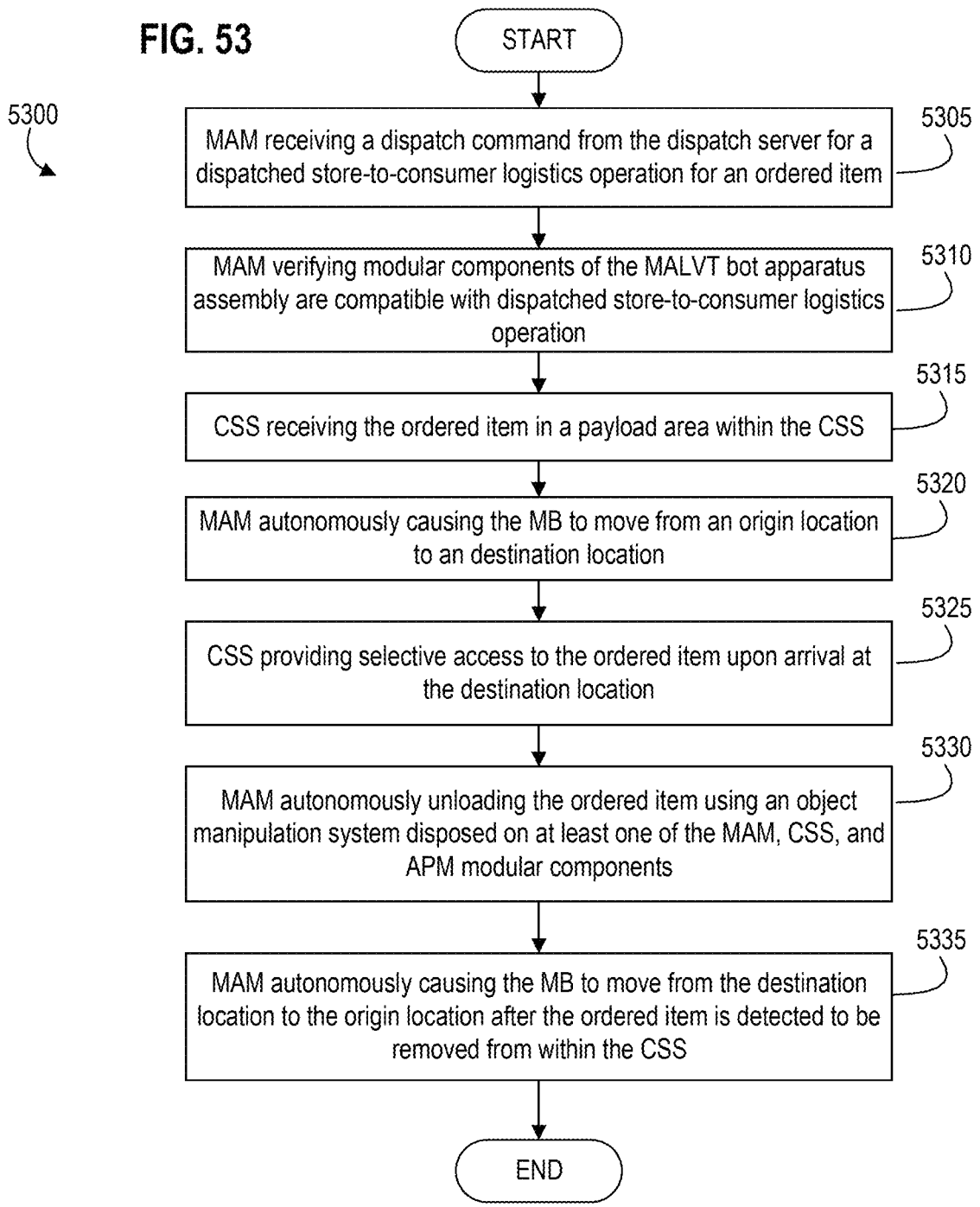
FIG. 53 is a flow diagram of an alternative embodiment of an exemplary method for performing a dispatched store-to-consumer logistics operation related to an ordered item and using a modular autonomous bot apparatus assembly (MALVT bot apparatus assembly) and a dispatch server in accordance with an embodiment of the invention.

FIG. 53 is a flow diagram of an alternative embodiment of an exemplary method for dispatched store-to-consumer logistics operation related to an ordered item and using a modular autonomous bot apparatus assembly (MALVT bot apparatus assembly) and a dispatch server in accordance with an embodiment of the invention. An embodiment of such a method 5300 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5300 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 5300.

Referring now to FIG. 53, exemplary method 5300 begins at step 5305 with the modular mobile autonomy control module receiving a dispatch command from the dispatch server. Such a dispatch command includes at least identifier information on the ordered item, transport parameters on the ordered item, and destination delivery information related to delivery of the ordered item.

At step 5310, method 5300 has the modular mobile autonomy control module verifying that each of the modular mobile autonomy control module, the modular mobility base, the modular auxiliary power module, and the modular cargo storage system are compatible with the dispatched store-to-consumer logistics operation based upon the dispatch command. Thereafter, at step 5315, method 5300 has the modular cargo storage system receiving the ordered item in a payload area within the modular cargo storage system.

At step 5320, method 5300 has the modular mobile autonomy control module autonomously causing the modular mobility base to move from an origin location on a route to a destination location identified by the destination delivery information. And then, at step 5325, method 5300 has the modular cargo storage system providing selective access to the ordered item within the modular cargo storage system upon arrival at the destination location.

At step 5330, method 5300 has the modular mobile autonomy control module, autonomously unloading the ordered item from within the modular cargo storage system using an object manipulation system disposed on at least one of the modular mobile autonomy control module, the modular cargo storage system, and the modular auxiliary power module. Thereafter, at step 5335, method 5300 has the modular mobile autonomy control module autonomously causing the modular mobility base to move from the destination location on a return route to the origin location after the ordered item is removed from within the modular cargo storage system by the object manipulation system.

In a further embodiment of method 5300, delivery authentication input may be provided by a facility node at the destination location. For example, in such a further embodiment of method 5300, the dispatch command may also include delivery authentication information related to an authorized facility node associated with the destination location. As such, method 5300 may include the step of receiving delivery authentication input by the modular mobile autonomy control module from an external wireless node disposed external to the modular autonomous bot apparatus assembly at the destination location. Accordingly, in this embodiment of method 5300, step 5325 may be implemented with the modular cargo storage system providing selective access to the ordered item within the modular cargo storage system (e.g., at the control of the autonomous control system 3100 in MAM 1725) only when the delivery authentication input received correlates to the delivery authentication information indicating that the external wireless node providing the delivery authentication input is the authorized facility node.

In still another embodiment of method 5300, a remote delivery recipient may be notified of the approaching delivery despite not being at the destination location. For example, in such a further embodiment of method 5300, the dispatch command may also include notification information for a designated notification recipient for the ordered item. As such, method 5300 may include the step of notifying, by the modular mobile autonomy control module, the designated notification recipient for the ordered item using the notification information, the step of notifying being triggered when the modular autonomous bot apparatus assembly is within a threshold notification range of the destination location identified by the destination information.

Consumer-to Store Use Cases—Returns

While the embodiments described above relate to store-to-consumer logistics operations, further embodiments may have the consumer sending something back to a supplier entity, such as a person that supplied the item, a retail store where the item was purchased, or another business entity where return of such an item may be arranged through that business entity. In such further embodiments, consumer-to-store logistics operations may involve dispatched exemplary MALVT bot apparatus assembly. For example, an embodiment may have a retailer provide a "return to local store" option within its normal returns process flow for customers and items that fit transport parameters for an exemplary MALVT bot apparatus (e.g., distance to store, size and value of items, etc.). In this general embodiment, a customer may select the return option, print return documentation, and select a desired time for return pickup (e.g., a 15 minute window/time for returns pickup). The return system with which the customer is interacting may then dispatch an exemplary MALVT bot apparatus from a logistics base at the retailer to coincide with the arrival window. The exemplary MALVT bot apparatus receives return information from the dispatch system, embarks from the base and travel to the customer (or designated pickup site). The exemplary MALVT bot apparatus may contact (e.g., via text/email/phone call) customer on route to reconfirm and transmit alerts upon arrival. The customer may then authenticate delivery via an app operating on the customer's user access device, e.g., via TRON node interactions for association-based authenticated delivery, or via interaction with the display screen on the MAM component. The customer then loads return items and paperwork into the CSS component of the exemplary MALVT bot apparatus. The exemplary MALVT bot apparatus then returns to the retailer's logistics base and alerts retail associate upon arrival (or as approaching) for timely assistance unloading & return processing. Aspects of TRON technology may be incorporated and leveraged for location, door & lock operation, elevator operation, and authentication using the various nodes (e.g., different nodes embedded in or in responsive communication with an actuated door, lock, or elevator) and node locating techniques described above.

Figure 54:
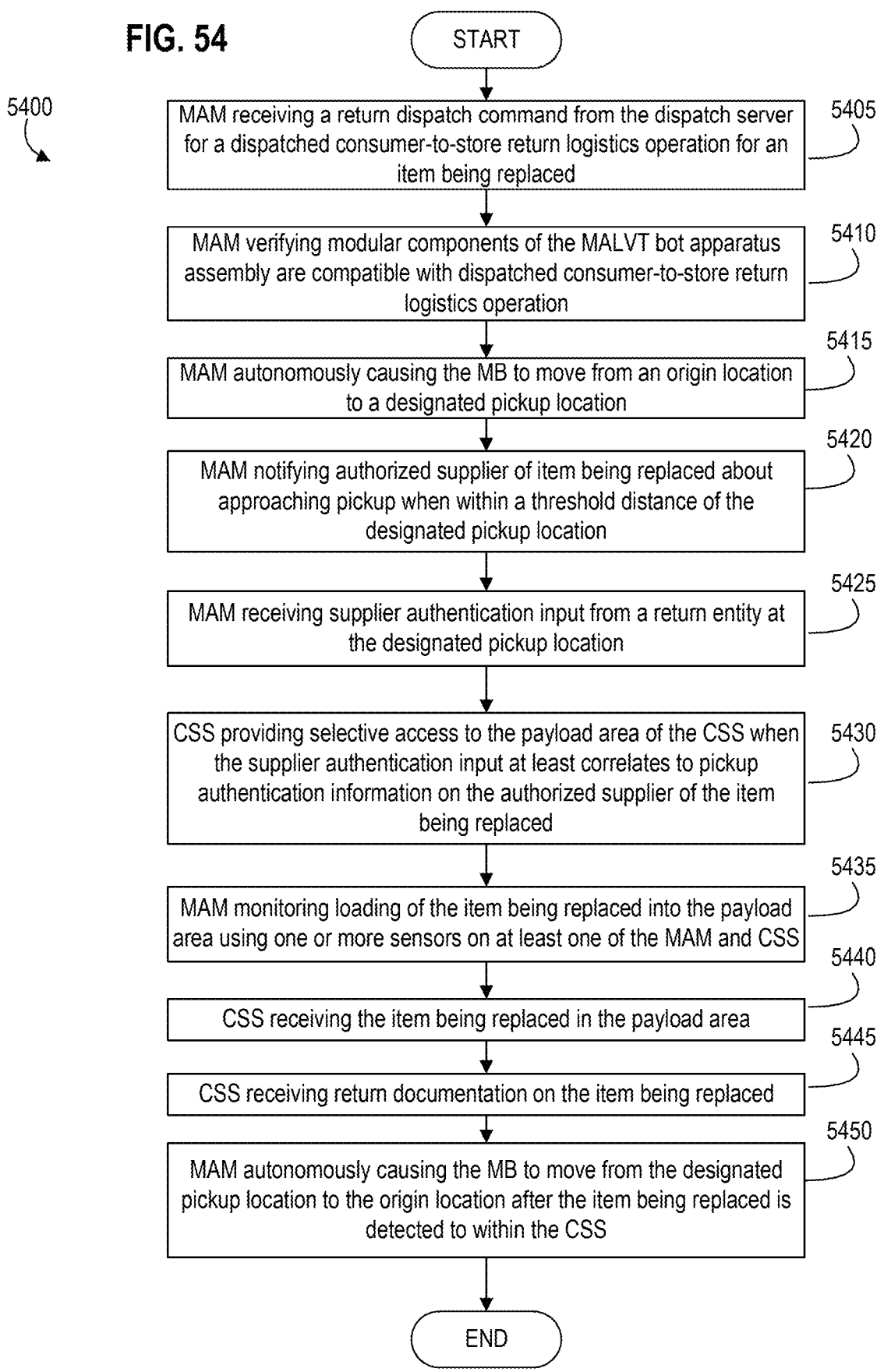
FIG. 54 is a flow diagram of an embodiment of an exemplary method for performing a dispatched consumer-to-store logistics operation related to an item being replaced and using a modular autonomous bot apparatus assembly (MALVT bot apparatus assembly) and a dispatch server in accordance with an embodiment of the invention.

FIG. 54 is a flow diagram of an embodiment of an exemplary method 5400 for performing a dispatched consumer-to-store logistics operation related to an item being replaced and using a modular autonomous bot apparatus assembly (MALVT bot apparatus assembly) and a dispatch server in accordance with an embodiment of the invention. An embodiment of method 5400 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5400 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 5400.

Referring now to FIG. 54, exemplary method 5400 begins at step 5405 with the modular mobile autonomy control module receiving a return operation dispatch command from the dispatch server. In one embodiment, the return operation dispatch command has at least identifier information on the item being replaced, transport parameters on the item being replaced, designated pickup information related to pickup of the item being replaced, and pickup authentication information related to an authorized supplier of the item being replaced.

In a further embodiment, step 5405 may have the modular mobile autonomy control module receiving a return order assignment message as the return operation dispatch command from a retail system (operating as the dispatch server) that received the return transaction order for the item being replaced. In such a further embodiment of step 5405, the designated pickup information related to the pickup of the item being replaced may include a pickup time and pickup date as selected in the return transaction order.

At step 5410, method 5400 proceeds with having the modular mobile autonomy control module verifying that each of the modular mobile autonomy control module, the modular mobility base, the modular auxiliary power module, and the modular cargo storage system are compatible with the dispatched consumer-to-store return logistics operation based upon the dispatch command. Once verified in step 5410, method 5400 proceeds to step 5415 where the modular mobile autonomy control module autonomously causes the modular mobility base to move from an origin location on a route or path to a designated pickup location identified by the designated pickup information.

At step 5420, method 5400 proceeds with having the modular mobile autonomy control module notifying the authorized supplier of the item being replaced of an approaching pickup for the item being replaced once the modular autonomous bot apparatus assembly is within a threshold notification range of the designated pickup location identified by the designated pickup information. This type of pre-pickup autonomously triggered notification of the entity providing the item being replaced may be conducted in various ways. For example, notifying as part of step 5420 may be implemented by generating a display alert for the authorized supplier of the item being replaced on a display on the modular mobile autonomy control module once the modular autonomous bot apparatus assembly is within the threshold notification range of the designated pickup location identified by the designated pickup information. In another example, notifying as part of step 5420 may be implemented by generating an audio notification for the authorized supplier of the item being replaced on a speaker on the modular mobile autonomy control module (or other part of the exemplary MALVT bot apparatus assembly) once the modular autonomous bot apparatus assembly is within the threshold notification range of the designated pickup location.

In still another example, notifying as part of step 5420 may be implemented by transmitting a pickup notification message (e.g., a text message, an electronic mail message, and a phone call) to an external wireless node (e.g., a smartphone) once the modular autonomous bot apparatus assembly is within the threshold notification range of the pickup location identified by the designated pickup information, where such an external wireless node may be related to the authorized supplier of the item being replaced, a designated third party, or the like. In yet another example, notifying as part of step 5420 may be implemented by transmitting a pickup notification message to such an external wireless node after the modular autonomous bot apparatus assembly moves from the origin location and before reaching such a threshold notification range instead of or in addition to a subsequent notification once within the threshold notification range. Such a notification may include an arrival estimate indicating an estimated time to arrive at the pickup location.

In an additional example, notifying as part of step 5420 may be implemented by the modular mobile autonomy control module transmitting a verification request to confirm pickup of the item being replaced to the authorized supplier of the item being replaced. Such a verification request may ask for a responsive confirmation that the item being replaced should be picked up by the modular autonomous bot apparatus assembly at the designated pickup location. After transmitting the verification request, the modular mobile autonomy control module may autonomously cause the modular mobility base to continue moving to the designated pickup location to complete the dispatched consumer-to-store return logistics operation unless the responsive confirmation from the authorized supplier indicated that the item being replaced should not be picked up at that designated pickup location or, alternatively, if a response indicates a changed designated pickup location.

At step 5425, method 5400 proceeds with receiving supplier authentication input by the modular mobile autonomy control module from a return entity disposed external to the modular autonomous bot apparatus assembly at the designated pickup location. The supplier authentication input received may, for example, be provided by the return entity through a user input panel (e.g., input in the form of an access code or biometric input from the return entity) disposed on the modular autonomous bot apparatus entity) coupled to the modular mobile autonomy control module. Additionally, similar supplier authentication input received may be provided by the return entity through an external wireless node disposed external to the modular autonomous bot apparatus assembly.

An embodiment of step 5425 may have the pickup authentication information including an identifier of the authorized supplier for the item being replaced as part of the dispatched consumer-to-store return logistics operation. As such, receiving the supplier authentication input may involve, for example, the modular mobile autonomy control module detecting an advertising signal as the supplier authentication input from an external wireless node within a predetermined range of the modular autonomous bot apparatus assembly once the modular autonomous bot apparatus assembly has arrived at the designated pickup location identified by the designated pickup information; and then authenticating that the external wireless node is associated with the authorized supplier for the item being replaced within the modular cargo storage system based upon the identifier of the authorized supplier and identifier information within the detected advertising signal broadcast from the external wireless node.

In another embodiment of step 545, the pickup authentication information related to the dispatched consumer-to-store return logistics operation may include an identifier of the authorized supplier for the item being replaced as part of the dispatched consumer-to-store return logistics operation. As such, the step of receiving the supplier authentication input may be implemented with the modular mobile autonomy control module detecting an unprompted advertising signal (e.g., not in response to an interrogation signal from the bot) from an external wireless node within a predetermined range of the modular autonomous bot apparatus assembly once the modular autonomous bot apparatus assembly has arrived at the designated pickup location identified by the designated pickup information; and establishing a secure association between the external node and the modular mobile autonomy control module after detecting the unprompted advertising signal from the external wireless node. Such a secure association between the external node and the modular mobile autonomy control module may reflect a logical permissive connection that allows secure sharing of information between the external node and the modular mobile autonomy control module. Such a secure association may be pre-authorized by the dispatch server as it relates to the dispatched consumer-to-store return logistics operation.

At step 5430, method 5400 proceeds with having the modular cargo storage system providing selective access to a payload area within the modular cargo storage system only when the supplier authentication input received correlates to the pickup authentication information indicating that the return entity providing the supplier authentication input is the authorized supplier of the item being replaced.

At step 5435, method 5400 proceeds with having the modular mobile autonomy control module monitoring the loading of the item being replaced into the payload area of the modular cargo storage system using one or more sensors on at least one of the modular mobile autonomy control module and the modular cargo storage system. As part of step 5435, monitoring the loading may involve generating a log entry in a custodial inventory data structure maintained on the MAM of the exemplary MALVT bot apparatus assembly when the item being replaced is detected to be within the modular cargo storage system. Such a log entry in the custodial inventory data structure kept in memory of the MAM reflects the receipt of the item being replaced within the modular cargo storage system.

In a further embodiment of method 5400, monitoring step 5435 may also be implemented by capturing sensor data from one or more of the sensors on at least one of the modular mobile autonomy control module and the modular cargo storage system, and then detecting when the item being replaced is received within the modular cargo storage system based upon the captured sensor data (e.g., using the captured sensor data as sensor data to be processed, and the processed sensor data indicating the item being replaced is located within the sensor range of the sensors and, thus, within the payload area of the modular cargo storage system). For example, the captured sensor data may be one or more visual images of what is disposed within the modular cargo storage system.

In a more detailed further example, step 5435 may be implemented by generating barcode scan data related to item being replaced as the item is received within the modular cargo storage system using a barcode scanner as one of the sensors, and processing the generated barcode scan data to monitor the ordered item as the ordered item is placed within the modular cargo storage system. In another more detailed further example, step 5435 may be implemented by generating image data related to item being replaced as the item is received within the modular cargo storage system using a camera as one of the sensors, and processing the generated image data to monitor the ordered item as the ordered item is placed within the modular cargo storage system. In still another more detailed further example, step 5435 may be implemented by generating video data related to item being replaced as the item is received within the modular cargo storage system using a video camera as one of the sensors, and processing the generated video data to monitor the ordered item as the ordered item is placed within the modular cargo storage system. In yet another more detailed further example, step 5435 may be implemented by capturing audio data using a microphone as one of the sensors disposed to record sound within and proximate to the modular cargo storage system as the item is received within the modular cargo storage system, and processing the captured audio data to monitor the ordered item as the ordered item is placed within the modular cargo storage system.

In an additional example, step 5435 may be implemented by detecting movement of a wireless node associated with the item being replaced as the node-enabled item is received within the modular cargo storage system based upon signals broadcast from the wireless node associated with the item being replaced. For example, a signal strength of the signals from the node-enabled item being replaced may peak above a threshold level when the item is received within the modular cargo storage system.

In an additional example, step 5435 may be implemented by detecting a change in location of a wireless node associated with the item being replaced from outside the modular cargo storage system to inside the modular cargo storage system as the node-enabled item being replaced is received within the modular cargo storage system as determined by the modular mobile autonomous control module. This may be accomplished using node location techniques described.

At step 5440, method 5400 proceeds with receiving, by the modular cargo storage system, the item being replaced in the payload area within the modular cargo storage system. Step 5430 of providing access, step 5435 of monitoring the loading and step 5440 of receiving the item being replaced may be implemented in an overlapping manner so as to allow access for loading, monitoring the loading of the item being replaced as part of receiving the item being replaced within the payload area.

In more detail, the loading that may be part of steps 5430-5440 may involve actuated and other object manipulation systems deployed on the exemplary MALVT bot apparatus assembly, such as actuated doors, joints, locks, sliding arms, grabbing arms, and the like. For example, step 5430 of providing access may involve actuating, by the modular mobile autonomy control module, an actuated cargo door (e.g., door 1715) disposed on the modular auxiliary power module (or modular CSS 1720) to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position. Actuating the door may, in some examples, involve actuating an actuated joint (e.g., a powered hinge) on the actuated cargo door to cause the actuated cargo door to move from the closed position to the open position. In further examples, the actuated cargo door may have an electro-mechanical lock so that providing access in step 5430 may involve actuating such an electro-mechanical lock on the actuated cargo door to cause the actuated cargo door to unlock before moving from the closed position to the open position as part of providing selective access to the payload area.

In a further example, step 5430 and/or step 5440 may involve actuating, by the modular mobile autonomy control module, an actuated sliding arm disposed on the modular cargo storage system to move the item being replaced into the payload area within the modular cargo storage system. In still another example, step 5430 and/or step 5440 may involve actuating, by the modular mobile autonomy control module, an actuated grabbing arm disposed on the modular cargo storage system to grab and move the item being replaced into the payload area within the modular cargo storage system as part of receiving the item being replaced. Further still, another example may have step 5430 and/or 5440 actuating, by the modular mobile autonomy control module, an actuated belt surface disposed on the modular auxiliary power module as a movable support surface exposed within the payload area inside the modular cargo storage system (or on the cargo door inner surface as a type of extended ramp), where the actuated belt surface causes the item being replaced on the actuated belt surface to move within the payload area as part of receiving the item being replaced.

At step 5445, method 5400 proceeds with having the modular cargo storage system also receiving return documentation provided by the authorized supplier of the item being return. The return documentation indicating the item being replaced is authorized to be returned in accordance with a return transaction order received by the dispatch server; and At step 5450, the embodiment of method 5400 concludes with the modular mobile autonomy control module autonomously causing the modular mobility base to move from the designated pickup location on a return route to the origin location after the item being replaced is detected within the modular cargo storage system based upon monitoring the loading of the item being replaced and after the return documentation is loaded within the modular cargo storage system with the item being replaced.

Further embodiments of method 5400 may further involve notifying upon approaching the return to the origin location. For example, an embodiment of method 5400 may also include the step of notifying, by the modular mobile autonomy control module, a retail entity at the origin location of an approaching delivery for the item being replaced once the modular autonomous bot apparatus assembly is within a threshold notification range of the origin location. In further example, an embodiment of method 5400 may also include the step of notifying, by the modular mobile autonomy control module, a retail entity at the origin location and/or the authorized supplier about delivery of the item being replaced after the modular autonomous bot apparatus assembly arrives at the origin location.

In more detailed embodiments of method 5400, the steps of 5415 and 5450 may involve further detailed actions of the exemplary MALVT bot apparatus assembly when moving from one location to another. For example, an embodiment of step 5415 may have the modular mobile autonomy control module autonomously causing the modular mobility base to move from the origin location to the designated pickup location while interacting with a wireless building facility node to actuate a pathway obstacle (e.g., an actuated door controlled by the wireless building facility node, an actuated elevator controlled by the wireless building facility node, an actuated lock controlled by the wireless building facility node, and the like) disposed in a path on the route to the designated pickup location. Interacting by the modular mobile autonomy control module with the wireless building facility node to actuate the pathway obstacle may, for example, involve establishing an authorized association pairing between the modular mobile autonomy control module and the wireless building facility node based upon the authentication information related to the dispatched logistics operation; and causing the wireless building facility node to actuate the pathway obstacle after establishing the authorized association pairing between the modular mobile autonomy control module and the wireless building facility node.

In further example embodiments of method 5400, the steps of 5415 and 5450 may involve manual interactions with pathway obstacles. For example, an embodiment of step 5415 may involve autonomously causing the modular mobility base to move from the origin location to the designated pickup location by having the modular mobile autonomy control module autonomously causing the modular mobility base to move from the origin location to the designated pickup location while manually/physically engaging a pathway obstacle (e.g., a manually actuated door, a manually actuated elevator, a manually actuated lock, and the like) disposed in a path on the route to the designated pickup location using one or more articulating arms (e.g., arm 4325) disposed on the modular autonomous bot apparatus assembly and using sensors disposed on at least one of the modular mobility base and the modular mobile autonomy control module. Such manual engagement of the pathway obstacle using the articulating arm and sensors may, in more detail, involve guiding, by the modular mobile autonomy control module, the articulating arm to a control element of the pathway obstacle using one or more of the sensors disposed on at least one of the modular mobility base and the modular mobile autonomy control module; and actuating the pathway obstacle, by the modular mobile autonomy control module, once the articulating arm engages the control element of the pathway obstacle. Examples of such a control element for the pathway obstacle may include, but not be limited to, a handle for the pathway obstacle, a button for the pathway obstacle, a switch for the pathway obstacle, and/or a portion of a control panel for the pathway obstacle (e.g., a touch panel, a keypad, and the like).

Consumer-to Store Use Cases—Consumable & Warranty/Repair Swaps

While the embodiments described above relate to consumer-to-store logistics operations, further embodiments may involve an exchange or swap of items that may be enhanced and improved with deploying an exemplary MALVT bot apparatus assembly. For example, a patient may be at home with home medical equipment (e.g., portable oxygen). The home medical equipment may need refilling with some type of consumable item swapped out, such as when the patient receives a full portable oxygen tank from a supplier in exchange for the empty tank at the patient's home. In such an embodiment, the supplier may dispatch an exemplary MALVT bot apparatus to help with such an exchange. Deliveries may be scheduled and/or on an ad hoc schedule based on the needs of the patient. Authentication needs may be dictated by patient/customer and/or supplier company. For example, the exemplary MALVT bot apparatus may alert the patient/customer when it is dispatched and give an estimated time of arrival. The receiving patient/customer may then authenticate delivery via an app operating on the recipient's user access device, via TRON node interactions for association-based authenticated delivery, or via interaction with the display screen on the MAM component. The patient or home care assistant at the patient's home may remove a full tank from the exemplary MALVT bot apparatus and load the empty tank into the exemplary MALVT bot apparatus for return trip. Such loading and unloading of items may be monitored by the exemplary MALVT bot apparatus to ensure cargo is securely in place prior to return to the supplier. The exemplary MALVT bot apparatus may be modified for easy collection and deposit of medical equipment by customers. This may involve articulated assist and manipulation of the swappable consumable (e.g., oxygen tank, bed linens, and the like) being delivered and picked up from the patient/customer. Aspects of TRON technology may be incorporated and leveraged for location, proper door identification, door & lock operation, elevator operation, receipt for swapping, and authentication using the various nodes (e.g., different nodes embedded in or in responsive communication with an actuated door, lock, or elevator) and node locating techniques described above.

In another embodiment, such an exchange or swap may involve a warranty or repair scenario. For example, a consumer may interact (in person or online with a retail sales system) with a company to request a replacement for an item still under warranty by the company. In such an embodiment, the consumer may select an appropriate time of day for the replacement to be delivered. The company may cause a dispatch system to dispatch an exemplary MALVT bot apparatus from its facility to the customer's desired location (e.g., office, home, or mobile location (such as a vehicle)) with a replacement item inside. The customer receives a notification of the exemplary MALVT bot apparatus being dispatched along with an estimated time of arrival. The exemplary MALVT bot apparatus arrives, and the consumer may then authenticate delivery via an app operating on the recipient's user access device, via TRON node interactions for association-based authenticated delivery, or via interaction with the display screen on the MAM component. As the customer unloads the exemplary MALVT bot apparatus, the exemplary MALVT bot apparatus may monitor unloading (e.g., making sure the replacement item is unloaded from the CSS), may monitor loading the damaged/malfunctioning item into the CSS of the exemplary MALVT bot apparatus, and then the exemplary MALVT bot apparatus returns to the company's dispatch base alerting an associate (or system) for unloading of the damaged/malfunctioning. Aspects of TRON technology may be incorporated and leveraged for location, door & lock operation, elevator operation, and authentication using the various nodes (e.g., different nodes embedded in or in responsive communication with an actuated door, lock, or elevator) and node locating techniques described above.

Figure 55:
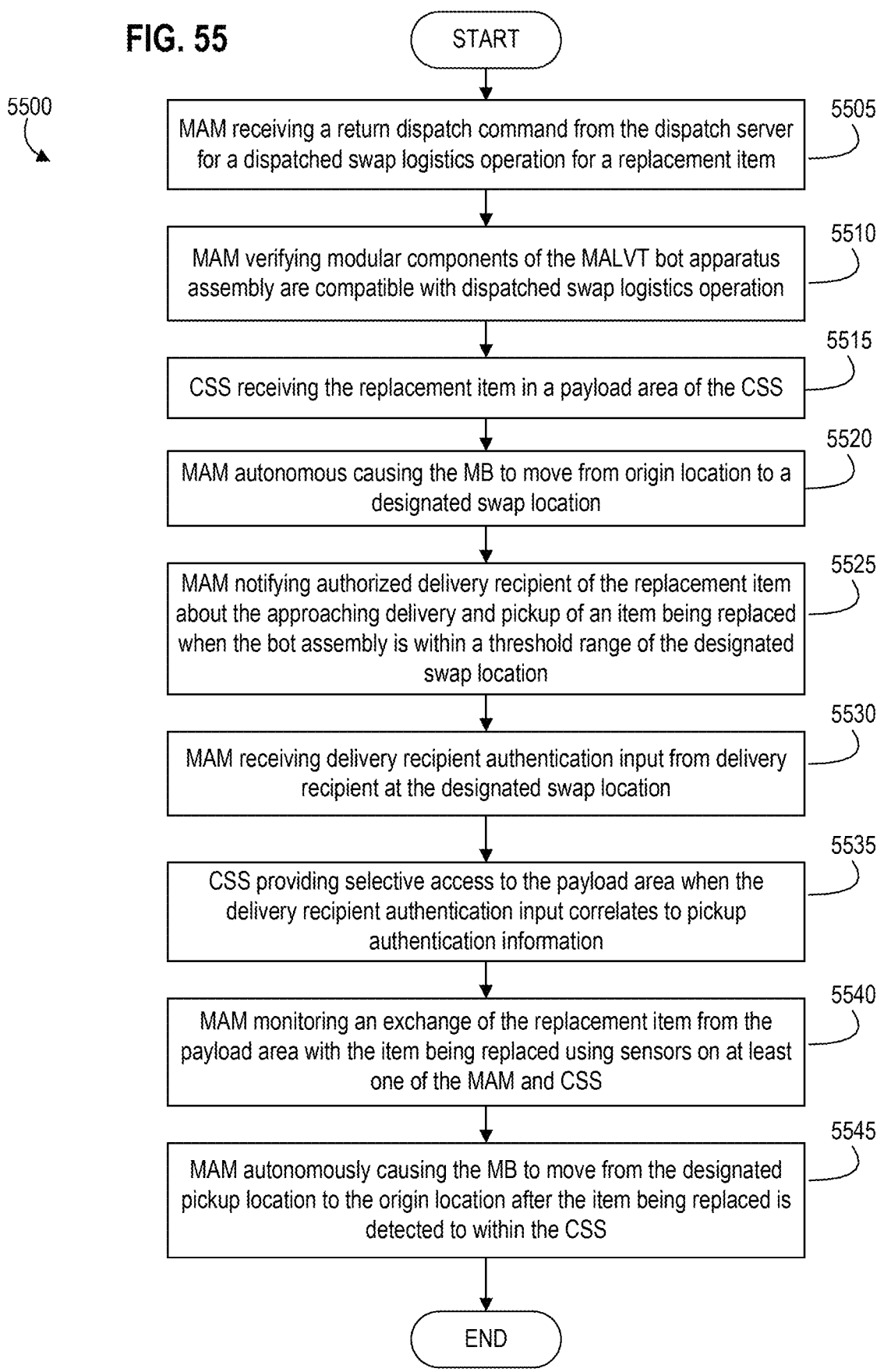
FIG. 55 is a flow diagram of an embodiment of an exemplary method for performing a dispatched swap logistics operation related to an item being replaced that is swapped for a replacement item and using a modular autonomous bot apparatus assembly (MALVT bot apparatus assembly) and a dispatch server in accordance with an embodiment of the invention.

FIG. 55 is a flow diagram of an embodiment of an exemplary method 5500 for performing a dispatched swap or exchange related logistics operation related to an item being replaced that is swapped for a replacement item and using a modular autonomous bot apparatus assembly (MALVT bot apparatus assembly) and a dispatch server in accordance with an embodiment of the invention. Such an item being replaced and a replacement item may, for example, be consumable items that are put to use or otherwise consumed over time. An embodiment of method 5500 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5500 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during the dispatched swap logistics operation involved with method 5500.

Referring now to FIG. 55, exemplary method 5500 begins at step 5505 with the modular mobile autonomy control module receiving a swap operation dispatch command from the dispatch server. The swap operation dispatch command includes at least identifier information on the item being replaced and identifier information on the replacement item, transport parameters on the item being replaced and the replacement item, designated pickup information related to swapping the item being replaced for the replacement item (e.g., a delivery time and delivery date as selected in the swap transaction order), and pickup authentication information related to an authorized delivery recipient of replacement item. In more detail, step 5505 may have the modular mobile autonomy control module receiving a replacement order message as the swap operation dispatch command from a retail system that received a swap transaction order for the replacement item, where the retail system may be operating as the dispatch server relative to the dispatched swap logistics operation.

At step 5510, method 5500 continues with verifying, by the modular mobile autonomy control module, that each of the modular mobile autonomy control module, the modular mobility base, the modular auxiliary power module, and the modular cargo storage system are compatible with the dispatched swap logistics operation based upon the swap operation dispatch command.

At step 5515, method 5500 has the modular cargo storage system receiving the replacement item in a payload area within the modular cargo storage system. In more detail, step 5515 may involve actuated devices and/or object manipulation systems on the exemplary MALVT bot apparatus assembly. For example, an embodiment of step 5515 may have the modular mobile autonomy control module actuating an actuated cargo door (e.g., door 1715) disposed on the modular auxiliary power module to an open position. As previously described, such an actuated cargo door provides a seal to the payload area within the modular cargo storage system when the actuated cargo door is in a closed position and the actuated cargo door provides access to the payload area within the modular cargo storage system when the actuated cargo door is in the open position. In another embodiment, step 5515 may have the modular mobile autonomy control module actuating the actuated cargo door by actuating an actuated joint on the actuated cargo door to cause the actuated cargo door to move from the closed position to the open position. Further embodiments of step 5515 may have the modular mobile autonomy control module actuating the actuated cargo door by actuating an electromechanical lock (e.g., lock 2025) on the actuated cargo door to cause the actuated cargo door to unlock before moving from the closed position to the open position. Still further embodiments of step 5515 may receive the replacement item with the modular mobile autonomy control module actuating an actuated sliding arm disposed on the modular cargo storage system to move the item being replaced into the payload area within the modular cargo storage system, and/or actuating an actuated grabbing arm disposed on the modular cargo storage system to grab and move the item being replaced into the payload area within the modular cargo storage system as part of receiving the item being replaced. And in another embodiment of step 5515, the modular mobile autonomy control module may actuate an actuated belt surface disposed on the modular auxiliary power module as a movable support surface exposed within the payload area inside the modular cargo storage system. Such an actuated belt surface causes the item as placed on the actuated belt surface to move within the payload area as part of receiving the item being replaced.

At step 5520, method 5500 continues with the modular mobile autonomy control module autonomously causing the modular mobility base to move from an origin location on a route to a designated swap location identified by the designated pickup information.

At step 5525, method 5500 continues with the modular mobile autonomy control module notifying the authorized delivery recipient of the replacement item of an approaching pickup for the item being replaced and delivery of the replacement item once the modular autonomous bot apparatus assembly is within a threshold notification range of the designated swap location identified by the designated pickup information. This type of pre-swap notification may take different forms in different embodiments. For example, step 5525 may involve notifying by generating a display alert for the authorized delivery recipient of the replacement item on a display on the modular mobile autonomy control module once the modular autonomous bot apparatus assembly is within the threshold notification range of the designated swap location identified by the designated pickup information. In another example, step 5525 may involve notifying by generating an audio notification for the authorized delivery recipient of the replacement item on a speaker on the modular mobile autonomy control module (or other component of the bot apparatus assembly) once the modular autonomous bot apparatus assembly is within the threshold notification range of the designated swap location identified by the designated pickup information.

Still further embodiments of step 5525 may involve notifying an external network device or user access device (generally referred to as an external wireless node), such as a smartphone, laptop, tablet, and the like. For example, step 5525 may implement the notifying step by transmitting a delivery notification message (e.g., a text message, an electronic mail message, and a phone call) to an external wireless node once the modular autonomous bot apparatus assembly is within the threshold notification range of the designated swap location identified by the designated pickup information (or alternatively once the bot apparatus assembly has moved from the origin location). In more detail, the external wireless node may be related to the authorized delivery recipient of the replacement item according to the designated pickup information or, alternatively to a designated third party authorized by the authorized delivery recipient according to the designated pickup information. Such pre-swap notifications may include transmitting an arrival estimate to the external wireless node, where the arrival estimate indicates an estimated time to arrive at the designated swap location.

In still another embodiment of step 5525, method 5500 may have the modular mobile autonomy control module transmitting a verification request to confirm pickup of the item being replaced to the authorized delivery recipient of the replacement item. Such a verification request asks for a responsive confirmation that the item being replaced should be picked up by the modular autonomous bot apparatus assembly at the designated swap location. Thereafter, the modular mobile autonomy control module autonomously causes the modular mobility base to continue moving to the designated swap location to complete the dispatched swap logistics operation unless the responsive confirmation from the authorized delivery recipient indicates that the item being replaced should not be picked up at the designated swap location or may be picked up at a redirected different swap location or at a different time (e.g., due to changes in weather, changes in the availability of the delivery recipient, and the like), or unless the responsive confirmation from the authorized delivery recipient indicates that the replacement item should not be delivered at the designated swap location or may be delivered to a redirected swap location or at a different time.

At step 5530, method 5500 continues with receiving delivery recipient authentication input by the modular mobile autonomy control module from a delivery recipient disposed external to the modular autonomous bot apparatus assembly at the designated swap location. Similar to that noted above regarding method 5100 (e.g., step 5130), such delivery recipient authentication input may be received in ways, such as involving a user input panel on the bot apparatus (that may receive an access code and/or biometric input and/or voice input, and the like) and/or involving input provided wirelessly from an external wireless node that may provide similar types of authentication input from a delivery recipient operating the external wireless node. In more detail, for example, an embodiment of method 5500 may have the pickup authentication information related to the dispatched swap logistics operation including an identifier of the authorized delivery recipient for the replacement item as part of the dispatched swap logistics operation. As such, step 5530 in that embodiment may receive the delivery recipient authentication input by having the modular mobile autonomy control module detecting an advertising signal as the delivery recipient authentication input from an external wireless node within a predetermined range of the modular autonomous bot apparatus assembly once the modular autonomous bot apparatus assembly has arrived at the designated swap location identified by the designated pickup information; and authenticating that the external wireless node is associated with the authorized delivery recipient for the item being replaced within the modular cargo storage system based upon the identifier of the authorized delivery recipient and identifier information within the detected advertising signal broadcast from the external wireless node.

In another example, an embodiment of method 5500 may have the pickup authentication information related to the dispatched swap logistics operation including an identifier of the authorized delivery recipient for the replacement item as part of the dispatched swap logistics operation. As such, step 5530 in that embodiment may receive the delivery recipient authentication input by having the modular mobile autonomy control module detecting an unprompted advertising signal from an external wireless node within a predetermined range of the modular autonomous bot apparatus assembly once the modular autonomous bot apparatus assembly has arrived at the designated swap location identified by the designated pickup information; and establishing a secure association between the external node and the modular mobile autonomy control module after detecting the unprompted advertising signal from the external wireless node. In this embodiment, the secure association between the external node and the modular mobile autonomy control module allows secure sharing of information between the external node and the modular mobile autonomy control module and may be pre-authorized by the dispatch server as it relates to the dispatched swap logistics operation.

At step 5535, method 5500 continues with the modular cargo storage system providing selective access to the payload area within the modular cargo storage system only when the delivery recipient authentication input received at least correlates to (or matches) relevant parts of the pickup authentication information indicating that the delivery recipient providing the delivery recipient authentication input is the authorized delivery recipient of the replacement item.

At step 5540, method 5500 has the modular mobile autonomy control module monitoring an exchange of the replacement item from the payload area of the modular cargo storage system with the item being replaced using one or more sensors on at least one of the modular mobile autonomy control module and the modular cargo storage system. In more detail, step 5540 of monitoring the exchange of the replacement item from the payload area of the modular cargo storage system with the item being replaced may involve having the modular mobile autonomy control module monitoring unloading of the replacement item from the payload area of the modular cargo storage system using the one or more sensors on at least one of the modular mobile autonomy control module and the modular cargo storage system; and monitoring the loading of the item being replaced into the modular cargo storage system using those sensors as the item being replaced is received into the payload area of the modular cargo storage system. Such monitoring as part of step 5540 may also include generating a log entry in a custodial inventory data structure when the replacement item is detected to be removed from the modular cargo storage system and the item being replaced is detected to be within the modular cargo storage system. Such a log entry reflects the exchange of the replacement item for the item being replacement and automatically provides chain of custody documentation for the exchange.

In more detailed embodiments, step 5540 may monitor the exchange using different types of sensors and processing the data generated by such sensors. For example, monitoring in step 5540 may involve capturing sensor data from the sensors on at least one of the modular mobile autonomy control module and the modular cargo storage system; and detecting when the replacement item is removed from the modular cargo storage system and when the item being replaced is received within the modular cargo storage system based upon the captured sensor data (e.g., as processed to identify the item being replaced and its relevant location). Such captured sensor data may, for example, be one or more visual images of what is disposed within the modular cargo storage system.

In even more detail, an embodiment of monitoring in step 5540 may involve generating barcode scan data related to the item being replaced and the replacement item as the item being replaced is swapped in for the replacement item using a barcode scanner as one of the sensors, and processing the generated barcode scan data to monitor the item being replaced and the replacement item as the item being replaced is swapped in for the replacement item that is removed from within the modular cargo storage system.

In another example, an embodiment of monitoring in step 5540 may involve generating image data related to item being replaced and the replacement item as the item being replaced is swapped in for the replacement item that is removed using a camera as one of the sensors, and processing the generated image data to monitor the item being replaced and the replacement item as the item being replaced is swapped in for the replacement item that is removed from within the modular cargo storage system.

In still another example, an embodiment of monitoring in step 5540 may involve generating video data related to item being replaced and the replacement item as the item being replaced is swapped in for the replacement item that is removed using a video camera as one of the sensors, and processing the generated video data to monitor the item being replaced and the replacement item as the item being replaced is swapped in for the replacement item that is removed from within the modular cargo storage system.

In yet another example, an embodiment of monitoring in step 5540 may involve capturing audio data using a microphone as one of the sensors disposed to record sound within and proximate to the modular cargo storage system as the item being replaced is swapped in for the replacement item that is removed from within the modular cargo storage system; and processing the captured audio data to monitor the item being replaced and the replacement item as the item being replaced is swapped in for the replacement item that is removed from within the modular cargo storage system.

Monitoring of what is in the payload area of the modular cargo storage system as part of step 5540 may also involve detecting movement of a wireless node associated with the item being replaces and/or replacement item. For example, step 5540 of monitoring the exchange of the replacement item from the payload area of the modular cargo storage system with the item being replaced may involve detecting movement of a wireless node associated with the item being replaced as the item being replaced is swapped in for the replacement item being removed from within the modular cargo storage system based upon signals broadcast from the wireless node associated with the item being replaced. In another example, step 5540 may involve detecting movement of a wireless node associated with the replacement item as the replacement item is swapped out from within the modular cargo storage system for the item being replaced based upon signals broadcast from the wireless node associated with replacement item.

Node locating techniques, as described in more detail above, may also be deployed as part of an embodiment of monitoring in step 5540. For example, step 5540 of monitoring the exchange of the replacement item from the payload area of the modular cargo storage system with the item being replaced may involve detecting a change in location of a wireless node associated with the item being replaced from a location outside the modular cargo storage system to the payload area as the item being replaced is swapped for the replacement item that is removed from within the modular cargo storage system as determined by the modular mobile autonomous control module. And in another example, step 5540 may involve detecting a change in location of a wireless node associated with the replacement item from inside the modular cargo storage system to outside the modular cargo storage system as the item being replaced is swapped in for the replacement item that is removed from within the modular cargo storage system as determined by the modular mobile autonomous control module.

Those skilled in the art will appreciate that embodiments involving monitoring the payload area of the modular cargo storage system may use multiple types of sensors, as described above, as part of such monitoring of the payload contents of the modular cargo storage system. Those skilled in the art will further appreciate that embodiments involving monitoring the payload area of the modular cargo storage system may also use a combination of sensor-based monitoring in concert with wireless node signal-based monitoring as described above.

At step 5545, method 5500 concludes with autonomously causing, by the modular mobile autonomy control module, the modular mobility base to move from the designated swap location on a return route to the origin location after the item being replaced is detected to be within the modular cargo storage system based upon the monitored loading of the item being replaced.

In further embodiments, method 5500 may also include sending notifications when approaching the return to the origin location and/or upon arrival back at the origin location. For example, a further embodiment of method 5500 may have the modular mobile autonomy control module notifying a retail entity at the origin location of an approaching return delivery of the item being replaced once the modular autonomous bot apparatus assembly is within a threshold notification range of the origin location. In another example, an embodiment of method 5500 may have the modular mobile autonomy control module notifying the retail entity at the origin location about delivery of the item being replaced after the modular autonomous bot apparatus assembly arrives at the origin location.

In still further embodiments of method 5500, the steps 5520 and 5545 of autonomously causing the modular mobility base to move between locations may involve interacting with facility nodes and pathway obstacles similar to that described above with respect to more detailed embodiments of method 5400 as it relates to step 5415 and 5450.

Additionally, further embodiments of method 5500 may involve more details related to providing access to the modular cargo storage system in step 5535 and the exchange unloading/loading that follows. For example, an embodiment of method 5500 may, after the providing step 5535, include the step of unloading, by the modular cargo storage system, the replacement item from within the payload area of the modular cargo storage system and loading the item being replaced into the payload area within the modular cargo storage system. This may, for example, have the steps of unloading the replacement item and loading the item being replaced having the modular mobile autonomy control module actuating an actuated cargo door disposed on the modular auxiliary power module to an open position (e.g., via an actuated joint on the door) once the delivery recipient authentication input correlates to a portion of the pickup authentication information related to the dispatched swap logistics operation. Actuating the actuated cargo door may, in other examples, involve actuating an electro-mechanical lock on the actuated cargo door to cause the actuated cargo door to unlock before moving from the closed position to the open position.

In more detail, additional embodiments of method 5500 may implement the step of unloading the replacement item with the modular mobile autonomy control module actuating an actuated sliding arm disposed on the modular cargo storage system to move the replacement item out from the payload area within the modular cargo storage system and loading the item being replaced by actuating the actuated sliding arm disposed on the modular cargo storage system to move the item being replaced into the payload area within the modular cargo storage system.

Additional embodiments of method 5500 may further implement the step of unloading the replacement item by having the modular mobile autonomy control module actuating an actuated grabbing arm disposed on the modular cargo storage system to grab and move the replacement item out from the payload area within the modular cargo storage system and loading the item being replaced by actuating the actuated grabbing arm disposed on the modular cargo storage system to move the item being replaced into the payload area within the modular cargo storage system.

Different types of actuated belt surfaces may also be used to remove the replacement item from the payload area and to place the item being replaced back in the payload area. For example, an embodiment of method 5500 may implement the step of unloading the replacement item by having the modular mobile autonomy control module actuating an actuated belt surface disposed on the modular auxiliary power module as a movable support surface exposed within the payload area inside the modular cargo storage system, where the actuated belt surface causes the replacement item as placed on the actuated belt surface to move out from within the payload area. In like manner, loading the item being replaced may have the modular mobile autonomy control module actuating the actuated belt surface to cause the item being replaced as placed on the actuated belt surface to move into the payload area.

In still further embodiments of method 5500, there may be different types of designated swap locations used. For example, an embodiment of method 5500 may have the designated swap location being a fixed address where the authorized delivery recipient receives the replacement item and provides the item being replaced within the mobile cargo storage system as part of dispatched swap logistics operation. However, in another example, the designated swap location may be a mobile location where the authorized delivery recipient receives the replacement item and provides the item being replaced within the mobile cargo storage system as part of dispatched swap logistics operation. Such a mobile location may be defined by the designated pickup information as a location of an external wireless mobile node being related to the authorized delivery recipient, and where the location of the external wireless mobile node may be determined with location data provided by the node and/or node locating techniques as described above in more detail.

Additional embodiments of method 5500 may also send alerts for removal assistance when the exemplary MALVT bot apparatus assembly returns back to the origin location with the item being replaces. For example, an embodiment of method 5500 may include the step of transmitting, by the modular mobile autonomy control module, an unload assistance request to the retail entity once the modular autonomous bot apparatus assembly is within a threshold notification range of the origin location or after the modular autonomous bot apparatus assembly arrives at the origin location.

Roundtrip Use Cases—Diagnostic/Treatment

In another embodiment, a customer who does not feel well may contact a pharmacy or medical clinic and describe their symptoms. Based upon customer's description of symptoms, the pharmacy/clinic may narrow their diagnosis to a small number of potential ailments. A clinic nurse/pharmacy tech may put together a particular type of diagnosis kit specific to the customer and their symptoms, and place it in an exemplary MALVT bot apparatus. The exemplary MALVT bot apparatus receives information related to the loaded diagnosis kit (including customer identification information and address/location information) and carries the diagnosis kit to customer's location (e.g., home, office, vehicle, etc.). The customer may then authenticate delivery via an app operating on the recipient's user access device, via TRON node interactions for association-based authenticated delivery, or via interaction with the display screen on the MAM component. The display screen on the MAM component may give instructions for customer who then conducts a sample/diagnostic test (e.g., swabs a relevant tissue from a swab kit in the diagnosis kit or other home diagnostic test that is part of the diagnosis kit sent by the pharmacy/clinic) and returns the kit and sample inside the waiting exemplary MALVT bot apparatus. The exemplary MALVT bot apparatus then returns swab/diagnosis kit to the pharmacy/clinic. The pharmacy/clinic uses sample obtained with the swab/diagnosis kit to finalize diagnosis and determine an appropriate treatment, consults with patient, and agrees upon a course of action. The pharmacy/clinic may then load treatment into the exemplary MALVT bot apparatus (e.g., could include not only prescription medication, medical supplies, but also tissues, food, heating pad, etc.). The customer then receives a notification that the exemplary MALVT bot apparatus has been dispatched again with the treatment load along with an estimated time of arrival. The exemplary MALVT bot apparatus delivers treatment load to the customer, who may then authenticate delivery via an app operating on the recipient's user access device, via TRON node interactions for association-based authenticated delivery, or via interaction with the display screen on the MAM component. The display screen of the MAM component may also offer any instructions or additional information for the customer. The display screen can also be leveraged as a warning of biological or hazardous contents of the cargo. As the customer unloads the treatment load from the exemplary MALVT bot apparatus, the exemplary MALVT bot apparatus may monitor unloading and ensure that all contents have been removed, and then the bot apparatus may return to the pharmacy/retail location. Enhanced security, recorded transaction records (e.g., automatic video/audio recorded loading/unloading), and multi-factor authentication (e.g., two factor/biometric) may be required given the chain of custody needs and the biological nature of the cargo. Ease of disinfection will be enhanced with modular swapped in and out self-contained CSS components that can be separately disinfected while another CSS component may be quickly used with the rest of the exemplary MALVT bot apparatus. TRON elements and locating techniques may be leveraged for location needs as well as authentication implementations.

Figure 56A:
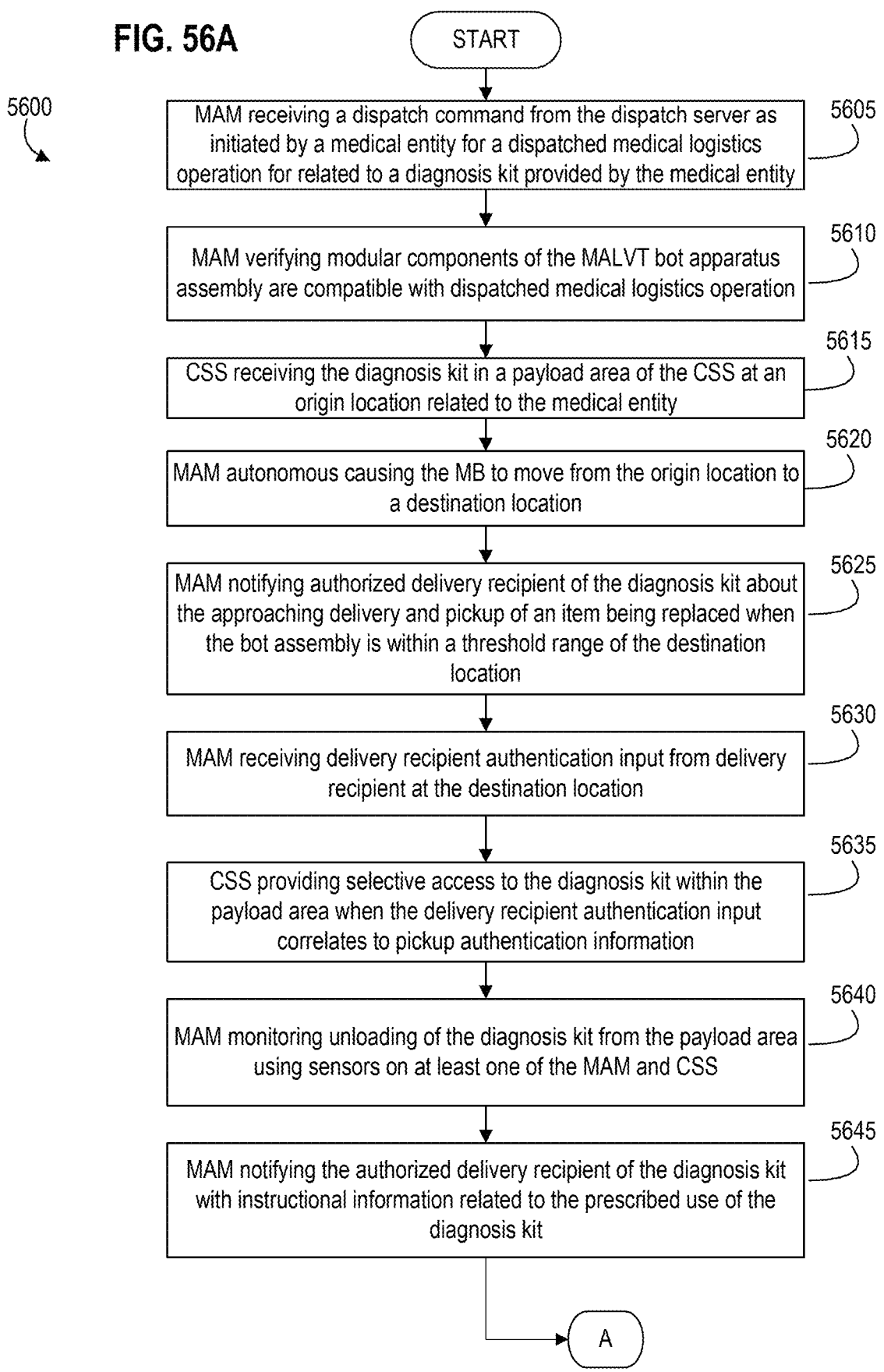
FIGS. 56A-56B are parts of a flow diagram of an embodiment of an exemplary method for performing an medical related dispatched logistics operation involving a diagnosis kit for treating a patient and using a modular autonomous bot apparatus assembly (MALVT bot apparatus assembly) and an dispatch server in accordance with an embodiment of the invention.
Figure 56B:
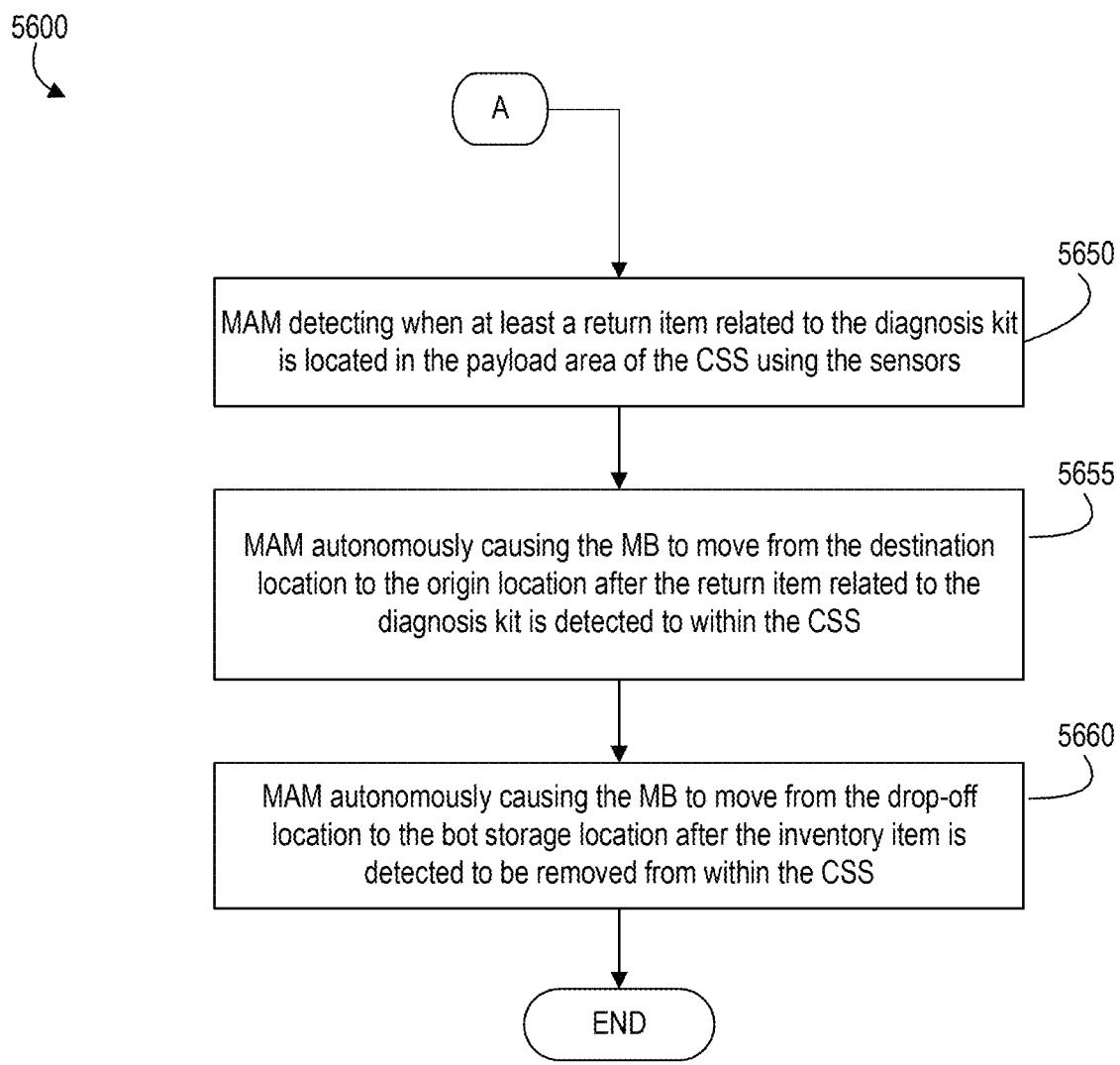

FIGS. 56A-56B are parts of a flow diagram of an embodiment of an exemplary method 5600 for performing an medical related dispatched logistics operation involving a diagnosis kit for treating a patient and using a modular autonomous bot apparatus assembly (MALVT bot apparatus assembly) and an dispatch server in accordance with an embodiment of the invention. An embodiment of method 5600 may use an embodiment of exemplary MALVT bot apparatus assembly 1700 (as assembled or after an on-demand assembly) and a dispatch server (e.g., server 4205, 4720). Exemplary modular autonomous bot apparatus assembly used (e.g., assembly 1700) as part of method 5600 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 5600.

Referring now to FIG. 56A, exemplary method 5600 begins at step 5605 with the modular mobile autonomy control module receiving a dispatch command from the dispatch server. In step 5605, the dispatch command is initiated by a medical entity providing the diagnosis kit, and the dispatch command includes at least identifier information on the diagnosis kit, transport parameters on the diagnosis kit, destination delivery information related to delivery of the diagnosis kit, and delivery authentication information related to an authorized delivery recipient of the diagnosis kit. Such an authorized delivery recipient may, for example, be the patient to be treated with the diagnosis kit or an authorized agent of the patient to be treated with the diagnosis kit (e.g., a parent of the patient, medical personnel authorized to treat the patient, and the like).

At step 5610, method 5600 proceeds with the modular mobile autonomy control module verifying that each of the modular mobile autonomy control module, the modular mobility base, the modular auxiliary power module, and the modular cargo storage system are compatible with the dispatched medical logistics operation based upon the dispatch command. As noted above, such a verification process may have the modular mobile autonomy control module (e.g., exemplary MAM 1725) interacting with each of the other modular components (e.g., the modular mobility base, the modular auxiliary power module, and the modular cargo storage system) to make the verification determination (i.e., a type of authentication of the exemplary MALVT bot apparatus assembly) or may have the modular mobile autonomy control module receiving results of component-to-component authentication performed when proximate modular components of the exemplary MALVT bot apparatus assembly are put together when building the exemplary MALVT bot apparatus assembly for the dispatched medical logistics operation.

At step 5615, method 5600 proceeds with receiving, by the modular cargo storage system, the diagnosis kit in a payload area within the modular cargo storage system at an origin location related to the medical entity. Such an origin location may be a bot storage location at the medical entity (e.g., a hospital, clinic, and the like).

As part of step 5615, an embodiment of method 5600 may implement more detailed ways to receive the diagnosis kit in the payload area within the modular cargo storage system using actuated and articulating systems that allow the exemplary MALVT bot apparatus assembly improved and enhance loading of the diagnosis kit. For example, an embodiment of step 5615 may receive the diagnosis kit with the modular mobile autonomy control module actuating an actuated cargo door disposed on the modular auxiliary power module to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position. Actuating such an actuated cargo door may, in some examples, involve actuating an actuated joint on the actuated cargo door to cause the actuated cargo door to move from the closed position to the open position, and/or actuating an electro-mechanical lock on the actuated cargo door to cause the actuated cargo door to unlock before moving from the closed position to the open position.

In a further example, an embodiment of step 5615 may receive the diagnosis kit with the modular mobile autonomy control module actuating an actuated sliding arm disposed on the modular cargo storage system to move the diagnosis kit into the payload area within the modular cargo storage system and/or actuating an actuated grabbing arm disposed on the modular cargo storage system to grab and move the diagnosis kit into the payload area within the modular cargo storage system as part of receiving the diagnosis kit.

Further still, another embodiment of step 5615 may have the modular mobile autonomy control module actuating an actuated belt surface disposed on the modular auxiliary power module as a movable support surface exposed within the payload area inside the modular cargo storage system.

Such an actuated belt surface, when operating, may cause the diagnosis kit as placed on the actuated belt surface to move within the payload area as part of receiving the diagnosis kit.

At step 5620, method 5600 continues and has the modular mobile autonomy control module autonomously causing the modular mobility base to move from the origin location on a route to a destination location identified by the destination delivery information.

At step 5625, method 5600 proceeds with the modular mobile autonomy control module notifying the authorized delivery recipient of the diagnosis kit of an approaching delivery once the modular autonomous bot apparatus assembly is within a threshold notification range of the destination location identified by the destination information. Such a notification may be implemented in a variety of ways as part of step 5625. For example, step 5625 may notify the authorized delivery recipient of the diagnosis kit of the approaching delivery by generating a display alert for the authorized delivery recipient on a display on the modular mobile autonomy control module; by generating an audio notification for the authorized delivery recipient on a speaker on the modular mobile autonomy control module; by transmitting a delivery notification message to the delivery recipient's external wireless node once the modular autonomous bot apparatus assembly is within the threshold notification range of the destination location identified by the destination information, and/or by transmitting a delivery notification message to an external wireless node after the modular autonomous bot apparatus assembly moves from the origin location, the external wireless node being related to the authorized delivery recipient according to the destination delivery information. Such notifications may include an arrival estimate indicating an estimated time to arrive at the destination location.

At step 5630, method 5600 proceeds with receiving delivery recipient authentication input by the modular mobile autonomy control module from a delivery recipient disposed external to the modular autonomous bot apparatus assembly at the destination location. Embodiments of method 5600 may have the modular mobile autonomy control module receiving the delivery recipient authentication input in different forms and through different ways. For example, an embodiment of step 5630 may have the delivery recipient authentication input received by the modular mobile autonomy control module being provided by the delivery recipient through a user input panel disposed on the modular autonomous bot apparatus coupled to the modular mobile autonomy control module (e.g., with an access code and/or biometric input provided through the user input panel) or being provided by the delivery recipient through an external wireless node disposed external to the modular autonomous bot apparatus assembly (e.g., with an access code and/or biometric input provided through an app on the external wireless node).

In still another example, an embodiment of method 5600 may have authentication information for the medically related dispatched operation including an identifier of the authorized delivery recipient for the diagnosis kit as part of the dispatched medical logistics operation. As such, step 5630 may be receiving the delivery recipient authentication input by having the modular mobile autonomy control module detecting an advertising signal as the delivery recipient authentication input from an external wireless node within a predetermined range of the modular autonomous bot apparatus assembly once the modular autonomous bot apparatus assembly has arrived at the destination location identified by the destination information; and authenticating that the external wireless node is associated with the authorized delivery recipient for the item being shipped within the modular cargo storage system based upon the identifier of the authorized delivery recipient and identifier information within the detected advertising signal broadcast from the external wireless node.

In yet another example, an embodiment of method 5600 may also have authentication information related to the dispatched medical logistics operation including an identifier of the authorized delivery recipient for the diagnosis kit as part of the dispatched operation. And as such, step 5630 may be implemented by having the modular mobile autonomy control module detecting an unprompted advertising signal from an external wireless node within a predetermined range of the modular autonomous bot apparatus assembly once the modular autonomous bot apparatus assembly has arrived at the destination location identified by the destination information; and establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched inventory operation.

At step 5635, method 5600 proceeds with the modular cargo storage system providing selective access to the diagnosis kit within the modular cargo storage system only when the delivery recipient authentication input correlates to the delivery authentication information indicating that the delivery recipient providing the delivery recipient authentication input is the authorized delivery recipient.

An embodiment of method 5600 may also involve unloading the diagnosis kit from within the payload area of the modular cargo storage system. This, for example, may be done manually in general after gaining access to the payload area, but in other examples unloading the diagnosis kit may involve the exemplary MALVT bot apparatus assembly actuating devices and/or articulating parts of an object manipulation system deployed onboard the exemplary MALVT bot apparatus assembly. For example, unloading of the diagnosis kit may involve the modular mobile autonomy control module actuating an actuated cargo door (e.g., door 1715 using actuated joint 2020) disposed on the modular auxiliary power module (or CSS) to an open position once the delivery recipient authentication input correlates to a portion of the authentication information related to the dispatched logistics operation; actuating an electro-mechanical lock on the actuated cargo door to cause the actuated cargo door to unlock before moving from the closed position to the open position; actuating an actuated sliding arm disposed on the modular cargo storage system to move the diagnosis kit out from the payload area within the modular cargo storage system; and/or actuating an actuated grabbing arm disposed on the modular cargo storage system to grab and move the diagnosis kit out from the payload area within the modular cargo storage system. Further still, unloading of the diagnosis kit may also have the modular mobile autonomy control module actuating an actuated belt surface disposed on the modular auxiliary power module as a movable support surface exposed within the payload area inside the modular cargo storage system to cause the diagnosis kit as placed on the actuated belt surface to move out from within the payload area.

At step 5640, method 5600 proceeds with the modular mobile autonomy control module monitoring unloading of the diagnosis kit from within the modular cargo storage system using one or more sensors on at least one of the modular mobile autonomy control module and the modular cargo storage system. In more detail, such monitoring of unloading the diagnosis kit may be accomplished by capturing sensor data from the sensors on at least one of the modular mobile autonomy control module and the modular cargo storage system, and detecting when the diagnosis kit is removed based upon the captured sensor data (such as when the sensor data is processed to identify the diagnosis kit and its movements).

In even more detail, such monitoring unloading of the diagnosis kit may involve generating barcode scan data related to the diagnosis kit as the diagnosis kit is removed from within the modular cargo storage system using a barcode scanner as one of the sensors; and processing the generated barcode scan data to monitor the diagnosis kit as the diagnosis kit is removed from within the modular cargo storage system. In another detailed example, monitoring unloading of the diagnosis kit may involve generating image data related to the diagnosis kit as the diagnosis kit is removed from within the modular cargo storage system using an image sensor as one of the sensors; and processing the generated image data to monitor the diagnosis kit as the diagnosis kit is removed from within the modular cargo storage system. Another example may implement such monitoring by generating video data related to the diagnosis kit as the diagnosis kit is removed from within the modular cargo storage system using a video camera as one of the sensors; and processing the generated video data to monitor the diagnosis kit as the diagnosis kit is removed from within the modular cargo storage system. Further still, in yet another example, monitoring unloading may be accomplished by capturing audio using a microphone as one of the sensors disposed to record sound within and proximate to the modular cargo storage system as the diagnosis kit is removed from within the modular cargo storage system; and processing the captured audio data to monitor the diagnosis kit as the diagnosis kit is removed from within the modular cargo storage system.

In other embodiments of method 5600, step 5640 may have the diagnosis kit including a wireless mobile node (such as an ID node or master node, where the node is attached to the kit, incorporated within the kit, integrated as part of the packaging of the kit, is simply disposed with the node as they are transported together as a unit). As such, the step of monitoring unloading of the diagnosis kit in step 5640 may be implemented by detecting movement of the wireless mobile node disposed with the diagnosis kit as the diagnosis kit is removed from within the modular cargo storage system based upon a plurality of signals broadcast from the wireless mobile node disposed with the diagnosis kit. In another example, monitoring unloading of such a node-enabled diagnosis kit may involve detecting a change in location of the wireless mobile node disposed with the diagnosis kit to outside the modular cargo storage system as the diagnosis kit is removed from within the modular cargo storage system as determined by the modular mobile autonomous control module.

Those skilled in the art will appreciate that with the various manners in which step 5640 may monitor the unloading of the diagnosis kit, further embodiments may combine the different types of sensors and/or use of wireless nodes with the diagnosis kit to implement step 5640 with an assessment of different types of processed sensor data and/or different monitored signals and locations of a node-enabled diagnosis kit when monitoring such unloading activity.

At step 5645, method 5600 proceeds with the modular mobile autonomy control module notifying the authorized delivery recipient of the diagnosis kit of instructional information related to prescribed use of the diagnosis kit. As such, the instruction information may be prescribed medical instructions for authorized medical personnel treating the patient using the transported diagnosis kit. According, as the diagnosis kit is removed (as monitored in step 5640), exemplary MAM 1725 may be triggered to issue or otherwise provide the instructional information related to the particular prescribed use of the diagnosis kit for the particular patient, which may be accomplished in several ways. For example, step 5645 may notify the authorized delivery recipient of the diagnosis kit of the instructional information by generating a display alert message (including the instruction information) for the authorized delivery recipient on a display (e.g., display 2815*a*, 2815*b*) on the modular mobile autonomy control module; by generating an audio alert message (including audible instructions as the instruction information) for the authorized delivery recipient using a speaker on the modular mobile autonomy control module; or having the modular mobile autonomy control module transmit an instructional message to an external wireless node related to the authorized delivery recipient according to the destination delivery information, where the instructional message includes or otherwise reflects the instructional information related to the prescribed use of the diagnosis kit. From step 5645 shown on FIG. 56A, method 5600 proceeds through transition A to step 5650 shown on FIG. 56B.

Referring now to FIG. 56B, method 5600 proceeds with step 5650 having the modular mobile autonomy control module detecting when at least a return item related to the diagnosis kit is located in the payload area of the modular cargo storage system using the one or more sensors. Such a return item may, for example, be one or more parts of the diagnosis kit used by the patient or one or more parts of the diagnosis kit still in its packaging and not used. In still another embodiment, such a return item related to the diagnosis kit may be a testing part of the diagnosis kit used by the patient as part of a medical test (e.g., a test strip indicating test results of heart testing, one or more blood vials drawn from the patient, images captured as part of the test using the test kit, and the like). In more detail, an embodiment may have such a testing part of the diagnosis kit used by the patient as part of the medical test being a sample from the patient gathered according to the instructional information related to the prescribed use of the diagnosis kit. Such a sample (e.g., blood) may then be part of the return item (e.g., blood within sealed vials) transported by the modular autonomous bot apparatus assembly back to the origin location for analysis by the medical entity.

As part of step 5650 (or as a separate step), method 5600 may more explicitly have the modular cargo storage system receiving the return item related to the diagnosis kit in the payload area within the modular cargo storage system at the destination location. For example, receiving the return item related to the diagnosis kit may have the modular mobile autonomy control module actuating an actuated sliding arm disposed on the modular cargo storage system to move the diagnosis kit's return item into the payload area within the modular cargo storage system; actuating an actuated grabbing arm disposed on the modular cargo storage system to grab and move the diagnosis kit's return item into the payload area within the modular cargo storage system as part of receiving the diagnosis kit's return item; and/or actuating, an actuated belt surface disposed on the modular auxiliary power module as a movable support surface exposed within the payload area inside the modular cargo storage system to cause the diagnosis kit's return item as placed on the actuated belt surface to move within the payload area as part of receiving the return item.

As part of an embodiment of step 5650 that detects when the diagnosis kit's return item is loaded, a further embodiment may have the modular mobile autonomy control module monitoring loading of the return item related to the diagnosis kit from within the modular cargo storage system using the one or more sensors. In one example, this step of monitoring the loading of the diagnosis kit's related return item may involve generating barcode scan data related to the return item as the return item is placed within the modular cargo storage system using a barcode scanner as one of the sensors 3130, and processing the generated barcode scan data to monitor the return item as the return item is placed within the modular cargo storage system. In another example, this step of monitoring the loading of the diagnosis kit's related return item may involve generating image data related to the return item as the return item is placed within the modular cargo storage system using an image sensor as one of the sensors 3130, and processing the generated image data to monitor the return item as the return item is placed within the modular cargo storage system. In still another example, this step of monitoring the loading of the diagnosis kit's related return item may involve generating video data related to the return item as the return item is placed within the modular cargo storage system using a video camera as one of the sensors 3130, and processing the generated video data to monitor the return item as the return item is placed within the modular cargo storage system. In yet another example, this step of monitoring the loading of the diagnosis kit's related return item may involve capturing audio data using a microphone as one of the sensors 3130 disposed to record sound within and proximate to the modular cargo storage system as the return item is placed within the modular cargo storage system, and processing the captured audio data to monitor the ordered item as the ordered item is placed within the modular cargo storage system.

In further examples with such monitored loading of the return item, the return item itself may include or otherwise be transported with its own wireless mobile node (similar to that described above for the diagnosis kit). As such, monitoring loading of the return item may involve detecting movement of the wireless mobile node disposed with the return item as the return item is placed within the modular cargo storage system based upon a plurality of signals broadcast from the wireless mobile node disposed with the return item; and/or detecting a change in location of the wireless mobile node disposed with the return item to outside the modular cargo storage system as the return item is placed within the modular cargo storage system as determined by the modular mobile autonomous control module.

At step 5655, method 5600 proceeds with the modular mobile autonomy control module autonomously causing the modular mobility base to move from the destination location on a return route to the origin location related to the medical entity after the return item related to the diagnosis kit is detected within the modular cargo storage system.

At step 5660, method 5600 concludes with the modular mobile autonomy control module notifying personnel associated with the medical entity about the return delivery of the return item related to the diagnosis kit when the modular autonomous bot apparatus assembly is at least within a return notification range of the origin location and/or once the modular autonomous bot apparatus assembly has arrived at the origin location. In this way, the notified personnel are proactively informed of the impending and/or actual arrival of the return item and can appropriately receive and unload the return item.

In some further embodiments of method 5600, chain of custody steps may be taken using the exemplary MALVT bot apparatus. For example, method 5600 may also have the modular mobile autonomy control module generating a first inventory data structure corresponding to the diagnosis kit. Such an inventory data structure (e.g., which may be stored as a type of profile data by autonomous control system 3100 on exemplary MAM 1725 for the particular dispatched medical logistics operation) may be generated upon detecting the diagnosis kit as received within the payload area, where the first inventory data structure includes different chain of custody entries. For example, the first inventory data structure may include a first chain of custody entry reflecting departure from the origin location for the diagnosis kit while in the custody of the modular autonomous bot apparatus assembly. In a further example, the modular mobile autonomy control module may generate a second chain of custody entry within the first inventory data structure after arrival at the destination location (where the second chain of custody reflects arrival at the destination location for delivery of the diagnosis kit from the custody of the modular autonomous bot apparatus assembly). In still a further example, the modular mobile autonomy control module may generate a third chain of custody entry within the first inventory data structure after arrival at the destination location and after detecting the diagnosis kit has been removed from within the modular cargo storage system (where the third chain of custody reflects the diagnosis kit changing custody to the authorized delivery recipient from the modular autonomous bot apparatus assembly). Likewise, the modular mobile autonomy control module may generate a fourth chain of custody entry within the first inventory data structure after arrival at the destination location and after detecting the return item has been placed within the modular cargo storage system (where the fourth chain of custody reflects at least the return item of the diagnosis kit changing custody from the authorized delivery recipient to the modular autonomous bot apparatus assembly).

Additional embodiments of method 5600 may also include steps of unloading the return item at the origin location related to the medical entity. For example, an embodiment of method 5600 may include the step of providing, by the modular cargo storage system, selective access to the return item within the modular cargo storage system when medical entity personnel submits return item authentication input to the modular mobile autonomy control module that correlates to a portion of the delivery authentication information indicating return item authentication information for the return item. Furthermore, such an embodiment of method 5600 may also include having the modular mobile autonomy control module monitoring unloading of the return item from within the modular cargo storage system using one or more sensors (e.g., on or more payload monitoring sensors 3130) and autonomously causing the modular mobility base to move to a bot storage location after the return item is detected as being removed from within the payload area of the modular cargo storage system using the one or more sensors. Such a further embodiment of method 5600 may also involve having the modular mobile autonomy control module transmitting a module replacement request to the dispatch server, the modular replacement request initiating a replacement of the modular cargo storage system for the modular autonomous bot apparatus assembly. For example, such a modular replacement request may initiate a disinfection process of one or more of the modular components of the exemplary MALVT bot apparatus assembly (e.g, the modular cargo storage system) after the return item has been removed from within the payload area of the modular cargo storage system.

In a further embodiment where the return item has been unloaded, an embodiment of method 5600 may also send treatment material back to the patient based upon testing of the return item. For example, in such a further embodiment, method 5600 may have the modular mobile autonomy control module receiving a follow-up dispatch command from the dispatch server for a follow-up dispatched medical logistics operation. The follow-up dispatch command is initiated by the medical entity after testing related to the return item and the patient, and may include at least identifier information on treatment material to be delivered to the authorized delivery recipient as a result of the testing related to the return item and the patient, transport parameters on the treatment material, and destination delivery information related to delivery of the treatment material. In this further embodiment of method 5600, may also have the modular mobile autonomy control module verifying that each of the modular mobile autonomy control module, the modular mobility base, the modular auxiliary power module, and a disinfected replacement for the modular cargo storage system are compatible with the follow-up dispatched medical logistics operation based upon the follow-up dispatch command; receiving, by the modular cargo storage system, the treatment material in the payload area within the disinfected replacement for the modular cargo storage system at the origin location related to the medical entity; and autonomously causing, by the modular mobile autonomy control module, the modular mobility base to move from the origin location back to the destination location identified by the destination delivery information for delivery of the treatment material (which may be different from the location where the diagnosis kit was delivered). Further, such an embodiment of method 5600 may continue with the modular mobile autonomy control module notifying the authorized delivery recipient an approaching delivery of the treatment material; receiving delivery recipient authentication input by the modular mobile autonomy control module from the delivery recipient disposed external to the modular autonomous bot apparatus assembly at the destination location; coordinating with the modular cargo storage system to provide selective access to the treatment material within the modular cargo storage system only when the delivery recipient authentication input correlates to the delivery authentication information indicating that the delivery recipient providing the delivery recipient authentication input is the authorized delivery recipient; monitoring unloading of the treatment material using one or more sensors on at least one of the modular mobile autonomy control module and the disinfected replacement for the modular cargo storage system; and then autonomously causing, by the modular mobile autonomy control module, the modular mobility base to move from the destination location to the origin location after the treatment material is no longer detected within the payload area within the disinfected replacement for the modular cargo storage system.

Those skilled in the art will further appreciate that embodiments of method 5600 may have the exemplary MALVT bot apparatus assembly used in method 5600 navigating and interacting with different pathway obstacles when moving from the origin location to the destination location. For example, step 5620 of autonomously causing the modular mobility base to move from the origin location to the destination location may be implemented with the modular mobile autonomy control module autonomously causing the modular mobility base to move from the origin location to the destination location while interacting with a wireless building facility node to actuate a pathway obstacle disposed in a path on the route to the destination location (e.g., an actuated door controlled by the wireless building facility node, an actuated elevator controlled by the wireless building facility node, an actuated lock controlled by the wireless building facility node, and the like). In more detail, such interactions with the wireless building facility node to actuate the pathway obstacle may involve establishing an authorized association pairing between the modular mobile autonomy control module and the wireless building facility node based upon the authentication information related to the dispatched store-to-consumer logistics operation (e.g., a tracked an authorized logically persistent pairing as reflected by locally generated association data on the MAM), and causing the wireless building facility node to actuate the pathway obstacle after establishing the authorized association pairing.

In further embodiments where pathway obstacles may not be controlled or actuated wirelessly, embodiments of method 5600 may have moving from the origin location to the destination location involve manual interactions by the exemplary MALVT bot apparatus assembly and such pathway obstacles. For example, step 5620 of autonomously causing the modular mobility base to move from the origin location to the destination location may have the modular mobile autonomy control module autonomously causing the modular mobility base to move from the origin location to the destination location while engaging a pathway obstacle disposed in a path on the route to the destination location using an articulating arm disposed on the modular autonomous bot apparatus assembly and using sensors disposed on at least one of the modular mobility base and the modular mobile autonomy control module. Such manually manipulated pathway obstacles may include, for example, a manually actuated door, a manually actuated elevator, a manually actuated lock, or a manually actuated control panel for the pathway obstacle. In more detail, engaging the pathway obstacle using the articulating arm and sensors may involve, for example, guiding, by the modular mobile autonomy control module, the articulating arm to a control element of the pathway obstacle using one or more of the sensors; and actuating the pathway obstacle, by the modular mobile autonomy control module, once the articulating arm engages the control element of the pathway obstacle. Such a pathway obstacle control element may, for example, be a handle for the pathway obstacle, a button for the pathway obstacle, a switch for the pathway obstacle, or a portion of a control panel for the pathway obstacle.

Courier Bot Assistant (Hand Cart & Freight)

Further embodiments may involve and deploy an alternative cart-version of an exemplary MALVT bot apparatus assembly (referred to herein as a modular autonomous cart apparatus assembly) where such an assembly may be deployed to assist a courier in distributing items being transported as part of an exemplary logistics operation (e.g., delivery, pickup, transfer, and the like as described herein). In general, such an embodiment may use the exemplary modular mobility base component of an exemplary MALVT bot apparatus assembly as the basis for a specially configured type of improved and enhanced hand cart with a handle that has a small sensing "hat" on top of the handle to help couriers who are carrying large amounts of objects. In a general example, an exemplary sensing hat on the handle provides further proximity and tracking sensors (similar to the autonomy module sensors 2810 on exemplary MAM 1725) to those disposed on the MB component itself, and provides control (similar to what exemplary MAM 1725 would provide) for the propulsion and steering system in the modular mobility base component. Such sensors may include, for example, multiple cameras, computer vision sensors, and mapping sensors (e.g., LiDAR/radar) so that this specially outfitted MB unit can track the courier while the courier is moving; predict & follow movement of the courier; detect, classify, and avoid objects (fixed and/or moving) while navigating; separately recognize and temporarily operate as a manual cart (with and without objects) so as to hover while the courier is making deliveries; and autonomously move and follow the moving courier with the additional objects to be delivered without burdening the courier.

An embodiment of an exemplary sensing hat (more generally referred to as a modular mobile cart autonomy control module) may include all features of an exemplary MAM 1725 but in a different form factor, and provide up to full autonomous operation with the addition of "follow-me" mode of the courier, another cart, and/or a vehicle. The cart handle (where the exemplary sensing hat is featured) may also allow localized human guidance should conditions such as regulatory limitations, or failure to sense require human intervention and interaction. In this situation, the exemplary sensing hat provides for an override capability based upon localize human input for this special type of improved and enhanced hand cart. In such a situation, the exemplary enhanced hand cart may function as a motor-assisted cart, guided by the local operator albeit in a temporary mode before switching back to an autonomous mode that follows the courier without any manual burden on the courier.

In a further embodiment, the exemplary enhanced hand cart may be instructed by a remote service networked device operated by a local operator or courier. Such a remote service networked device may, for example, be implemented as a master node communicating with an ID node or master node embedded as part of an exemplary sensing hat (e.g., the autonomous controller in the exemplary sensing hat similar to autonomous control system 3100 in exemplary MAM 1725). The master node of the remote service networked device knows of or has determined a location of the ID node in such an exemplary sensing hat using TRON locating techniques described above or where the control system in the exemplary sensing hat has location circuitry (e.g., a GPS receiver) and is capable of self-locating (i.e., where the control system is implemented with a master node that has built-in location circuitry). Such a remote service networked device, more generally referred to as a wireless mobile courier node, allows for communications of instructions between the local courier operating such a device and the exemplary enhanced hand cart. Such instructions may be related to regulatory limitations, which may come in the form of attributes describing a limitation of use for at least the exemplary enhanced hand cart based upon the cart's proximity to a location, geofence, or the like. In an embodiment, local operation of the exemplary enhanced hand cart may also include an awareness of local limiting factors as captured on the ground, such as by visual recognition by sensors on the exemplary enhanced hand cart of a hazardous object, symbol, or sign (e.g., a tanker truck with gasoline having a hazardous material sign or explosive triangle visual symbol on the truck or on a warning sign placed near the truck). With such awareness, the exemplary enhanced hand cart (i.e., an exemplary modular autonomous cart apparatus assembly) may alter its course and speed in compliance with or to avoid issues with such local limiting factors.

Figure 57A:
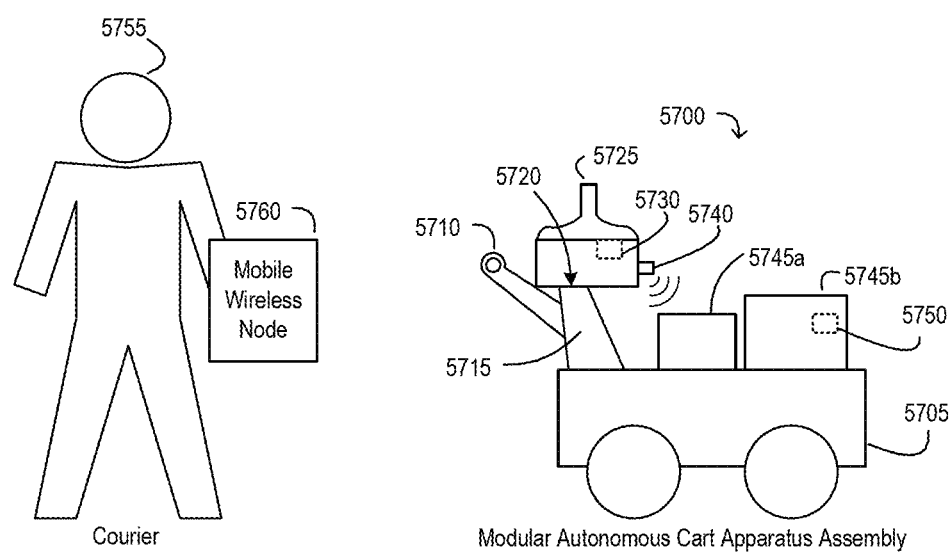
FIG. 57A is a diagram of an exemplary modular autonomous cart apparatus assembly in accordance with an embodiment of the invention.

FIG. 57A is a diagram of an exemplary modular autonomous cart apparatus assembly 5700 in accordance with an embodiment of the invention. Referring now to FIG. 57A, exemplary courier personnel 5755 is shown next to exemplary modular autonomous cart apparatus assembly 5700, which is supporting items 5745a, 5745b as items being shipped that may, for example, be involved in a logistics operation for pickup and/or delivery where the courier 5755 picks up or delivers such items as transported on exemplary modular autonomous cart apparatus assembly 5700. Such items may be conventional objects, packages, or items being transported as part of such a logistics operation. In the illustrated embodiment, courier 5755 has possession of and operates exemplary courier mobile wireless node 5760, which may be implemented similar to that described above as a remote service networked devices (e.g., smartphone, table, and the like) or as node-based mobile user access device 3310. For example, exemplary courier mobile wireless node 5760 may be implemented as a master node with onboard location circuitry that identifies the current location of the wireless mobile courier node. In more detail, courier mobile wireless node 5760 may be a master node traveling with courier personnel 5755 as part of delivering an item being shipped (e.g., item 5745a), where the master node includes onboard GPS location circuitry that identifies the current location of the wireless mobile courier node 5760. In still other examples, the wireless mobile courier node 5760 may be a master node disposed on a vehicle transporting courier personnel tasked with delivering the item being shipped, wherein the master node includes onboard location circuitry that identifies the current location of the wireless mobile courier node. Further still, an example may implement the wireless mobile courier node 5760 as a master node disposed on another modular autonomous cart apparatus assembly where the master node on the other cart apparatus assembly has onboard location circuitry that identifies the current location of the wireless mobile courier node 5760.

Exemplary modular autonomous cart apparatus assembly 5700 generally includes modular components that may be assembled ahead of time (with component-to-component authentication) or assembled in an on-demand manner with respect to a targeted dispatched logistics operation. As shown in FIG. 57A, exemplary modular autonomous cart apparatus assembly 5700 generally includes an exemplary modular mobility base 5705, an exemplary modular cart handle (e.g., comprised of handle grip 5710 and handle base 5715) mounted to the base platform of the mobility base 5705, and an exemplary modular mobile cart autonomy control module 5725 mounted to the cart handle. In general, the exemplary modular mobile cart autonomy control module 5725 (e.g., an exemplary "sensing hat") may be implemented as a specialized type of exemplary MAM 1725 and be deployed as having the same components as exemplary MAM 1725 as shown in FIG. 31. In one example, exemplary modular mobile cart autonomy control module 5725 is shown in FIG. 57A with an exemplary autonomous controller 5730 (e.g., an embodiment of which may be implemented similar to autonomous control system 3100) and payload monitoring sensors 5740 (e.g., an embodiment of which may be implemented similar to sensors 3130 or deployed in sensor pods detachably connected to the outside of control module 5725 so that such sensors 5740 may monitor what is supported on the base adapter plate of mobility based 5705).

Such payload monitoring sensors 5740 may be mounted on the detachable modular housing of control module 5725 so as to be focused and operative to monitor a payload area on the mobility base platform on mobility base 5705 where items 5745a-5745b are supported when the modular mobility base 5705 is moving.

However, those skilled in the art will appreciate that while not shown in FIG. 57A, exemplary modular mobile cart autonomy control module 5725 may also be implemented with an appropriately shaped detachable modular housing, latching points for secure modular connections to the cart handle, displays, light panels, additional sensors (also referred to as autonomy module sensors that generate onboard sensor data about an environment external to the control module 5725), lights, a user input panel, a wireless transceiver, and location circuitry as described relative to exemplary MAM 1725.

Figure 57B:
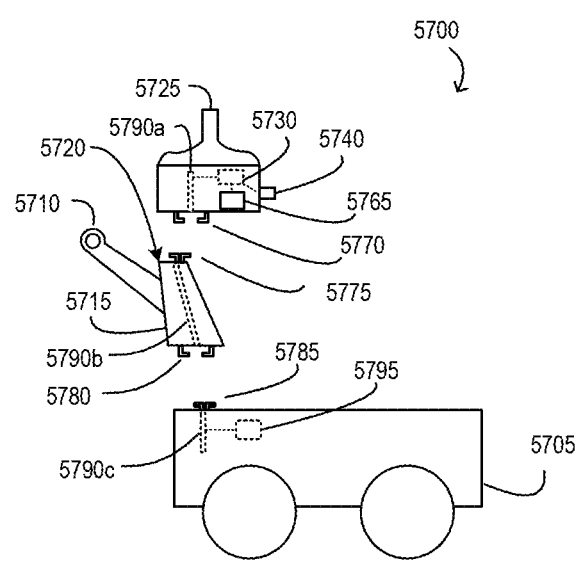
FIG. 57B is a more detailed diagram of the exemplary modular autonomous cart apparatus assembly from FIG. 57A in accordance with an embodiment of the invention.

FIG. 57B is a more detailed diagram of the exemplary modular autonomous cart apparatus assembly 5700 from FIG. 57A in accordance with an embodiment of the invention. Referring now to FIG. 57B, the general components of exemplary modular autonomous cart apparatus assembly 5700 described above are shown in a separated configuration to better reveal exemplary latching points 5770, 5785 (e.g., interlocking latches) and actuated latches 5775, 5780 that mate to the latching points during assembly of exemplary modular autonomous cart apparatus assembly 5700. As shown in FIG. 57B, the embodiment of exemplary modular mobility base 5705 is illustrated with exemplary common power and data conduit bus 5790c, exemplary mobility controller 5895 coupled to the bus 5790c, as well as an embodiment of latching points or latches 5785 disposed on the top of mobility base 5705 (e.g., similar to latches 1855 but located at a point on the top of mobility base 5705 to appropriate mate with the modular cart handle). However, those skilled in the art will appreciate that, while not shown in detail in FIG. 57B, exemplary modular mobility base 5705 may be implemented with essentially the same type of components as that described above for exemplary modular mobility base 1705 in FIG. 18c (e.g., having a mobile base platform, alignment interfaces, latching elements, mobility controller, wheels, sensors, lights, steering system, propulsion system, wireless transceiver, common power and data conduit bus, and the like).

As shown in FIG. 57B, the embodiment of exemplary modular cart handle includes exemplary handle grip 5710 and exemplary handle base 5715. The handle base 5715 has a top end and bottom end, with latches 5775 and 5780 on both ends that may be actuated, for example, via actuation in response to signals from controller 5730 (similar to handle actuator 2225 that actuates latches 2110a, 2110b in response to signals from autonomous control system 3100) and/or via manual actuation with a handle, lever, or other manual control element similar to the actuation of the latching elements shown and described on FIG. 22B using locking handle 2115. Exemplary handle base 5715, in such a way, may be detachably connected to the exemplary mobility base 5705 and to exemplary modular mobile cart autonomy control module 5725 (via, for example, an alignment seat 5720 for control module 5725 on the top end of handle base 5715). Further, exemplary handle base 5715 is shown having exemplary common power and data conduit bus 5790b that connects with aligned mated interfaces for bus 5790a in the control module 5725 and bus 5790c in the mobility base 5705. Exemplary handle grip 5710 is shown extending from handle base 5715, but other embodiments of grip 5710 may attached directly to mobility base 5705.

And as shown in FIG. 57B, exemplary modular mobile cart autonomy control module 5725 (e.g., an exemplary "sensing hat") has exemplary autonomous controller 5730 (e.g., an embodiment of which may be implemented similar to autonomous control system 3100), exemplary payload monitoring sensors 5740 (e.g., an embodiment of which may be implemented similar to sensors 3130 or deployed in sensor pods detachably connected to the outside of control module 5725 so that such sensors 5740 may monitor what is supported on the base adapter plate of mobility based 5705), as well as an exemplary user input panel 5765 and latching points 5770 (e.g., similar to points 5785) that mate to and/or interlock with actuating latching structure 5775. Again, those skilled in the art will appreciate that while not shown in FIG. 57B, exemplary modular mobile cart autonomy control module 5725 may also be implemented with an appropriately shaped detachable modular housing, displays, light panels, additional autonomy module sensors, lights, a wireless transceiver, and location circuitry as described relative to exemplary MAM 1725.

One or more items being shipped on assembly 5700 may also have a node (e.g., ID node, master node) disposed with an item (e.g., item 5745b) that may associate with and securely communicate with autonomous controller 5730 as part of identifying the item, tracking the item, locating the item, and the like. For example, item 5745b has a wireless ID node 5750 with (e.g., attached to, disposed within, integrated as part of) item 5745b. In such an example, the wireless ID node 5750 may maintain shipping information on the item 5745b including at least identifier information on the item 5745b, recipient information on the item 5745b, and destination information on the item 5745b. As such, the autonomous controller 5730 of the modular mobile cart autonomy control module 5725 may be further programmatically adapted and configured to be operative to generate association data that establishes and reflects a secure association between the wireless ID node 5750 and the modular mobile cart autonomy control module 5725 (e.g., the autonomous controller 5730 in control module 5725) after detecting an advertising signal from the wireless ID node 5760. This secure association between the wireless ID node 5750 and the modular mobile cart autonomy control module 5725 allows secure sharing of at least the shipping information between the wireless ID node 5750 and the modular mobile cart autonomy control module 5725, and further embodiments may then responsively generate notifications related to delivery of such an node-enabled item 5745b.

The exemplary modular autonomous cart apparatus assembly 5700 may, in some embodiments, advantageously and automatically provide notifications for courier 5755 related to what is being transported on the assembly 5700. For example, the autonomous controller 5730 of the modular mobile cart autonomy control module 5725 may be further programmatically adapted and configured to be operative to generate a delivery notification in response to receiving at least a portion of the shipping information from the wireless ID node 5750. Such a delivery notification may, for example, be a delivery location information notification indicating the destination information on the item being shipped and the identifier information on the item being shipped. Such a delivery notification may be triggered, for example, when the current location of the modular autonomous cart apparatus assembly is within a threshold distance from a delivery location indicated by the destination information.

Such delivery notifications may take several forms. For example, the autonomous controller 5730 of the modular mobile cart autonomy control module 5725 may be programmatically adapted and configured to generate the delivery notification as a delivery warning on at least one display disposed on the detachable modular housing of control module 5725, where the delivery warning identifies the item 5745b based upon the shipping information from that item's node 5750 and where the delivery warning also indicates the destination information on the item being shipped. In other examples, such a delivery warning may be generated as an audible delivery warning through a speaker disposed on the detachable modular housing and operatively coupled to the autonomous controller 5730.

In further examples, the delivery notification may be through wireless interactions with the courier's wireless mobile courier node 5760. For example, the autonomous controller 5730 of the modular mobile cart autonomy control module 3725 may be programmatically adapted and configured to be operative to generate the delivery notification wirelessly notifying the wireless mobile courier node 5760 with the delivery notification, which may appear on a screen on the courier node 5760 or with an audible warning generated by the courier node 5760.

An exemplary delivery notification generated by the autonomous controller 5730 may, in another example, be a delivery location information notification indicating the destination information on the item and identifier information on the item being shipped. The generations of such deliver location information notification may be triggered, by autonomous controller 5730, for wireless notification of wireless mobile courier node 5760 when the current location of the modular autonomous cart apparatus assembly 5700 is within a threshold distance from a delivery location indicated by the destination information.

An embodiment of exemplary modular autonomous cart apparatus assembly 5700 may be capable, configured, and programmed to predict movement of the courier 5755, and autonomously cause exemplary modular autonomous cart apparatus assembly 5700 to move (e.g., the modular mobility base 5705 to move) based upon such predicted movement. For example, the autonomous controller 5730 of the modular mobile cart autonomy control module 5725 in exemplary modular autonomous cart apparatus assembly 5700 may be further programmatically adapted and configured to be operative to generate a predicted path of movement for the wireless mobile courier node 5760 based upon a destination location maintained by the modular mobile cart autonomy control module 5725; and generate the steering control command and the propulsion control command for systems in mobility base 5705 based at least upon the location data from the location circuitry in module 5725, the received information on the base feedback sensor data from the mobility controller in mobility base 5705, the onboard sensor data as received by the autonomous controller 5730 from the autonomy module sensors, and the determined location of the wireless mobile courier node 5760.

In more detail, the location of the wireless mobile courier node 5760 may be determined by the autonomous controller 5730 of the modular mobile cart autonomy control module receiving a location message from the wireless mobile courier node 5760 and where the location message provides the current location of the wireless mobile courier node 5760 (and the location of the assembly 5700 may be provided to controller 5730 through location circuitry deployed as part of control module 5725).

Similar to modular components from exemplary MALVT bot apparatus assembly 1700 as described above, an embodiment of exemplary modular autonomous cart apparatus assembly 5700 may be deployed that uses only authenticated modular components. For example, an embodiment of exemplary modular autonomous cart apparatus assembly 5700 may have modular mobility base 5705, modular cart handle 5710/5715, and the modular mobile cart autonomy control module 5725 being each authenticated modular components based upon a component-to-component secure handshaking between proximately attached ones of the modular mobility base 5705, modular cart handle 5710/5715, and the modular mobile cart autonomy control module 5725. In more detail, the component-to-component secure handshaking may involve a challenge and security credential response between proximately attached ones of the modular mobility base 5705, modular cart handle 5710/5715, and the modular mobile cart autonomy control module 5725 (such as explained with reference to FIG. 34). Such authentication of the modular components may, for example, be implemented with verification of authenticated modular components for the modular autonomous cart apparatus assembly 5700 as each of the modular mobility base 5705, modular cart handle 5710/5715, and the modular mobile cart autonomy control module 5725 are assembled into the modular autonomous cart apparatus assembly 5700. And like that explained with reference to FIG. 34, the component-to-component secure handshaking may be based upon one or more regulatory rules, one or more contractual rules, and/or one or more safety rules. Further, an embodiment may have the component-to-component secure handshaking of modular components of assembly 5700 being based upon logistical constraint information on a determined work environment for the modular autonomous bot apparatus assembly 5700. Examples of such logical constraint information may be identified as part of the security credential response. In more detail, examples of such logistical constraint information may identify a size limitation for the modular autonomous cart apparatus assembly 5700, a weight limitation for the modular autonomous cart apparatus assembly 5700, and/or a readiness limitation for the modular autonomous cart apparatus assembly. In even more detail, such a readiness limitation may be one or more performance thresholds for the modular autonomous bot apparatus assembly 5700 in an anticipated deployment operation of the modular autonomous cart apparatus assembly 5700 (e.g., a minimum charge on the power source used onboard assembly 5700, and the like).

If the modular components of exemplary modular autonomous cart apparatus assembly 5700 are not authenticated, actions may be initiated on the modular autonomous cart apparatus assembly 5700. For example, the autonomous controller 5730 of the modular mobile cart autonomy control module 3725 may be further programmatically adapted and configured to be operative to notify a server (such as a dispatch server or assembly server) over the wireless radio transceiver on control module 3725 that one or more of the modular mobility base 5705, modular cart handle 5710/5715, and the modular mobile cart autonomy control module 5725 are not authenticated modular components based upon the component-to-component secure handshaking between the modular mobile cart autonomy control module 5725 and each of the modular mobility base 5705 and the modular cart handle 5710/5715. Such a notification may include or be followed by request by the autonomous controller 5730 for a replacement component for the one or more of the modular mobility base 5705 and the modular cart handle 5710/5715 that are not authenticated modular components in the assembly 5700.

In another example of actions that may be initiated for non-authenticated modular components, the autonomous controller 5730 of the modular mobile cart autonomy control module 5725 may be further programmatically adapted and configured to be operative to generate a component replacement request message on at least one of the displays disposed on the detachable modular housing of control module 5725 when one or more of the modular mobility base 5705 and the modular cart handle 5710/5715 are not authenticated modular components based upon the component-to-component secure handshaking. Such a component replacement request message may request a replacement component for the one or more of the modular mobility base 5705 and the modular cart handle 5710/5715 that are not authenticated modular components.

In still another example, the autonomous controller 5730 of the modular mobile autonomy control module 5725 may be further programmatically adapted and configured to receive an authentication result from one of the modular mobility base and the modular cart handle, where the authentication result indicates that at least one of the modular mobility base and the modular cart handle are not authenticated modular components based upon the component-to-component secure handshaking. Based upon the authentication result received by the autonomous controller 5730, the autonomous controller 5730 may then notify a server (such as a dispatch server or assembly server) over the wireless radio transceiver in control module 5725 that one or more of the modular mobility base and modular cart handle are not authenticated modular components to initiate replacement of the non-authenticated component(s). A further example may, instead of or in addition to notifying the server, generate a component replacement request message on at least one of the displays disposed on the detachable modular housing of control module 5725 based upon the authentication result received.

In further embodiments involving the authentication of modular components on exemplary modular autonomous cart apparatus assembly 5700, the component-to-component secure handshaking may be performed between the modular mobile cart autonomy control module 5725 and each of the modular mobility base 5705 and the modular cart handle 5710/5715. Thus, while the control module 5730 may not be proximately attached to modular mobility base 5705, the component identifiers and relevant security credentials of non-proximate modular components may be verified and authenticated by the control module 5730 through communications over buses 5790a-5790c. As such, the component-to-component secure handshaking may involve a challenge and security credential response between the modular mobile cart autonomy control module 5725 and respectively each of the modular mobility base 5705 and the modular cart handle 5710/5715. As with the component-to-component secure handshaking described above relative to assembly 5700, such secure handshaking with the modular mobile cart autonomy control module 5725 may involve regulatory rules, contractual rules, and safety rules, logistical constraint information on a determined work environment for the modular autonomous cart apparatus (e.g., a size limitation for the modular autonomous cart apparatus assembly, a weight limitation for the modular autonomous cart apparatus assembly, a readiness limitation for the modular autonomous cart apparatus assembly, performance thresholds for the modular autonomous cart apparatus assembly in an anticipated deployment operation of the modular autonomous cart apparatus assembly, and the like). Those skilled in the art will further appreciate that similar notifications and responsive actions (e.g., request replacements) for non-authenticated modular components may also be taken based upon the secure handshaking undertaken by the modular mobile cart autonomy control module 5725.

Further still, an embodiment may have such authentication of the modular components of exemplary modular autonomous cart apparatus assembly 5700 in the context of a particular logistics operation assigned to the exemplary modular autonomous cart apparatus assembly 5700. For example, the modular mobility base 5705, modular cart handle 5710/5715, and the modular mobile cart autonomy control module 5725 may be each verified to be compatible with an assigned logistics operation for the modular autonomous cart apparatus assembly 5700 based upon a component-to-component secure handshaking between proximately attached ones of the modular mobility base 5705, modular cart handle 5710/5715, and the modular mobile cart autonomy control module 5725.

Figure 58:
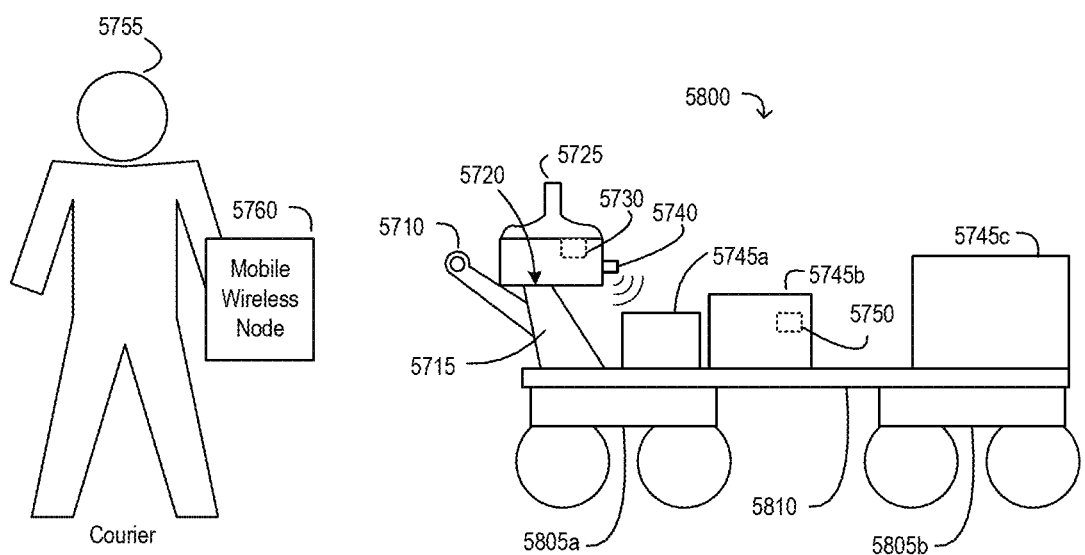
FIG. 58 is a diagram of the exemplary modular autonomous cart apparatus assembly that uses a mobility base sub-assembly having an extended base adapter plate and two mobility base units in accordance with an embodiment of the invention.

FIG. 58 is a diagram of the exemplary modular autonomous cart apparatus assembly 5800 that uses two mobility bases as a sub-assembly having an extended base adapter plate in accordance with an embodiment of the invention. The pair of mobility base components may cooperate as a combined larger format follower-enhanced MB-based in order to move heavy or hard to handle freight that can follow a courier to a delivery destination. The exemplary MB pair in this embodiment may be able to cooperate via TRON technology (e.g., association based coupling, wireless node-to-node communication, etc.) acting as one larger combined platform able to carry heavier encumbering loads than a courier could carry on his own. The coupled/combined MB pair may follow the courier via autonomous following as described above and with the various location enablement techniques described herein (e.g., via GPS, mapping, or TRON enablement).

Referring now to FIG. 58, exemplary modular autonomous cart apparatus assembly 5800 is setup similar to that of assembly 5700, but it includes two mobility bases 5805a, 5805b and an extended base adapter plate 5810. As such, this part of assembly 5800 is similar to exemplary assembly 1900 as shown in FIG. 19 with multiple modular mobility base components 1705a, 1705b paired with an exemplary extended base adapter plate module (BAPM) 1905. Further, mobility bases 5805a, 5805b may include multi/all-wheel independent drive (propulsion) and multi/all-wheel independent steering as discussed with respect to exemplary modular mobility base 1705. In such a configuration, exemplary modular autonomous cart apparatus assembly 5800 may be deployed to carry an increased payload (e.g., items 5745a-5745c) atop extended base adapter plate 5810 but still be used with courier 5755 and courier mobile wireless node 5760 as described herein.

As such and in more detail, an embodiment of modular autonomous cart apparatus assembly 5800 implements a combined mobility base with a mobility base sub-assembly that has an extended base adapter plate 5810 as the mobile base platform, a front mobility base unit 5805a coupled to a bottom of the extended base adapter plate 5810, and a rear mobility base unit 5805b coupled to the bottom of the extended base adapter plate 5810. In light of the discussion above related to exemplary modular mobility base 1705, those skilled in the art will appreciate that the collective propulsion system for the modular mobility base is connected to the extended base adapter plate 5810, and uses a front propulsion system responsive to a first propulsion control input from the mobility controller to cause changes in speed of the front mobility base unit 5805a, and a second propulsion system responsive to a second propulsion control input from the mobility controller to cause changes in speed of the rear mobility base unit 5805*b*. The steering system for the combined modular mobility base has a first steering system connected to the front mobility base unit 5805*a* and coupled to the first propulsion system (where the first steering system responds to a first steering control input from the mobility controller to cause changes to directional movement of the front mobility base unit 5805*a*) and a second steering system connected to the second mobility base unit 5805*b* and coupled to the second propulsion system (where the second steering system responds to a second steering control input from the mobility controller and to cause changes to directional movement of the rear mobility base unit 5805*b*). Such an exemplary mobility base sub-assembly also has mobility base sensors coupled to the mobility control system for the sub-assembly, where the mobility base sensors have a first portion disposed on the front mobility base unit 5805*a* and a second portion disposed on the rear mobility base unit 5805*b*. Such mobility base sensors (similar to sensors 1815) are operative to autonomously detect an object in the path of assembly 5800 and provide base feedback sensor data to the mobility controller on the detected object.

An embodiment of assembly 5800 may use a single mobility controller as a mobility control system that separately generates coordinated control signals to control each of the mobility base units 5805*a*, 5805*b*. In another embodiment, assembly 5800 may have different mobility controllers in each of the mobility base units 5805*a*, 5805*b* where the two mobility controllers coordinate similar to that described above relative to FIG. 19 and exemplary modular multiple mobility base assembly apparatus 1900. As such, in this other embodiment, one unit 5805*a* may operate as a master controller with respect to the mobility base sub-assembly and the other unit 5805*b* may operate as a slave controller (e.g., taking direction for propulsion and steering from the master controller in unit 5805*a* as master control input and providing sensor data by the slave controller in unit 5805*b* to the master controller in the first unit 5805*a*).

Exemplary assembly 5800 may also have an interface to a common modular component power and data transport bus (similar to that shown as bus 5790*c*) that provides a power conduit for the modular mobility base (e.g., both of mobility base units 5805*a*, 5805*b*) and a command and data interface conduit for at least the mobility controller (e.g., for the respective mobility controllers in each of mobility base units 5805*a*, 5805*b*).

Figure 59A:
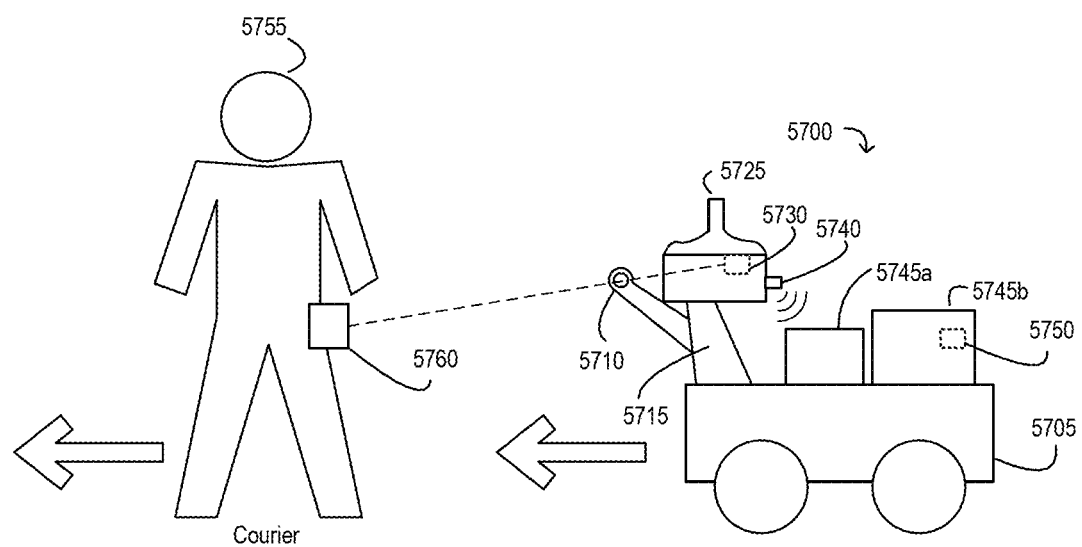
FIGS. 59A-59C are diagrams of an exemplary modular autonomous cart apparatus assembly as deployed and used in different operating modes with an exemplary wireless mobile courier node in accordance with an embodiment of the invention.
Figure 59B:
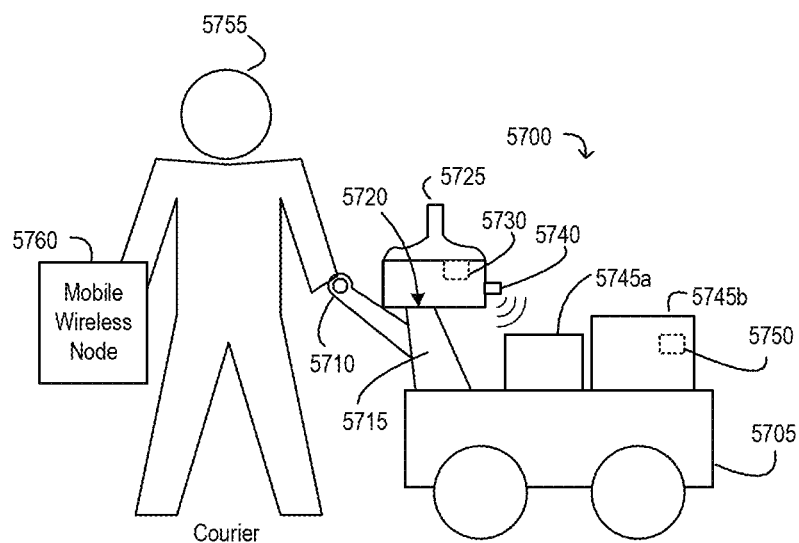
Figure 59C:
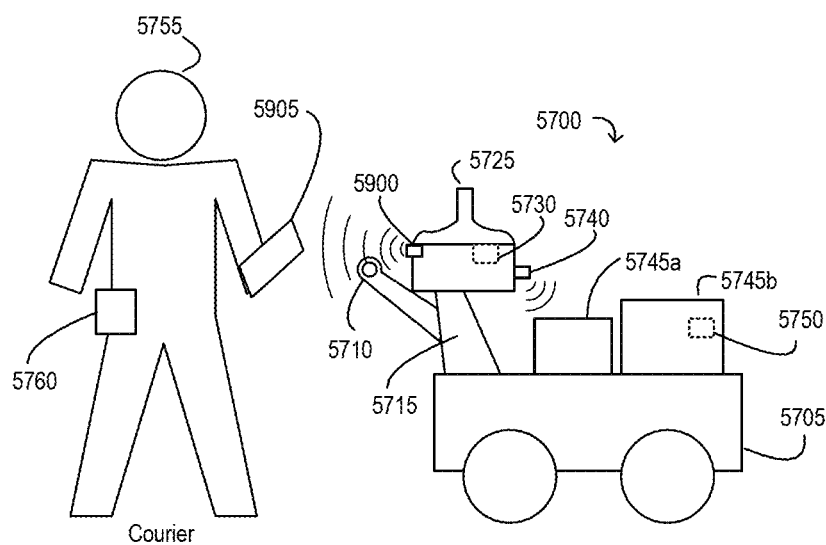

FIGS. 59A-59C are diagrams of exemplary modular autonomous cart apparatus assembly 5700 as deployed and used with exemplary wireless mobile courier node 5760 operated by courier 5755 in different operating modes—e.g., a follow mode, a manual or directed override mode, and a hover mode in accordance with an embodiment of the invention. In general, FIG. 59A illustrates exemplary modular autonomous cart apparatus assembly 5700 operating in the follow mode where the exemplary modular autonomous cart apparatus assembly 5700 autonomously tracks and follows the current location of the wireless mobile courier node 5760 as the wireless mobile courier node 5760 moves and while maintaining a predetermined follow distance from the current location of the wireless mobile courier node 5760. In more detail, and referring now to the exemplary embodiment shown in FIG. 59A, an embodiment of exemplary modular autonomous cart apparatus assembly 5700 operate in follow mode with the autonomous controller 5730 of modular mobile cart autonomy control module 5725 being programmatically adapted and configured to be operative to perform functions (a)-(i) as described below. This includes having the autonomous controller 5730 being programmatically operative to (a) detect, using the wireless radio transceiver on control module 5725, an advertising signal from a wireless mobile courier node 5760 and then (b) generate association data that establishes and reflects a secure association between the wireless mobile courier node 5760 and the modular mobile cart autonomy control module 5725 after detecting the advertising signal from the wireless mobile courier node 5760 (where the secure association between the wireless mobile courier node 5760 and the modular mobile cart autonomy control module 5725 enables and allows secure sharing of information between the wireless mobile courier node 5760 and the modular mobile cart autonomy control module 5725. The autonomous controller 5730 may be further programmatically operative to (c) determine a current location of the wireless mobile courier node 5760 (e.g., through information provided by node 5760, through node locating techniques described herein, and the like); (d) determine a current location of the modular autonomous cart apparatus assembly 5700 through, for example, location data generated by location circuitry within control module 5725; (e) receive information on base feedback sensor data from the mobility controller 5795 through the common modular component power and data transport bus (e.g., buses 5790*a*-5790*c*); (f) receive the onboard sensor data from the autonomy module sensors on control module 5725; and then (g) generate a steering control command and a propulsion control command based at least upon the current location of the modular autonomous cart apparatus assembly 5700, the current location of the wireless mobile courier node 5760, the received information on the base feedback sensor data from the mobility controller 5795, and the onboard sensor data as received by the autonomous controller 5730 from the autonomy module sensors on control module 3725. Additionally, the autonomous controller 5730 may be further programmatically operative to (h) transmit the steering control command and the propulsion control command through the common modular component power and data transport bus (e.g., buses 5790*a*-5790*c*) for receipt by the mobility controller 5730 in control module 5725; and then (i) repeat functions (c)-(h) to autonomously track and follow the current location of the wireless mobile courier node 5760 as the wireless mobile courier node 5760 moves and while maintaining a predetermined follow distance from the current location of the wireless mobile courier node 5760. In this way, an embodiment of exemplary modular autonomous cart apparatus assembly 5700 may operate in a type of follow mode that unburdens the courier 5755 and allows the courier 5755 an entirely new freedom of movement without the need to consciously guide the assembly 5700.

A further embodiment may extend such a follow mode for the exemplary modular autonomous cart apparatus assembly 5700 with a handoff to another node, such as another mobile node (e.g., one associated with a vehicle or separate person other than courier 5755) or one or more facility nodes disposed in an environment external to the assemble 5700 (e.g., building facility nodes placed in different locations within an office area or at different locations within the building). Such a handoff from the wireless mobile courier node 5760 to another node (such as one or more facility nodes) may, in essence, have exemplary modular autonomous cart apparatus assembly 5700 engage in a type of follow mode where what is followed may change from the courier mobile wireless node 5760 to a "virtual" courier represented by the other node (whether mobile or stationary types of nodes). For example, a further embodiment of the exemplary modular autonomous cart apparatus assembly 5700, when operating in follow mode, may have the autonomous controller 5730 of the modular mobile cart autonomy control module 5725 being further programmatically adapted and configured to be operative to (j) detect, using the wireless radio transceiver, a first wireless facility node; and (k) repeat functions (c)-(i) using the first wireless building facility node as the wireless mobile courier node. As such, assembly 5700 may shift from moving towards the courier mobile wireless node and transition to moving towards the first wireless facility node, which effectively implements a follow mode handoff.

In more detail, such a follow mode handoff embodiment may have the autonomous controller 5730 of the modular mobile cart autonomy control module 5725 being operative to perform function (j) by being further programmatically adapted and configured to be operative to detect, using the wireless radio transceiver, an advertising signal from the first wireless facility node; and generate association data that establishes and reflects a secure association between the first wireless facility node and the modular mobile cart autonomy control module 5725 after detecting the advertising signal from the first wireless facility node. Here, the secure association between the first wireless facility node and the modular mobile cart autonomy control module 5725 (e.g., the autonomous controller 5730 within the control module 5725) allows for secure sharing of information between the first wireless facility node and the modular mobile cart autonomy control module 5725. Such securely shared information allows the first wireless facility node to guide the modular autonomous cart apparatus assembly 5700 from the current location of the modular autonomous cart apparatus assembly 5700 to the current location of the first wireless facility node. For example, if the first wireless facility node was a node deployed in the lobby of a building, exemplary modular autonomous cart apparatus assembly 5700 may operate in follow mode to follow courier 5755 (i.e., wireless mobile courier node 5760) to an entrance of the building where the assembly shifts to now "follow" or move towards the current location of the lobby node. Those skilled in the art will appreciate that the building facility node may be stationary or mobile, but in either case, the assembly 5700 performing a follow mode handoff will move relative to the building facility node in the future rather than towards or relative to the wireless mobile courier node 5760. A further embodiment may have the autonomous controller 5730 implement a "return to courier" mode after such a handoff, where the autonomous controller 5730 detects completion of a delivery or pickup (e.g., using sensors 5740 and/or node communications with a node-enabled item being transported for pickup or delivery), notifies the wireless mobile courier node 5760 and autonomously causes the modular mobility base 5705 to move back to the current location of the wireless mobile courier node 5760 (or to a separate pickup or delivery location for an additional logistics operation before returning to the courier autonomously after being handed off to follow such a virtual courier).

An embodiment may extend the follow mode handoff exemplary by having assembly 5700 shift again from following the first building facility node to another node for additional handoffs. For example, the autonomous controller 5730 of the modular mobile cart autonomy control module 5725 may be further programmatically adapted and configured to be operative to detect, using the wireless radio transceiver, a second wireless building facility node located past the first wireless building facility node; and repeat functions (c)-(i) using the second wireless building facility node as the wireless mobile courier node. As such, in the example where the first wireless building facility node is a lobby node, the exemplary modular autonomous cart apparatus assembly 5700 may switch from following the courier mobile wireless node 5760 upon entering the building to moving towards the lobby node (despite it not moving). Once close enough to the lobby node, assembly 5700 may shift again and begin following or moving towards a building facility node located in a particular conference room. Thus, as the assembly "follows" and moves towards and arrives at the conference room node, a pickup or delivery may occur with an item being transported on mobility base 5705, and assembly 5700 may return to the courier 5755 without the courier 5755 ever needed to enter the building or move from the entrance area.

In still another embodiment, the securely shared information between the associated devices may extend this follow mode to where the securely shared information allows the first wireless facility node to guide the modular autonomous cart apparatus assembly 5700 from the current location of the modular autonomous cart apparatus assembly 5700 to a remote location within a transmission range of the first wireless facility node. As such, the "virtual" courier may provide a point to follow as well as directions to follow towards the remote location. In other words, an embodiment may have the autonomous controller 5730 of the modular mobile cart autonomy control module 5725 being further programmatically adapted and configured to be operative to repeat functions (d)-(h) using the first wireless building facility node as the wireless mobile courier node and to autonomously cause the modular autonomous cart apparatus assembly to move towards the remote location.

In some circumstances, exemplary modular autonomous cart apparatus assembly 5700 may use localized human guidance input to override autonomous movement of the assembly 5700. In such an embodiment, as shown in FIG. 59B, courier 5755 manually engages the modular cart handle grip 5710 to initiate a manual override mode of assembly 5700. For example, in such an embodiment, the modular cart handle may have a localized guidance input detector (e.g., button, switch, or touch-sensitive detector responsive to a degree of pressure exerted on the detector) disposed on the handle grip 5710 and operatively coupled to the autonomy controller 5730 through bus 5790*b* within the modular cart handle. The localized guidance input detector operates in this embodiment to sense external contact with local personnel (e.g., the hand of courier 5755 as it engages grip 5710 and the localized guidance input detector on the grip 5710) as an override control input for the modular autonomous cart apparatus assembly 5700. As such, the autonomous controller 5730 of the modular mobile cart autonomy control module 5725 may be further programmatically adapted and configured to be operative to, in response to receiving the override control input from the localized guidance input detector, to generate the steering control command and the propulsion control command based at least upon the sensed external contact with the local personnel to provide power-assisted movement of the modular mobility base 5705 at the direction of the local personnel, such as courier 5755.

In more detail, an embodiment may have the autonomous controller 5730 of the modular mobile cart autonomy control module 5725 being further programmatically adapted and configured to be operative to, in response to receiving the override control input from the localized guidance input detector, to generate the steering control command and the propulsion control command based at least upon (a) the sensed external contact with the local personnel to provide power-assisted movement of the modular mobility base at the direction of the local personnel, (b) the received information on the base feedback sensor data from the mobility controller, and (c) the onboard sensor data as received by the autonomous controller from the autonomy module sensors so as to provide the power-assisted movement of the modular mobility base 5705 at the direction of the local personnel while avoiding collisions and objects in the path of the modular mobility base 5705 using the received information on the base feedback sensor data and the onboard sensor data. Thus, in response to detecting an object in the path of the modular mobility base 5705 while in this manual override mode, the autonomous controller 5730 of the modular mobile cart autonomy control module 5725 may be further programmatically adapted and configured to be operative to alter at least one of the steering control command and the propulsion control command to implement a type of collision avoidance intervention despite the manual override mode. In one example, at least one of the base feedback sensor data and the onboard sensor data may be proximity sensor data related to the object in the path of the modular mobility base being avoided by at least one of the steering control command and the propulsion control command. In another example, at least one of the base feedback sensor data and the onboard sensor data includes visual sensor data related to an image of the object in the path of the modular mobility base being avoided by at least one of the steering control command and the propulsion control command. For example, when the sensors noted above identify the object in the path of the modular mobility base 5705 as being in a class of pathway objects to be avoided (e.g., a predetermined class of hazardous objects (such as fuel tankers), a predetermined class of symbols (such as symbols for hazardous waste), and a predetermined class of signs (such as STOP signs)).

The override mode described above is a manual override mode based upon local human input, but another type of override mode may be deployed in an exemplary modular autonomous cart apparatus assembly 5700. In more detail, a directed override mode may use limitations of use attributes based on restrictions of operations for the assembly 5700 to automatically switch into a different directed mode of operation for the assembly 5700. For example, a further embodiment of exemplary modular autonomous cart apparatus assembly 5700 may have the autonomous controller 5730 of control module 5725 maintaining a location limitation profile in its memory as a type of profile data (e.g., profile data 430 when controller 5730 is implemented as a type of master node), where the location limitation profile identifies one or more restricted locations for the modular autonomous cart apparatus assembly 5700 to avoid. In this further embodiment, the autonomous controller 5730 of the modular mobile cart autonomy control module 5725 may then be further programmatically adapted and configured to be operative to (g) generate the steering control command and the propulsion control command based at least upon the current location of the modular autonomous cart apparatus assembly 5700, the current location of the wireless mobile courier node 5760, the received information on the base feedback sensor data from the mobility controller 5795, the onboard sensor data as received by the autonomous controller 5730 from the autonomy module sensors, and the one or more restricted locations as identified in the location limitation profile. Such a location limitation profile may be downloaded wirelessly from a remote service network device (e.g., a dispatch or assembly server, a user access device external to the assembly 5700, and the like) to the autonomous controller 5830 in control module 5725 of modular autonomous cart apparatus assembly 5700

In yet a further embodiment of exemplary modular autonomous cart apparatus assembly 5700, autonomous operation of the assembly may rely on historic context data, such as location information and sensor-based information from prior logistics operations in the vicinity of where the assembly 5700 is currently operating. For example, an embodiment of exemplary modular autonomous cart apparatus assembly 5700 may have its autonomous controller 5730 of control module 5725 maintaining context data in memory related to prior movement of the modular autonomous cart apparatus assembly 5700. As such, the autonomous controller 5730 of the modular mobile cart autonomy control module 5725 may be further programmatically adapted and configured to repeat functions (c)-(h) as described above to autonomously track and follow the current location of the wireless mobile courier node 5760 as the wireless mobile courier node 5760 moves and while maintaining the predetermined follow distance from the current location of the wireless mobile courier node 5760 based also upon the context data related to prior movements of the modular autonomous cart apparatus assembly. In other words, any of the embodiments described herein may use such historic context data (e.g., a type of context data, shared data, and/or historic data 575 used by node-enabled components) in order for the apparatus to enhance its autonomous movement operations with a finer degree of location and sensory data keyed to locations where the assembly (or other assemblies) have been.

In such an embodiment and in more detail, the autonomous controller 5730 of the modular mobile cart autonomy control module 5725 may be programmatically adapted and configured to perform function (g) by being further programmatically adapted and configured to generate the steering control command and the propulsion control command based at least upon the current location of the modular autonomous cart apparatus assembly 5700, the current location of the wireless mobile courier node 5760, the received information on the base feedback sensor data from the mobility controller 5795, the onboard sensor data as received by the autonomous controller 5730 from the autonomy module sensors, and the context data related to prior movements of at least the modular autonomous cart apparatus assembly 5700.

For example, such context data may be historic data related to prior movement of the modular mobility base 5705 at one or more locations within a range distance from the current location of the modular autonomous cart apparatus assembly 5700. In another example, such context data, as historic data, may include historic pathway obstacle data indicating at least one identified pathway obstacle within the range distance from the current location of the modular autonomous cart apparatus assembly 5700. Such historic pathway obstacle data may be based upon previously processed onboard sensor data, previously processed base feedback sensor data, and previously processed location data on the prior location of the modular autonomous cart apparatus assembly 5700.

In still another example, such historic data may be historic building data indicating at least one identified building feature disposed external to the modular autonomous cart apparatus assembly where the identified building feature is within the range distance from the current location of the modular autonomous cart apparatus assembly. Such historic building data may be based upon previously processed onboard sensor data, previously processed base feedback sensor data, and previously processed location data on the prior location of the modular autonomous cart apparatus assembly.

Further still, historic data in yet another example, may include historic origin location context data and/or historic destination location context data. Historic origin location context data indicates at least one identified origin location environment feature disposed external to the modular autonomous cart apparatus assembly 5700 where the identified origin location environment feature is within the range distance from the current location of the modular autonomous cart apparatus assembly. Such historic origin location context data is based upon previously processed onboard sensor data, previously processed base feedback sensor data, and previously processed location data on the prior location of the modular autonomous cart apparatus assembly 5700. The historic destination location context data indicates at least one identified destination location environment feature disposed external to the modular autonomous cart apparatus assembly 5700 where the identified destination location environment feature is within the range distance from the current location of the modular autonomous cart apparatus assembly 5700. Such historic destination location context data is based upon previously processed onboard sensor data, previously processed base feedback sensor data, and previously processed location data on the prior location of the modular autonomous cart apparatus assembly 5700.

In addition to the follow mode and override modes described above, an embodiment of exemplary modular autonomous cart apparatus assembly 5700 may transition to a "hover" mode where the modular autonomous cart apparatus assembly 5700 temporarily halts movement based upon one or more types of control input from the courier 5755. For example, such an embodiment of exemplary modular autonomous cart apparatus assembly 5700 may have the autonomous controller 5730 of the modular mobile cart autonomy control module 5725 being further programmatically adapted and configured to be operative to (i) repeat functions (c)-(h) as described above relative to follow mode until the autonomy controller 5730 receives a delivery control input that activates a hover mode for the modular autonomous cart apparatus assembly 5700 temporarily halting movement of the modular mobility base 5705 that was otherwise autonomously tracking and following the current location of the wireless mobile courier node 5760. The delivery control input may, for example, be a wireless delivery control input from the wireless mobile courier node 5760 (e.g., a control signal generated by an app on node 5760 and wirelessly transmitted from node 5760 to autonomous controller 5730 to activate the hover mode that temporarily halts movement of assembly 5700). In other examples, the delivery control input may be provided through user input panel 5765 on control module 5725 based upon manual input received at the user input panel 5765 (e.g., depressing a switch, pressing a button, responding to a voice command via a microphone in user input panel 5765, and the like).

In still other examples, the delivery control input may be provided as a recognized gesture, such as a hand gesture (such as a particular hand gesture that represents activation of hover mode and another hand gesture that represents resume follow mode or end of hover mode). In more detail, an example of such an embodiment may have the delivery control input being a gesture control input received through at least one from the autonomy module sensors and the mobility base sensors. In more detail, the one from the autonomy module sensors and the mobility base sensors may be a scanning sensor that generates scanning sensor data representing a halt hand gesture from an operator (e.g., the courier 5755) of the wireless mobile courier node 5760. As received by autonomous controller 5730, such scanning sensor data representing the halt hand gesture as the gesture control input may be used as the delivery control input that activates hover mode on exemplary modular autonomous cart apparatus assembly 5700. Those skilled in the art will appreciate that any of the embodiments described herein may deploy sensors on the component (or as part of a user input panel) to provide H2M input via machine-recognized gestures that represent input (e.g., an access code, a predetermined pattern used to represent an authorized or designated entity providing the input, and the like).

To de-activate hover mode, the autonomous controller 5730 of the modular mobile cart autonomy control module 5725 may be further programmatically adapted and configured to be operative to resume, in response to receiving a resume control input that deactivates the hover mode repeating, functions (c)-(h) to autonomously track and follow the current location of the wireless mobile courier node as the wireless mobile courier node moves and while maintaining the predetermined follow distance from the current location of the wireless mobile courier node. Such a resume control input may be a wireless delivery control input from the wireless mobile courier node, an input from user input panel 5765 in its various forms as discussed above, or a gesture control input received through at least one from the autonomy module sensors and the mobility base sensors (scanning sensor data generated that represents a resume hand gesture from an operator of the wireless mobile courier node 5760).

Figure 60:
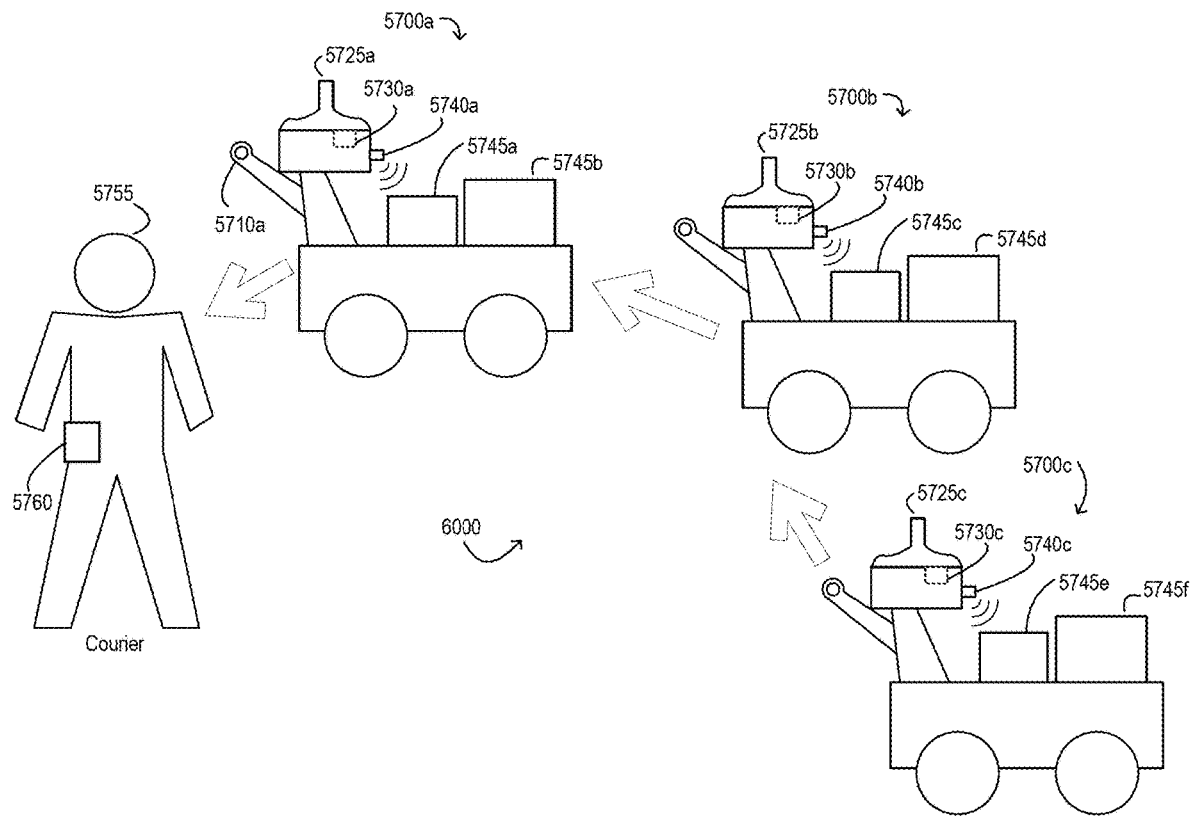
FIGS. 60-61 are diagrams of an exemplary system of multiple modular autonomous cart apparatus assemblies for transporting different items in accordance with an embodiment of the invention.
Figure 61:
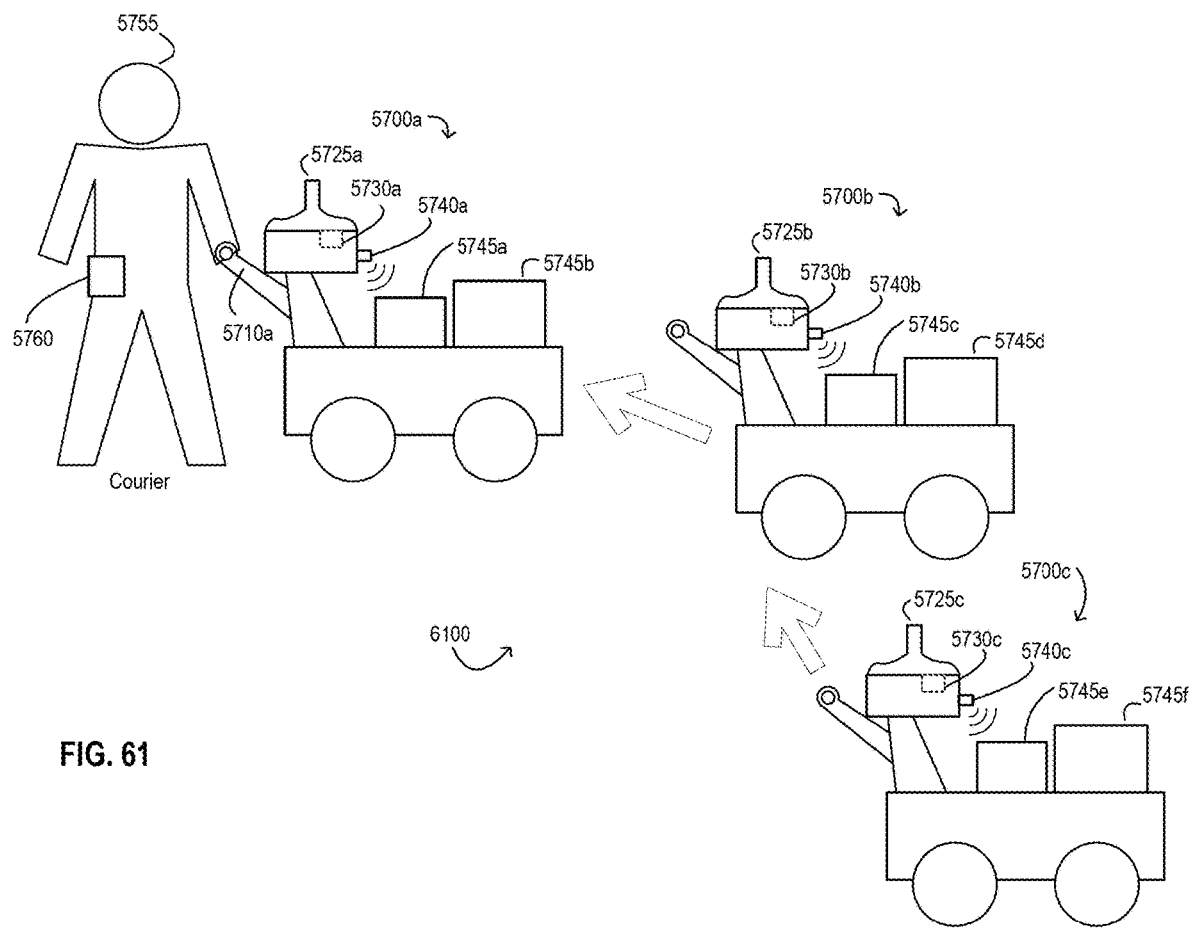

FIGS. 60-61 are diagrams of an exemplary system of multiple modular autonomous cart apparatus assemblies for transporting different items in accordance with an embodiment of the invention. In a large city environment example, where couriers typically use carts to carry multiple objects once a parking spot is attained, an embodiment may have a courier using multiple modular autonomous cart apparatus assemblies—e.g., one cart that may be manually pushed (or an MB with a manual control on a handle that allows the courier to direct and control the propulsion and steering system on the MB) with one or more additional cart assemblies in follow mode that are autonomously following in order to increase productivity. An embodiment may leverage TRON technology and/or sensors in order to follow couriers as they make deliveries. For example, the courier may have a handheld user access device (e.g., exemplary courier mobile wireless node 5760) operating as a type of master node while the follower-enhanced MB-based cart may have its small sensing hat (e.g., control module 5725) operating as a type of master/container/ID node. Further embodiments, may have the follower-enhanced MB-based cart interactively communicating with the courier's handheld user access device for locating purposes as well as tracking/monitoring what is on the respective carts. Different ID node enabled items (e.g., item 5475*b* with associated node 5750) may be loaded onto the different cart assemblies, where such ID nodes proactively and automatically allow the courier (via the courier's handheld user access device or a display on the follower-enhanced MB-based cart or both) to know what item (or object) is on which cart assembly and allow for proactive and automatic notifications of where such items/objects need to be delivered as the courier moves on a delivery route. Further embodiments may have a courier using multiple follower-enhanced MB-based carts where each can autonomously follow the courier in the group of cart assemblies with wireless communication between each cart assembly (e.g., between each respective control module 5725) allowing for logging of deliveries and notification regarding where particular objects are on specific carts.

FIG. 60 is a diagram of an exemplary system 6000 where the different modular autonomous cart apparatus assemblies 5700a-5700c are in follow mode so that assembly 5700a is following courier 5755 via exemplary courier mobile wireless node 5760, while assembly 5700b is following assembly 5700a via communications with autonomous controller 5730a in the control module 5725a of assembly 5700a and assembly 5700c is following assembly 5700b via communications with autonomous controller 5730b in the control module 5725b of assembly 5700b. Those skilled in the art will appreciate that each of assemblies 5700a-5700b in system 6000 may be implemented similar to that shown and described herein as exemplary modular autonomous cart apparatus assembly 5700 and the particular components described and explained as used in such an assembly 5700.

In such a system example, an embodiment of an exemplary system for transporting multiple items (e.g., items 5745a-5745f) includes a first modular autonomous cart apparatus assembly for transporting a first of the items being shipped and a second modular autonomous cart apparatus assembly for transporting a second of the items. In this system, the first modular autonomous cart apparatus assembly (e.g., assembly 5700a similar to assembly 5700) is equipped with a first propelled sensor-based modular mobility base (similar to mobility base 5705) having a first support base platform that supports the first of the items being shipped; a first modular cart handle (similar to handle 5710/5715) detachably mounted to the first modular mobility base (where the first modular cart handle has a first handle grip (similar to grip 5710) and a first common modular component power and data transport bus as a first conduit (similar to bus 5790b) through the first modular cart handle); and a first modular sensor-based cart autonomy control module (e.g., control module 5725a similar to control module 5725) detachably mounted to the first modular cart handle and including a first wireless radio transceiver (similar to wireless radio transceiver 3125). As such, the first modular sensor-based cart autonomy control module (e.g., autonomous controller 5730a in control module 5725a) is operative to generate first onboard sensor data related to an environment proximate the first modular sensor-based cart autonomy control module, receive first base sensor data from the first modular mobility base through the first conduit, where the first base sensor data is related to an environment proximate the first modular mobility base, and provide a first mobility control input as navigation control to the first modular mobility base through the first conduit based at least upon the onboard sensor data and the received base sensor data.

The second modular autonomous cart apparatus assembly in the system is similarly configured to the first modular autonomous cart apparatus assembly with its respective propelled sensor-based modular mobility base, modular cart handle, and modular sensor-based cart autonomy control module. In this second assembly of the system, its modular sensor-based cart autonomy control module (e.g., autonomous controller 5730b in control module 5725b) is operative to generate second onboard sensor data related to an environment proximate the second modular sensor-based cart autonomy control module, receive second base sensor data from the second modular mobility base through the second conduit (where the second base sensor data is related to an environment proximate the second modular mobility base), and provide a second mobility control input as navigation control to the second modular mobility base through the second conduit based at least upon the second onboard sensor data and the received second base sensor data.

In this system configuration, the first modular sensor-based cart autonomy control module is further operative to determine a location of a wireless mobile courier node (e.g., node 5760) operated by courier personnel involved in delivering the items being shipped (e.g., courier 5755), and autonomously cause the first modular mobility base to follow the wireless courier node while maintaining a first predetermined follow distance from the location of the wireless mobile courier node as the wireless mobile courier node moves on a delivery route. In other words, the first modular sensor-based cart autonomy control module operates the first cart assembly in a follow mode where the first cart assembly is autonomously tracking and following the wireless courier node. At the same time, the second modular sensor-based cart autonomy control module is further operative to determine a location of the first modular sensor-based cart autonomy module, and autonomously cause the second modular mobility base to follow the first modular sensor-based cart autonomy module while maintaining a second predetermined follow distance from the location of the first modular sensor-based cart autonomy module as the first modular sensor-based cart autonomy module follows the wireless mobile courier node on the delivery route.

In a further system embodiment, a third cart assembly (e.g., assembly 5700c) may be in follow mode to autonomously track and follow the second cart assembly (e.g., assembly 5700b). In more detail, such a further embodiment may have the system including a third modular autonomous cart apparatus assembly for transporting a third of the items being shipped. Such a third modular autonomous cart apparatus assembly is similarly configured to the second (and first) modular autonomous cart apparatus assembly with its respective propelled sensor-based modular mobility base, modular cart handle, and modular sensor-based cart autonomy control module. In this third assembly of the system, its modular sensor-based cart autonomy control module (e.g., autonomous controller 5730c in control module 5725c) is operative to generate third onboard sensor data related to an environment proximate the third modular sensor-based cart autonomy control module, receive third base sensor data from the third modular mobility base through the conduit (where the third base sensor data is related to an environment proximate the third modular mobility base), and provide a third mobility control input as navigation control to the third modular mobility base through conduit based at least upon the third onboard sensor data and the received third base sensor data. In this configuration, the third modular sensor-based cart autonomy control module (e.g., control module 5725c via its autonomous controller 5730c) is further operative to determine a location of the second modular sensor-based cart autonomy module, and autonomously cause the third modular mobility base to follow the second modular sensor-based cart autonomy module while maintaining a second predetermined follow distance from the location of the second modular sensor-based cart autonomy module as the second modular sensor-based cart autonomy module follows the first modular sensor-based cart autonomy module.

With node-enabled items being shipped on one or more of the modular autonomous cart apparatus assemblies in this system, further embodiments of the system may involve node-to-node secure associations and secure communications, which may facilitate the generation, presentation, and responses to various type of delivery notifications based on shared information from such node-enabled items with respective modular autonomous cart apparatus assemblies and/or the courier mobile wireless node operated by the attendant courier personnel. in more detail, a further system embodiment may have the first of the items being shipped having a first wireless ID node with the first of the items being shipped (e.g., ID node 5750 with item 5745b on cart apparatus assembly 5700a). This first wireless ID node maintains shipping information on the first of the items being shipped including at least identifier information on the first of the items being shipped, recipient information on the first of the items being shipped, and destination information on the first of the items being shipped. As such, the first modular sensor-based cart autonomy control module (e.g., autonomous controller 5730a in control module 5725a) is further programmatically adapted and configured to be operative to generate association data that establishes and reflects a secure association between the first wireless ID node and the first modular sensor-based cart autonomy control module after detecting an advertising signal from the first wireless ID node. This secure association between the first wireless ID node and the first modular sensor-based cart autonomy control module allows secure sharing of at least the shipping information between the first wireless ID node and the first modular sensor-based cart autonomy control module. A further example may have an item (e.g., the second of the items being shipped) also being a node-enabled item that may be similarly associated with the control module on the second cart apparatus assembly so that shipping information about the second of the items being shipped may be securely communicated and shared through the ID node with the second item to the autonomous controller in the control module of the second cart apparatus assembly.

In still further embodiments, notifications about delivery of the ID node-enabled items may be responsively generated based on the shared shipping information. For example, the first modular sensor-based cart autonomy control module may be further programmatically adapted and configured to be operative to generate a delivery notification in response to receiving at least a portion of the shipping information from the first wireless ID node. In like manner, the second modular sensor-based cart autonomy control module may be further programmatically adapted and configured to be operative to generate a delivery notification in response to receiving at least a portion of the shipping information from the second wireless ID node.

Such delivery notifications may include delivery location information. For example, the delivery notification generated by the first control module may be delivery location information notification indicating the destination information on the first of the items being shipped and the identifier information on the first of the items being shipped. And in like manner, the delivery notification generated by the second control module may be delivery location information notification indicating the destination information on the second of the items being shipped and the identifier information on the second of the items being shipped.

These delivery notifications generated by control modules in the first and/or second cart apparatus assemblies in the system may be triggered when the current location of the relevant modular autonomous cart apparatus assembly is within a threshold distance from a delivery location indicated by the destination information.

The form of such delivery notifications generated by the first and second modular sensor-based cart autonomy control modules may, for example, be a delivery warning on a display disposed on the respective one of the two modular sensor-based cart autonomy control modules in the system. Such a delivery warning identifies the item based upon the shipping information provided from its accompanying ID node and indicates the destination information on the respective item that is the subject of the displayed warning. Other forms of such delivery notifications generated by the respective first and second modular sensor-based cart autonomy control modules may, for example, be an audible delivery warning through a speaker on the respective control module. Such an audible delivery warning identifies the item based upon the shipping information provided from its accompanying ID node and indicates the destination information on the respective item that is the subject of the audible warning.

Further forms of such delivery notification may take the form of a wireless notification to the courier. For example, the first and second modular sensor-based cart autonomy control modules may each be programmatically adapted and configured to be operative to generate their respective delivery notification by being further operative to wirelessly notify the wireless mobile courier node 5760 with the relevant delivery notification (which may include destination information and identifier information on the relevant item) and where notification may be triggered when the current location of the respective modular autonomous cart apparatus assembly is within a threshold distance from a delivery location indicated by the destination information.

In a further embodiment of such a system, inventory data structures may be deployed on one or more of the respective modular autonomous cart apparatus assemblies to log deliveries as monitored items are removed with updates being provided to the courier mobile wireless node. In such a further embodiment, for example, the first modular sensor-based cart autonomy control module may maintain a first inventory data structure identifying which of the items are disposed on the first support base, and the first modular sensor-based autonomy control module may have at least a first payload monitoring sensor (e.g., sensor 5740a) that monitors any of the items disposed on the first support base (e.g., items 5475a, 5475b). As such, the first modular sensor-based cart autonomy control module may be programmatically adapted and configured to be operative to detect, using first payload sensor data from the first payload monitoring sensor, when the first of the items being shipped has been removed from the first support base; update the first inventory data structure to reflect the detected removal of the first of the items being shipped, and notify the wireless mobile courier node that the first of the items being shipped has been removed from the first support base. In another example in such a further embodiment, the second cart assembly may be similarly configured to detect remove of items and notify the wireless mobile courier node about the items removed.

Further still, an embodiment of this multi-assembly system may have the first and/or second modular sensor-based cart autonomy control module notifying the courier node about the location of a particular item on their respective cart. For example, an embodiment may have the first modular sensor-based cart autonomy control module being programmatically adapted and configured to be operative to monitor at least the first of the items being shipped on the first support base; identify a location of the first of the items being shipped as located on the first support base (e.g., via machine vision, image detection, node location, proximity sensing, and the like); and notify the wireless mobile courier node about the identified location of the first of the items being shipped. In another example in such a further embodiment, the second cart assembly may be similarly configured to locate and report on the location of items.

FIG. 61 is a diagram of an exemplary system 6100 where a first modular autonomous cart apparatus assembly 5700a is manually controller and while the remaining two modular autonomous cart apparatus assemblies 5700b-5700c are in follow mode so that assembly 5700a is manually controlled by courier 5755 in a temporary override mode, while assembly 5700b is following assembly 5700a via communications with autonomous controller 5730a in the control module 5725a of assembly 5700a and assembly 5700c is following assembly 5700b via communications with autonomous controller 5730b in the control module 5725b of assembly 5700b. Those skilled in the art will appreciate that each of assemblies 5700a-5700b in system 6000 may be implemented similar to that shown and described herein in exemplary system 6100 as exemplary modular autonomous cart apparatus assembly 5700 and the particular components described and explained as used in such an assembly 5700.

In such a system 6100, an embodiment of an exemplary system for transporting a multiple items being shipped includes a first modular autonomous cart apparatus assembly 5700a for transporting a first of the items being shipped and a second modular autonomous cart apparatus assembly 5700b for transporting a first of the items being shipped. In system 6100, the first modular autonomous cart apparatus assembly 5700a is equipped with a first propelled sensor-based modular mobility base having a support base platform that supports the first of the items being shipped, a first modular cart handle detachably mounted to the first modular mobility base, and a first modular sensor-based cart autonomy control module. The first modular cart handle has a first handle grip, a localized guidance input detector disposed on the handle grip, and a first common modular component power and data transport bus as a first conduit through the first modular cart handle. The first modular sensor-based cart autonomy control module is detachably mounted to the first modular cart handle, and has an autonomous controller and a first wireless radio transceiver. As such, the first modular sensor-based cart autonomy control module is operative to generate first onboard sensor data related to an environment proximate the first modular sensor-based cart autonomy control module; receive first base sensor data from the first modular mobility base through the conduit (where the first base sensor data is related to an environment proximate the first modular mobility base); receive override control input from the localized guidance input detector on the first cart handle (and where the override control input received is provided through the first conduit); and provide a first mobility control input as navigation control to the first modular mobility base through the first conduit based at least upon the onboard sensor data, the received base sensor data, and the override control input.

The second modular autonomous cart apparatus assembly 5700b in system 6100 is similarly configured to the first modular autonomous cart apparatus assembly 5700a with its respective propelled sensor-based modular mobility base, modular cart handle, and modular sensor-based cart autonomy control module. However, rather than be in override mode, the second modular autonomous cart apparatus assembly 5700b has its second modular sensor-based cart autonomy control module being operative to generate second onboard sensor data related to an environment proximate the second modular sensor-based cart autonomy control module; receive second base sensor data from the second modular mobility base through the second conduit, where the second base sensor data is related to an environment proximate the second modular mobility base; and provide a second mobility control input as navigation control to the second modular mobility base through the second conduit based at least upon the second onboard sensor data and the received second base sensor data. Thus, in system 6100, the first modular sensor-based cart autonomy control module is further operative to respond to the override control input and autonomously cause the first modular mobility base to move based on the provided first mobility control input to initiate and cause power-assisted movement of the first modular mobility base at the direction of local personnel in external contact with the localized guidance input detector. And, in system 6100, the second modular sensor-based cart autonomy control module is further operative to determine a location of the first modular sensor-based cart autonomy module, and autonomously cause the second modular mobility base to follow the first modular sensor-based cart autonomy module while maintaining a second predetermined follow distance from the location of the first modular sensor-based cart autonomy module.

A further embodiment of system 6100 has a third modular autonomous cart apparatus assembly 5700c that, similar to that described with respect to system 6000, is in follow mode to autonomously track and follow the second modular autonomous cart apparatus assembly 5700b.

Hold-at-Location (HAL) Related Logistics Operations

In further embodiments, a customer's item being shipped may be designated a "hold at location" (HAL) delivery, which may be an auto-redirect or self-selected designation. In this manner, the deliverable item may be delivered to a particular holding place (generally referred as a HAL location or a hold-at-location logistics facility), held temporarily in storage at the HAL location, and may be picked up directly at the HAL location or taken out to be delivered to a customer from the HAL location.

In a general example, the customer may have an option for robotic delivery of the deliverable item from the HAL location (which may be standard or may be for a small fee). In this example, the customer selects a time window for delivery and sets a delivery location. An attendant at the HAL location loads an exemplary MALVT bot apparatus. Once loaded, the exemplary MALVT bot apparatus initiates delivery. As such, the exemplary MALVT bot apparatus is dispatched and the customer is informed when the exemplary MALVT bot apparatus begins the delivery journey from the HAL location with an estimated time of arrival. The exemplary MALVT bot apparatus arrives at the HAL location and notifies the customer. The customer may then authenticate delivery via an app operating on the recipient's user access device, via TRON node interactions for association-based authenticated delivery, or via interaction with the display screen on the MAM component. After authentication, the CSS is opened and the customer receives the object. As the customer unloads the exemplary MALVT bot apparatus, the exemplary MALVT bot apparatus may monitor unloading and ensure that all contents for the customer have been removed, and then the bot apparatus may return to the HAL location for the next delivery (or if carrying multiple objects left at the same HAL location for other customers, the bot apparatus may continue to the next delivery location to drop off the next object to another customer). The customer may also request a pick up, if needed, and reload the exemplary MALVT bot apparatus with an additional object to return to the HAL station for tender to a courier service or other logistics service. Aspects of TRON technology may be incorporated and leveraged for location, door & lock operation, elevator operation, and authentication using the various nodes (e.g., different nodes embedded in or in responsive communication with an actuated door, lock, or elevator) and node locating techniques described above.

Figure 62:
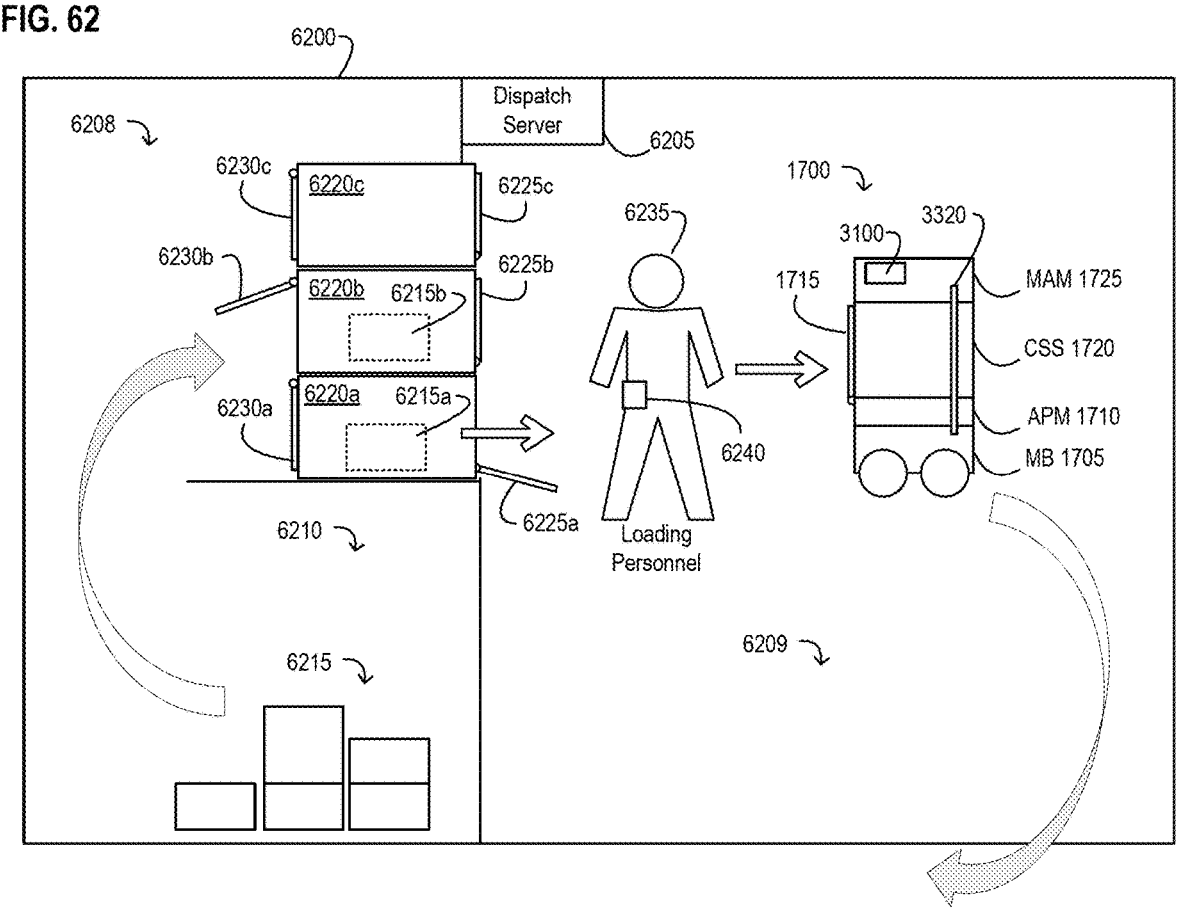
FIG. 62 is a diagram of an exemplary modular autonomous logistics transport vehicle apparatus (MALVT bot apparatus assembly) at an exemplary hold-at-location logistics facility in accordance with an embodiment of the invention.

FIG. 62 is a diagram of an exemplary MALVT bot apparatus assembly 1700 at an exemplary hold-at-location logistics facility 6200 in accordance with an embodiment of the invention. As shown in FIG. 62, exemplary hold-at-location logistics facility 6200 has a dispatch server 6205, which may be implemented similar to servers 4205, 4720 or may be part of an assembly server (e.g., server 4205) onside at the facility 6200. While not shown in FIG. 62, those skilled in the art will appreciate that exemplary hold-at-location logistics facility 6200 may include a bot storage depot location (similar to that of exemplary bot storage depot location 4125) with vending systems for organizing, storing, and dispensing particular modular components that may be used to build an exemplary MALVT bot apparatus assembly that can go on to deliver an item from the hold-at-location logistics facility 6200.

Referring back to the example embodiment shown in FIG. 62, exemplary hold-at-location logistics facility 6200 is shown with a temporary storage area 6210, a secure storage area 6208, and an access area 6209. Temporary storage area 6210, in this example, is where deliverable items 6125 may be received from a separate delivery to the facility, so that such items 6215 may be later placed by personnel (such as personnel 6235) in a secure storage area 6208. In secure storage area 6208, for example, a deliverable item 6215 may be placed into one of the secure storage enclosures 6220a-6220c (e.g., storage receptacles, secure locker receptacles for items, such as shown for items 6215a, 6215b in respective enclosures 6220a, 6220b) through services doors 6230a-6230c. In this way, the stored items (e.g., deliverable items 6125a, 6215b) may be retrieved through respective customer accessible doors 6225a-6225c by an authorized delivery recipient (or person designated by the authorized delivery recipient) for pickup or further delivery operations from the particular secure storage enclosure/receptacle having the relevant deliverable item.

Picking up or accessing the relevant deliverable item (e.g., item 6215a) may be accomplished through access area 6209. As shown in FIG. 62, attendant personnel 6235 that may be involved in loading assembly 1700 is shown in access area 6209. Personnel 6235 may be equipped with and operating a personnel mobile wireless node 6240 (similar to node 5760, such as a smartphone, tablet, or other wireless user access device). Exemplary MALVT bot apparatus assembly 1700 may be dispatched to the hold-at-location logistics facility 6200 (from a bot storage location onsite or from a separate location) by dispatch server 6205 so as to receive a deliverable item (e.g., deliverable item 6215a), and then take it on a dispatched logistics operation to deliver the item to the appropriate delivery recipient.

FIG. 63 is a flow diagram of an embodiment of an exemplary method 6300 for performing a dispatched logistics operation for a deliverable item (e.g., deliverable item 6215a) from a hold-at-location logistics facility having a secured storage and using an exemplary MALVT bot apparatus assembly 1700 and a dispatch server 6205 in accordance with an embodiment of the invention. An embodiment of method 6300 may use an embodiment of exemplary MALVT bot apparatus assembly 1700 (as assembled or after an on-demand assembly at the hold-at-location logistics facility 6200) and dispatch server 6205. The exemplary modular autonomous bot apparatus assembly used (e.g., assembly 1700) as part of method 6300 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 6300.

Referring now to FIG. 63, exemplary method 6300 begins at step 6305 with the modular mobile autonomy control module of assembly 1700 receiving a delivery dispatch command from the dispatch server 6205. The received delivery dispatch command has at least identifier information on the deliverable item, transport parameters on the deliverable item, destination delivery information related to drop-off of the deliverable item, and delivery authentication information related to an authorized delivery recipient of the deliverable item. In more detail, the delivery dispatch command may be an auto redirect dispatch command initiated by the dispatch system 6205 when the deliverable item is detected at a temporary storage within the hold-at-location logistics facility (e.g., storage 6210 where item 6215a was dropped off for placement within secured storage 6220a). For example, personnel mobile wireless node 6240 may detect or log the presence of deliverable item 6215a once it arrives at exemplary hold-at-location logistics facility 6200 (or once it is ready for placement within secured storage 6220a). As such, node 6240 may notify dispatch server 6205, which them may initiate the delivery dispatch command depending on transaction information related to the deliverable item 6145a (e.g., use of further robotic delivery or an alternative notification for the authorized delivery recipient to know the item 6215a is at the facility 6200). As such, the delivery dispatch command may be implemented as a self-selected designated dispatch command initiated by the dispatch system when the deliverable item is detected at the temporary storage within the hold-at-location logistics facility and in response to a delivery request received by the dispatch system from the authorized delivery recipient.

Receiving the delivery dispatch command in step 6305 may also, in some embodiments of method 6300, be triggered as a result of a separate logistics operation related to the deliverable item. For example, such a separate logistics operation related to the deliverable item 6215a may involve a prior unsuccessful attempt for delivery of the deliverable item 6215a to the authorized delivery recipient. The authorized delivery recipient may not have been home, and as a result, the deliverable item 6215a may have been brought to the hold-at-location logistics facility 6200 and placed in secure storage enclosure 6220a. Such a prior unsuccessful attempt for delivery of deliverable item 6215a may have been a prior dispatched logistics operation for autonomous delivery of the deliverable item 6215a to the authorized delivery recipient (e.g., via the same or different exemplary MALVT bot apparatus assembly), or alternatively may have been a prior manual delivery attempt delivery of the deliverable item 6215a to the authorized delivery recipient.

In still another example, the dispatched logistics operation for the delivery of the deliverable item 6215a from the hold-at-location logistics facility 6200 may be a planned second part of an overall delivery operation. For example, as part of an embodiment of method 6300, the separate logistics operation related to the deliverable item 6415a may be a pre-designated first stage of an overall logistics operation to deliver the deliverable item 6215a to the authorized delivery recipient where the pre-designated first stage provides the deliverable item 6215a to the secured storage at the hold-at-location logistics facility 6200 (e.g., via delivery to temporary storage area 6210 then as moved to secured storage enclosure 6220a in secured storage area 6208) as a designated interim handoff location for the dispatched logistics operation from the hold-at-location logistics facility 6200 involving the modular autonomous bot apparatus assembly 1700.

As part of step 6305, the identifier information in the received delivery dispatch command may be implemented, for example, with data that uniquely identifies the deliverable item (such as a machine readable identification of the deliverable item, or human readable information disposed on the deliverable item that identifies the deliverable item).

At step 6310, method 6300 proceeds with the modular mobile autonomy control module verifying that each of the modular mobile autonomy control module, the modular mobility base, the modular auxiliary power module, and the modular cargo storage system are compatible with the dispatched logistics operation for the deliverable item based upon the delivery dispatch command At step 6315, method 6300 proceeds with the modular cargo storage system receiving the deliverable item from the secured storage at the hold-at-location logistics facility into a payload area within the modular cargo storage system at the hold-at-location logistics facility. In more detail, step 6315 may involve loading the deliverable item 6215a into the payload area within the modular cargo storage system of exemplary MALVT bot apparatus assembly 1700 at the hold-at-location logistics facility 6200. Such loading, in a more detailed example of step 6315, may be in response to a load request message from the dispatch system 6200 (e.g., a load request message being sent from the dispatch system 6200 to loading personnel 6235 via that person's personnel mobile wireless node 6240 while at the hold-at-location logistics facility 6200).

Still further details on how deliverable item 6215a may be loaded as part of step 6315 may involve actuated and/or articulating structure on the exemplary MALVT bot apparatus assembly 1700. For example, the step of receiving the deliverable item may be accomplished in an embodiment of step 6315 with the modular mobile autonomy control module actuating an actuated cargo door 1715 disposed on the modular auxiliary power module to an open position (similar to that described above relative to exemplary cargo door 1715). This may involve actuating an actuated joint 2020 on the actuated cargo door 1715 to cause the actuated cargo door to move from the closed position to the open position, and/or actuating an electro-mechanical lock 2025 on the actuated cargo door 1715 to cause the actuated cargo door to unlock before the door 1715 moves from the closed position to the open position.

In a further example, step 6315 may implement receiving the deliverable item by having the modular mobile autonomy control module actuating an actuated sliding arm disposed on the modular cargo storage system to move the deliverable item into a payload area within the modular cargo storage system, and/or actuating an actuated grabbing arm disposed on the modular cargo storage system to grab and move the deliverable item into a payload area within the modular cargo storage system as part of receiving the deliverable item, and/or actuating an actuated belt surface disposed on the modular auxiliary power module as a movable support surface exposed within a payload area inside the modular cargo storage system to cause the deliverable item as placed on the actuated belt surface to move within the payload area as part of receiving the deliverable item.

At step 6320, method 6300 proceeds with the modular mobile autonomy control module autonomously causing the modular mobility base to move from the hold-at-location logistics facility 6200 (e.g., where loaded in step 6315 within the access area 6209) on a route to a destination location identified by the destination delivery information. As noted above, movement of the exemplary MALVT bot apparatus assembly 1700 may involve interactions with facility nodes and pathway obstacles. For example, an embodiment of step 6320 may have the modular mobile autonomy control module autonomously causing the modular mobility base to move from the hold-at-location logistics facility 6200 to the destination location while interacting with a wireless building facility node to actuate a pathway obstacle disposed in a path on the route to the destination location. Such a pathway obstacle may, for example, be an actuated door controlled by the wireless building facility node, an actuated elevator controlled by the wireless building facility node, or an actuated lock controlled by the wireless building facility node. When interacting with the wireless building facility node to actuate the pathway obstacle as part of step 6320, the method may have the modular mobile autonomy control module establishing an authorized association pairing between the modular mobile autonomy control module and the wireless building facility node based upon the authentication information related to the dispatched logistics operation; and causing the wireless building facility node to actuate the pathway obstacle after establishing the authorized association pairing between the modular mobile autonomy control module and the wireless building facility node.

In another embodiment of step 6320, the method 6300 may have the exemplary MALVT bot apparatus assembly manually interacting with pathway obstacles. For example, step of autonomously causing the modular mobility base to move from the hold-at-location logistics facility to the destination location comprises autonomously in step 6320 may be accomplished by having the modular mobile autonomy control module autonomously causing the modular mobility base to move from the hold-at-location logistics facility to the destination location while engaging a pathway obstacle disposed in a path on the route to the destination location using an articulating arm (e.g., arm 4325) disposed on the modular autonomous bot apparatus assembly and using sensors disposed on at least one of the modular mobility base and the modular mobile autonomy control module. For example, such a pathway obstacle may be a manually actuated door, a manually actuated elevator, or a manually actuated lock. When engaging the pathway obstacle using the articulating arm and sensors as part of step 6320, method 6300 may have the modular mobile autonomy control module guiding the articulating arm to a control element of the pathway obstacle (e.g., a handle for the pathway obstacle, a button for the pathway obstacle, a switch for the pathway obstacle, and a portion of a control panel for the pathway obstacle) using one or more of the sensors disposed on at least one of the modular mobility base and the modular mobile autonomy control module; and then actuating the pathway obstacle once the articulating arm engages the control element of the pathway obstacle.

At step 6325, method 6300 proceeds with notifying, by the modular mobile autonomy control module, the authorized delivery recipient of the deliverable item of an approaching delivery (e.g., with an estimated time of arrival in some embodiments) when the modular autonomous bot apparatus assembly is within a threshold notification range of the destination location identified by the destination information. In more detail, step 6325 may involve, for example, generating a display alert for the authorized delivery recipient on a display on the modular mobile autonomy control module once the modular autonomous bot apparatus assembly is within the threshold notification range of the destination location identified by the destination information; and/or generating an audio notification for the authorized delivery recipient on a speaker on the modular mobile autonomy control module once the modular autonomous bot apparatus assembly is within the threshold notification range of the destination location identified by the destination information.

In another example, step 6325 may implement notifications of the approaching delivery wirelessly. For example, step 6325 may have method 6300 proceeding with transmitting a delivery notification message (e.g., with an estimated time of arrival) to an external wireless node once the modular autonomous bot apparatus assembly is within the threshold notification range of the destination location identified by the destination information, where the external wireless node is related to the authorized delivery recipient according to the destination delivery information; and/or transmitting a delivery notification message to such an external wireless node after the modular autonomous bot apparatus assembly moves from the hold-at-location logistics facility itself.

At step 6330, method 6300 proceeds with the modular mobile autonomy control module monitoring, using its wireless radio transceiver, for delivery recipient authentication input. If delivery recipient authentication input is received, as monitored by the modular mobile autonomy control module, from a delivery recipient disposed external to the modular autonomous bot apparatus assembly at the destination location, then step 6330 proceeds to decision step 6335 where the modular mobile autonomy control module determines if the delivery recipient input received in step 6330 correlates to the delivery authentication information (i.e., indicating that the delivery recipient providing the delivery recipient authentication input is the authorized delivery recipient). Thus, when the delivery recipient input correlates to the deliver authentication information (e.g., matches to at least part of the authentication information), step 6335 proceeds to step 6340. If not, then step 6335 returns to step 6330 for continued monitoring.

In more detail, step 6330 may receive recipient authentication input in various ways in different embodiments of method 6300. For example, the delivery recipient authentication input received by the modular mobile autonomy control module may be provided by the delivery recipient through a user input panel disposed on the modular autonomous bot apparatus coupled to the modular mobile autonomy control module (e.g., with an access code provided by the delivery recipient through the user input panel, and/or biometric input provided by the delivery recipient through the user input panel) and/or may be provided by the delivery recipient through an external wireless node disposed external to the modular autonomous bot apparatus assembly (e.g., with wirelessly provided access code input and/or biometric input provided through an app on the external wireless node disposed external to the modular autonomous bot apparatus assembly).

In a further example of step 6330, the authentication information related to the dispatched logistics operation from the hold-at-location logistics facility may include an identifier of the authorized delivery recipient for the deliverable item for transport as part of the dispatched logistics operation from the hold-at-location logistics facility. In such a situation, the step of receiving the delivery recipient authentication input may have the modular mobile autonomy control module detecting an advertising signal as the delivery recipient authentication input from an external wireless node within a predetermined range of the modular autonomous bot apparatus assembly once the modular autonomous bot apparatus assembly has arrived at the destination location identified by the destination information; and authenticating that the external wireless node is associated with the authorized delivery recipient for the item being shipped within the modular cargo storage system based upon the identifier of the authorized delivery recipient and identifier information within the detected advertising signal broadcast from the external wireless node.

In still another example of step 6330, the authentication information related to the dispatched logistics operation from the hold-at-location logistics facility may include an identifier of the authorized delivery recipient for the deliverable item for transport as part of the dispatched logistics operation from the hold-at-location logistics facility. As such, the step of receiving the delivery recipient authentication input may have the modular mobile autonomy control module detecting an unprompted (e.g., not as a result of interrogating) advertising signal from an external wireless node within a predetermined range of the modular autonomous bot apparatus assembly once the modular autonomous bot apparatus assembly has arrived at the destination location identified by the destination information; and establishing a secure association between the external node and the modular mobile autonomy control module after detecting the unprompted advertising signal from the external wireless node. In this example, the secure association between the external node and the modular mobile autonomy control module enables and allows secure sharing of information between the external node and the modular mobile autonomy control module and being pre-authorized by the dispatch server as it relates to the dispatched logistics operation from the hold-at-location logistics facility.

At step 6340, method 6300 proceeds with the modular cargo storage system providing selective access to the deliverable item within the modular cargo storage system only when the delivery recipient authentication input correlates to the delivery authentication information indicating that the delivery recipient providing the delivery recipient authentication input is the authorized delivery recipient. In more detail, step 6340 may provide selective access to the deliverable item with the modular mobile autonomy control module actuating (or otherwise activating or causing movement of) an actuated cargo door disposed on the modular auxiliary power module to an open position once the delivery recipient authentication input correlates to a portion of the authentication information related to the dispatched logistics operation.

A further example of step 6340 may involve the modular mobile autonomy control module actuating the actuated cargo door comprises actuating an actuated joint on the actuated cargo door to cause the actuated cargo door to move from the closed position to the open position; actuating an electro-mechanical lock on the actuated cargo door to cause the actuated cargo door to unlock before moving from the closed position to the open position; actuating an actuated sliding arm disposed on the modular cargo storage system to move the deliverable item out from a payload area within the modular cargo storage system; actuating an actuated grabbing arm disposed on the modular cargo storage system to grab and move the deliverable item out from a payload area within the modular cargo storage system; and or actuating an actuated belt surface disposed on the modular auxiliary power module as a movable support surface exposed within a payload area inside the modular cargo storage system, the actuated belt surface being operative when actuated to cause the deliverable item as placed on the actuated belt surface to move out from within the payload area.

At step 6345, method 6300 proceeds with the modular mobile autonomy control module monitoring unloading of the deliverable item from within the modular cargo storage system using one or more sensors on at least one of the modular mobile autonomy control module and the modular cargo storage system. In more detail, such monitoring of unloading the deliverable item may be accomplished by capturing sensor data from the sensors on at least one of the modular mobile autonomy control module and the modular cargo storage system, and detecting when the deliverable item is removed based upon the captured sensor data (such as when the sensor data is processed to identify the deliverable item and its movements).

In even more detail, such monitoring unloading of the deliverable item may involve generating barcode scan data related to the deliverable item as the deliverable item is removed from within the modular cargo storage system using a barcode scanner as one of the sensors; and processing the generated barcode scan data to monitor the deliverable item as the deliverable item is removed from within the modular cargo storage system. In another detailed example, monitoring unloading of the deliverable item may involve generating image data related to the deliverable item as the deliverable item is removed from within the modular cargo storage system using an image sensor as one of the sensors; and processing the generated image data to monitor the deliverable item as the deliverable item is removed from within the modular cargo storage system. Another example may implement such monitoring by generating video data related to the deliverable item as the deliverable item is removed from within the modular cargo storage system using a video camera as one of the sensors; and processing the generated video data to monitor the deliverable item as the deliverable item is removed from within the modular cargo storage system. Further still, in yet another example, monitoring unloading may be accomplished by capturing audio using a microphone as one of the sensors disposed to record sound within and proximate to the modular cargo storage system as the deliverable item is removed from within the modular cargo storage system; and processing the captured audio data to monitor the deliverable item as the deliverable item is removed from within the modular cargo storage system.

In other embodiments of method 6300, step 6345 may have the deliverable item including a wireless mobile node (such as an ID node or master node, where the node is attached to the item, incorporated within the item, integrated as part of the packaging of the item, is simply disposed with the node as they are transported together as a unit). As such, the step of monitoring unloading of the deliverable item in step 5640 may be implemented by detecting movement of the wireless mobile node disposed with the deliverable item as the deliverable item is removed from within the modular cargo storage system based upon a plurality of signals broadcast from the wireless mobile node disposed with the deliverable item. In another example, monitoring unloading of such a node-enabled deliverable item may involve detecting a change in location of the wireless mobile node disposed with the deliverable item to outside the modular cargo storage system as the deliverable item is removed from within the modular cargo storage system as determined by the modular mobile autonomous control module.

Those skilled in the art will appreciate that with the various manners in which step 6345 may monitor the unloading of the deliverable item, further embodiments may combine the different types of sensors and/or use of wireless nodes with the deliverable item to implement step 6345 with an assessment of different types of processed sensor data and/or different monitored signals and locations of a node-enabled deliverable item when monitoring such unloading activity.

At step 6350, method 6300 proceeds with autonomously causing, by the modular mobile autonomy control module, the modular mobility base to move from the destination location on a return route to the hold-at-location logistics facility after the deliverable item is no longer detected within the modular cargo storage system.

A further embodiment of method 6300 may involve a requested pickup of a return deliverable item at the destination location for the exemplary MALVT bot apparatus to take back to the hold-at-location logistics facility for tendering to a separate courier from there. For example, method 6300 may implement step 6350 by having the modular mobile autonomy control module receiving a return delivery dispatch command from the dispatch server before the modular mobility base leaves from the destination location. Such a return delivery dispatch command may, for example, be initiated by the authorized delivery recipient of the deliverable item in a way that has the return delivery dispatch command extending the dispatched logistics operation. As such, the return deliver dispatch command may have at least identifier information on a return deliverable item, transport parameters on the return deliverable item, and courier authentication information related to an authorized pickup courier for the return deliverable item. Beyond receiving such a return delivery dispatch command, this example of step 6350 may also have the modular mobile autonomy control module verifying that each of the modular mobile autonomy control module, the modular mobility base, the modular auxiliary power module, and the modular cargo storage system are compatible with the extended dispatched logistics operation for the return deliverable item based upon the return delivery dispatch command; receiving, by the modular cargo storage system, the return deliverable item from the authorized delivery recipient into the payload area within the modular cargo storage system at the destination location after the deliverable item is no longer detected within the modular cargo storage system; and having the modular mobile autonomy control module autonomously causing the modular mobility base to move from the destination location to the hold-at-location logistics facility after the return deliverable item is detected by the payload monitoring sensors as being placed within the modular cargo storage system.

This further embodiment involving the return deliverable item may also have method 6300 having the modular mobile autonomy control module notifying personnel at the hold-at-location logistics facility (e.g., personnel 6235) about an approaching delivery (and estimated time of arrival in some examples) of the return deliverable item when the modular autonomous bot apparatus assembly is within a threshold notification range of the hold-at-location logistics facility. Such notifications may, for example, come in the form of generating display alert about the return deliverable item shown on one or more of the displays on the modular mobile autonomy control module once the modular autonomous bot apparatus assembly is within the threshold notification range of the hold-at-location logistics facility; generating an audio notification about the return deliverable item on a speaker on the modular mobile autonomy control module once the modular autonomous bot apparatus assembly is within the threshold notification range of the hold-at-location logistics facility; transmitting a delivery notification message to an external wireless node once the modular autonomous bot apparatus assembly is within the threshold notification range of the hold-at-location logistics facility, the external wireless node being related to the personnel at the hold-at-location logistics facility; and/or transmitting a delivery notification message to an external wireless node after the modular autonomous bot apparatus assembly moves from the destination location with the return deliverable item, the external wireless node being related to the personnel at the hold-at-location logistics facility. An embodiment of method 6300 may also include providing, by the modular cargo storage system, selective access to the return deliverable item within the modular cargo storage system after the modular mobile base arrives at the hold-at-location logistics facility.

Rather than coming back with a return deliverable item, further embodiments of method 6300 may have the exemplary MALVT bot apparatus assembly dispatched for the particular deliverable item dropped off at the destination continuing to another destination location to deliver another deliverable item for another customer. In more detail, an example of such a further embodiment of method 6300 may have the delivery dispatch command received in step 6305 further including identifier information on an additional deliverable item, additional destination delivery information related to drop-off of the additional deliverable item, and additional delivery authentication information related to a secondary authorized delivery recipient of the additional deliverable item. Additionally, this further embodiment of method 6300 may further include having the modular cargo storage system receiving the additional (or secondary) deliverable item from the secured storage at the hold-at-location logistics facility into the payload area within the modular cargo storage system at the hold-at-location logistics facility (e.g., into a different partitioned compartment of the payload area within exemplary CSS 1720). As such in this embodiment of method 6300 involving multiple deliverable items being transported from the hold-at-location logistics facility, step 6340 of providing selective access to the deliverable item within the modular cargo storage system may be implemented with the modular cargo storage system providing selective access to only the first deliverable item (not the additional deliverable item) within the modular cargo storage system when the delivery recipient authentication input correlates to the delivery authentication information indicating that the delivery recipient providing the delivery recipient authentication input is the authorized delivery recipient. And also in this embodiment of method 6300 involving multiple deliverable items being transported from the hold-at-location logistics facility, step 6350 may be implemented by with the sub-steps of (a) autonomously causing, by the modular mobile autonomy control module, the modular mobility base to move from the destination location to a secondary delivery location after the deliverable item is detected to be removed from within the modular cargo storage system at the destination location (where the secondary delivery location is identified by the additional destination delivery information in the delivery dispatch command); (b) receiving secondary delivery recipient authentication input by the modular mobile autonomy control module from a second delivery recipient disposed external to the modular autonomous bot apparatus assembly at the secondary destination location; (c) providing, by the modular cargo storage system, selective access to only the additional deliverable item within the modular cargo storage system when the secondary delivery recipient authentication input correlates to the secondary delivery authentication information indicating that the second delivery recipient providing the secondary delivery recipient authentication input is the secondary authorized delivery recipient of the additional deliverable item; and (d) autonomously causing, by the modular mobile autonomy control module, the modular mobility base to move from the secondary delivery location to the hold-at-location logistics facility after the additional deliverable item is no longer detected within the modular cargo storage system.

In the embodiments shown and discussed above relative to FIGS. 62 and 63, the secured storage enclosure or logistics receptacle was not required to be an interactive or remotely controlled secure storage enclosure or logistics receptacle. But in further embodiments, an exemplary MALVT bot apparatus assembly (such as assembly 1700) may interact with and exemplary enhanced, remotely controlled secure storage enclosure or logistics receptacle that can even further improve and enhance automated dispatched logistics operations. For example, an exemplary MALVT bot apparatus may be alerted of object at a logistics receptacle (such as a drop box or a "ship & get" (SNG) parcel locker for parcel drop-off and pickup). A dispatch system (such as a dispatch server) may dispatch the exemplary MALVT bot apparatus to the drop box. The drop box may be a self-monitoring box with wireless communications (e.g., NFC, Bluetooth, Wi-Fi, cellular, ZigBee, and the like) and sensor-enabled so that the exemplary MALVT bot apparatus may communicate with the drop box using such wireless formats and/or using TRON advertising and associating techniques that allow for secure exchange of data. The exemplary MALVT bot apparatus may interact with the drop box/SNG to, for example, dock with the drop box/SNG, gain access to and custody of the object (e.g., a deliverable item) from the drop box/SNG.

In general, such an improved drop box (generally referred to as a remotely controlled or actuated logistics receptacle) may include a remote access module that responsively actuates an access door for the drop box and SNG. Such an improved drop box may also have remotely controlled actuators that cause the object to move out of the drop box/SNG (e.g., via tilting of a base support, articulation of a pushing arm to push the object out of the opened access door, and the like). As such, the exemplary MALVT bot apparatus may communicate with the drop box/SNG to cause the box to open and cause the object to be removed from the box and placed into the exemplary MALVT bot apparatus (e.g., on an open cargo access door of the CSS component, and then slid into the storage area of the CSS component) so as to allow the exemplary MALVT bot apparatus to autonomously operate the box and make unmanned pick-ups. In more detail, the drop box may be operative to alert a dispatch system when it has a pickup ready within its storage contents, which in turn the dispatch system to dispatches an appropriately configured exemplary MALVT bot apparatus to pick up the object (e.g., an appropriately sized and capable MALVT bot apparatus configured to support and handle the size and weight of the object to be picked up). The selective nature of assembling the right type and configuration of an exemplary MALVT bot apparatus for a particular one or more objects to be picked up allows for enhanced pickup services for the drop box. The exemplary MALVT bot apparatus operates with the modular drop-box in order to retrieve the object, ensure that the exemplary MALVT bot apparatus has all items from the box's inventory, and returns to the dispatching station (or another waypoint location) to inject one or more of the picked up objects into a further delivery network.

Figure 64A:
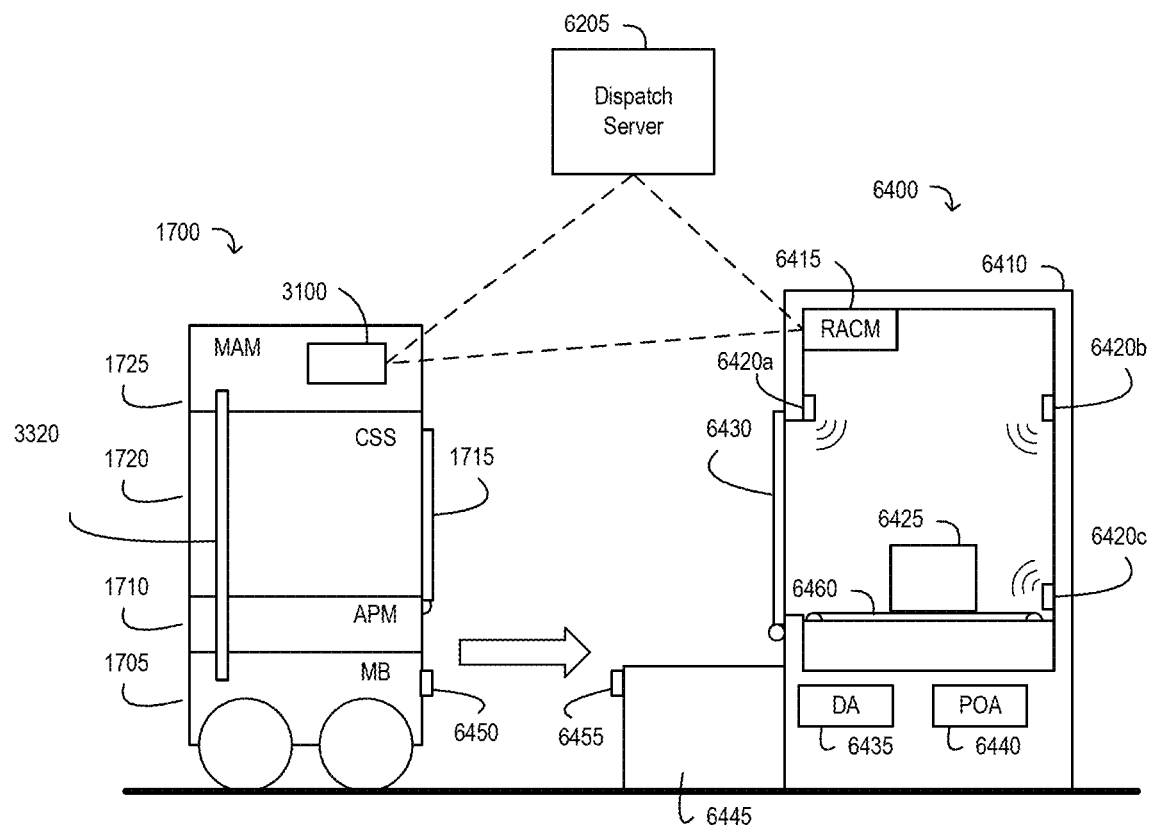
FIGS. 64A-64H are diagrams of an exemplary modular autonomous logistics transport vehicle apparatus (MALVT bot apparatus assembly) interfacing and interacting with an exemplary remotely-actuated logistics receptacle that may be located at a hold-at-location logistics facility in accordance with an embodiment of the invention.

FIGS. 64A-64H are diagrams of an exemplary modular autonomous logistics transport vehicle apparatus (MALVT bot apparatus) interfacing and interacting with an exemplary remotely-actuated logistics receptacle that may be located at a hold-at-location logistics facility in accordance with an embodiment of the invention. Referring now to FIG. 64A, an embodiment of exemplary MALVT bot apparatus assembly 1700 is shown approaching exemplary remotely-actuated logistics receptacle 6400 in order to interactively dock with receptacle 6400 and pick up deliverable item 6425 using enhanced and improved actuation features on each of assembly 1700 and receptacle 6400. In more detail, exemplary remotely-actuated logistics receptacle 6400 is shown having logistics receptacle 6410 for receiving and temporarily maintaining an object deposited for shipment (e.g., deliverable item 6425). In one embodiment, the logistics receptacle 6410 may, for example, be a drop box receptacle or parcel locker receptacle. In another embodiment, such a logistics receptacle 6410 may be implemented as one of multiple of secure storage logistic receptacles (e.g., secured storage enclosures 6220a-6220c) at a location, such as hold-at-location logistics facility 6200.

Exemplary logistics receptacle 6410 is generally an example of a storage enclosure having an entrance opening that may be sealed/closed or accessed/opened by access door 6430. The storage enclosure formed by logistics receptacle 6410 defines a temporary storage area within which deliverable item 6425 may be temporarily maintained. The entrance opening covered by door 6430 is an opening through which item 6425 can pass when the item 6425 is being retrieved from the storage enclosure formed by logistics receptacle 6410.

An exemplary wireless node-based remote access control module 6415, as part of receptacle 6400, is shown disposed with the logistics receptacle 6410 and operatively connected to at least sensors 6420a-6420c (for monitoring the interior of receptacle 6410 and detecting deposits of items within receptacle 6410), door actuator 6435, and parcel object actuator 6440. Those skilled in the art will appreciate that control module 6415 may be implemented as a processing-based, programmable device such as an ID node or master node with communications connectivity to dispatch server 6205, and having an integrated wireless radio transceiver for communications with at least autonomous controller 3100 of exemplary MAM 1725 on exemplary MALVT bot apparatus assembly 1700. As such, an embodiment of wireless node-based remote access control module 6415 may have such a controller as wells a control module memory coupled to the controller and a wireless communication interface (e.g., a wireless radio transceiver) coupled to the controller. The control module memory maintains at least remote storage access program code and pickup authentication information related to an authorized pickup logistics operation for the object (e.g., deliverable item 6425) by the dispatched mobile autonomous delivery vehicle as an authorized pickup entity for the object deposited for shipment. The wireless communication interface operatively coupled to the controller provides a wireless communication path to the dispatched mobile autonomous delivery vehicle (e.g., exemplary MALVT bot apparatus assembly 1700).

The door actuator 6435 as shown in FIG. 64A as part of exemplary remotely-actuated logistics receptacle 6400 couples the access door 6430 and the storage enclosure of receptacle 6410 so that door actuator 6435, as operatively activated by the controller, selectively causing the access door 6430 to open when activated to move from the closed position to the open position and selectively cause the access door 6430 close when activated to move the access door from the open position to closed position. While shown in a general position in FIG. 64A, those skilled in the art will appreciate that embodiments of door actuator 6435 may be implemented with hinge or joint actuators, actuated shock assemblies, or other actuated mechanical, magnetic, hydraulic or other manners of actuated movement that causes a change of position for door 6430 between open and closed positions in response to control input from the controller of control module 6415.

The parcel object actuator 6440, as shown in FIG. 64A, is shown with a an exemplary moving belt surface 6460 controlled by actuator 6440 in response to operative activation by the controller in control module 6415. As such, the parcel object actuator 6440 (and its moving belt surface 6460) selectively causes item 6425 to move out of the temporary storage area within receptacle 6410 and through the entrance opening normally sealed by door 6430.

FIG. 64A also shows structure that may be used for securely docking the exemplary MALVT bot apparatus assembly 1700 and the exemplary remotely-actuated logistics receptacle 6400. As shown in FIG. 64A, a docking interface is shown as a mated alignment interface 6455 disposed on extended engagement barrier 6445 disposed on the exterior of the logistics receptacle 6410 and below the entrance opening. In general, such a docking interface extends from the logistics receptacle 6410 as a contact registration point for engaging the dispatched mobile autonomous delivery vehicle when the dispatched mobile autonomous delivery vehicle approaches the remotely-actuated logistics receptacle apparatus 6400 as part of an authorized pickup logistics operation. The contact registration point may be a mated alignment interface 6455 configured to fit with a corresponding mated alignment interface 6450 on the dispatched mobile autonomous delivery vehicle when the dispatched mobile autonomous delivery vehicle approaches and engages the remotely-actuated logistics receptacle apparatus as part of the authorized pickup logistics operation.

Figure 64B:
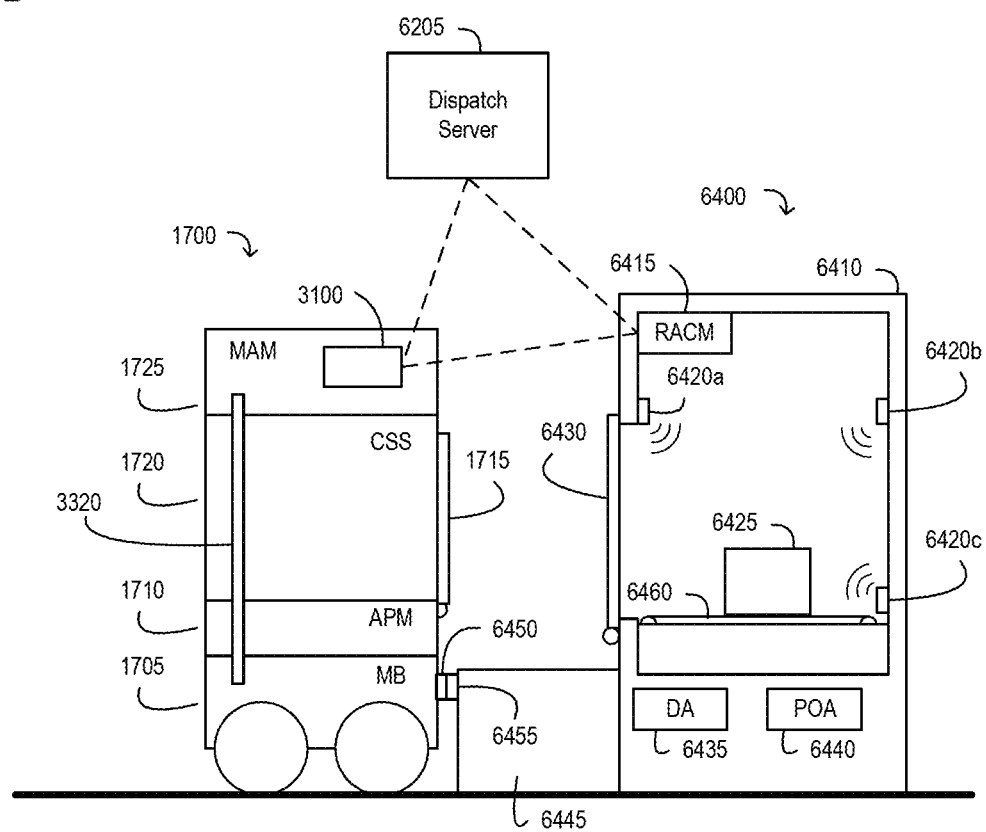
Figure 64C:
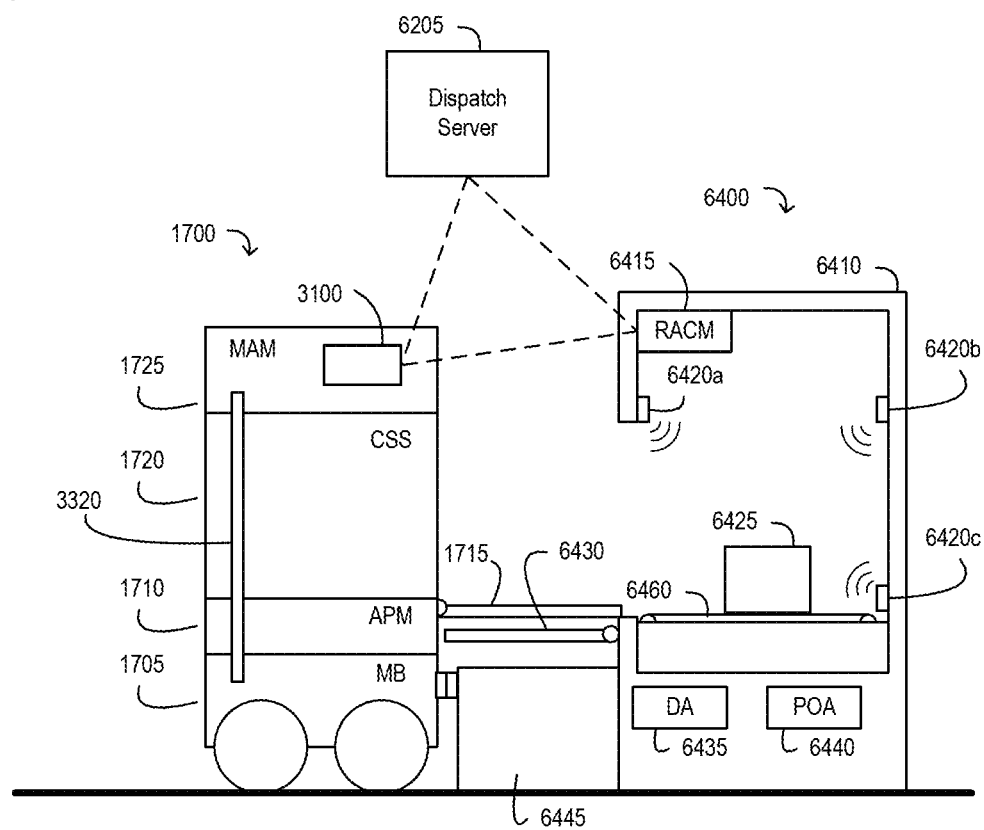

In the example shown in FIG. 64A, extended engagement barrier 6445 allows for docking to occur (between mated alignment interface 6455 that fits with a corresponding mated alignment interface 6450 on the exemplary modular mobility base 1705 of the dispatched MALVT bot apparatus assembly 1700) so as to allow for room for respective doors on the receptacle 6400 and assembly 1700 to be deployed (as shown in FIG. 64C). However, in other embodiments, receptacle 6400 and assembly 1700 may securely dock in closer proximity where the respective openings in each of receptacle 6400 and the CSS 1720 on assembly 1700 can line up in a closer manner to allow for enhanced transfer of the item 6425 from the receptacle 6400 into the CSS 1720 of assembly 1700.

In one embodiment, such as that shown in FIG. 64A, the docking interfaces (e.g., mated alignment interfaces 6450/6455) may be implemented by one or more sets of latches disposed on an outward peripheral edge of the extended engagement barrier, where such latches are configured and disposed to mate with a set of complementary latches on the dispatched mobile autonomous delivery vehicle (e.g., an outward peripheral edge of the exemplary mobility base 1705). Such latches may be implemented as recessed latches, interlocking latches, and/or as actuated latches activated by a controller on the respective structure (e.g., one set of latches actuated by the controller in control module 6415 to move and engage a mated set of latches on the dispatched mobile autonomous delivery vehicle to secure the dispatched mobile autonomous delivery vehicle to the extended engagement barrier of the logistics receptacle). In like manner, the latches on the dispatched mobile autonomous delivery vehicle (e.g., assembly 1700) may be actuated to move and engage a mated set of latches on the exemplary remotely-actuated logistics receptacle. Actuation of such latches may be initiated through proximity sensor data and signals provided by, for example, autonomous control system 3100 on exemplary MAM 1725 based on sensor data provided by the mobility controller on exemplary mobility base 1705, as well as communication of such processed proximity sensor data between autonomous control system 3100 and the controller in control module 6415. Actuation of such latches may be initiated through proximity sensor data and signals provided by, in another example, receptacle 6400 when equipped with its own proximity sensors operatively coupled to the controller in control module 6415 to generate responsive latch control signals for latches 6455 while in communication with autonomous control system 3100 on exemplary MAM 1725. As such, when the exemplary MALVT bot apparatus assembly 1700 approaches exemplary remotely-actuated logistics receptacle 6400, the respective control systems may communicate and implement secure docking of the exemplary MALVT bot apparatus assembly 1700 and exemplary remotely-actuated logistics receptacle 6400.

In the context of such exemplary remotely-actuated logistics receptacle 6400 and as the exemplary MALVT bot apparatus assembly 1700 approached the exemplary remotely-actuated logistics receptacle 6400 to pickup deliverable item 6425, the controller in control module 6415, when executing the remote storage access program code, is operative to receive a pickup authentication signal over the wireless communication interface from an external wireless node (such as the autonomous control system 3100 in exemplary MAM). In some embodiments, the pickup authentication signal may be received before secure docking and simply while on assembly 1700 is on approach as part of an authorized pickup logistics operation. However, in other embodiments, the pickup authentication signal may be received only after secure docking, as shown in FIG. 64B.

Referring now to FIG. 64C, the controller in the control module 6415, when executing the remote storage access program code, is operative to transmit a first remote control actuation signal to the door actuator 6435 only if the received pickup authentication signal is determined to be from the dispatched mobile autonomous delivery vehicle as the authorized pickup entity according to the pickup authentication information in the control module memory. As such, the first remote control actuation signal activating the door actuator 6435 causes the access door 6430 to open. As shown in the example of FIG. 64C, access door 6430 opens first. The controller in control module 6415 may transmit an open door acknowledgement signal to autonomous control system 3100, which then actuates cargo door 1715 to open as shown in FIG. 64C.

Figure 64D:
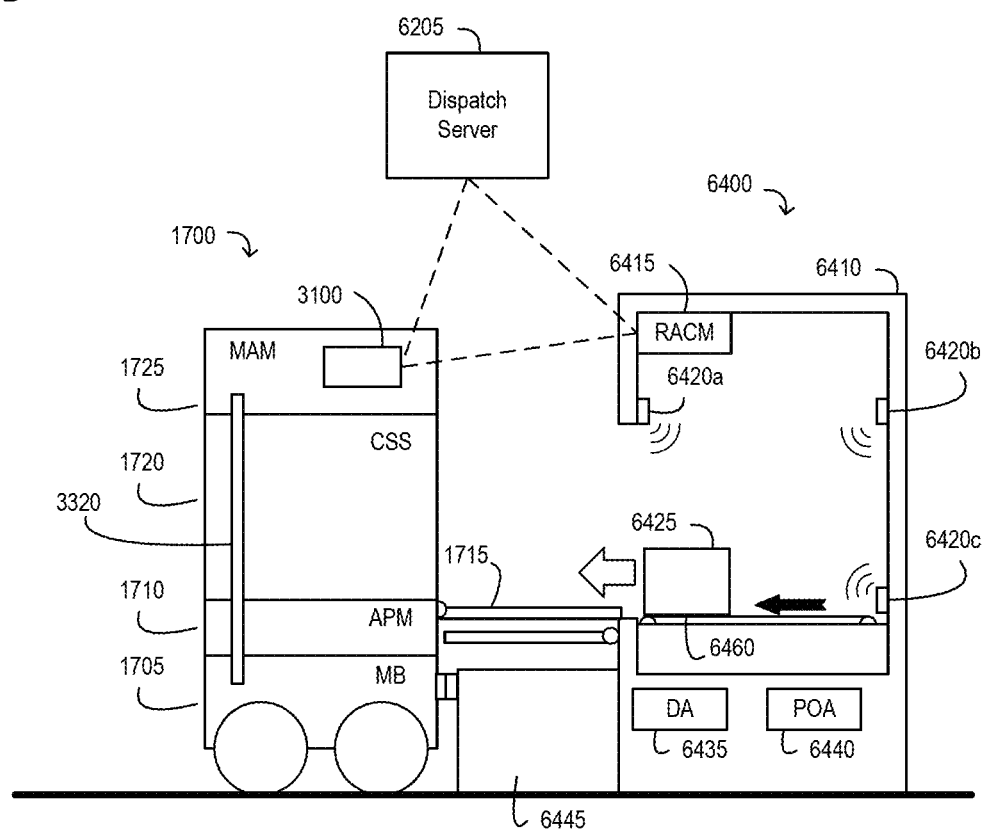

Referring now to FIG. 64D, deliverable item 6425 is then moved out of receptacle 6400 automatically. This may have the controller of the control module 6415, when executing the remote storage access program code, transmitting a remote control actuation signal to the parcel object actuator 6440 once the access door is open and only if the received pickup authentication signal is determined to be from the dispatched mobile autonomous delivery vehicle as the authorized pickup entity according to the pickup authentication information in the control module memory. As such, the remote control actuation signal activating the parcel object actuator 6440 causes moving belt surface 6460 to move as part of the parcel object actuator), which causes the deliverable item 6425 to move towards and through the entrance opening.

Figure 64E:
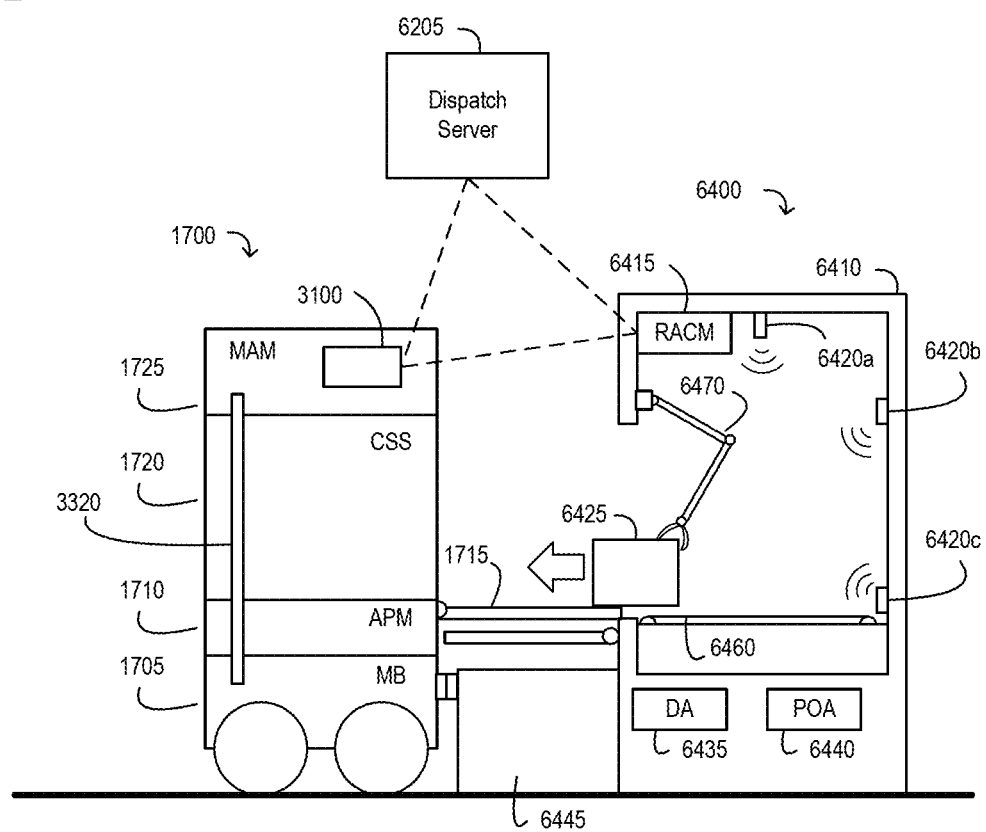
Figure 64F:
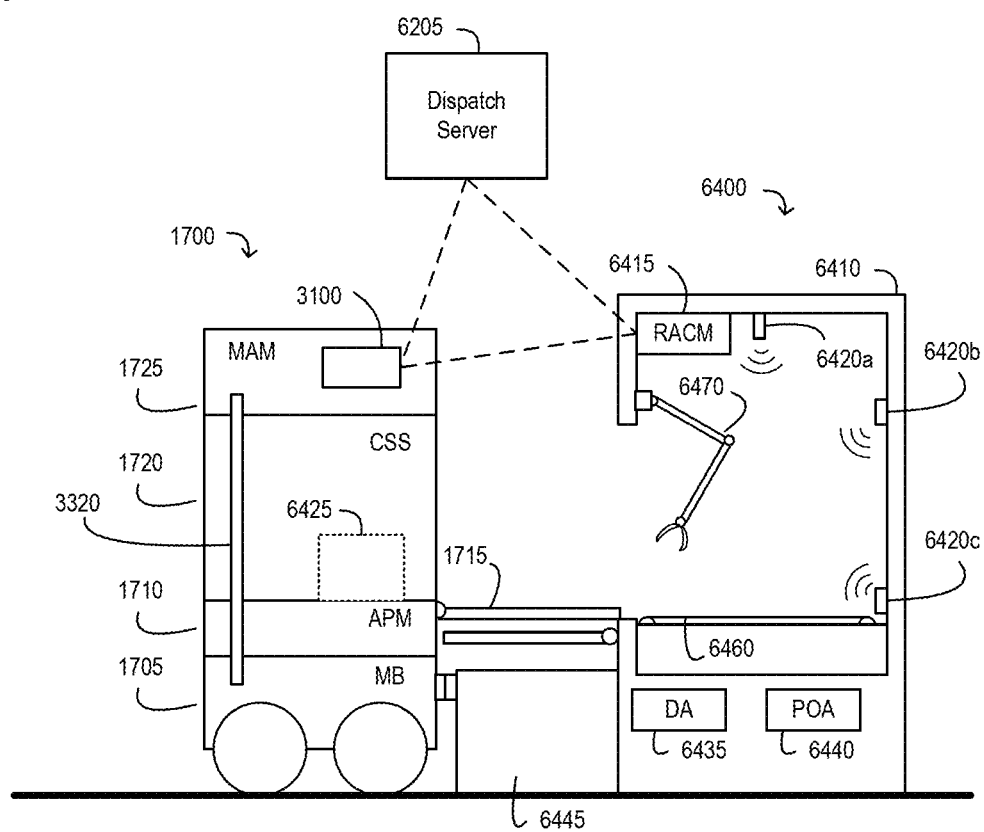

As shown in FIG. 64E, dispensing delivery item 6425 may also be accomplished through another type of parcel object actuator 6440—namely, an articulating arm 6470 that is activated to cause the deliverable item 6425 to be removed from the temporary storage area of receptacle 6400 and placed into custody of the dispatched mobile autonomous delivery vehicle (e.g., into exemplary CSS 1720 of assembly 1700 as shown in FIG. 64F). In further embodiments, the parcel object actuator 6440 may be implemented as an actuated support base that temporarily maintains the deliverable item 6425 deposited for shipment, and where the actuated support base is operative when actuated to tilt towards the entrance opening (e.g., a tiltable base in place of the moving belt surface 6460) causing the deliverable item 6425 being shipped to at least slide towards the entrance opening. In another example, the parcel object actuator may be implemented as an actuated pushing arm (similar to piston like arm that pushes the item in a particular direction) that is operative when actuated to contact the deliverable item 6425 being shipped and at least push the deliverable item 6425 being shipped towards the entrance opening. Further examples may have an actuated sliding arm and/or actuated grabbing arm (similar to sweeping arms 2085, 2700, and grabbing arms 2090, 2710) as the parcel object actuator to manipulate the deliverable item 6425 and remove it from receptacle 6400 and onto/into assembly 1700.

Movement/dispensing of the deliverable item 6425 may, in some embodiments, only occur after the controller in the control module 6415 receives a "ready" indication signal from the autonomous control system 3100 in exemplary MAM 1725 of assembly 1700. For example, the controller in the control module 6415, when executing the remote storage access program code, may be further operative to receive a ready confirmation signal over the wireless communication interface from the dispatched mobile autonomous deliver vehicle as the authorized pickup entity. In such an embodiment, only after the controller received the ready confirmation signal from the dispatched mobile autonomous deliver vehicle (e.g., assembly 1700) as the authorized pickup entity does the controller transmit the remote control actuation signal to the parcel object actuator causing the object to move through the entrance opening as shown in FIGS. 64D and 64E.

Figure 64G:
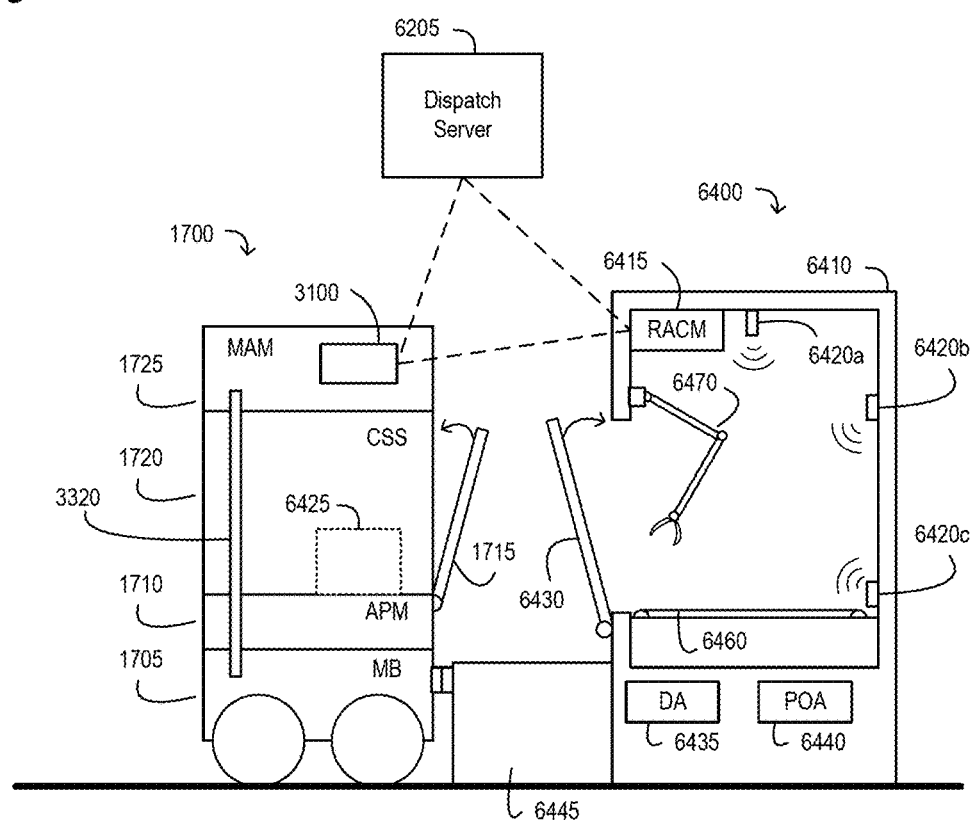
Figure 64H:
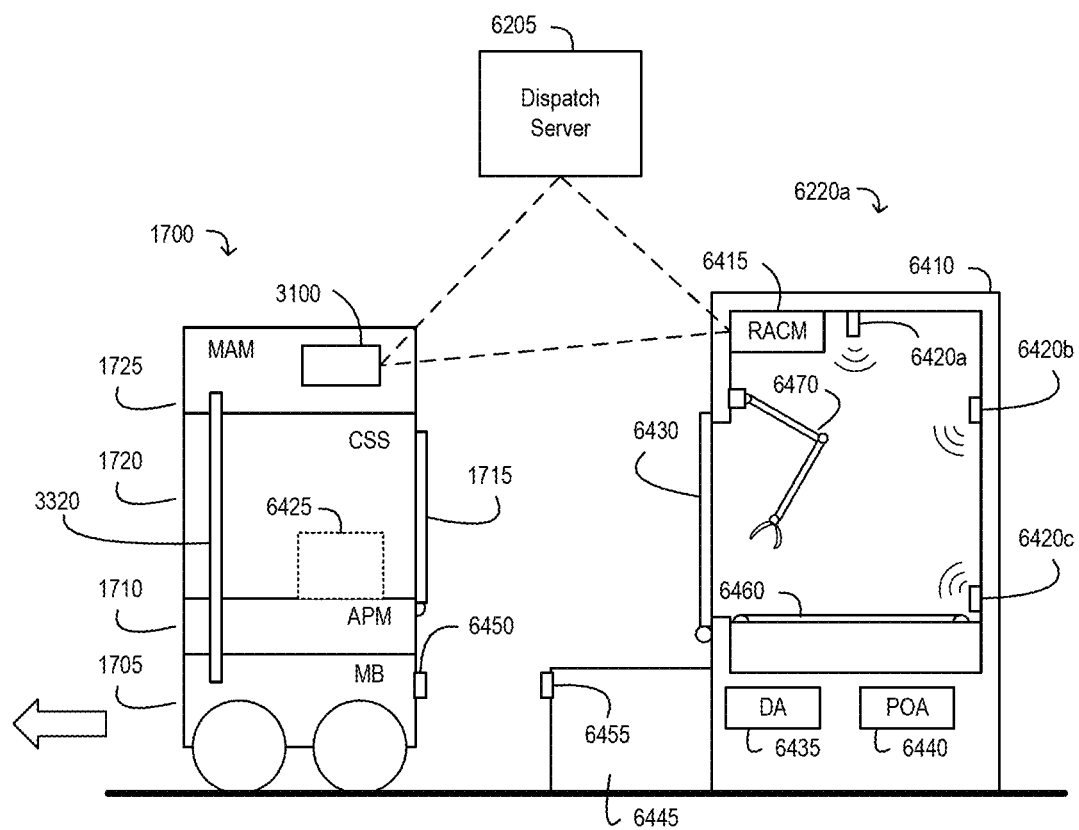

In FIG. 64G, the process of automatically transferring the deliverable item 6425 from the exemplary remotely-actuated logistics receptacle 6400 to the exemplary MALVT bot apparatus assembly 1700 has been completes, so the respective controllers actuate their respective doors to a closed position and undock so exemplary MALVT bot apparatus assembly 1700 can move away and proceed to deliver the item 6425 to another location as shown in FIG. 64H.

In a further embodiment, the pickup authentication process between exemplary remotely-actuated logistics receptacle 6400 and exemplary MALVT bot apparatus assembly 1700 may involve node association in order to first establish a secure communication path between the exemplary remotely-actuated logistics receptacle 6400 and exemplary MALVT bot apparatus assembly 1700. In such an embodiment, for example, the controller of the control module 6415 may be operative to determine if the received pickup authentication signal from the dispatched mobile autonomous delivery vehicle is from the authorized pickup entity according to the pickup authentication information in the control module memory by being operative to generate association data indicating a secure association between the external node (e.g., the autonomous control system 3100 in MAM 1725) and the controller in control module 6415 after detecting the pickup authentication signal from the external wireless node. Such secure association between the external node and the controller allows secure sharing of information between the external node and the controller and being pre-authorized by the dispatch server 6205 as indicated by the pickup authentication information related to the authorized pickup logistics operation. Such pickup authentication information may be received from the dispatch server over the wireless communication interface.

As noted above, sensors 6420a-6420c may be used for monitoring the interior of receptacle 6410 and detecting deposits of items within receptacle 6410. For example, when one or more of sensors 6420a-6420c detect a change in what is in the receptacle 6410, the controller of control module 6415, when executing the remote storage access program code, may be further operative to receive the sensor data from the sensor, process such data (i.e., the processed sensor data reflecting the detected deposit of the item deposited for shipment within the storage enclosure of receptacle 6410), and responsively transmit a dispatch request message over the wireless communication interface to the dispatch server 6205 to initiate dispatch of the dispatched mobile autonomous delivery vehicle (e.g., assembly 1700) for the authorized pickup logistics operation.

In light of the interactive operations of each of exemplary remotely-actuated logistics receptacle 6400 and exemplary MALVT bot apparatus assembly 1700 as described above, a more detailed method may encompass such operations that take place as part of a dispatched logistics operation. FIGS. 65A-65B represent a flow diagram of such an embodiment of an exemplary method for performing a dispatched logistics operation for a deliverable item maintained within a remotely-actuated logistics receptacle and using a modular autonomous bot apparatus assembly (MALVT bot apparatus assembly) and a dispatch server in accordance with an embodiment of the invention. An embodiment of method 6500 may use an embodiment of exemplary remotely-actuated logistics receptacle 6400, an embodiment of exemplary MALVT bot apparatus assembly 1700 (as assembled or after an on-demand assembly) and dispatch server 6205. The exemplary modular autonomous bot apparatus assembly used (e.g., assembly 1700) as part of method 6500 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 6500.

Referring now to FIG. 65A, exemplary method 6500 begins at step 6505 with the remotely-actuated logistics receptacle detecting the deposit of the deliverable item based upon sensor data generated by a sensor within the remotely-actuated logistics receptacle. For example, one of the sensors may be an impact sensor and detect the impact from the deposit of the deliverable item. In another example, such sensor data may be proximity data reflecting a change in what is nearest to one of the sensors. In other examples, such sensor data that reflects the deposit of the deliverable item may come from machine vision sensors, image sensors, and the like. For node-enabled deliverable items, detecting the deposit of the deliverable item may involve locating the node with the deliverable item using the wireless radio transceiver in the control module of the remotely-actuated logistics receptacle using node locating techniques as described herein.

At step 6510, method 6500 continues with the remotely-actuated logistics receptacle transmitting a dispatch request message to the dispatch server in response to the detected deposit of the deliverable item. The dispatch request message includes shipping information on the deliverable item and identifier information on the remotely-actuated logistics receptacle. In some embodiments, the dispatch request message may include identifier information on the deliverable item (e.g., an imaged tracking number, barcode scan data on the deliverable item, and the like), which may allow the dispatch server to look up or request the shipping information on the deliverable item that may then be included with any dispatch command generated by the dispatch server.

At step 6515, method 6500 continues with the modular mobile autonomy control module receiving a dispatch command from the dispatch server. The dispatch command has at least identifier information on the deliverable item based upon the shipping information, transport parameters on the deliverable item based upon the shipping information, destination delivery information related to pickup of the deliverable item, and pickup authentication information related to the modular autonomous bot assembly as an authorized pickup entity for the deliverable item. In more detail, the destination delivery information related to pickup of the deliverable item may include an identifier of one of several secure storage enclosures within the remotely-actuated logistics receptacle that temporarily maintains the deliverable item.

At step 6520, method 6500 has the modular mobile autonomy control module verifying that each of the modular mobile autonomy control module, the modular mobility base, the modular auxiliary power module, and the modular cargo storage system are compatible with transporting the deliverable item as part of the dispatched logistics operation for the deliverable item based upon the dispatch command. In one example, step 6520 may be implemented by verifying that at least the modular cargo storage system is compatible with a size of the deliverable item according to the transport parameters identified on the deliverable item in the dispatch command. In another example, step 6520 may be implemented by verifying that at least the modular cargo storage system is compatible with a weight of the deliverable item according to the transport parameters on the deliverable item identified in the dispatch command.

In a more detail example, a further embodiment of step 6520 may have the modular mobile autonomy control module verifying that at least the modular cargo storage system is compatible with the transport parameters on the deliverable item identified in the dispatch command; and then transmitting a configuration change request to the dispatch server if the at least modular cargo storage system is verified to be incompatible with the transport parameters on the deliverable item, the configuration change request identifying that the at least modular cargo storage system are incompatible with the transport parameters on the deliverable item. In more detail, the modular mobile autonomy control module may transmit the configuration change request to the dispatch server if the at least modular cargo storage system is verified to be incompatible with the transport parameters on the deliverable item prior to when the modular mobile autonomy control module causes the modular mobility base to move from the bot storage location.

At step 6525, method 6500 continues with the modular mobile autonomy control module autonomously causing the modular mobility base to move from a bot storage location to a location of the remotely-actuated logistics receptacle as identified by the destination delivery information in the dispatch command. On approach to the location of the remotely-actuated logistics receptacle, method 6500 has the modular mobile autonomy control module broadcasting, at step 6530, a pickup authentication signal when the modular autonomous bot apparatus assembly is within a threshold notification range of the location of the remotely-actuated logistics receptacle. At step 6535, method 6500 continues with the modular mobile autonomy control module autonomously causing the modular mobility base to move to a receiving position proximate an access door on the remotely-actuated logistics receptacle upon arrival at the location of the remotely-actuated logistics receptacle.

At step 6540, method 6500 has the remotely-actuated logistics receptacle detecting the pickup authentication signal from the modular mobile autonomy control module. In some embodiments of step 6540, detecting the pickup authentication signal may involve node association actions taken to establish a secure association between the remotely-actuated logistics receptacle and the modular mobile autonomy control module. In more detail, an embodiment of step 6540 may be accomplished with the remotely-actuated logistics receptacle detecting an advertising signal from the modular mobile autonomy control module; and then establishing a secure association between the remotely-actuated logistics receptacle and the modular mobile autonomy control module after detecting the advertising signal. The establishment of such a secure association is done by generating association data stored on the remotely-actuated logistics receptacle indicating the secure association and allowing secure sharing of information between the remotely-actuated logistics receptacle and the modular mobile autonomy control module. Such a secure association is pre-authorized by the dispatch server as it relates to the dispatched logistics operation for the deliverable item. This embodiment of step 6540 continues by having the modular mobile autonomy control module securely transmitting the pickup authentication signal to the remotely-actuated logistics receptacle once the secure association is established and the association data is generated; and securely receiving, by the remotely-actuated logistics receptacle, the pickup authentication signal from the modular mobile autonomy control module.

After step 6540, method 6500 continues through transition A to step 6545 on FIG. 65B. Referring now to step 6545 on FIG. 65B, method 6500 continues with authenticating, by the remotely-actuated logistics receptacle, that the modular autonomous bot apparatus assembly is the authorized pickup entity for the deliverable item when authentication information in the pickup authentication signal correlates to the pickup authentication information from the dispatch command.

At step 6550, method 6500 continues with the remotely-actuated logistics receptacle activating a door actuator on the remotely actuated logistics receptacle after authenticating that the modular autonomous bot apparatus assembly is the authorized pickup entity based upon the pickup authentication signal. Activating the door actuator causes the access door on the remotely-actuated logistics receptacle to move from a secure closed position to an open position, such as shown in FIG. 64C. In more detail, activating the door actuator may involve activating, by the remotely-actuated logistics receptacle, the door actuator on the remotely actuated logistics receptacle (a) after authenticating that the modular autonomous bot apparatus assembly is the authorized pickup entity based upon the pickup authentication signal and (b) after receiving a door activation request signal from the modular mobile autonomy control module.

At step 6555, method 6500 continues with the modular mobile autonomy control module broadcasting a ready confirmation signal once the modular mobility base is located at the receiving position proximate the access door on the remotely-actuated logistics receptacle. Thereafter, at step 6560, method 6500 continues with the remotely-actuated logistics receptacle activating a parcel object actuator (i.e., a type of object manipulation device or system) on the remotely-actuated logistics receptacle in response to the ready confirmation signal from the modular mobile autonomy control module and only if the authentication information in the pickup authentication signal correlates to the pickup authentication information from the dispatch command. Activating the parcel object actuator moves the deliverable item from where it is maintained in the remotely-actuated logistics receptacle and into the custody of the modular cargo storage system.

In more detail, further embodiments of step 6560 involving activing the parcel object actuator may activate the parcel object actuator by causing the parcel object actuator to remove the deliverable item from the remotely-actuated logistics receptacle and transfer the deliverable item to an articulating object receiver (e.g., an articulating arm, an actuated sliding arm, an actuated grabbing arm, an actuated belt surface, and the like) on the modular cargo storage system being controlled by the modular mobile autonomy control module. Additionally, this may involve the further steps of receiving, by the articulating object receiver on the modular cargo storage system under control of the modular mobile autonomy control module, the deliverable item from the parcel object actuator on the remotely-actuated logistics receptacle; and placing, by the articulating object receiver on the modular cargo storage system under control of the modular mobile autonomy control module, the deliverable item within the modular cargo storage system.

In still another embodiment of step 6560, more detailed types of parcel object actuators may be deployed. For example, step 6560 may involve activating, by the remotely-actuated logistics receptacle, an actuated support base within a storage compartment of the remotely-actuated logistics receptacle in response to the ready confirmation signal. Such a support base, when activated, may cause the actuated support base to tilt towards an entrance opening to the storage compartment at the access door and cause the deliverable item to at least slide towards the entrance opening. Such an actuated support base may have an adjustable suspension system, similar to that described above relative to exemplary modular mobility base 1705 and its ability to tilt and lift.

In another example, step 6560 may involve activating, by the remotely-actuated logistics receptacle, an actuated pushing arm within a storage compartment of the remotely-actuated logistics receptacle in response to the ready confirmation signal, where activating the actuated pushing arm causes the actuated pushing arm to contact the deliverable item and at least push the deliverable item towards an entrance opening to the storage compartment at the access door. Further still, another example of step 6560 may involve activating, by the remotely-actuated logistics receptacle, an actuated sliding arm within a storage compartment of the remotely-actuated logistics receptacle in response to the ready confirmation signal, where activating the actuated sliding arm causes the actuated sliding arm to contact the deliverable item and at least slide the deliverable item towards an entrance opening to the storage compartment at the access door. Such an actuated sliding arm may be implemented similar to that described above regarding actuated sliding arms 2085.

In yet another example of step 6560, activating the parcel object actuator may involve activating, by the remotely-actuated logistics receptacle, an actuated grabbing arm within a storage compartment of the remotely-actuated logistics receptacle in response to the ready confirmation signal, wherein activating the actuated grabbing arm causes the actuated grabbing arm to engage the deliverable item, move the deliverable item towards and through an entrance opening to the storage compartment at the access door, and place the deliverable item into the modular cargo storage system. Such an actuated grabbing arm may be implemented similar to that described above regarding actuated grabbing arm 2090.

In yet another example of step 6560, activating the parcel object actuator may involve activating, by the remotely-actuated logistics receptacle, an actuated belt surface in response to the ready confirmation signal, the actuated belt surface temporarily supporting the deliverable item within a storage compartment of the remotely-actuated logistics receptacle, where activating the actuated belt surface causes the actuated moving surface to move the deliverable item towards and through an entrance opening to the storage compartment at the access door. Such an actuated belt surface may be implemented similar to that described above regarding actuated belt surface 2080b. Furthermore, such an actuated belt surface in step 6560 may include an actuated belt surface on an inner surface of the actuated door (similar to that of belt surface 2080a).

At step 6565, method 6500 continues with autonomously causing, by the modular mobile autonomy control module, the modular mobility base to move from the remotely-actuated logistics receptacle to a destination location for delivery of the deliverable item, the destination location being identified as part of the destination delivery information from the dispatch command.

A further embodiment of method 6500 may also have the dispatch server initiating a configuration change operation on the modular autonomous bot apparatus assembly to change at least one of the modular mobile autonomy control module, the modular mobility base, the modular auxiliary power module, and the modular cargo storage system that are verified to be incompatible with transporting the deliverable item as part of the dispatched logistics operation for the deliverable item based upon the dispatch command prior to when the modular mobile autonomy control module causes the modular mobility base to move from the bot storage location.

Figure 66:
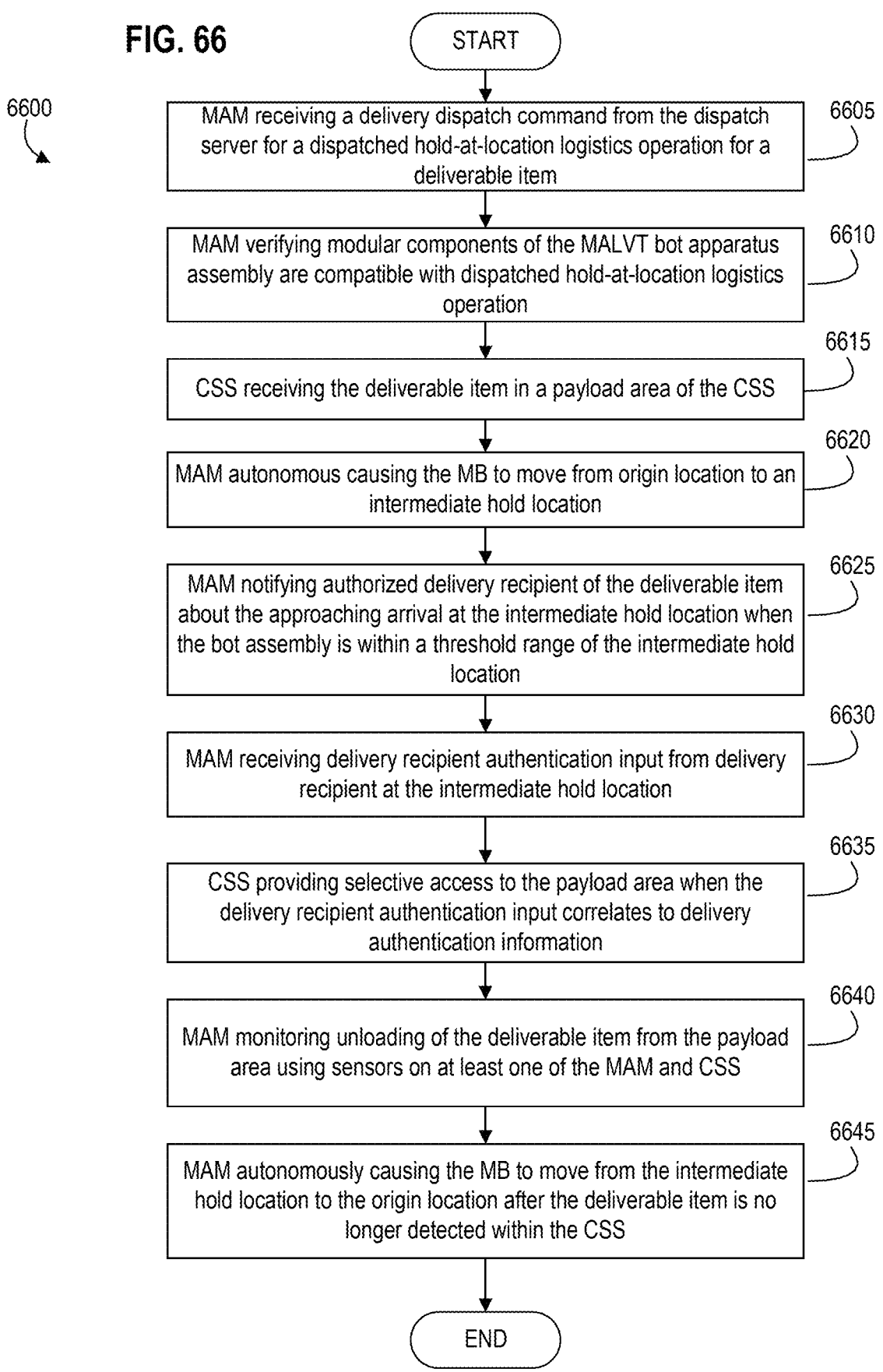
FIG. 66 is a flow diagram of an embodiment of an exemplary method for performing a dispatched hold-at-location logistics operation for a deliverable item from an origin location using a modular autonomous bot apparatus assembly operating as a temporary hold-at-location logistics receptacle and a dispatch server in accordance with an embodiment of the invention.

In still a further embodiment, an exemplary MALVT bot apparatus assembly, such as assembly 1700, may itself be configured to deploy and operate as a temporary hold-at-location secure storage while on the dispatched logistics operation. FIG. 66 is a flow diagram of an embodiment of an exemplary method for performing a dispatched hold-at-location logistics operation for a deliverable item from an origin location using a modular autonomous bot apparatus assembly operating as a temporary hold-at-location logistics receptacle and a dispatch server in accordance with an embodiment of the invention. An embodiment of method 6600 may use an embodiment of exemplary MALVT bot apparatus assembly 1700 (as assembled or after an on-demand assembly) and dispatch server 6205. The exemplary modular autonomous bot apparatus assembly used (e.g., assembly 1700) as part of method 6600 is equipped with at least a modular mobility base (e.g., exemplary MB 1705) propelling the exemplary MALVT bot apparatus assembly 1700, a modular auxiliary power module (e.g., exemplary APM 1710) providing power for exemplary MALVT bot apparatus assembly 1700, a modular cargo storage system (e.g., exemplary CSS 1720) configured to temporarily maintain what is transported within the exemplary MALVT bot apparatus assembly 1700, and a modular mobile autonomy control module (e.g., exemplary MAM 1725) with its autonomous controller (e.g., autonomous control system 3100) that autonomously controls operation of the exemplary MALVT bot apparatus assembly 1700 during method 6600.

Referring now to FIG. 66, method 6600 begins at step 6605 with (a) the modular mobile autonomy control module receiving a delivery dispatch command for the dispatched hold-at-location logistics operation from the dispatch server. The delivery dispatch command received from the dispatch server has at least identifier information on the deliverable item, transport parameters on the deliverable item, hold-at-location information related to an intermediate hold location for the deliverable item as maintained within the modular autonomous bot apparatus assembly, and delivery authentication information related to an authorized delivery recipient of the deliverable item.

In more detail, an embodiment of step 6605 may have the hold-at-location information related to the intermediate hold location identifying that location being at a hold-at-location logistics facility (such as facility 6200). In other embodiments, the intermediate hold location may be designated, according to the dispatch command, to be the location of a mobile external wireless node designated as part of the hold-at-location information. Such a mobile external wireless node may, for example, be a delivery vehicle master node disposed with a delivery vehicle (such as a courier's remotely located delivery vehicle), a delivery courier master node operated by delivery personnel (such as exemplary courier mobile wireless node 5760), or a mobile master node operated by a designated alternative recipient (who is identified by the authorized delivery recipient according to the hold-at-location information and the delivery authentication information in the dispatch command).

At step 6610, method 6600 proceeds with (b) the modular mobile autonomy control module verifying that each of the modular mobile autonomy control module, the modular mobility base, the modular auxiliary power module, and the modular cargo storage system are compatible with the dispatched hold-at-location logistics operation for the deliverable item based upon the delivery dispatch command. In this way, as described above, replacement modular components may be swapped out so that the exemplary MALVT bot apparatus assembly being dispatched for this particular logistics operation has, for example, components of the right size, the sufficient level of readiness (e.g., calibration state on sensors, charge state on power sources), and use of components that are authorized to be used for such a dispatched hold-at-location logistics operation.

Once verification has been accomplished in step 6610, method 6600 proceeds to step 6615 with (c) the modular cargo storage system receiving the deliverable item into a payload area within the modular cargo storage system at the origin location. Thereafter, at step 6620, method 6600 proceeds with (d) the modular mobile autonomy control module autonomously causing the modular mobility base to move from the original on a route to the intermediate hold location identified by the hold-at-location information.

At step 6625, method 6600 continues with (e) the modular mobile autonomy control module notifying the authorized delivery recipient of the deliverable item of an approaching arrival at the intermediate hold location when the modular autonomous bot apparatus assembly is within a threshold notification range of the intermediate hold location identified by the hold-at-location information. Such a step may be accomplished in the variety of manners similar that described above relative to step 6530.

At step 6630, method 6600 proceeds with (f) receiving delivery recipient authentication input by the modular mobile autonomy control module from a delivery recipient disposed external to the modular autonomous bot apparatus assembly at the intermediate hold location. Thus, the exemplary MALVT bot apparatus assembly that has been sent on this dispatched hold-at-location logistics operation waits at the intermediate hold location (as a type of secured storage itself) and monitors for delivery recipient authentication input from the reception range of the wireless radio transceiver that is part of the exemplary MAM on this exemplary MALVT bot apparatus assembly.

At step 6635, method 6600 proceeds with (g) the modular cargo storage system providing selective access to the deliverable item within the modular cargo storage system only when the delivery recipient authentication input correlates to the delivery authentication information indicating that the delivery recipient providing the delivery recipient authentication input is the authorized delivery recipient.

At step 6640, method 6600 proceeds with (h) the modular mobile autonomy control module monitoring unloading of the deliverable item from within the modular cargo storage system using one or more sensors on at least one of the modular mobile autonomy control module and the modular cargo storage system. Such monitoring of the unloading process may involve different types of sensors and processing of such sensor data generated to identify and track the deliverable item as it is removed from within the modular cargo storage system similar to that described with respect to step 5140 and its variations.

At step 6645, method 6600 proceeds with (i) the modular mobile autonomy control module autonomously causing the modular mobility base to move from the intermediate hold location on a return route to the origin location after the deliverable item is no longer detected within the modular cargo storage system.

In more detail, an embodiment of method 6600 may implement steps (f) and (g) in more detail as involving waiting for the required delivery recipient authentication input prior to a time deadline (e.g., closing of the hold-at-location logistics facility 6200 where the exemplary MALVT bot apparatus assembly dispatched on this particular hold-at-location logistics operation is waiting at the intermediate hold location). For example, this may have an embodiment of method 6600 implementing the steps of (f) receiving delivery recipient authentication input and (g) providing selective access to the deliverable item by having the modular mobile autonomy control module autonomously causing the modular mobility base to wait at the intermediate hold location for at least until a pre-determined closing time of the hold-at-location facility; and then having the modular cargo storage system at the direction of the modular mobile autonomy control module providing selective access to the deliverable item when the modular mobile autonomy control module detects the delivery recipient authentication input and determines the detected delivery authentication input indicates the delivery recipient providing the delivery recipient authentication input is the authorized delivery recipient and the pre-determined deadline for closing of the hold-at-location facility has not yet expired.

In another example, this type of embodiment may have method implementing steps (f)-(i) by having the modular mobile autonomy control module autonomously causing the modular mobility base to wait at the intermediate hold location for at least until a pre-determined closing time of the hold-at-location facility, and then monitoring for receipt of delivery recipient authentication input from the authorized delivery recipient according to the delivery authentication information. The modular mobile autonomy control module is then, as part of this embodiment of method 6600, autonomously causing the modular mobility base to move from the intermediate hold location to the origin location when the pre-determined deadline for closing of the hold-at-location facility has expired and the monitoring has not indicated receipt of the delivery recipient authentication input from the authorized delivery recipient. Thereafter, this embodiment of method 6600 repeats steps (d)-(i) after a subsequent pre-determined opening time of the hold-at-location facility. As such, the exemplary MALVT bot apparatus assembly dispatched to be the hold-at-location secure storage can adaptively locate as a dynamically autonomous and relocatable hold-at-location secure storage as part of delivering the deliverable item.

Single Logistics Operation in Multiple Legs Using Different Autonomous Bots

As noted above, an exemplary system embodiment may deploy multiple exemplary modular components (e.g., MB units, MAM units) operating in a "collaboration mode" as part of an exemplary MALVT bot apparatus assembly. This ability to have exemplary MALVT bot apparatus assemblies (or modular components of such assemblies) cooperate may be extended for use on general autonomous logistics vehicle transports and improved pickup/delivery/transfer operations to involve directed and/or autonomous vehicle-to-vehicle transfers of the deliverable item.

In further embodiments, multiple MALVT bot apparatus assemblies may be used as part of a single logistics operation, such as a pickup operation or a delivery operation, having multiple legs of the operation (e.g., a first leg that involves pickup from an initial location and transit to a waypoint location for transfer to another for a second leg, and where the second leg involves receipt of the payload and transit from the waypoint location to a second location). In other words, this additional type of embodiment may implement a single multi-leg logistics operation with multiple different node-enabled autonomous vehicle transports (also referenced as node-enabled autonomous transport vehicles (NEATV), node-enabled autonomous vehicles (NEAVs) or autonomous transport vehicles (AVs)). For example, an exemplary node-enabled autonomous transport vehicle (NEAVT) may be implemented by exemplary MALVT bot apparatus assembly. In other examples, an exemplary node-enabled autonomous transport vehicle (NEAVT) may be implemented by an autonomous transport vehicle that is node-enabled but not necessarily a modular assembly of swappable components that may be assembled on-demand.

In a general embodiment, an exemplary system of multiple AVs may be used to conduct a single multi-leg logistics operation. In some embodiments, one of the AVs may be deemed a "main" or "primary" AV and cover one part of the logistics operation, while the other may be a "secondary" AV to cover the remainder of the logistics operation. As part of the overall logistic operation, whether a pickup or delivery operation, the different AV devices (e.g., different exemplary MALVT bot apparatus assemblies, which may be referred to herein as different node-enabled AVs) may be dispatched and meet in a coordinated manner to align with each other and transfer the cargo/payload of what is being transported (e.g., the item being transported, a payload container that maintains one or more items being transported) from one of the AV units/assemblies to the other, which then has the other AV unit/assembly moving on to complete the logistics operation (which may involve a further transfer to another AV or delivery at a designated location).

Figure 67:
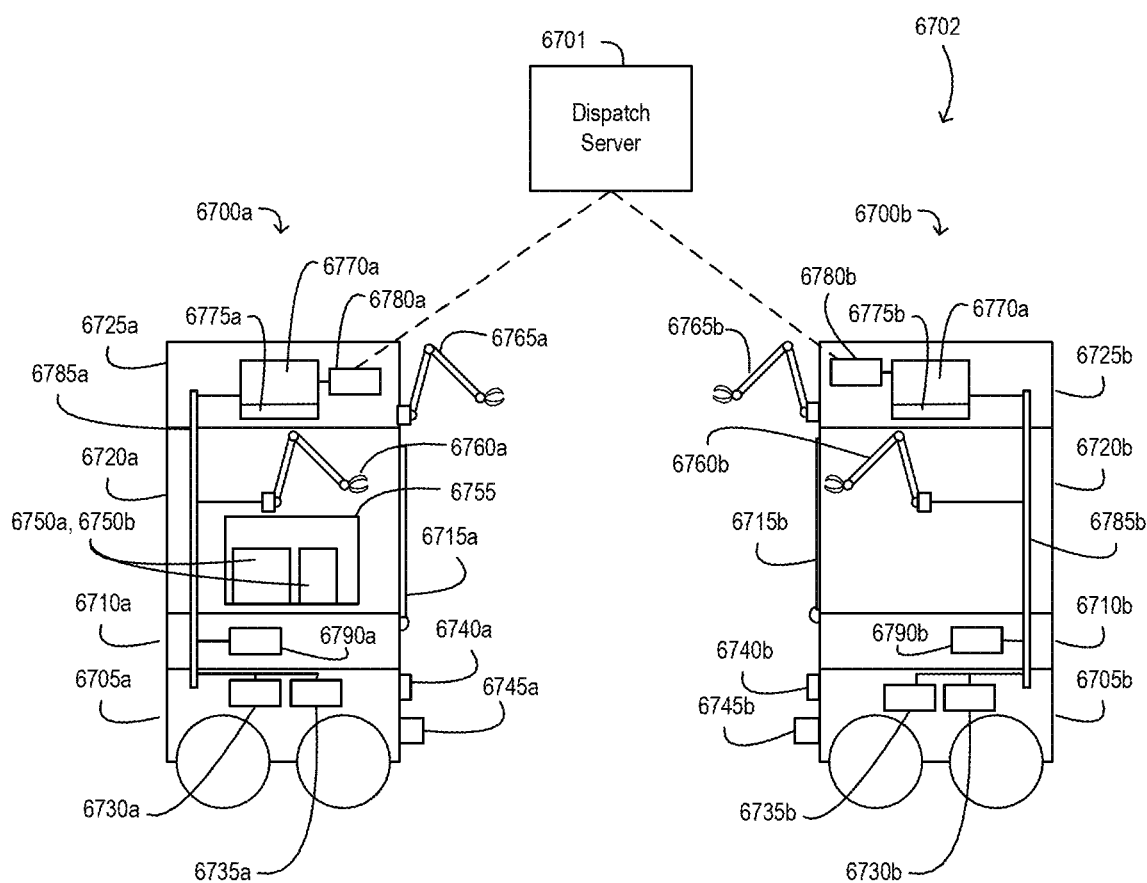
FIG. 67 is a diagram of multiple exemplary node-enabled autonomous transport vehicles in accordance with an embodiment of the invention.

FIG. 67 is a diagram of an exemplary system 6702 having multiple exemplary node-enabled autonomous transport vehicles 6700a, 6700b and a dispatch server 6701 that may communicate with each of vehicles 6700a, 6700b in accordance with an embodiment of the invention. Exemplary node-enabled autonomous transport vehicles 6700a, 6700b in the embodiment shown in FIG. 67 may be implemented similar to exemplary MALVT bot apparatus assembly 1700 and those skilled in the art will appreciate that components described above related to assembly 1700 may deployed on either of exemplary node-enabled autonomous transport vehicles 6700a, 6700b. Referring now to FIG. 67, exemplary node-enabled autonomous transport vehicle 6700a is shown in a configurations with mobility base 6705a, auxiliary power module 6710a, cargo storage system 6720a, and a modular autonomy module 6725a. Exemplary mobility base 6705a is an example of a mobile transport vehicle base the propels vehicle 6700a. Base 6705a includes exemplary propulsion system 6730a and steering system 6735a (similar to propulsion system 1830 and steering system 1835 on exemplary modular mobility base 1705) that may be controlled locally through a mobility controller (not shown but similar to mobility controller 1825) on base 6705a or may be controlled by controller 6770a through connections over bus 6785a (a common power and data conduit or transport bus similar to that of buses 1860, 2050, 2250, 3115 explained above). As such, exemplary propulsion system 6730a and steering system 6735a are configured to control and move the exemplary mobile transport vehicle base 6705a in response to a control input from controller 6770a.

Mobility base 6705a also includes sensors 6740a (similar to sensors 1815) that may include, for example, front AV sensors, such as cameras, proximity sensors, IR sensors, LiDAR sensors, environmental sensors, light sensors, motion detectors, tilt sensors, impact sensors, and the like. Such sensors 6740a may be accompanied with lights to aid with the generation of useful sensor data by sensors 6740a. Sensor data generated by sensors 6740a is provided via bus 6785a to controller 6770a for processing and use during operation of vehicle 6700a.

An exemplary docking interface 6745a is shown disposed on mobility base 6705a in the illustrated embodiment of FIG. 67. Such a docking interface 6745a may be implemented as a contact registration point for engaging vehicle 6700a with another AV (such as vehicle 6700b). Further embodiments of docking interface 6745a may include one or more sets of latches disposed on an outward peripheral edge of the mobility base 6705a, where such latches are configured and disposed to mate with a set of complementary latches on other vehicles (e.g., complementary latches that implement docking interface 6745b on an outward peripheral edge of the exemplary mobility base 6705b). Such latches may be implemented as recessed latches, interlocking latches, and/or as actuated latches activated by controller 6770a on the respective structure (e.g., one set of latches actuated by the controller 6770a in module 6725a (e.g., an exemplary mobile master node) to move and engage a mated set of latches on another mobile autonomous vehicle 6700b to secure vehicle 6700a to vehicle 6700b). In like manner, the latches 6745b on vehicle 6700b may be actuated to move and engage the mated set of latches 6745a on vehicle 6700a. Actuation of such latches may be initiated, for example, based upon proximity sensor data and signals provided to controller 6770a as vehicle 6700a approaches exemplary vehicle 6700b.

While exemplary docking interface 6745a is shown on the mobility base 6705a, those skilled in the art will appreciate that such a docking interface may be more than a securable contact point, such as sealed passageway that may extend from the cargo storage system 6720a to engage the cargo storage system on another AV and allow for transfer of items being carried by vehicle 6700a into vehicle 6700b through such a sealed passageway, which may be actuated to deploy, seal, and retract in response to control signals from controller 6770a. Further those skilled in the art will appreciate that other embodiments of exemplary docking interface 6745a may be disposed on different parts of vehicle 6700a and may provide a secured engagement between vehicle 6700a and another vehicle with other securing structure, such as keyed capture appendages, abutting seals with actuated clamps to hold the seals together, and the like.

Exemplary auxiliary power module 6710a on exemplary vehicle 6700a (similar to exemplary APM 1710) includes a power source 6790a that provides power over bus 6785a and may actuate door 6715a. Exemplary cargo storage system 6720a on exemplary vehicle 6700a (similar to exemplary CSS 1720) provides a payload storage that is configured to temporarily maintain at least one object (such as payload container 6755 and deliverable items 6750a, 6750b) and also provides part of bus 6785a. Exemplary articulating arm 6760a is shown disposed within cargo storage system 6720a and coupled to bus 6785a as an example implementation of an object manipulation system that may be used within the payload area of CSS 6720a to manipulate the contents of the payload area. A further embodiment may have exemplary articulating arm 6760a disposed on auxiliary power module 6710a and coupled to bus 6785a as another example implementation of an object manipulation system.

Exemplary modular autonomy module 6725a (similar to autonomous control system 3100) is implemented in this embodiment as a mobile master node having controller 6770a with memory 6775a and a wireless communication interface 6780a. Modular autonomy 6725a, as a mobile master node for vehicle 6700a, is disposed on the mobile transport vehicle base 6705a, albeit along with the APM 6710a and cargo storage system 6720a. Such a wireless communication interface 6780a may be implemented with a wireless radio transceiver (e.g., a hardware radio, a wireless transceiver implemented with a combination of hardware and software, or a software defined radio (SDR) implementation of a wireless radio transceiver capable of providing the functionality of a short, medium, and long range wireless communications interface. Memory 6775a maintains, for example, an autonomous navigation program module that may be executed by controller 6770a to be operative as described herein to control movement of the vehicle 6700a, alignment of the vehicle with other vehicles when docking and transferring items from the vehicle to another, controlling the transfer of items via actuator control signals, and interacting with other vehicles and nodes as part of a logistics operation.

Exemplary vehicle 6700a may further have exemplary articulating arm 6765a operatively coupled to controller 6770a and disposed, as another example of an object manipulation system onboard vehicle 6700a, to reach and move items outside of the vehicle 6700a (or in combination with articulating arm 6760a or other object manipulation system structure, such as a moving belt surface, sweeping arms, grabbing arms, tilting wheelbases, and the like).

Those skilled in the art will further appreciate that the second exemplary node-enabled autonomous transport vehicle 6700b shown in FIG. 67 in a similar configuration with similar exemplary components as shown for vehicle 6700a, but is currently not holding the payload container 6755 or any deliverable items. And such a second exemplary node-enabled autonomous transport vehicle 6700b may interact with the first exemplary node-enabled autonomous transport vehicle 6700a in a manner to carry out a single multi-leg logistics operation. For example, in an exemplary embodiment, these two different node-enabled AVs 6700a, 6700b (which may be implemented with different exemplary MALVT bot apparatus assemblies) are deployed for a single multi-leg logistics operation where one (the master or main or primary) node-enabled AV 6700a travels to a location near an object delivery point (or waypoint), and transfers the object or item being transported to a shorter range or secondary node-enabled AV 6700b that can complete the delivery. A similar type of example may be used where the second node-enabled AV 6700b picks up the object and transfers it to the main node-enabled AV 6700a, which can then complete the pickup operation (e.g., ending with the autonomous transfer or with further transit to a courier vehicle, such as exemplary courier transport vehicle 6805 shown in FIG. 68A). In this embodiment, those skilled in the art will appreciate that the primary and secondary node-enabled AV units 6700a, 6700b may be implemented with similar or differently configured exemplary MALVT bot apparatus assemblies tailored to carry the appropriate object(s)/item(s) and configured to implement transfer of the payload from one to the other as part of the single, multi-leg logistics operation.

Figure 68A:
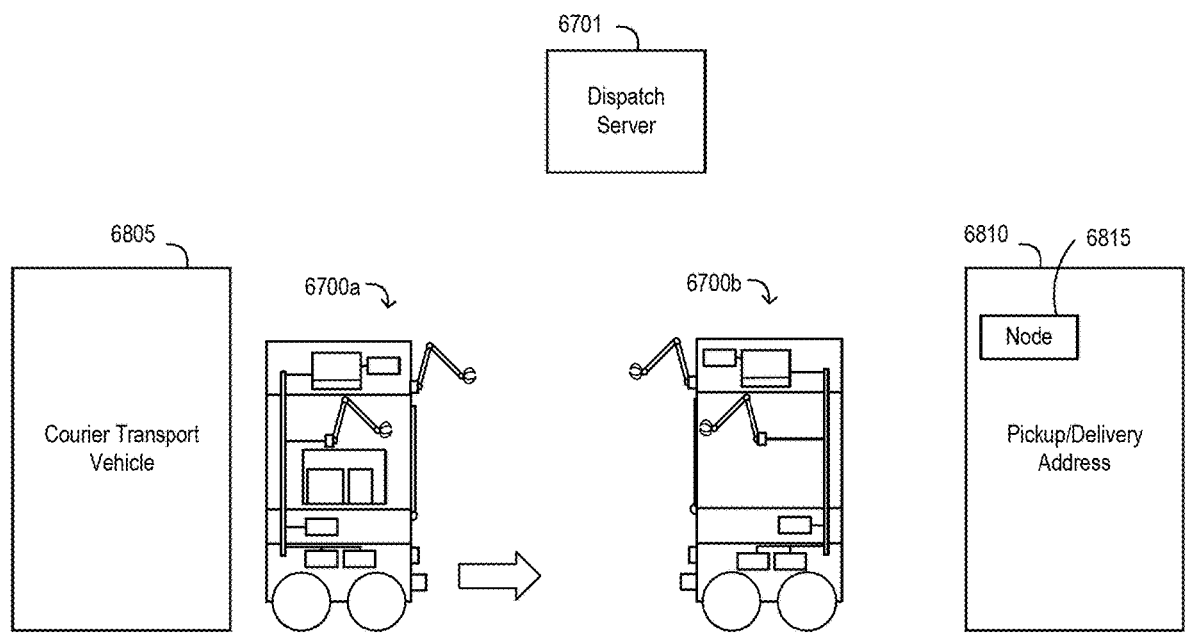
FIGS. 68A-68E are diagrams of an exemplary system using multiple exemplary node-enabled autonomous transport vehicles when navigating between an exemplary courier transport vehicle and a designated shipping location with an item being shipped as part of a multi-leg autonomous logistics operation for the item being shipped in accordance with an embodiment of the invention.

FIGS. 68A-68E are diagrams of an exemplary system using multiple exemplary node-enabled autonomous transport vehicles 6700a, 6700b when navigating between an exemplary courier transport vehicle 6805 and a designated shipping location 6810 with an item being shipped as part of a multi-leg autonomous logistics operation for the item being shipped in accordance with an embodiment of the invention. Referring now to FIG. 68A, exemplary node-enabled autonomous transport vehicle 6700a may be referred to a primary vehicle, and has been loaded with at least one object (e.g., items 6750a, 6750b within a payload container 6755 as shown specifically in FIG. 67). In an example where such an object or object may be loaded, the mobile master node 6725a, when executing the autonomous navigation program module from memory 6775a, is operative to initiate a loading operation of items 6750a, 6750b and payload container 6755 as the payload at a pickup location using the primary object manipulating system (e.g., articulating arm 6765a and/or articulating arm 6760a) on the primary node-enabled autonomous transport vehicle. In one embodiment, the pickup location may, for example and as shown in FIG. 68A, be in the courier transport vehicle 6850 where the logistics operation is delivery to delivery address 6810 as the designated shipping location. Those skilled in the art will appreciate that in another embodiment, the pickup location may, for example, be at the delivery address 6810 where the logistics operation is delivery to the courier transport vehicle 6850.

Once the object has been picked up by the primary exemplary node-enabled autonomous transport vehicle 6700a, exemplary node-enabled autonomous transport vehicle 6700a may approach the secondary exemplary node-enabled autonomous transport vehicle 6700b in order to handoff the object and for the secondary exemplary node-enabled autonomous transport vehicle 6700b to complete the logistics operation. In more detail, an embodiment may have the mobile master node 6725a in primary vehicle 6700a, when executing the first autonomous navigation program module in memory 6775a, being operative to detect a signal broadcast from the mobile master node 6725b of vehicle 6700b via the primary wireless communication interface 6780a and then transmit an instruction over the primary wireless communication interface 6780a to the mobile master node 6725b in vehicle 6700b to alter a power level of the signal broadcast from mobile master node 6725b. Mobile master node 6725a is further operative to identify the signal broadcast from mobile master node 6725b with the altered power level, determine a direction of mobile master node 6725b relative to mobile master node 6725a based upon the detected signal from mobile master node 6725b with the altered power level; and generate onboard control input for steering and propulsion systems 6730a, 6735a to cause the primary node-enabled autonomous transport vehicle 6700a to navigate to mobile master node 6725b based upon the determined direction of mobile master node 6725b relative to mobile master node 6725a.

Figure 68B:
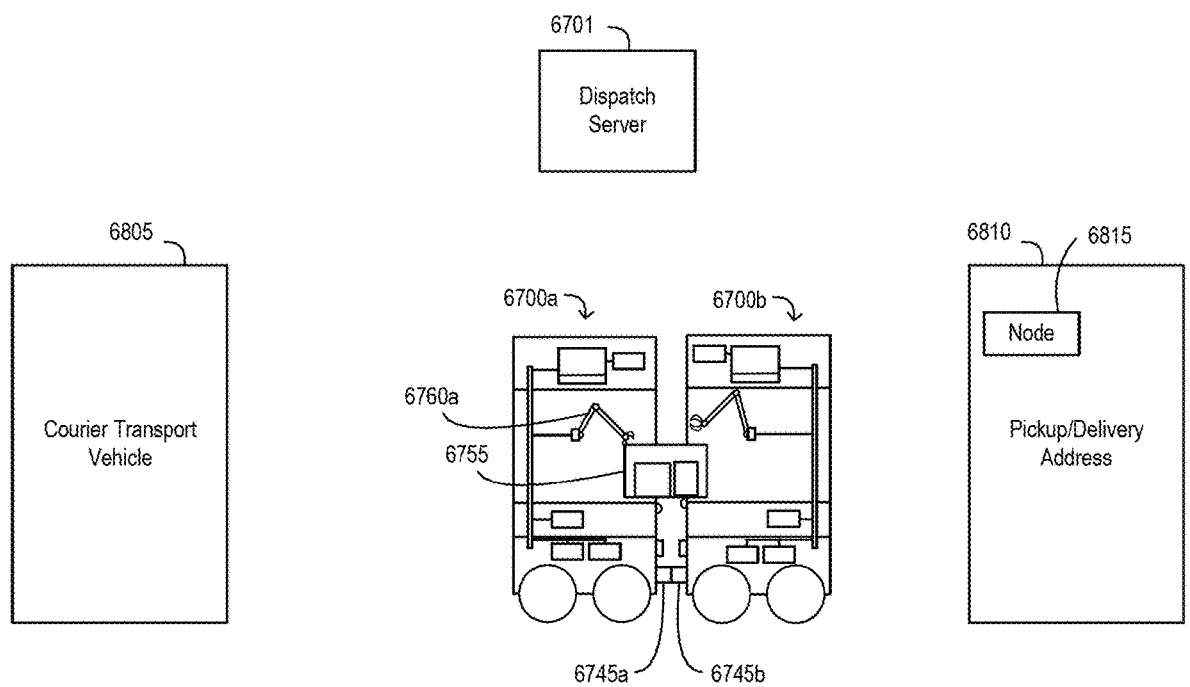

As shown in FIG. 68B, the primary exemplary node-enabled autonomous transport vehicle 6700b has moved towards secondary exemplary node-enabled autonomous transport vehicle 6700b so that they can align, dock, and begin transferring payload container 6755 having items 6750a, 6750b. In more detail, an embodiment may have the mobile master node 6725a in primary vehicle 6700a, when executing the first autonomous navigation program module in memory 6775a, being operative to generate the appropriate onboard control input (based upon, for example, location data, sensor data, and the like) to cause the primary node-enabled autonomous transport vehicle 6700a to navigate to the mobile master node 6725b in the secondary vehicle 6700b by being further operative to generate such control input to cause the primary node-enabled autonomous transport vehicle 6700a to navigate to docking interface 6745b disposed on the secondary node-enabled autonomous transport vehicle 6700b based upon the determined direction of the mobile master node 6725b of the secondary vehicle 6700b relative to mobile master node 6725a and engage the docking interface 6745a disposed on the primary node-enabled autonomous transport vehicle 6700a at the waypoint location of the secondary node-enabled autonomous transport vehicle 6700b. Once the vehicles 6700a, 6700b are engaged via their respective docking interfaces 6745a, 6745b (which may be actuated latches), the mobile master node 6725a on the primary vehicle 6700a, when executing the first autonomous navigation program module in memory 6775a, is operative to cause the primary object manipulation system 6760a to transfer the payload container 6755 (and the items being transported in the container) once the docking interface 6745a on the primary node-enabled autonomous transport vehicle 6700a is secured to the docking interface 6745b on the secondary node-enabled autonomous transport vehicle 6700b at the waypoint location.

Figure 68C:
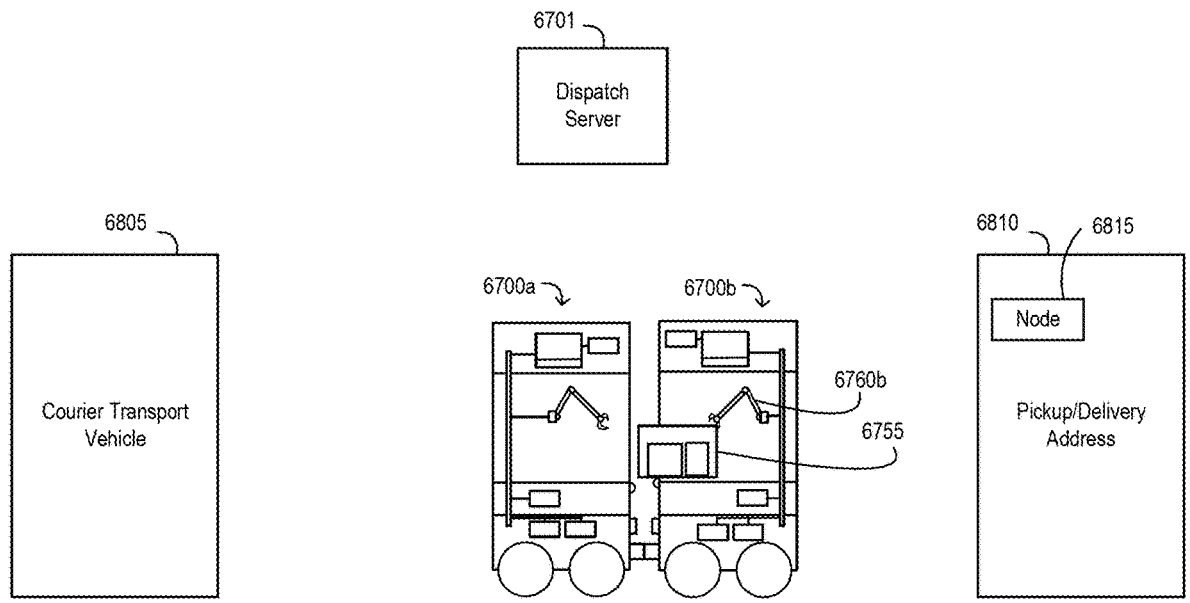

As shown in FIG. 68B, the primary object manipulation system 6760a (e.g., an articulating arm in the CSS 6720 of primary vehicle 6700a) begins transfer of the container 6755 with items 6750a, 6750b). Other types of object manipulation systems on the primary vehicle may be deployed, such actuated or articulating belts, arms, and the like as described herein relative to assembly 1700) to initiate and carry out transfer of such a container and items. Further exemplary object manipulation systems for use in transferring such a container and items from primary vehicle 6700a to secondary vehicle 6700b may include articulating arm 6765a. Those skilled in the art will further appreciate that mobile master node 6725a may activate and actuate multiple object manipulation systems onboard primary vehicle 6700a to transfer the container and items to the secondary vehicle 6700b. Likewise, those skilled in the art will further appreciate the mobile master node 6725b may activate and actuate similar multiple object manipulation systems onboard primary vehicle 6700b to receive and stow away the container and items within the secondary vehicle 6700b as shown in FIG. 68C.

Figure 68D:
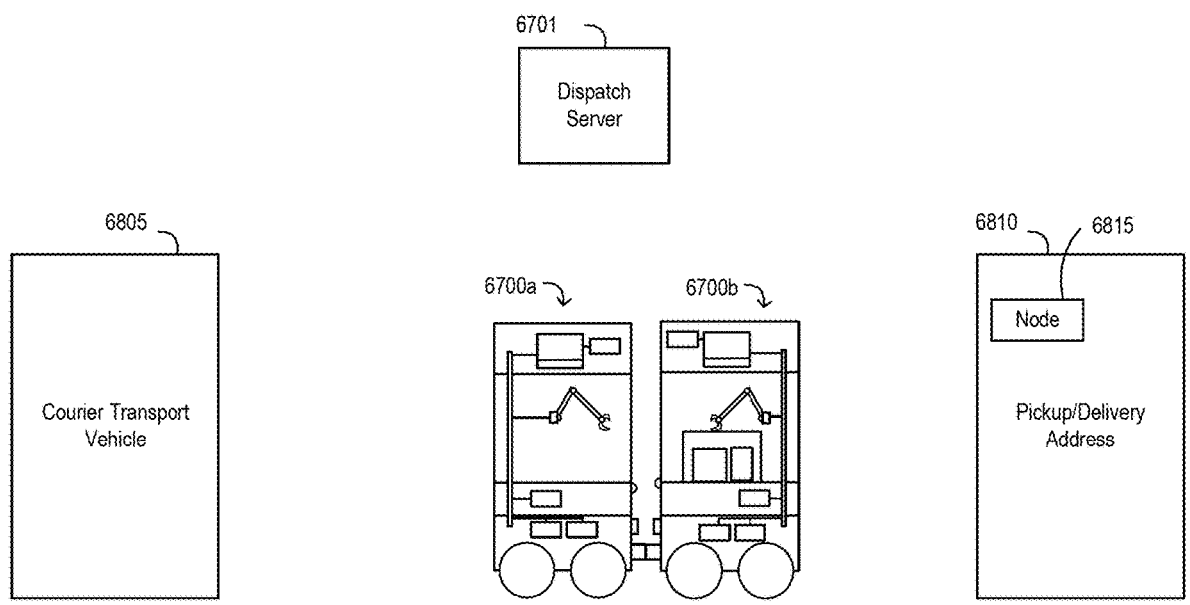
Figure 68E:
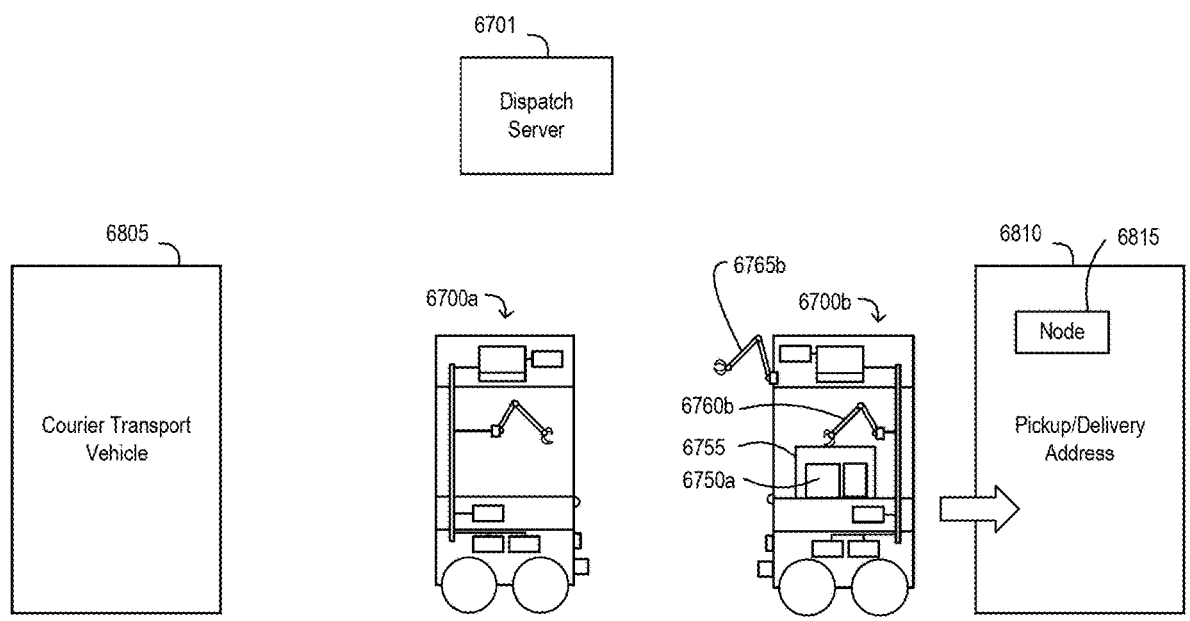

As shown in FIG. 68D, the transfer of the payload container 6755 and items 6750a, 6750b is complete with such a payload now on the secondary vehicle 6700b. Then, as shown in FIG. 68E, the vehicles 6700a, 6700b undock, and the secondary vehicle 6700b moves towards its destination (e.g., delivery address 6810). In more detail, an embodiment may have mobile master node 6725b in secondary vehicle 6700b, when executing the second autonomous navigation program module in memory 6775b, being further operative to detect a signal broadcast from another node associated with the designated shipping location for the payload (e.g. facility node 6815, which may also be implemented as a mobile wireless node-based user access device of the delivery recipient of the payload delivery) and transmit an instruction over the secondary wireless communication interface 6780b to node 6815 to alter a power level of the signal broadcast from that node 6815. The mobile master node 6725b in the secondary vehicle 6700b is further operative to then identify the signal broadcast from node 6815 with the altered power level; determine a direction of node 6815 relative to mobile master node 6725b in secondary vehicle 6700b based upon the detected signal from node 6815 with the altered power level; generate onboard control input to cause the secondary node-enabled autonomous transport vehicle 6700b to navigate to node 6815 based upon the determined direction; and cause the secondary object manipulation system (e.g., articulating arm 6760b, arm 6765b, or other object manipulation devices that are actuated/activated by mobile master node 6725b (such as moving belt surfaces, sweeping arms, grabbing arms, and the like) to transfer the payload container 6755 and items 6750a, 6750b being shipped off the secondary mobile transport vehicle base 6705b to at the designated shipping location (e.g., whether the delivery address 6810 or the courier transport vehicle 6805 if the primary vehicle 6700a picked up the payload from address 6810).

In further embodiments, such a system with the primary vehicle 6700a and secondary vehicle 6700b may involve updating a server, such as a backed server (e.g., dispatch server 6701) about the logistics operation as it happens. For example, in such a system embodiment, the mobile master node 6725a on the primary vehicle 6700a may, when executing the autonomous navigation program module from memory 6775a, be further operative to transmit an updated location of mobile master node 6725a to a server (such as server 6701) over the primary wireless communication interface 6780a as mobile master node 6725a approaches the second mobile master node 6725b. In this embodiment, the second mobile master node 6725b, when executing the autonomous navigation program module from memory 6775b, may be further operative to transmit an updated location of the second mobile master node 6725b to the server 6701 over the secondary wireless communication interface 6780b as the second mobile master node 6725b approaches the mobile master node 6725a on the primary vehicle 6700a. In more detail, the locations involved in such updates may come from location circuitry (e.g., GPS circuitry, similar to location positioning circuitry 475) disposed on the respective primary vehicle 6700a or secondary vehicle 6700b and coupled to the respective master node controllers on such vehicles. A further example may be that the primary vehicle 6700a and/or secondary vehicle 6700b further includes an inertial navigation unit as such location circuitry, which relies less on receiving external signals for positioning and may be used in combination with other location circuitry.

Figure 69A:
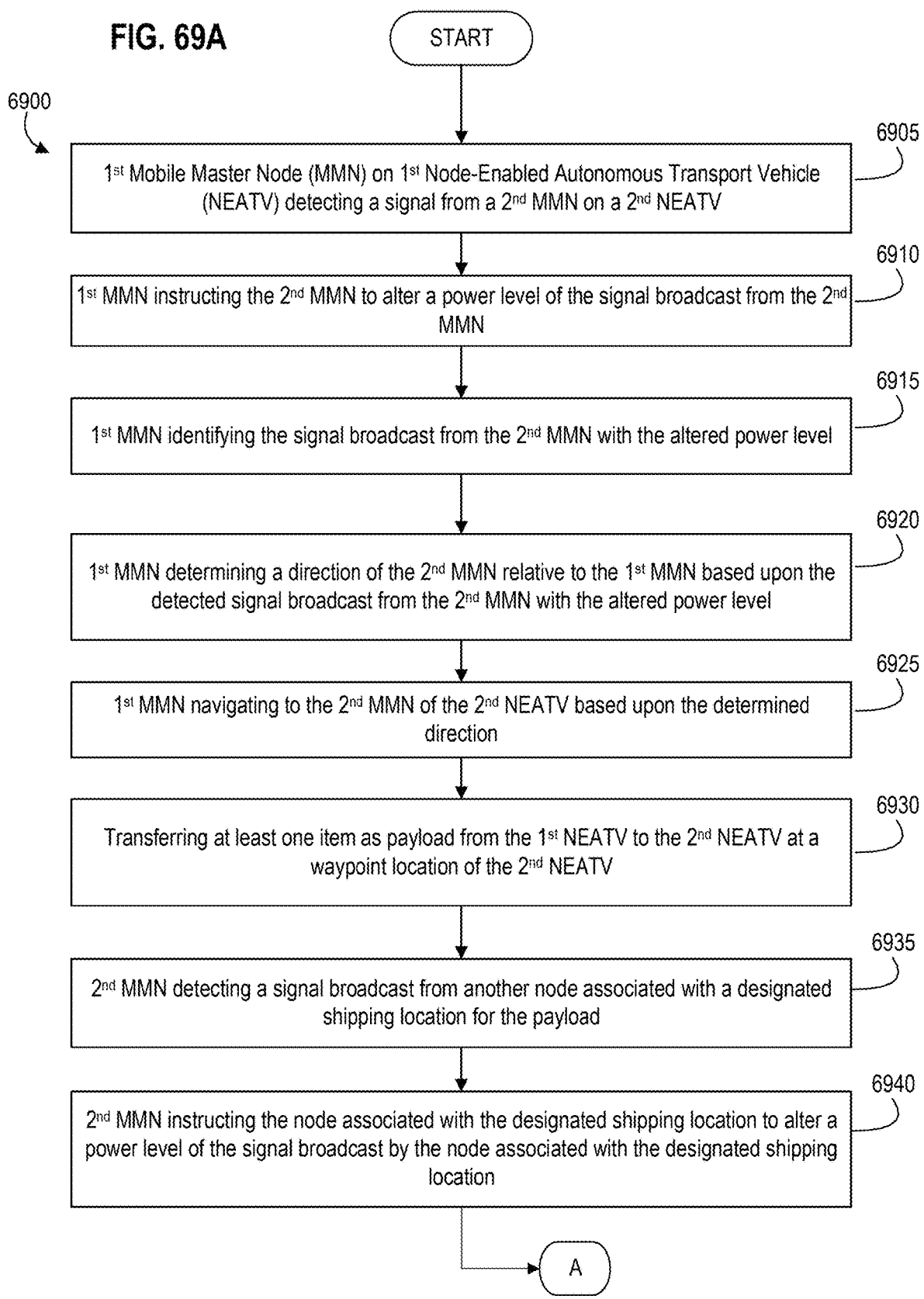
FIGS. 69A-69B are flow diagrams of an embodiment of an exemplary method for navigating to a designated shipping location as part of a multi-leg logistics operation using multiple nodes in a wireless node network, a server in the network, and multiple node-enabled autonomous transport vehicles in the network in accordance with an embodiment of the invention.
Figure 69B:
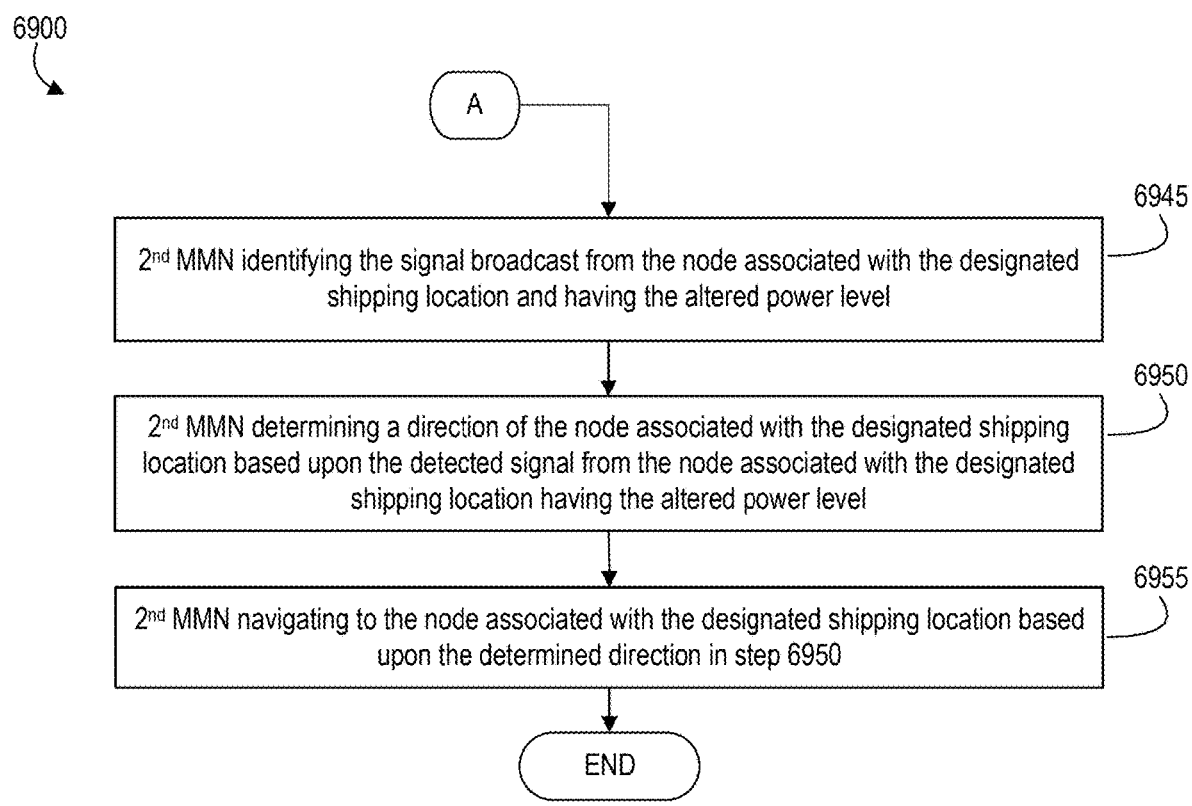

In light of the system described above in FIGS. 67 and 68A-68E, a further embodiment may include an exemplary method for navigating to a designated shipping location (e.g., pickup/delivery address 6810) as part of a multi-leg logistics operation using different node-enabled autonomous transport vehicles. FIGS. 69A-69B are, collectively, a flow diagram of an embodiment of such an exemplary method 6900 for navigating to a designated shipping location as part of a multi-leg logistics operation using multiple nodes in a wireless node network, a server in the network, and multiple node-enabled autonomous transport vehicles in the network in accordance with an embodiment of the invention.

Referring now to FIG. 69A, method 6900 begins at step 6905 with a first mobile master node of the nodes detecting a signal broadcast from a second mobile master node of the nodes, where the first mobile master node (e.g., mobile master node 6725a) is associated with a first of the node-enabled autonomous transport vehicles (e.g., vehicle 6700a) and the second mobile master node (e.g., mobile master node 6725b) is associated with a second of the node-enabled autonomous transport vehicles (e.g., vehicle 6700b).

At step 6910, method 6900 proceeds with the first mobile master node instructing the second mobile master node to alter a power level of the signal broadcast from the second mobile master node, and then identifying the signal broadcast from the second mobile master node with the altered power level at step 6915.

At step 6920, method 6900 proceeds with the first mobile master node determining a direction of the second mobile master node relative to the first mobile master node based upon the detected signal from the second mobile master node with the altered power level.

At step 6925, method 6900 proceeds with the first mobile master node navigating to the second mobile master node associated with the second vehicle (e.g., vehicle 6700*b*) based upon the determined direction of the second mobile master node relative to the first mobile master node. In more detail, step 6925 may involve navigating, by the first mobile master node, to the second mobile master node as the power level of the signal broadcast from the second mobile master node is incrementally decreased over time as the first mobile master node approaches the second mobile master node. In a further example, the first mobile master node may be associated with a control system of the first autonomous transport vehicles (e.g., a control system that provides steering and propulsion control signals to respective steering and propulsion systems on the first vehicle). As such, the step of navigating by the first mobile master node may have the first mobile master node providing the determined direction of the second mobile master node relative to the first mobile master node to an input of the control system of the first of the autonomous transport vehicles. Additionally, an example may have the first mobile master node causing the first autonomous transport vehicles to stop moving when a current location of the first mobile master node is within a predetermined range of the second mobile master node.

In a further embodiment, step 6925 may implement navigating by the first mobile master node using context data. For example, implementing step 6925 with the first mobile master node may involve, in such a further embodiment, accessing first context data that relates to an operating environment of the second mobile master node; and the navigating to the second mobile master node with reference to the accessed first context data as the power level of the signal broadcast from the second mobile master node is incrementally decreased over time and as the first mobile master node approaches the second mobile master node. In even more detail, such context data relates to the anticipated operating environment for the second mobile master node. By relying on using this type of context data about the operating environment that is known or anticipated to be faced by the second mobile master node (and the node-enabled autonomous transport vehicle it operates on), the first mobile master node may better navigate towards its destination.

At step 6930, method 6900 proceeds with transferring at least one item (which may include a payload container) as payload from the first node-enabled autonomous transport vehicle to the second node-enabled autonomous transport vehicle at a waypoint location of the second node-enabled autonomous transport vehicle. For example, as shown in FIGS. 68B-68B, exemplary items 6750*a*, 6750*b* in payload container 6755 are shown transferred from node-enabled autonomous transport vehicle 6700*a* to the second node-enabled autonomous transport vehicle 6700*b* at a waypoint location of the second node-enabled autonomous transport vehicle 6700*b*.

In more detail, an embodiment of method 6900 may implement step 6930 with the first master node (a) detecting the second node-enabled autonomous transport vehicle by a proximity sensor (e.g., sensor 6740*a*) on the first node-enabled autonomous transport vehicle as the first vehicle navigates towards and approaches the second vehicle; (b) causing, by the first mobile master node, a transfer alignment configuration of the first vehicle and the second vehicle as the first mobile master node controls movement of the first vehicle; and (c) initiating, by the first mobile master node, transfer of the item (or payload container with one or more items) from the first vehicles to the second vehicle while the first and second vehicles are in the transfer alignment configuration. In this example, the step of causing the transfer alignment configuration of the first node-enabled autonomous transport vehicle and the second node-enabled autonomous transport vehicle may have the first mobile master node aligning a first docking interface (e.g., docking interface 6745*a*) disposed on the first node-enabled autonomous transport vehicle with a second docking interface (e.g., docking interface 6745*b*) disposed on the second node-enabled autonomous transport vehicle as the first mobile master node controls movement of the first node-enabled autonomous transport vehicle. In even more detail, causing such a transfer alignment configuration may also have the first mobile master node securing the first docking interface to the second docking interface (e.g., with actuated latches as such docking interfaces) to create the transfer alignment orientation.

Additionally, the initiating step in this further embodiment of step 6930 may, for example, be implemented by having the first mobile master node deploy an object manipulation system on the first node-enabled autonomous transport vehicle (e.g., articulating arms 6765*a*, 6760*a*, or other actuated devices, such as movable belt surfaces, sweeping arms, or grabbing arms deployed on the CSS or APM parts of vehicle 6700*a*) to initiate control of the item being transferred while on the first node-enabled autonomous transport vehicle. Then, the first mobile master node may move the item from the first node-enabled autonomous transport vehicle to the second node-enabled autonomous transport vehicle using such an object manipulation system on the first node-enabled autonomous transport vehicle (e.g., via sending control signals to the object manipulation system, which contacts and moves the item/container as shown in FIG. 68B).

In still another embodiment of step 6930, the step of transferring may be implemented with (a) detecting the first of the node-enabled autonomous transport vehicles by a proximity sensor on the second node-enabled autonomous transport vehicle (e.g., via sensor 6740*b*), as the first node-enabled autonomous transport vehicle navigates towards and approaches the second node-enabled autonomous transport vehicle; (b) having the second mobile master node causing a transfer alignment configuration of the first node-enabled autonomous transport vehicle and the second node-enabled autonomous transport vehicle as the second mobile master node controls movement of the second node-enabled autonomous transport vehicle relative to the first node-enabled autonomous transport vehicle; and then (c) initiating, by the second mobile master node, transfer of the item to the second node-enabled autonomous transport vehicle while the first and second node-enabled autonomous transport vehicle are in the transfer alignment configuration. In more detail, the step of causing the transfer alignment configuration of the first and second node-enabled autonomous transport vehicle may have the second mobile master node aligning a second docking interface (e.g., docking interface 6745*b*) disposed on the second of the node-enabled autonomous transport vehicles with a first docking interface (e.g., docking interface 6745*a*) disposed on the first node-enabled autonomous transport vehicle as the second mobile master node controls movement of the second node-enabled autonomous transport vehicle relative to the first node-enabled autonomous transport vehicle. This may also involve securing the second docking interface to the first docking interface (e.g., with one or more actuated interlocking latches) to create the transfer alignment orientation. Additionally, in this embodiment of step 6930, the initiating step may be implemented with the second mobile master node deploying an object manipulation system on the second node-enabled autonomous transport vehicle (e.g., articulating arms 6765b, 6760b, or other actuated devices, such as movable belt surfaces, sweeping arms, or grabbing arms deployed on the CSS or APM parts of vehicle 6700b) to initiate control of the item (and/or payload container) while on the first node-enabled autonomous transport vehicle; and having the second mobile master node move the at least one item from the first of the node-enabled autonomous transport vehicles to the second of the node-enabled autonomous transport vehicles using the object manipulation system on the second of the node-enabled autonomous transport vehicles (e.g., via sending control signals to the object manipulation system, which contacts and moves the item/container as shown in FIG. 68C).

In still another embodiment of step 6930, such transferring may be implemented in a more coordinated manner with both autonomous vehicles using proximity sensing and moving to transfer positions. In more detail, such an embodiment of step 6930 may begin with the first mobile master node navigating to the waypoint location of the second node-enabled autonomous transport vehicle; detecting the first node-enabled autonomous transport vehicle by a proximity sensor on the second node-enabled autonomous transport vehicle (e.g., sensor 6740b) as the first node-enabled autonomous transport vehicle navigates towards and approaches the second vehicle. Then, this further embodiment of step 6930 continues by detecting the second node-enabled autonomous transport vehicle by a proximity sensor on the first node-enabled autonomous transport vehicle (e.g., sensor 6740a), as the first node-enabled autonomous transport vehicle navigates towards and approaches the second vehicle. Thereafter, in this further embodiment of step 6930 has the first mobile master node controlling a position of the first node-enabled autonomous transport vehicle by moving the first node-enabled autonomous transport vehicle into a first transfer position; has the second mobile master node controlling a position of the second node-enabled autonomous transport vehicle by moving the second node-enabled autonomous transport vehicle into a second transfer position; refining the relative alignment of the first transfer position and the second transfer position to cause the first and second vehicles to be in a transfer alignment orientation; and moving the item from the first vehicle to the second vehicle using object manipulation systems deployed on respective ones of the first and second vehicles.

At step 6935, method 6900 proceeds with the second mobile master node detecting a signal broadcast from a node associated with the designated shipping location for the payload (e.g., facility node 6815 at the pickup/delivery address 6810). At step 6940, method 6900 has the second mobile master node instructing this other node to alter a power level of the signal broadcast from the another node. Step 6940 continues through transition A to step 6945 on FIG. 69B, where method 6900 proceeds with the second mobile master node identifying the signal broadcast from the other node with the altered power level.

At step 6950, method 6900 proceeds with the second mobile master node determining a direction of the other node relative to the second mobile master node based upon the detected signal from the other node with the altered power level.

At step 6955, method 6900 has the second mobile master node navigating to the other node at step 6955 based upon the determined direction of the other node relative to the second mobile master node. In one example, such a step of navigating by the second mobile master node may involve accessing second context data that relates to an operating environment of the other node; and navigating, by the second mobile master node, to the other node with reference to the accessed second context data as the power level of the signal broadcast from the other node is incrementally decreased over time and as the second mobile master node approaches the other node. In another example, step 6955 may have the second mobile master node navigating to the other node as the power level of the signal broadcast from the other node is incrementally decreased over time and as the second mobile master node approaches that node. Further still, an example of step 6955 may implement such navigating with the second mobile master node providing the determined direction of the another node relative to the second mobile master node to an input of the control system of the second of the autonomous transport vehicles. Still in another example as part of navigating in step 6955, the second mobile master node may cause the second of the autonomous transport vehicles to stop moving when a current location of the second mobile master node is within a predetermined range of the another node.

In a further embodiment of method 6900, the method may involve offloading the second vehicle at the delivery location. For example, an embodiment of method 6900 may further have the second mobile master node initiating an offload operation of the item as the payload (and/or the payload container that maintains one or more items) at the designated shipping location (e.g., courier transport vehicle 6805 or delivery address 6810 for the item) using an object manipulating system on the second node-enabled autonomous transport vehicle.

Likewise, a further embodiment of method 6900 may involve loading the first vehicle at a pickup location. For example, an embodiment of method 6900 may further have the first mobile master node initiating a loading operation of the item (and/or payload container that maintains one or more items) as the payload at a pickup location (e.g., courier transport vehicle 6805 or delivery address 6810 for the item) using an object manipulating system on the first node-enabled autonomous transport vehicle.

In still another further embodiment of method 6900, the method may have the mobile master nodes on the respective vehicles updating a server with locations of the vehicles. For example, an embodiment of method 6900 may further include the steps of transmitting, by the first mobile master node to the server (e.g., server 6701), an updated location of the first mobile master node as the first mobile master node approaches the second mobile master node; and transmitting, by the second mobile master node to the server, an updated location of the second mobile master node as the second mobile master node approaches the another node. As noted above, the locations involved in such updates may come from location circuitry (e.g., GPS circuitry, similar to location positioning circuitry 475) disposed on the respective first and second vehicle and coupled to the respective master node controllers on such vehicles. A further example may be that one or both of the first and second vehicles may include an inertial navigation unit as such location circuitry, which relies less on receiving external signals for positioning and may be used in combination with other location circuitry.

Method 6900 is described as using node-enabled autonomous transport vehicles, but in a more detailed embodiment, such vehicles may be implemented with an exemplary MALVT bot apparatus assembly as discussed above relative to FIG. 67. For example, the first of the node-enabled autonomous transport vehicles in method 6900 may be a modular autonomous bot apparatus assembly having a modular mobility base propelling the modular autonomous bot apparatus assembly, a modular auxiliary power module providing power for the modular autonomous bot apparatus assembly, a modular cargo storage system configured to at least temporarily maintain the at least one item within the modular autonomous bot apparatus assembly, and a modular mobile autonomy control module as the first mobile master node that autonomously controls operation of the modular autonomous bot apparatus assembly. In like manner, an embodiment of method 6900 may also have the second of the node-enabled autonomous transport vehicles being a modular autonomous bot apparatus assembly having a modular mobility base propelling the modular autonomous bot apparatus assembly, a modular auxiliary power module providing power for the modular autonomous bot apparatus assembly, a modular cargo storage system configured to at least receive and temporarily maintain the at least one item within the modular autonomous bot apparatus assembly, and a modular mobile autonomy control module as the second mobile master node that autonomously controls operation of the modular autonomous bot apparatus assembly.

In still another embodiment of method 6900, one of the vehicles interacts with the other vehicle and takes over during the alignment, docking and transferring aspects of method 6900. For example, an embodiment of step 6930 in method 6900 may be implemented by (a) detecting the second node-enabled autonomous transport vehicle by a proximity sensor on the first node-enabled autonomous transport vehicle (e.g., sensor 6740a) as the first node-enabled autonomous transport vehicle navigates towards and approaches the second node-enabled autonomous transport vehicle; (b) causing, by the first mobile master node, a transfer alignment configuration of the first and second vehicles as the first mobile master node controls movement of the first vehicle and remotely controls movement of the second vehicle through interaction with the second mobile master node; and (c) initiating, by the first mobile master node, transfer of the item (and/or payload container) from the first vehicle to the second vehicle while the first and second vehicles are in the transfer alignment configuration. In this example, step of causing the transfer alignment configuration of the first and second vehicles may have the first mobile master node aligning a first docking interface (e.g., docking interface 6745a) disposed on the first vehicle with a second docking interface (e.g., docking interface 6745b) disposed on the second vehicle as the first mobile master node controls movement of the first vehicle and remotely controls movement of the second vehicle through wireless interaction with the second mobile master node. This may also involve securing the first docking interface to the second docking interface to create the transfer alignment orientation (e.g., via actuating one or more latches as one or more of these docking interfaces). Transferring, as initiated in this further embodiment, may have the first mobile master node deploying an object manipulation system on the first vehicle to initiate control of the item (and/or payload container) while on the first node-enabled autonomous transport vehicle, and having the first mobile master node move the at least one item from the first node-enabled autonomous transport vehicle to the second node-enabled autonomous transport vehicle using the object manipulation system on the first node-enabled autonomous transport vehicle.

A similar example may be implemented for step 6930 with the second mobile master node controlling movement of the second vehicle and remotely controlling movement of the first vehicle as part of aligning with the respective docking interfaces and transferring as noted above.

Those skilled in the art will appreciate that such a method embodiment as disclosed and explained above may be implemented with multiple node-enabled autonomous transport vehicles (e.g., multiple exemplary MALVT bot apparatus assemblies) or a system with such multiple AVs and implemented with the above-described suite of sensors, and different processor modules/controller modules, and the different software modules running on the different processor/controller modules as described relative to node-enabled autonomous transport vehicles using TRON type nodes (e.g., exemplary mobile master nodes) or as described above relative to an exemplary MALVT bot apparatus assembly. Such software modules may be stored on non-transitory computer-readable medium in each of the processor/controller modules. Thus, when executing such software modules, the collective processor/controller modules of the enhanced system or distinct AVs may be operative to perform the operations or steps from the exemplary method 6900 disclosed above, including variations of that method.

In another exemplary embodiment, one of the node-enabled AVs may be configured and able to selectively get another type of node-enabled AV to help with the multi-leg logistics operation. In this manner, the embodiment highlights selective use of multiple node-enabled AV for a multi-leg logistics operation, and may enhance the operation due to the selective inclusion of an appropriately configured second node-enabled AV. In a general example, a main node-enabled AV may dynamically select one of multiple types of shorter range second node-enabled AVs to use for a given logistics operation (pickup or delivery) based on shipping information and/or context data (e.g., weight of the object or objects, need for temperature control, requirement for specialized mechanical manipulation, the desire to interact with a home automation system at the delivery/pickup location, regulatory information on the object and its use, compliance information on the object and its use). So this may have multiple short range second node-enabled AVs at the disposal of the main node-enabled AV—e.g., locally traveling with the main node-enabled AV or dispatched by the main AV from a courier vehicle.

FIG. 70 is a flow diagram of an embodiment of an exemplary method 7000 for navigating to a designated shipping location as part of a multi-leg logistics operation using multiple nodes in a wireless node network, a server in the network, a first node-enabled autonomous transport vehicle in the network, and a selected one of a group of other node-enabled autonomous transport vehicles in accordance with an embodiment of the invention. Referring now to FIG. 70, method 7000 begins at step 7005 with a first mobile master node of the nodes receiving logistics information related to an item being shipped on a primary one of the node-enabled autonomous transport vehicles. Such a first mobile master node is associated with the primary one of the node-enabled autonomous transport vehicles (e.g., mobile master node 6725a on primary vehicle 6700a) and where the primary vehicle is responsible for a first leg of the multi-leg logistics operation. For example, such dispatching logistics information received in step 7005 may be at least shipping information on where the item is being shipped and context information about the item being shipped. Such context information may, for example, include the weight and size information on the item being shipped, environmental condition requirement information on the item being shipped, manipulation requirement information on the item being shipped (e.g., fragile nature of the item, where the item may be engaged for actuated object manipulation, and the like), delivery address automation information related to the item being shipped, and/or regulatory/compliance information related to the pickup, transport, and/or delivery of the item.

At step 7010, method 7000 has the first mobile master node accessing the logistics information from a memory on the first mobile master node (e.g., memory 6775a) where the logistics information at least generally indicates characteristic parameters about the item being shipped.

At step 7015, method 7000 has the first mobile master node selecting a secondary one of the node-enabled autonomous transport vehicles to be deployed for a second leg of the multi-leg logistics operation based upon the logistics information about the item being shipped. For example, some of the potential other node-enabled autonomous transport vehicles may not be equipped to transport the particular item involved with the logistics operation due to weight, size, or other characteristic parameters on the item being shipped. Additionally, some of the potential other node-enabled autonomous transport vehicles may not be allowed to participate in the second leg of the logistics operation for regulatory or contractual reasons (e.g., a particular customer has not leased the use of certain types of the node-enabled autonomous transport vehicles).

At step 7020, method 7000 continues with the first mobile master node detecting a signal broadcast from a second mobile master node of the nodes, where the second mobile master node is associated with the selected secondary one of the node-enabled autonomous transport vehicles.

At step 7025, method 7000 continues with the first mobile master node navigating to the selected secondary node-enabled autonomous transport vehicle in a direction determined by the first mobile master node to be towards the second mobile master node relative to the first mobile master node based upon the detected signal broadcast from the second mobile master node.

At step 7030, method 7000 continues with autonomously transferring the item from the primary node-enabled autonomous transport vehicle to the selected secondary node-enabled autonomous transport vehicle at a waypoint location of the selected secondary node-enabled autonomous transport vehicle. This transferring step 7030 may involve, in some embodiments, transferring a payload container (and one or more items in it) as payload the primary node-enabled autonomous transport vehicle to the selected secondary node-enabled autonomous transport vehicle at the waypoint location.

At step 7035, method 7000 has the second mobile master node detecting a signal broadcast from another of the nodes, such as a node associated with the designated shipping location (e.g., facility node 6810). Then, at step 7040, method 7000 has the second mobile master node navigating to the designated shipping location in a direction determined by the second mobile master node to be towards the other node relative to the second mobile master node based upon the detected signal broadcast from the other node.

A further embodiment of method 7000 may involve offloading the item/payload container by the selected secondary vehicle at the designated shipping location. For example, such a further embodiment of method 7000 may have the second mobile master node initiating an offload operation of the item being shipped at the designated shipping location (e.g., the delivery address for the item) using an object manipulating system on the selected secondary one of the node-enabled autonomous transport vehicles that is operative to move the item being shipped off of the selected secondary one of the node-enabled autonomous transport vehicles.

In like manner, a further embodiment of method 7000 may involve loading the item into the primary vehicle. For example, such a further embodiment of method 7000 may include the step of receiving, by the primary one of the node-enabled autonomous transport vehicles, the item being shipped (which may be received, transported, and offloaded as maintained in a removable payload container, such as container 6755 shown in FIG. 67). This further step of receiving the item may, in some embodiments, have the first mobile master node initiating a load operation of the item being shipped using an object manipulating system on the primary node-enabled autonomous transport vehicle that is operative to place the item being shipped onto and/or within the primary node-enabled autonomous transport vehicle.

In still a further embodiment of method 7000, step 7025 may be implemented in more detail with the first mobile master node (a) instructing the second mobile master node to alter a power level of the signal broadcast from the second mobile master node; (b) identifying the signal broadcast from the second mobile master node with the altered power level; (c) determining the direction towards the second mobile master node relative to the first mobile master node based upon the detected signal from the second mobile master node with the altered power level; and (d) navigating to the selected secondary node-enabled autonomous transport vehicle in the determined direction towards the second mobile master node relative to the first mobile master node.

In like manner, step 7040 may be implemented in more detail with the second mobile master node navigating to the designated shipping location by having the second mobile master node (a) instructing the other node to alter a power level of the signal broadcast from the other node; (b) identifying the signal broadcast from the other node with the altered power level; (c) determining the direction towards the other node relative to the second mobile master node based upon the detected signal from the other node with the altered power level; and (d) navigating to the designated shipping location in the determined direction towards the other node relative to the second mobile master node.

A more detailed embodiment of method 7000 may implement autonomous transferring in step 7030 by (a) detecting the selected secondary node-enabled autonomous transport vehicle by a proximity sensor on the primary node-enabled autonomous transport vehicle, as the primary node-enabled autonomous transport vehicle navigates towards and approaches the selected secondary node-enabled autonomous transport vehicle; (b) causing, by the first mobile master node, a transfer alignment configuration of the primary and selected secondary vehicles as the first mobile master node controls movement of the primary node-enabled autonomous transport vehicles; and (c) initiating, by the first mobile master node, transfer of the item being shipped from the primary node-enabled autonomous transport vehicle to the selected secondary node-enabled autonomous transport vehicle while the primary node-enabled autonomous transport vehicle and the selected secondary node-enabled autonomous transport vehicle are in the transfer alignment configuration. In this example, the step of causing the transfer alignment configuration of the primary and selected secondary vehicles may have the first mobile master node aligning a first docking interface disposed on the primary vehicle with a second docking interface disposed on the selected secondary vehicle as the first mobile master node controls movement of the primary node-enabled autonomous transport vehicle. In this same example, the initiating step may be implemented with the first mobile master node deploying an object manipulation system on the primary node-enabled autonomous transport vehicles to initiate control of the item being shipped while on the primary node-enabled autonomous transport vehicle; and moving the item being shipped from the primary vehicle to the selected secondary vehicle using the object manipulation system on the primary node-enabled autonomous transport vehicle.

In even more detail, the step 7030 of transferring may be implemented by (a) detecting the primary node-enabled autonomous transport vehicle by a proximity sensor on the selected secondary node-enabled autonomous transport vehicle as the primary vehicle navigates towards and approaches the selected secondary node-enabled autonomous transport vehicle; (b) causing, by the second mobile master node, a transfer alignment configuration of the primary vehicle and the selected secondary vehicle as the second mobile master node controls movement of the selected secondary node-enabled autonomous transport vehicle relative to the primary node-enabled autonomous transport vehicle; and (c) initiating, by the second mobile master node, transfer of the item being shipped from the primary node-enabled autonomous transport vehicles to the selected secondary node-enabled autonomous transport vehicle while the primary node-enabled autonomous transport vehicle and the selected secondary node-enabled autonomous transport vehicle are in the transfer alignment configuration. Here, the step of causing the transfer alignment configuration of the primary vehicle and the selected secondary vehicle may have the first mobile master node aligning a first docking interface disposed on the primary node-enabled autonomous transport vehicle with a second docking interface disposed on the selected secondary node-enabled autonomous transport vehicle as the first mobile master node controls movement of the primary node-enabled autonomous transport vehicle. Additionally, the initiating step in this example may be implemented with the second mobile master node deploying an object manipulation system on the selected secondary node-enabled autonomous transport vehicle to initiate control of the item being shipped while on the primary node-enabled autonomous transport vehicles; and moving the item being shipped from the primary one of the node-enabled autonomous transport vehicles to the selected secondary one of the node-enabled autonomous transport vehicles using the object manipulation system on the selected secondary one of the node-enabled autonomous transport vehicles.

In still more detail, an embodiment of step 7030 of method 7000 may implement the step of transferring the item (and/or the payload container having the item) by (a) navigating, by the first mobile master node, the primary vehicle to the waypoint location of the selected secondary vehicle; (b) detecting the selected secondary vehicle by a proximity sensor on the primary vehicle as the primary vehicle navigates towards and approaches the selected secondary node-enabled autonomous transport vehicle; (c) detecting the primary vehicle by a proximity sensor on the selected secondary vehicle as the primary vehicle navigates towards and approaches the selected secondary vehicle; (d) controlling, by the first mobile master node, a position of the primary vehicle by moving the primary vehicle into a first transfer position; (e) controlling, by the second mobile master node, a position of the selected secondary vehicle by moving the selected secondary vehicle into a second transfer position; (f) refining the relative alignment of the first transfer position and the second transfer position to cause the primary and the selected secondary node-enabled autonomous transport vehicle to be in a transfer alignment orientation; and (g) moving the item being shipped from the primary vehicle to the selected secondary vehicle using a first object manipulation system on the primary vehicle and a second object manipulation system on the selected secondary node-enabled autonomous transport vehicle. In this detailed example, the step of refining the relative alignment of the first transfer position and the second transfer position to cause the primary one of the node-enabled autonomous transport vehicles and the selected secondary one of the node-enabled autonomous transport vehicles to be in the transfer alignment orientation may be accomplished, for example, by causing the first mobile master node to align a first docking interface disposed on the primary node-enabled autonomous transport vehicle to a second docking interface disposed on the selected secondary node-enabled autonomous transport vehicle. In another example, this may be accomplished by causing the second mobile master node to align a second docking interface disposed on the selected secondary vehicle to a first docking interface disposed on the primary node-enabled autonomous transport vehicle.

Furthermore, in this detailed example, the step of controlling the position of the primary node-enabled autonomous transport vehicle by moving the primary node-enabled autonomous transport vehicle into the first transfer position may be accomplished with the first mobile master node controlling the position of the primary node-enabled autonomous transport vehicle by moving a first docking interface disposed on the primary vehicle proximate a second docking interface disposed on the selected secondary vehicle as the first transfer position. And the step of controlling the position of the selected secondary vehicle by moving the selected secondary node-enabled autonomous transport vehicle into the second transfer position may be accomplished with the second mobile master node controlling the position of the selected secondary node-enabled autonomous transport vehicle by moving the second docking interface proximate the first docking interface as the second transfer position. As such, refining the relative alignment of the first transfer position and the second transfer position to cause the primary vehicle and the selected secondary vehicle to be in the transfer alignment orientation may be accomplished by securing a first docking interface disposed on the primary vehicle to a second docking interface disposed on the selected secondary vehicle to create the transfer alignment orientation.

Another embodiment of method 7000 may have step 7025 implemented with the first mobile master node navigating to the second mobile master node as the power level of the signal broadcast from the second mobile master node is incrementally decreased over time and as the first mobile master node approaches the second mobile master node; and have step 7040 implemented with the second mobile master node navigating to the other node as the power level of the signal broadcast from the other node is incrementally decreased over time and as the second mobile master node approaches the other node.

Further details with an embodiment of method 7000 may more specifically have the mobile master nodes of the respective node-enabled autonomous transport vehicles associated with, communicating with, or implementing a control system that controls the propulsion and steering related to the respective vehicle. As such, the steps involving navigating by respective mobile master nodes may have those mobile master nodes providing determined node directional information to the control system (or using that information itself) as an input to the control system as part of navigating. Furthermore, such an embodiment of method 7000 may have first mobile master node causing the primary autonomous transport vehicles to stop moving when a current location of the first mobile master node is within a predetermined range of the second mobile master node; and in like manner, have the second mobile master node causing the selected secondary one of the autonomous transport vehicles to stop moving when a current location of the second mobile master node is within a predetermined range of the another node.

Similar to that of method 6900, an embodiment of method 7000 may implement the respective node-enabled autonomous transport vehicles using different exemplary embodiments of an MALVT bot apparatus assembly (e.g., assembly 1700). For example, an embodiment of method 7000 may have the primary one of the node-enabled autonomous transport vehicles being a modular autonomous bot apparatus assembly having a modular mobility base propelling the modular autonomous bot apparatus assembly, a modular auxiliary power module providing power for the modular autonomous bot apparatus assembly, a modular cargo storage system configured to at least temporarily maintain the at least one item within the modular autonomous bot apparatus assembly, and a modular mobile autonomy control module as the first mobile master node that autonomously controls operation of the modular autonomous bot apparatus assembly. Likewise, an embodiment of method 7000 may have the selected secondary one of the node-enabled autonomous transport vehicles being a modular autonomous bot apparatus assembly having a modular mobility base propelling the modular autonomous bot apparatus assembly, a modular auxiliary power module providing power for the modular autonomous bot apparatus assembly, a modular cargo storage system configured to at least receive and temporarily maintain the at least one item within the modular autonomous bot apparatus assembly, and a modular mobile autonomy control module as the second mobile master node that autonomously controls operation of the modular autonomous bot apparatus assembly.

In such an embodiment of method 7000 using embodiments of exemplary MALVT bot apparatus assembly as the node-enabled autonomous transport vehicles, the step of selecting the secondary one of the node-enabled autonomous transport vehicles to be deployed for the second leg of the multi-leg logistics operation may be based upon compatibility of at least the modular cargo storage system and the item being shipped according to the logistics information; based upon compatibility of at least the modular mobility base and the logistics information; based upon compatibility of at least the modular auxiliary power module and the logistics information; based upon compatibility of at least the modular mobile autonomy control module and the logistics information; and/or based upon compatibility of the logistics information as compared with the combination of the modular mobility base, the modular auxiliary power module, the modular cargo storage system, and the modular mobile autonomy control module as configured in the modular autonomous bot apparatus assembly.

Those skilled in the art will appreciate that such a method embodiment as disclosed and explained above involving selective involvement of the second node-enabled autonomous transport vehicle may be implemented with multiple node-enabled autonomous transport vehicles (e.g., multiple exemplary MALVT bot apparatus assemblies) or a system with such multiple AVs and implemented with the above-described suite of sensors, and different processor modules/controller modules, and the different software modules running on the different processor/controller modules as described relative to node-enabled autonomous transport vehicles as generally described above with mobile master nodes as explained herein or as described above relative to an exemplary MALVT bot apparatus assembly. Such software modules may be stored on non-transitory computer-readable medium in each of the processor/controller modules. Thus, when executing such software modules, the collective processor/controller modules of the enhanced system or distinct AVs may be operative to perform the operations or steps from the exemplary method 7000 disclosed above, including variations of that method.

In still further embodiments, one of the node-enabled autonomous transport vehicles may cooperate and coordinate with the other node-enabled autonomous transport vehicle as part of a multi-leg logistics operation and have one of the vehicles being in a "master" role where the control of the second autonomous transport vehicle is, at least in part, transferred to the master during portions of the logistics operation. FIG. 71 is a flow diagram of an embodiment of another exemplary method 7100 for navigating to a designated shipping location as part of a multi-leg logistics operation using multiple nodes in a wireless node network, a server in the network, and multiple node-enabled autonomous transport vehicles in the network where one of the node-enabled autonomous transport vehicles operates as master to control at least docking and transferring operations as part of the multi-leg logistics operation in accordance with an embodiment of the invention. Referring now to FIG. 71, exemplary method 7100 begins at step 7150 has a first mobile master node of the nodes in the network is detecting a signal broadcast from a second mobile master node of the nodes in the network. Here, the first mobile master node is associated with and disposed on a first of the node-enabled autonomous transport vehicles (e.g., node-enabled autonomous transport vehicle 6700*a*) and the second mobile master node is associated with and disposed on a second of the node-enabled autonomous transport vehicles (e.g., node-enabled autonomous transport vehicle 6700*b*).

At step 7110, method 7100 proceeds with the first mobile master node instructing the second mobile master node to alter a power level of the signal broadcast from the second mobile master node. At step 7115, method 7100 has the first mobile master node identifying the signal broadcast from the second mobile master node with the altered power level. At step 7120, method 7100 has the first mobile master node determining a direction of the second mobile master node relative to the first mobile master node based upon the detected signal from the second mobile master node with the altered power level. Then, at step 7125, method 7100 has the first mobile master node navigating to the second mobile master node associated with the second node-enabled autonomous transport vehicle based upon the determined direction of the second mobile master node relative to the first mobile master node.

At step 7130, method 7100 proceeds with the first mobile master node causing a first docking interface on the first node-enabled autonomous transport vehicle (e.g., docking interface 6745*a*) to securely engage a second docking interface on the second node-enabled autonomous transport vehicle (e.g., docking interface 6745*b*) at a waypoint location of the second of the node-enable autonomous transport vehicles as the first mobile master node controls movement of the first vehicle and remotely controls movement of the second node-enabled autonomous transport vehicle through interaction with the second mobile master node.

At step 7135, method 7100 proceeds with the first mobile master node initiating transfer of the item (e.g., the item itself, such as item 6570a, or a payload container 6744 that maintains the item) from the first node-enabled autonomous transport vehicle to the second node-enabled autonomous transport vehicle while the first node-enabled autonomous transport vehicle and the second node-enabled autonomous transport vehicle are securely engaged (e.g., via one or more actuated clamps, interlocking latches, and the like).

At step 7140, method 7100 proceeds has the first mobile master node causing the first docking interface to disengage from the second docking interface after the at least one item is no longer present on the first of the node-enabled autonomous transport vehicles based upon monitoring by one or more payload monitoring sensors on the first of the node-enabled autonomous transport vehicles. The engagement and disengagement of such docking interfaces may be accomplished, for example, through master node controlled actuators disposed on the respective first and second node-enabled autonomous transport vehicle. In more detail, an embodiment of method 7100 may have the first docking interface and the second docking interface implemented as at least one mated set of latches that has at least one from the mated set of latches being disposed on the first node-enabled autonomous transport vehicle and a matching other from the mated set of latches being disposed on the second node-enabled autonomous transport vehicle. These mated set of latches may be an actuated set of latches activated by the first mobile master node to securely engage the first docking interface to the second docking interface. In another example, the matching other from the mated set of latches on the second node-enabled autonomous transport vehicle may be an actuated set of latches activated by the second mobile master node to securely engage the first docking interface to the second docking interface.

Those skilled in the art will appreciate that such a method embodiment as disclosed and explained above more specifically involving docking of the second node-enabled autonomous transport vehicle and the first node-enabled autonomous transport vehicle may be implemented with multiple node-enabled autonomous transport vehicles (e.g., multiple exemplary MALVT bot apparatus assemblies) or a system with such multiple AVs and implemented with the above-described suite of sensors, and different processor modules/controller modules, and the different software modules running on the different processor/controller modules as described relative to node-enabled autonomous transport vehicles as generally described using mobile master nodes or as described above relative to an exemplary MALVT bot apparatus assembly. Such software modules may be stored on non-transitory computer-readable medium in each of the processor/controller modules. Thus, when executing such software modules, the collective processor/controller modules of the enhanced system or distinct AVs may be operative to perform the operations or steps from the exemplary method 7100 disclosed above, including variations of that method.

FURTHER PARTICULAR EMBODIMENTS

What follows below is a listing of exemplary categorized sets of particular embodiments focusing on one or more aspects of the different embodiments described above. Each of the different sets of particular embodiments respectively effect improvements to the technology of modular autonomous logistics vehicle transports and assemblies using modular components of the same. As such, within each further embodiment heading are numbered aspects describing a specific technological and practical application as explicitly explained and supported by the disclosure above. Each numbered aspect appearing below a particular heading may make reference to other numbered aspects that appear below that particular heading in a dependent relationship.

Further Embodiment A—Modular Mobility Base for a Modular Autonomous Logistics Vehicle Transport Apparatus 1. A modular mobility base for a modular autonomous bot apparatus that transports an item being shipped, the modular mobility base comprising:
   a mobile base platform;
   a modular component alignment interface disposed on the mobile base platform, the modular alignment interface providing at least one channel into which another modular component of the modular autonomous bot apparatus can be placed and secured on the mobile base platform;
   a mobility controller disposed as part of the mobile base platform, the mobility controller being operative to generate a propulsion control signal for controlling speed of the modular mobility base and a steering control signal for controlling navigation of the modular mobility base;
   a propulsion system connected to the mobile base platform, the propulsion system being responsive to the propulsion control signal from the mobility controller and operative to cause changes to the speed of the modular mobility base;
   a steering system connected to the mobile base platform and coupled to the propulsion system, the steering system being responsive to the steering control signal from the mobility controller and operative to cause changes to directional movement of the modular mobility base; and
   a plurality of sensors coupled to the mobility controller, wherein each of the sensors being disposed on the mobile base platform, wherein the sensors being operative to autonomously generate and provide feedback sensor data to the mobility controller about a condition of the modular mobility base.

2. The modular mobility base of embodiment 1, wherein the mobile base platform comprises:
   a support base having the modular alignment interface and the sensors, the support base comprising at least (a) a top support surface on which the modular alignment interface is disposed and (b) a plurality of peripheral edges on which the sensors are disposed; and
   a set of wheels coupled to the support base, wherein at least a first portion of the set of wheels being further coupled to the propulsion system and wherein at least a second portion of the set of wheels being further coupled to the steering system.

3. The modular mobility base of embodiment 2, wherein the set of wheels comprises a set of tracks.

4. The modular mobility base of embodiment 2, wherein the mobile base platform further comprises a selectively adjustable suspension system that couples the set of wheels to the support base, the selectively adjustable suspension system activating to change an oriented configuration of the support base relative to the set of wheels from a first orientation state to a second orientation state in response to a support base orientation control signal from the mobility controller.

5. The modular mobility base of embodiment 4, wherein the oriented configuration of the support base comprises a lifted attitude orientation.

6. The modular mobility base of embodiment 4, wherein the oriented configuration of the support base comprises a tilted attitude orientation.

7. The modular mobility base of embodiment 4, wherein the oriented configuration of the support base comprises a combination lift and tilt attitude orientation.

8. The modular mobility base of embodiment 4, wherein the selectively adjustable suspension system comprises a plurality of actuators individually responsive to one of a plurality of actuator control signals as part of the support base orientation control signal from the mobility controller.

9. The modular mobility base of embodiment 4, wherein the mobility controller generates the support base orientation control signal to cause the selectively adjustable suspension system to activate and change the oriented configuration of the support base relative to the set of wheels from the first orientation state to the second orientation state based upon and in response to feedback sensor data from at least one of the sensors.

10. The modular mobility base of embodiment 4, wherein the mobility controller generates the support base orientation control signal to cause the selectively adjustable suspension system to activate and change the oriented configuration of the support base relative to the set of wheels from the first orientation state to the second orientation state based upon and in response to a control command from the another modular component of the modular autonomous bot apparatus.

11. The modular mobility base of embodiment 4 further comprising a wireless transceiver operatively coupled to the mobility controller, the wireless transceiver providing a bi-directional wireless data path between the mobility controller and an external wireless node disposed external to the modular autonomous bot apparatus; and
   wherein the mobility controller generates the support base orientation control signal to cause the selectively adjustable suspension system to activate and change the oriented configuration of the support base relative to the set of wheels from the first orientation state to the second orientation state based upon and in response to a wireless control command from the external wireless node disposed external to the modular autonomous bot apparatus.

12. The modular mobility base of embodiment 2, wherein the modular component alignment interface comprises:
   a registration interface disposed on the top support surface of the mobile base platform as the at least one channel into which the another modular component of the modular autonomous bot apparatus can be placed and secured on the mobile base platform; and
   a coupling receiver disposed on the top support surface of the mobile base platform, the coupling receiver providing a secure receiving latch element for a mated coupling latch element on the another modular component of the modular autonomous bot apparatus, wherein the secure receiving latch element being operative to temporarily attach to the mated coupling latch element on the another modular component of the modular autonomous bot apparatus.

13. The modular mobility base of embodiment 12, wherein the registration interface comprises a plurality of raised alignment channels.

14. The modular mobility base of embodiment 12, wherein the registration interface comprises a plurality of recessed alignment channels.

15. The modular mobility base of embodiment 12, wherein the registration interface comprises a plurality of alignment channels where each of the alignment channels are disposed proximate one of the peripheral edges of the support base.

16. The module mobility base of embodiment 12, wherein the secure receiving latch element comprises an interlocking latch element for a mated interlocking coupling latch element on the another modular component of the modular autonomous bot apparatus.

17. The modular mobility base of embodiment 12, wherein the modular component alignment interface further comprising a modular component electronics interface disposed on the top support surface of the mobile base platform, the modular component electronics interface being operatively coupled to the mobility controller as a power and data mated interface to at least the another modular component of the modular autonomous bot apparatus.

18. The modular mobility base of embodiment 17 further comprising an onboard power source that supplies electrical power to at least the mobility controller, the propulsion system, the steering system, and the sensors; and
   wherein the power and data mated interface is operatively connected to the onboard power source, the power and data mated interface further including a power output connection that provides electrical power to the another modular component of the modular autonomous bot apparatus.

19. The modular mobility base of embodiment 18 further comprising an onboard power controller that selectively applies the electrical power to at least the mobility controller, the propulsion system, the steering system, and the sensors from the one of the onboard power source, from an external power source, and both the onboard power source and the external power source; and
   wherein the power and data mated interface further including a power input connection that receives externally supplied electrical power from the external power source.

20. The modular mobility base of embodiment 12, wherein the modular component electronics interface comprising a modular mated bus interface connection for relaying feedback sensor data from the sensors coupled to the mobility controller and for receiving control commands that responsively causes the mobility controller to generate the propulsion control signal and the steering control signal.

21. The modular mobility base of embodiment 2, wherein the propulsion system comprises at least one motor coupled to at least one in the set of wheels, the motor being responsive to the propulsion control signal from the mobility controller to alter rotation of the at least one in the set of wheels.

22. The modular mobility base of embodiment 2, wherein the propulsion system comprises a set of motors coupled to respective ones in the set of wheels, the set of motors being responsive to the propulsion control signal from the mobility controller to alter rotation of each of wheels in the set of wheels.

23. The modular mobility base of embodiment 2, wherein the propulsion system comprises a set of motors integrated with respective wheels in the set of wheels, the set of motors integrated with wheels being responsive to the propulsion control signal from the mobility controller to alter rotation of each of wheels in the set of wheels.

24. The modular mobility base of embodiment 1, wherein different ones of the sensors are operative to detect a tilt characteristic of the mobile base platform, to detect an environmental characteristic next to the mobile base platform, and to detect a proximity characteristic about what is next to the mobile base platform.

25. The modular mobility base of embodiment 1, wherein at least one of the sensors being a proximity sensor operative to autonomously detect an object in a movement path of the modular mobility base and provide proximity sensor data to the mobility controller on the detected object as the feedback sensor data.

26. The modular mobility base of embodiment 25, wherein mobility controller is operative to receive the feedback sensor data from at least the proximity sensor and responsively generate a change to at least one of the propulsion control signal and the steering control signal.

27. The modular mobility base of embodiment 1 further comprising at least one light disposed on the mobile base platform, wherein the at least one light being focused external to the mobile base platform.

28. The modular mobility base of embodiment 27, wherein the at least one light comprises a multi-spectral light providing multi-spectral visibility to facilitate sensor detection by at least one of the sensors.

29. The modular mobility base of embodiment 1 further comprising a wireless transceiver operatively coupled to the mobility controller, the wireless transceiver providing a bi-directional wireless data path between the mobility controller and at least the another modular component of the modular autonomous bot apparatus.

30. The modular mobility base of embodiment 1 further comprising a wireless transceiver operatively coupled to the mobility controller, the wireless transceiver providing a bi-directional wireless data path between the mobility controller and an external wireless node disposed external to the modular autonomous bot apparatus.

31. The modular mobility base of embodiment 17 further comprising a wireless transceiver operatively coupled to the mobility controller, the wireless transceiver providing a bi-directional wireless data path for the mobility controller and at least the another modular component of the modular autonomous bot apparatus.

32. The modular mobility base of embodiment 29, wherein the wireless transceiver providing the bi-directional wireless data path between the mobility controller and the another modular component of the modular autonomous bot apparatus to enable remote wireless control of the modular mobility base by the another modular component of the modular autonomous bot apparatus.

33. The modular mobility base of embodiment 30, wherein the wireless transceiver providing the bi-directional wireless data path between the mobility controller and the external wireless node disposed external to the modular autonomous bot apparatus to enable remote wireless control of the modular mobility base by the external wireless node.

34. A modular mobility base for a modular autonomous bot apparatus that transports an item being shipped, the modular mobility base comprising:
  a selectively adjustable mobile base platform comprising
    a support base having a top support surface,
    a plurality of peripheral edges on the support base,
    a wheelbase frame,
    a set of motorized wheels coupled to the wheelbase frame, the motorized set of wheels operating as a propulsion system for the modular mobility base,
    a selectively adjustable suspension system coupling the wheelbase frame to the support base, the selectively adjustable suspension system activating to change an oriented configuration of the support base relative to the wheelbase frame from a first orientation state to a second orientation state in response to a support base orientation control signal from the mobility controller;
  a modular component alignment interface disposed on the selectively adjustable mobile base platform, the modular alignment interface comprising
    at least one alignment channel into which another modular component of the modular autonomous bot apparatus can be placed and secured on the selectively adjustable mobile base platform;
    a coupling receiver disposed on the top support surface of the selectively adjustable mobile base platform, the coupling receiver providing a secure interlocking receiving latch element for a mated interlocking coupling latch element on the another modular component of the modular autonomous bot apparatus, wherein the secure interlocking receiving latch element being operative to temporarily attach to the mated interlocking coupling latch element on the another modular component of the modular autonomous bot apparatus;
  a mobility controller disposed as part of the selectively adjustable mobile base platform, the mobility controller being operative to generate a propulsion control signal for controlling speed of the modular mobility base and a steering control signal for controlling navigation of the modular mobility base;
  a plurality of sensors coupled to the mobility controller, wherein each of the sensors being disposed on the selectively adjustable mobile base platform, wherein the sensors being operative to autonomously generate and provide feedback sensor data to the mobility controller about a condition of the modular mobility base; and
  a steering system connected to the selectively adjustable mobile base platform and coupled to the propulsion system, the steering system being responsive to the steering control signal from the mobility controller and operative to cause changes to directional movement of the modular mobility base; and
  wherein the set of motorized wheels is responsive to the propulsion control signal from the mobility controller and operative to cause changes to the speed of the modular mobility base.

Further Embodiment B—Modular Multiple Mobility Base Assembly Apparatus for Transporting an Item Being Shipped 1. A modular multiple mobility base assembly apparatus for transporting an item being shipped, the modular mobility base comprising:
  a base adapter plate having a top side and a bottom side, wherein the top side provides a transport area for supporting the item being shipped;
  a first modular mobility base coupled to the bottom side of the base adapter plate, the first modular mobility base operating as a master autonomous mobile vehicle, the first modular mobility base comprising
    a first mobile base platform;
    a first mobility controller disposed as part of the first mobile base platform, the first mobility controller being operative to generate a master propulsion control signal for controlling speed of the first modular mobility base and a master steering control signal for controlling navigation of the first modular mobility base;

a first propulsion system connected to the first mobile base platform, the first propulsion system being responsive to the master propulsion control signal from the first mobility controller and operative to cause changes to the speed of the first modular mobility base;

a first steering system connected to the mobile base platform and coupled to the first propulsion system, the first steering system being responsive to the master steering control signal from the first mobility controller and operative to cause changes to directional movement of the first modular mobility base;

a first wireless transceiver operatively coupled to the first mobility controller, the first wireless transceiver providing a first bi-directional wireless data and command interface for the first mobility controller;

a plurality of first sensors coupled to the first mobility controller, wherein each of the first sensors being disposed on the first mobile base platform, wherein the first sensors being operative to autonomously generate and provide first feedback sensor data to the first mobility controller about a condition of the first modular mobility base; and a second modular mobility base coupled to the bottom side of the base adapter plate, the second modular mobility base wirelessly paired to the first modular mobility base and operating as a slave autonomous mobile vehicle under control of the first modular mobility base, the second modular mobility base comprising a second mobile base platform;

a second mobility controller disposed as part of the second mobile base platform, the second mobility controller being operative to generate a responsive propulsion control signal for controlling speed of the second modular mobility base and generate a responsive steering control signal for controlling navigation of the second modular mobility base, wherein the responsive propulsion control signal and the responsive steering control signal are generated by the second mobility controller based upon master control input received from the first modular mobility base;

a second propulsion system connected to the second mobile base platform, the second propulsion system being responsive to the responsive propulsion control signal from the second mobility controller and operative to cause changes to the speed of the second modular mobility base;

a second steering system connected to the second mobile base platform and coupled to the second propulsion system, the second steering system being responsive to the responsive steering control signal from the second mobility controller and operative to cause changes to directional movement of the second modular mobility base;

a second wireless transceiver operatively coupled to the second mobility controller, the second wireless transceiver providing a second bi-directional wireless data and command interface for the second mobility controller, wherein the second mobility controller is operative to communicate with at least the first mobility controller and receive the master control input over a secure paired wireless connection between the first bi-directional wireless data and command interface for the first mobility controller and the second bi-directional wireless data and command interface for the second mobility controller; and a plurality of second sensors coupled to the second mobility controller, wherein each of the second sensors being disposed on the second mobile base platform, wherein the second sensors being operative to autonomously generate and provide second feedback sensor data to the second mobility controller about a condition of the second modular mobility base.

2. The modular multiple mobility base assembly apparatus of embodiment 1, wherein the first mobile base platform on the first modular mobility base further having a first support plate alignment channel disposed on a top of the first mobile base platform;

wherein the second mobile base platform on the second modular mobility base further having a second support plate alignment channel disposed on a top of the second mobile base platform; and wherein the base adapter plate further comprises a first support plate alignment seat and a second support plate alignment seat disposed on the bottom side of the base adapter plate, wherein the first support plate alignment seat providing a mated interface to the first support plate alignment channel where the base adapter plate is coupled to the first modular mobility base, and wherein the second support plate alignment seat providing a mated interface to the second support plate alignment channel where the base adapter plate is coupled to the second modular mobility base.

3. The modular multiple mobility base assembly apparatus of embodiment 2, wherein the first support plate alignment channel comprises a first raised channel protruding from the first mobile base platform; and wherein the second support plate alignment channel comprises a second raised channel protruding from the second mobile base platform.

4. The modular multiple mobility base assembly apparatus of embodiment 2, wherein the first support plate alignment seat comprises a first recessed channel on the bottom side of the base adapter plate; and wherein the second support plate alignment seat comprises a second recessed channel on the bottom side of the base adapter plate.

5. The modular multiple mobility base assembly apparatus of embodiment 1, wherein the first modular mobility base is secured to the bottom side of the base adapter plate using a first detachable coupling that allows the first modular mobility base to be latched and locked to the bottom side of the base adapter plate; and wherein the second modular mobility base is secured to the bottom side of the base adapter plate using a second detachable coupling that allows the second modular mobility base to be latched and locked to the bottom side of the base adapter plate.

6. The modular multiple mobility base assembly apparatus of embodiment 1, wherein the first detachable coupling on the first modular mobility base comprises a first interlocking latch that detachably mates with the bottom side of the base adapter plate; and wherein the second detachable coupling on the second modular mobility base comprises a second interlocking latch that detachably mates with the bottom side of the base adapter plate 7. The modular multiple mobility base assembly apparatus of embodiment 1, wherein the first mobility controller detects a pairing request using the first wireless transceiver, the pairing request being broadcast from the second mobility controller, and wherein the first mobility controller is further operative to establish the secure paired wireless connection with the second mobility controller in response to the detected pairing request.

8. The modular multiple mobility base assembly apparatus of embodiment 7, wherein the first mobility controller is further operative to establish an authorized association with the second mobility controller in response to the detected pairing request and based upon a security credential sent to the first mobility controller from the second mobility controller, the established authorization allowing the first mobility controller to generate and provide the second mobility controller with the master control input over the secure paired wireless connection and for the second mobility controller to receive and respond to the master control input.

9. The modular multiple mobility base assembly apparatus of embodiment 8, wherein the first mobility controller is further operative to receive the second feedback sensor data from the second mobility controller about the condition of the second modular mobility base.

10. The modular multiple mobility base assembly apparatus of embodiment 9, wherein the first mobility controller is further operative to generate updated master control input based upon the received second feedback sensor data from the second mobility controller about the condition of the second modular mobility base and provide the second mobility controller with the updated master control input over the secure paired wireless connection and for the second mobility controller to receive and respond to the updated master control input.

11. The modular multiple mobility base assembly apparatus of embodiment 1, wherein the first mobile base platform comprises a first support base, a first set of wheels, and a selectively adjustable first suspension system that couples the first support base to the first set of wheels, the selectively adjustable first suspension system being operative to change an oriented configuration of the first support base relative to the first set of wheels from a first orientation state to a second orientation state in response to a first support base orientation control signal from the first mobility controller; and wherein the second mobile base platform comprises a second support base, a second set of wheels, and a selectively adjustable second suspension system that couples the second support base to the second set of wheels, the selectively adjustable second suspension system being operative to change an oriented configuration of the second support base relative to the second set of wheels from a third orientation state to a fourth orientation state in response to a second support base orientation control signal from the second mobility controller.

12. The modular multiple mobility base assembly apparatus of embodiment 11, wherein the second support base orientation control signal is generated by the second mobility controller in response to a coordinated support base orientation control signal from the first mobility controller.

13. The modular multiple mobility base assembly apparatus of embodiment 12, wherein the first mobility controller is operative to maintain a desired orientation configuration of the base adapter plate by periodically generating an update for the first support base orientation control signal and generating an update for the coordinated support base orientation control signal.

14. The modular multiple mobility base assembly apparatus of embodiment 13, wherein the desired orientation configuration comprises a desired lifted attitude configuration of the base adapter plate.

15. The modular multiple mobility base assembly apparatus of embodiment 13, wherein the desired orientation configuration comprises a desired tilted attitude configuration of the base adapter plate.

16. The modular multiple mobility base assembly apparatus of embodiment 14, wherein the desired orientation configuration comprises a desired combination lift and tilt attitude configuration of the base adapter plate.

17. The modular multiple mobility base assembly apparatus of embodiment 11, wherein the selectively adjustable first suspension system comprising a plurality of first support base actuators individually responsive to one of a plurality of first support base actuator control signals as part of the first support base orientation control signal from the first mobility controller; and wherein the selectively adjustable second suspension system comprising a plurality of second support base actuators individually responsive to one of a plurality of second support base actuator control signals as part of the second support base orientation control signal generated by the second mobility controller in response to a coordinated support base orientation control signal from the first mobility controller.

18. The modular multiple mobility base assembly apparatus of embodiment 17, wherein the first support base actuator control signals from the first mobility controller cause the first support base actuators to raise the first support base relative to the first set of wheels; and wherein the second support base actuator control signals based upon the coordinated support base orientation control signal from the first mobility controller cause the second support base actuators to lower the second support base relative to the second set of wheels.

19. The modular multiple mobility base assembly apparatus of embodiment 17, wherein the first mobility controller is operative to responsively generate an update to the first support base orientation control signal and the coordinated support base orientation control signal based upon a combination of (a) the first feedback sensor data and (b) the second feedback sensor data as provided by the second mobility controller to the first mobility controller.

20. The modular multiple mobility base assembly apparatus of embodiment 17, wherein the first mobility controller is operative to responsively generate an update to the first support base orientation control signal and the coordinated support base orientation control signal based upon and in response to a control command received by the first mobility controller over the first wireless transceiver.

21. The modular multiple mobility base assembly apparatus of embodiment 1, wherein the base adapter plate further comprises:

an auxiliary power source disposed as part of the base adapter plate;

a first output power connection disposed on the bottom side of the base adapter plate, the first output power connection being coupled to the auxiliary power source and providing access by the first modular mobility base to the auxiliary power source; and a second output power connection disposed on the bottom side of the base adapter plate, the second output power connection being coupled to the auxiliary power source and providing access by the second modular mobility base to the auxiliary power source.

Further Embodiment C—Modular Auxiliary Power Module for a Modular Autonomous Bot Apparatus that Transports an Item Being Shipped 1. A modular auxiliary power module for a modular autonomous bot apparatus that transports an item being shipped, the auxiliary power module comprising:
   a base adapter platform having a top side, a bottom side, and a plurality of peripheral edges, wherein the top side of the base adapter platform having a cargo support area configured to support the item being shipped, wherein the top side of the base adapter platform includes at least a first interlocking alignment interface and wherein the bottom side of the base adapter platform includes at least a second interlocking alignment interface;
   a cargo door movably attached to and extending from one of the peripheral edges of the base adapter platform;
   an auxiliary power source disposed as part of the base adapter platform; and
   an output power outlet disposed as part of the base adapter platform, the output power outlet being coupled to the auxiliary power source and providing access by a first component of the modular autonomous bot apparatus to the auxiliary power source.

2. The modular auxiliary power module of embodiment 1, wherein the first interlocking alignment interface comprises a plurality of top alignment channels disposed on the peripheral edges of the base adapter platform not having the cargo door.

3. The modular auxiliary power module of embodiment 2, wherein the first interlocking alignment interface further comprises a plurality of latches, wherein each of the latches being disposed on one of the top alignment channels disposed on the peripheral edges of the base adapter platform not having the cargo door, wherein each of the latches configured to secure another mated component of the modular autonomous bot apparatus to the top side of the base adapter platform.

4. The modular auxiliary power module of embodiment 1, wherein the second interlocking alignment interface comprises at least one bottom alignment registration interface on the bottom side of the base adapter platform configured to mate with at least one alignment registration interface on a mobility base component of the modular autonomous bot apparatus.

5. The modular auxiliary power module of embodiment 4, where the second interlocking alignment interface further comprises a plurality of latches configured to secure the base adapter platform to the mobility base component of the modular autonomous bot apparatus.

6. The modular auxiliary power module of embodiment 1, wherein the auxiliary power source comprises a removable power pack.

7. The modular auxiliary power module of embodiment 1, wherein the auxiliary power source comprises an extendible power pack that is configured to receive at least one additional power pack to extend the available output power provided by the auxiliary power source.

8. The modular auxiliary power module of embodiment 1 further comprising a modular component electronics interface disposed on the base adapter platform, the modular component electronics interface providing (a) the output power outlet and (b) a command and data communication interface, the modular component electronics interface provided on the base adapter platform to at least the another modular component of the modular autonomous bot apparatus.

9. The modular auxiliary power module of embodiment 8, wherein the modular component electronics interface comprises a top side modular component electronics interface disposed on the top side of the base adapter platform and a bottom side modular component electronics interface disposed on the bottom side of the base adapter platform; and
   wherein the output power outlet comprises:
      a first output power connection integrated as part of the bottom side modular component electronics interface, the first output power connection being coupled to the auxiliary power source and providing access by a first component of the modular autonomous bot apparatus to the auxiliary power source, the first component of the modular autonomous bot apparatus being disposed below the modular auxiliary power module; and
      a second output power connection integrated as part of the top side modular component electronics interface, the second output power connection being coupled to the auxiliary power source and providing access by a second component of the modular autonomous bot apparatus to the auxiliary power source, the second component of the modular autonomous bot apparatus being disposed above the modular auxiliary power module.

10. The modular auxiliary power module of embodiment 1, wherein the cargo door is movably attached to the one of the peripheral edges of the base adapter platform using an actuated joint.

11. The modular auxiliary power module of embodiment 1, wherein the actuated joint comprises an actuated hinge.

12. The modular auxiliary power module of embodiment 10, wherein the actuated joint comprises a spring actuated joint that is self-closing.

13. The modular auxiliary power module of embodiment 8, wherein the cargo door is movably attached to the one of the peripheral edges of the base adapter platform using a joint; and
   further comprising
      a door actuator fixed to the base adapter platform and operative to move the cargo door, and
      a door actuator driver coupled to the door actuator and responsive to a cargo door control input from a control component of the modular autonomous bot apparatus received over the command and data communication interface of the modular component electronics interface, the door actuator driver causing the door actuator to move the cargo door relative to the base adapter platform in response to the cargo door control input.

14. The modular auxiliary power module of embodiment 1, wherein the cargo door is movably attached to the one of the peripheral edges of the base adapter platform using a joint; and
   further comprising
      a door actuator fixed to the base adapter platform and operative to move the cargo door, and
      a door actuator driver coupled to the door actuator and responsive to an authorized wireless cargo door control input from a control component of the modular autonomous bot apparatus, the authorized wireless cargo door control input being wirelessly received by the door actuator driver causing the door actuator to move the cargo door relative to the base adapter platform in response to the authorized wireless cargo door control input.

15. The modular auxiliary power module of embodiment 1, wherein the cargo door is movably attached to the one of the peripheral edges of the base adapter platform using a joint; and further comprising
a door actuator fixed to the base adapter platform and operative to move the cargo door, and
a door actuator driver coupled to the door actuator and responsive to an authorized wireless cargo door control input from an external wireless node disposed external to the modular autonomous bot apparatus, the authorized wireless cargo door control input being wirelessly received by the door actuator driver causing the door actuator to move the cargo door relative to the base adapter platform and in response to the authorized wireless cargo door control input.

16. The modular auxiliary power module of embodiment 8, wherein the cargo door further comprises at least one actuated electro-mechanical lock responsive to a door lock control input from a control component of the modular autonomous bot apparatus, the door lock control input being received by the actuated electro-mechanical lock over the command and data communication interface of the modular component electronics interface, the actuated electro-mechanical lock being operative to activate to secure the cargo door when the cargo door is in a raised closed position in response to the door lock control input.

17. The modular auxiliary power module of embodiment 1, wherein the cargo door further comprises at least one actuated electro-mechanical lock responsive to an authorized wireless door lock control input from a control component of the modular autonomous bot apparatus, the wireless door lock control input being wirelessly received by the actuated electro-mechanical lock causing the actuated electro-mechanical lock to activate to secure the cargo door when the cargo door is in a raised closed position in response to the authorized wireless door lock control input.

18. The modular auxiliary power module of embodiment 1, wherein the cargo door further comprises at least one actuated electro-mechanical lock responsive to an authorized wireless door lock control input from an external wireless node disposed external to the modular autonomous bot apparatus, the authorized wireless door lock control input being wirelessly received by the actuated electro-mechanical lock causing the actuated electro-mechanical lock to activate to secure the cargo door when the cargo door is in a raised closed position in response to the authorized wireless door lock control input.

19. The modular auxiliary power module of embodiment 8, wherein the cargo door further comprises an electronic display interface coupled to the command and data communication interface of the modular component electronics interface, the electronic display interface being operative to generate a visual message on the cargo door.

20. The modular auxiliary power module of embodiment 19, wherein the electronic display interface comprises a translucent panel that allows visibility through the cargo door while also being operative to generate the visual message on the cargo door with generated characters.

21. The modular auxiliary power module of embodiment 19, wherein the visual message comprises prompted instructions related to delivery of the item being shipped.

22. The modular auxiliary power module of embodiment 8, wherein the base adapter platform further comprises:
an actuated belt surface disposed on the top side of the base adapter platform; and
a belt actuator driver coupled to the actuated belt surface and responsive to a belt control input generated by a control component of the modular autonomous bot apparatus, the belt actuator driver causing the actuated belt surface to move relative to the cargo door of the base adapter platform in response to the belt control input.

23. The modular auxiliary power module of embodiment 8, wherein the base adapter platform further comprises:
an actuated belt surface disposed on the top side of the base adapter platform; and
a belt actuator driver coupled to the actuated belt surface and responsive to an authorized belt control input generated by an external wireless node disposed external to the modular autonomous bot apparatus, the belt actuator driver causing the actuated belt surface to move relative to the cargo door of the base adapter platform in response to the authorized belt control input.

24. The modular auxiliary power module of embodiment 8, wherein the base adapter platform further comprises:
an actuated belt surface disposed on an inner side of the cargo door; and
a belt actuator driver coupled to the actuated belt surface and responsive to a belt control input generated by a control component of the modular autonomous bot apparatus, the belt actuator driver causing the actuated belt surface to move relative to the cargo door in response to the belt control input once the cargo door is in a deployed position.

25. The modular auxiliary power module of embodiment 8, wherein the base adapter platform further comprises:
an actuated belt surface disposed on an inner side of the cargo door; and
a belt actuator driver coupled to the actuated belt surface and responsive to an authorized belt control input generated by an external wireless node disposed external to the modular autonomous bot apparatus, the belt actuator driver causing the actuated belt surface to move relative to the cargo door in response to the authorized belt control input once the cargo door is in a deployed position.

26. The modular auxiliary power module of embodiment 1, wherein the cargo door further comprises an extendible ramp that articulates out from an opposing end of the cargo door opposite the one of the peripheral edges of the base adapter platform.

27. The modular auxiliary power module of embodiment 8, wherein the cargo door further comprises an extendible ramp that articulates out from an opposing end of the cargo door opposite the one of the peripheral edges of the base adapter platform, wherein the extendible ramp being responsive to a ramp deploy control input generated by a control component of the modular autonomous bot apparatus to articulate the extendible ramp relative to the cargo door.

28. The modular auxiliary power module of embodiment 27, wherein the extendible ramp further comprises:
an actuated belt surface disposed on a top side of the extendible ramp; and a belt actuator driver coupled to the actuated belt surface and responsive to a belt control input generated by a control component of the modular autonomous bot apparatus, the belt actuator driver causing the actuated belt surface to move relative to the extendible ramp in response to the belt control input once the cargo door is in a deployed position.

29. The modular auxiliary power module of embodiment 8, wherein the base adapter platform further comprises:
an actuated belt surface disposed on a top side of the extendible ramp; and
a belt actuator driver coupled to the actuated belt surface and responsive to an authorized belt control input generated by an external wireless node disposed external to the modular autonomous bot apparatus, the belt actuator driver causing the actuated belt surface to move relative to the extendible ramp in response to the authorized belt control input once the cargo door is in a deployed position.

30. The modular auxiliary power module of embodiment 8, wherein the base adapter platform further comprises:
at least one actuated sliding arm disposed above the top side of the base adapter platform; and
a sliding arm actuator driver coupled to the at least one actuated sliding arm and responsive to a sliding arm control input generated by a control component of the modular autonomous bot apparatus, the sliding arm actuator driver causing the actuated sliding arm to move at least towards the cargo door of the base adapter platform in response to the sliding arm control input.

31. The modular auxiliary power module of embodiment 8, wherein the base adapter platform further comprises:
at least one actuated sliding arm disposed above the top side of the base adapter platform; and
a sliding arm actuator driver coupled to the at least one actuated sliding arm and responsive to an authorized sliding arm control input generated by an external wireless node disposed external to the modular autonomous bot apparatus, the sliding arm actuator driver causing the actuated sliding arm to move at least towards the cargo door of the base adapter platform in response to the authorized sliding arm control input.

32. The modular auxiliary power module of embodiment 8, wherein the base adapter platform further comprises:
an actuated grabbing arm disposed above the top side of the base adapter platform, the actuated grabbing arm having a stationary base coupled to the top side of the base adapter platform, a movable grabbing arm coupled to the stationary base with multiple degrees of freedom of movement, and grip head disposed on the distal end of the movable grabbing arm where the grip head is articulable to grab onto the item being shipped as disposed on the top side of the base adapter platform; and
a grabbing arm actuator driver coupled to the actuated grabbing arm and responsive to a grabbing arm control input generated by a control component of the modular autonomous bot apparatus, the grabbing arm actuator driver (a) causing the actuated grabbing arm to move towards the item being shipped, (b) causing the grip head to grab onto the item being shipped, and (c) causing the actuated grabbing arm to move the item being shipped as maintained within the grip head at least towards the cargo door of the base adapter platform in response to the grabbing arm control input.

33. The modular auxiliary power module of embodiment 8, wherein the base adapter platform further comprises:
an actuated grabbing arm disposed above the top side of the base adapter platform, the actuated grabbing arm having a stationary base coupled to the top side of the base adapter platform, a movable grabbing arm coupled to the stationary base with multiple degrees of freedom of movement, and grip head disposed on the distal end of the movable grabbing arm where the grip head is articulable to grab onto the item being shipped as disposed on the top side of the base adapter platform; and
a grabbing arm actuator driver coupled to the actuated grabbing arm and responsive to an authorized grabbing arm control input generated by an external wireless node disposed external to the modular autonomous bot apparatus, the grabbing arm actuator driver (a) causing the actuated grabbing arm to move towards the item being shipped, (b) causing the grip head to grab onto the item being shipped, and (c) causing the actuated grabbing arm to move the item being shipped as maintained within the grip head at least towards the cargo door of the base adapter platform in response to the authorized grabbing arm control input.

34. A modular auxiliary power module for a modular autonomous bot apparatus that transports an item being shipped, the auxiliary power module comprising:
a base adapter platform having a top side, a bottom side, and a plurality of peripheral edges, wherein the top side of the base adapter platform having a cargo support area configured to support the item being shipped, wherein the top side of the base adapter platform includes at least a first interlocking alignment interface and wherein the bottom side of the base adapter platform includes at least a second interlocking alignment interface;
a modular component electronics interface disposed as a conduit from the top side of the base adapter platform to the bottom side of the base adapter platform, the modular component electronics interface providing (a) an output power outlet for at least another modular component of the modular autonomous bot apparatus and (b) a command and data communication interface to at least the another modular component of the modular autonomous bot apparatus;
an auxiliary power source disposed as part of the base adapter platform, the auxiliary power source being coupled to the output power outlet of the modular component electronics interface; and
a cargo door coupled to one of the peripheral edges of the base adapter platform by at least one joint;
a door actuator fixed to the base adapter platform and to the cargo door, the door actuator being operative to move the cargo door; and
a door actuator driver coupled to the door actuator and responsive to a cargo door control input from a control component of the modular autonomous bot apparatus received over the command and data communication interface of the modular component electronics interface, the door actuator driver causing the door actuator to move the cargo door relative to the base adapter platform in response to the cargo door control input.

35. A modular auxiliary power module for a modular autonomous bot apparatus that transports an item being shipped, the auxiliary power module comprising:
a base adapter platform having a top side, a bottom side, and a plurality of peripheral edges, wherein the top side of the base adapter platform having a cargo support area configured to support the item being shipped, wherein the top side of the base adapter platform includes at least a first interlocking alignment interface and wherein the bottom side of the base adapter platform includes at least a second interlocking alignment interface;

an auxiliary power source disposed as part of the base adapter platform; and a modular component electronics interface disposed as a conduit from the top side of the base adapter platform to the bottom side of the base adapter platform, the modular component electronics interface providing (a) an output power outlet coupled to the auxiliary power source and (b) a command and data communication interface to at least another modular component of the modular autonomous bot apparatus, wherein the modular component electronics interface comprises a top side modular component electronics interface disposed on the top side of the base adapter platform, and a bottom side modular component electronics interface disposed on the bottom side of the base adapter platform, and wherein the output power outlet comprises:

a first output power connection integrated as part of the bottom side modular component electronics interface, the first output power connection being coupled to the auxiliary power source and providing access by a first component of the modular autonomous bot apparatus to the auxiliary power source, the first component of the modular autonomous bot apparatus being disposed below the modular auxiliary power module; and a second output power connection integrated as part of the top side modular component electronics interface, the second output power connection being coupled to the auxiliary power source and providing access by a second component of the modular autonomous bot apparatus to the auxiliary power source, the second component of the modular autonomous bot apparatus being disposed above the modular auxiliary power module.

Further Embodiment D—a Modular Cargo Storage Apparatus for Use on a Base Platform of a Modular Autonomous Bot Apparatus that Transports an Item being Shipped 1. A modular cargo storage apparatus for use on a base platform of a modular autonomous bot apparatus that transports an item being shipped, the modular cargo storage apparatus comprising:

a set of folding structural walls configured to at least partially enclose a payload area above the base platform and on at least three sides above the base platform and forming a set of vertical boundaries on the at least three sides of the payload area;

an interlocking alignment interface disposed on at least one of the folding structural walls, the interlocking alignment interface comprising a set of latches disposed on the at least one of the folding structural walls, and a locking handle coupled to the set of latches, the locking handle actuating the set of latches to cause the set of latches to interlock with at least the base platform; and a modular component power and data transport bus disposed on the at least one of the folding structural walls, the modular component power and data transport bus having a top side modular component electronics interface and a bottom side modular component electronics interface, wherein the top side modular component electronics interface being disposed on a top edge of the at least one of the folding structural walls and wherein the bottom side modular component electronics interface being disposed on a bottom edge of the at least one of the folding structural walls, wherein each of the top side modular component electronics interface and the bottom side modular component electronics interface having (a) a power conduit outlet and (b) a command and data communication interface.

2. The modular cargo storage apparatus of embodiment 1, wherein the set of latches comprises a pair of longitudinal support latches slidably attached to the at least one of the folding structural walls and coupled to the locking handle, wherein each of the longitudinal support latches having a top interlocking latch disposed above a top of the at least one of the folding structural walls and a bottom interlocking latch disposed above a bottom of the at least one of the folding structural walls; and wherein the locking handle actuates a sliding movement of at least one of the longitudinal support latches relative to the other of the longitudinal support latches in a first direction to engage the set of latches, and wherein the locking handle actuates the sliding movement of at least one of the longitudinal support latches relative to the other of the longitudinal support latches in an opposite direction to engage the set of latches.

3. The modular cargo storage apparatus of embodiment 1, wherein the locking handle actuates the sliding movement at least one of the longitudinal support latches relative to the other of the longitudinal support latches by rotation of the locking handle relative to the pair of longitudinal support latches.

4. The modular cargo storage apparatus of embodiment 2, wherein the sliding movement of both of the longitudinal support latches in response to actuation of the locking handle moves the top interlocking latches on each of the longitudinal support latches towards each other above the top of the at least one of the folding structural walls to engage a mating set of latches on a component of the modular autonomous bot apparatus disposed above the modular cargo storage apparatus; and wherein the sliding movement of both of the longitudinal support latches in response to actuation of the locking handle also moves the bottom interlocking latches on each of the longitudinal support latches towards each other below the bottom of the at least one of the folding structural walls to engage a mating set of latches on the base platform below the modular cargo storage apparatus.

5. The modular cargo storage apparatus of embodiment 4, wherein the component of the modular autonomous bot apparatus disposed above the modular cargo storage apparatus comprises a modular mobile autonomy module component secured to the modular cargo storage apparatus by the mating set of latches on the mobile autonomy module component in engagement with the top interlocking latches as a result of actuating the locking handle.

6. The modular cargo storage apparatus of embodiment 4, wherein the base platform of the modular autonomous bot apparatus disposed below the modular cargo storage apparatus comprises a modular auxiliary power module component secured to the modular cargo storage apparatus by the mating set of latches on the auxiliary power module component in engagement with the bottom interlocking latches as a result of actuating the locking handle.

7. The modular cargo storage apparatus of embodiment 1, wherein the locking handle comprises an actuated electro-mechanical locking handle responsive to a latch locking control input from a control component of the modular autonomous bot apparatus, the latch locking control input being received by the actuated electro-mechanical locking handle over the modular component power and data transport bus, the actuated electro-mechanical locking handle being operative to actuate the set of latches in response to the latch locking control input.

8. The modular cargo storage apparatus of embodiment 1, wherein the locking handle further comprises an actuated electro-mechanical locking handle responsive to an authorized wireless latch locking control input from a control component of the modular autonomous bot apparatus, the wireless latch locking control input being wirelessly received by the actuated electro-mechanical locking handle causing the actuated electro-mechanical locking handle to actuate the set of latches in response to the authorized wireless latch locking control input.

9. The modular cargo storage apparatus of embodiment 1, wherein the locking handle further comprises an actuated electro-mechanical locking handle responsive to an authorized wireless latch locking control input from an external wireless node disposed external to the modular autonomous bot apparatus, the authorized wireless latch locking control input being wirelessly received by the actuated electro-mechanical locking handle causing the actuated electro-mechanical locking handle to actuate the set of latches in response to the authorized wireless latch locking control input.

10. The modular cargo storage apparatus of embodiment 1, wherein the locking handle comprises:
a user input panel disposed on the at least one of the folding structural walls, the user input panel accepting a latch locking control input from a user; and
an actuated electro-mechanical locking handle operatively coupled to the user input panel to receive the latch locking control input, the actuated electro-mechanical locking handle being responsive to the latch locking control input from the user input panel to actuate the set of latches in response to the latch locking control input.

11. The modular cargo storage apparatus of embodiment 1, wherein the base platform of the modular autonomous bot apparatus disposed below the modular cargo storage apparatus has a cargo door that when in a closed position mates with the folding structural walls of the modular cargo storage apparatus to form a set of vertical boundaries on all sides of the payload area.

12. The modular cargo storage apparatus of embodiment 1, wherein the set of folding structural walls comprises at least a set of four cargo storage structural walls configured to vertically enclose the payload area above the base platform, wherein one of the folding structural walls comprises a cargo door movably attached to another of the folding structural walls, the cargo door being selectively opened to provide access to within the payload area.

13. The modular auxiliary power module of embodiment 12, wherein the cargo door is movably attached to the another of the folding structural walls using a self-closing actuated joint.

14. The modular auxiliary power module of embodiment 13, wherein the self-closing actuated joint comprises a spring-loaded hinge.

15. The modular cargo storage apparatus of embodiment 12 further comprising
a door actuator fixed to the another of the folding structural walls having the cargo door, the door actuator being operative to selectively move the cargo door to provide access to within the payload area, and
a door actuator driver coupled to the door actuator and responsive to a cargo door control input from a control component of the modular autonomous bot apparatus, the cargo door control input being received over the modular component power and data transport bus causing the door actuator to selectively move the cargo door in response to the cargo door control input.

16. The modular cargo storage apparatus of embodiment 12 further comprising
a door actuator fixed to the another of the folding structural walls having the cargo door, the door actuator being operative to selectively move the cargo door to provide access to within the payload area, and
a door actuator driver coupled to the door actuator and responsive to an authorized wireless cargo door control input from a control component of the modular autonomous bot apparatus, the authorized wireless cargo door control input being wirelessly received by the door actuator driver and causing the door actuator to move the cargo door in response to the authorized wireless cargo door control input.

17. The modular cargo storage apparatus of embodiment 12 further comprising
a door actuator fixed to the another of the folding structural walls having the cargo door, the door actuator being operative to selectively move the cargo door to provide access to within the payload area, and
a door actuator driver coupled to the door actuator and responsive to an authorized wireless cargo door control input from an external wireless node disposed external to the modular autonomous bot apparatus, the authorized wireless cargo door control input being wirelessly received by the door actuator driver and causing the door actuator to move the cargo door in response to the authorized wireless cargo door control input.

18. The modular cargo storage apparatus of embodiment 12, wherein the cargo door further comprises an actuated electro-mechanical lock responsive to a door lock control input from a control component of the modular autonomous bot apparatus, the door lock control input being received by the actuated electro-mechanical lock over the modular component power and data transport bus, the actuated electro-mechanical lock being operative to selectively secure or unlock the cargo door in response to the door lock control input.

19. The modular cargo storage apparatus of embodiment 12, wherein the cargo door further comprises an actuated electro-mechanical lock responsive to an authorized wireless door lock control input from a control component of the modular autonomous bot apparatus, the wireless door lock control input being wirelessly received by the actuated electro-mechanical lock causing the actuated electro-mechanical lock to selectively secure or unlock the cargo door in response to the authorized wireless door lock control input.

20. The modular cargo storage apparatus of embodiment 12, wherein the cargo door further comprises an actuated electro-mechanical lock responsive to an authorized wireless door lock control input from an external wireless node disposed external to the modular autonomous bot apparatus, the authorized wireless door lock control input being wirelessly received by the actuated electro-mechanical lock causing the actuated electro-mechanical lock to selectively secure or unlock the cargo door in response to the authorized wireless door lock control input.

21. The modular cargo storage apparatus of embodiment 1 further comprising an electronic display interface disposed on one of the folding structural walls, the electronic display interface being coupled to the modular component power and data transport bus, the electronic display interface being operative to generate a visual message on the one of the folding structural walls.

22. The modular cargo storage apparatus of embodiment 21, wherein the electronic display interface comprises a translucent panel that allows visibility through the cargo door while also being operative to generate the visual message on the cargo door with generated characters.

23. The modular cargo storage apparatus of embodiment 21, wherein the visual message comprises prompted instructions related to delivery of the item being shipped.

24. The modular cargo storage apparatus of embodiment 21, wherein the visual message comprises electronically displayed information about the item being shipped.

25. The modular cargo storage apparatus of embodiment 1 further comprising one or more sensors disposed on an internal side of at least one of the folding structural walls, the sensors being operative to monitor contents of the modular cargo storage apparatus in the payload area.

26. The modular cargo storage apparatus of embodiment 25, wherein at least one of the sensors comprising a proximity sensor for detecting a position of the item being shipped as the item is maintained within the payload area.

27. The modular cargo storage apparatus of embodiment 25, wherein at least one of the sensors comprising a proximity sensor for detecting a height of the item being shipped as the item is maintained within the payload area.

28. The modular cargo storage apparatus of embodiment 25, wherein at least one of the sensors comprising an environmental sensor for detecting a current environmental condition within the payload area.

29. The modular cargo storage apparatus of embodiment 25, wherein the sensors being operatively coupled to the modular component power and data transport bus for reporting sensor data from the sensors over the modular component power and data transport bus.

30. The modular cargo storage apparatus of embodiment 25 further comprising a sensor wireless transceiver disposed on one of the folding structure walls and coupled to each of the sensors, and wherein the sensor wireless transceiver wirelessly providing the sensor data to an authorized control component of the modular autonomous bot apparatus.

31. The modular cargo storage apparatus of embodiment 25 further comprising a sensor wireless transceiver disposed on one of the folding structure walls and coupled to each of the sensors, and wherein the sensor wireless transceiver wirelessly providing the sensor data to an authorized external wireless node disposed external to the modular autonomous bot apparatus.

32. The modular cargo storage apparatus of embodiment 1 further comprising climate control module attached to one of the folding structural walls, the climate control module being coupled to the modular component power and data transport bus to at least power the climate control module, wherein the climate control module being operative to alter an environment next to the climate control module to maintain a desired environment next to the climate control module.

33. The modular cargo storage apparatus of embodiment 32, wherein the set of folding structural walls comprises a set of folding insulated structural walls.

34. The modular cargo storage apparatus of embodiment 32, wherein the climate control module is temporarily attached to the one of the folding insulated structural walls so that the climate control module is removable when the set of folding insulated structural walls is configured in a folded stored state.

35. The modular cargo storage apparatus of embodiment 32, wherein the climate control module is self-regulating with a built-in environmental sensor to sense the environment next to the climate control module and a feedback thermostat using sensor data from the environmental sensor as a basis for altering the environment next to the climate control module to maintain the desired environment next to the climate control module.

36. The modular cargo storage apparatus of embodiment 32, wherein the climate control module is responsive to a climate control input from a control component of the modular autonomous bot apparatus, the climate control input being received by the climate control module over the modular component power and data transport bus, the climate control module being operative to alter the environment next to the climate control module to maintain the desired environment next to the climate control module in response to the climate control input.

37. The modular cargo storage apparatus of embodiment 32, wherein the climate control module is responsive to an authorized wireless climate control input from a control component of the modular autonomous bot apparatus, the wireless climate control input being wirelessly received by the climate control module causing the climate control module to alter the environment next to the climate control module to maintain the desired environment next to the climate control module in response to the authorized wireless climate control input.

38. The modular cargo storage apparatus of embodiment 32, wherein the climate control module is responsive to an authorized wireless climate control input from an external wireless node disposed external to the modular autonomous bot apparatus, the authorized wireless climate control input being wirelessly received by the climate control module causing the climate control module to alter the environment next to the climate control module to maintain the desired environment next to the climate control module in response to the authorized wireless climate control input.

39. The modular cargo storage apparatus of embodiment 32, wherein the set of folding structural walls comprises a set of folding insulated structural walls.

40. The modular cargo storage apparatus of embodiment 1 further comprising an actuated sliding arm assembly attached to one of the folding structural walls, the actuated sliding arm assembly being coupled to the modular component power and data transport bus to at least power the actuated sliding arm assembly, wherein the actuated sliding arm assembly comprises:
  an actuated sliding arm removably affixed to the one of the folding structural walls; and
  a sliding arm actuator driver coupled to the at least one actuated sliding arm and responsive to a sliding arm control input generated by a control component of the modular autonomous bot apparatus, the sliding arm actuator driver causing the actuated sliding arm to move the item being shipped within the payload area in response to the sliding arm control input.

41. The modular cargo storage apparatus of embodiment 1 further comprising an actuated sliding arm assembly attached to one of the folding structural walls, the actuated sliding arm assembly being coupled to the modular component power and data transport bus to at least power the actuated sliding arm assembly, wherein the actuated sliding arm assembly comprises:
  an actuated sliding arm removably affixed to the one of the folding structural walls; and
  a sliding arm actuator driver coupled to the at least one actuated sliding arm and responsive to an authorized wireless sliding arm control input generated by an external wireless node disposed external to the modular autonomous bot apparatus, the sliding arm actuator driver causing the actuated sliding arm to move the item being shipped within the payload area in response to the authorized wireless sliding arm control input.

42. The modular cargo storage apparatus of embodiment 25 further comprising an actuated grabbing arm assembly attached to one of the folding structural walls, the actuated grabbing arm assembly being coupled to the modular component power and data transport bus to at least power the actuated grabbing arm assembly, wherein the actuated grabbing arm assembly comprises:
  an actuated grabbing arm removably coupled to the one of the folding structural walls, the actuated grabbing arm having
    a stationary base removably attached to the one of the folding structural walls,
    a movable grabbing arm coupled to the stationary base with multiple degrees of freedom of movement, and
    a grip head disposed on the distal end of the movable grabbing arm where the grip head is articulable to grab onto the item being shipped as disposed on the top side of the base adapter platform; and
  a grabbing arm actuator driver coupled to the actuated grabbing arm and the sensors, the grabbing arm actuator driver being responsive to a grabbing arm control input generated by a control component of the modular autonomous bot apparatus and sensor data from the sensors, the grabbing arm actuator driver (a) detecting the item being shipped using the sensor data, (b) causing the actuated grabbing arm to move towards the item being shipped, (c) causing the grip head to grab onto the item being shipped, and (d) causing the actuated grabbing arm to move the item being shipped as maintained within the grip head from within the payload area to outside the payload area in response to the grabbing arm control input.

43. The modular cargo storage apparatus of embodiment 25 further comprising an actuated grabbing arm assembly attached to one of the folding structural walls, the actuated grabbing arm assembly being coupled to the modular component power and data transport bus to at least power the actuated grabbing arm assembly, wherein the actuated grabbing arm assembly comprises:
  an actuated grabbing arm removably coupled to the one of the folding structural walls, the actuated grabbing arm having
    a stationary base removably attached to the one of the folding structural walls,
    a movable grabbing arm coupled to the stationary base with multiple degrees of freedom of movement, and
    a grip head disposed on the distal end of the movable grabbing arm where the grip head is articulable to grab onto the item being shipped as disposed on the top side of the base adapter platform; and
  a grabbing arm actuator driver coupled to the actuated grabbing arm and the sensors, the grabbing arm actuator driver being responsive to an authorized wireless grabbing arm control input generated by an external wireless node disposed external to the modular autonomous bot apparatus and sensor data from the sensors, the grabbing arm actuator driver (a) detecting the item being shipped using the sensor data, (b) causing the actuated grabbing arm to move towards the item being shipped, (c) causing the grip head to grab onto the item being shipped, and (d) causing the actuated grabbing arm to move the item being shipped as maintained within the grip head from within the payload area to outside the payload area in response to the authorized wireless grabbing arm control input.

Further Embodiment E—Detachable Modular Mobile Autonomy Control Module for a Modular Autonomous Bot Apparatus 1. A detachable modular mobile autonomy control module for a modular autonomous bot apparatus that transports an item being shipped, the modular autonomous bot apparatus having at least a modular mobile base component that propels the modular autonomous bot apparatus, the modular bot apparatus further having a modular cargo storage component having a payload area disposed below and open to the detachable modular mobile autonomy control module when assembled as part of the modular autonomous bot apparatus, the detachable modular mobile autonomy control module comprising:
  a detachable modular housing comprising
    a horizontally-oriented base cover configured to detachably cover the payload area when the modular mobile autonomy control module is attached to the modular cargo storage component as part of the modular autonomous bot apparatus, the base cover comprising at least a top side, a bottom side, and a plurality of peripheral sides,
    a plurality of latching points on the bottom side of the base cover, the latching points operative to detachably couple the detachable modular housing to the modular cargo storage component of the modular autonomous bot apparatus;
  an autonomous control system disposed within the detachable modular housing;
  location circuitry disposed within the detachable modular housing, the location circuitry being operatively coupled to the autonomous control system, the location circuitry generating location data on a location of the detachable modular mobile autonomy control module and providing the location data to the autonomous control system;
  a plurality of external sensors disposed on the detachable modular housing, the sensors being operatively coupled to the autonomous control system, the external sensors generating external sensor data on an environment external to the detachable modular mobile autonomy control module as detected by the external sensors and providing the sensor data to the autonomous control system;
  a plurality of multi-element light panels disposed on at least a subset of the peripheral sides of the base cover and operatively coupled to the autonomous control system, the multi-element light panels being operatively driven by the autonomous control system; and a modular component power and data transport bus disposed within the detachable modular housing, the modular component power and data transport bus having a bottom side modular component electronics interface disposed on the bottom side of the detachable modular housing that mates to a corresponding modular component electronics interface on the modular cargo storage component, wherein the bottom side modular component electronics interface having (a) a power conduit input interface and (b) a command and data communication interface, wherein the power conduit input interface operatively coupled to the autonomous control system, the location circuitry, and the multi-element light panels; and wherein the autonomous control system is programmatically adapted and configured to be operative to at least receive the sensor data from the external sensors disposed on the detachable modular housing, receive outside sensor data from additional sensors disposed on the modular mobile base component, the outside sensor data being received over the command and data communication interface of the modular component power and data transport bus, generate steering and propulsion control output signals based on the location data from the location circuitry, the sensor data from the external sensors, the outside sensor data, and destination information data maintained by the autonomous control system, generate first autonomous transport information to provide on selective ones of the multi-element light panels, and generate autonomous delivery information to provide on at least one of the multi-element light panels.

2. The detachable modular mobile autonomy control module of embodiment 1, wherein the detachable modular housing further comprises a vertically-oriented raised display support protruding up from the top side of the base cover; and further comprising a first display interface disposed on a front side of the vertically-oriented raised display support and operatively coupled to the autonomous control system, the first display interface being operatively driven by the autonomous control system;

a second display interface disposed on a rear side of the vertically-oriented raised display support and operatively coupled to the autonomous control system, the second display interface being operatively driven by the autonomous control system;

wherein the power conduit input interface is also operatively coupled to the first display interface and the second display interface; and wherein the autonomous control system is programmatically adapted and configured to be further operative to:

generate second autonomous transport information to provide on the first display interface and second display interface, and generate the autonomous delivery information to provide on at least one of the first display interface, the second display interface, and on at least one of the multi-element light panels.

3. The detachable modular mobile autonomy control module of embodiment 1, wherein the latching points disposed on the bottom side of the base cover comprise at least one set of passive latches that engage an opposing set of movable latches on the modular cargo storage component, wherein the detachable modular mobile autonomy control module is secured to the modular cargo storage component and covers the payload area when the at least one set of passive latches are engaged with the opposing set of movable latches on the modular cardo storage component.

4. The detachable modular mobile autonomy control module of embodiment 3, wherein the set of passive latches comprises a set of interlocking latches that mate to the opposing set of movable latches.

5. The detachable modular mobile autonomy control module of embodiment 1, wherein the plurality of external sensors disposed on the detachable modular housing are of different types of sensors.

6. The detachable modular mobile autonomy control module of embodiment 1, wherein at least a subset of the plurality of external sensors are implemented in a sensor pod removably attached to the detachable modular housing.

7. The detachable modular mobile autonomy control module of embodiment 1, wherein a plurality of subsets of the plurality of external sensors are respectively implemented in a plurality of interchangeable sensor pods, wherein each of the interchangeable sensor pods being removably attached to the detachable modular housing and having a characteristic type of sensors in the subset of the external sensors.

8. The detachable modular mobile autonomy control module of embodiment 1 further comprising one or more payload monitoring sensors disposed on the bottom side of the base cover, the one or more payload monitoring sensors generating payload sensor data on the payload area disposed below the detachable modular mobile autonomy control module when the detachable modular mobile autonomy control module is attached to the modular cargo storage component using the latching points, the one or more payload monitoring sensors providing the payload sensor data to the autonomous control system.

9. The detachable modular mobile autonomy control module of embodiment 8, wherein the one or more payload monitoring sensors are implemented in a sensor pod removably attached to the bottom side of the base cover.

10. The detachable modular mobile autonomy control module of embodiment 1 further comprising a wireless radio transceiver interface disposed within the detachable modular housing and being operatively coupled to the autonomous control system, the wireless radio transceiver being operative to communicate with an actuated component on the modular autonomous bot apparatus.

11. The detachable modular mobile autonomy control module of embodiment 1 further comprising a wireless radio transceiver interface disposed within the detachable modular housing and being operatively coupled to the autonomous control system, the wireless radio transceiver being operative to communicate with an external wireless node disposed external to the modular autonomous bot apparatus having the detachable modular mobile autonomy control module.

12. The detachable modular mobile autonomy control module of embodiment 11, wherein wireless radio transceiver being operative to receive command inputs from the external wireless node as a remote control input from a delivery recipient.

13. The detachable modular mobile autonomy control module of embodiment 11, wherein wireless radio transceiver being operative to receive command inputs from the external wireless node as a remote control input from a delivery supplier.

14. The detachable modular mobile autonomy control module of embodiment 11, wherein wireless radio transceiver being operative to request and receive navigation assistance from the external wireless node.

15. The detachable modular mobile autonomy control module of embodiment 11, wherein wireless radio transceiver being operative to request and receive navigation assistance from a backend server as the external wireless node.

16. The detachable modular mobile autonomy control module of embodiment 1, wherein the detachable modular housing further comprises a plurality of externally focused lights disposed on one or more of the peripheral sides of the base cover, the externally focused lights being selectively powered by the autonomous control system to enhance processing of the sensor data from the external sensors and enhance processing of the outside sensor data from the additional sensors disposed on the modular mobile base component.

17. The detachable modular mobile autonomy control module of embodiment 8, wherein the detachable modular housing further comprises one or more payload focused lights disposed on the bottom of the base cover, the payload focused lights being selectively powered by the autonomous control system to enhance processing of the payload sensor data from the payload monitoring sensors disposed on the bottom side of the base cover.

18. The detachable modular mobile autonomy control module of embodiment 1 further comprising a secondary power source disposed within the detachable modular housing, wherein the second power source being operatively coupled to provide backup power to at least the autonomous control system.

19. The detachable modular mobile autonomy control module of embodiment 1, wherein the autonomous control system is further programmatically adapted and configured to be operative to process at least the sensor data from the external sensors disposed on the detachable modular housing for object detection and collision avoidance as part of generating the steering and propulsion control output signals.

20. The detachable modular mobile autonomy control module of embodiment 1, wherein the autonomous control system is further programmatically adapted and configured to be operative to process at least the sensor data from the external sensors disposed on the detachable modular housing and process the outside sensor data from the additional sensors disposed on the modular mobile base component for object detection and collision avoidance as part of generating the steering and propulsion control output signals.

21. The detachable modular mobile autonomy control module of embodiment 1, wherein the autonomous control system is further programmatically adapted and configured to be operative to generate an actuator control signal as part of a logistics operation once the location data from the location circuitry indicates the detachable modular mobile autonomy control module is at a desired logistics location.

22. The detachable modular mobile autonomy control module of embodiment 21, wherein the actuator control signal comprises a lock actuator control signal provided to an electro-mechanically actuated lock on the modular bot apparatus that selectively secures and unsecures access to the payload area.

23. The detachable modular mobile autonomy control module of embodiment 21, wherein the actuator control signal comprises a handle actuator control signal provided to an electro-mechanically actuated lock on the modular bot apparatus that selectively secures and unsecures access to the payload area.

24. The detachable modular mobile autonomy control module of embodiment 21, wherein the actuator control signal comprises a door actuator control signal provided to a door actuator on the modular bot apparatus that selectively opens and closes access to the payload area.

25. The detachable modular mobile autonomy control module of embodiment 21, wherein the actuator control signal comprises a belt actuator control signal provided to a belt actuator on the modular bot apparatus that selectively moves the item being shipped from within the payload area.

26. The detachable modular mobile autonomy control module of embodiment 21, wherein the actuator control signal comprises a climate control signal for a climate control module on the modular cargo storage component, the climate control signal being provided to the climate control module for selectively modifying an environment within the payload area.

27. The detachable modular mobile autonomy control module of embodiment 21, wherein the actuator control signal comprises a sliding arm actuator control signal provided to a sliding arm actuator within the payload area that responsively moves the item being shipped in response to the sliding arm actuator control signal.

28. The detachable modular mobile autonomy control module of embodiment 21, wherein the actuator control signal comprises a grabbing arm actuator control signal provided to a grabbing arm actuator within the payload area that responsively grasps the item being shipped and moves the item being shipped in response to the grabbing arm actuator control signal.

29. The detachable modular mobile autonomy control module of embodiment 21, wherein the actuator control signal comprises a support base actuator control signal provided to a selectively adjustable suspension system on the modular mobile base component that responsively changes an orientation state of the modular mobile base component in response to the support base actuator control signal.

30. The detachable modular mobile autonomy control module of embodiment 1, further comprising an authentication interface coupled to the autonomous control system, the authentication interface being operative to verify another modular component attached to the latching points is an authenticated modular component based upon component-to-component secure handshaking with a corresponding authentication interface on the another modular component.

31. The detachable modular mobile autonomy control module of embodiment 30, wherein the component-to-component secure handshaking comprises a challenge and security credential response between the authentication interface on the detachable modular mobility autonomy control module and the authentication interface on the another modular component.

32. The detachable modular mobile autonomy control module of embodiment 31, wherein the component-to-component secure handshaking comprises a comparison of the security credential response from the authentication interface on the another modular component to a security credential maintained as part of the authentication interface on the detachable modular mobility autonomy control module, and wherein the another modular component attached to the latching points is verified to be the authenticated modular component based upon the comparison.

33. The detachable modular mobile autonomy control module of embodiment 30, wherein the component-to-component secure handshaking is based upon at least one from a group comprising one or more regulatory rules, one or more contractual rules, and one or more safety rules.

34. The detachable modular mobile autonomy control module of embodiment 30, wherein the component-to-component secure handshaking is based upon logistical constraint information on a determined work environment for the detachable modular mobile autonomy control module, the logical constraint information being identified as part of a security credential maintained as part of the authentication interface on the detachable modular mobility autonomy control module.

35. The detachable modular mobile autonomy control module of embodiment 34, wherein the logistical constraint information identifies a size limitation for the detachable modular mobile autonomy control module.

36. The detachable modular mobile autonomy control module of embodiment 34, wherein the logistical constraint information identifies a weight limitation for the detachable modular mobile autonomy control module.

37. The detachable modular mobile autonomy control module of embodiment 34, wherein the logistical constraint information identifies a readiness limitation for the detachable modular mobile autonomy control module.

38. The detachable modular mobile autonomy control module of embodiment 37, wherein the readiness limitation comprising one or more performance thresholds for the detachable modular mobile autonomy control module in an anticipated deployment operation of the detachable modular mobile autonomy control module.

39. The detachable modular mobile autonomy control module of embodiment 30, further comprising a wireless radio transceiver interface disposed within the detachable modular housing and being operatively coupled to the autonomous control system, the wireless radio transceiver being operative to communicate with a server;
  wherein the autonomous control system is further programmatically adapted and configured to be operative to
    notify the server over the wireless radio transceiver that another modular component attached to the latching points is not verified to be the authenticated modular component based upon the authentication interface on the detachable modular mobility autonomy control module and the authentication interface on the another modular component.

Further Embodiment F—A Modular Autonomous Bot Apparatus Assembly for Transporting an Item Being Shipped 1. A modular autonomous bot apparatus assembly for transporting an item being shipped, comprising:
  a modular mobility base comprising
    a mobile base platform,
    a mobility controller disposed as part of the base platform,
    a propulsion system connected to the mobile base platform, the propulsion system being responsive to a propulsion control input from the mobility controller to cause changes in speed of the modular mobility base,
    a steering system connected to the mobile base platform and coupled to the propulsion system, the steering system responsive to a steering control input from the mobility controller and operative to cause changes to directional movement of the modular mobility base,
    a plurality of mobility base sensors coupled to the mobility controller and disposed on the base platform, the mobility base sensors being operative to autonomously detect an object in the path of the modular mobility base and provide base feedback sensor data to the mobility controller on the detected object, and
    a first interface to a common modular component power and data transport bus, the first interface providing a power conduit for the modular mobility base and a command and data interface conduit for at least the mobility controller;
  a modular auxiliary power module detachably attached to the modular mobility base, the modular auxiliary power module comprising
    a base adapter platform detachably mounted to the mobile base platform of the modular mobility base, the base adapter platform having a payload support surface area, a top interlocking alignment interface, and a bottom interlocking alignment interface, wherein the payload support surface area is disposed on a top of the base adapter platform to support the item being shipped, and wherein the bottom interlocking alignment interface is disposed on a bottom of the base adapter platform to latch to the mobile base platform,
    an articulating cargo door movably attached to and extending from the base adapter platform,
    an auxiliary power source disposed as part of the base adapter platform, and
    a second interface to the common modular component power and data transport bus, the second interface providing a power conduit for the modular auxiliary power module and a command and data interface conduit for the modular auxiliary power module, wherein the power conduit for the modular auxiliary power module is coupled to the auxiliary power source and provides access to power provided by the auxiliary power source;
  a modular cargo storage system detachably attached to the modular auxiliary power module, the modular cargo storage system comprising
    a set of folding structural walls configured to partially enclose the payload support area above the base adapter platform of the modular auxiliary power module, the folding structural walls forming vertical boundaries above the payload support area with the articulating cargo door of the auxiliary power module,
    an actuated set of latches disposed on the at least one of the folding structural walls, and
    a locking handle coupled to the actuated set of latches, the locking handle causing the actuated set of latches to detachably interlock with at least the base adapter platform of the modular auxiliary power module; and
    a third interface to the common modular component power and data transport bus, the third interface providing a power conduit for the modular cargo storage system and a command and data interface conduit for the modular cargo storage system, wherein the power conduit for the modular auxiliary power module is operatively coupled to the auxiliary power source and provides access to power provided by the auxiliary power source; and a modular mobile autonomy control module detachably attached to a top edge of the folding structure walls of the modular cargo storage system, the modular mobile autonomy control module completing the enclosure of the payload support area when connected to the top edge of the folding structure walls of the modular cargo storage system, the modular mobile autonomy control module comprising a detachable modular housing detachably connected to the top edge of the folding structure walls of the cargo storage system, a plurality of latching points disposed on the detachable modular housing, the latching points engaging the actuated set of latches when the locking handle detachably interlocks the actuated set of latches to the latching points, an autonomous controller disposed within the detachable modular housing, a plurality of human interaction interfaces disposed on the detachable modular housing, wherein each of the human interaction interfaces being operatively coupled to the autonomous controller, location circuitry disposed within the detachable modular housing, the location circuitry being operatively coupled to the autonomous controller, the location circuitry generating location data on a location of the modular autonomous bot apparatus assembly and providing the location data to the autonomous controller;

a plurality of autonomy module sensors disposed on the mobile autonomy control module and operatively coupled to the autonomous controller, wherein the autonomy module sensors being operative to generate onboard sensor data on an environment external to the modular mobile autonomy control module as detected by the autonomy module sensors and providing the onboard sensor data to the autonomous controller, and a fourth interface to the common modular component power and data transport bus, the fourth interface providing a power conduit for the modular mobile autonomy control module and a command and data interface conduit for the modular mobile autonomy control module, wherein the command and data interface conduit is operatively coupled to at least the autonomous controller; and wherein the autonomous controller of the modular mobile autonomy control module is programmatically adapted and configured to be operative to at least receive information from the mobility controller through the common modular component power and data transport bus, the received information being about the base feedback sensor data, receive the onboard sensor data from the autonomy module sensors, generate a steering control command and a propulsion control command based at least upon the location data from the location circuitry, the received information on the base feedback sensor data from the mobility controller, the onboard sensor data as received by the autonomous controller from the autonomy module sensors, and destination information data maintained by the autonomous controller, transmit the steering control command and the propulsion control command through the common modular component power and data transport bus for receipt by the mobility controller, and generate transport and delivery information to provide on the human interaction interfaces.

2. The modular autonomous bot apparatus assembly of embodiment 1, wherein the modular mobility base, the modular auxiliary power module, the modular cargo storage system, and the modular mobile autonomy control module are each authenticated modular components based upon a component-to-component secure handshaking between proximately attached ones of the modular mobility base, the modular auxiliary power module, the modular cargo storage system, and the modular mobile autonomy control module.

3. The modular autonomous bot apparatus assembly of embodiment 2, wherein the component-to-component secure handshaking comprises a challenge and security credential response between proximately attached ones of the modular mobility base, the modular auxiliary power module, the modular cargo storage system, and the modular mobile autonomy control module.

4. The modular autonomous bot apparatus assembly of embodiment 1, wherein the modular mobility base, the modular auxiliary power module, the modular cargo storage system, and the modular mobile autonomy control module are verified to be authenticated modular components for the modular autonomous bot apparatus assembly as each of the modular mobility base, the modular auxiliary power module, the modular cargo storage system, and the modular mobile autonomy control module are assembled into the modular autonomous bot apparatus assembly.

5. The modular autonomous bot apparatus assembly of embodiment 2, wherein the component-to-component secure handshaking is based upon at least one from a group comprising one or more regulatory rules, one or more contractual rules, and one or more safety rules.

6. The modular autonomous bot apparatus assembly of embodiment 2, wherein the component-to-component secure handshaking is based upon logistical constraint information on a determined work environment for the modular autonomous bot apparatus assembly.

7. The modular autonomous bot apparatus assembly of embodiment 6, wherein the logical constraint information being identified as part of the security credential response.

8. The modular autonomous bot apparatus assembly of embodiment 6, wherein the logistical constraint information identifies a size limitation for the modular autonomous bot apparatus assembly.

9. The modular autonomous bot apparatus assembly of embodiment 6, wherein the logistical constraint information identifies a weight limitation for the modular autonomous bot apparatus assembly.

10. The modular autonomous bot apparatus assembly of embodiment 6, wherein the logistical constraint information identifies a readiness limitation for the modular autonomous bot apparatus assembly.

11. The modular autonomous bot apparatus assembly of embodiment 10, wherein the readiness limitation comprising one or more performance thresholds for the modular autonomous bot apparatus assembly in an anticipated deployment operation of the modular autonomous bot apparatus assembly.

12. The modular autonomous bot apparatus assembly of embodiment 2, wherein the modular mobile autonomy control module further comprises a wireless radio transceiver operatively coupled to the autonomous controller; and wherein the autonomous controller of the modular mobile autonomy control module is further programmatically adapted and configured to be operative to notify a server over the wireless radio transceiver that one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system, and request a replacement component for the one or more of the modular mobility base, the modular auxiliary power module, and the modular cargo storage system that are not authenticated modular components.

13. The modular autonomous bot apparatus assembly of embodiment 2, wherein the autonomous controller of the modular mobile autonomy control module is further programmatically adapted and configured to be operative to generate a component replacement request message on at least one of the human interaction interfaces disposed on the detachable modular housing when one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system, the component replacement request message requesting a replacement component for the one or more of the modular mobility base, the modular auxiliary power module, and the modular cargo storage system that are not authenticated modular components.

14. The modular autonomous bot apparatus assembly of embodiment 2, wherein the autonomous controller of the modular mobile autonomy control module is further programmatically adapted and configured to receive an authentication result from one of the modular mobility base, the modular auxiliary power module, and the modular cargo storage system, wherein the authentication result indicating that at least one of the modular mobility base, the modular auxiliary power module, and the modular cargo storage system are not authenticated modular components based upon the component-to-component secure handshaking between proximate ones of the modular mobility base, the modular auxiliary power module, the modular cargo storage system, and the modular mobile autonomy control module; and notify a server over the wireless radio transceiver that one or more of the modular mobility base, the modular auxiliary power module, and the modular cargo storage system are not authenticated modular components based upon the authentication result received.

15. The modular autonomous bot apparatus assembly of embodiment 2, wherein the autonomous controller of the modular mobile autonomy control module is further programmatically adapted and configured to receive an authentication result from one of the modular mobility base, the modular auxiliary power module, and the modular cargo storage system, wherein the authentication result indicating that at least one of the modular mobility base, the modular auxiliary power module, and the modular cargo storage system are not authenticated modular components based upon the component-to-component secure handshaking between proximate ones of the modular mobility base, the modular auxiliary power module, the modular cargo storage system, and the modular mobile autonomy control module; and generate a component replacement request message on at least one of the human interaction interfaces disposed on the detachable modular housing based upon the authentication result received.

16. The modular autonomous bot apparatus assembly of embodiment 1, wherein each of the modular mobility base, the modular auxiliary power module, and the modular cargo storage system are authenticated modular components based upon a component-to-component secure handshaking between the modular mobile autonomy control module and each of the modular mobility base, the modular auxiliary power module, and the modular cargo storage system.

17. The modular autonomous bot apparatus assembly of embodiment 16, wherein the component-to-component secure handshaking comprises a challenge and security credential response between the modular mobile autonomy control module and each of the modular mobility base, the modular auxiliary power module, and the modular cargo storage system.

18. The modular autonomous bot apparatus assembly of embodiment 16, wherein the component-to-component secure handshaking is based upon at least one from a group comprising one or more regulatory rules, one or more contractual rules, and one or more safety rules.

19. The modular autonomous bot apparatus assembly of embodiment 16, wherein the component-to-component secure handshaking is based upon logistical constraint information on a determined work environment for the modular autonomous bot apparatus assembly.

20. The modular autonomous bot apparatus assembly of embodiment 20, wherein the logistical constraint information identifies a size limitation for the modular autonomous bot apparatus assembly.

21. The modular autonomous bot apparatus assembly of embodiment 20, wherein the logistical constraint information identifies a weight limitation for the modular autonomous bot apparatus assembly.

22. The modular autonomous bot apparatus assembly of embodiment 20, wherein the logistical constraint information identifies a readiness limitation for the modular autonomous bot apparatus assembly.

23. The modular autonomous bot apparatus assembly of embodiment 22, wherein the readiness limitation comprising one or more performance thresholds for the modular autonomous bot apparatus assembly in an anticipated deployment operation of the modular autonomous bot apparatus assembly.

24. The modular autonomous bot apparatus assembly of embodiment 16, wherein the modular mobile autonomy control module further comprises a wireless radio transceiver operatively coupled to the autonomous controller; and wherein the autonomous controller of the modular mobile autonomy control module is further programmatically adapted and configured to be operative to notify a server over the wireless radio transceiver that one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system, and request a replacement component for the one or more of the modular mobility base, the modular auxiliary power module, and the modular cargo storage system that are not authenticated modular components.

25. The modular autonomous bot apparatus assembly of embodiment 14, wherein the autonomous controller of the modular mobile autonomy control module is further programmatically adapted and configured to be operative to generate a component replacement request message on at least one of the human interaction interfaces disposed on the detachable modular housing when one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system, the component replacement request message requesting a replacement component for the one or more of the modular mobility base, the modular auxiliary power module, and the modular cargo storage system that are not authenticated modular components.

26. The modular autonomous bot apparatus assembly of embodiment 1, wherein the modular mobility base further comprises a set of suspension orientation actuators disposed within the mobile base platform, the set of suspension orientation actuators being operative to responsively alter an orientation of the mobile base platform relative to a ground surface on which the mobile base platform is supported in response to a support base orientation control command generated by the autonomous controller and provided to the mobility controller over the common modular component power and data transport bus.

27. The modular autonomous bot apparatus assembly of embodiment 1, wherein the modular auxiliary power module further comprises a cargo door actuator disposed on the base adapter platform, the cargo door actuator being operative to responsively move the articulating cargo door in response to a cargo door control command generated by the autonomous controller and provided to a door actuator driver on the base adapter platform over the common modular component power and data transport bus.

28. The modular autonomous bot apparatus assembly of embodiment 1, wherein the modular auxiliary power module further comprises a belt actuator disposed on the base adapter platform, the belt actuator being operative to responsively move an actuated belt surface disposed on the base adapter platform in response to a belt control command generated by the autonomous controller and provided to a belt actuator driver on the base adapter platform over the common modular component power and data transport bus.

29. The modular autonomous bot apparatus assembly of embodiment 1, wherein the modular auxiliary power module further comprises a ramp belt actuator disposed on the articulating cargo door, the ramp belt actuator being operative to responsively move an actuated ramp belt surface disposed on the articulating cargo door in response to a ramp belt control command generated by the autonomous controller and provided to a ramp belt actuator driver on the articulating cargo door over the common modular component power and data transport bus.

30. The modular autonomous bot apparatus assembly of embodiment 1, wherein the modular auxiliary power module further comprises an actuated electro-mechanical lock disposed on the modular auxiliary power module, the actuated electro-mechanical lock being operative to responsively secure the articulating cargo door in response to a door lock control command generated by the autonomous controller and provided to the actuated electro-mechanical lock on the modular auxiliary power module over the common modular component power and data transport bus.

31. The modular autonomous bot apparatus assembly of embodiment 1, wherein the modular cargo storage system further comprises an actuated electro-mechanical lock disposed on the modular cargo storage system, the actuated electro-mechanical lock being operative to responsively secure the articulating cargo door in response to a door lock control command generated by the autonomous controller and provided to the actuated electro-mechanical lock on the modular cargo storage system over the common modular component power and data transport bus.

32. The modular autonomous bot apparatus assembly of embodiment 1, wherein the modular cargo storage system further comprises an actuated electro-mechanical lock disposed on the modular cargo storage system, the actuated electro-mechanical lock being operative to responsively actuate the set of actuated latches in response to a latch locking control command generated by the autonomous controller and provided to the actuated electro-mechanical lock on the modular cargo storage system over the common modular component power and data transport bus.

33. The modular autonomous bot apparatus assembly of embodiment 1, wherein the modular cargo storage system further comprises climate control module disposed within the modular cargo storage system, the climate control module being operative to responsively alter an environment of the payload support area to maintain a desired environment within the payload support area in response to a climate control command generated by the autonomous controller and provided to the climate control module on the modular cargo storage system over the common modular component power and data transport bus.

34. The modular autonomous bot apparatus assembly of embodiment 1, wherein the modular cargo storage system further comprises an actuated sliding arm disposed on the modular cargo storage system, the actuated sliding arm being operative to responsively move the item being shipped within the payload support area in response to a sliding arm control command generated by the autonomous controller and provided to the actuated sliding arm on the modular cargo storage system over the common modular component power and data transport bus.

35. The modular autonomous bot apparatus assembly of embodiment 1, wherein the modular cargo storage system further comprises an actuated grabbing arm disposed on the modular cargo storage system, the actuated grabbing arm being operative to responsively obtain and move the item being shipped within the payload support area in response to a grabbing arm control command generated by the autonomous controller and provided to the actuated grabbing arm on the modular cargo storage system over the common modular component power and data transport bus.

36. The modular autonomous bot apparatus assembly of embodiment 1, wherein the modular mobile autonomy control module further comprises one or more payload monitoring sensors disposed on a bottom side of the detachable modular housing and operatively coupled to the autonomous controller, the one or more payload monitoring sensors generating payload sensor data on the payload support area and providing the payload sensor data to the autonomous controller; and wherein the autonomous controller is further programmatically adapted and configured to be operative to monitor the payload sensor data.

37. The modular autonomous bot apparatus assembly of embodiment 36, wherein the one or more payload monitoring sensors are implemented in a detachable sensor pod attached to the bottom side of the detachable modular housing and operatively coupled to the autonomous controller while assembling the modular autonomous bot apparatus assembly.

38. The modular autonomous bot apparatus assembly of embodiment 37, wherein the detachable sensor pod includes at least some of the payload monitoring sensors of a predetermined sensor type correlating to an assigned dispatch use profile maintained by the autonomous controller.

39. The modular autonomous bot apparatus assembly of embodiment 38, wherein the assigned dispatch use profile maintained by the autonomous controller comprises data received by the autonomous controller on the assigned dispatch operation for the modular autonomous bot apparatus.

40. The modular autonomous bot apparatus assembly of embodiment 1, wherein one or more of the autonomy module sensors are implemented in a detachable sensor pod attached to the detachable modular housing and operatively coupled to the autonomous controller while assembling the modular autonomous bot apparatus assembly.

41. The modular autonomous bot apparatus assembly of embodiment 40, wherein the detachable sensor pod includes at least some of the autonomy module sensors of a predetermined sensor type correlating to an assigned dispatch use profile maintained by the autonomous controller.

42. The modular autonomous bot apparatus assembly of embodiment 41, wherein the assigned dispatch use profile maintained by the autonomous controller comprises data received by the autonomous controller on the assigned dispatch operation for the modular autonomous bot apparatus.

43. The modular autonomous bot apparatus assembly of embodiment 1, wherein the modular mobile autonomy control module further comprises a wireless radio transceiver interface disposed within the detachable modular housing and being operatively coupled to the autonomous controller, the wireless radio transceiver being operative to communicate with an external wireless node disposed external to the modular autonomous bot apparatus.

44. The modular autonomous bot apparatus assembly of embodiment 43, wherein the external wireless node comprises a handheld wireless user access device.

45. The modular autonomous bot apparatus assembly of embodiment 43, wherein the external wireless node comprises a server disposed external to the modular autonomous bot apparatus.

46. The modular autonomous bot apparatus assembly of embodiment 43, wherein the autonomous controller is further programmatically adapted and configured to be operative to receive an assigned dispatch use profile for the modular autonomous bot apparatus from the server, wherein the assigned dispatch use profile identifying a type of each of the modular mobility base, the modular auxiliary power module, the modular cargo storage system, and the modular mobile autonomy control module used as part of the modular autonomous bot apparatus assembly.

47. The modular autonomous bot apparatus assembly of embodiment 46, wherein the assigned dispatch use profile for the modular autonomous bot apparatus providing authentication information used for verifying an authentication status for each of the modular mobility base, the modular auxiliary power module, the modular cargo storage system, and the modular mobile autonomy control module used as part of the modular autonomous bot apparatus assembly.

48. The modular autonomous bot apparatus assembly of embodiment 43, wherein the autonomous controller is further programmatically adapted and configured to be operative to wirelessly receive a remote command input for the modular autonomous bot apparatus from the external wireless node through the wireless radio transceiver interface.

49. The modular autonomous bot apparatus assembly of embodiment 48, wherein the remote command input comprises a remote control input from a delivery supplier.

50. The modular autonomous bot apparatus assembly of embodiment 48, wherein the remote command input comprises a remote control input from a delivery recipient.

51. The modular autonomous bot apparatus assembly of embodiment 43, wherein the autonomous controller is further programmatically adapted and configured to be operative to wirelessly request and receive navigation assistance from a backend server as the external wireless node.

52. The modular autonomous bot apparatus assembly of embodiment 43, wherein the autonomous controller is further programmatically adapted and configured to be operative to wirelessly request and receive navigation assistance from an authorized handheld wireless user access device as the external wireless node.

53. The modular autonomous bot apparatus assembly of embodiment 43, wherein the autonomous controller is further programmatically adapted and configured to be operative to
 detect when a current location of the modular autonomous bot apparatus is within a threshold distance from a destination point for the modular autonomous bot apparatus assembly according to an assigned dispatch use profile for the modular autonomous bot apparatus;
 transmit a remote control request over the wireless radio transceiver interface to the external wireless node;
 receive a series of remote control command inputs from the external wireless node through the wireless radio transceiver;
 generate responsive steering control commands and responsive propulsion control command based upon the series of remote control command inputs; and
 transmit the responsive steering control commands and the responsive propulsion control commands to the mobility controller through the common modular component power and data transport bus for receipt by the mobility controller allowing the external wireless node to control navigation of the modular autonomous bot apparatus assembly during a final segment of a deployment operation of the modular autonomous bot apparatus assembly as the modular autonomous bot apparatus assembly moves to the destination point.

54. The modular autonomous bot apparatus assembly of embodiment 53, wherein the autonomous controller is further programmatically adapted and configured to be operative to
 receive the base feedback sensor data from the mobility controller during the final segment of the deployment operation of the modular autonomous bot apparatus assembly as the modular autonomous bot apparatus assembly moves to the destination point;
 receive the onboard sensor data from the autonomy module sensors during the final segment of the deployment operation of the modular autonomous bot apparatus assembly as the modular autonomous bot apparatus assembly moves to the destination point; and transmit a subset of the received base feedback sensor data and the received onboard sensor data to the external wireless node as remote navigation feedback information.

55. The modular autonomous bot apparatus assembly of embodiment 53, wherein the autonomous controller is further programmatically adapted and configured to be operative to update onboard routing information on the autonomous controller with at least a portion of the received base feedback sensor data and the received onboard sensor data.

56. The modular autonomous bot apparatus assembly of embodiment 55, wherein the onboard routing information comprises a database of mapping information; and
wherein the portion of the received base feedback sensor data and the received onboard sensor data that update the database of mapping information provides a higher definition information than exists within the database of mapping information for the final segment of the deployment operation.

57. The modular autonomous bot apparatus assembly of embodiment 32, wherein the autonomous controller is further programmatically adapted and configured to be operative to:
receive the base feedback sensor data from the mobility controller;
receive the onboard sensor data from the autonomy module sensors;
detect an adverse approaching impact based upon the base feedback sensor data and the onboard sensor data;
generate a failsafe mode unlock signal for the actuated electro-mechanical lock disposed on the modular cargo storage system in response to the detected adverse approaching impact; and
transmit the failsafe mode unlock signal to the actuated electro-mechanical lock on the modular cargo storage system over the common modular component power and data transport bus to cause the actuated electro-mechanical lock to unlock the set of actuated set of latches in response to the detected adverse approaching impact.

58. The modular autonomous bot apparatus assembly of embodiment 32, wherein the autonomous controller is further programmatically adapted and configured to be operative to:
detect an adverse power level of the auxiliary power source below a failure threshold power level;
generate a failsafe mode unlock signal for the actuated electro-mechanical lock disposed on the modular cargo storage system in response to the detected adverse power level of the auxiliary power source; and
transmit the failsafe mode unlock signal to the actuated electro-mechanical lock on the modular cargo storage system over the common modular component power and data transport bus to cause the actuated electro-mechanical lock to unlock the set of actuated set of latches in response to the detected adverse power level of the auxiliary power source.

59. The modular autonomous bot apparatus assembly of embodiment 32, wherein the autonomous controller is further programmatically adapted and configured to be operative to:
generate a failsafe mode unlock signal for the actuated electro-mechanical lock disposed on the modular cargo storage system after transmitting a request for assistance to a server; and
transmit the failsafe mode unlock signal to the actuated electro-mechanical lock on the modular cargo storage system over the common modular component power and data transport bus to cause the actuated electro-mechanical lock to unlock the set of actuated set of latches in response to the detected adverse power level of the auxiliary power source.

60. The modular autonomous bot apparatus assembly of embodiment 32, wherein the autonomous controller is further programmatically adapted and configured to be operative to:
generate a failsafe mode unlock signal for the actuated electro-mechanical lock disposed on the modular cargo storage system after transmitting a request for assistance to an external wireless node; and
transmit the failsafe mode unlock signal to the actuated electro-mechanical lock on the modular cargo storage system over the common modular component power and data transport bus to cause the actuated electro-mechanical lock to unlock the set of actuated set of latches in response to the detected adverse power level of the auxiliary power source.

60. The modular autonomous bot apparatus assembly of embodiment 1, wherein the modular cargo storage system further comprises at least one shelving separator disposed within the payload support area and detachable mounted to at least one of the folding structural walls, the shelving separator partioning the payload area into a plurality of payload compartments.

61. The modular autonomous bot apparatus assembly of embodiment 60, wherein the modular cargo storage system further comprises a climate control module disposed within one of the payload compartments, the climate control module being coupled to the common modular component power and data transport bus to at least power the climate control module, wherein the climate control module being operative to alter an environment within the one of the payload compartments to maintain a desired environment within the one of the payload compartments.

62. The modular autonomous bot apparatus assembly of embodiment 61, wherein the climate control module is attached to one of the folding structural walls.

63. The modular autonomous bot apparatus assembly of embodiment 61, wherein the climate control module is attached to the at least one shelving separator.

64. The modular autonomous bot apparatus assembly of embodiment 61, wherein the climate control module is detachably disposed within the one of the payload compartments.

65. The modular autonomous bot apparatus assembly of embodiment 60, wherein the modular cargo storage system further comprises:
a first detachable climate control module disposed within a first of the payload compartments, the first climate control module being coupled to the common modular component power and data transport bus to at least power the first climate control module, wherein the first climate control module being operative to alter an environment within the first of the payload compartments to maintain a first desired environment within the first of the payload compartments; and
a second detachable climate control module disposed within a second of the payload compartments, the second climate control module being coupled to the common modular component power and data transport bus to at least power the second climate control module, wherein the second climate control module being operative to alter an environment within the second of the payload compartments to maintain a second desired environment within the second of the payload compartments.

65. A modular autonomous bot apparatus assembly for transporting an item being shipped, comprising:
   a modular mobility base comprising
      a steerable powered base platform responsive to navigation inputs to cause changes to a movement and path of the steerable powered base platform,
      a plurality of base sensors disposed on the steerable powered base platform, the sensors being operative to generate base feedback sensor data on an object in the path of the modular mobility base,
      a set of actuators for tilting an orientation of the steerable powered base platform relative to the ground,
      a mobility controller disposed as part of the base platform, the mobility controller being coupled to the base sensors and the set of actuators, the mobility controller being operative to receive the base feedback sensor data and generate the navigation inputs, and
      a first interface to a common modular component power and data transport bus, the common modular component power and data transport bus being coupled to at least the mobility controller;
   a modular auxiliary power module detachably connected to the modular mobility base, the modular auxiliary power module comprising
      a base adapter platform having a payload area on top of the base adapter platform,
      an auxiliary power source disposed as part of the base adapter platform,
      an articulating cargo door extending from a side of the base adapter platform, and
      a second interface to the common modular component power and data transport bus, the common modular component power and data transport bus being coupled to at least the auxiliary power source so as to supply power onto the common modular component power and data transport bus;
   a modular cargo storage module detachably connected to the modular auxiliary power module, the modular cargo storage module comprising
      a set of folding structural walls assembled on the base adapter platform to partially enclose a payload area on at least three sides above the base adapter platform and forming vertical boundaries above the payload area with the articulating cargo door of the modular auxiliary power module,
      a locking handle that causes the modular cargo storage system to latch to the base adapter platform, and
      a third interface to the common modular component power and data transport bus;
   a modular mobile autonomy module detachably connected to a top of the folding structure walls of the modular cargo storage module, the modular mobile autonomy module completing the enclosure of the payload area when connected to the top of the folding structure walls of the modular cargo storage module, the modular mobile autonomy module comprising
      a plurality of human interaction interfaces disposed on the modular mobile autonomy module,
      a plurality of autonomy module sensors disposed on the modular mobile autonomy module,
      an autonomous controller with interfacing circuitry coupled to the human interaction interfaces and the autonomy module sensors on the modular mobile autonomy module,
      a fourth interface to the common modular component power and data transport bus, the common modular component power and data transport bus being coupled to at least the autonomous controller, and
      a wireless communication interface coupled to the autonomous controller, the wireless communication interface being operative to provide a wireless communication path to an external wireless node disposed external to the modular autonomous bot apparatus assembly.
   wherein the autonomous controller of the modular mobile autonomy control module is programmatically adapted and configured to be operative to at least
      receive information from the mobility controller through at least the first common modular component power and data transport bus, the received information being about the base feedback sensor data,
      receive onboard sensor data from the autonomy module sensors,
      generate a steering control command and a propulsion control command based at least upon the location data from the location circuitry, the received information on the base feedback sensor data from the mobility controller, the onboard sensor data as received by the autonomous controller from the autonomy module sensors, and destination information data maintained by the autonomous controller,
      transmit the steering control command and the propulsion control command through at least the fourth common modular component power and data transport bus to the first common modular component power and data transport bus for receipt by the mobility controller, and
      generate transport and delivery information to provide on the human interaction interfaces.

66. A modular autonomous bot apparatus assembly for transporting an item being shipped, comprising:
   a modular mobility base comprising
      a base platform,
      a mobility controller disposed as part of the base platform,
      a propulsion system on the base platform, the propulsion system being responsive to inputs from the mobility controller,
      a steering system coupled to the propulsion system, the steering system responsive to inputs from the mobility controller and operative to cause changes to movement of the modular mobility base,
      a plurality of sensors coupled to the mobility controller and disposed on the base platform, the sensors being operative to autonomously detect objects and obstacles in the path of the modular mobility base and provide feedback data to the mobility controller on detections, and
      a set of actuators for tilting the orientation of the base platform relative to the parts of the propulsion system that contact the ground;
   a modular auxiliary power module affixed to the powered mobility base, the auxiliary power module comprising at least
      a power connection that provides power to the powered mobility base, and an articulating cargo door extending from a side of the auxiliary power module;
a modular cargo storage system affixed to the auxiliary power module, the modular cargo storage system comprising
a set of folding structural walls configured to partially enclose a payload area on at least three sides above the base platform and forming vertical boundaries of the payload area with the articulating cargo door of the auxiliary power module
a locking handle that causes the modular cargo storage system to latch to the base platform, and
a power and data transport bus that provides communication and power conduit up from the modular auxiliary power module and the modular mobility base; and
a modular mobile autonomy module connected to a top edge of the folding structure walls of the cargo storage system, the mobile autonomy module completing the enclosure of the payload area when connected to the top edge of the folding structure walls of the modular cargo storage system, the mobile autonomy module comprising
a plurality of human interaction interfaces disposed on edges of the mobile autonomy module,
a plurality of sensors disposed on the mobile autonomy module,
a controller with interfacing circuitry coupled to the human interaction interfaces and sensors on the mobile autonomy module and with the power and data transport bus for operative communications with the powered mobility base, and
a wireless communication interface coupled to the controller.

67. A method of on-demand building of a modular autonomous bot apparatus assembly that transports an item being shipped, the method comprising the steps of:
receiving, by an assembly server, a request for assembly of the modular autonomous bot apparatus assembly;
generating, by the assembly server, an assigned dispatch use profile that identifies a type of each of a modular mobility base, a modular auxiliary power module, a modular cargo storage system, and a modular mobile autonomy control module to be used as authorized parts of the modular autonomous bot apparatus assembly based on the request for assembly;
detachably mounting a selected modular mobility base to a selected modular auxiliary power module using an interlocking alignment interface disposed on each of the selected modular mobility base and the selected modular auxiliary power module;
detachably mounting a selected modular cargo storage system to a top of the selected modular auxiliary power module;
detachably mounting a selected modular mobile autonomy control module to a top of the selected modular cargo storage system;
securing the selected modular cargo storage system to each of the selected modular auxiliary power module and the selected modular mobile autonomy control module using a locking handle actuating at least one set of actuated latches disposed on the selected modular cargo storage system;
downloading, by the assembly server, the assigned dispatch use profile for the modular autonomous bot apparatus assembly to the selected modular mobile autonomy control module; and
authenticating each of the selected modular mobility base, the selected modular auxiliary power module, the selected modular cargo storage system according to authentication information in the assigned dispatch use profile.

68. The method of embodiment 67, wherein the authenticating step comprises a component-to-component secure handshaking between proximately attached ones of the selected modular mobility base, the selected modular auxiliary power module, the selected modular cargo storage system, and the selected modular mobile autonomy control module.

69. The method of embodiment 68, wherein the component-to-component secure handshaking comprises a challenge and security credential response between proximately attached ones of the selected modular mobility base, the selected modular auxiliary power module, the selected modular cargo storage system, and the selected modular mobile autonomy control module.

70. The method of embodiment 67, wherein the authenticating step comprises authenticating, by the selected modular mobile autonomy control module, each of the selected modular mobility base, the selected modular auxiliary power module, and the selected modular cargo storage system according to the authentication information in the assigned dispatch use profile.

71. The method of embodiment 67, wherein the authenticating step comprises a component-to-component secure handshaking between the selected modular mobile autonomy control module and each of the selected modular mobility base, the selected modular auxiliary power module, and the selected modular cargo storage system according to the authentication information in the assigned dispatch use profile.

72. The method of embodiment 71, wherein the component-to-component secure handshaking comprises a challenge and security credential response between the selected modular mobile autonomy control module and each of the selected modular mobility base, the selected modular auxiliary power module, and the selected modular cargo storage system according to the authentication information in the assigned dispatch use profile.

73. The method of embodiment 71 further comprising the step of transmitting a replacement component request message to the assembly server by the selected modular mobile autonomy control module, the replacement component request message indicating that one or more of the selected modular mobility base, the selected modular auxiliary power module, and the selected modular cargo storage system are not authenticated modular components based upon the component-to-component secure handshaking between the selected modular mobile autonomy control module and each of the selected modular mobility base, the selected modular auxiliary power module, and the selected modular cargo storage system.

74. The method of embodiment 73, wherein receipt of the replacement component request message causing the assembly server to initiate replacement of the one of the selected modular mobility base, the selected modular auxiliary power module, and the selected modular cargo storage system indicated as being not authenticated modular components for the modular autonomous bot apparatus assembly according to the authentication information in the assigned dispatch use profile.

75. The method of embodiment 67 further comprising the step of causing, by the assembly server, each of the selected modular mobility base, the selected modular auxiliary power module, the selected modular cargo storage system, and the selected modular mobile autonomy control module to be pulled from a modular bot component storage according to the assigned dispatch use profile.

76. The method of embodiment 67 further comprising the step of causing, by the assembly server, each of the selected modular mobility base, the selected modular auxiliary power module, the selected modular cargo storage system, and the selected modular mobile autonomy control module to be selected from a modular bot component storage according to a desired logistics operation identified in the assigned dispatch use profile.

77. The method of embodiment 76, wherein the selected modular cargo storage system from the modular bot component storage is selected based upon a cargo size characteristic for the desired logistics operation.

78. The method of embodiment 76, wherein the selected modular cargo storage system from the modular bot component storage is selected based upon an organized storage characteristic for the desired logistics operation.

79. The method of embodiment 76, wherein the selected modular cargo storage system from the modular bot component storage is selected based upon an environmental storage characteristic for the desired logistics operation.

80. The method of embodiment 76, wherein the selected modular mobility base from the modular bot component storage is selected based upon an anticipated path for the desired logistics operation.

81. The method of embodiment 76, wherein the selected modular mobility base from the modular bot component storage is selected based upon a base sensor requirement for the desired logistics operation.

82. The method of embodiment 76, wherein the selected modular auxiliary power module from the modular bot component storage is selected based upon a power requirement for the desired logistics operation.

83. The method of embodiment 76, wherein the selected modular auxiliary power module from the modular bot component storage is selected based upon an articulated delivery assistance requirement for the desired logistics operation.

84. The method of embodiment 76, wherein the selected modular mobile autonomy control module from the modular bot component storage is selected based upon an autonomy module sensor requirement for the desired logistics operation.

85. The method of embodiment 67 further comprising the step of causing, by the assembly server, each of the selected modular mobility base, the selected modular auxiliary power module, the selected modular cargo storage system, and the selected modular mobile autonomy control module to be pulled from a fleet modular bot component storage according to one of a plurality of licensed fleet use profiles, the one of the licensed fleet use profiles being the assigned dispatch use profile.

86. The method of embodiment 67 further comprising the step of dispensing at least one of the selected modular mobility base, the selected modular auxiliary power module, the selected modular cargo storage system, and the selected modular mobile autonomy control module from a vending machine.

87. The method of embodiment 67 further comprising the step of dispensing the selected modular cargo storage system to be used as one of the authorized parts of the modular autonomous bot apparatus assembly from a vending machine maintaining a plurality of different sized modular cargo storage systems.

88. The method of embodiment 67 further comprising the steps of:
receiving, by a vending machine, a selection of at least one of the selected modular mobility base, the selected modular auxiliary power module, the selected modular cargo storage system, and the selected modular mobile autonomy control module, the selection being received from the assembly server in response to the request for assembly of the modular autonomous bot apparatus assembly, the selection being consistent with the assigned dispatch use profile identifying the type of each of the selected modular mobility base, the selected modular auxiliary power module, the selected modular cargo storage system, and the selected modular mobile autonomy control module to be used as the authorized parts of the modular autonomous bot apparatus assembly based on the request for assembly; and
dispensing the selected one of the modular mobility base, the selected auxiliary power module, the selected modular cargo storage system, and the selected modular mobile autonomy control module from the vending machine.

89. The method of embodiment 67 further comprising the step of dispensing a detachable module from a vending machine, the detachable module for deployment within the selected modular cargo storage system comprising one from a group consisting of a detachable climate control module, a detachable sensor pod, and a detachable separator.

90. The method of embodiment 89, wherein the detachable climate control module dispensed from the vending machine comprises one of a plurality of types of detachable climate control modules available for dispensing from the vending machine, wherein each of the different types of detachable climate control modules has a different environmental control range.

91. The method of embodiment 89, wherein the detachable sensor pod dispensed from the vending machine comprises one of a plurality of types of detachable sensor pods available for dispensing from the vending machine, wherein each of the different types of detachable sensor pods having a different characteristic type of sensor.

Further Embodiment G—Methods of Performing a Dispatched Logistics Operation Related to an Item Being Shipped and Using a Modular Autonomous Bot Apparatus Assembly and a Dispatch Server 1. A method of performing a dispatched logistics operation related to an item being shipped and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to temporarily maintain the item being shipped within the modular autonomous bot apparatus assembly, and a modular mobile autonomy control module that autonomously controls operation of the modular autonomous bot apparatus assembly, the method comprising the steps of:
receiving, by the modular mobile autonomy control module, a dispatch command from the dispatch server, the dispatch command including at least destination information and authentication information related to a dispatched logistics operation;
authenticating, by the modular mobile autonomy control module, that each of the modular mobile autonomy control module, the modular mobility base, the modular auxiliary power module, and the modular cargo storage system are compatible with the dispatched logistics operation;

receiving, by the modular cargo storage system, the item being shipped;

autonomously causing, by the modular mobile autonomy control module, the modular mobility base to move from an origin location on a route to a destination location identified by the destination information;

receiving delivery recipient authentication input by the modular mobile autonomy control module from a delivery recipient disposed external to the modular autonomous bot apparatus assembly, the delivery recipient authentication input correlating to a portion of the authentication information related to the dispatched logistics operation indicating the delivery recipient that provided the delivery recipient authentication input is an authorized delivery recipient for the item being shipped within the module cargo storage system;

providing, by the modular cargo storage system, selective access to the item being shipped within the modular cargo storage system after the delivery recipient authentication input received correlates to the portion of the authentication information indicating the delivery recipient providing the delivery recipient authentication input is the authorized delivery recipient; and autonomously causing, by the modular mobile autonomy control module, the modular mobility base to move from the destination location on a return route to the origin location after the item being shipped is detected to be removed from within the modular cargo storage system.

2. The method of embodiment 1, wherein the step of autonomously causing the modular mobility base to move from the origin location on the route to the destination location identified by the destination information comprises autonomously causing, by the modular mobile autonomy control module, the modular mobility base to move from the origin location to the destination location while avoiding a collision with an obstacle in a path on the route to the destination location using a plurality of sensors disposed on at least one of the modular mobility base and the modular mobile autonomy control module.

3. The method of embodiment 1, wherein the step of autonomously causing the modular mobility base to move from the origin location on the route to the destination location identified by the destination information comprises autonomously causing, by the modular mobile autonomy control module, the modular mobility base to move from the origin location to the destination location while interacting with a wireless building facility node to actuate a pathway obstacle disposed in a path on the route to the destination location.

4. The method of embodiment 3, wherein the pathway obstacle comprises an actuated door controlled by the wireless building facility node.

5. The method of embodiment 3, wherein the pathway obstacle comprises an actuated elevator controlled by the wireless building facility node.

6. The method of embodiment 3, wherein the pathway obstacle comprises an actuated lock controlled by the wireless building facility node.

7. The method of embodiment 3, wherein interacting with the wireless building facility node to actuate the pathway obstacle comprises:

establishing an authorized association pairing between the modular mobile autonomy control module and the wireless building facility node based upon the authentication information related to the dispatched logistics operation; and causing the wireless building facility node to actuate the pathway obstacle after establishing the authorized association pairing between the modular mobile autonomy control module and the wireless building facility node.

8. The method of embodiment 1, wherein the step of autonomously causing the modular mobility base to move from the origin location on the route to the destination location identified by the destination information comprises autonomously causing, by the modular mobile autonomy control module, the modular mobility base to move from the original location to the destination location while engaging a pathway obstacle disposed in a path on the route to the destination location using an articulating arm disposed on the modular autonomous bot apparatus assembly and using a plurality of sensors disposed on at least one of the modular mobility base and the modular mobile autonomy control module.

9. The method of embodiment 8, wherein the pathway obstacle comprises a manually actuated door.

10. The method of embodiment 8, wherein the pathway obstacle comprises a manually actuated elevator.

11. The method of embodiment 8, wherein the pathway obstacle comprises a manually actuated lock.

12. The method of embodiment 8, wherein engaging the pathway obstacle using the articulating arm and sensors comprises:

guiding, by the modular mobile autonomy control module, the articulating arm to a control element of the pathway obstacle using one or more of the sensors disposed on at least one of the modular mobility base and the modular mobile autonomy control module; and actuating the pathway obstacle, by the modular mobile autonomy control module, once the articulating arm engages the control element of the pathway obstacle.

13. The method of embodiment 12, wherein the control element of the pathway obstacle comprises one from the group consisting of a handle for the pathway obstacle, a button for the pathway obstacle, a switch for the pathway obstacle, and a portion of a control panel for the pathway obstacle.

14. The method of embodiment 1, wherein the authentication information related to the dispatched logistics operation includes logistical constraint information on the dispatched logistics operation; and wherein the step of authenticating, by the modular mobile autonomy control module, that each of the modular mobility base, the modular auxiliary power module, and the modular cargo storage system are compatible with the dispatched logistics operation is based at least upon a comparison of each of the modular mobility base, the modular auxiliary power module, and the modular cargo storage system to the logistical constraint information on the dispatched logistics operation.

15. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

16. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

17. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

18. The method of embodiment 1, wherein the delivery recipient authentication input received by the modular mobile autonomy control module is provided by the delivery recipient through an external wireless node disposed external to the modular autonomous bot apparatus assembly.

19. The method of embodiment 18, wherein the delivery recipient authentication input received by the modular mobile autonomy control module comprises an access code provided by the delivery recipient through the external wireless node disposed external to the modular autonomous bot apparatus assembly.

20. The method of embodiment 18, wherein the delivery recipient authentication input received by the modular mobile autonomy control module comprises a biometric input provided by the delivery recipient through the external wireless node disposed external to the modular autonomous bot apparatus assembly.

21. The method of embodiment 1, wherein the authentication information related to the dispatched logistics operation includes an identifier of the authorized delivery recipient for the item being shipped as part of the dispatched logistics operation; and
wherein the step of receiving the delivery recipient authentication input comprises:
detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
authenticating, by the modular mobile autonomy control module, that the external wireless node is associated with the authorized delivery recipient for the item being shipped within the modular cargo storage system based upon the identifier of the authorized delivery recipient and identifier information within the detected advertising signal broadcast from the external wireless node.

22. The method of embodiment 1, wherein the authentication information related to the dispatched logistics operation includes an identifier of the authorized delivery recipient for the item being shipped as part of the dispatched logistics operation; and
wherein the step of receiving the delivery recipient authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched logistics operation.

23. The method of embodiment 1, wherein the step of receiving the item being shipped comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

24. The method of embodiment 23, wherein actuating, by the modular mobile autonomy control module, the actuated cargo door comprises actuating an actuated joint on the actuated cargo door to cause the actuated cargo door to move from the closed position to the open position.

25. The method of embodiment 23, wherein actuating, by the modular mobile autonomy control module, the actuated cargo door further comprises actuating an electro-mechanical lock on the actuated cargo door to cause the actuated cargo door to unlock before moving from the closed position to the open position.

26. The method of embodiment 1, wherein the step of receiving the item being shipped comprises actuating, by the modular mobile autonomy control module, an actuated sliding arm disposed on the modular cargo storage system to move the item being shipped into a payload area within the modular cargo storage system.

27. The method of embodiment 1, wherein the step of receiving the item being shipped comprises actuating, by the modular mobile autonomy control module, an actuated grabbing arm disposed on the modular cargo storage system to grab and move the item being shipped into a payload area within the modular cargo storage system as part of receiving the item being shipped.

28. The method of embodiment 1, wherein the step of receiving the item being shipped comprises actuating, by the modular mobile autonomy control module, an actuated belt surface disposed on the modular auxiliary power module as a movable support surface exposed within a payload area inside the modular cargo storage system, the actuated belt surface being operative when actuated to cause the item being shipped as placed on the actuated belt surface to move within the payload area as part of receiving the item being shipped.

29. The method of embodiment 1, wherein the step of providing selective access to the item being shipped comprises actuating, by the modular mobile autonomy control module, an actuated cargo door disposed on the modular auxiliary power module to an open position once the delivery recipient authentication input correlates to a portion of the authentication information related to the dispatched logistics operation, wherein the actuated cargo door provides a seal to a payload area within the modular cargo storage system when the actuated cargo door is in a closed position and the actuated cargo door provides access to the payload area within the modular cargo storage system when the actuated cargo door is in the open position.

30. The method of embodiment 29, wherein actuating, by the modular mobile autonomy control module, the actuated cargo door comprises actuating an actuated joint on the actuated cargo door to cause the actuated cargo door to move from the closed position to the open position.

31. The method of embodiment 29, wherein actuating, by the modular mobile autonomy control module, the actuated cargo door further comprises actuating an electro-mechanical lock on the actuated cargo door to cause the actuated cargo door to unlock before moving from the closed position to the open position.

32. The method of embodiment 1, wherein the step of providing selective access to the item being shipped comprises actuating, by the modular mobile autonomy control module, an actuated sliding arm disposed on the modular cargo storage system to move the item being shipped out from a payload area within the modular cargo storage system.

33. The method of embodiment 1, wherein the step of providing selective access to the item being shipped comprises actuating, by the modular mobile autonomy control module, an actuated grabbing arm disposed on the modular cargo storage system to grab and move the item being shipped out from a payload area within the modular cargo storage system.

34. The method of embodiment 1, wherein the step of providing selective access to the item being shipped comprises actuating, by the modular mobile autonomy control module, an actuated belt surface disposed on the modular auxiliary power module as a movable support surface exposed within a payload area inside the modular cargo storage system, the actuated belt surface being operative when actuated to cause the item being shipped as placed on the actuated belt surface to move out from within the payload area.

35. The method of embodiment 1, wherein the step of receiving the item being shipped further comprises:
    confirming that the item received corresponds to the dispatched logistics operation based upon a readable identification on the item received; and
    receiving, by the modular mobile autonomy control module, a confirmation input acknowledging that the item received corresponds to the dispatched logistics operation based upon the readable identification on the item received.

36. The method of embodiment 35, wherein the readable identification comprises a human readable identification disposed on the item received.

37. The method of embodiment 35, wherein the readable identification comprises a machine readable identification disposed on the item received.

38. The method of embodiment 35, wherein the confirmation input comprises input received on a user input panel disposed on the modular cargo storage system and operatively coupled to the modular mobile autonomy control module.

39. The method of embodiment 1, wherein the step of receiving the item being shipped further comprises:
    scanning, by a payload monitoring sensor on the modular mobile autonomy control module, a payload area within the modular cargo storage system;
    detecting, by modular mobile autonomy control module, the item being shipped within the payload area based upon scan data generated by the payload monitoring sensor; and
    confirming that the item detected within the payload area corresponds to the dispatched logistics operation based upon a machine readable identification on the item received as indicated by the scan data generated by the payload monitoring sensor.

40. The method of embodiment 1, further comprising generating a display alert for the authorized delivery recipient on a display on the modular mobile autonomy control module once the modular autonomous bot apparatus assembly is within a threshold notification range of the destination location identified by the destination information.

41. The method of embodiment 1, further comprising generating an audio notification for the authorized delivery recipient on a speaker on the modular mobile autonomy control module once the modular autonomous bot apparatus assembly is within a threshold notification range of the destination location identified by the destination information.

42. The method of embodiment 1, further comprising transmitting a delivery notification message to an external wireless node identified to be related to the delivery recipient once the modular autonomous bot apparatus assembly is within a threshold notification range of the destination location identified by the destination information.

43. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

44. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

45. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

46. The method of embodiment 1, wherein the origin location comprises a storage location on a predetermined floor of a multi-level facility where the modular autonomous bot apparatus assembly is maintained until dispatched for the dispatched logistics operation; and
    wherein the destination location is located on another floor of the multi-level facility.

47. The method of embodiment 1, wherein the origin location comprises a multi-component storage location on a predetermined floor of a multi-level facility where each of the modular mobility base, the modular auxiliary power module, the modular cargo storage system, and the modular mobile autonomy control module used as part of the modular autonomous bot apparatus assembly is maintained in an unassembled form until on-demand assembly of the modular autonomous bot apparatus assembly occurs in response to the dispatch command from the dispatch server; and
    wherein the destination location is located on another floor of the multi-level facility.

48. The method of embodiment 1, wherein the origin location comprises a multi-component storage location on a predetermined floor of a multi-level facility where each of the modular mobility base, the modular auxiliary power module, the modular cargo storage system, and the modular mobile autonomy control module are leased components used as part of the modular autonomous bot apparatus assembly and where each of the leased components is maintained until dispatched as part of the modular autonomous bot apparatus assembly for the dispatched logistics operation; and wherein the destination location is located on another floor of the multi-level facility.

49. The method of embodiment 1, wherein the origin location for the dispatched logistics operation comprises a bot storage location where the modular autonomous bot apparatus assembly is initially maintained and wherein the destination information defines an intermediate loading location defined as part of the destination information;

wherein the step of receiving the item being shipped comprises
autonomously causing, by the modular mobile autonomy control module, the modular mobility base to move from the bot storage location to the intermediate loading location, and
receiving, by the modular cargo storage system, the item being shipped at the intermediate loading location; and wherein the step of autonomously causing the modular mobility base to move from the origin location on the route to the destination location identified by the destination information comprises causing, by the modular mobile autonomy control module, the modular mobility base to move from the intermediate loading location on an intermediate delivery route to the destination location identified by the destination information; and wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the destination location on the return route to the bot storage location after the item being shipped is detected to be removed from within the modular cargo storage system.

50. The method of embodiment 49, wherein the step of autonomously causing the modular mobility base to move from the bot storage location to the intermediate loading location comprises autonomously causing, by the modular mobile autonomy control module, the modular mobility base to move from the bot storage location to the intermediate loading location after receipt of a confirmation message from the dispatch server, the confirmation message verifying the intermediate loading location as provided by a sender of the item being shipped.

51. The method of embodiment 49, wherein the intermediate loading location comprises location coordinates.

52. The method of embodiment 49, wherein the intermediate loading location comprises an identified location relative to an office mapping.

53. The method of embodiment 49, wherein the intermediate loading location comprises a location of an external wireless node disposed outside of the modular autonomous bot apparatus assembly and related to a sender of the item being shipped.

54. The method of embodiment 49, wherein the intermediate loading location comprises a location of a master node disposed as part of a facility.

55. The method of embodiment 49, wherein the intermediate loading location comprises a lobby location of a multi-floor facility.

56. The method of embodiment 55, wherein the modular autonomous bot apparatus assembly is temporarily disposed at the lobby of the multi-floor facility as a hold-at-location logistics receptacle to receive the item being shipped before autonomously moving to the destination location with the item being shipped.

57. The method of embodiment 49, wherein the dispatch command from the dispatch server is initiated by a hotel customer request received by the dispatch server for delivery of the item being shipped;
wherein the bot storage location comprises a storage facility within a hotel building;
wherein the intermediate loading location defined as part of the destination information for the modular autonomous bot apparatus assembly comprises a location within the hotel designated by the delivery recipient sending the hotel customer request; and
further comprising the step of notifying the delivery recipient of an approaching delivery once the modular autonomous bot apparatus assembly is within a threshold notification range of the destination location identified by the destination information.

58. The method of embodiment 57, wherein the location within the hotel designated by the delivery recipient sending the hotel customer request comprises a designated hotel room within the hotel building.

59. The method of embodiment 57, wherein the location within the hotel designated by the delivery recipient sending the hotel customer request comprises a designated services area within the hotel building.

60. The method of embodiment 57, wherein the location within the hotel designated by the delivery recipient sending the hotel customer request comprises a designated conference room within the hotel building.

61. The method of embodiment 57, wherein the location within the hotel designated by the delivery recipient sending the hotel customer request comprises a location of an external mobile wireless node related to the delivery recipient.

61. The method of embodiment 49, wherein the dispatch command from the dispatch server is initiated by a hotel customer request received by the dispatch server for intermediate pickup and delivery of the item being shipped;
wherein the bot storage location comprises a storage facility within a hotel building;
wherein the intermediate loading location defined as part of the destination information for the modular autonomous bot apparatus assembly comprises a location within the hotel designated by the delivery recipient sending the hotel customer request; and
further comprising the step of notifying the delivery recipient of an approaching delivery once the modular autonomous bot apparatus assembly is within a threshold notification range of the destination location identified by the destination information.

63. The method of embodiment 1, wherein the origin location for the dispatched logistics operation comprises a bot storage location within a hotel building where the modular autonomous bot apparatus is initially maintained;
wherein the destination information comprises an intermediate loading location and a drop-off location;
wherein the step of receiving the item being shipped comprises
autonomously causing, by the modular mobile autonomy control module, the modular mobility base to move from the bot storage location to the intermediate loading location, notifying the delivery recipient of an approaching pickup once the modular autonomous bot apparatus assembly is within a threshold notification range of the intermediate loading location identified by the destination information, and receiving, by the modular cargo storage system, the item being shipped at the intermediate locating location; and wherein the step of autonomously causing the modular mobility base to move from the origin location on the route to the destination location identified by the destination information comprises causing, by the modular mobile autonomy control module, the modular mobility base to move from the intermediate loading location on an intermediate delivery route to the drop-off location identified by the destination information as the destination location; and wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the drop-off location on the return route to the bot storage location after the item being shipped is detected to be removed from within the modular cargo storage system.

64. The method of embodiment 63, wherein the step of autonomously causing, by the modular mobile autonomy control module, the modular mobility base to move from the intermediate loading location on the intermediate delivery route to the drop-off location identified by the destination information as the destination location comprises:

autonomously causing, by the modular mobile autonomy control module, the modular mobility base to move from the intermediate loading location on the intermediate delivery route to the drop-off location and holding at the drop-off location as a first holding location identified as part of the destination information, and autonomously causing, by the modular mobile autonomy control module, the modular mobility base to move from the first holding location to a secondary drop-off location identified as the location of an external mobile wireless node related to the delivery recipient.

65. The method of embodiment 64, wherein the step of autonomously causing, by the modular mobile autonomy control module, the modular mobility base to move from the first holding location to a secondary drop-off location identified as the location of an external mobile wireless node related to the delivery recipient comprises:

detecting, by the modular mobile autonomy control module, an advertising signal from the external mobile wireless node related to the delivery recipient;

establishing, by the modular mobile autonomy control module, an authorized secure association between the modular mobile autonomy control module and the external mobile wireless node based upon the authentication information related to the dispatched logistics operation; and autonomously causing, by the modular mobile autonomy control module, the modular mobility base to move from the first holding location to the secondary drop-off location after establishing the authorized secure association.

66. The method of embodiment 64, wherein the step of autonomously causing, by the modular mobile autonomy control module, the modular mobility base to move from the drop-off location on the return route to the bot storage location after the item being shipped is detected to be removed from within the modular cargo storage system comprises autonomously causing, by the modular mobile autonomy control module, the modular mobility base to move from the secondary drop-off location to the bot storage location after the item being shipped is detected to be removed from within the modular cargo storage system at the secondary drop-off location.

67. The method of embodiment 1, wherein the origin location for the dispatched logistics operation comprises a bot storage location within a hotel building where the modular autonomous bot apparatus is initially maintained;

wherein the destination information comprises an intermediate loading location and a drop-off location;

wherein the step of receiving the item being shipped comprises autonomously causing, by the modular mobile autonomy control module, the modular mobility base to move from the bot storage location to the intermediate loading location, detecting, by the modular mobile autonomy control module, an advertising signal from an external mobile wireless node related to the delivery recipient;

establishing, by the modular mobile autonomy control module, an authorized secure association between the modular mobile autonomy control module and the external mobile wireless node based upon the authentication information related to the dispatched logistics operation, the established authorized secure association authenticating the delivery recipient related to the external mobile wireless node;

transmitting, by the modular mobile autonomy control module, an impending pickup message to the external mobile wireless node about an approaching pickup of the item being shipped once the modular autonomous bot apparatus assembly has established the authorized secure association between the modular mobile autonomy control module and the external mobile wireless node; and receiving, by the modular cargo storage system, the item being shipped at the intermediate locating location;

wherein the step of autonomously causing the modular mobility base to move from the origin location on the route to the destination location identified by the destination information comprises causing, by the modular mobile autonomy control module, the modular mobility base move from the intermediate loading location towards the external mobile wireless node in a following mode as the external mobile wireless node moves towards the drop-off location; and wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the drop-off location to the bot storage location after the item being shipped is detected to be removed from within the modular cargo storage system at the drop-off location.

68. The method of embodiment 1, wherein the modular mobility base comprises a master mobility base, a slave mobility base, and an extended base adapter plate coupled to each of the master mobility base and the slave mobility base to support the item being shipped, each of the master mobility base and the slave mobility base being responsive to control input from the modular mobile autonomy control module to cause coordinated movement of the modular mobility base.

69. The method of embodiment 1, wherein the origin location for the dispatched logistics operation comprises a centralized bot storage location within a warehouse where the modular autonomous bot apparatus is initially maintained;
　　wherein the dispatch command sent by the dispatch server is initiated based upon a dispatch request received by the dispatch server, the dispatch request being sent from an authorized maintenance person related to the dispatched logistics operation, the dispatch command including identifier information of an external mobile wireless node operated by the authorized maintenance person; and
　　wherein the destination information comprises a mobile node location of the external mobile wireless node operated by the authorized maintenance person.

70. The method of embodiment 69, wherein the step of receiving the delivery recipient authentication input comprises:
　　detecting, by the modular mobile autonomy control module, an advertising signal from the external mobile wireless node as the delivery recipient authentication input as the modular autonomous bot apparatus assembly approaches the mobile node location of the external mobile wireless node; and
　　authenticating, by the modular mobile autonomy control module, that the external mobile wireless node is associated with the authorized delivery recipient for the item being shipped within the modular cargo storage system based upon (a) the identifier information of the external mobile wireless node from the dispatch command and (b) identifier information within the detected advertising signal broadcast from the external mobile wireless node.

71. The method of embodiment 69, wherein the delivery recipient authentication input received by the modular mobile autonomy control module is provided by the delivery recipient through a user input panel disposed on the modular autonomous bot apparatus coupled to the modular mobile autonomy control module.

72. The method of embodiment 69, wherein the delivery recipient authentication input received by the modular mobile autonomy control module comprises an access code provided by the delivery recipient through the user input panel disposed on the modular cargo storage system and operatively coupled to the modular mobile autonomy control module.

73. The method of embodiment 69, wherein the delivery recipient authentication input received by the modular mobile autonomy control module comprises a biometric input provided by the delivery recipient through the user input panel disposed on the modular cargo storage system and operatively coupled to the modular mobile autonomy control module.

74. The method of embodiment 69, wherein the modular mobility base compatible with the dispatched logistics operation comprises a master mobility base, a slave mobility base, and an extended base adapter plate coupled to each of the master mobility base and the slave mobility base to support the item being shipped, each of the master mobility base and the slave mobility base being responsive to control input from the modular mobile autonomy control module to cause coordinated movement of the modular mobility base.

75. The method of embodiment 69, wherein the modular cargo storage system compatible with the dispatched logistics operation comprises one of a plurality of different sized modular cargo storage systems, the one of the different sized modular cargo storage systems being compatible with a size parameter for the item being shipped as part of the dispatched logistics operation.

76. The method of embodiment 75, wherein the modular mobile autonomy control module compatible with the dispatched logistics operation comprises one of a plurality of different sized modular mobile autonomy control modules, the one of the different sized modular mobile autonomy control module being compatible with the one of the different sized modular cargo storage systems compatible with the size parameter for the item being shipped as part of the dispatched logistics operation.

77. The method of embodiment 49, wherein the bot storage location for the dispatched logistics operation comprises a centralized bot storage location within a hospital where the modular autonomous bot apparatus is initially maintained;
　　wherein the dispatch command sent by the dispatch server is initiated based upon a dispatch request received by the dispatch server, the dispatch request being sent from an authorized hospital staff related to the dispatched logistics operation, the dispatch command including identifier information of an external mobile wireless node operated by the authorized hospital staff; and
　　wherein the intermediate loading location comprises a medical supply storage.

78. The method of embodiment 77, wherein the medical supply storage comprises a pharmaceutical supply storage and the item being shipped comprises a prescribed medicine according to the dispatched logistics operation.

79. The method of embodiment 77, wherein the destination location comprises a predetermined location within the hospital for a patient currently located within the hospital.

80. The method of embodiment 77, wherein the destination information comprises a mobile node location of the external mobile wireless node operated by the authorized hospital staff.

81. The method of embodiment 77, further comprising the step of storing, by the modular mobile autonomy control module, the delivery recipient authentication input as chain of custody information for the item being shipped.

82. The method of embodiment 49, wherein the bot storage location for the dispatched logistics operation comprises a centralized bot storage location within a hospital where the modular autonomous bot apparatus is initially maintained;
　　wherein the dispatch command sent by the dispatch server is initiated based upon a dispatch request received by the dispatch server, the dispatch request being sent from an authorized hospital staff related to the dispatched logistics operation;
　　wherein the intermediate loading location comprises a hospital meal supply location;
　　wherein the modular cargo storage system having a segmented and insulated payload area for transporting a plurality of meals as the item being shipped, the modular cargo storage system further having a detachable climate control module responsive to climate control input from the modular mobile autonomy control module to maintain a desired environment within the modular cargo storage system.

83. The method of embodiment 49, wherein the bot storage location for the dispatched logistics operation comprises a centralized bot storage location within a hospital where the modular autonomous bot apparatus is initially maintained;
wherein the dispatch command sent by the dispatch server is initiated based upon a dispatch request received by the dispatch server, the dispatch request being sent from an authorized hospital staff related to the dispatched logistics operation;
wherein the intermediate loading location comprises a biohazard material repository location;
wherein the destination location comprises a biohazard material disposal location.

84. The method of embodiment 77, further comprising the steps of:
receiving, by the modular mobile autonomy control module, a wireless hospital alarm signal during the dispatched logistics operation; and
autonomously causing, by the modular mobile autonomy control module, the modular mobility base to interrupt movement and position the modular mobility base in a predetermined unobstructive position within a current environment of the modular autonomous bot apparatus assembly.

85. The method of embodiment 84, wherein the predetermined unobstructive position within the current environment of the modular autonomous bot apparatus assembly comprises a position against a wall within the current environment of the modular autonomous bot apparatus assembly as sensed by one or more sensors on the modular autonomous bot apparatus assembly.

86. The method of embodiment 85, wherein the predetermined unobstructive position within the current environment of the modular autonomous bot apparatus assembly comprises a position within the current environment of the modular autonomous bot apparatus assembly and sensed by the modular mobile autonomy control module to be unoccupied relative to movement sensed within the current environment of the modular autonomous bot apparatus assembly.

87. The method of embodiment 77, wherein the modular mobility base compatible with the dispatched logistics operation comprises a master mobility base, a slave mobility base, and an extended base adapter plate coupled to each of the master mobility base and the slave mobility base to support the item being shipped, each of the master mobility base and the slave mobility base being responsive to control input from the modular mobile autonomy control module to cause coordinated movement of the modular mobility base.

88. The method of embodiment 77, wherein the modular cargo storage system compatible with the dispatched logistics operation within the hospital comprises one of a plurality of different sized modular cargo storage systems, the one of the different sized modular cargo storage systems being compatible with a size parameter for the item being shipped as part of the dispatched logistics operation within the hospital.

89. The method of embodiment 88, wherein the modular mobile autonomy control module compatible with the dispatched logistics operation within the hospital comprises one of a plurality of different sized modular mobile autonomy control modules, the one of the different sized modular mobile autonomy control module being compatible with the one of the different sized modular cargo storage systems compatible with the size parameter for the item being shipped as part of the dispatched logistics operation within the hospital.

90. The method of embodiment 77, further comprising the step of generating, by the modular mobile autonomy control module, warning information on a display disposed on the modular mobile autonomy control module, wherein the warning information being related to the item being shipped within the modular cargo storage system as part of the dispatched logistics operation within the hospital.

91. The method of embodiment 77, wherein the warning information comprising a biohazard warning related to the item being shipped within the modular cargo storage system as part of the dispatched logistics operation within the hospital.

92. The method of embodiment 77, wherein the warning information comprising medical administration information related to medication being shipped within the modular cargo storage system as the item being shipped for the dispatched logistics operation within the hospital.

93. The method of embodiment 1, wherein the dispatch command sent by the dispatch server is initiated based upon a dispatch request received by the dispatch server, the dispatch request being sent from a sending entity related to the dispatched logistics operation, the dispatch command including sender identifier information of an external mobile wireless node operated by the sending entity and delivery recipient identifier information related to a delivery recipient for the item being shipped;
wherein the origin location for the dispatched logistics operation comprises a bot storage location where the modular autonomous bot apparatus is initially maintained and wherein the destination information defines an intermediate loading location defined as part of the destination information;
wherein the step of receiving the item being shipped comprises
autonomously causing, by the modular mobile autonomy control module, the modular mobility base to move from the bot storage location to the intermediate loading location,
receiving sending entity authentication input by the modular mobile autonomy control module from the sending entity, the sending entity authentication input correlating to a portion of the authentication information related to the dispatched logistics operation indicating the sending entity that provided the sending entity authentication input is an authorized provider for the item being shipped within the module cargo storage system as part of the dispatched logistics operation,
providing, by the modular cargo storage system, selective access to within the modular cargo storage system after the sending entity authentication input received correlates to the portion of the authentication information indicating the sending entity providing the sending entity authentication input is the authorized provider for the item being shipped,
receiving, by the modular cargo storage system, the item being shipped at the intermediate locating location, and
securing, by the modular mobile autonomy control module, the item being shipped within the modular cargo storage system;
wherein the step of autonomously causing the modular mobility base to move from the origin location on the route to the destination location identified by the destination information comprises causing, by the modular mobile autonomy control module, the modular mobility base to move from the intermediate loading location on an intermediate delivery route to the destination location identified by the destination information; and
wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the destination location on the return route to the bot storage location after the item being shipped is detected to be removed from within the modular cargo storage system.

94. The method of embodiment 93, wherein the item being shipped comprises one or more documents to be transported within the modular cargo storage system.

95. The method of embodiment 93, wherein the intermediate loading location comprises a mobile node location of the external mobile wireless node operated by the sending entity.

96. The method of embodiment 93, wherein the destination location comprises a mobile node location of an external mobile wireless node operated by the delivery recipient.

97. The method of embodiment 93, wherein the step of receiving the sending entity authentication input comprises:
detecting, by the modular mobile autonomy control module, an advertising signal from the external mobile wireless node operated by the sending entity as the sending entity authentication input as the modular autonomous bot apparatus assembly approaches the mobile node location of the external mobile wireless node operated by the sending entity; and
authenticating, by the modular mobile autonomy control module, that the external mobile wireless node operated by the sending entity is associated with the sending entity for the item being shipped within the modular cargo storage system based upon (a) the identifier information of the external mobile wireless node operated by the sending entity from the dispatch command and (b) identifier information within the detected advertising signal.

98. The method of embodiment 93, wherein the sending entity authentication input received by the modular mobile autonomy control module is provided by the sending entity through a user input panel disposed on the modular autonomous bot apparatus coupled to the modular mobile autonomy control module.

99. The method of embodiment 93, wherein the sending entity authentication input received by the modular mobile autonomy control module comprises an access code provided by the sending entity through the user input panel disposed on the modular cargo storage system and operatively coupled to the modular mobile autonomy control module.

100. The method of embodiment 93, wherein the sending entity authentication input received by the modular mobile autonomy control module comprises a biometric input provided by the sending entity through the user input panel disposed on the modular cargo storage system and operatively coupled to the modular mobile autonomy control module.

101. The method of embodiment 93, wherein the step of receiving the delivery recipient authentication input comprises:
detecting, by the modular mobile autonomy control module, an advertising signal from an external mobile wireless node operated by the delivery recipient as the delivery recipient authentication input as the modular autonomous bot apparatus assembly approaches the mobile node location of the external mobile wireless node operated by the delivery recipient; and
authenticating, by the modular mobile autonomy control module, that the external mobile wireless node operated by the delivery recipient is associated with the delivery recipient for the item being shipped within the modular cargo storage system based upon (a) the delivery recipient identifier information from the dispatch command and (b) identifier information of the external mobile wireless node operated by the delivery recipient within the detected advertising signal.

102. The method of embodiment 93, wherein the delivery recipient authentication input received by the modular mobile autonomy control module is provided by the delivery recipient through a user input panel disposed on the modular autonomous bot apparatus coupled to the modular mobile autonomy control module.

103. The method of embodiment 93, wherein the delivery recipient authentication input received by the modular mobile autonomy control module comprises an access code provided by the delivery recipient through the user input panel disposed on the modular cargo storage system and operatively coupled to the modular mobile autonomy control module.

104. The method of embodiment 93, wherein the delivery recipient authentication input received by the modular mobile autonomy control module comprises a biometric input provided by the delivery recipient through the user input panel disposed on the modular cargo storage system and operatively coupled to the modular mobile autonomy control module.

105. The method of embodiment 93, further comprising the step of transmitting, by the modular mobile autonomy control module, a pickup notification to the sending entity of an approaching pickup as part of the dispatched logistics operation once the modular autonomous bot apparatus assembly is within a threshold notification range of the intermediate loading location identified by the destination information.

106. The method of embodiment 93, further comprising the step of transmitting, by the modular mobile autonomy control module, a departure notification to the delivery recipient of an estimated drop-off as part of the dispatched logistics operation once the modular autonomous bot apparatus assembly moves a threshold departure distance from the intermediate loading location.

107. The method of embodiment 106, wherein the departure notification includes an estimated time of arrival for the modular autonomous bot apparatus assembly to arrive at the destination location from a current location of the modular autonomous bot apparatus assembly.

108. The method of embodiment 93, further comprising the step of transmitting, by the modular mobile autonomy control module, a drop-off notification to the delivery recipient of an approaching drop-off as part of the dispatched logistics operation once the modular autonomous bot apparatus assembly is within a threshold notification range of the destination location identified by the destination information.

109. The method of embodiment 93, wherein the step of autonomously causing the modular mobility base to move from the destination location on the return route to the bot storage location after the item being shipped is detected to be removed from within the modular cargo storage system comprises:
   autonomously causing, by the modular mobile autonomy control module, the modular mobility base to move from the destination location back to the intermediate loading location after the item being shipped is detected to be removed from within the modular cargo storage system at the destination location and an additional item is detected to be placed within the modular cargo storage system at the destination location; and
   autonomously causing, by the modular mobile autonomy control module, the modular mobility base to move from the intermediate loading location to the bot storage location after the additional item is detected to be removed from within the modular cargo storage system at the intermediate loading location.

110. The method of embodiment 109, further comprising the steps of:
   receiving secondary sending entity authentication input by the modular mobile autonomy control module from the sending entity while at the intermediate loading location after the modular mobility base returns to the intermediate loading location, the secondary sending entity authentication input correlating to the portion of the authentication information related to the dispatched logistics operation indicating the sending entity that provided the secondary sending entity authentication input is the authorized provider for the item being shipped within the module cargo storage system as part of the dispatched logistics operation; and
   providing, by the modular cargo storage system, selective access to within the modular cargo storage system for removal of the additional item after the secondary sending entity authentication input received correlates to the portion of the authentication information indicating the sending entity providing the secondary sending entity authentication input is the authorized provider for the item being shipped.

111. The method of embodiment 93, wherein the step of autonomously causing the modular mobility base to move from the destination location on the return route to the bot storage location after the item being shipped is detected to be removed from within the modular cargo storage system comprises:
   autonomously causing, by the modular mobile autonomy control module, the modular mobility base to move from the destination location to a secondary delivery location after the item being shipped is detected to be removed from within the modular cargo storage system at the destination location and after an additional item is detected within the modular cargo storage system while at the destination location, the secondary delivery location being identified as part of the destination information related to the dispatched logistics operation; and
   autonomously causing, by the modular mobile autonomy control module, the modular mobility base to move from the secondary delivery location to the bot storage location after the additional item is detected to be removed from within the modular cargo storage system at the secondary delivery location.

112. The method of embodiment 111, further comprising the steps of:
   receiving third party entity authentication input by the modular mobile autonomy control module from a third party entity while at the secondary delivery location after the modular mobility base arrives at the secondary delivery location, the third party entity authentication input correlating to a portion of the authentication information related to the dispatched logistics operation indicating the third party entity that provided the third party entity authentication input is an authorized third party recipient for the additional item within the module cargo storage system as part of the dispatched logistics operation; and
   providing, by the modular cargo storage system, selective access to within the modular cargo storage system for removal of the additional item after the third party entity authentication input received correlates to the portion of the authentication information indicating the third party entity providing the third party entity authentication input is the authorized third party recipient for the additional item.

113. The method of embodiment 1, wherein the item being shipped comprises at least one of a plurality of components of a medical kit used for a medical procedure, the at least one of the components of the medical kit being unused as part of the medical procedure and in condition for use in a second medical procedure;
   wherein the origin location for the dispatched logistics operation comprises a bot storage location where the modular autonomous bot apparatus is initially maintained and wherein the destination information defines an intermediate return loading location defined as part of the destination information;
   wherein the destination location for the dispatched logistics operation comprises a centralized return location for one or more of the components of the medical kit;
   wherein the step of receiving the item being shipped comprises
      autonomously causing, by the modular mobile autonomy control module, the modular mobility base to move from the bot storage location to the intermediate return loading location,
      receiving returning entity medical personnel authentication input by the modular mobile autonomy control module from returning entity medical personnel related to the dispatched logistics operation, the returning entity medical personnel authentication input correlating to a portion of the authentication information related to the dispatched logistics operation indicating the returning entity medical personnel that provided the returning entity medical personnel authentication input is an authorized return supplier for the item being shipped within the module cargo storage system as part of the dispatched logistics operation,
      providing, by the modular cargo storage system, selective access to within the modular cargo storage system after the returning entity medical personnel authentication input received correlates to the portion of the authentication information indicating the returning entity medical personnel providing the returning entity medical personnel authentication input is the authorized return supplier for the item being shipped,
      receiving, by the modular cargo storage system, the item being shipped at the intermediate locating location, and securing, by the modular mobile autonomy control module, the item being shipped within the modular cargo storage system;

wherein the step of autonomously causing the modular mobility base to move from the origin location on the route to the destination location identified by the destination information comprises causing, by the modular mobile autonomy control module, the modular mobility base to move from the intermediate loading location on an intermediate delivery route to the destination location identified by the destination information; and wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the destination location on the return route to the bot storage location after the item being shipped is detected to be removed from within the modular cargo storage system.

114. The method of embodiment 113, wherein the intermediate loading location comprises a mobile node location of an external mobile wireless node operated by the returning entity medical personnel.

115. The method of embodiment 113, wherein the step of receiving the returning entity medical personnel authentication input comprises:

detecting, by the modular mobile autonomy control module, an advertising signal from the external mobile wireless node operated by the returning entity medical personnel as the returning entity medical personnel authentication input when the modular autonomous bot apparatus assembly approaches the mobile node location of the external mobile wireless node operated by the returning entity medical personnel; and authenticating, by the modular mobile autonomy control module, that the external mobile wireless node operated by the returning entity medical personnel is associated with the returning entity medical personnel for the item being shipped within the modular cargo storage system based upon (a) the identifier information of the external mobile wireless node operated by the returning entity medical personnel from the dispatch command and (b) identifier information within the detected advertising signal.

116. The method of embodiment 113, wherein the returning entity medical personnel authentication input received by the modular mobile autonomy control module is provided by the returning entity medical personnel through a user input panel disposed on the modular autonomous bot apparatus coupled to the modular mobile autonomy control module.

117. The method of embodiment 113, wherein the returning entity medical personnel authentication input received by the modular mobile autonomy control module comprises an access code provided by the returning entity medical personnel through the user input panel disposed on the modular cargo storage system and operatively coupled to the modular mobile autonomy control module.

118. The method of embodiment 113, wherein the returning entity medical personnel authentication input received by the modular mobile autonomy control module comprises a biometric input provided by the returning entity medical personnel through the user input panel disposed on the modular cargo storage system and operatively coupled to the modular mobile autonomy control module.

119. The method of embodiment 113, wherein the step of receiving the delivery recipient authentication input comprises:

detecting, by the modular mobile autonomy control module, an advertising signal from an external mobile wireless node operated by a centralized return location recipient as the delivery recipient authentication input as the modular autonomous bot apparatus assembly approaches the mobile node location of the external mobile wireless node operated by the centralized return location recipient; and authenticating, by the modular mobile autonomy control module, that the external mobile wireless node operated by the centralized return location recipient is associated with the centralized return location recipient for the item being shipped within the modular cargo storage system based upon (a) the delivery recipient identifier information from the dispatch command and (b) identifier information of the external mobile wireless node operated by the centralized return location recipient within the detected advertising signal.

120. The method of embodiment 113, wherein the delivery recipient authentication input received by the modular mobile autonomy control module is provided by the centralized return location recipient through a user input panel disposed on the modular autonomous bot apparatus coupled to the modular mobile autonomy control module.

121. The method of embodiment 113, wherein the delivery recipient authentication input received by the modular mobile autonomy control module comprises an access code provided by the centralized return location recipient through the user input panel disposed on the modular cargo storage system and operatively coupled to the modular mobile autonomy control module.

122. The method of embodiment 113, wherein the delivery recipient authentication input received by the modular mobile autonomy control module comprises a biometric input provided by the centralized return location recipient through the user input panel disposed on the modular cargo storage system and operatively coupled to the modular mobile autonomy control module.

123. The method of embodiment 113, further comprising the step of transmitting, by the modular mobile autonomy control module, a pickup notification to the returning entity medical personnel of an approaching pickup as part of the dispatched logistics operation once the modular autonomous bot apparatus assembly is within a threshold notification range of the intermediate loading location identified by the destination information.

124. The method of embodiment 113, further comprising the step of transmitting, by the modular mobile autonomy control module, a departure notification to a centralized return location recipient of an estimated drop-off as part of the dispatched logistics operation once the modular autonomous bot apparatus assembly moves a threshold departure distance from the intermediate loading location.

125. The method of embodiment 124, wherein the departure notification includes an estimated time of arrival for the modular autonomous bot apparatus assembly to arrive at the destination location from a current location of the modular autonomous bot apparatus assembly.

126. The method of embodiment 113, further comprising the step of transmitting, by the modular mobile autonomy control module, a drop-off notification to the centralized return location recipient of an approaching drop-off as part of the dispatched logistics operation once the modular autonomous bot apparatus assembly is within a threshold notification range of the destination location identified by the destination information.

127. The method of embodiment 93, wherein the step of autonomously causing the modular mobility base to move from the destination location on the return route to the bot storage location after the item being shipped is detected to be removed from within the modular cargo storage system comprises:
  autonomously causing, by the modular mobile autonomy control module, the modular mobility base to move from the destination location back to the intermediate loading location after the item being shipped is detected to be removed from within the modular cargo storage system at the destination location and an additional item is detected to have been placed within the modular cargo storage system at the destination location; and
  autonomously causing, by the modular mobile autonomy control module, the modular mobility base to move from the intermediate loading location to the bot storage location after the additional item is detected to be removed from within the modular cargo storage system at the intermediate loading location.

128. The method of embodiment 127, wherein the additional item comprises a replacement medical kit.

129. The method of embodiment 127, wherein the additional item comprises a second medical kit for a different type of medical procedure.

130. The method of embodiment 49, wherein the item being shipped comprises a plurality of documents collected for secure shredding;
  wherein the destination location comprises a centralized shred pickup facility; and
  wherein the intermediate loading location comprises a location of a container maintaining the documents collected for secure shredding.

131. The method of embodiment 130, wherein the item being shipped further comprises a container securely maintaining the plurality of documents collected for secure shredding.

132. The method of embodiment 130, wherein the intermediate loading location comprises an identified location relative to an office mapping of the container maintaining the documents collected for secure shredding.

133. The method of embodiment 130, wherein the intermediate loading location comprises a location of an external wireless node disposed outside of the modular autonomous bot apparatus assembly, the external wireless node being a part of the container maintaining the documents collected for secure shredding.

134. The method of embodiment 130, wherein the intermediate loading location comprises a mobile location of the external wireless node that is part of a mobile container maintaining the documents collected for secure shredding.

135. The method of embodiment 130, where the step of receiving the item being shipped comprises:
  receiving pickup authentication input by the modular mobile autonomy control module from a document supplier through a user input panel disposed on the modular autonomous bot apparatus coupled to the modular mobile autonomy control module; and
  providing, by the modular cargo storage system, selective access to within the modular cargo storage system for loading of the item being shipped after the pickup authentication input received correlates to a portion of the authentication information related to an authorized document supplier.

136. The method of embodiment 135, wherein the pickup recipient authentication input received by the modular mobile autonomy control module comprises an access code provided by the document supplier through the user input panel disposed on the modular cargo storage system and operatively coupled to the modular mobile autonomy control module.

137. The method of embodiment 135, wherein the pickup recipient authentication input received by the modular mobile autonomy control module comprises a biometric input provided by the document supplier through the user input panel disposed on the modular cargo storage system and operatively coupled to the modular mobile autonomy control module.

138. The method of embodiment 135, wherein the step of receiving the pickup recipient authentication input comprises:
  receiving pickup authentication input by the modular mobile autonomy control module by detecting an advertising signal from the external wireless node that is part of the container maintaining the documents collected for secure shredding and verifying the detected advertising signal includes identifier information that correlates to a portion of the authentication information related to an authorized document supplier for the container; and
  providing, by the modular cargo storage system, selective access to within the modular cargo storage system for loading of the item being shipped after the pickup authentication input received correlates to the portion of the authentication information related to the authorized document supplier.

139. The method of embodiment 130, where the delivery receipt authentication input comprises information received through a user input panel disposed on the modular autonomous bot apparatus coupled to the modular mobile autonomy control module.

140. The method of embodiment 130, wherein the delivery recipient authentication input comprises an access code provided by the delivery recipient through the user input panel disposed on the modular cargo storage system and operatively coupled to the modular mobile autonomy control module.

141. The method of embodiment 130, wherein the pickup recipient authentication input comprises a biometric input provided by the delivery recipient through the user input panel disposed on the modular cargo storage system and operatively coupled to the modular mobile autonomy control module.

142. The method of embodiment 133, wherein the authentication information related to the dispatched logistics operation includes an identifier of the authorized delivery recipient for the item being shipped as part of the dispatched logistics operation; and
  wherein the step of receiving the delivery recipient authentication input comprises:
    detecting, by the modular mobile autonomy control module, an advertising signal as the delivery recipient authentication input from an external wireless node related to the destination location within a predetermined range of the modular autonomous bot apparatus assembly once the modular autonomous bot apparatus assembly has arrived at the destination location identified by the destination information; and authenticating, by the modular mobile autonomy control module, that the external wireless node related to the destination location is associated with the authorized delivery recipient for the item being shipped within the modular cargo storage system based upon the identifier of the authorized delivery recipient and identifier information within the detected advertising signal broadcast from the external wireless node related to the destination location.

143. The method of embodiment 130, wherein the step of receiving the item being shipped comprises deploying an articulating arm disposed on the modular autonomous bot apparatus assembly and using a plurality of proximity and vision sensors disposed on at least one of the modular mobility base and the modular mobile autonomy control module to engage the item being shipped and placing the item being shipped within the modular cargo storage system.

144. The method of embodiment 130, wherein the step of receiving the item being shipped comprises:
guiding, by the modular mobile autonomy control module, the articulating arm to the item being shipped using one or more of the proximity and vision sensors disposed on at least one of the modular mobility base and the modular mobile autonomy control module;
engaging, by the articulating arm, the item being shipped; and
moving, by the articulating arm, the item being shipped to a position within the modular cargo storage system.

145. The method of embodiment 133, wherein the step of receiving the item being shipped comprises:
guiding, by the modular mobile autonomy control module, the articulating arm to a closable access point on the container using one or more of the proximity and vision sensors disposed on at least one of the modular mobility base and the modular mobile autonomy control module;
engaging, by the articulating arm, the closable access point on the container to enabled access to within the container;
engaging, by the articulating arm, the documents collected for secure shredding; and
moving, by the articulating arm, the documents collected for secure shredding to a position within the modular cargo storage system.

146. The method of embodiment 133, wherein the step of receiving the item being shipped comprises deploying an articulating arm disposed on the modular autonomous bot apparatus assembly and using a plurality of proximity and vision sensors disposed on at least one of the modular mobility base and the modular mobile autonomy control module to engage the container and place the container within the modular cargo storage system.

147. The method of embodiment 1, wherein the item being shipped comprises a plurality of documents collected for secure shredding;
wherein the destination location comprises a centralized shred pickup facility;
wherein the origin location for the dispatched logistics operation comprises a bot storage location where the modular autonomous bot apparatus is initially maintained and wherein the destination information defines a plurality of intermediate loading locations defined as part of the destination information;
wherein the step of receiving the item being shipped comprises:
autonomously causing, by the modular mobile autonomy control module, the modular mobility base to move from the bot storage location to a first of the intermediate loading locations,
receiving, by the modular cargo storage system, a first portion of the item being shipped at first of the intermediate locating locations,
autonomously causing, by the modular mobile autonomy control module, the modular mobility base to move from the first intermediate loading location to a second of the intermediate loading locations,
receiving, by the modular cargo storage system, a second portion of the item being shipped at first of the intermediate locating locations; and
wherein the step of autonomously causing the modular mobility base to move from the origin location on the route to the destination location identified by the destination information comprises causing, by the modular mobile autonomy control module, the modular mobility base to move from the second of the intermediate loading locations to the destination location identified by the destination information; and
wherein the step of autonomously causing the modular mobility base to move from the destination location on the return route to the origin location after the item being shipped is detected to be removed from within the modular cargo storage system comprises autonomously causing, by the modular mobile autonomy control module, the modular mobility base to move from the destination location on the return route to the bot storage location after each of at least the first portion of the item being shipped and the second portion of the item being shipped are detected to be removed from within the modular cargo storage system.

148. The method of embodiment 1, wherein the origin location comprises an extended hour centralized base depot for pharmaceutical prescription supplies where the modular autonomous bot apparatus is initially maintained;
wherein the dispatch command sent by the dispatch server is initiated based upon a dispatch request received by the dispatch server, the dispatch request being sent from an authorized pharmaceutical personnel at a remote pharmaceutical outlet served by the extended hour centralized base depot for pharmaceutical prescription supplies, the dispatch command being related to the dispatched logistics operation, the dispatch command including identifier information of an external mobile wireless node operated by the authorized pharmaceutical personnel; and
wherein the destination location identified by the destination information comprising a location of the remote pharmaceutical outlet.

149. The method of embodiment 148, wherein the destination information comprises a mobile node location of an external mobile wireless node operated by the authorized pharmaceutical person.

150. The method of embodiment 148, further comprising the step of generating, by the modular mobile autonomy control module, a first inventory data structure corresponding to the item being shipped upon receiving the item being shipped, wherein the first inventory data structure including a first chain of custody entry reflecting departure from the extended hour centralized base depot for pharmaceutical prescription supplies for the item being shipped in the custody of the modular autonomous bot apparatus assembly.

151. The method of embodiment 150, further comprising the step of generating, by the modular mobile autonomy control module, a second chain of custody entry within the first inventory data structure after arrival at the remote pharmaceutical outlet, the second chain of custody reflecting arrival from the extended hour centralized base depot for pharmaceutical prescription supplies for the item being shipped to the remote pharmaceutical outlet in the custody of the modular autonomous bot apparatus assembly.

152. The method of embodiment 151, further comprising the step of generating, by the modular mobile autonomy control module, a third chain of custody entry within the first inventory data structure after arrival at the remote pharmaceutical outlet and after detecting the item being shipped has been removed from within the modular cargo storage system, the third chain of custody reflecting the item being shipped changing custody to the remote pharmaceutical outlet from the modular autonomous bot apparatus assembly.

153. The method of embodiment 152, wherein the step of autonomously causing, by the modular mobile autonomy control module, the modular mobility base to move from the destination location on a return route to the origin location after the item being shipped is detected to be removed from within the modular cargo storage system comprises:
   monitoring, by the modular mobile autonomy control module, an unloading status of the modular cargo storage system using at least one sensor on at least one of the modular mobile autonomy control module and the modular cargo storage system;
   detecting when the item being shipped is removed from within the modular cargo storage system based upon sensor data from the at least one sensor; and
   generating the third chain of custody entry within the first inventory data structure when the sensor data reflects the item being shipped is no longer within the modular cargo storage system.

154. The method of embodiment 148, wherein the dispatch command sent by the dispatch server comprises one of a plurality of dispatch commands for different dispatched logistics operations from the extended hour centralized base depot for pharmaceutical prescription supplies to the remote pharmaceutical outlet, the dispatch commands being sent on a predetermined schedule for the remote pharmaceutical outlet.

155. The method of embodiment 148, wherein the dispatch command sent by the dispatch server comprises one of a plurality of dispatch commands for different dispatched logistics operations from the extended hour centralized base depot for pharmaceutical prescription supplies to a plurality of serviced remote pharmaceutical outlets, where the remote pharmaceutical outlet is one of the serviced remote pharmaceutical outlets by the extended hour centralized base depot for pharmaceutical prescription supplies.

156. The method of embodiment 148, wherein the authentication information related to the dispatched logistics operation comprises multi-level authentication information.

157. The method of embodiment 156, wherein the multi-level authentication information comprises at least (a) passcode authentication information and (b) identifier information of an external mobile wireless node operated by the authorized delivery recipient.

158. The method of embodiment 156, wherein the multi-level authentication information comprises at least (a) a first passcode authentication information related to a first communication path with the delivery recipient and (b) a second passcode authentication information related to a second communication path with the delivery recipient, wherein the first communication path being distinct from the second communication path.

159. The method of embodiment 148, wherein the multi-level authentication information comprises at least two from the group consisting of passcode authentication information, biometric scanning authentication information, device signature authentication information, and voice authentication information.

160. The method of embodiment 49, wherein the origin location comprises a location of a business entity for delivery services where the modular autonomous bot apparatus is initially maintained;
   wherein the dispatch command sent by the dispatch server is initiated based upon a dispatch request received by the dispatch server, the dispatch request being sent from the delivery recipient;
   further comprising the step of determining, by the dispatch server, if the dispatched logistics operation related to the dispatch request is a fulfillable type of dispatch logistics operation for the business entity for delivery services based upon a plurality of fulfillment requirements for the dispatched logistics operation related to the dispatch request, the determining step being performed prior to the authenticating step;
   wherein the step of authenticating, by the modular mobile autonomy control module, that each of the modular mobile autonomy control module, the modular mobility base, the modular auxiliary power module, and the modular cargo storage system are compatible with the dispatched logistics operation comprises verifying, by the modular autonomy control module, whether each of the modular mobile autonomy control module, the modular mobility base, the modular auxiliary power module, and the modular cargo storage system are compatible with the fulfillment requirements for the dispatched logistics operation related to the dispatch request prior to moving from the origin location; and
   further comprising the steps of:
      notifying, by the modular mobile autonomy control module, a supplier of the item being shipped of (a) an approaching pickup at the intermediate loading location and (b) an estimated time of arrival at the intermediate loading location before arriving at the intermediate loading location;
      receiving supplier authentication input by the modular mobile autonomy control module from the supplier disposed external to the modular autonomous bot apparatus assembly at the intermediate loading location before receiving the item being shipped, the supplier authentication input correlating to a portion of the authentication information related to the dispatched logistics operation indicating the supplier that provided the supplier authentication input is an authorized supplier for the item being shipped related to the dispatched logistics operation; and
      notifying, by the modular mobile autonomy control module, the delivery recipient of an approaching delivery after receiving the item being shipped at the intermediate loading location and notifying the delivery recipient of an estimated time of arrival at the destination location.

161. The method of embodiment 160, wherein the modular autonomous bot apparatus assembly comprises one of a plurality of leased modular autonomous bot apparatus assemblies to the business entity at the origin location.

162. The method of embodiment 160, wherein the modular autonomous bot apparatus assembly comprises a modular assembly of leased modular autonomous bot apparatus components under lease by the business entity at the origin location.

163. The method of embodiment 160, wherein at least one of the fulfillment requirements comprises a location parameter, the location parameter including the origin location and the destination location.

164. The method of embodiment 160, wherein at least one of the fulfillment requirements comprises a timing parameter for conducting the dispatched logistics operation relate to the dispatch request.

165. The method of embodiment 160, wherein at least one of the fulfillment requirements comprises a payload parameter for transporting the item being shipped as part of the dispatched logistics operation relate to the dispatch request.

166. The method of embodiment 160, wherein the step of receiving the item being shipped at the intermediate loading location comprises:
  generating, by the modular mobile autonomy control module, a loading assistance prompt message on a display disposed on the modular mobile autonomy control module, wherein the loading assistance prompt message providing information on the item being shipped to be provided by the supplier and instructions for placing the item being shipped within the modular cargo storage system as part of the dispatched logistics operation.

167. The method of embodiment 160, wherein the step of notifying, by the modular mobile autonomy control module, the delivery recipient of an approaching delivery after receiving the item being shipped at the intermediate loading location and notifying the delivery recipient of an estimated time of arrival at the destination location is performed after receiving the item being shipped at the intermediate loading location and before the modular mobility based moves from the intermediate loading location.

168. The method of embodiment 160, wherein the step of notifying, by the modular mobile autonomy control module, the delivery recipient of an approaching delivery after receiving the item being shipped at the intermediate loading location and notifying the delivery recipient of an estimated time of arrival at the destination location is performed once the modular autonomous bot apparatus assembly is within a threshold notification range of the destination location identified by the destination information.

169. The method of embodiment 160, further comprising the steps of:
  receiving, by the modular mobile autonomy control module, a delivery change notification in response to notifying the delivery recipient of the approaching delivery at the destination location; and
  altering, by the modular mobile autonomy control module, the intermediate delivery route according to the delivery change notification, the altering of the intermediate delivery route resulting in a modified delivery for the item being shipped according to the delivery change notification.

170. The method of embodiment 169, wherein the modified delivery comprises an altered time for delivery at the destination location.

171. The method of embodiment 169, wherein the modified delivery comprises an altered destination location for delivery of the item being shipped.

172. The method of embodiment 169, wherein the modified delivery comprises autonomously causing, by the modular mobile autonomy control module, the modular mobility base to move on a modified return route to a holding location before moving to an altered destination location for delivery of the item being shipped at an altered time for delivery at the altered destination location.

173. The method of embodiment 172, wherein the holding location comprises the intermediate loading location.

174. The method of embodiment 160, further comprising the step of verifying, by the modular mobile autonomy control module, an unload status of the item being shipped using one or more sensors on the modular mobile autonomy control module that monitors a payload area of the modular cargo storage system.

175. The method of embodiment 174, wherein the unload status reflects an identifier of the item being shipped that has been removed from within the modular cargo storage system.

176. The method of embodiment 160, further comprising the step of verifying, by the modular mobile autonomy control module, that an object removed from within the payload area of the modular cargo storage system using the one or more sensors is the item being shipped and authorized to be removed at the destination location according to the dispatched logistics operation.

177. The method of embodiment 176, further comprising a step of transmitting a warning message by the modular mobile autonomy control module to the dispatch server when the object removed from within the payload area of the modular cargo storage system using the one or more sensors is not the item being shipped and authorized to be removed at the destination location according to the dispatched logistics operation, the warning message indicating an unauthorized unloading of the modular cargo storage system and including sensor data from the one or more sensors.

178. The method of embodiment 176, further comprising a step of generating an audio warning message by the modular mobile autonomy control module when the object removed from within the payload area of the modular cargo storage system using the one or more sensors is not the item being shipped and authorized to be removed at the destination location according to the dispatched logistics operation, the audio warning message indicating an unauthorized unloading of the modular cargo storage system and requesting replacement of the object removed.

179. A method of performing a dispatched pickup logistics operation related to an item being shipped and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to temporarily maintain the item being shipped within the modular autonomous bot apparatus assembly, and a modular mobile autonomy control module that autonomously controls operation of the modular autonomous bot apparatus assembly, the method comprising the steps of:
  receiving, by the modular mobile autonomy control module and from the dispatch server, a dispatch command related to the dispatched pickup logistics operation, the dispatch command including at least destination information related to a pickup location, authentication information related to an authorized pickup entity, and shipment characteristics of the item being shipped;

authenticating, by the modular mobile autonomy control module, that each of the modular mobile autonomy control module, the modular mobility base, the modular auxiliary power module, and the modular cargo storage system are compatible with the dispatched pickup logistics operation based upon the shipment characteristics of the item being shipped as indicated in the dispatch command;

autonomously causing, by the modular mobile autonomy control module, the modular mobility base to move from an origin location on a route to the pickup location identified by the destination information;

receiving pickup entity authentication input by the modular mobile autonomy control module from a pickup entity disposed external to the modular autonomous bot apparatus assembly;

determining if the pickup entity authentication input correlates to the authentication information related to the authorized pickup entity according to the dispatch command;

providing, by the modular cargo storage system, selective access to the item being shipped within the modular cargo storage system only after the pickup entity authentication input received correlates to the authentication information related to the authorized pickup entity according to the dispatch command;

receiving, by the modular cargo storage system, the item being shipped; and autonomously causing, by the modular mobile autonomy control module, the modular mobility base to move from the pickup location on a return route to the origin location after the item being shipped is detected to be received within the modular cargo storage system.

180. The method of embodiment 179, wherein the dispatch command sent by the dispatch server is initiated based upon a dispatch request received by the dispatch server, the dispatch request being sent by the pickup entity related to the dispatched logistics operation, the dispatch command including identifier information of an external mobile wireless node operated by the authorized pickup entity as part of the authentication information.

181. The method of embodiment 180, wherein the pickup location comprises a mobile location of the external mobile wireless node operated by the authorized pickup entity.

182. The method of embodiment 179, wherein the step of receiving the item being shipped comprises:
monitoring, by the modular mobile autonomy control module, a payload area within the modular cargo storage system using at least one sensor on at least one of the modular mobile autonomy control module and the modular cargo storage system; and
detecting when the item being shipped is received within the modular cargo storage system based upon sensor data from the at least one sensor.

183. The method of embodiment 179, wherein the step of receiving the item being shipped comprises:
monitoring, by the modular mobile autonomy control module, a payload area within the modular cargo storage system for a wireless node associated with the item being shipped; and
detecting when the item being shipped is received within the modular cargo storage system when the wireless node associated with the item being shipped is determined to be located within the payload area within the modular cargo storage system based upon one or more detected signals broadcast by the wireless node associated with the item being shipped.

184. The method of embodiment 179, wherein the step of autonomously causing, by the modular mobile autonomy control module, the modular mobility base to move from the pickup location on a return route to the origin location after the item being shipped is detected to be received within the modular cargo storage system comprises:
autonomously causing, by the modular mobile autonomy control module, the modular mobility base to move from the pickup location to a secondary pickup location for an additional item being shipped according to a secondary dispatched logistics operation identified in a subsequent dispatch commend received by the modular mobile autonomy control module and from the dispatch server;
receiving, by the modular cargo storage system, the additional item being shipped; and
autonomously causing, by the modular mobile autonomy control module, the modular mobility base to move from the secondary pickup location to the origin location after the additional item being shipped is detected to be received within the modular cargo storage system.

185. The method of embodiment 179, wherein the step of receiving the item being shipped comprises deploying an articulating arm disposed on the modular autonomous bot apparatus assembly and using a plurality of proximity and vision sensors disposed on at least one of the modular mobility base and the modular mobile autonomy control module to engage the item being shipped and place the item being shipped within the modular cargo storage system.

186. The method of embodiment 179, wherein the step of receiving the item being shipped comprises:
deploying an articulating arm disposed on the modular autonomous bot apparatus assembly and using a plurality of proximity and vision sensors disposed on at least one of the modular mobility base and the modular mobile autonomy control module to engage a logistics receptacle currently maintaining the item being shipped;
guiding, by the modular mobile autonomy control module, the articulating arm to a closable access point on the logistics receptacle using one or more of the proximity and vision sensors disposed on at least one of the modular mobility base and the modular mobile autonomy control module;
engaging, by the articulating arm, the closable access point on the container to enabled access to within the logistics receptacle;
engaging, by the articulating arm, the item being shipped while maintained within the logistics receptacle; and
moving, by the articulating arm, the item being shipped from within the logistics receptacle to a position within the modular cargo storage system.

187. A method of performing a dispatched logistics operation related to an item being shipped and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to temporarily maintain the item being shipped within the modular autonomous bot apparatus assembly, and a modular mobile autonomy control module that autonomously controls operation of the modular autonomous bot apparatus assembly, the method comprising the steps of:
receiving, by the modular mobile autonomy control module, a dispatch command from the dispatch server, the dispatch command including at least destination information and authentication information related to the dispatched logistics operation;

authenticating, by the modular mobile autonomy control module, that each of the modular mobility base, the modular auxiliary power module, and the modular cargo storage system are compatible with the dispatched logistics operation;

receiving, by the modular cargo storage system, the item being shipped at an origin location;

autonomously causing, by the modular mobile autonomy control module, the modular mobility base to move from the origin location on a route to an object holding location identified by the destination information;

transmitting, by the modular mobile autonomy control module, a delivery notification message to an external mobile wireless node operated by a delivery recipient for the item being shipped, the delivery notification message being transmitted when the modular autonomous bot apparatus assembly is within a threshold distance from the object holding location identified by the destination information;

receiving, by the modular mobile autonomy control module, a responsive final delivery message from the external mobile wireless node, the responsive final delivery message including at least a delivery location for the item being shipped;

autonomously causing, by the modular mobile autonomy control module, the modular mobility base to move from the object holding location to the delivery location identified by the responsive final delivery message from the external mobile wireless node;

receiving authentication input by the modular mobile autonomy control module from the delivery recipient, the authentication input correlating to a portion of the authentication information related to the dispatched logistics operation indicating the delivery recipient that provided the authentication input is an authorized delivery recipient for the item being shipped within the module cargo storage system; and providing, by the modular cargo storage system, selective access to the item being shipped within the modular cargo storage system after the authentication input received correlates to the portion of the authentication information indicating the delivery recipient providing the authentication input is the authorized delivery recipient.

188. The method of embodiment 187, further comprising the step of autonomously causing, by the modular mobile autonomy control module, the modular mobility base to move from the delivery location to the origin location after the item being shipped is detected to be removed from within the modular cargo storage system.

189. The method of embodiment 187, further comprising the step of autonomously causing, by the modular mobile autonomy control module, the modular mobility base to move from the delivery location to the object holding location after the item being shipped is detected to be removed from within the modular cargo storage system.

190. The method of embodiment 189, further comprising the step of autonomously causing, by the modular mobile autonomy control module, the modular mobility base to move from the delivery location to the object holding location after the item being shipped is detected to be removed from within the modular cargo storage system;

transmitting, by the modular mobile autonomy control module, a second delivery notification message to a second external mobile wireless node operated by a second delivery recipient for an additional item maintained within the modular cargo storage system, the second delivery notification message being transmitted when the modular autonomous bot apparatus assembly is within the threshold distance from the object holding location;

receiving, by the modular mobile autonomy control module, a second responsive final delivery message from the second external mobile wireless node, the second responsive final delivery message including at least a second delivery location for the additional item maintained within the modular cargo system; and autonomously causing, by the modular mobile autonomy control module, the modular mobility base to move from the object holding location to the second delivery location identified by the second responsive final delivery message from the external mobile wireless node.

191. The method of embodiment 189, further comprising the step of receiving, by the modular mobile autonomy control module, a second dispatch command from the dispatch server, the second dispatch command including at least second destination information and second authentication information related to a second dispatched logistics operation;

autonomously causing, by the modular mobile autonomy control module, the modular mobility base to move from the delivery location to the object holding location after the item being shipped is detected to be removed from within the modular cargo storage system;

receiving, by the modular cargo storage system, a second item being shipped at the object holding location;

transmitting, by the modular mobile autonomy control module, a second delivery notification message to a second external mobile wireless node operated by a second delivery recipient for the second item;

receiving, by the modular mobile autonomy control module, a second responsive final delivery message from the second external mobile wireless node, the second responsive final delivery message including at least a second delivery location for the second item; and autonomously causing, by the modular mobile autonomy control module, the modular mobility base to move from the object holding location to the second delivery location identified by the second responsive final delivery message from the second external mobile wireless node.

Further Embodiment H—Methods of Performing an Inventory Management Related Dispatched Logistics Item for an Inventory Item Using a Modular Autonomous Bot Apparatus Assembly and a Dispatch Server 1. A method of performing a dispatched inventory operation related to an inventory item for transport within a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to maintain the inventory item for transport within the modular autonomous bot apparatus assembly, and a modular mobile autonomy control module that autonomously controls operation of the modular autonomous bot apparatus assembly, the dispatched inventory operation involving an inventory hub location and a plurality of remote business facilities external to the inventory hub location, the method comprising the steps of:
- (a) receiving, by the modular mobile autonomy control module, an inventory dispatch command from the dispatch server, wherein the inventory dispatch command includes at least destination information and authentication information related to the dispatched inventory operation for the inventory item for transport, the inventory dispatch command further assigning the inventory item for transport to the modular autonomous bot apparatus assembly from the contents of an inventory order received at the inventory hub location;
- (b) receiving, by the modular cargo storage system, the inventory item for transport at the inventory hub location;
- (c) autonomously causing, by the modular mobile autonomy control module, the modular mobility base to move from the inventory hub location on a route outside of the inventory hub location to one of the remote business facilities as a destination location identified by the destination information for the dispatched inventory operation;
- (d) receiving delivery recipient authentication input by the modular mobile autonomy control module from a delivery recipient disposed external to the modular autonomous bot apparatus assembly and at the destination location, the delivery recipient authentication input at least correlates to a portion of the authentication information related to the dispatched inventory operation indicating the delivery recipient that provided the delivery recipient authentication input is an authorized delivery recipient for the inventory item for transport within the module cargo storage system;
- (e) providing, by the modular cargo storage system, selective access to the inventory item for transport within the modular cargo storage system after the delivery recipient authentication input received correlates to the portion of the authentication information indicating the delivery recipient providing the delivery recipient authentication input is the authorized delivery recipient;
- (f) detecting, by the modular mobile autonomy control module, removal of the inventory item for transport from within the modular cargo storage system; and
- (g) autonomously causing, by the modular mobile autonomy control module, the modular mobility base to move from the destination location on a return route to the inventory hub location after the inventory item for transport is detected to be removed from within the modular cargo storage system.

2. The method of embodiment 1, further comprising the step of authenticating, by the modular mobile autonomy control module, that each of the modular mobile autonomy control module, the modular mobility base, the modular auxiliary power module, and the modular cargo storage system are compatible with the dispatched inventory operation prior to receiving the inventory item for transport;

3. The method of embodiment 2, wherein the modular cargo storage system compatible with the dispatched logistics operation comprises one of a plurality of different sized modular cargo storage systems, the one of the different sized modular cargo storage systems being compatible with a size parameter for the inventory item for transport as part of the dispatched inventory operation.

4. The method of embodiment 2, wherein the modular mobile autonomy control module compatible with the dispatched logistics operation comprises one of a plurality of different sized modular mobile autonomy control modules, the one of the different sized modular mobile autonomy control module being compatible with the one of the different sized modular cargo storage systems compatible with the size parameter for the inventory item for transport as part of the dispatched inventory operation.

5. The method of embodiment 2, further comprising the step of autonomously causing, by the modular mobile autonomy control module, the mobility base to move to an assembly area at the inventory hub location when one of the modular mobile autonomy control module, the modular mobility base, the modular auxiliary power module, or the modular cargo storage system are found to be not compatible with the dispatched inventory operation during the authenticating step.

6. The method of embodiment 5, further comprising the step of transmitting, by the modular mobile autonomy control module, a replacement request to the dispatch server, the replacement request causing the dispatch server to assign another modular autonomous bot apparatus assembly to the dispatched inventory operation to operate in place of the modular autonomous bot apparatus assembly.

7. The method of embodiment 5, further comprising the step of transmitting, by the modular mobile autonomy control module, a module replacement request to the dispatch server, the module replacement request instructing the dispatch server to cause the one of the modular mobile autonomy control module, the modular mobility base, the modular auxiliary power module, or the modular cargo storage system are found to be not compatible with the dispatched inventory operation to be replaced.

8. The method of embodiment 1, wherein the contents of the inventory order received at the inventory hub location comprises the inventory item for transport involved with the dispatched inventory operation and a plurality of additional inventory items to be supplied to others of the remote business facilities.

9. The method of embodiment 8, wherein the inventory item for transport removed from within the modular cargo storage system at the destination location comprises a restocking supply of one or more retail items sold at the one of the remote business facilities.

10. The method of embodiment 8, wherein the inventory item for transport removed from within the modular cargo storage system at the destination location comprises a rebalancing supply of one or more retail items sold at the one of the remote business facilities compared to a current inventory maintained in the others of the remote business facilities and the inventory hub location.

11. The method of embodiment 1, wherein the step of autonomously causing, by the modular mobile autonomy control module, the modular mobility base to move from the destination location on the return route to the inventory hub location after the inventory item for transport is detected to be removed from within the modular cargo storage system comprises:
- autonomously causing, by the modular mobile autonomy control module, the modular mobility base to hold at the destination location and wait for a subsequent inventory dispatch command from the dispatch server, the subsequent inventory dispatch command related to a subsequent dispatched inventory operation involving the modular autonomous bot apparatus assembly; and
- autonomously causing, by the modular mobile autonomy control module, the modular mobility base to return to the inventory hub location after the modular autonomous bot apparatus assembly completes the subsequent dispatched inventory operation.

12. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

13. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

14. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

15. The method of embodiment 1, wherein the delivery recipient authentication input received by the modular mobile autonomy control module is provided by the delivery recipient through an external wireless node disposed external to the modular autonomous bot apparatus assembly.

16. The method of embodiment 15, wherein the delivery recipient authentication input received by the modular mobile autonomy control module comprises an access code provided by the delivery recipient through the external wireless node disposed external to the modular autonomous bot apparatus assembly.

17. The method of embodiment 15, wherein the delivery recipient authentication input received by the modular mobile autonomy control module comprises a biometric input provided by the delivery recipient through the external wireless node disposed external to the modular autonomous bot apparatus assembly.

18. The method of embodiment 1, wherein the authentication information related to the dispatched inventory operation includes an identifier of the authorized delivery recipient for the inventory item for transport as part of the dispatched inventory operation; and wherein the step of receiving the delivery recipient authentication input comprises:
  detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
  authenticating, by the modular mobile autonomy control module, that the external wireless node is associated with the authorized delivery recipient for the item being shipped within the modular cargo storage system based upon the identifier of the authorized delivery recipient and identifier information within the detected advertising signal broadcast from the external wireless node.

19. The method of embodiment 1, wherein the authentication information related to the dispatched inventory operation includes an identifier of the authorized delivery recipient for the inventory item for transport as part of the dispatched inventory operation; and wherein the step of receiving the delivery recipient authentication input comprises:
  detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
  establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched inventory operation.

20. The method of embodiment 1, wherein the inventory item for transport is a portion from a plurality of inventory order items in a received inventory order; and further comprising the steps of repeating steps (a)-(g) for the remaining portions from the inventory order items in the received inventory order using additional modular autonomous bot apparatus assemblies to concurrently transport each of the remaining portions from the inventory order items in the received inventory order from the inventory hub location to respective others of the remote business facilities.

21. The method of embodiment 1, wherein the step (c) of autonomously causing the modular mobility base to move from the inventory hub location to the destination location comprises autonomously causing, by the modular mobile autonomy control module, the modular mobility base to move from the inventory hub location to the destination location while interacting with a wireless building facility node to actuate a pathway obstacle disposed in a path on the route to the destination location.

22. The method of embodiment 21, wherein the pathway obstacle comprises an actuated door controlled by the wireless building facility node.

23. The method of embodiment 21, wherein the pathway obstacle comprises an actuated elevator controlled by the wireless building facility node.

24. The method of embodiment 21, wherein the pathway obstacle comprises an actuated lock controlled by the wireless building facility node.

25. The method of embodiment 21, wherein interacting with the wireless building facility node to actuate the pathway obstacle comprises:
  establishing an authorized association pairing between the modular mobile autonomy control module and the wireless building facility node based upon the authentication information related to the dispatched logistics operation; and
  causing the wireless building facility node to actuate the pathway obstacle after establishing the authorized association pairing between the modular mobile autonomy control module and the wireless building facility node.

26. The method of embodiment 1, wherein the step (c) of autonomously causing the modular mobility base to move from the inventory hub location to the destination location comprises autonomously causing, by the modular mobile autonomy control module, the modular mobility base to move from the inventory hub location to the destination location while engaging a pathway obstacle disposed in a path on the route to the destination location using an articulating arm disposed on the modular autonomous bot apparatus assembly and using a plurality of sensors disposed on at least one of the modular mobility base and the modular mobile autonomy control module.

27. The method of embodiment 26, wherein the pathway obstacle comprises a manually actuated door.

28. The method of embodiment 26, wherein the pathway obstacle comprises a manually actuated elevator.

29. The method of embodiment 26, wherein the pathway obstacle comprises a manually actuated lock.

30. The method of embodiment 26, wherein engaging the pathway obstacle using the articulating arm and sensors comprises:
    guiding, by the modular mobile autonomy control module, the articulating arm to a control element of the pathway obstacle using one or more of the sensors disposed on at least one of the modular mobility base and the modular mobile autonomy control module; and
    actuating the pathway obstacle, by the modular mobile autonomy control module, once the articulating arm engages the control element of the pathway obstacle.

31. The method of embodiment 30, wherein the control element of the pathway obstacle comprises one from the group consisting of a handle for the pathway obstacle, a button for the pathway obstacle, a switch for the pathway obstacle, and a portion of a control panel for the pathway obstacle.

32. The method of embodiment 1, wherein step (b) comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

33. The method of embodiment 32, wherein actuating, by the modular mobile autonomy control module, the actuated cargo door comprises actuating an actuated joint on the actuated cargo door to cause the actuated cargo door to move from the closed position to the open position.

34. The method of embodiment 32, wherein actuating, by the modular mobile autonomy control module, the actuated cargo door further comprises actuating an electro-mechanical lock on the actuated cargo door to cause the actuated cargo door to unlock before moving from the closed position to the open position.

35. The method of embodiment 1, wherein step (b) comprises actuating, by the modular mobile autonomy control module, an actuated sliding arm disposed on the modular cargo storage system to move the inventory item into a payload area within the modular cargo storage system.

36. The method of embodiment 1, wherein step (b) comprises actuating, by the modular mobile autonomy control module, an actuated grabbing arm disposed on the modular cargo storage system to grab and move the inventory item into a payload area within the modular cargo storage system as part of receiving the inventory item.

37. The method of embodiment 1, wherein step (b) comprises actuating, by the modular mobile autonomy control module, an actuated belt surface disposed on the modular auxiliary power module as a movable support surface exposed within a payload area inside the modular cargo storage system, the actuated belt surface being operative when actuated to cause the inventory item as placed on the actuated belt surface to move within the payload area as part of receiving the inventory item.

38. The method of embodiment 1, wherein step (e) comprises actuating, by the modular mobile autonomy control module, an actuated cargo door disposed on the modular auxiliary power module to an open position once the delivery recipient authentication input correlates to a portion of the authentication information related to the dispatched logistics operation, wherein the actuated cargo door provides a seal to a payload area within the modular cargo storage system when the actuated cargo door is in a closed position and the actuated cargo door provides access to the payload area within the modular cargo storage system when the actuated cargo door is in the open position.

39. The method of embodiment 38, wherein actuating, by the modular mobile autonomy control module, the actuated cargo door comprises actuating an actuated joint on the actuated cargo door to cause the actuated cargo door to move from the closed position to the open position.

40. The method of embodiment 38, wherein actuating, by the modular mobile autonomy control module, the actuated cargo door further comprises actuating an electro-mechanical lock on the actuated cargo door to cause the actuated cargo door to unlock before moving from the closed position to the open position.

41. The method of embodiment 1, wherein step (e) comprises actuating, by the modular mobile autonomy control module, an actuated sliding arm disposed on the modular cargo storage system to move the inventory item out from a payload area within the modular cargo storage system.

42. The method of embodiment 1, wherein step (e) comprises actuating, by the modular mobile autonomy control module, an actuated grabbing arm disposed on the modular cargo storage system to grab and move the inventory item out from a payload area within the modular cargo storage system.

43. The method of embodiment 1, wherein step (e) comprises actuating, by the modular mobile autonomy control module, an actuated belt surface disposed on the modular auxiliary power module as a movable support surface exposed within a payload area inside the modular cargo storage system, the actuated belt surface being operative when actuated to cause the inventory item as placed on the actuated belt surface to move out from within the payload area.

44. The method of embodiment 1, wherein the inventory dispatch command further includes a shelving system identifier corresponding to a node-enabled shelving system maintaining the inventory item at the inventory hub location; and
    wherein step (b) comprises:
        notifying, by the modular mobile autonomy control module, the node-enabled shelving system of an approaching pickup of the inventory item;
        autonomously causing, by the modular mobile autonomy control module, the modular mobility base to move to the node-enabled shelving system as an intermediate loading location at the inventory hub location;
        detecting, by a vision sensor disposed on the modular autonomous bot apparatus assembly, an activated light element on the node-enabled shelving system proximate to the inventory item as maintained on the node-enabled shelving system, the light element having been activated in response to the modular mobile autonomy control module notifying the node-enabled shelving system of the approaching pickup of the inventory item;

autonomously causing, by the modular mobile autonomy control module, the modular mobility base to move to the detected activated light element on the node-enabled shelving system as a refined intermediate loading location at the first of the remote business facilities;

receiving pickup authentication input by the modular mobile autonomy control module from the node-enabled shelving system at the intermediate loading location;

providing, by the modular cargo storage system, selective access to within the modular cargo storage system when the pickup authentication input received correlates to the shelving system identifier from the inventory dispatch command, and receiving, by the modular cargo storage system, the inventory item for transport from the node-enabled shelving system at the intermediate loading location.

45. The method of embodiment 44, wherein the step of receiving the inventory item for transport from the node-enabled shelving system at the intermediate loading location comprises deploying an articulating arm disposed on the modular autonomous bot apparatus assembly and using at least the vision sensor and a proximity senor disposed on at least one of the modular mobility base and the modular mobile autonomy control module to engage the inventory item as maintained on the node-enabled shelving system and place the inventory item within the modular cargo storage system.

46. The method of embodiment 44, wherein the step of receiving the inventory item for transport from the node-enabled shelving system at the intermediate loading location comprises:

guiding, by the modular mobile autonomy control module, the articulating arm to the inventory item on the node-enabled shelving system using at least the vision sensor and a proximity senor disposed on at least one of the modular mobility base and the modular mobile autonomy control module;

engaging, by the articulating arm, the inventory item; and moving, by the articulating arm, the inventory item to a position within the modular cargo storage system.

47. The method of embodiment 1, wherein the inventory dispatch command further includes a shelving system identifier corresponding to a node-enabled shelving system at the destination location;

wherein steps (d) and (e) comprising:

notifying, by the modular mobile autonomy control module, the node-enabled shelving system at the destination location of an approaching delivery of the inventory item;

autonomously causing, by the modular mobile autonomy control module, the modular mobility base to move to the node-enabled shelving system at the destination location as an intermediate unloading location at the one of the remote business facilities;

detecting, by a vision sensor disposed on the modular autonomous bot apparatus assembly, an activated light element on the node-enabled shelving system proximate to the inventory item as maintained on the node-enabled shelving system, the light element having been activated in response to the modular mobile autonomy control module notifying the node-enabled shelving system of the approaching delivery of the inventory item;

autonomously causing, by the modular mobile autonomy control module, the modular mobility base to move to the detected activated light element on the node-enabled shelving system as a refined intermediate loading location at the first of the remote business facilities;

receiving delivery authentication input by the modular mobile autonomy control module from the node-enabled shelving system at the intermediate loading location; and providing, by the modular cargo storage system, selective access to within the modular cargo storage system when the delivery authentication input received correlates to the shelving system identifier from the inventory dispatch command.

48. The method of embodiment 47, wherein the step (f) of detecting, by the modular mobile autonomy control module, removal of the inventory item for transport from within the modular cargo storage system comprises:

deploying an articulating arm disposed on the modular autonomous bot apparatus assembly and using at least the vision sensor and a proximity senor disposed on at least one of the modular mobility base and the modular mobile autonomy control module to engage the inventory item as maintained within the modulator cargo storage system and place the inventory item on the node-enabled shelving system.

49. The method of embodiment 47, wherein the step (f) of detecting, by the modular mobile autonomy control module, removal of the inventory item for transport from within the modular cargo storage system comprises:

engaging, by the articulating arm, the inventory item within the modular cargo storage system; and moving, by the articulating arm, the inventory item from within the modular cargo storage system to a position within the modular cargo storage system.

50. A method of performing a dispatched inventory balancing operation related to an inventory item for transport within a modular autonomous bot apparatus assembly and an inventory management server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to maintain the inventory item for transport within the modular autonomous bot apparatus assembly, and a modular mobile autonomy control module that autonomously controls operation of the modular autonomous bot apparatus assembly, the dispatched inventory balancing operation involving a bot storage location and a plurality of remote business facilities external to the bot storage location, the method comprising the steps of:

detecting, by the inventory management server, an inventory imbalance between a first of the remote business facilities and a second of the remote business facilities based upon updated inventories reported from each of the first of the remote business facilities and the second of the remote business facilities;

transmitting, by the inventory management server, an inventory dispatch command to the modular mobile autonomy control module, the inventory dispatch command related to the dispatched inventory balancing operation between the first of the remote business facilities and the second of the remote business facilities;

receiving, by the modular mobile autonomy control module, the inventory dispatch command from the inventory management server, wherein the inventory dispatch command includes at least destination information on an intermediate loading location at the first of the remote business facilities and a drop-off location at the second of the remote business facilities, wherein the inventory dispatch command further includes authentication information related to the dispatched inventory balancing operation for the inventory item for transport;

autonomously causing, by the modular mobile autonomy control module, the modular mobility base to move from the bot storage location to the intermediate loading location at the first of the remote business facilities, receiving pickup authentication input by the modular mobile autonomy control module from a pickup entity disposed external to the modular autonomous bot apparatus assembly and at the intermediate loading location, the pickup authentication input at least correlates to a first portion of the authentication information related to the dispatched inventory balancing operation indicating the pickup entity that provided the pickup authentication input is an authorized inventory item supplier for the inventory item for transport within the module cargo storage system;

providing, by the modular cargo storage system, selective access to within the modular cargo storage system after the pickup authentication input received correlates to the first portion of the authentication information;

receiving, by the modular cargo storage system, the inventory item for transport at the intermediate loading location;

autonomously causing, by the modular mobile autonomy control module, the modular mobility base to move from the intermediate loading location to the drop-off location at the second of the remote business facilities;

receiving delivery recipient authentication input by the modular mobile autonomy control module from a delivery recipient disposed external to the modular autonomous bot apparatus assembly and at the drop-off location, the delivery recipient authentication input at least correlates to a portion of the authentication information related to the dispatched inventory balancing operation indicating the delivery recipient that provided the delivery recipient authentication input is an authorized delivery recipient for the inventory item for transport within the module cargo storage system;

providing, by the modular cargo storage system, selective access to the inventory item for transport within the modular cargo storage system after the delivery recipient authentication input received correlates to the portion of the authentication information indicating the delivery recipient providing the delivery recipient authentication input is the authorized delivery recipient;

detecting, by the modular mobile autonomy control module, removal of the inventory item for transport from within the modular cargo storage system; and autonomously causing, by the modular mobile autonomy control module, the modular mobility base to move from the drop-off location on a return route to the bot storage location after the inventory item for transport is detected to be removed from within the modular cargo storage system.

51. The method of embodiment 50, wherein the step of autonomously causing, by the modular mobile autonomy control module, the modular mobility base to move from the drop-off location on the return route to the bot storage location after the inventory item for transport is detected to be removed from within the modular cargo storage system comprises:

autonomously causing, by the modular mobile autonomy control module, the modular mobility base to hold at the drop-off location in a ready for dispatch mode and wait for a subsequent inventory dispatch command from the dispatch server, the subsequent inventory dispatch command related to a subsequent dispatched inventory operation involving the modular autonomous bot apparatus assembly; and autonomously causing, by the modular mobile autonomy control module, the modular mobility base to return to the inventory hub location after the modular autonomous bot apparatus assembly completes the subsequent dispatched inventory operation.

52. The method of embodiment 50, further comprising the step of authenticating, by the modular mobile autonomy control module, that each of the modular mobile autonomy control module, the modular mobility base, the modular auxiliary power module, and the modular cargo storage system are compatible with the dispatched inventory operation prior to receiving the inventory item for transport.

53. The method of embodiment 52, wherein the modular cargo storage system compatible with the dispatched logistics operation comprises one of a plurality of different sized modular cargo storage systems, the one of the different sized modular cargo storage systems being compatible with a size parameter for the inventory item for transport as part of the dispatched inventory operation.

54. The method of embodiment 52, wherein the modular mobile autonomy control module compatible with the dispatched logistics operation comprises one of a plurality of different sized modular mobile autonomy control modules, the one of the different sized modular mobile autonomy control module being compatible with the one of the different sized modular cargo storage systems compatible with the size parameter for the inventory item for transport as part of the dispatched inventory operation.

55. The method of embodiment 52, further comprising the step of autonomously causing, by the modular mobile autonomy control module, the mobility base to move to an assembly area at the bot storage location when one of the modular mobile autonomy control module, the modular mobility base, the modular auxiliary power module, or the modular cargo storage system are found to be not compatible with the dispatched inventory operation during the authenticating step.

56. The method of embodiment 55, further comprising the step of transmitting, by the modular mobile autonomy control module, a replacement request to the dispatch server, the replacement request causing the dispatch server to assign another modular autonomous bot apparatus assembly to the dispatched inventory operation to operate in place of the modular autonomous bot apparatus assembly.

57. The method of embodiment 55, further comprising the step of transmitting, by the modular mobile autonomy control module, a module replacement request to the dispatch server, the module replacement request instructing the dispatch server cause the one of the modular mobile autonomy control module, the modular mobility base, the modular auxiliary power module, or the modular cargo storage system are found to be not compatible with the dispatched inventory operation to be replaced.

58. The method of embodiment 50, wherein the delivery recipient authentication input received by the modular mobile autonomy control module is provided by the delivery recipient through a user input panel disposed on the modular autonomous bot apparatus coupled to the modular mobile autonomy control module.

59. The method of embodiment 50, wherein the delivery recipient authentication input received by the modular mobile autonomy control module comprises an access code provided by the delivery recipient through the user input panel disposed on the modular cargo storage system and operatively coupled to the modular mobile autonomy control module.

60. The method of embodiment 50, wherein the delivery recipient authentication input received by the modular mobile autonomy control module comprises a biometric input provided by the delivery recipient through the user input panel disposed on the modular cargo storage system and operatively coupled to the modular mobile autonomy control module.

61. The method of embodiment 50, wherein the delivery recipient authentication input received by the modular mobile autonomy control module is provided by the delivery recipient through an external wireless node disposed external to the modular autonomous bot apparatus assembly.

62. The method of embodiment 61, wherein the delivery recipient authentication input received by the modular mobile autonomy control module comprises an access code provided by the delivery recipient through the external wireless node disposed external to the modular autonomous bot apparatus assembly.

63. The method of embodiment 61, wherein the delivery recipient authentication input received by the modular mobile autonomy control module comprises a biometric input provided by the delivery recipient through the external wireless node disposed external to the modular autonomous bot apparatus assembly.

64. The method of embodiment 50, wherein the authentication information related to the dispatched inventory operation includes an identifier of the authorized delivery recipient for the inventory item for transport as part of the dispatched inventory operation; and
wherein the step of receiving the delivery recipient authentication input comprises:
detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
authenticating, by the modular mobile autonomy control module, that the external wireless node is associated with the authorized delivery recipient for the item being shipped within the modular cargo storage system based upon the identifier of the authorized delivery recipient and identifier information within the detected advertising signal broadcast from the external wireless node.

65. The method of embodiment 50, wherein the authentication information related to the dispatched inventory operation includes an identifier of the authorized delivery recipient for the inventory item for transport as part of the dispatched inventory operation; and
wherein the step of receiving the delivery recipient authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched inventory operation.

66. The method of embodiment 50, wherein the step of autonomously causing the modular mobility base to move from the bot storage location to the intermediate loading location comprises autonomously causing, by the modular mobile autonomy control module, the modular mobility base to move from the bot storage location to the intermediate loading location while interacting with a wireless building facility node to actuate a pathway obstacle disposed in a path on the route to the intermediate loading location.

67. The method of embodiment 66, wherein the pathway obstacle comprises an actuated door controlled by the wireless building facility node.

68. The method of embodiment 66, wherein the pathway obstacle comprises an actuated elevator controlled by the wireless building facility node.

69. The method of embodiment 66, wherein the pathway obstacle comprises an actuated lock controlled by the wireless building facility node.

70. The method of embodiment 66, wherein interacting with the wireless building facility node to actuate the pathway obstacle comprises:
establishing an authorized association pairing between the modular mobile autonomy control module and the wireless building facility node based upon the authentication information related to the dispatched logistics operation; and
causing the wireless building facility node to actuate the pathway obstacle after establishing the authorized association pairing between the modular mobile autonomy control module and the wireless building facility node.

71. The method of embodiment 50, wherein the step of autonomously causing the modular mobility base to move from the bot storage location to the intermediate loading location comprises autonomously causing, by the modular mobile autonomy control module, the modular mobility base to move from the bot storage location to the intermediate loading location while engaging a pathway obstacle disposed in a path on the route to the intermediate loading location using an articulating arm disposed on the modular autonomous bot apparatus assembly and using a plurality of sensors disposed on at least one of the modular mobility base and the modular mobile autonomy control module.

72. The method of embodiment 71, wherein the pathway obstacle comprises a manually actuated door.

73. The method of embodiment 71, wherein the pathway obstacle comprises a manually actuated elevator.

74. The method of embodiment 71, wherein the pathway obstacle comprises a manually actuated lock.

75. The method of embodiment 71, wherein engaging the pathway obstacle using the articulating arm and sensors comprises:
    guiding, by the modular mobile autonomy control module, the articulating arm to a control element of the pathway obstacle using one or more of the sensors disposed on at least one of the modular mobility base and the modular mobile autonomy control module; and
    actuating the pathway obstacle, by the modular mobile autonomy control module, once the articulating arm engages the control element of the pathway obstacle.

76. The method of embodiment 75, wherein the control element of the pathway obstacle comprises one from the group consisting of a handle for the pathway obstacle, a button for the pathway obstacle, a switch for the pathway obstacle, and a portion of a control panel for the pathway obstacle.

77. The method of embodiment 50, wherein the step of receiving, by the modular cargo storage system, the inventory item for transport at the intermediate loading location comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

78. The method of embodiment 77, wherein actuating, by the modular mobile autonomy control module, the actuated cargo door comprises actuating an actuated joint on the actuated cargo door to cause the actuated cargo door to move from the closed position to the open position.

79. The method of embodiment 77, wherein actuating, by the modular mobile autonomy control module, the actuated cargo door further comprises actuating an electro-mechanical lock on the actuated cargo door to cause the actuated cargo door to unlock before moving from the closed position to the open position.

80. The method of embodiment 50, wherein step of receiving, by the modular cargo storage system, the inventory item for transport at the intermediate loading location comprises actuating, by the modular mobile autonomy control module, an actuated sliding arm disposed on the modular cargo storage system to move the inventory item into a payload area within the modular cargo storage system.

81. The method of embodiment 50, wherein step of receiving, by the modular cargo storage system, the inventory item for transport at the intermediate loading location comprises actuating, by the modular mobile autonomy control module, an actuated grabbing arm disposed on the modular cargo storage system to grab and move the inventory item into a payload area within the modular cargo storage system as part of receiving the inventory item.

82. The method of embodiment 50, wherein step of receiving, by the modular cargo storage system, the inventory item for transport at the intermediate loading location comprises actuating, by the modular mobile autonomy control module, an actuated belt surface disposed on the modular auxiliary power module as a movable support surface exposed within a payload area inside the modular cargo storage system, the actuated belt surface being operative when actuated to cause the inventory item as placed on the actuated belt surface to move within the payload area as part of receiving the inventory item.

83. The method of embodiment 50, wherein step of providing, by the modular cargo storage system, selective access to the inventory item for transport within the modular cargo storage system comprises actuating, by the modular mobile autonomy control module, an actuated cargo door disposed on the modular auxiliary power module to an open position once the delivery recipient authentication input correlates to a portion of the authentication information related to the dispatched logistics operation, wherein the actuated cargo door provides a seal to a payload area within the modular cargo storage system when the actuated cargo door is in a closed position and the actuated cargo door provides access to the payload area within the modular cargo storage system when the actuated cargo door is in the open position.

84. The method of embodiment 83, wherein actuating, by the modular mobile autonomy control module, the actuated cargo door comprises actuating an actuated joint on the actuated cargo door to cause the actuated cargo door to move from the closed position to the open position.

85. The method of embodiment 83, wherein actuating, by the modular mobile autonomy control module, the actuated cargo door further comprises actuating an electro-mechanical lock on the actuated cargo door to cause the actuated cargo door to unlock before moving from the closed position to the open position.

86. The method of embodiment 50, wherein step of providing, by the modular cargo storage system, selective access to the inventory item for transport within the modular cargo storage system comprises actuating, by the modular mobile autonomy control module, an actuated sliding arm disposed on the modular cargo storage system to move the inventory item out from a payload area within the modular cargo storage system.

87. The method of embodiment 50, wherein step of providing, by the modular cargo storage system, selective access to the inventory item for transport within the modular cargo storage system comprises actuating, by the modular mobile autonomy control module, an actuated grabbing arm disposed on the modular cargo storage system to grab and move the inventory item out from a payload area within the modular cargo storage system.

88. The method of embodiment 50, wherein step of providing, by the modular cargo storage system, selective access to the inventory item for transport within the modular cargo storage system comprises actuating, by the modular mobile autonomy control module, an actuated belt surface disposed on the modular auxiliary power module as a movable support surface exposed within a payload area inside the modular cargo storage system, the actuated belt surface being operative when actuated to cause the inventory item as placed on the actuated belt surface to move out from within the payload area.

89. The method of embodiment 50, wherein the inventory dispatch command further includes a shelving system identifier corresponding to a node-enabled shelving system maintaining the inventory item at the intermediate loading location; and
    wherein the step of receiving, by the modular cargo storage system, the inventory item for transport at the intermediate loading location comprises:
        notifying, by the modular mobile autonomy control module, the node-enabled shelving system of an approaching pickup of the inventory item;

autonomously causing, by the modular mobile autonomy control module, the modular mobility base to move to the node-enabled shelving system at the intermediate loading location;

detecting, by a vision sensor disposed on the modular autonomous bot apparatus assembly, an activated light element on the node-enabled shelving system proximate to the inventory item as maintained on the node-enabled shelving system, the light element having been activated in response to the modular mobile autonomy control module notifying the node-enabled shelving system of the approaching pickup of the inventory item;

autonomously causing, by the modular mobile autonomy control module, the modular mobility base to move to the detected activated light element on the node-enabled shelving system as a refined intermediate loading location at the first of the remote business facilities;

receiving pickup authentication input by the modular mobile autonomy control module from the node-enabled shelving system at the intermediate loading location;

providing, by the modular cargo storage system, selective access to within the modular cargo storage system when the pickup authentication input received correlates to the shelving system identifier from the inventory dispatch command for the node-enabled shelving system at the intermediate loading location, and receiving, by the modular cargo storage system, the inventory item for transport from the node-enabled shelving system at the intermediate loading location.

90. The method of embodiment 89, wherein the step of receiving the inventory item for transport from the node-enabled shelving system at the intermediate loading location comprises deploying an articulating arm disposed on the modular autonomous bot apparatus assembly and using at least the vision sensor and a proximity senor disposed on at least one of the modular mobility base and the modular mobile autonomy control module to engage the inventory item as maintained on the node-enabled shelving system and place the inventory item within the modular cargo storage system.

91. The method of embodiment 89, wherein the step of receiving the inventory item for transport from the node-enabled shelving system at the intermediate loading location comprises:
guiding, by the modular mobile autonomy control module, the articulating arm to the inventory item on the node-enabled shelving system using at least the vision sensor and a proximity senor disposed on at least one of the modular mobility base and the modular mobile autonomy control module;
engaging, by the articulating arm, the inventory item; and
moving, by the articulating arm, the inventory item to a position within the modular cargo storage system.

92. The method of embodiment 50, wherein the inventory dispatch command further includes a shelving system identifier corresponding to a node-enabled shelving system at the drop-off location at the second of the remote business facilities;
wherein the steps of providing the selective access to the inventory item and detecting removal of the inventory item comprising:

notifying, by the modular mobile autonomy control module, the node-enabled shelving system at the drop-off location of an approaching delivery of the inventory item;

autonomously causing, by the modular mobile autonomy control module, the modular mobility base to move to the node-enabled shelving system at the drop-off location;

detecting, by a vision sensor disposed on the modular autonomous bot apparatus assembly, an activated light element on the node-enabled shelving system proximate to the inventory item as maintained on the node-enabled shelving system, the light element having been activated in response to the modular mobile autonomy control module notifying the node-enabled shelving system of the approaching delivery of the inventory item;

autonomously causing, by the modular mobile autonomy control module, the modular mobility base to move to the detected activated light element on the node-enabled shelving system as a refined intermediate unloading location at the second of the remote business facilities;

receiving delivery authentication input by the modular mobile autonomy control module from the node-enabled shelving system at the refined intermediate loading location; and providing, by the modular cargo storage system, selective access to within the modular cargo storage system when the delivery authentication input received correlates to the shelving system identifier from the inventory dispatch command at the drop-off location.

93. The method of embodiment 92, wherein the step of detecting, by the modular mobile autonomy control module, removal of the inventory item for transport from within the modular cargo storage system comprises:
deploying an articulating arm disposed on the modular autonomous bot apparatus assembly and using at least the vision sensor and a proximity senor disposed on at least one of the modular mobility base and the modular mobile autonomy control module to engage the inventory item as maintained within the modulator cargo storage system and place the inventory item on the node-enabled shelving system.

94. The method of embodiment 92, wherein the step of detecting, by the modular mobile autonomy control module, removal of the inventory item for transport from within the modular cargo storage system comprises:
engaging, by the articulating arm, the inventory item within the modular cargo storage system; and
moving, by the articulating arm, the inventory item from within the modular cargo storage system to a position on the node-enabled shelving system corresponding to the activated light element.

Further Embodiment I—Methods of Performing a Dispatched Store-to-Consumer Logistics Operation Related to an Ordered Item and Using a Modular Autonomous Bot Apparatus Assembly and a Dispatch Server 1. A method of performing a dispatched store-to-consumer logistics operation related to an ordered item and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to maintain the ordered item within the modular autonomous bot apparatus assembly, and a modular mobile autonomy control module that autonomously controls operation of the modular autonomous bot apparatus assembly, the method comprising the steps of:

receiving, by the modular mobile autonomy control module, a dispatch command from the dispatch server, the dispatch command comprising at least
        identifier information on the ordered item,
        transport parameters on the ordered item,
        destination delivery information related to delivery of the ordered item, and
        delivery authentication information related to an authorized delivery recipient of the ordered item;
    verifying, by the modular mobile autonomy control module, that each of the modular mobile autonomy control module, the modular mobility base, the modular auxiliary power module, and the modular cargo storage system are compatible with the dispatched store-to-consumer logistics operation based upon the dispatch command;
    receiving, by the modular cargo storage system, the ordered item in a payload area within the modular cargo storage system;
    autonomously causing, by the modular mobile autonomy control module, the modular mobility base to move from an origin location on a route to a destination location identified by the destination delivery information;
    notifying, by the modular mobile autonomy control module, the authorized delivery recipient of the ordered item of an approaching delivery once the modular autonomous bot apparatus assembly is within a threshold notification range of the destination location identified by the destination information;
    receiving delivery recipient authentication input by the modular mobile autonomy control module from a delivery recipient disposed external to the modular autonomous bot apparatus assembly at the destination location;
    providing, by the modular cargo storage system, selective access to the ordered item within the modular cargo storage system only when the delivery recipient authentication input received correlates to the delivery authentication information indicating that the delivery recipient providing the delivery recipient authentication input is the authorized delivery recipient;
    monitoring, by the modular mobile autonomy control module, unloading of the ordered item from within the modular cargo storage system using one or more sensors on at least one of the modular mobile autonomy control module and the modular cargo storage system; and
    autonomously causing, by the modular mobile autonomy control module, the modular mobility base to move from the destination location on a return route to the origin location after the ordered item is detected to be removed from within the modular cargo storage system based upon monitoring the unloading of the ordered item.

2. The method of embodiment 1, wherein the dispatch command further comprising supplier authentication information related to an authorized supplier of the ordered item to be transported within the modular cargo storage system, and wherein the step of receiving the ordered item comprises:
        receiving supplier authentication input by the modular mobile autonomy control module from a loading entity disposed external to the modular autonomous bot apparatus assembly at the origin location; and
        providing, by the modular cargo storage system, selective access to within the modular cargo storage system only when the supplier authentication input received correlates to the supplier authentication information indicating that the loading entity providing the supplier authentication input is the authorized supplier of the ordered item to be transported within the modular cargo storage system during the dispatched store-to-consumer logistics operations.

3. The method of embodiment 1, wherein the notifying step comprises generating a display alert for the authorized delivery recipient on a display on the modular mobile autonomy control module once the modular autonomous bot apparatus assembly is within the threshold notification range of the destination location identified by the destination information.

4. The method of embodiment 1, wherein the notifying step comprises generating an audio notification for the authorized delivery recipient on a speaker on the modular mobile autonomy control module once the modular autonomous bot apparatus assembly is within the threshold notification range of the destination location identified by the destination information.

5. The method of embodiment 1, wherein the notifying step comprises transmitting a delivery notification message to an external wireless node once the modular autonomous bot apparatus assembly is within the threshold notification range of the destination location identified by the destination information.

6. The method of embodiment 5, wherein the external wireless node being related to a designated wireless user identified in the dispatch command.

7. The method of embodiment 5, wherein the external wireless node being related to the authorized delivery recipient according to the destination delivery information.

8. The method of embodiment 1, wherein the notifying step comprises transmitting a delivery notification message to an external wireless node after the modular autonomous bot apparatus assembly moves from the origin location, the external wireless node being related to the authorized delivery recipient according to the destination delivery information.

9. The method of embodiment 8, wherein the notifying step further comprises transmitting an arrival estimate to the external wireless node, the arrival estimate indicating an estimated time to arrive at the destination location.

10. The method of embodiment 1, wherein the step of receiving the dispatch command from the dispatch server comprises receiving, by the modular mobile autonomy control module, a delivery order assignment message as the dispatch command from a retail system that received a transaction order for the ordered item, wherein the retail system operating as the dispatch server.

11. The method of embodiment 1, wherein the step of monitoring unloading of the ordered item comprises generating a log entry in a custodial inventory data structure when the ordered item is detected to be removed from within the modular cargo storage system, the log entry reflecting the removal of the ordered item from within the modular cargo storage system.

12. The method of embodiment 1, wherein the step of monitoring unloading of the ordered item comprises:
   capturing sensor data from the one or more sensors on at least one of the modular mobile autonomy control module and the modular cargo storage system; and
   detecting when the ordered item is removed from within the modular cargo storage system based upon the captured sensor data.

13. The method of embodiment 12, wherein the captured sensor data comprises visual images of what is disposed within the modular cargo storage system.

14. The method of embodiment 1, wherein the step of monitoring unloading of the ordered item comprises:
   generating barcode scan data related to the ordered item as the ordered item is removed from within the modular cargo storage system using a barcode scanner as one of the one or more sensors; and
   processing the generated barcode scan data to monitor the ordered item as the ordered item is removed from within the modular cargo storage system.

15. The method of embodiment 1, wherein the step of monitoring unloading of the ordered item comprises:
   detecting advertising data related to a node with the ordered item as the ordered item is removed from within the modular cargo storage system; and
   processing the generated advertising data to monitor the location of the node with the ordered item as the ordered item is removed from within the modular cargo storage system.

16. The method of embodiment 1, wherein the step of monitoring unloading of the ordered item comprises:
   generating image data related to the ordered item as the ordered item is removed from within the modular cargo storage system using a camera as one of the one or more sensors; and
   processing the generated image data to monitor the ordered item as the ordered item is removed from within the modular cargo storage system.

17. The method of embodiment 1, wherein the step of monitoring unloading of the ordered item comprises:
   generating video data related to the ordered item as the ordered item is removed from within the modular cargo storage system using a video camera as one of the one or more sensors; and
   processing the generated video data to monitor the ordered item as the ordered item is removed from within the modular cargo storage system.

18. The method of embodiment 1, wherein the step of monitoring unloading of the ordered item comprises:
   capturing audio data using a microphone as one of the one or more sensors disposed to record sound within and proximate to the modular cargo storage system as the ordered item is removed from within the modular cargo storage system; and
   processing the captured audio data to monitor the ordered item as the ordered item is removed from within the modular cargo storage system.

19. The method of embodiment 1, wherein the step of monitoring unloading of the ordered item comprises detecting movement of a wireless node associated with the ordered item as the ordered item is removed from within the modular cargo storage system based upon a plurality of signals broadcast from the wireless node associated with the ordered item.

20. The method of embodiment 1, wherein the step of monitoring unloading of the ordered item comprises detecting a change in location of a wireless node associated with the ordered item to outside the modular cargo storage system as the ordered item is removed from within the modular cargo storage system as determined by the modular mobile autonomous control module 21. The method of embodiment 1, further comprising the step of generating, by the modular mobile autonomy control module, a first inventory data structure corresponding to the ordered item upon receiving the ordered item, wherein the first inventory data structure including a first chain of custody entry reflecting departure from the origin location for the ordered item while in the custody of the modular autonomous bot apparatus assembly.

22. The method of embodiment 21, further comprising the step of generating, by the modular mobile autonomy control module, a second chain of custody entry within the first inventory data structure after arrival at the destination location, the second chain of custody reflecting arrival from the destination location for delivery of the ordered item from the custody of the modular autonomous bot apparatus assembly.

23. The method of embodiment 22, further comprising the step of generating, by the modular mobile autonomy control module, a third chain of custody entry within the first inventory data structure after arrival at the destination location and after detecting the ordered item has been removed from within the modular cargo storage system, the third chain of custody reflecting the ordered item changing custody to the authorized delivery recipient from the modular autonomous bot apparatus assembly.

24. The method of embodiment 1, wherein the step of autonomously causing the modular mobility base to move from the origin location to the destination location comprises autonomously causing, by the modular mobile autonomy control module, the modular mobility base to move from the origin location to the destination location while interacting with a wireless building facility node to actuate a pathway obstacle disposed in a path on the route to the destination location.

25. The method of embodiment 24, wherein the pathway obstacle comprises an actuated door controlled by the wireless building facility node.

26. The method of embodiment 24, wherein the pathway obstacle comprises an actuated elevator controlled by the wireless building facility node.

27. The method of embodiment 24, wherein the pathway obstacle comprises an actuated lock controlled by the wireless building facility node.

28. The method of embodiment 24, wherein interacting with the wireless building facility node to actuate the pathway obstacle comprises:
   establishing an authorized association pairing between the modular mobile autonomy control module and the wireless building facility node based upon the authentication information related to the dispatched store-to-consumer logistics operation; and
   causing the wireless building facility node to actuate the pathway obstacle after establishing the authorized association pairing between the modular mobile autonomy control module and the wireless building facility node.

29. The method of embodiment 1, wherein the step of autonomously causing the modular mobility base to move from the origin location to the destination location comprises autonomously causing, by the modular mobile autonomy control module, the modular mobility base to move from the origin location to the destination location while engaging a pathway obstacle disposed in a path on the route to the destination location using an articulating arm disposed on the modular autonomous bot apparatus assembly and using a plurality of sensors disposed on at least one of the modular mobility base and the modular mobile autonomy control module.

30. The method of embodiment 29, wherein the pathway obstacle comprises a manually actuated door.

31. The method of embodiment 29, wherein the pathway obstacle comprises a manually actuated elevator.

32. The method of embodiment 29, wherein the pathway obstacle comprises a manually actuated lock.

33. The method of embodiment 29, wherein engaging the pathway obstacle using the articulating arm and sensors comprises:
  guiding, by the modular mobile autonomy control module, the articulating arm to a control element of the pathway obstacle using one or more of the sensors disposed on at least one of the modular mobility base and the modular mobile autonomy control module; and
  actuating the pathway obstacle, by the modular mobile autonomy control module, once the articulating arm engages the control element of the pathway obstacle.

34. The method of embodiment 33, wherein the control element of the pathway obstacle comprises one from the group consisting of a handle for the pathway obstacle, a button for the pathway obstacle, a switch for the pathway obstacle, and a portion of a control panel for the pathway obstacle.

35. The method of embodiment 1, wherein the step of receiving the ordered item in the payload area within the modular cargo storage system comprises actuating, by the modular mobile autonomy control module, an actuated cargo door disposed on the modular auxiliary power module to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position.

36. The method of embodiment 35, wherein actuating, by the modular mobile autonomy control module, the actuated cargo door comprises actuating an actuated joint on the actuated cargo door to cause the actuated cargo door to move from the closed position to the open position.

37. The method of embodiment 35, wherein actuating, by the modular mobile autonomy control module, the actuated cargo door further comprises actuating an electro-mechanical lock on the actuated cargo door to cause the actuated cargo door to unlock before moving from the closed position to the open position.

38. The method of embodiment 1, wherein step of receiving the ordered item in the payload area within the modular cargo storage system comprises actuating, by the modular mobile autonomy control module, an actuated sliding arm disposed on the modular cargo storage system to move the ordered item into the payload area within the modular cargo storage system.

39. The method of embodiment 1, wherein step of receiving the ordered item in the payload area within the modular cargo storage system comprises actuating, by the modular mobile autonomy control module, an actuated grabbing arm disposed on the modular cargo storage system to grab and move the ordered item into the payload area within the modular cargo storage system as part of receiving the ordered item.

40. The method of embodiment 1, wherein step of receiving the ordered item in the payload area within the modular cargo storage system comprises actuating, by the modular mobile autonomy control module, an actuated belt surface disposed on the modular auxiliary power module as a movable support surface exposed within the payload area inside the modular cargo storage system, the actuated belt surface being operative when actuated to cause the ordered item as placed on the actuated belt surface to move within the payload area as part of receiving the ordered item.

41. The method of embodiment 1, wherein the step of providing, by the modular cargo storage system, selective access to the ordered item within the modular cargo storage system comprises actuating, by the modular mobile autonomy control module, an actuated cargo door disposed on the modular auxiliary power module to an open position once the delivery recipient authentication input correlates to a portion of the authentication information related to the dispatched store-to-consumer logistics operation, wherein the actuated cargo door provides a seal to the payload area within the modular cargo storage system when the actuated cargo door is in a closed position and the actuated cargo door provides access to the payload area within the modular cargo storage system when the actuated cargo door is in the open position.

42. The method of embodiment 41, wherein actuating, by the modular mobile autonomy control module, the actuated cargo door comprises actuating an actuated joint on the actuated cargo door to cause the actuated cargo door to move from the closed position to the open position.

43. The method of embodiment 41, wherein actuating, by the modular mobile autonomy control module, the actuated cargo door further comprises actuating an electro-mechanical lock on the actuated cargo door to cause the actuated cargo door to unlock before moving from the closed position to the open position.

44. The method of embodiment 1, wherein the step of providing, by the modular cargo storage system, selective access to the ordered item within the modular cargo storage system comprises actuating, by the modular mobile autonomy control module, an actuated sliding arm disposed on the modular cargo storage system to move the ordered item out from the payload area within the modular cargo storage system.

45. The method of embodiment 1, wherein the step of providing, by the modular cargo storage system, selective access to the ordered item within the modular cargo storage system comprises actuating, by the modular mobile autonomy control module, an actuated grabbing arm disposed on the modular cargo storage system to grab and move the ordered item out from the payload area within the modular cargo storage system.

46. The method of embodiment 1, wherein the step of providing, by the modular cargo storage system, selective access to the ordered item within the modular cargo storage system comprises actuating, by the modular mobile autonomy control module, an actuated belt surface disposed on the modular auxiliary power module as a movable support surface exposed within the payload area inside the modular cargo storage system, the actuated belt surface being operative when actuated to cause the ordered item as placed on the actuated belt surface to move out from within the payload area.

47. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

48. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

49. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

50. The method of embodiment 1, wherein the delivery recipient authentication input received by the modular mobile autonomy control module is provided by the delivery recipient through an external wireless node disposed external to the modular autonomous bot apparatus assembly.

51. The method of embodiment 50, wherein the delivery recipient authentication input received by the modular mobile autonomy control module comprises an access code provided by the delivery recipient through the external wireless node disposed external to the modular autonomous bot apparatus assembly.

52. The method of embodiment 50, wherein the delivery recipient authentication input received by the modular mobile autonomy control module comprises a biometric input provided by the delivery recipient through the external wireless node disposed external to the modular autonomous bot apparatus assembly.

53. The method of embodiment 1, wherein the delivery authentication information related to the dispatched store-to-consumer logistics operation includes an identifier of the authorized delivery recipient for the ordered item as part of the dispatched store-to-consumer logistics operation; and
wherein the step of receiving the delivery recipient authentication input comprises:
detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
authenticating, by the modular mobile autonomy control module, that the external wireless node is associated with the authorized delivery recipient for the ordered item within the modular cargo storage system based upon the identifier of the authorized delivery recipient and identifier information within the detected advertising signal broadcast from the external wireless node.

54. The method of embodiment 1, wherein the delivery authentication information related to the dispatched store-to-consumer logistics operation includes an identifier of the authorized delivery recipient for the ordered item as part of the dispatched store-to-consumer logistics operation; and
wherein the step of receiving the delivery recipient authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched store-to-consumer logistics operation.

55. The method of embodiment 1, wherein the ordered item comprises a pharmaceutical item;
wherein the step of receiving the ordered item in the payload area within the modular cargo storage system comprises receiving, by the modular cargo storage system, the pharmaceutical item as part of a pharmaceutical transaction between a pharmacy and the authorized delivery recipient of the pharmaceutical item.

56. The method of embodiment 1, wherein the destination delivery information related to the delivery of the ordered item comprises a requested time of day for the modular autonomous bot apparatus assembly to arrive at the destination location for the delivery of the ordered item to the authorized delivery recipient.

57. The method of embodiment 1, wherein the destination delivery information related to the delivery of the ordered item comprises a requested day of the week for the modular autonomous bot apparatus assembly to arrive at the destination location for the delivery of the ordered item to the authorized delivery recipient.

58. The method of embodiment 1, wherein the destination delivery information related to the delivery of the ordered item comprises contact information for the authorized delivery recipient to use when notifying the authorized delivery recipient.

59. The method of embodiment 1, wherein the destination delivery information related to the delivery of the ordered item comprises a special delivery instruction for delivery of the ordered item.

60. The method of embodiment 2, wherein the step of receiving the ordered item comprises notifying, by the dispatch server, the loading entity of a load time deadline for placing the ordered item within the modular cargo storage system as part of the dispatched store-to-consumer logistics operation for the ordered item, the step of notifying the loading entity of the load time deadline occurring prior to receiving the supplier authentication input.

61. The method of embodiment 1, wherein the step of receiving the delivery recipient authentication input comprises receiving multiple-factor delivery recipient authentication input from the delivery recipient, and wherein the delivery authentication information including multiple-factor authentication input answers that when collectively correlating to the multiple-factor delivery recipient authentication input from the delivery recipient indicates the delivery recipient is the authorized delivery recipient.

62. The method of embodiment 1, wherein the destination delivery information comprises a selected delivery timeframe for presenting the ordered item to the authorized delivery recipient, wherein the selected delivery timeframe corresponds to a range of time over which the modular autonomous bot apparatus will autonomously arrive at the destination location for monitored unloading of the ordered item as part of the dispatched store-to-consumer logistics operation.

63. The method of embodiment 1, wherein the dispatch command further comprising supplier authentication information related to an authorized retail personnel that obtains and provides the ordered item to the modular cargo storage system, and
  wherein the step of receiving the ordered item comprises:
    receiving supplier authentication input by the modular mobile autonomy control module from a loading retail personnel disposed external to the modular autonomous bot apparatus assembly at the origin location; and
    providing, by the modular cargo storage system, selective access to within the modular cargo storage system only when the supplier authentication input received correlates to the supplier authentication information indicating that the loading retail personnel providing the supplier authentication input is the authorized retail personnel for obtaining and providing the ordered item.

64. The method of embodiment 63, wherein the authorized retail personnel obtains and provides the ordered item within the modular cargo storage system after the dispatch server instructs the authorized retail personnel to obtain obtains and provides the ordered item to the modular cargo storage system as part of the dispatched store-to-consumer logistics operation.

65. The method of embodiment 63, wherein the step of receiving the ordered item further comprises monitoring, by the modular mobile autonomy control module, loading of the ordered item from within the modular cargo storage system as the ordered item is received within the modular cargo storage system, the monitoring using one or more sensors on at least one of the modular mobile autonomy control module and the modular cargo storage system.

66. The method of embodiment 65, wherein the step of monitoring loading of the ordered item comprises generating a log entry in a custodial inventory data structure when the ordered item is detected to be placed within the modular cargo storage system, the log entry reflecting placement of the ordered item within the modular cargo storage system.

67. The method of embodiment 65, wherein the step of monitoring loading of the ordered item comprises:
  capturing sensor data from the one or more sensors on at least one of the modular mobile autonomy control module and the modular cargo storage system; and
  detecting when the ordered item is placed within the modular cargo storage system based upon the captured sensor data.

68. The method of embodiment 67, wherein the captured sensor data comprises visual images of what is disposed within the modular cargo storage system.

69. The method of embodiment 65, wherein the step of monitoring loading of the ordered item comprises generating barcode scan data related to ordered item as the ordered item is placed within the modular cargo storage system using a barcode scanner as one of the one or more sensors.

70. The method of embodiment 65, wherein the step of monitoring loading of the ordered item comprises generating image data related to ordered item as the ordered item is placed within the modular cargo storage system using a camera as one of the one or more sensors.

71. The method of embodiment 65, wherein the step of monitoring loading of the ordered item comprises generating video data related to ordered item as the ordered item is placed within the modular cargo storage system using a video camera as one of the one or more sensors.

72. The method of embodiment 65, wherein the step of monitoring loading of the ordered item comprises capturing audio data using a microphone as one of the one or more sensors disposed to record sound within and proximate to the modular cargo storage system as the ordered item is placed within the modular cargo storage system.

73. The method of embodiment 65, wherein the step of monitoring loading of the ordered item comprises detecting movement of a wireless node associated with the ordered item as the ordered item is placed within the modular cargo storage system based upon a plurality of signals broadcast from the wireless node associated with the ordered item.

74. The method of embodiment 65, wherein the step of monitoring loading of the ordered item comprises detecting a change in location of a wireless node associated with the ordered item from outside the modular cargo storage system to inside the modular cargo storage system as the ordered item is placed within the modular cargo storage system as determined by the modular mobile autonomous control module.

75. The method of embodiment 1, further comprising the steps of:
  notifying, by the modular mobile autonomy control module, the authorized delivery recipient of an anticipated delivery time of the ordered item at the destination location prior to receiving the ordered item in the modular cargo storage system; and
  receiving, by the modular mobile autonomy control module, a responsive confirmation from the authorized delivery recipient related to the anticipated delivery of the ordered item;
  wherein the step of receiving the ordered item within the payload area within the modular cargo storage system depends on the responsive confirmation from the authorized delivery recipient.

76. The method of embodiment 75, the step of receiving the ordered item within the payload area within the modular cargo storage system permissively proceeds upon receipt of the responsive confirmation when the responsive confirmation from the authorized delivery recipient indicates acceptance of the anticipated delivery time of the ordered item.

77. The method of embodiment 75, the step of receiving the ordered item within the payload area within the modular cargo storage system is delayed upon receipt of the responsive confirmation when the responsive confirmation from the authorized delivery recipient indicates an alternative delivery time of the ordered item.

78. The method of embodiment 75, wherein the step of notifying the authorized delivery recipient of the anticipated delivery time comprises transmitting, by the modular mobile autonomy control module, a wireless notification message directly to an external wireless node identified to be related to the authorized delivery recipient based upon the delivery authentication information, where the wireless notification message provides the anticipated delivery time to the authorized delivery recipient; and
  wherein the step of receiving the responsive confirmation from the authorized delivery recipient comprises receiving a wireless confirmation message directly from the external wireless node identified to be related to the authorized delivery recipient, where the wireless confirmation message provides the responsive confirmation from the authorized delivery recipient.

79. The method of embodiment 75, wherein the step of notifying the authorized delivery recipient of the anticipated delivery time comprises transmitting, by the modular mobile autonomy control module, a notification message indirectly through the dispatch server to the authorized delivery recipient, where the notification message provides the anticipated delivery time to the authorized delivery recipient; and wherein the step of receiving the responsive confirmation from the authorized delivery recipient comprises receiving a confirmation message indirectly from the authorized delivery recipient through the dispatch server, where the confirmation message provides the responsive confirmation from the authorized delivery recipient.

80. The method of embodiment 1, wherein the step of receiving the delivery recipient authentication input conforms to a store-selected security protocol for verifying the delivery recipient authentication input is from the authorized delivery recipient so that the ordered item is provided only to the authorized delivery recipient.

81. The method of embodiment 80, wherein the store-selected security protocol has the delivery recipient authentication input received by the modular mobile autonomy control module being provided by the delivery recipient through a user input panel disposed on the modular autonomous bot apparatus coupled to the modular mobile autonomy control module.

82. The method of embodiment 80, wherein the store-selected security protocol has the delivery recipient authentication input received by the modular mobile autonomy control module comprising an access code provided by the delivery recipient through the user input panel disposed on the modular cargo storage system and operatively coupled to the modular mobile autonomy control module.

83. The method of embodiment 80, wherein the store-selected security protocol has the delivery recipient authentication input received by the modular mobile autonomy control module comprising a biometric input provided by the delivery recipient through the user input panel disposed on the modular cargo storage system and operatively coupled to the modular mobile autonomy control module.

84. The method of embodiment 80, wherein the store-selected security protocol has the delivery recipient authentication input received by the modular mobile autonomy control module being provided by the delivery recipient through an external wireless node disposed external to the modular autonomous bot apparatus assembly.

85. The method of embodiment 84, wherein the store-selected security protocol has the delivery recipient authentication input received by the modular mobile autonomy control module comprising an access code provided by the delivery recipient through the external wireless node disposed external to the modular autonomous bot apparatus assembly.

86. The method of embodiment 84, wherein the store-selected security protocol has the delivery recipient authentication input received by the modular mobile autonomy control module comprising a biometric input provided by the delivery recipient through the external wireless node disposed external to the modular autonomous bot apparatus assembly.

87. The method of embodiment 80, wherein the authentication information related to the dispatched store-to-customer logistics operation includes an identifier of the authorized delivery recipient for the ordered item as part of the dispatched store-to-consumer logistics operation; and wherein the step of receiving the delivery recipient authentication input using the store-selected security protocol comprises:

detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and authenticating, by the modular mobile autonomy control module, that the external wireless node is associated with the authorized delivery recipient for the ordered item within the modular cargo storage system based upon the identifier of the authorized delivery recipient and identifier information within the detected advertising signal broadcast from the external wireless node.

88. The method of embodiment 80, wherein the authentication information related to the dispatched store-to-customer logistics operation includes an identifier of the authorized delivery recipient for the ordered item as part of the dispatched store-to-customer logistics operation; and wherein the step of receiving the delivery recipient authentication input using the store-selected security protocol comprises:

detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched store-to-customer logistics operation.

89. The method of embodiment 1, wherein the step of monitoring the unloading of the ordered item comprises:

detecting, by the modular mobile autonomy control module, that the ordered item has been removed from within the modular cargo storage system based upon sensor data generated by the one or more sensors;

receiving, by the modular mobile autonomy control module, a satisfaction indicator input from the authorized delivery recipient after detecting that the ordered item has been removed from within the modular cargo storage system;

receiving, by the modular cargo storage system, the ordered item back within the modular cargo storage system only when the satisfaction indicator input reflects the authorized delivery recipient is returning the ordered item; and wherein the step of autonomously causing the modular mobility base to move from the destination location to the origin location comprises autonomously causing, by the modular mobile autonomy control module, the modular mobility base to move from the destination location on the return route to the origin location after receiving the satisfaction indicator input and transporting contents of the payload area within the modular cargo storage system depending upon the satisfaction indicator input.

90. The method of embodiment 1, further comprising the step of transmitting, by the modular mobile autonomy control module, a dispatch command acceptance response to the dispatch server acknowledging acceptance of the dispatched store-to-consumer logistics operation based upon the dispatch command and a status of the modular autonomous bot apparatus assembly.

91. The method of embodiment 90, wherein the step of transmitting the dispatch command acceptance response comprises:
  accessing, by the modular mobility autonomy control module, context data on environmental conditions about the origin location and the destination location;
  generating the dispatch command acceptance response based upon the dispatch command, the status of the modular autonomous bot apparatus assembly, and the accessed context data on the environmental conditions about the origin location and the destination location; and
  transmitting the generated dispatch command acceptance response to the dispatch server.

92. The method of embodiment 90, further comprising the step of transmitting, by the modular mobile autonomy control module, a dispatch command decline response to the dispatch server informing the dispatch server that the modular autonomous bot apparatus assembly is unable to perform the dispatched store-to-consumer logistics operation based upon the dispatch command and the status of the modular autonomous bot apparatus assembly and that the dispatch server must send the dispatch command to another modular autonomous bot apparatus assembly at the origin location in order to complete the dispatched store-to-consumer logistics operation.

93. The method of embodiment 90, wherein the step of transmitting the dispatch command decline response comprises:
  identifying, by the modular mobility autonomy control module, an adverse transit condition based upon context data on environmental conditions about the origin location and the destination location;
  generating the dispatch command decline response based upon the dispatch command, the status of the modular autonomous bot apparatus assembly, and the adverse transit condition related to the context data on the environmental conditions about the origin location and the destination location; and
  transmitting the generated dispatch command decline response to the dispatch server.

94. The method of embodiment 93, wherein the context data on the environmental conditions about the origin location and the destination location being part of the dispatch command received from the dispatch server.

95. The method of embodiment 1, further comprising the step of transmitting, by the modular mobile autonomy control module, a dispatch command redirect response to the dispatch server requesting a change to the dispatched store-to-consumer logistics operation based upon context data on the environmental conditions about at least one of the origin location and the destination location.

96. The method of embodiment 1, wherein the modular cargo storage system verified to be compatible with the dispatched store-to-consumer logistics operation comprises climate control module disposed within the payload area and operative to maintain a desired environment in the payload area of the modular cargo storage system for the ordered item according to the transport parameters on the ordered item.

97. The method of embodiment 96, wherein the payload area comprises at least a partially insulated area within modular cargo storage system.

98. The method of embodiment 96, further comprising the step of transmitting, by the modular mobile autonomy control module, a climate control input to the climate control module to alter an environment next to the climate control module to maintain the desired environment in the payload area according to the transport parameters on the ordered item.

99. The method of embodiment 3, wherein the display alert generated on the display on the modular mobile autonomy control module comprises a heat caution related to the ordered item.

100. The method of embodiment 3, wherein the display alert generated on the display on the modular mobile autonomy control module comprises branded information on a food service entity that supplies the ordered item.

101. The method of embodiment 3, wherein the display alert generated on the display on the modular mobile autonomy control module comprises instructional information related to the ordered item.

102. The method of embodiment 3, wherein the display alert comprises branded information from a food service entity that supplies the ordered item, the branded information including information about additional items available for order from the food service entity.

103. The method of embodiment 2, wherein the ordered item comprises a plurality of food stuffs gathered by the loading entity.

104. The method of embodiment 2, wherein the ordered item comprises a plurality of retail items sold by a business entity that employs the loading entity.

105. The method of embodiment 1, wherein the step of autonomously causing the modular mobility base to move from the destination location on the return route to the origin location after the ordered item is detected to be removed from within the modular cargo storage system comprises:
  autonomously causing, by the modular mobile autonomy control module, the modular mobility base to move from the destination location to a secondary delivery location after the ordered item is detected to be removed from within the modular cargo storage system at the destination location and after an additional item is detected within the modular cargo storage system while at the destination location, the secondary delivery location being identified as part of the destination information related to the dispatched store-to-consumer logistics operation; and
  autonomously causing, by the modular mobile autonomy control module, the modular mobility base to move from the secondary delivery location to the origin location after the additional item is detected to be removed from within the modular cargo storage system at the secondary delivery location.

106. The method of embodiment 105, further comprising the steps of:
  receiving third party entity authentication input by the modular mobile autonomy control module from a third party entity while at the secondary delivery location after the modular mobility base arrives at the secondary delivery location, the third party entity authentication input correlating to a portion of the authentication information related to the dispatched store-to-consumer logistics operation indicating the third party entity that provided the third party entity authentication input is an authorized third party recipient for the additional item within the module cargo storage system as part of the dispatched store-to-consumer logistics operation; and providing, by the modular cargo storage system, selective access to within the modular cargo storage system for removal of the additional item after the third party entity authentication input received correlates to the portion of the authentication information indicating the third party entity providing the third party entity authentication input is the authorized third party recipient for the additional item.

107. The method of embodiment 1, wherein the step of receiving the ordered item in the payload area comprises receiving, by the modular cargo storage system, the ordered item in a first compartment of a plurality of separated storage compartments within the payload area within the modular cargo storage system;

wherein the step of monitoring unloading of the ordered item comprises monitoring, by the modular mobile autonomy control module, unloading of the ordered item from the first compartment within the modular cargo storage system using the one or more sensors on at least one of the modular mobile autonomy control module and the modular cargo storage system; and wherein the step of autonomously causing the modular mobility base to move from the destination location on the return route to the origin location after the ordered item is detected to be removed from within the modular cargo storage system comprises:

autonomously causing, by the modular mobile autonomy control module, the modular mobility base to move from the destination location to a secondary delivery location after the ordered item is detected to be removed from the first compartment within the modular cargo storage system at the destination location and after the additional item is detected within a second compartment of the separated storage compartments within the modular cargo storage system while at the destination location, the secondary delivery location being identified as part of the destination information related to the dispatched store-to-consumer logistics operation; and autonomously causing, by the modular mobile autonomy control module, the modular mobility base to move from the secondary delivery location to the origin location after the additional item is detected to be removed from the second compartment within the modular cargo storage system at the secondary delivery location.

108. The method of embodiment 107, wherein the step of providing selective access to the ordered item within the modular cargo storage system comprises providing, by the modular cargo storage system, selective access to the first compartment maintaining the ordered item within the modular cargo storage system while limiting access to others of the separated storage compartments including the second compartment, selective access to the first compartment being provided only when the delivery recipient authentication input received correlates to the delivery authentication information indicating that the delivery recipient providing the delivery recipient authentication input is the authorized delivery recipient.

109. The method of embodiment 107, further comprising the step of setting, by the modular mobile autonomy control module, a first detachable climate control module disposed within the first compartment of the separated storage compartments within the payload area to first desired temperature according to the transport parameters on the ordered item.

110. The method of embodiment 107, further comprising the step of setting, by the modular mobile autonomy control module, a second detachable climate control module disposed within the second compartment of the separated storage compartments within the payload area to second desired temperature according to a transport parameter on the additional item, the transport parameter on the additional item being included in the dispatch command and related to the dispatched store-to-consumer logistics operation.

111. The method of embodiment 1, wherein the step of receiving the dispatch command comprises receiving, by the modular mobile autonomy control module, a pre-screened dispatch command from the dispatch server, the pre-screened dispatch command indicating the dispatch server has verified the dispatched store-to-consumer logistics operation is an autonomous delivery eligible logistics operation, the pre-screened dispatch command comprising at least identifier information on the ordered item, transport parameters on the ordered item, destination delivery information related to delivery of the ordered item, and delivery authentication information related to an authorized delivery recipient of the ordered item.

112. The method of embodiment 1, further comprising the steps, prior to receiving the dispatch command, of:

receiving, by the dispatch server, an autonomous delivery order for the ordered item priced at an autonomous delivery option level below a non-autonomous delivery option level for the same ordered item; and transmitting, by the dispatch server, the dispatch command to the modular mobile autonomy control module of the modular autonomous bot apparatus assembly.

113. The method of embodiment 1, wherein the step of autonomously causing the modular mobility base to move from the destination location on the return route to the bot storage location after the ordered item is detected to be removed from within the modular cargo storage system comprises autonomously causing, by the modular mobile autonomy control module, the modular mobility base to move from the destination location back to the origin location after the ordered item is detected to be removed from within the modular cargo storage system at the destination location and an additional item is detected to be placed within the modular cargo storage system at the destination location, the additional item to be returned to the origin location as a new retail work order from the authorized delivery recipient.

114. The method of embodiment 113, further comprising the step of autonomously causing, by the modular mobile autonomy control module, transfer of the additional item out from the payload area the modular cargo storage system at the origin location for processing of the additional item according to the new retail work order by a retail processing system located at the original location.

115. The method of embodiment 1, wherein the origin location is a warehousing location for warehoused ordered items and wherein the dispatch command further comprises a pickup location within the warehousing location where the ordered item is to be provided by a wireless node-enabled pick and place machine from the warehoused ordered items;

wherein the step of receiving the ordered item in the payload area within the modular cargo storage system comprises:

autonomously causing, by the modular mobile autonomy control module, the modular mobility base to move from within the warehousing location to the pickup location;

detecting, by the modular mobile autonomy control module, an unprompted advertising signal from the wireless node-enable pick and pack machine as the modular mobility base approaches the pickup location;

establishing a secure association between the modular mobile autonomy control module and the wireless node-enabled pick and place machine after detecting the unprompted advertising signal from the wireless node-enabled pick and place machine, the secure association between the wireless node-enabled pick and place machine and the modular mobile autonomy control module allowing secure sharing of information between the wireless node-enabled pick and place machine and the modular mobile autonomy control module and being pre-authorized by the dispatch server as it relates to the dispatched store-to-consumer logistics operation;

securely sharing, by the modular mobile autonomy control module, the identifier of the ordered item involved in the dispatched store-to-consumer logistics operation with the wireless node-enabled pick and place machine; and receiving, by the modular cargo storage system, the ordered item in the payload area within the modular cargo storage system from the wireless node-enabled pick and place machine.

116. The method of embodiment 115, wherein the step of receiving, by the modular cargo storage system, the ordered item in the payload area within the modular cargo storage system from the wireless node-enabled pick and place machine comprises:

requesting, by the modular mobile autonomy control module, the wireless node-enabled pick and place machine to obtain the ordered item based upon the identifier of the ordered item securely shared with the wireless node-enabled pick and place machine; and receiving, by the modular cargo storage system, the ordered item from the wireless node-enabled pick and place machine in response to the requesting step, wherein the ordered item received from the wireless node-enabled pick and place machine is placed by the wireless node-enabled pick and place machine within the payload area of the modular cargo storage system.

117. The method of embodiment 115, wherein the step of receiving, by the modular cargo storage system, the ordered item in the payload area within the modular cargo storage system from the wireless node-enabled pick and place machine comprises:

requesting, by the modular mobile autonomy control module, the wireless node-enabled pick and place machine to obtain the ordered item based upon the identifier of the ordered item securely shared with the wireless node-enabled pick and place machine;

receiving, by the modular cargo storage system, the ordered item from the wireless node-enabled pick and place machine in response to the requesting step, wherein the ordered item received from the wireless node-enabled pick and place machine is placed by the wireless node-enabled pick and place machine on an actuated belt surface of the modular cargo storage system; and actuating, by the modular mobile autonomy control module, the actuated belt surface to move the ordered item placed on the actuated belt surface to within the payload area of the modular cargo storage system.

118. The method of embodiment 115, wherein the step of receiving, by the modular cargo storage system, the ordered item in the payload area within the modular cargo storage system from the wireless node-enabled pick and place machine comprises:

requesting, by the modular mobile autonomy control module, the wireless node-enabled pick and place machine to obtain the ordered item based upon the identifier of the ordered item securely shared with the wireless node-enabled pick and place machine;

receiving, by the modular cargo storage system, the ordered item from the wireless node-enabled pick and place machine in response to the requesting step, wherein the ordered item received from the wireless node-enabled pick and place machine is placed by the wireless node-enabled pick and place machine on an extended ramp of the modular cargo storage system; and actuating, by the modular mobile autonomy control module, an actuated grabbing arm disposed within the modular cargo system to move the ordered item from on the extended ramp to within the payload area of the modular cargo storage system.

119. The method of embodiment 115, wherein the step of receiving, by the modular cargo storage system, the ordered item in the payload area within the modular cargo storage system from the wireless node-enabled pick and place machine comprises:

requesting, by the modular mobile autonomy control module, the wireless node-enabled pick and place machine to obtain the ordered item based upon the identifier of the ordered item securely shared with the wireless node-enabled pick and place machine;

receiving, by the modular cargo storage system, the ordered item from the wireless node-enabled pick and place machine in response to the requesting step, wherein the ordered item received from the wireless node-enabled pick and place machine is placed by the wireless node-enabled pick and place machine within the modular cargo storage system; and actuating, by the modular mobile autonomy control module, an actuated sliding arm disposed within the modular cargo system to move the ordered item as placed within the modular cargo storage system to within the payload area of the modular cargo storage system.

120. The method of embodiment 1, wherein the identifier information on the ordered item further comprises a node identifier corresponding to a wireless node associated with the ordered item.

121. The method of embodiment 120, wherein the step of receiving the ordered item in the payload area within the modular cargo storage system comprises:

detecting, by the modular mobile autonomy control module, an unprompted advertising signal from the wireless node associated with the ordered item;

establishing a secure association between the modular mobile autonomy control module and the wireless node associated with the ordered item after detecting the unprompted advertising signal from the wireless node associated with the ordered item, the secure association between the wireless node associated with the ordered item and the modular mobile autonomy control module allowing secure sharing of information between the wireless node associated with the ordered item and the modular mobile autonomy control module, the secure association being pre-authorized by the dispatch server as it relates to the dispatched store-to-consumer logistics operation;

receiving, by the modular cargo storage system, the ordered item in the payload area within the modular cargo storage system after establishing the secure association.

122. The method of embodiment 121, wherein the step of monitoring unloading of the ordered item from within the modular cargo storage system comprises:

monitoring a location of the wireless node associated with the ordered item operating as an ID node by the modular mobile autonomy control module operating as a master node; and detecting, by the modular mobile autonomy control module, when the location of the wireless node associated with the ordered item is outside the modular autonomous bot apparatus assembly.

123. The method of embodiment 1, wherein the ordered item comprises a plurality of trial items being sent to the authorized delivery recipient for satisfaction assessment before purchase;

wherein the step of monitoring the unloading of the ordered item comprises:

detecting, by the modular mobile autonomy control module, that each of the trial items have been removed from within the modular cargo storage system based upon sensor data generated by the one or more sensors, receiving, by the modular mobile autonomy control module, a satisfaction indicator input from the authorized delivery recipient after detecting that the trial items have been removed from within the modular cargo storage system, the satisfaction indicator input reflecting one or more of the trial items are to be returned after the satisfaction assessment by the authorized delivery recipient, and receiving, by the modular cargo storage system, the one or more trial items to be returned within the modular cargo storage system; and wherein the step of autonomously causing the modular mobility base to move from the destination location to the origin location comprises autonomously causing, by the modular mobile autonomy control module, the modular mobility base to move from the destination location on the return route to the origin location after receiving the satisfaction indicator input and receiving the one or more of the trial items to be returned in the payload area within the modular cargo storage system.

124. The method of embodiment 123, wherein the trial items comprise retail clothing items of differing sizes.

125. The method of embodiment 123, wherein the trial items comprise retail clothing items of differing designs.

126. The method of embodiment 123, wherein the trial items comprise retail clothing items of differing colors.

127. The method of embodiment 1, wherein the ordered item comprises a plurality of trial items being sent to the authorized delivery recipient for satisfaction assessment before purchase;

wherein the step of monitoring the unloading of the ordered item comprises:

detecting, by the modular mobile autonomy control module, that each of the trial items have been removed from within the modular cargo storage system based upon sensor data generated by the one or more sensors, and causing, by the modular mobile autonomy control module, the modular mobility base to remain stationary for a predetermined period of time awaiting a satisfaction indicator input from the authorized delivery recipient after detecting that the trial items have been removed from within the modular cargo storage system; and wherein the step of autonomously causing the modular mobility base to move from the destination location to the origin location comprises autonomously causing, by the modular mobile autonomy control module, the modular mobility base to move from the destination location on the return route to the origin location after the predetermined period of time expires without receiving the satisfaction indicator input.

128. The method of embodiment 1, wherein the ordered item comprises a plurality of trial items being sent to the authorized delivery recipient for satisfaction assessment before purchase;

wherein the step of monitoring the unloading of the ordered item comprises:

detecting, by the modular mobile autonomy control module, that each of the trial items have been removed from within the modular cargo storage system based upon sensor data generated by the one or more sensors, causing, by the modular mobile autonomy control module, the modular mobility base to remain stationary up to a predetermined period of time awaiting a satisfaction indicator input from the authorized delivery recipient after detecting that the trial items have been removed from within the modular cargo storage system; and receiving, by the modular mobile autonomy control module, a satisfaction indicator input from the authorized delivery recipient after detecting that the trial items have been removed from within the modular cargo storage system and prior to the end of the predetermined period of time, the satisfaction indicator input reflecting one or more of the trial items are to be returned after the satisfaction assessment by the authorized delivery recipient, and receiving, by the modular cargo storage system, the one or more trial items to be returned within the modular cargo storage system; and wherein the step of autonomously causing the modular mobility base to move from the destination location to the origin location comprises autonomously causing, by the modular mobile autonomy control module, the modular mobility base to move from the destination location on the return route to the origin location after receiving the satisfaction indicator input and receiving the one or more of the trial items to be returned in the payload area within the modular cargo storage system.

129. The method of embodiment 1, wherein the step of receiving the dispatch command comprises receiving, by the modular mobile autonomy control module, a pre-screened dispatch command from the dispatch server, the pre-screened dispatch command indicating the dispatch server has verified the dispatched store-to-consumer logistics operation is an autonomous delivery eligible logistics operation according to a weight of the ordered item, the pre-screened dispatch command comprising at least identifier information on the ordered item, transport parameters on the ordered item,
destination delivery information related to delivery of the ordered item, and
delivery authentication information related to an authorized delivery recipient of the ordered item.

130. The method of embodiment 1, wherein the transport parameters on the ordered item comprise at least weight information about the ordered item to be transported within the modular autonomous bot apparatus assembly; and
wherein the verifying step comprises verifying, by the modular mobile autonomy control module, that each of the modular mobile autonomy control module, the modular mobility base, the modular auxiliary power module, and the modular cargo storage system are compatible with weight information about the ordered item.

131. The method of embodiment 1, wherein the transport parameters on the ordered item comprise at least weight information about the ordered item to be transported within the modular autonomous bot apparatus assembly; and
wherein the verifying step comprises verifying, by the modular mobile autonomy control module, that the modular autonomous bot apparatus assembly has a transport capacity that is compatible with the weight information about the ordered item.

132. The method of embodiment 1, wherein the dispatch command further comprises a delivery schedule for what is to be delivered from contents of the modular cargo storage system;
wherein the transport parameters on the ordered item comprise at least weight information about the ordered item to be transported within the modular autonomous bot apparatus assembly; and
wherein the verifying step comprises
verifying, by the modular mobile autonomy control module, that the modular autonomous bot apparatus assembly has a transport capacity that is compatible with the weight information about the ordered item; and
verifying, by the modular mobile autonomy control module, that the delivery schedule is compatible with the weight information about the ordered item.

133. The method of embodiment 132, wherein the delivery schedule comprises at least one pickup logistics operation to be performed as part of the dispatched store-to-consumer logistics operation, wherein the at least one pickup logistics operation anticipated to add an additional item having additional weight in the payload area with the ordered item.

134. A method of performing a dispatched store-to-consumer logistics operation related to an ordered item and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to maintain the ordered item within the modular autonomous bot apparatus assembly, and a modular mobile autonomy control module that autonomously controls operation of the modular autonomous bot apparatus assembly, the method comprising the steps of:
receiving, by the modular mobile autonomy control module, a dispatch command from the dispatch server, the dispatch command comprising at least
identifier information on the ordered item,
transport parameters on the ordered item, and
destination delivery information related to delivery of the ordered item;
verifying, by the modular mobile autonomy control module, that each of the modular mobile autonomy control module, the modular mobility base, the modular auxiliary power module, and the modular cargo storage system are compatible with the dispatched store-to-consumer logistics operation based upon the dispatch command;
receiving, by the modular cargo storage system, the ordered item in a payload area within the modular cargo storage system;
autonomously causing, by the modular mobile autonomy control module, the modular mobility base to move from an origin location on a route to a destination location identified by the destination delivery information;
providing, by the modular cargo storage system, selective access to the ordered item within the modular cargo storage system upon arrival at the destination location;
autonomously, by the modular mobile autonomy control module, unloading the ordered item from within the modular cargo storage system using an object manipulation system disposed on at least one of the modular mobile autonomy control module, the modular cargo storage system, and the modular auxiliary power module; and
autonomously causing, by the modular mobile autonomy control module, the modular mobility base to move from the destination location on a return route to the origin location after the ordered item is removed from within the modular cargo storage system by the object manipulation system.

135. The method of embodiment 134, wherein the dispatch command further comprises delivery authentication information related to an authorized facility node associated with the destination location; and
further comprising the step of receiving delivery authentication input by the modular mobile autonomy control module from an external wireless node disposed external to the modular autonomous bot apparatus assembly at the destination location; and
wherein the providing step comprises providing, by the modular cargo storage system, selective access to the ordered item within the modular cargo storage system only when the delivery authentication input received correlates to the delivery authentication information indicating that the external wireless node providing the delivery authentication input is the authorized facility node.

136. The method of embodiment 134, wherein the dispatch command further comprises notification information for a designated notification recipient for the ordered item; and
further comprising the step of notifying, by the modular mobile autonomy control module, the designated notification recipient for the ordered item using the notification information, the step of notifying being triggered when the modular autonomous bot apparatus assembly is within a threshold notification range of the destination location identified by the destination information.

Further Embodiment J—Methods of Performing a Dispatched Consumer-to-Store Return or Swap Logistics Operation Related to an Item being Replaced and Using a Modular Autonomous Bot Apparatus Assembly and a Dispatch Server 1. A method of performing a dispatched consumer-to-store return logistics operation related to an item being replaced and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to at least temporarily maintain the item being replaced within the modular autonomous bot apparatus assembly, and a modular mobile autonomy control module that autonomously controls operation of the modular autonomous bot apparatus assembly during the dispatched consumer-to-store return logistics operation, the method comprising the steps of:

- receiving, by the modular mobile autonomy control module, a return operation dispatch command from the dispatch server, the return operation dispatch command comprising at least
  - identifier information on the item being replaced,
  - transport parameters on the item being replaced,
  - designated pickup information related to pickup of the item being replaced, and
  - pickup authentication information related to an authorized supplier of the item being replaced;
- verifying, by the modular mobile autonomy control module, that each of the modular mobile autonomy control module, the modular mobility base, the modular auxiliary power module, and the modular cargo storage system are compatible with the dispatched consumer-to-store return logistics operation based upon the dispatch command;
- autonomously causing, by the modular mobile autonomy control module, the modular mobility base to move from an origin location on a route to a designated pickup location identified by the designated pickup information;
- notifying, by the modular mobile autonomy control module, the authorized supplier of the item being replaced of an approaching pickup for the item being replaced once the modular autonomous bot apparatus assembly is within a threshold notification range of the designated pickup location identified by the designated pickup information;
- receiving supplier authentication input by the modular mobile autonomy control module from a return entity disposed external to the modular autonomous bot apparatus assembly at the designated pickup location;
- providing, by the modular cargo storage system, selective access to a payload area within the modular cargo storage system only when the supplier authentication input received correlates to the pickup authentication information indicating that the return entity providing the supplier authentication input is the authorized supplier of the item being replaced;
- monitoring, by the modular mobile autonomy control module, loading of the item being replaced into the payload area of the modular cargo storage system using one or more sensors on at least one of the modular mobile autonomy control module and the modular cargo storage system;
- receiving, by the modular cargo storage system, the item being replaced in the payload area within the modular cargo storage system;
- receiving, by the modular cargo storage system, return documentation provided by the authorized supplier of the item being return, the return documentation indicating the item being replaced is authorized to be returned in accordance with a return transaction order received by the dispatch server; and
- autonomously causing, by the modular mobile autonomy control module, the modular mobility base to move from the designated pickup location on a return route to the origin location after the item being replaced is detected to be within the modular cargo storage system based upon monitoring the loading of the item being replaced and the return documentation is loaded within the modular cargo storage system with the item being replaced.

2. The method of embodiment 1, wherein the notifying step comprises generating a display alert for the authorized supplier of the item being replaced on a display on the modular mobile autonomy control module once the modular autonomous bot apparatus assembly is within the threshold notification range of the designated pickup location identified by the designated pickup information.

3. The method of embodiment 1, wherein the notifying step comprises generating an audio notification for the authorized supplier of the item being replaced on a speaker on the modular mobile autonomy control module once the modular autonomous bot apparatus assembly is within the threshold notification range of the pickup location identified by the designated pickup information.

4. The method of embodiment 1, wherein the notifying step comprises transmitting a pickup notification message to an external wireless node once the modular autonomous bot apparatus assembly is within the threshold notification range of the pickup location identified by the designated pickup information, the external wireless node being related to the authorized supplier of the item being replaced according to the designated pickup information.

5. The method of embodiment 1, wherein the notifying step comprises transmitting a pickup notification message to an external wireless node after the modular autonomous bot apparatus assembly moves from the origin location, the external wireless node being related to the authorized supplier of the item being replaced according to the designated pickup information.

6. The method of embodiment 5, wherein the pickup notification message comprises one from a group consisting of a text message, an electronic mail message, and a phone call.

7. The method of embodiment 5, wherein the notifying step further comprises transmitting an arrival estimate to the external wireless node, the arrival estimate indicating an estimated time to arrive at the pickup location.

8. The method of embodiment 1, wherein the notifying step further comprising the steps of:
  - transmitting, by the modular mobile autonomy control module, a verification request to confirm pickup of the item being replaced to the authorized supplier of the item being replaced, the verification request asking for a responsive confirmation that the item being replaced should be picked up by the modular autonomous bot apparatus assembly at the designated pickup location; and
  - autonomously causing, by the modular mobile autonomy control module, the modular mobility base to continue moving to the designated pickup location to complete the dispatched consumer-to-store return logistics operation unless the responsive confirmation from the authorized supplier indicated that the item being replaced should not be picked up at that designated pickup location.

9. The method of embodiment 1, wherein the step of receiving the return operation dispatch command from the dispatch server comprises receiving, by the modular mobile autonomy control module, a return order assignment message as the return operation dispatch command from a retail system that received the return transaction order for the item being replaced, wherein the retail system operating as the dispatch server.

10. The method of embodiment 9, wherein the designated pickup information related to the pickup of the item being replaced includes a pickup time and pickup date as selected in the return transaction order.

11. The method of embodiment 1, wherein the step of monitoring loading of the item being replaced comprises generating a log entry in a custodial inventory data structure when the item being replaced is detected to be within the modular cargo storage system, the log entry reflecting receipt of the item being replaced within the modular cargo storage system.

12. The method of embodiment 1, wherein the step of monitoring loading of the item being replaced comprises:
capturing sensor data from the one or more sensors on at least one of the modular mobile autonomy control module and the modular cargo storage system; and
detecting when the item being replaced is received within the modular cargo storage system based upon the captured sensor data.

13. The method of embodiment 12, wherein the captured sensor data comprises visual images of what is disposed within the modular cargo storage system.

14. The method of embodiment 1, wherein the step of monitoring loading of the item being replaced comprises:
generating barcode scan data related to item being replaced as the item being replaced is received within the modular cargo storage system using a barcode scanner as one of the one or more sensors; and
processing the generated barcode scan data to monitor the ordered item as the ordered item is placed within the modular cargo storage system.

15. The method of embodiment 1, wherein the step of monitoring loading of the item being replaced comprises:
generating image data related to item being replaced as the item being replaced is received within the modular cargo storage system using a camera as one of the one or more sensors;
processing the generated image data to monitor the ordered item as the ordered item is placed within the modular cargo storage system.

16. The method of embodiment 1, wherein the step of monitoring loading of the item being replaced comprises:
generating video data related to item being replaced as the item being replaced is received within the modular cargo storage system using a video camera as one of the one or more sensors; and
processing the generated video data to monitor the ordered item as the ordered item is placed within the modular cargo storage system.

17. The method of embodiment 1, wherein the step of monitoring loading of the item being replaced comprises:
capturing audio data using a microphone as one of the one or more sensors disposed to record sound within and proximate to the modular cargo storage system as the item being replaced is received within the modular cargo storage system; and
processing the captured audio data to monitor the ordered item as the ordered item is placed within the modular cargo storage system.

18. The method of embodiment 1, wherein the step of monitoring loading of the item being replaced comprises detecting movement of a wireless node associated with the item being replaced as the item being replaced is received within the modular cargo storage system based upon a plurality of signals broadcast from the wireless node associated with the item being replaced.

19. The method of embodiment 1, wherein the step of monitoring loading of the item being replaced comprises detecting a change in location of a wireless node associated with the item being replaced from outside the modular cargo storage system to inside the modular cargo storage system as the item being replaced is received within the modular cargo storage system as determined by the modular mobile autonomous control module.

20. The method of embodiment 1, further comprising the step of notifying, by the modular mobile autonomy control module, a retail entity at the origin location of an approaching delivery for the item being replaced once the modular autonomous bot apparatus assembly is within a threshold notification range of the origin location.

21. The method of embodiment 1, further comprising the step of notifying, by the modular mobile autonomy control module, a retail entity at the origin location about delivery of the item being replaced after the modular autonomous bot apparatus assembly arrives at the origin location.

22. The method of embodiment 1, further comprising the step of notifying, by the modular mobile autonomy control module, the authorized supplier about delivery of the item being replaced after the modular autonomous bot apparatus assembly arrives at the origin location.

23. The method of embodiment 1, wherein the step of autonomously causing the modular mobility base to move from the origin location to the designated pickup location comprises autonomously causing, by the modular mobile autonomy control module, the modular mobility base to move from the origin location to the designated pickup location while interacting with a wireless building facility node to actuate a pathway obstacle disposed in a path on the route to the designated pickup location.

24. The method of embodiment 23, wherein the pathway obstacle comprises an actuated door controlled by the wireless building facility node.

25. The method of embodiment 23, wherein the pathway obstacle comprises an actuated elevator controlled by the wireless building facility node.

26. The method of embodiment 23, wherein the pathway obstacle comprises an actuated lock controlled by the wireless building facility node.

27. The method of embodiment 23, wherein interacting with the wireless building facility node to actuate the pathway obstacle comprises:
establishing an authorized association pairing between the modular mobile autonomy control module and the wireless building facility node based upon the authentication information related to the dispatched logistics operation; and
causing the wireless building facility node to actuate the pathway obstacle after establishing the authorized association pairing between the modular mobile autonomy control module and the wireless building facility node.

28. The method of embodiment 1, wherein the step of autonomously causing the modular mobility base to move from the origin location to the designated pickup location comprises autonomously causing, by the modular mobile autonomy control module, the modular mobility base to move from the origin location to the designated pickup location while engaging a pathway obstacle disposed in a path on the route to the designated pickup location using an articulating arm disposed on the modular autonomous bot apparatus assembly and using a plurality of sensors disposed on at least one of the modular mobility base and the modular mobile autonomy control module.

29. The method of embodiment 28, wherein the pathway obstacle comprises a manually actuated door.

30. The method of embodiment 28, wherein the pathway obstacle comprises a manually actuated elevator.

31. The method of embodiment 28, wherein the pathway obstacle comprises a manually actuated lock.

32. The method of embodiment 28, wherein engaging the pathway obstacle using the articulating arm and sensors comprises:
- guiding, by the modular mobile autonomy control module, the articulating arm to a control element of the pathway obstacle using one or more of the sensors disposed on at least one of the modular mobility base and the modular mobile autonomy control module; and
- actuating the pathway obstacle, by the modular mobile autonomy control module, once the articulating arm engages the control element of the pathway obstacle.

33. The method of embodiment 32, wherein the control element of the pathway obstacle comprises one from the group consisting of a handle for the pathway obstacle, a button for the pathway obstacle, a switch for the pathway obstacle, and a portion of a control panel for the pathway obstacle.

34. The method of embodiment 1, wherein the providing step comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

35. The method of embodiment 34, wherein actuating, by the modular mobile autonomy control module, the actuated cargo door comprises actuating an actuated joint on the actuated cargo door to cause the actuated cargo door to move from the closed position to the open position.

36. The method of embodiment 34, wherein actuating, by the modular mobile autonomy control module, the actuated cargo door further comprises actuating an electro-mechanical lock on the actuated cargo door to cause the actuated cargo door to unlock before moving from the closed position to the open position.

37. The method of embodiment 1, wherein the providing step comprises actuating, by the modular mobile autonomy control module, an actuated sliding arm disposed on the modular cargo storage system to move the item being replaced into the payload area within the modular cargo storage system.

38. The method of embodiment 1, wherein the providing step comprises actuating, by the modular mobile autonomy control module, an actuated grabbing arm disposed on the modular cargo storage system to grab and move the item being replaced into the payload area within the modular cargo storage system as part of receiving the item being replaced.

39. The method of embodiment 1, wherein the providing step comprises actuating, by the modular mobile autonomy control module, an actuated belt surface disposed on the modular auxiliary power module as a movable support surface exposed within a payload area inside the modular cargo storage system, the actuated belt surface being operative when actuated to cause the item being replaced on the actuated belt surface to move within the payload area as part of receiving the item being replaced.

40. The method of embodiment 1, wherein the supplier authentication input received by the modular mobile autonomy control module is provided by the return entity through a user input panel disposed on the modular autonomous bot apparatus coupled to the modular mobile autonomy control module.

41. The method of embodiment 1, wherein the supplier authentication input received by the modular mobile autonomy control module comprises an access code provided by the return entity through the user input panel disposed on the modular cargo storage system and operatively coupled to the modular mobile autonomy control module.

42. The method of embodiment 1, wherein the supplier authentication input received by the modular mobile autonomy control module comprises a biometric input provided by the return entity through the user input panel disposed on the modular cargo storage system and operatively coupled to the modular mobile autonomy control module.

43. The method of embodiment 1, wherein the supplier authentication input received by the modular mobile autonomy control module is provided by the return entity through an external wireless node disposed external to the modular autonomous bot apparatus assembly.

44. The method of embodiment 43, wherein the supplier authentication input received by the modular mobile autonomy control module comprises an access code provided by the return entity through the external wireless node disposed external to the modular autonomous bot apparatus assembly.

45. The method of embodiment 43, wherein the supplier authentication input received by the modular mobile autonomy control module comprises a biometric input provided by the return entity through the external wireless node disposed external to the modular autonomous bot apparatus assembly.

46. The method of embodiment 1, wherein the pickup authentication information related to the dispatched consumer-to-store return logistics operation includes an identifier of the authorized supplier for the item being replaced as part of the dispatched consumer-to-store return logistics operation; and
- wherein the step of receiving the supplier authentication input comprises:
  - detecting, by the modular mobile autonomy control module, an advertising signal as the supplier authentication input from an external wireless node within a predetermined range of the modular autonomous bot apparatus assembly once the modular autonomous bot apparatus assembly has arrived at the designated pickup location identified by the designated pickup information; and
  - authenticating, by the modular mobile autonomy control module, that the external wireless node is associated with the authorized supplier for the item being replaced within the modular cargo storage system based upon the identifier of the authorized supplier and identifier information within the detected advertising signal broadcast from the external wireless node.

47. The method of embodiment 1, wherein the pickup authentication information related to the dispatched consumer-to-store return logistics operation includes an identifier of the authorized supplier for the item being replaced as part of the dispatched consumer-to-store return logistics operation; and wherein the step of receiving the supplier authentication input comprises:

detecting, by the modular mobile autonomy control module, an unprompted advertising signal from an external wireless node within a predetermined range of the modular autonomous bot apparatus assembly once the modular autonomous bot apparatus assembly has arrived at the designated pickup location identified by the designated pickup information; and establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched consumer-to-store return logistics operation.

48. A method of performing a dispatched swap logistics operation related to an item being replaced being swapped for a replacement item and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least maintain the item being replaced within the modular autonomous bot apparatus assembly, and a modular mobile autonomy control module that autonomously controls operation of the modular autonomous bot apparatus assembly during the dispatched swap logistics operation, the method comprising the steps of:

receiving, by the modular mobile autonomy control module, a swap operation dispatch command from the dispatch server, the swap operation dispatch command comprising at least identifier information on the item being replaced and identifier information on the replacement item, transport parameters on the item being replaced and the replacement item, designated pickup information related to swapping the item being replaced for the replacement item, and pickup authentication information related to an authorized delivery recipient of replacement item;

verifying, by the modular mobile autonomy control module, that each of the modular mobile autonomy control module, the modular mobility base, the modular auxiliary power module, and the modular cargo storage system are compatible with the dispatched swap logistics operation based upon the swap operation dispatch command;

receiving, by the modular cargo storage system, the replacement item in a payload area within the modular cargo storage system;

autonomously causing, by the modular mobile autonomy control module, the modular mobility base to move from an origin location on a route to a designated swap location identified by the designated pickup information;

notifying, by the modular mobile autonomy control module, the authorized delivery recipient of the replacement item of an approaching pickup for the item being replaced and delivery of the replacement item once the modular autonomous bot apparatus assembly is within a threshold notification range of the designated swap location identified by the designated pickup information;

receiving delivery recipient authentication input by the modular mobile autonomy control module from a delivery recipient disposed external to the modular autonomous bot apparatus assembly at the designated swap location;

providing, by the modular cargo storage system, selective access to the payload area within the modular cargo storage system only when the delivery recipient authentication input received correlates to the pickup authentication information indicating that the delivery recipient providing the delivery recipient authentication input is the authorized delivery recipient of the replacement item;

monitoring, by the modular mobile autonomy control module, an exchange of the replacement item from the payload area of the modular cargo storage system with the item being replaced using one or more sensors on at least one of the modular mobile autonomy control module and the modular cargo storage system; and autonomously causing, by the modular mobile autonomy control module, the modular mobility base to move from the designated swap location on a return route to the origin location after the item being replaced is detected to be within the modular cargo storage system based upon the monitored loading of the item being replaced.

49. The method of embodiment 48, wherein the item being replaced and the replacement items are consumable items.

50. The method of embodiment 48, wherein the notifying step comprises generating a display alert for the authorized delivery recipient of the replacement item on a display on the modular mobile autonomy control module once the modular autonomous bot apparatus assembly is within the threshold notification range of the designated swap location identified by the designated pickup information.

51. The method of embodiment 48, wherein the notifying step comprises generating an audio notification for the authorized delivery recipient of the replacement item on a speaker on the modular mobile autonomy control module once the modular autonomous bot apparatus assembly is within the threshold notification range of the designated swap location identified by the designated pickup information.

52. The method of embodiment 48, wherein the notifying step comprises transmitting a delivery notification message to an external wireless node once the modular autonomous bot apparatus assembly is within the threshold notification range of the designated swap location identified by the designated pickup information, the external wireless node being related to the authorized delivery recipient of the replacement item according to the designated pickup information.

53. The method of embodiment 48, wherein the notifying step comprises transmitting a delivery notification message to an external wireless node after the modular autonomous bot apparatus assembly moves from the origin location, the external wireless node being related to the authorized delivery recipient of the replacement item according to the designated pickup information.

54. The method of embodiment 53, wherein the delivery notification message comprises one from a group consisting of a text message, an electronic mail message, and a phone call.

55. The method of embodiment 53, wherein the notifying step further comprises transmitting an arrival estimate to the external wireless node, the arrival estimate indicating an estimated time to arrive at the designated swap location.

56. The method of embodiment 48, wherein the notifying step further comprising the steps of:
- transmitting, by the modular mobile autonomy control module, a verification request to confirm pickup of the item being replaced to the authorized delivery recipient of the replacement item, the verification request asking for a responsive confirmation that the item being replaced should be picked up by the modular autonomous bot apparatus assembly at the designated swap location; and
- autonomously causing, by the modular mobile autonomy control module, the modular mobility base to continue moving to the designated swap location to complete the dispatched swap logistics operation unless the responsive confirmation from the authorized delivery recipient indicates that the item being replaced should not be picked up at the designated swap location 57. The method of embodiment 48, wherein the notifying step further comprising the steps of:
- transmitting, by the modular mobile autonomy control module, a verification request to confirm pickup of the item being replaced to the authorized delivery recipient of the replacement item, the verification request asking for a responsive confirmation that the item being replaced should be picked up by the modular autonomous bot apparatus assembly at the designated swap location; and
- autonomously causing, by the modular mobile autonomy control module, the modular mobility base to continue moving to the designated swap location to complete the dispatched swap logistics operation unless the responsive confirmation from the authorized delivery recipient indicates that the replacement item should not be delivered at the designated swap location.

58. The method of embodiment 48, wherein the step of receiving the swap operation dispatch command from the dispatch server comprises receiving, by the modular mobile autonomy control module, a replacement order message as the swap operation dispatch command from a retail system that received a swap transaction order for the replacement item, wherein the retail system operating as the dispatch server.

59. The method of embodiment 58, wherein designated pickup information related to swapping the item being replaced for the replacement item includes a delivery time and delivery date as selected in the swap transaction order.

60. The method of embodiment 48, wherein the step of monitoring the exchange of the replacement item from the payload area of the modular cargo storage system with the item being replaced comprises the steps of:
- monitoring, by the modular mobile autonomy control module, unloading of the replacement item from the payload area of the modular cargo storage system using the one or more sensors on at least one of the modular mobile autonomy control module and the modular cargo storage system; and
- monitoring, by the modular mobile autonomy control module, loading of the item being replaced into the modular cargo storage system using the one or more sensors as the item being replaced is received into the payload area of the modular cargo storage system.

61. The method of embodiment 48, wherein the step of monitoring the exchange of the replacement item from the payload area of the modular cargo storage system with the item being replaced comprises generating a log entry in a custodial inventory data structure when the replacement item is detected to be removed from the modular cargo storage system and the item being replaced is detected to be within the modular cargo storage system, the log entry reflecting the exchange of the replacement item for the item being replacement.

62. The method of embodiment 48, wherein the step of monitoring the exchange of the replacement item from the payload area of the modular cargo storage system with the item being replaced comprises:
- capturing sensor data from the one or more sensors on at least one of the modular mobile autonomy control module and the modular cargo storage system; and
- detecting when the replacement item is removed from the modular cargo storage system and when the item being replaced is received within the modular cargo storage system based upon the captured sensor data.

63. The method of embodiment 62, wherein the captured sensor data comprises visual images of what is disposed within the modular cargo storage system.

64. The method of embodiment 48, wherein the step of monitoring the exchange of the replacement item from the payload area of the modular cargo storage system with the item being replaced comprises:
- generating barcode scan data related to the item being replaced and the replacement item as the item being replaced is swapped in for the replacement item that is removed from within the modular cargo storage system using a barcode scanner as one of the one or more sensors; and
- processing the generated barcode scan data to monitor the item being replaced and the replacement item as the item being replaced is swapped in for the replacement item that is removed from within the modular cargo storage system.

65. The method of embodiment 48, wherein the step of monitoring the exchange of the replacement item from the payload area of the modular cargo storage system with the item being replaced comprises:
- generating image data related to item being replaced and the replacement item as the item being replaced is swapped in for the replacement item that is removed from within the modular cargo storage system using a camera as one of the one or more sensors; and
- processing the generated image data to monitor the item being replaced and the replacement item as the item being replaced is swapped in for the replacement item that is removed from within the modular cargo storage system.

66. The method of embodiment 48, wherein the step of monitoring the exchange of the replacement item from the payload area of the modular cargo storage system with the item being replaced comprises:
- generating video data related to item being replaced and the replacement item as the item being replaced is swapped in for the replacement item that is removed from within the modular cargo storage system using a video camera as one of the one or more sensors; and processing the generated video data to monitor the item being replaced and the replacement item as the item being replaced is swapped in for the replacement item that is removed from within the modular cargo storage system.

67. The method of embodiment 48, wherein the step of monitoring the exchange of the replacement item from the payload area of the modular cargo storage system with the item being replaced comprises:

capturing audio data using a microphone as one of the one or more sensors disposed to record sound within and proximate to the modular cargo storage system as the item being replaced is swapped in for the replacement item that is removed from within the modular cargo storage system; and processing the captured audio data to monitor the item being replaced and the replacement item as the item being replaced is swapped in for the replacement item that is removed from within the modular cargo storage system.

68. The method of embodiment 48, wherein the step of monitoring the exchange of the replacement item from the payload area of the modular cargo storage system with the item being replaced comprises detecting movement of a wireless node associated with the item being replaced as the item being replaced is swapped in for the replacement item being removed from within the modular cargo storage system based upon a plurality of signals broadcast from the wireless node associated with the item being replaced.

69. The method of embodiment 48, wherein the step of monitoring the exchange of the replacement item from the payload area of the modular cargo storage system with the item being replaced comprises detecting movement of a wireless node associated with the replacement item as the replacement item is swapped out from within the modular cargo storage system for the item being replaced based upon a plurality of signals broadcast from the wireless node associated with replacement item.

70. The method of embodiment 48, wherein the step of monitoring the exchange of the replacement item from the payload area of the modular cargo storage system with the item being replaced comprises detecting a change in location of a wireless node associated with the item being replaced from a location outside the modular cargo storage system to the payload area inside the modular cargo storage system as the item being replaced is swapped for the replacement item that is removed from within the modular cargo storage system as determined by the modular mobile autonomous control module.

71. The method of embodiment 48, wherein the step of monitoring the exchange of the replacement item from the payload area of the modular cargo storage system with the item being replaced comprises detecting a change in location of a wireless node associated with the replacement item from inside the modular cargo storage system to outside the modular cargo storage system as the item being replaced is swapped in for the replacement item that is removed from within the modular cargo storage system as determined by the modular mobile autonomous control module.

72. The method of embodiment 48 further comprising the step of notifying, by the modular mobile autonomy control module, a retail entity at the origin location of an approaching return delivery of the item being replaced once the modular autonomous bot apparatus assembly is within a threshold notification range of the origin location.

73. The method of embodiment 48, further comprising the step of notifying, by the modular mobile autonomy control module, a retail entity at the origin location about delivery of the item being replaced after the modular autonomous bot apparatus assembly arrives at the origin location.

74. The method of embodiment 48, wherein the step of autonomously causing the modular mobility base to move from the origin location to the designated swap location comprises autonomously causing, by the modular mobile autonomy control module, the modular mobility base to move from the origin location to the designated swap location while interacting with a wireless building facility node to actuate a pathway obstacle disposed in a path on the route to the designated swap location.

75. The method of embodiment 74, wherein the pathway obstacle comprises an actuated door controlled by the wireless building facility node.

76. The method of embodiment 74, wherein the pathway obstacle comprises an actuated elevator controlled by the wireless building facility node.

77. The method of embodiment 74, wherein the pathway obstacle comprises an actuated lock controlled by the wireless building facility node.

78. The method of embodiment 74, wherein interacting with the wireless building facility node to actuate the pathway obstacle comprises:

establishing an authorized association pairing between the modular mobile autonomy control module and the wireless building facility node based upon the authentication information related to the dispatched swap logistics operation; and causing the wireless building facility node to actuate the pathway obstacle after establishing the authorized association pairing between the modular mobile autonomy control module and the wireless building facility node.

79. The method of embodiment 48, wherein the step of autonomously causing the modular mobility base to move from the origin location to the designated swap location comprises autonomously causing, by the modular mobile autonomy control module, the modular mobility base to move from the origin location to the designated swap location while engaging a pathway obstacle disposed in a path on the route to the designated swap location using an articulating arm disposed on the modular autonomous bot apparatus assembly and using a plurality of sensors disposed on at least one of the modular mobility base and the modular mobile autonomy control module.

80. The method of embodiment 79, wherein the pathway obstacle comprises a manually actuated door.

81. The method of embodiment 79, wherein the pathway obstacle comprises a manually actuated elevator.

82. The method of embodiment 79, wherein the pathway obstacle comprises a manually actuated lock.

83. The method of embodiment 79, wherein engaging the pathway obstacle using the articulating arm and the sensors comprises:

guiding, by the modular mobile autonomy control module, the articulating arm to a control element of the pathway obstacle using one or more of the sensors disposed on at least one of the modular mobility base and the modular mobile autonomy control module; and actuating the pathway obstacle, by the modular mobile autonomy control module, once the articulating arm engages the control element of the pathway obstacle.

84. The method of embodiment 83, wherein the control element of the pathway obstacle comprises one from the group consisting of a handle for the pathway obstacle, a button for the pathway obstacle, a switch for the pathway obstacle, and a portion of a control panel for the pathway obstacle.

85. The method of embodiment 48, wherein the receiving step comprises actuating, by the modular mobile autonomy control module, an actuated cargo door disposed on the modular auxiliary power module to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position.

86. The method of embodiment 85, wherein actuating, by the modular mobile autonomy control module, the actuated cargo door comprises actuating an actuated joint on the actuated cargo door to cause the actuated cargo door to move from the closed position to the open position.

87. The method of embodiment 85, wherein actuating, by the modular mobile autonomy control module, the actuated cargo door further comprises actuating an electro-mechanical lock on the actuated cargo door to cause the actuated cargo door to unlock before moving from the closed position to the open position.

88. The method of embodiment 48, wherein the receiving step comprises actuating, by the modular mobile autonomy control module, an actuated sliding arm disposed on the modular cargo storage system to move the item being replaced into the payload area within the modular cargo storage system.

89. The method of embodiment 48, wherein the receiving step comprises actuating, by the modular mobile autonomy control module, an actuated grabbing arm disposed on the modular cargo storage system to grab and move the item being replaced into the payload area within the modular cargo storage system as part of receiving the item being replaced.

90. The method of embodiment 48, wherein the receiving step comprises actuating, by the modular mobile autonomy control module, an actuated belt surface disposed on the modular auxiliary power module as a movable support surface exposed within the payload area inside the modular cargo storage system, the actuated belt surface being operative when actuated to cause the item being replaced as placed on the actuated belt surface to move within the payload area as part of receiving the item being replaced.

91. The method of embodiment 48 further comprising, after the providing step, unloading, by the modular cargo storage system, the replacement item from within the payload area of the modular cargo storage system and loading the item being replaced into the payload area within the modular cargo storage system.

92. The method of embodiment 91, wherein each of the steps of unloading the replacement item and loading the item being replaced comprises actuating, by the modular mobile autonomy control module, an actuated cargo door disposed on the modular auxiliary power module to an open position once the delivery recipient authentication input correlates to a portion of the pickup authentication information related to the dispatched swap logistics operation, wherein the actuated cargo door provides a seal to the payload area within the modular cargo storage system when the actuated cargo door is in a closed position and the actuated cargo door provides access to the payload area within the modular cargo storage system when the actuated cargo door is in the open position.

93. The method of embodiment 92, wherein actuating, by the modular mobile autonomy control module, the actuated cargo door comprises actuating an actuated joint on the actuated cargo door to cause the actuated cargo door to move from the closed position to the open position.

94. The method of embodiment 92, wherein actuating, by the modular mobile autonomy control module, the actuated cargo door further comprises actuating an electro-mechanical lock on the actuated cargo door to cause the actuated cargo door to unlock before moving from the closed position to the open position.

95. The method of embodiment 91, wherein the step of unloading the replacement item comprises actuating, by the modular mobile autonomy control module, an actuated sliding arm disposed on the modular cargo storage system to move the replacement item out from the payload area within the modular cargo storage system.

96. The method of embodiment 91, wherein the step of loading the item being replaced comprises actuating, by the modular mobile autonomy control module, an actuated sliding arm disposed on the modular cargo storage system to move the item being replaced into the payload area within the modular cargo storage system.

97. The method of embodiment 91, wherein the step of unloading the replacement item comprises actuating, by the modular mobile autonomy control module, an actuated grabbing arm disposed on the modular cargo storage system to grab and move the replacement item out from the payload area within the modular cargo storage system.

98. The method of embodiment 91, wherein the step of loading the item being replaced comprises actuating, by the modular mobile autonomy control module, an actuated grabbing arm disposed on the modular cargo storage system to move the item being replaced into the payload area within the modular cargo storage system.

99. The method of embodiment 91, wherein the step of unloading the replacement item comprises actuating, by the modular mobile autonomy control module, an actuated belt surface disposed on the modular auxiliary power module as a movable support surface exposed within the payload area inside the modular cargo storage system, the actuated belt surface being operative when actuated to cause the replacement item as placed on the actuated belt surface to move out from within the payload area.

100. The method of embodiment 91, wherein the step of loading the item being replaced comprises actuating, by the modular mobile autonomy control module, an actuated belt surface disposed on the modular auxiliary power module as a movable support surface exposed within the payload area inside the modular cargo storage system, the actuated belt surface being operative when actuated to cause the item being replaced as placed on the actuated belt surface to move into the payload area.

101. The method of embodiment 48, wherein the delivery recipient authentication input received by the modular mobile autonomy control module is provided by the delivery recipient through a user input panel disposed on the modular autonomous bot apparatus coupled to the modular mobile autonomy control module.

102. The method of embodiment 48, wherein the delivery recipient authentication input received by the modular mobile autonomy control module comprises an access code provided by the delivery recipient through the user input panel disposed on the modular cargo storage system and operatively coupled to the modular mobile autonomy control module.

103. The method of embodiment 48, wherein the delivery recipient authentication input received by the modular mobile autonomy control module comprises a biometric input provided by the delivery recipient through the user input panel disposed on the modular cargo storage system and operatively coupled to the modular mobile autonomy control module.

104. The method of embodiment 48, wherein the delivery recipient authentication input received by the modular mobile autonomy control module is provided by the delivery recipient through an external wireless node disposed external to the modular autonomous bot apparatus assembly.

105. The method of embodiment 104, wherein the delivery recipient authentication input received by the modular mobile autonomy control module comprises an access code provided by the delivery recipient through the external wireless node disposed external to the modular autonomous bot apparatus assembly.

106. The method of embodiment 104, wherein the delivery recipient authentication input received by the modular mobile autonomy control module comprises a biometric input provided by the delivery recipient through the external wireless node disposed external to the modular autonomous bot apparatus assembly.

107. The method of embodiment 48, wherein the pickup authentication information related to the dispatched swap logistics operation includes an identifier of the authorized delivery recipient for the replacement item as part of the dispatched swap logistics operation; and
  wherein the step of receiving the delivery recipient authentication input comprises:
    detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the designated swap location identified by the designated pickup information; and
    authenticating, by the modular mobile autonomy control module, that the external wireless node is associated with the authorized delivery recipient for the item being replaced within the modular cargo storage system based upon the identifier of the authorized delivery recipient and identifier information within the detected advertising signal broadcast from the external wireless node.

108. The method of embodiment 48, wherein the pickup authentication information related to the dispatched swap logistics operation includes an identifier of the authorized delivery recipient for the replacement item as part of the dispatched swap logistics operation; and
  wherein the step of receiving the delivery recipient authentication input comprises:
    detecting, by the modular mobile autonomy control module, an unprompted advertising signal from an external wireless node within a predetermined range of the modular autonomous bot apparatus assembly once the modular autonomous bot apparatus assembly has arrived at the designated swap location identified by the designated pickup information; and
    establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched swap logistics operation.

109. The method of embodiment 48, wherein the designated swap location comprises a fixed address where the authorized delivery recipient receives the replacement item and provides the item being replaced within the mobile cargo storage system as part of dispatched swap logistics operation.

110. The method of embodiment 48, wherein the designated swap location comprises a mobile location where the authorized delivery recipient receives the replacement item and provides the item being replaced within the mobile cargo storage system as part of dispatched swap logistics operation, wherein the mobile location being defined by the designated pickup information as a location of an external wireless mobile node being related to the authorized delivery recipient.

111. The method of embodiment 107, further comprising the step of transmitting, by the modular mobile autonomy control module, an unload assistance request to the retail entity once the modular autonomous bot apparatus assembly is within a threshold notification range of the origin location.

112. The method of embodiment 108, further comprising the step of transmitting, by the modular mobile autonomy control module, an unload assistance request to the retail entity after the modular autonomous bot apparatus assembly arrives at the origin location.

Further Embodiment K—Methods of Performing a Dispatched Medical Logistics Operation Related to a Diagnosis Kit for Treating a Patient and Using a Modular Autonomous Bot Apparatus Assembly and a Dispatch Server 1. A method of performing a dispatched medical logistics operation related to a diagnosis kit for treating a patient and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least temporarily maintain the diagnosis kit within the modular autonomous bot apparatus assembly, and a modular mobile autonomy control module that autonomously controls operation of the modular autonomous bot apparatus assembly during the dispatched medical logistics operation, the method comprising the steps of:
  receiving, by the modular mobile autonomy control module, a dispatch command from the dispatch server, the dispatch command initiated by a medical entity providing the diagnosis kit, the dispatch command comprising at least
    identifier information on the diagnosis kit,
    transport parameters on the diagnosis kit,
    destination delivery information related to delivery of the diagnosis kit, and
    delivery authentication information related to an authorized delivery recipient of the diagnosis kit;
  verifying, by the modular mobile autonomy control module, that each of the modular mobile autonomy control module, the modular mobility base, the modular auxiliary power module, and the modular cargo storage system are compatible with the dispatched medical logistics operation based upon the dispatch command;

receiving, by the modular cargo storage system, the diagnosis kit in a payload area within the modular cargo storage system at an origin location related to the medical entity;

autonomously causing, by the modular mobile autonomy control module, the modular mobility base to move from the origin location on a route to a destination location identified by the destination delivery information;

notifying, by the modular mobile autonomy control module, the authorized delivery recipient of the diagnosis kit of an approaching delivery once the modular autonomous bot apparatus assembly is within a threshold notification range of the destination location identified by the destination information;

receiving delivery recipient authentication input by the modular mobile autonomy control module from a delivery recipient disposed external to the modular autonomous bot apparatus assembly at the destination location;

providing, by the modular cargo storage system, selective access to the diagnosis kit within the modular cargo storage system only when the delivery recipient authentication input correlates to the delivery authentication information indicating that the delivery recipient providing the delivery recipient authentication input is the authorized delivery recipient;

monitoring, by the modular mobile autonomy control module, unloading of the diagnosis kit from within the modular cargo storage system using one or more sensors on at least one of the modular mobile autonomy control module and the modular cargo storage system;

notifying, by the modular mobile autonomy control module, the authorized delivery recipient of the diagnosis kit of instructional information related to prescribed use of the diagnosis kit;

detecting, by the modular mobile autonomy control module, when at least a return item related to the diagnosis kit is located in the payload area of the modular cargo storage system using the one or more sensors;

autonomously causing, by the modular mobile autonomy control module, the modular mobility base to move from the destination location on a return route to the origin location after the return item related to the diagnosis kit is detected within the modular cargo storage system; and notifying, by the modular mobile autonomy control module, personnel associated with the medical entity about a return delivery of the return item related to the diagnosis kit when the modular autonomous bot apparatus assembly is at least within a return notification range of the origin location.

2. The method of embodiment 1, wherein the authorized delivery recipient is the patient to be treated with the diagnosis kit.

3. The method of embodiment 1, wherein the authorized delivery recipient is an authorized agent of the patient to be treated with the diagnosis kit.

4. The method of embodiment 1, wherein the step of notifying the authorized delivery recipient of the diagnosis kit of the approaching delivery comprises generating a display alert for the authorized delivery recipient on a display on the modular mobile autonomy control module once the modular autonomous bot apparatus assembly is within the threshold notification range of the destination location identified by the destination information.

5. The method of embodiment 1, wherein the step of notifying the authorized delivery recipient of the diagnosis kit of the approaching delivery comprises generating an audio notification for the authorized delivery recipient on a speaker on the modular mobile autonomy control module once the modular autonomous bot apparatus assembly is within the threshold notification range of the destination location identified by the destination information.

6. The method of embodiment 1, wherein the step of notifying the authorized delivery recipient of the diagnosis kit of the approaching delivery comprises transmitting a delivery notification message to an external wireless node once the modular autonomous bot apparatus assembly is within the threshold notification range of the destination location identified by the destination information, the external wireless node being related to the authorized delivery recipient according to the destination delivery information.

7. The method of embodiment 1, wherein the step of notifying the authorized delivery recipient of the diagnosis kit of the approaching delivery comprises transmitting a delivery notification message to an external wireless node after the modular autonomous bot apparatus assembly moves from the origin location, the external wireless node being related to the authorized delivery recipient according to the destination delivery information.

8. The method of embodiment 6, the step of notifying the authorized delivery recipient of the diagnosis kit of the approaching delivery further comprises transmitting an arrival estimate to the external wireless node, the arrival estimate indicating an estimated time to arrive at the destination location.

9. The method of embodiment 1, wherein the step of monitoring unloading of the diagnosis kit comprises:
capturing sensor data from the one or more sensors on at least one of the modular mobile autonomy control module and the modular cargo storage system; and
detecting when the diagnosis kit is removed from within the modular cargo storage system based upon the captured sensor data.

10. The method of embodiment 1, wherein the step of monitoring unloading of the diagnosis kit comprises:
generating barcode scan data related to the diagnosis kit as the diagnosis kit is removed from within the modular cargo storage system using a barcode scanner as one of the one or more sensors; and
processing the generated barcode scan data to monitor the diagnosis kit as the diagnosis kit is removed from within the modular cargo storage system.

11. The method of embodiment 1, wherein the step of monitoring unloading of the diagnosis kit comprises:
generating image data related to the diagnosis kit as the diagnosis kit is removed from within the modular cargo storage system using an image sensor as one of the one or more sensors; and
processing the generated image data to monitor the diagnosis kit as the diagnosis kit is removed from within the modular cargo storage system.

12. The method of embodiment 1, wherein the step of monitoring unloading of the diagnosis kit comprises:
generating video data related to the diagnosis kit as the diagnosis kit is removed from within the modular cargo storage system using a video camera as one of the one or more sensors; and processing the generated video data to monitor the diagnosis kit as the diagnosis kit is removed from within the modular cargo storage system.

13. The method of embodiment 1, wherein the step of monitoring unloading of the diagnosis kit comprises:
capturing audio using a microphone as one of the one or more sensors disposed to record sound within and proximate to the modular cargo storage system as the diagnosis kit is removed from within the modular cargo storage system; and
processing the captured audio data to monitor the diagnosis kit as the diagnosis kit is removed from within the modular cargo storage system.

14. The method of embodiment 1, wherein the diagnosis kit includes a wireless mobile node; and
wherein the step of monitoring unloading of the diagnosis kit comprises detecting movement of the wireless mobile node disposed with the diagnosis kit as the diagnosis kit is removed from within the modular cargo storage system based upon a plurality of signals broadcast from the wireless mobile node disposed with the diagnosis kit.

15. The method of embodiment 1, wherein the diagnosis kit includes a wireless mobile node; and
wherein the step of monitoring unloading of the diagnosis kit comprises detecting a change in location of the wireless mobile node disposed with the diagnosis kit to outside the modular cargo storage system as the diagnosis kit is removed from within the modular cargo storage system as determined by the modular mobile autonomous control module.

16. The method of embodiment 1, wherein the step of detecting when at least the return item related to the diagnosis kit is located in the payload area of the modular cargo storage system comprises monitoring, by the modular mobile autonomy control module, loading of the return item related to the diagnosis kit from within the modular cargo storage system using the one or more sensors.

17. The method of embodiment 16, wherein the step of monitoring loading of the return item comprises:
generating barcode scan data related to the return item as the return item is placed within the modular cargo storage system using a barcode scanner as one of the one or more sensors; and
processing the generated barcode scan data to monitor the return item as the return item is placed within the modular cargo storage system.

18. The method of embodiment 16, wherein the step of monitoring loading of the return item comprises:
generating image data related to the return item as the return item is placed within the modular cargo storage system using an image sensor as one of the one or more sensors; and
processing the generated image data to monitor the return item as the return item is placed within the modular cargo storage system.

19. The method of embodiment 16, wherein the step of monitoring loading of the return item comprises:
generating video data related to the return item as the return item is placed within the modular cargo storage system using a video camera as one of the one or more sensors; and
processing the generated video data to monitor the return item as the return item is placed within the modular cargo storage system.

20. The method of embodiment 16, wherein the step of monitoring loading of the return item comprises:
capturing audio data using a microphone as one of the one or more sensors disposed to record sound within and proximate to the modular cargo storage system as the return item is placed within the modular cargo storage system; and
processing the captured audio data to monitor the ordered item as the ordered item is placed within the modular cargo storage system.

21. The method of embodiment 16, wherein the return item related to the diagnosis kit includes a wireless mobile node; and
wherein the step of monitoring loading of the return item comprises detecting movement of the wireless mobile node disposed with the return item as the return item is placed within the modular cargo storage system based upon a plurality of signals broadcast from the wireless mobile node disposed with the return item.

22. The method of embodiment 16, wherein the return item related to the diagnosis kit includes a wireless mobile node; and
wherein the step of monitoring loading of the return item comprises detecting a change in location of the wireless mobile node disposed with the return item to outside the modular cargo storage system as the return item is placed within the modular cargo storage system as determined by the modular mobile autonomous control module.

23. The method of embodiment 1, wherein the return item comprises one or more parts of the diagnosis kit used by the patient.

24. The method of embodiment 1, wherein the return item comprises a testing part of the diagnosis kit used by the patient as part of a medical test.

25. The method of embodiment 24, wherein the testing part of the diagnosis kit used by the patient as part of the medical test comprises a sample from the patient gathered according to the instructional information related to the prescribed use of the diagnosis kit, the sample being part of the return item transported by the modular autonomous bot apparatus assembly back to the origin location for analysis by the medical entity.

26. The method of embodiment 1, further comprising the step of generating, by the modular mobile autonomy control module, a first inventory data structure corresponding to the diagnosis kit and stored on the modular mobile autonomy control module upon detecting the diagnosis kit as received within the payload area, wherein the first inventory data structure including a first chain of custody entry reflecting departure from the origin location for the diagnosis kit while in the custody of the modular autonomous bot apparatus assembly.

27. The method of embodiment 26, further comprising the step of generating, by the modular mobile autonomy control module, a second chain of custody entry within the first inventory data structure after arrival at the destination location, the second chain of custody reflecting arrival at the destination location for delivery of the diagnosis kit from the custody of the modular autonomous bot apparatus assembly.

28. The method of embodiment 27, further comprising the step of generating, by the modular mobile autonomy control module, a third chain of custody entry within the first inventory data structure after arrival at the destination location and after detecting the diagnosis kit has been removed from within the modular cargo storage system, the third chain of custody reflecting the diagnosis kit changing custody to the authorized delivery recipient from the modular autonomous bot apparatus assembly.

29. The method of embodiment 28, further comprising the step of generating, by the modular mobile autonomy control module, a fourth chain of custody entry within the first inventory data structure after arrival at the destination location and after detecting the return item has been placed within the modular cargo storage system, the fourth chain of custody reflecting at least the return item of the diagnosis kit changing custody from the authorized delivery recipient to the modular autonomous bot apparatus assembly.

30. The method of embodiment 1, wherein the step of notifying the authorized delivery recipient of the diagnosis kit of the instructional information comprises generating a display alert message for the authorized delivery recipient on a display on the modular mobile autonomy control module, the display alert message including the instructional information related to the prescribed use of the diagnosis kit.

31. The method of embodiment 1, wherein the step of notifying the authorized delivery recipient of the diagnosis kit of the instructional information comprises generating an audio alert message for the authorized delivery recipient using a speaker on the modular mobile autonomy control module, the audio alert message including the audible instructions as the instructional information related to the prescribed use of the diagnosis kit.

32. The method of embodiment 1, wherein the step of notifying the authorized delivery recipient of the diagnosis kit of the instructional information comprises transmitting, by the modular mobile autonomy control module, an instructional message to an external wireless node related to the authorized delivery recipient according to the destination delivery information, the instructional message reflecting the instructional information related to the prescribed use of the diagnosis kit.

33. The method of embodiment 1, further comprising the step of notifying, by the modular mobile autonomy control module, the personnel associated with the medical entity about the return delivery of the return item related to the diagnosis kit once the modular autonomous bot apparatus assembly has arrived at the origin location.

34. The method of embodiment 1, further comprising providing, by the modular cargo storage system, selective access to the return item within the modular cargo storage system when medical entity personnel submits return item authentication input to the modular mobile autonomy control module that correlates to a portion of the delivery authentication information indicating return item authentication information for the return item.

35. The method of embodiment 34, further comprising monitoring, by the modular mobile autonomy control module, unloading of the return item from within the modular cargo storage system using the one or more sensors.

36. The method of embodiment 35, further comprising autonomously causing, by the modular mobile autonomy control module, the modular mobility base to move to a bot storage location after the return item is detected as being removed from within the payload area of the modular cargo storage system using the one or more sensors.

37. The method of embodiment 35, further comprising transmitting, by the modular mobile autonomy control module, a module replacement request to the dispatch server, the modular replacement request initiating a replacement of the modular cargo storage system for the modular autonomous bot apparatus assembly.

38. The method of embodiment 37, wherein the modular replacement request further initiating a disinfection process of the modular cargo storage system after the return item has been removed from within the payload area of the modular cargo storage system.

39. The method of embodiment 35, further comprising the steps of:
  receiving, by the modular mobile autonomy control module, a follow-up dispatch command from the dispatch server for a follow-up dispatched medical logistics operation, the follow-up dispatch command initiated by the medical entity after testing related to the return item and the patient, the follow-up dispatch command comprising at least
    identifier information on treatment material to be delivered to the authorized delivery recipient as a result of the testing related to the return item and the patient,
    transport parameters on the treatment material, and
    destination delivery information related to delivery of the treatment material;
  verifying, by the modular mobile autonomy control module, that each of the modular mobile autonomy control module, the modular mobility base, the modular auxiliary power module, and a disinfected replacement for the modular cargo storage system are compatible with the follow-up dispatched medical logistics operation based upon the follow-up dispatch command;
  receiving, by the modular cargo storage system, the treatment material in the payload area within the disinfected replacement for the modular cargo storage system at the origin location related to the medical entity;
  autonomously causing, by the modular mobile autonomy control module, the modular mobility base to move from the origin location to the destination location identified by the destination delivery information;
  notifying, by the modular mobile autonomy control module, the authorized delivery recipient an approaching delivery of the treatment material;
  receiving delivery recipient authentication input by the modular mobile autonomy control module from the delivery recipient disposed external to the modular autonomous bot apparatus assembly at the destination location;
  providing, by the modular cargo storage system, selective access to the treatment material within the modular cargo storage system only when the delivery recipient authentication input correlates to the delivery authentication information indicating that the delivery recipient providing the delivery recipient authentication input is the authorized delivery recipient;
  monitoring, by the modular mobile autonomy control module, unloading of the treatment material using one or more sensors on at least one of the modular mobile autonomy control module and the disinfected replacement for the modular cargo storage system;
  autonomously causing, by the modular mobile autonomy control module, the modular mobility base to move from the destination location to the origin location after the treatment material is no longer detected within the payload area within the disinfected replacement for the modular cargo storage system.

40. The method of embodiment 1, wherein the step of autonomously causing the modular mobility base to move from the origin location to the destination location comprises autonomously causing, by the modular mobile autonomy control module, the modular mobility base to move from the origin location to the destination location while interacting with a wireless building facility node to actuate a pathway obstacle disposed in a path on the route to the destination location.

41. The method of embodiment 40, wherein the pathway obstacle comprises an actuated door controlled by the wireless building facility node.

42. The method of embodiment 40, wherein the pathway obstacle comprises an actuated elevator controlled by the wireless building facility node.

43. The method of embodiment 40, wherein the pathway obstacle comprises an actuated lock controlled by the wireless building facility node.

44. The method of embodiment 40, wherein interacting with the wireless building facility node to actuate the pathway obstacle comprises:
   establishing an authorized association pairing between the modular mobile autonomy control module and the wireless building facility node based upon the authentication information related to the dispatched logistics operation; and
   causing the wireless building facility node to actuate the pathway obstacle after establishing the authorized association pairing between the modular mobile autonomy control module and the wireless building facility node.

45. The method of embodiment 1, wherein the step of autonomously causing the modular mobility base to move from the origin location to the destination location comprises autonomously causing, by the modular mobile autonomy control module, the modular mobility base to move from the origin location to the destination location while engaging a pathway obstacle disposed in a path on the route to the destination location using an articulating arm disposed on the modular autonomous bot apparatus assembly and using a plurality of sensors disposed on at least one of the modular mobility base and the modular mobile autonomy control module.

46. The method of embodiment 45, wherein the pathway obstacle comprises a manually actuated door.

47. The method of embodiment 45, wherein the pathway obstacle comprises a manually actuated elevator.

48. The method of embodiment 45, wherein the pathway obstacle comprises a manually actuated lock.

49. The method of embodiment 45, wherein engaging the pathway obstacle using the articulating arm and sensors comprises:
   guiding, by the modular mobile autonomy control module, the articulating arm to a control element of the pathway obstacle using one or more of the sensors disposed on at least one of the modular mobility base and the modular mobile autonomy control module; and
   actuating the pathway obstacle, by the modular mobile autonomy control module, once the articulating arm engages the control element of the pathway obstacle.

50. The method of embodiment 49, wherein the control element of the pathway obstacle comprises one from the group consisting of a handle for the pathway obstacle, a button for the pathway obstacle, a switch for the pathway obstacle, and a portion of a control panel for the pathway obstacle.

51. The method of embodiment 1, wherein the step of receiving the diagnosis kit comprises actuating, by the modular mobile autonomy control module, an actuated cargo door disposed on the modular auxiliary power module to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position.

52. The method of embodiment 51, wherein actuating, by the modular mobile autonomy control module, the actuated cargo door comprises actuating an actuated joint on the actuated cargo door to cause the actuated cargo door to move from the closed position to the open position.

53. The method of embodiment 51, wherein actuating, by the modular mobile autonomy control module, the actuated cargo door further comprises actuating an electro-mechanical lock on the actuated cargo door to cause the actuated cargo door to unlock before moving from the closed position to the open position.

54. The method of embodiment 1, wherein the step of receiving the diagnosis kit comprises actuating, by the modular mobile autonomy control module, an actuated sliding arm disposed on the modular cargo storage system to move the diagnosis kit into the payload area within the modular cargo storage system.

55. The method of embodiment 1, wherein the step of receiving the diagnosis kit comprises actuating, by the modular mobile autonomy control module, an actuated grabbing arm disposed on the modular cargo storage system to grab and move the diagnosis kit into the payload area within the modular cargo storage system as part of receiving the diagnosis kit.

56. The method of embodiment 1, wherein the step of receiving the diagnosis kit comprises actuating, by the modular mobile autonomy control module, an actuated belt surface disposed on the modular auxiliary power module as a movable support surface exposed within the payload area inside the modular cargo storage system, the actuated belt surface being operative when actuated to cause the diagnosis kit as placed on the actuated belt surface to move within the payload area as part of receiving the diagnosis kit.

57. The method of embodiment 1, wherein unloading of the diagnosis kit comprises actuating, by the modular mobile autonomy control module, an actuated cargo door disposed on the modular auxiliary power module to an open position once the delivery recipient authentication input correlates to a portion of the authentication information related to the dispatched logistics operation, wherein the actuated cargo door provides a seal to the payload area within the modular cargo storage system when the actuated cargo door is in a closed position and the actuated cargo door provides access to the payload area within the modular cargo storage system when the actuated cargo door is in the open position.

58. The method of embodiment 57, wherein actuating, by the modular mobile autonomy control module, the actuated cargo door comprises actuating an actuated joint on the actuated cargo door to cause the actuated cargo door to move from the closed position to the open position.

59. The method of embodiment 57, wherein actuating, by the modular mobile autonomy control module, the actuated cargo door further comprises actuating an electro-mechanical lock on the actuated cargo door to cause the actuated cargo door to unlock before moving from the closed position to the open position.

60. The method of embodiment 1, wherein unloading of the diagnosis kit comprises actuating, by the modular mobile autonomy control module, an actuated sliding arm disposed on the modular cargo storage system to move the diagnosis kit out from the payload area within the modular cargo storage system.

61. The method of embodiment 1, wherein unloading of the diagnosis kit comprises actuating, by the modular mobile autonomy control module, an actuated grabbing arm disposed on the modular cargo storage system to grab and move the diagnosis kit out from the payload area within the modular cargo storage system.

62. The method of embodiment 1, wherein unloading of the diagnosis kit comprises actuating, by the modular mobile autonomy control module, an actuated belt surface disposed on the modular auxiliary power module as a movable support surface exposed within the payload area inside the modular cargo storage system, the actuated belt surface being operative when actuated to cause the diagnosis kit as placed on the actuated belt surface to move out from within the payload area.

63. The method of embodiment 1, further comprising receiving, by the modular cargo storage system, the return item related to the diagnosis kit in the payload area within the modular cargo storage system at the destination location.

64. The method of embodiment 63, wherein the step of receiving the return item related to the diagnosis kit comprises actuating, by the modular mobile autonomy control module, an actuated sliding arm disposed on the modular cargo storage system to move the return item related to the diagnosis kit into the payload area within the modular cargo storage system.

65. The method of embodiment 63, wherein the step of receiving the return item related to the diagnosis kit comprises actuating, by the modular mobile autonomy control module, an actuated grabbing arm disposed on the modular cargo storage system to grab and move the return item related to the diagnosis kit into the payload area within the modular cargo storage system as part of receiving the return item related to the diagnosis kit.

66. The method of embodiment 63, wherein the step of receiving the return item related to the diagnosis kit comprises actuating, by the modular mobile autonomy control module, an actuated belt surface disposed on the modular auxiliary power module as a movable support surface exposed within the payload area inside the modular cargo storage system, the actuated belt surface being operative when actuated to cause the return item related to the diagnosis kit as placed on the actuated belt surface to move within the payload area as part of receiving the return item related to the diagnosis kit.

67. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

68. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

69. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

70. The method of embodiment 1, wherein the delivery recipient authentication input received by the modular mobile autonomy control module is provided by the delivery recipient through an external wireless node disposed external to the modular autonomous bot apparatus assembly.

71. The method of embodiment 70, wherein the delivery recipient authentication input received by the modular mobile autonomy control module comprises an access code provided by the delivery recipient through the external wireless node disposed external to the modular autonomous bot apparatus assembly.

72. The method of embodiment 70, wherein the delivery recipient authentication input received by the modular mobile autonomy control module comprises a biometric input provided by the delivery recipient through the external wireless node disposed external to the modular autonomous bot apparatus assembly.

73. The method of embodiment 1, wherein the authentication information related to the dispatched medical logistics operation includes an identifier of the authorized delivery recipient for the diagnosis kit as part of the dispatched medical logistics operation; and
wherein the step of receiving the delivery recipient authentication input comprises:
detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
authenticating, by the modular mobile autonomy control module, that the external wireless node is associated with the authorized delivery recipient for the item being shipped within the modular cargo storage system based upon the identifier of the authorized delivery recipient and identifier information within the detected advertising signal broadcast from the external wireless node.

74. The method of embodiment 1, wherein the authentication information related to the dispatched medical logistics operation includes an identifier of the authorized delivery recipient for the diagnosis kit as part of the dispatched medical logistics operation; and
wherein the step of receiving the delivery recipient authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched inventory operation.

Further Embodiment L—Apparatus and Systems of a Modular Autonomous Cart Apparatus Assembly for Transporting an Item being Shipped 1. A modular autonomous cart apparatus assembly for transporting an item being shipped, comprising:
a modular mobility base comprising
a mobile base platform,
a mobility controller disposed as part of the mobile base platform, a propulsion system connected to the mobile base platform, the propulsion system being responsive to a propulsion control input from the mobility controller to cause changes in speed of the modular mobility base, a steering system connected to the mobile base platform and coupled to the propulsion system, the steering system responsive to a steering control input from the mobility controller and operative to cause changes to directional movement of the modular mobility base, a plurality of mobility base sensors coupled to the mobility controller and disposed on the mobile base platform, the mobility base sensors being operative to autonomously detect an object in the path of the modular mobility base and provide base feedback sensor data to the mobility controller on the detected object, and a first interface to a common modular component power and data transport bus, the first interface providing a power conduit for the modular mobility base and a command and data interface conduit for at least the mobility controller;

a modular cart handle detachably mounted to the modular mobility base, the modular cart handle comprising
  a handle base having a first end and a second end, wherein the first end is detachably connected to the modular mobility base,
  a handle grip disposed on the handle base,
  a handle seat disposed on the second end of the handle base,
  an actuated set of latches disposed on the handle top seat, and
  a second interface to the common modular component power and data transport bus, the second interface providing a power conduit through the modular cart handle and a command and data interface conduit through the modular cart handle; and a modular mobile cart autonomy control module detachably attached to the modular handle, the modular mobile cart autonomy control module comprising
  a detachable modular housing detachably connected to the handle top seat,
  a plurality of latching points disposed on the detachable modular housing, the latching points configured to interlock with the actuated set of latches disposed on the handle top seat,
  an autonomous controller disposed within the detachable modular housing,
  at least one display disposed on the detachable modular housing, wherein the display being operatively coupled to the autonomous controller,
  a user input panel disposed on the detachable modular housing, the user input panel being operatively coupled to the autonomous controller, the user input panel receiving localized input to supplement autonomous operation of the modular autonomous cart apparatus assembly,
  a wireless radio transceiver operatively coupled to the autonomous controller,
  a plurality of autonomy module sensors disposed on the detachable modular housing and operatively coupled to the autonomous controller, wherein the autonomy module sensors being operative to generate onboard sensor data on an environment external to the modular mobile cart autonomy control module as detected by the autonomy module sensors and providing the onboard sensor data to the autonomous controller, and
  a third interface to the common modular component power and data transport bus, the third interface providing a power conduit for the modular mobile cart autonomy control module and a command and data interface conduit for the modular mobile cart autonomy control module, wherein the command and data interface conduit is operatively coupled to at least the autonomous controller; and wherein the autonomous controller of the modular mobile cart autonomy control module is programmatically adapted and configured to be operative to at least
  (a) detect, using the wireless radio transceiver, an advertising signal from a wireless mobile courier node;
  (b) generate association data that establishes and reflects a secure association between the wireless mobile courier node and the modular mobile cart autonomy control module after detecting the advertising signal from the wireless mobile courier node, the secure association between the wireless mobile courier node and the modular mobile cart autonomy control module allowing secure sharing of information between the wireless mobile courier node and the modular mobile cart autonomy control module;
  (c) determine a current location of the wireless mobile courier node;
  (d) determine a current location of the modular autonomous cart apparatus assembly;
  (e) receive information from the mobility controller through the common modular component power and data transport bus, the received information being about the base feedback sensor data;
  (f) receive the onboard sensor data from the autonomy module sensors;
  (g) generate a steering control command and a propulsion control command based at least upon the current location of the modular autonomous cart apparatus assembly, the current location of the wireless mobile courier node, the received information on the base feedback sensor data from the mobility controller, and the onboard sensor data as received by the autonomous controller from the autonomy module sensors;
  (h) transmit the steering control command and the propulsion control command through the common modular component power and data transport bus for receipt by the mobility controller; and
  (i) repeat functions (c)-(h) to autonomously track and follow the current location of the wireless mobile courier node as the wireless mobile courier node moves and while maintaining a predetermined follow distance from the current location of the wireless mobile courier node.

2. The modular autonomous cart apparatus assembly of embodiment 1, wherein the autonomous controller of the modular mobile cart autonomy control module is further programmatically adapted and configured to be operative to:

generate a predicted path of movement for the wireless mobile courier node based upon a destination location maintained by the modular mobile cart autonomy control module; and generate the steering control command and the propulsion control command based at least upon the location data from the location circuitry, the received information on the base feedback sensor data from the mobility controller, the onboard sensor data as received by the autonomous controller from the autonomy module sensors, and the determined location of the wireless mobile courier node.

3. The modular autonomous cart apparatus assembly of embodiment 1, wherein the autonomous controller of the modular mobile cart autonomy control module is further programmatically adapted and configured to be operative to determine the current location of the wireless mobile courier node by receiving a location message from the wireless mobile courier node, the location message providing the current location of the wireless mobile courier node.

4. The modular autonomous cart apparatus assembly of embodiment 1, wherein the modular mobile cart autonomy control module further comprises location circuitry disposed within the detachable modular housing, the location circuitry being operatively coupled to the autonomous controller, the location circuitry generating location data on the current location of the modular autonomous cart apparatus assembly and providing the location data to the autonomous controller.

5. The modular autonomous cart apparatus assembly of embodiment 1, wherein the wireless mobile courier node comprises a master node with onboard location circuitry that identifies the current location of the wireless mobile courier node.

6. The modular autonomous cart apparatus assembly of embodiment 1, wherein the wireless mobile courier node comprises a master node traveling with courier personnel delivering the item being shipped, wherein the master node includes onboard location circuitry that identifies the current location of the wireless mobile courier node.

7. The modular autonomous cart apparatus assembly of embodiment 1, wherein the wireless mobile courier node comprises a master node disposed on a vehicle transporting courier personnel tasked with delivering the item being shipped, wherein the master node includes onboard location circuitry that identifies the current location of the wireless mobile courier node.

8. The modular autonomous cart apparatus assembly of embodiment 1, wherein the wireless mobile courier node comprises a master node disposed on a second modular autonomous cart apparatus assembly, the master node operating as the modular mobile cart autonomy control module on the second modular autonomous cart apparatus, wherein the master node includes onboard location circuitry that identifies the current location of the wireless mobile courier node.

9. The modular autonomous cart apparatus assembly of embodiment 1, wherein one or more of the autonomy modular sensors are mounted on the detachable modular housing so as to be focused and operative to monitor a payload area on the mobility base platform where the item being shipped is supported when the modular mobility base is moving.

10. The modular autonomous cart apparatus assembly of embodiment 1, wherein the item being shipped comprises a wireless ID node with the item being shipped, the wireless ID node maintaining shipping information on the item being shipped including at least identifier information on the item being shipped, recipient information on the item being shipped, and destination information on the item being shipped; and wherein the autonomous controller of the modular mobile cart autonomy control module is further programmatically adapted and configured to be operative to generate association data that establishes and reflects a secure association between the wireless ID node and the modular mobile cart autonomy control module after detecting an advertising signal from the wireless ID node, the secure association between the wireless ID node and the modular mobile cart autonomy control module allowing secure sharing of at least the shipping information between the wireless ID node and the modular mobile cart autonomy control module.

11. The modular autonomous cart apparatus assembly of embodiment 10, wherein the autonomous controller of the modular mobile cart autonomy control module is further programmatically adapted and configured to be operative to generate a delivery notification in response to receiving at least a portion of the shipping information from the wireless ID node.

12. The modular autonomous cart apparatus assembly of embodiment 11, wherein the delivery notification comprises a delivery location information notification indicating the destination information on the item being shipped and the identifier information on the item being shipped.

13. The modular autonomous cart apparatus assembly of embodiment 12, wherein the autonomous controller of the modular mobile cart autonomy control module is programmatically adapted and configured to be operative to trigger generation of the delivery notification when the current location of the modular autonomous cart apparatus assembly is within a threshold distance from a delivery location indicated by the destination information.

14. The modular autonomous cart apparatus assembly of embodiment 11, wherein the autonomous controller of the modular mobile cart autonomy control module is programmatically adapted and configured to be operative to generate the delivery notification by being further operative to generate a delivery warning on the at least one display disposed on the detachable modular housing, the delivery warning identifying the item being shipped based upon the shipping information, the delivery warning also indicating the destination information on the item being shipped.

15. The modular autonomous cart apparatus assembly of embodiment 11, wherein the modular mobile cart autonomy control module further comprises a speaker disposed on the detachable modular housing and operatively coupled to the autonomous controller; and wherein the autonomous controller of the modular mobile cart autonomy control module is programmatically adapted and configured to be operative to generate the delivery notification by being further operative to generate an audible delivery warning through the speaker disposed on the detachable modular housing, the audible delivery warning identifying the item being shipped based upon the shipping information, the audible delivery warning also indicating the destination information on the item being shipped.

16. The modular autonomous cart apparatus assembly of embodiment 11, wherein the autonomous controller of the modular mobile cart autonomy control module is programmatically adapted and configured to be operative to generate the delivery notification by being further operative to wirelessly notify the wireless mobile courier node with the delivery notification.

17. The modular autonomous cart apparatus assembly of embodiment 16, wherein the delivery notification comprises a delivery location information notification indicating the destination information on the item being shipped and the identifier information on the item being shipped.

18. The modular autonomous cart apparatus assembly of embodiment 17, wherein the autonomous controller of the modular mobile cart autonomy control module is programmatically adapted and configured to be operative to trigger generation of the delivery notification and the wireless notification of the wireless mobile courier node when the current location of the modular autonomous cart apparatus assembly is within a threshold distance from a delivery location indicated by the destination information.

19. The modular autonomous cart apparatus assembly of embodiment 1, wherein the autonomous controller of the modular mobile cart autonomy control module is further programmatically adapted and configured to be operative to (i) repeat functions (c)-(h) to autonomously track and follow the current location of the wireless mobile courier node as the wireless mobile courier node moves and while maintaining the predetermined follow distance from the current location of the wireless mobile courier node until the autonomous controller receives a delivery control input, the delivery control input activating a hover mode for the modular autonomous cart apparatus assembly that temporarily halts movement of the modular mobility base that autonomously tracks and follows the current location of the wireless mobile courier node.

20. The modular autonomous cart apparatus assembly of embodiment 19, wherein the delivery control input comprises a wireless delivery control input from the wireless mobile courier node.

21. The modular autonomous cart apparatus assembly of embodiment 19, wherein the modular mobile cart autonomy control module further comprises a user input panel disposed on the detachable modular housing, the user input panel being operatively coupled to the autonomous controller and configured to generate the delivery control input based upon manual input received at the user input panel.

22. The modular autonomous cart apparatus assembly of embodiment 19, wherein the delivery control input comprises a gesture control input received through at least one from the autonomy module sensors and the mobility base sensors.

23. The modular autonomous cart apparatus assembly of embodiment 22, wherein the at least one from the autonomy module sensors and the mobility base sensors comprises a scanning sensor operative to generate scanning sensor data representing a halt hand gesture from an operator of the wireless mobile courier node.

24. The modular autonomous cart apparatus assembly of embodiment 19, wherein the autonomous controller of the modular mobile cart autonomy control module is further programmatically adapted and configured to be operative to resume, in response to receiving a resume control input that deactivates the hover mode repeating, functions (c)-(h) to autonomously track and follow the current location of the wireless mobile courier node as the wireless mobile courier node moves and while maintaining the predetermined follow distance from the current location of the wireless mobile courier node.

25. The modular autonomous cart apparatus assembly of embodiment 24, wherein the resume control input comprises a wireless delivery control input from the wireless mobile courier node.

26. The modular autonomous cart apparatus assembly of embodiment 24, wherein the modular mobile cart autonomy control module further comprises a user input panel disposed on the detachable modular housing, the user input panel being operatively coupled to the autonomous controller and configured to generate the resume control input based upon manual input received at the user input panel.

27. The modular autonomous cart apparatus assembly of embodiment 24, wherein the resume control input comprises a gesture control input received through at least one from the autonomy module sensors and the mobility base sensors.

28. The modular autonomous cart apparatus assembly of embodiment 27, wherein the at least one from the autonomy module sensors and the mobility base sensors comprises a scanning sensor operative to generate scanning sensor data representing a resume hand gesture from an operator of the wireless mobile courier node.

29. The modular autonomous cart apparatus assembly of embodiment 1, wherein the modular cart handle further comprises a localized guidance input detector disposed on the handle grip and operatively coupled to the autonomy controller through the second interface of the modular cart handle, the localized guidance input detector sensing external contact with local personnel as an override control input for the modular autonomous cart apparatus assembly; and
wherein the autonomous controller of the modular mobile cart autonomy control module is further programmatically adapted and configured to be operative to, in response to receiving the override control input from the localized guidance input detector, to generate the steering control command and the propulsion control command based at least upon the sensed external contact with the local personnel to provide power-assisted movement of the modular mobility base at the direction of the local personnel.

30. The modular autonomous cart apparatus assembly of embodiment 29, wherein the autonomous controller of the modular mobile cart autonomy control module is further programmatically adapted and configured to be operative to, in response to receiving the override control input from the localized guidance input detector, to generate the steering control command and the propulsion control command based at least upon the sensed external contact with the local personnel to provide power-assisted movement of the modular mobility base at the direction of the local personnel, the received information on the base feedback sensor data from the mobility controller, and the onboard sensor data as received by the autonomous controller from the autonomy module sensors so as to provide the power-assisted movement of the modular mobility base at the direction of the local personnel while avoiding the object in the path of the modular mobility base using the received information on the base feedback sensor data and the onboard sensor data.

31. The modular autonomous cart apparatus assembly of embodiment 30, wherein the autonomous controller of the modular mobile cart autonomy control module is further programmatically adapted and configured to be operative to alter at least one of the steering control command and the propulsion control command in response to detecting the object in the path of the modular mobility base.

32. The modular autonomous cart apparatus assembly of embodiment 29, wherein at least one of the base feedback sensor data and the onboard sensor data includes proximity sensor data related to the object in the path of the modular mobility base being avoided by at least one of the steering control command and the propulsion control command.

33. The modular autonomous cart apparatus assembly of embodiment 29, wherein at least one of the base feedback sensor data and the onboard sensor data includes visual sensor data related to an image of the object in the path of the modular mobility base being avoided by at least one of the steering control command and the propulsion control command.

34. The modular autonomous cart apparatus assembly of embodiment 33, wherein the autonomous controller of the modular mobile cart autonomy control module is further programmatically adapted and configured to be operative to alter at least one of the steering control command and the propulsion control command to avoid the object in the path of the modular mobility base when the image of the object in the path of the modular mobility base is identified as being in a class of pathway objects to be avoided.

35. The modular autonomous cart apparatus assembly of embodiment 34, wherein the class of pathway objects to be avoided comprises at least one from the group consisting of a predetermined class of hazardous objects, a predetermined class of symbols, and a predetermined class of signs.

36. The modular autonomous cart apparatus assembly of embodiment 1, wherein the autonomous controller of the modular mobile cart autonomy control module maintains a location limitation profile identifying one or more restricted locations for the modular autonomous cart apparatus assembly to avoid; and wherein the autonomous controller of the modular mobile cart autonomy control module is further programmatically adapted and configured to be operative to (g) generate the steering control command and the propulsion control command based at least upon the current location of the modular autonomous cart apparatus assembly, the current location of the wireless mobile courier node, the received information on the base feedback sensor data from the mobility controller, the onboard sensor data as received by the autonomous controller from the autonomy module sensors, and the one or more restricted locations as identified in the location limitation profile.

37. The modular autonomous cart apparatus assembly of embodiment 1, wherein the autonomous controller of the modular mobile cart autonomy control module is further programmatically adapted and configured to be operative to receive, using the wireless radio transceiver, the location limitation profile from a remote service networked device.

38. The modular autonomous cart apparatus assembly of embodiment 1, wherein the autonomous controller maintains context data related to prior movement of the modular autonomous cart apparatus assembly; and wherein the autonomous controller of the modular mobile cart autonomy control module is further programmatically adapted and configured to repeat functions (c)-(h) to autonomously track and follow the current location of the wireless mobile courier node as the wireless mobile courier node moves and while maintaining the predetermined follow distance from the current location of the wireless mobile courier node based also upon the context data related to prior movements of the modular autonomous cart apparatus assembly.

39. The modular autonomous cart apparatus assembly of embodiment 38, wherein the autonomous controller of the modular mobile cart autonomy control module is programmatically adapted and configured to perform function (g) by being further programmatically adapted and configured to generate the steering control command and the propulsion control command based at least upon the current location of the modular autonomous cart apparatus assembly, the current location of the wireless mobile courier node, the received information on the base feedback sensor data from the mobility controller, the onboard sensor data as received by the autonomous controller from the autonomy module sensors, and the context data related to prior movements of the modular autonomous cart apparatus assembly.

40. The modular autonomous cart apparatus assembly of embodiment 38, wherein the modular mobile cart autonomy control module further comprises:

a memory coupled to the autonomous controller, the memory maintaining at least the context data; and location circuitry disposed within the detachable modular housing, the location circuitry being operatively coupled to the autonomous controller, the location circuitry generating location data on the current location of the modular autonomous cart apparatus assembly and providing the location data to the autonomous controller; and wherein the context data comprises historic data related to prior movement of the modular mobility base at one or more locations within a range distance from the current location of the modular autonomous cart apparatus assembly.

41. The modular autonomous cart apparatus assembly of embodiment 40, wherein the historic data comprises historic pathway obstacle data indicating at least one identified pathway obstacle within the range distance from the current location of the modular autonomous cart apparatus assembly, the historic pathway obstacle data being based upon previously processed onboard sensor data, previously processed base feedback sensor data, and previously processed location data on the prior location of the modular autonomous cart apparatus assembly.

42. The modular autonomous cart apparatus assembly of embodiment 40, wherein the historic data comprises historic building data indicating at least one identified building feature disposed external to the modular autonomous cart apparatus assembly where the identified building feature is within the range distance from the current location of the modular autonomous cart apparatus assembly, the historic building data being based upon previously processed onboard sensor data, previously processed base feedback sensor data, and previously processed location data on the prior location of the modular autonomous cart apparatus assembly.

43. The modular autonomous cart apparatus assembly of embodiment 40, wherein the historic data comprises historic origin location context data indicating at least one identified origin location environment feature disposed external to the modular autonomous cart apparatus assembly where the identified origin location environment feature is within the range distance from the current location of the modular autonomous cart apparatus assembly, the historic origin location context data being based upon previously processed onboard sensor data, previously processed base feedback sensor data, and previously processed location data on the prior location of the modular autonomous cart apparatus assembly.

44. The modular autonomous cart apparatus assembly of embodiment 40, wherein the historic data comprises historic destination location context data indicating at least one identified destination location environment feature disposed external to the modular autonomous cart apparatus assembly where the identified destination location environment feature is within the range distance from the current location of the modular autonomous cart apparatus assembly, the historic destination location context data being based upon previously processed onboard sensor data, previously processed base feedback sensor data, and previously processed location data on the prior location of the modular autonomous cart apparatus assembly.

45. The modular autonomous cart apparatus assembly of embodiment 1, wherein the autonomous controller of the modular mobile cart autonomy control module is further programmatically adapted and configured to be operative to:
(j) detect, using the wireless radio transceiver, a first wireless facility node; and
(k) repeat functions (c)-(i) using the first wireless building facility node as the wireless mobile courier node.

46. The modular autonomous cart apparatus assembly of embodiment 45, wherein the autonomous controller of the modular mobile cart autonomy control module is further programmatically adapted and configured to be operative to
(l) detect, using the wireless radio transceiver, a second wireless building facility node located past the first wireless building facility node; and
(m) repeat functions (c)-(i) using the second wireless building facility node as the wireless mobile courier node.

47. The modular autonomous cart apparatus assembly of embodiment 45, wherein the autonomous controller of the modular mobile cart autonomy control module is operative to perform function (j) by being further programmatically adapted and configured to be operative to
(n) detect, using the wireless radio transceiver, an advertising signal from the first wireless facility node; and
(o) generate association data that establishes and reflects a secure association between the first wireless facility node and the modular mobile cart autonomy control module after detecting the advertising signal from the first wireless facility node, the secure association between the first wireless facility node and the modular mobile cart autonomy control module allowing secure sharing of information between the first wireless facility node and the modular mobile cart autonomy control module.

48. The modular autonomous cart apparatus assembly of embodiment 47, wherein the secure sharing of information between the first wireless facility node and the modular mobile cart autonomy control module allows the first wireless facility node to guide the modular autonomous cart apparatus assembly from the current location of the modular autonomous cart apparatus assembly to the current location of the first wireless facility node.

49. The modular autonomous cart apparatus assembly of embodiment 47, wherein the secure sharing of information between the first wireless facility node and the modular mobile cart autonomy control module allows the first wireless facility node to guide the modular autonomous cart apparatus assembly from the current location of the modular autonomous cart apparatus assembly to a remote location within a transmission range of the first wireless facility node.

50. The modular autonomous cart apparatus assembly of embodiment 49, wherein the autonomous controller of the modular mobile cart autonomy control module is further programmatically adapted and configured to be operative to repeat functions (d)-(h) using the first wireless building facility node as the wireless mobile courier node and to autonomously cause the modular autonomous cart apparatus assembly to move towards the remote location.

51. The modular autonomous cart apparatus assembly of embodiment 1, wherein the modular mobility base, modular cart handle, and the modular mobile cart autonomy control module are each authenticated modular components based upon a component-to-component secure handshaking between proximately attached ones of the modular mobility base, modular cart handle, and the modular mobile cart autonomy control module.

52. The modular autonomous cart apparatus assembly of embodiment 51, wherein the component-to-component secure handshaking comprises a challenge and security credential response between proximately attached ones of the modular mobility base, modular cart handle, and the modular mobile cart autonomy control module.

53. The modular autonomous cart apparatus assembly of embodiment 1, wherein the modular mobility base, modular cart handle, and the modular mobile cart autonomy control module are verified to be authenticated modular components for the modular autonomous cart apparatus assembly as each of the modular mobility base, modular cart handle, and the modular mobile cart autonomy control module are assembled into the modular autonomous cart apparatus assembly.

54. The modular autonomous cart apparatus assembly of embodiment 51, wherein the component-to-component secure handshaking is based upon at least one from a group comprising one or more regulatory rules, one or more contractual rules, and one or more safety rules.

55. The modular autonomous cart apparatus assembly of embodiment 51, wherein the component-to-component secure handshaking is based upon logistical constraint information on a determined work environment for the modular autonomous bot apparatus assembly.

56. The modular autonomous cart apparatus assembly of embodiment 55, wherein the logical constraint information being identified as part of the security credential response.

57. The modular autonomous cart apparatus assembly of embodiment 55, wherein the logistical constraint information identifies a size limitation for the modular autonomous cart apparatus assembly.

58. The modular autonomous cart apparatus assembly of embodiment 55, wherein the logistical constraint information identifies a weight limitation for the modular autonomous cart apparatus assembly.

59. The modular autonomous cart apparatus assembly of embodiment 55, wherein the logistical constraint information identifies a readiness limitation for the modular autonomous cart apparatus assembly.

60. The modular autonomous cart apparatus assembly of embodiment 59, wherein the readiness limitation comprising one or more performance thresholds for the modular autonomous bot apparatus assembly in an anticipated deployment operation of the modular autonomous cart apparatus assembly.

61. The modular autonomous cart apparatus assembly of embodiment 51, wherein the autonomous controller of the modular mobile cart autonomy control module is further programmatically adapted and configured to be operative to:
notify a server over the wireless radio transceiver that one or more of the modular mobility base, modular cart handle, and the modular mobile cart autonomy control module are not authenticated modular components based upon the component-to-component secure handshaking between the modular mobile cart autonomy control module and each of the modular mobility base and the modular cart handle; and request a replacement component for the one or more of the modular mobility base and the modular cart handle that are not authenticated modular components.

62. The modular autonomous cart apparatus assembly of embodiment 51, wherein the autonomous controller of the modular mobile cart autonomy control module is further programmatically adapted and configured to be operative to generate a component replacement request message on at least one of the displays disposed on the detachable modular housing when one or more of the modular mobility base and the modular cart handle are not authenticated modular components based upon the component-to-component secure handshaking between the modular mobile autonomy control module and each of the modular mobility base and the modular cart handle, the component replacement request message requesting a replacement component for the one or more of the modular mobility base and the modular cart handle that are not authenticated modular components.

63. The modular autonomous cart apparatus assembly of embodiment 51, wherein the autonomous controller of the modular mobile autonomy control module is further programmatically adapted and configured to:
receive an authentication result from one of the modular mobility base and the modular cart handle, wherein the authentication result indicating that at least one of the modular mobility base and the modular cart handle are not authenticated modular components based upon the component-to-component secure handshaking between proximate ones of the modular mobility base, the modular cart handle, and the modular mobile autonomy control module; and
notify a server over the wireless radio transceiver that one or more of the modular mobility base and modular cart handle are not authenticated modular components based upon the authentication result received.

64. The modular autonomous cart apparatus assembly of embodiment 51, wherein the autonomous controller of the modular mobile autonomy control module is further programmatically adapted and configured to
receive an authentication result from one of the modular mobility base, the modular auxiliary power module, and the modular cargo storage system, wherein the authentication result indicating that at least one of the modular mobility base, the modular auxiliary power module, and the modular cargo storage system are not authenticated modular components based upon the component-to-component secure handshaking between proximate ones of the modular mobility base, the modular auxiliary power module, the modular cargo storage system, and the modular mobile autonomy control module; and
generate a component replacement request message on at least one of the displays disposed on the detachable modular housing based upon the authentication result received.

65. The modular autonomous cart apparatus assembly of embodiment 1, wherein each of the modular mobility base and modular cart handle are authenticated modular components based upon a component-to-component secure handshaking between the modular mobile cart autonomy control module and each of the modular mobility base and the modular cart handle.

66. The modular autonomous cart apparatus assembly of embodiment 65, wherein the component-to-component secure handshaking comprises a challenge and security credential response between the modular mobile cart autonomy control module and each of the modular mobility base and the modular cart handle.

67. The modular autonomous cart apparatus assembly of embodiment 65, wherein the component-to-component secure handshaking is based upon at least one from a group comprising one or more regulatory rules, one or more contractual rules, and one or more safety rules.

68. The modular autonomous cart apparatus assembly of embodiment 65, wherein the component-to-component secure handshaking is based upon logistical constraint information on a determined work environment for the modular autonomous cart apparatus assembly.

69. The modular autonomous cart apparatus assembly of embodiment 68, wherein the logistical constraint information identifies a size limitation for the modular autonomous cart apparatus assembly.

71. The modular autonomous cart apparatus assembly of embodiment 68, wherein the logistical constraint information identifies a weight limitation for the modular autonomous cart apparatus assembly.

72. The modular autonomous cart apparatus assembly of embodiment 68, wherein the logistical constraint information identifies a readiness limitation for the modular autonomous cart apparatus assembly.

73. The modular autonomous cart apparatus assembly of embodiment 72, wherein the readiness limitation comprising one or more performance thresholds for the modular autonomous cart apparatus assembly in an anticipated deployment operation of the modular autonomous cart apparatus assembly.

74. The modular autonomous cart apparatus assembly of embodiment 65, wherein the autonomous controller of the modular mobile autonomy control module is further programmatically adapted and configured to be operative to
notify a server over the wireless radio transceiver that one or more of the modular mobility base and the modular cart handle are not authenticated modular components based upon the component-to-component secure handshaking between the modular mobile autonomy control module and each of the modular mobility base, the modular auxiliary power module, and the modular cargo storage system, and
request a replacement component for the one or more of the modular mobility base and the modular cart handle that are not authenticated modular components.

75. The modular autonomous cart apparatus assembly of embodiment 63, wherein the autonomous controller of the modular mobile autonomy control module is further programmatically adapted and configured to be operative to generate a component replacement request message on at least one of the displays disposed on the detachable modular housing when one or more of the modular mobility base, the modular auxiliary power module, and the modular cargo storage system are not authenticated modular components based upon the component-to-component secure handshaking between the modular mobile autonomy control module and each of the modular mobility base, the modular auxiliary power module, and the modular cargo storage system, the component replacement request message requesting a replacement component for the one or more of the modular mobility base, the modular auxiliary power module, and the modular cargo storage system that are not authenticated modular components.

76. The modular autonomous cart apparatus assembly of embodiment 1, wherein the modular mobility base, modular cart handle, and the modular mobile cart autonomy control module are each verified to be compatible with an assigned logistics operation for the modular autonomous cart apparatus assembly based upon a component-to-component secure handshaking between proximately attached ones of the modular mobility base, modular cart handle, and the modular mobile cart autonomy control module.

77. The modular autonomous cart apparatus assembly of embodiment 1, wherein the modular mobility base comprises a mobility base sub-assembly, wherein the mobility base subassembly comprising
an extended base adapter plate as the mobile base platform,
a front mobility base unit coupled to a bottom of the extended base adapter plate, and
a rear mobility base unit coupled to the bottom of the extended base adapter plate,
wherein the propulsion system for the modular mobility base being connected to the extended base adapter plate, the propulsion system comprising
a front propulsion system responsive to a first propulsion control input from the mobility controller to cause changes in speed of the front mobility base unit,
a second propulsion system responsive to a second propulsion control input from the mobility controller to cause changes in speed of the rear mobility base unit,
wherein the steering system for the modular mobility base comprising
a first steering system connected to the front mobility base unit and coupled to the first propulsion system, the first steering system responsive to a first steering control input from the mobility controller and operative to cause changes to directional movement of the front mobility base unit,
a second steering system connected to the second mobility base unit and coupled to the second propulsion system, the second steering system responsive to a second steering control input from the mobility controller and operative to cause changes to directional movement of the rear mobility base unit,
a plurality of mobility base sensors coupled to the mobility controller, the mobility base sensors having a first portion being disposed on the front mobility base unit and a second portion being disposed on the rear mobility base unit, the mobility base sensors being operative to autonomously detect an object in the path of the modular mobility base and provide base feedback sensor data to the mobility controller on the detected object, and
a first interface to a common modular component power and data transport bus, the first interface providing a power conduit for the modular mobility base and a command and data interface conduit for at least the mobility controller.

78. A system for transporting a plurality of items being shipped, the system comprising
a first modular autonomous cart apparatus assembly for transporting a first of the items being shipped, the first modular autonomous cart apparatus assembly comprising:
a first propelled sensor-based modular mobility base having a first support base platform that supports the first of the items being shipped,
a first modular cart handle detachably mounted to the first modular mobility base, the first modular cart handle comprising a first handle grip and a first common modular component power and data transport bus as a first conduit through the first modular cart handle, and
a first modular sensor-based cart autonomy control module detachably mounted to the first modular cart handle, the first modular sensor-based cart autonomy control module further comprising a first wireless radio transceiver, wherein the first modular sensor-based cart autonomy control module being operative to
generate first onboard sensor data related to an environment proximate the first modular sensor-based cart autonomy control module,
receive first base sensor data from the first modular mobility base through the first conduit, where the first base sensor data is related to an environment proximate the first modular mobility base, and
provide a first mobility control input as navigation control to the first modular mobility base through the first conduit based at least upon the onboard sensor data and the received base sensor data; and
a second modular autonomous cart apparatus assembly for transporting a second of the items being shipped, the second modular autonomous cart apparatus assembly comprising:
a second propelled sensor-based modular mobility base having a second support base platform that supports the second of the items being shipped,
a second modular cart handle detachably mounted to the second modular mobility base, the second modular cart handle comprising a second handle grip and a second common modular component power and data transport bus as a second conduit through the second modular cart handle, and
a second modular sensor-based cart autonomy control module detachably mounted to the second modular cart handle, the second modular sensor-based cart autonomy control module further comprising a second wireless radio transceiver, wherein the second modular sensor-based cart autonomy control module being operative to
generate second onboard sensor data related to an environment proximate the second modular sensor-based cart autonomy control module,
receive second base sensor data from the second modular mobility base through the second conduit, where the second base sensor data is related to an environment proximate the second modular mobility base, and
provide a second mobility control input as navigation control to the second modular mobility base through the second conduit based at least upon the second onboard sensor data and the received second base sensor data; and
wherein the first modular sensor-based cart autonomy control module is further operative to
determine a location of a wireless mobile courier node operated by courier personnel involved in delivering the items being shipped, and
autonomously cause the first modular mobility base to follow the wireless courier node while maintaining a first predetermined follow distance from the location of the wireless mobile courier node as the wireless mobile courier node moves on a delivery route, and
wherein the second modular sensor-based cart autonomy control module is further operative to determine a location of the first modular sensor-based cart autonomy module, and autonomously cause the second modular mobility base to follow the first modular sensor-based cart autonomy module while maintaining a second predetermined follow distance from the location of the first modular sensor-based cart autonomy module as the first modular sensor-based cart autonomy module follows the wireless mobile courier node on the delivery route.

79. The system of embodiment 78, further comprising a third modular autonomous cart apparatus assembly for transporting a third of the items being shipped, the third modular autonomous cart apparatus assembly comprising:

a third propelled sensor-based modular mobility base having a support base platform that supports the third of the items being shipped, a third modular cart handle detachably mounted to the third modular mobility base, the third modular cart handle comprising a third handle grip and a third common modular component power and data transport bus as a third conduit through the third modular cart handle, and a third modular sensor-based cart autonomy control module detachably mounted to the third modular cart handle, the third modular sensor-based cart autonomy control module further comprising a third wireless radio transceiver, wherein the third modular sensor-based cart autonomy control module being operative to generate third onboard sensor data related to an environment proximate the third modular sensor-based cart autonomy control module, receive third base sensor data from the third modular mobility base through the conduit, where the third base sensor data is related to an environment proximate the third modular mobility base, and provide a third mobility control input as navigation control to the third modular mobility base through conduit based at least upon the third onboard sensor data and the received third base sensor data; and wherein the third modular sensor-based cart autonomy control module is further operative to determine a location of the second modular sensor-based cart autonomy module, and autonomously cause the third modular mobility base to follow the second modular sensor-based cart autonomy module while maintaining a second predetermined follow distance from the location of the second modular sensor-based cart autonomy module as the second modular sensor-based cart autonomy module follows the first modular sensor-based cart autonomy module.

80. The system of embodiment 78, wherein the first of the items being shipped comprises a first wireless ID node with the first of the items being shipped, the first wireless ID node maintaining shipping information on the first of the items being shipped including at least identifier information on the first of the items being shipped, recipient information on the first of the items being shipped, and destination information on the first of the items being shipped; and wherein the first modular sensor-based cart autonomy control module is further programmatically adapted and configured to be operative to generate association data that establishes and reflects a secure association between the first wireless ID node and the first modular sensor-based cart autonomy control module after detecting an advertising signal from the first wireless ID node, the secure association between the first wireless ID node and the first modular sensor-based cart autonomy control module allowing secure sharing of at least the shipping information between the first wireless ID node and the first modular sensor-based cart autonomy control module.

81. The system of embodiment 78, wherein the second of the items being shipped comprises a second wireless ID node with the second of the items being shipped, the second wireless ID node maintaining shipping information on the second of the items being shipped including at least identifier information on the second of the items being shipped, recipient information on the second of the items being shipped, and destination information on the second of the items being shipped; and wherein the second modular sensor-based cart autonomy control module is further programmatically adapted and configured to be operative to generate association data that establishes and reflects a secure association between the second wireless ID node and the second modular sensor-based cart autonomy control module after detecting an advertising signal from the second wireless ID node, the secure association between the second wireless ID node and the second modular sensor-based cart autonomy control module allowing secure sharing of at least the shipping information between the second wireless ID node and the second modular sensor-based cart autonomy control module.

82. The system of embodiment 80, wherein the first modular sensor-based cart autonomy control module is further programmatically adapted and configured to be operative to generate a delivery notification in response to receiving at least a portion of the shipping information from the first wireless ID node.

83. The system of embodiment 81, wherein the second modular sensor-based cart autonomy control module is further programmatically adapted and configured to be operative to generate a delivery notification in response to receiving at least a portion of the shipping information from the second wireless ID node.

84. The system of embodiment 82, wherein the delivery notification comprises a delivery location information notification indicating the destination information on the first of the items being shipped and the identifier information on the first of the items being shipped.

85. The system of embodiment 83, wherein the delivery notification comprises a delivery location information notification indicating the destination information on the second of the items being shipped and the identifier information on the second of the items being shipped.

86. The system of embodiment 84, wherein the first modular sensor-based cart autonomy control module is programmatically adapted and configured to be operative to trigger generation of the delivery notification when the current location of the first modular autonomous cart apparatus assembly is within a threshold distance from a delivery location indicated by the destination information.

87. The system of embodiment 85, wherein the second modular sensor-based cart autonomy control module is programmatically adapted and configured to be operative to trigger generation of the delivery notification when the current location of the second modular autonomous cart apparatus assembly is within a threshold distance from a delivery location indicated by the destination information.

88. The system of embodiment 82, wherein the first modular sensor-based cart autonomy control module is programmatically adapted and configured to be operative to generate the delivery notification by being further operative to generate a delivery warning on a display disposed on the first modular sensor-based cart autonomy control module, the delivery warning identifying the first of the items being shipped based upon the shipping information, the delivery warning also indicating the destination information on the first of the items being shipped.

89. The system of embodiment 83, wherein the second modular sensor-based cart autonomy control module is programmatically adapted and configured to be operative to generate the delivery notification by being further operative to generate a delivery warning on a display disposed on the second modular sensor-based cart autonomy control module, the delivery warning identifying the second of the items being shipped based upon the shipping information, the delivery warning also indicating the destination information on the second of the items being shipped.

90. The system of embodiment 82, wherein the first modular sensor-based cart autonomy control module further comprises a speaker; and
    wherein the first modular sensor-based cart autonomy control module is programmatically adapted and configured to be operative to generate the delivery notification by being further operative to generate an audible delivery warning through the speaker, the audible delivery warning identifying the first of the items being shipped based upon the shipping information, the audible delivery warning also indicating the destination information on the first of the items being shipped.

91. The system of embodiment 83, wherein the second modular sensor-based cart autonomy control module further comprises a speaker; and
    wherein the second modular sensor-based cart autonomy control module is programmatically adapted and configured to be operative to generate the delivery notification by being further operative to generate an audible delivery warning through the speaker, the audible delivery warning identifying the second of the items being shipped based upon the shipping information, the audible delivery warning also indicating the destination information on the second of the items being shipped.

92. The system of embodiment 82, wherein the first modular sensor-based cart autonomy control module is programmatically adapted and configured to be operative to generate the delivery notification by being further operative to wirelessly notify the wireless mobile courier node with the delivery notification.

93. The system of embodiment 83, wherein the second modular sensor-based cart autonomy control module is programmatically adapted and configured to be operative to generate the delivery notification by being further operative to wirelessly notify the wireless mobile courier node with the delivery notification.

94. The system of embodiment 92, wherein the delivery notification comprises a delivery location information notification indicating the destination information on the first of the items being shipped and the identifier information on the first of the items being shipped.

95. The system of embodiment 93, wherein the delivery notification comprises a delivery location information notification indicating the destination information on the second of the items being shipped and the identifier information on the second of the items being shipped.

96. The system of embodiment 94, wherein the first modular sensor-based cart autonomy control module is programmatically adapted and configured to be operative to trigger generation of the delivery notification and the wireless notification of the wireless mobile courier node when the current location of the first modular autonomous cart apparatus assembly is within a threshold distance from a delivery location indicated by the destination information.

97. The system of embodiment 95, wherein the second modular sensor-based cart autonomy control module is programmatically adapted and configured to be operative to trigger generation of the delivery notification and the wireless notification of the wireless mobile courier node when the current location of the second modular autonomous cart apparatus assembly is within a threshold distance from a delivery location indicated by the destination information.

98. The system of embodiment 78, wherein the first modular sensor-based cart autonomy control module maintains a first inventory data structure identifying which of the items are disposed on the first support base;
    wherein the first modular sensor-based autonomy control module further comprises at least a first payload monitoring sensor that monitors any of the items disposed on the first support base; and
    wherein the first modular sensor-based cart autonomy control module is programmatically adapted and configured to be operative to
        detect, using first payload sensor data from the first payload monitoring sensor, when the first of the items being shipped has been removed from the first support base,
        update the first inventory data structure to reflect the detected removal of the first of the items being shipped, and
        notify the wireless mobile courier node that the first of the items being shipped has been removed from the first support base.

99. The system of embodiment 78, wherein the second modular sensor-based cart autonomy control module maintains a second inventory data structure identifying which of the items are disposed on the second support base;
    wherein the second modular sensor-based autonomy control module further comprises at least a second payload monitoring sensor that monitors any of the items disposed on the second support base; and
    wherein the second modular sensor-based cart autonomy control module is programmatically adapted and configured to be operative to
        detect, using second payload sensor data from the second payload monitoring sensor, when the second of the items being shipped has been removed from the second support base,
        update the second inventory data structure to reflect the detected removal of the second of the items being shipped, and
        notify the wireless mobile courier node that the second of the items being shipped has been removed from the second support base.

100. The system of embodiment 78, wherein the first modular sensor-based cart autonomy control module is programmatically adapted and configured to be operative to
    monitor at least the first of the items being shipped on the first support base;
    identify a location of the first of the items being shipped as located on the first support base; and
    notify the wireless mobile courier node about the identified location of the first of the items being shipped.

101. The system of embodiment 78, wherein the second modular sensor-based cart autonomy control module is programmatically adapted and configured to be operative to monitor at least the second of the items being shipped on the second support base;
identify a location of the second of the items being shipped as located on the second support base; and
notify the wireless mobile courier node about the identified location of the second of the items being shipped.

102. A system for transporting a plurality of items being shipped, the system comprising
a first modular autonomous cart apparatus assembly for transporting a first of the items being shipped, the first modular autonomous cart apparatus assembly comprising:
  a first propelled sensor-based modular mobility base having a support base platform that supports the first of the items being shipped,
  a first modular cart handle detachably mounted to the first modular mobility base, the first modular cart handle comprising
    a first handle grip,
    a localized guidance input detector disposed on the handle grip, and
    a first common modular component power and data transport bus as a first conduit through the first modular cart handle, and
  a first modular sensor-based cart autonomy control module detachably mounted to the first modular cart handle, the first modular sensor-based cart autonomy control module further comprising a first wireless radio transceiver, wherein the first modular sensor-based cart autonomy control module being operative to
    generate first onboard sensor data related to an environment proximate the first modular sensor-based cart autonomy control module,
    receive first base sensor data from the first modular mobility base through the conduit, where the first base sensor data is related to an environment proximate the first modular mobility base,
    receive override control input from the localized guidance input detector and through the first conduit, and
    provide a first mobility control input as navigation control to the first modular mobility base through the first conduit based at least upon the onboard sensor data, the received base sensor data, and the override control input; and
a second modular autonomous cart apparatus assembly for transporting a second of the items being shipped, the second modular autonomous cart apparatus assembly comprising:
  a second propelled sensor-based modular mobility base having a support base platform that supports the second of the items being shipped,
  a second modular cart handle detachably mounted to the second modular mobility base, the second modular cart handle comprising a second handle grip and a second common modular component power and data transport bus as a second conduit through the second modular cart handle, and
  a second modular sensor-based cart autonomy control module detachably mounted to the second modular cart handle, the second modular sensor-based cart autonomy control module further comprising a second wireless radio transceiver, wherein the second modular sensor-based cart autonomy control module being operative to
    generate second onboard sensor data related to an environment proximate the second modular sensor-based cart autonomy control module,
    receive second base sensor data from the second modular mobility base through the second conduit, where the second base sensor data is related to an environment proximate the second modular mobility base, and
    provide a second mobility control input as navigation control to the second modular mobility base through the second conduit based at least upon the second onboard sensor data and the received second base sensor data; and
  wherein the first modular sensor-based cart autonomy control module is further operative to respond to the override control input and autonomously cause the first modular mobility base to move based on the provided first mobility control input to initiate and cause power-assisted movement of the first modular mobility base at the direction of local personnel in external contact with the localized guidance input detector, and
  wherein the second modular sensor-based cart autonomy control module is further operative to
    determine a location of the first modular sensor-based cart autonomy module, and
    autonomously cause the second modular mobility base to follow the first modular sensor-based cart autonomy module while maintaining a second predetermined follow distance from the location of the first modular sensor-based cart autonomy module.

103. The system of embodiment 102, further comprising
a third modular autonomous cart apparatus assembly for transporting a third of the items being shipped, the third modular autonomous cart apparatus assembly comprising:
  a third propelled sensor-based modular mobility base having a support base platform that supports the third of the items being shipped,
  a third modular cart handle detachably mounted to the third modular mobility base, the third modular cart handle comprising a third handle grip and a third common modular component power and data transport bus as a third conduit through the third modular cart handle, and
  a third modular sensor-based cart autonomy control module detachably mounted to the third modular cart handle, the third modular sensor-based cart autonomy control module further comprising a third wireless radio transceiver, wherein the third modular sensor-based cart autonomy control module being operative to
    generate third onboard sensor data related to an environment proximate the third modular sensor-based cart autonomy control module,
    receive third base sensor data from the third modular mobility base through the conduit, where the third base sensor data is related to an environment proximate the third modular mobility base, and
    provide a third mobility control input as navigation control to the third modular mobility base through conduit based at least upon the third onboard sensor data and the received third base sensor data; and
  wherein the third modular sensor-based cart autonomy control module is further operative to
  determine a location of the second modular sensor-based cart autonomy module, and
  autonomously cause the third modular mobility base to follow the second modular sensor-based cart autonomy module while maintaining a second predetermined follow distance from the location of the second modular sensor-based cart autonomy module as the second modular sensor-based cart autonomy module follows the first modular sensor-based cart autonomy module.

Further Embodiment M—Apparatus, Systems, and Methods for Performing a Dispatched Logistics Operation for a Deliverable Item from a Hold-at-Location Logistics Facility Using a Modular Autonomous Bot Apparatus Assembly, a Dispatch Server, and an Enhanced Remotely-Actuated Logistics Receptacle Apparatus 1. A method of performing a dispatched logistics operation for a deliverable item from a hold-at-location logistics facility having a secured storage and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least temporarily maintain the deliverable item within the modular autonomous bot apparatus assembly, and a modular mobile autonomy control module that autonomously controls operation of the modular autonomous bot apparatus assembly during the dispatched logistics operation from the hold-at-location logistics facility, the method comprising the steps of:
receiving, by the modular mobile autonomy control module, a delivery dispatch command from the dispatch server, the delivery dispatch command comprising at least
identifier information on the deliverable item,
transport parameters on the deliverable item,
destination delivery information related to drop-off of the deliverable item, and
delivery authentication information related to an authorized delivery recipient of the deliverable item;
verifying, by the modular mobile autonomy control module, that each of the modular mobile autonomy control module, the modular mobility base, the modular auxiliary power module, and the modular cargo storage system are compatible with the dispatched logistics operation for the deliverable item based upon the delivery dispatch command;
receiving, by the modular cargo storage system, the deliverable item from the secured storage at the hold-at-location logistics facility into a payload area within the modular cargo storage system at the hold-at-location logistics facility;
autonomously causing, by the modular mobile autonomy control module, the modular mobility base to move from the hold-at-location logistics facility on a route to a destination location identified by the destination delivery information;
notifying, by the modular mobile autonomy control module, the authorized delivery recipient of the deliverable item of an approaching delivery when the modular autonomous bot apparatus assembly is within a threshold notification range of the destination location identified by the destination information;
receiving delivery recipient authentication input by the modular mobile autonomy control module from a delivery recipient disposed external to the modular autonomous bot apparatus assembly at the destination location;
providing, by the modular cargo storage system, selective access to the deliverable item within the modular cargo storage system only when the delivery recipient authentication input correlates to the delivery authentication information indicating that the delivery recipient providing the delivery recipient authentication input is the authorized delivery recipient;
monitoring, by the modular mobile autonomy control module, unloading of the deliverable item from within the modular cargo storage system using one or more sensors on at least one of the modular mobile autonomy control module and the modular cargo storage system; and
autonomously causing, by the modular mobile autonomy control module, the modular mobility base to move from the destination location on a return route to the hold-at-location logistics facility after the deliverable item is no longer detected within the modular cargo storage system.

2. The method of embodiment 1, wherein the hold-at-location logistics facility comprises a logistics location having a temporary storage for receipt of the deliverable item and where a designated one of a plurality of secure storage enclosures as the secured storage.

3. The method of embodiment 2, wherein the secure storage enclosures comprise a plurality of secure locker receptacles.

4. The method of embodiment 2, wherein the designated one of the secure storage enclosures comprises a secure locker receptacle accessible by the authorized delivery recipient.

5. The method of embodiment 2, wherein the designated one of the secure storage enclosures comprises a secure locker receptacle accessible by personnel designated by the authorized delivery recipient.

6. The method of embodiment 1, wherein the delivery dispatch command comprises an auto redirect dispatch command initiated by the dispatch system when the deliverable item is detected at a temporary storage within the hold-at-location logistics facility.

7. The method of embodiment 1, wherein the delivery dispatch command comprises a self-selected designated dispatch command initiated by the dispatch system when the deliverable item is detected at a temporary storage within the hold-at-location logistics facility and in response to a delivery request received by the dispatch system from the authorized delivery recipient.

8. The method of embodiment 1, wherein the step of receiving the delivery dispatch command is triggered as a result of a separate logistics operation related to the deliverable item.

9. The method of embodiment 8, wherein the separate logistics operation related to the deliverable item comprises a prior unsuccessful attempt for delivery of the deliverable item to the authorized delivery recipient.

10. The method of embodiment 8, wherein the prior unsuccessful attempt for delivery of the deliverable item to the authorized delivery recipient comprises a prior dispatched logistics operation for autonomous delivery of the deliverable item to the authorized delivery recipient.

11. The method of embodiment 8, wherein the prior unsuccessful attempt for delivery of the deliverable item to the authorized delivery recipient comprises a prior manual delivery attempt delivery of the deliverable item to the authorized delivery recipient.

12. The method of embodiment 8, wherein the separate logistics operation related to the deliverable item comprises a pre-designated first stage of an overall logistics operation to deliver the deliverable item to the authorized delivery recipient, wherein the pre-designated first stage of the overall logistics operation provides the deliverable item to the secured storage at the hold-at-location logistics facility as a designated interim handoff location for the dispatched logistics operation from the hold-at-location logistics facility involving the modular autonomous bot apparatus assembly 13. The method of embodiment 1, wherein the identifier information comprises data that uniquely identifies the deliverable item.

14. The method of embodiment 1, wherein the identifier information comprises a machine readable identification of the deliverable item.

15. The method of embodiment 1, wherein the identifier information comprises human readable information disposed on the deliverable item that identifies the deliverable item.

16. The method of embodiment 1, wherein the step of receiving the deliverable item comprises loading the deliverable item into the payload area within the modular cargo storage system at the hold-at-location logistics facility.

17. The method of embodiment 16, wherein the step of loading the deliverable item comprises receiving, by the modular cargo storage system, the deliverable item in response to a load request message from the dispatch system.

18. The method of embodiment 16, wherein the load request message being sent from the dispatch system to loading personnel at the hold-at-location logistics facility.

19. The method of embodiment 1, wherein the step of notifying the authorized delivery recipient of the deliverable item of the approaching delivery comprises generating a display alert for the authorized delivery recipient on a display on the modular mobile autonomy control module once the modular autonomous bot apparatus assembly is within the threshold notification range of the destination location identified by the destination information.

20. The method of embodiment 1, wherein the step of notifying the authorized delivery recipient of the deliverable item of the approaching delivery comprises generating an audio notification for the authorized delivery recipient on a speaker on the modular mobile autonomy control module once the modular autonomous bot apparatus assembly is within the threshold notification range of the destination location identified by the destination information.

21. The method of embodiment 1, wherein the step of notifying the authorized delivery recipient of the deliverable item of the approaching delivery comprises transmitting a delivery notification message to an external wireless node once the modular autonomous bot apparatus assembly is within the threshold notification range of the destination location identified by the destination information, the external wireless node being related to the authorized delivery recipient according to the destination delivery information.

22. The method of embodiment 1, wherein the step of notifying the authorized delivery recipient of the deliverable item of the approaching delivery comprises transmitting a delivery notification message to an external wireless node after the modular autonomous bot apparatus assembly moves from the hold-at-location logistics facility, the external wireless node being related to the authorized delivery recipient according to the destination delivery information.

23. The method of embodiment 21, the step of notifying the authorized delivery recipient of the deliverable item of the approaching delivery further comprises transmitting an arrival estimate to the external wireless node, the arrival estimate indicating an estimated time to arrive at the destination location.

24. The method of embodiment 1, wherein the step of monitoring unloading of the deliverable item comprises:
capturing sensor data from the one or more sensors on at least one of the modular mobile autonomy control module and the modular cargo storage system; and
detecting when the deliverable item is removed from within the modular cargo storage system based upon the captured sensor data.

25. The method of embodiment 1, wherein the step of monitoring unloading of the deliverable item comprises:
generating barcode scan data related to the deliverable item as the deliverable item is removed from within the modular cargo storage system using a barcode scanner as one of the one or more sensors; and
processing the generated barcode scan data to monitor the deliverable item as the deliverable item is removed from within the modular cargo storage system.

26. The method of embodiment 1, wherein the step of monitoring unloading of the deliverable item comprises:
generating image data related to the deliverable item as the deliverable item is removed from within the modular cargo storage system using an image sensor as one of the one or more sensors; and
processing the generated image data to monitor the deliverable item as the deliverable item is removed from within the modular cargo storage system.

27. The method of embodiment 1, wherein the step of monitoring unloading of the deliverable item comprises:
generating video data related to the deliverable item as the deliverable item is removed from within the modular cargo storage system using an image sensor as one of the one or more sensors; and
processing the generated video data to monitor the deliverable item as the deliverable item is removed from within the modular cargo storage system.

28. The method of embodiment 1, wherein the step of monitoring unloading of the deliverable item comprises:
capturing audio using a microphone as one of the one or more sensors disposed to record sound within and proximate to the modular cargo storage system as the deliverable item is removed from within the modular cargo storage system; and
processing the captured audio data to monitor the deliverable item as the deliverable item is removed from within the modular cargo storage system.

29. The method of embodiment 1, wherein the deliverable item includes a wireless mobile node; and
wherein the step of monitoring unloading of the deliverable item comprises detecting movement of the wireless mobile node disposed with the deliverable item as the deliverable item is removed from within the modular cargo storage system based upon a plurality of signals broadcast from the wireless mobile node disposed with the deliverable item.

30. The method of embodiment 1, wherein the deliverable item includes a wireless mobile node; and
wherein the step of monitoring unloading of the deliverable item comprises detecting a change in location of the wireless mobile node disposed with the deliverable item to outside the modular cargo storage system as the deliverable item is removed from within the modular cargo storage system as determined by the modular mobile autonomous control module.

31. The method of embodiment 1, wherein the delivery dispatch command further comprises identifier information on an additional deliverable item, additional destination delivery information related to drop-off of the additional deliverable item, and additional delivery authentication information related to a secondary authorized delivery recipient of the additional deliverable item;
- further comprising the step of receiving, by the modular cargo storage system, the additional deliverable item from the secured storage at the hold-at-location logistics facility into the payload area within the modular cargo storage system at the hold-at-location logistics facility;
- wherein the step of providing selective access to the deliverable item within the modular cargo storage system comprises providing, by the modular cargo storage system, selective access to only the deliverable item within the modular cargo storage system when the delivery recipient authentication input correlates to the delivery authentication information indicating that the delivery recipient providing the delivery recipient authentication input is the authorized delivery recipient;
- wherein the step of autonomously causing the modular mobility base to move from the destination location on the return route to the hold-at-location logistics facility after the deliverable item is no longer detected within the modular cargo storage system comprises:
    - autonomously causing, by the modular mobile autonomy control module, the modular mobility base to move from the destination location to a secondary delivery location after the deliverable item is detected to be removed from within the modular cargo storage system at the destination location, the secondary delivery location identified by the additional destination delivery information in the delivery dispatch command;
    - receiving secondary delivery recipient authentication input by the modular mobile autonomy control module from a second delivery recipient disposed external to the modular autonomous bot apparatus assembly at the secondary destination location;
    - providing, by the modular cargo storage system, selective access to only the additional deliverable item within the modular cargo storage system when the secondary delivery recipient authentication input correlates to the secondary delivery authentication information indicating that the second delivery recipient providing the secondary delivery recipient authentication input is the secondary authorized delivery recipient of the additional deliverable item; and
    - autonomously causing, by the modular mobile autonomy control module, the modular mobility base to move from the secondary delivery location to the hold-at-location logistics facility after the additional deliverable item is no longer detected within the modular cargo storage system.

32. The method of embodiment 1, wherein the step of autonomously causing the modular mobility base to move from the destination location on the return route to the hold-at-location logistics facility after the deliverable item is no longer detected within the modular cargo storage system comprises:
- receiving, by the modular mobile autonomy control module, a return delivery dispatch command from the dispatch server before the modular mobility base leaves from the destination location, the return delivery dispatch command being initiated by the authorized delivery recipient of the deliverable item, the return delivery dispatch command extending the dispatched logistics operation and comprising at least identifier information on a return deliverable item, transport parameters on the return deliverable item, and courier authentication information related to an authorized pickup courier for the return deliverable item;
- verifying, by the modular mobile autonomy control module, that each of the modular mobile autonomy control module, the modular mobility base, the modular auxiliary power module, and the modular cargo storage system are compatible with the extended dispatched logistics operation for the return deliverable item based upon the return delivery dispatch command;
- receiving, by the modular cargo storage system, the return deliverable item from the authorized delivery recipient into the payload area within the modular cargo storage system at the destination location after the deliverable item is no longer detected within the modular cargo storage system; and
- autonomously causing, by the modular mobile autonomy control module, the modular mobility base to move from the destination location to the hold-at-location logistics facility after the return deliverable item is detected by the one or more sensors as being placed within the modular cargo storage system.

33. The method of embodiment 32, further comprising the step of notifying, by the modular mobile autonomy control module, personnel at the hold-at-location logistics facility about an approaching delivery of the return deliverable item when the modular autonomous bot apparatus assembly is within a threshold notification range of the hold-at-location logistics facility.

34. The method of embodiment 33, wherein the step of notifying the personnel at the hold-at-location logistics facility about the approaching delivery of the return deliverable item comprises generating a display alert about the return deliverable item on a display on the modular mobile autonomy control module once the modular autonomous bot apparatus assembly is within the threshold notification range of the hold-at-location logistics facility.

35. The method of embodiment 33, wherein the step of notifying the personnel at the hold-at-location logistics facility about the approaching delivery of the return deliverable item comprises generating an audio notification about the return deliverable item on a speaker on the modular mobile autonomy control module once the modular autonomous bot apparatus assembly is within the threshold notification range of the hold-at-location logistics facility.

36. The method of embodiment 33, wherein the step of notifying the personnel at the hold-at-location logistics facility about the approaching delivery of the return deliverable item comprises transmitting a delivery notification message to an external wireless node once the modular autonomous bot apparatus assembly is within the threshold notification range of the hold-at-location logistics facility, the external wireless node being related to the personnel at the hold-at-location logistics facility.

37. The method of embodiment 33, wherein the step of notifying the personnel at the hold-at-location logistics facility about the approaching delivery of the return deliverable item comprises transmitting a delivery notification message to an external wireless node after the modular autonomous bot apparatus assembly moves from the destination location with the return deliverable item, the external wireless node being related to the personnel at the hold-at-location logistics facility.

38. The method of embodiment 36, the step of notifying the authorized delivery recipient of the deliverable item of the approaching delivery further comprises transmitting an arrival estimate to the external wireless node, the arrival estimate indicating an estimated time to arrive at the hold-at-location logistics facility.

39. The method of embodiment 32, further comprising the step of providing, by the modular cargo storage system, selective access to the return deliverable item within the modular cargo storage system after the modular mobile base arrives at the hold-at-location logistics facility.

40. The method of embodiment 1, wherein the step of autonomously causing the modular mobility base to move from the hold-at-location logistics facility to the destination location comprises autonomously causing, by the modular mobile autonomy control module, the modular mobility base to move from the hold-at-location logistics facility to the destination location while interacting with a wireless building facility node to actuate a pathway obstacle disposed in a path on the route to the destination location.

41. The method of embodiment 40, wherein the pathway obstacle comprises an actuated door controlled by the wireless building facility node.

42. The method of embodiment 40, wherein the pathway obstacle comprises an actuated elevator controlled by the wireless building facility node.

43. The method of embodiment 40, wherein the pathway obstacle comprises an actuated lock controlled by the wireless building facility node.

44. The method of embodiment 40, wherein interacting with the wireless building facility node to actuate the pathway obstacle comprises:
   establishing an authorized association pairing between the modular mobile autonomy control module and the wireless building facility node based upon the authentication information related to the dispatched logistics operation; and
   causing the wireless building facility node to actuate the pathway obstacle after establishing the authorized association pairing between the modular mobile autonomy control module and the wireless building facility node.

45. The method of embodiment 1, wherein the step of autonomously causing the modular mobility base to move from the hold-at-location logistics facility to the destination location comprises autonomously causing, by the modular mobile autonomy control module, the modular mobility base to move from the hold-at-location logistics facility to the destination location while engaging a pathway obstacle disposed in a path on the route to the destination location using an articulating arm disposed on the modular autonomous bot apparatus assembly and using a plurality of sensors disposed on at least one of the modular mobility base and the modular mobile autonomy control module.

46. The method of embodiment 45, wherein the pathway obstacle comprises a manually actuated door.

47. The method of embodiment 45, wherein the pathway obstacle comprises a manually actuated elevator.

48. The method of embodiment 45, wherein the pathway obstacle comprises a manually actuated lock.

49. The method of embodiment 45, wherein engaging the pathway obstacle using the articulating arm and sensors comprises:
   guiding, by the modular mobile autonomy control module, the articulating arm to a control element of the pathway obstacle using one or more of the sensors disposed on at least one of the modular mobility base and the modular mobile autonomy control module; and
   actuating the pathway obstacle, by the modular mobile autonomy control module, once the articulating arm engages the control element of the pathway obstacle.

50. The method of embodiment 49, wherein the control element of the pathway obstacle comprises one from the group consisting of a handle for the pathway obstacle, a button for the pathway obstacle, a switch for the pathway obstacle, and a portion of a control panel for the pathway obstacle.

51. The method of embodiment 1, wherein the delivery recipient authentication input received by the modular mobile autonomy control module is provided by the delivery recipient through a user input panel disposed on the modular autonomous bot apparatus coupled to the modular mobile autonomy control module.

52. The method of embodiment 1, wherein the delivery recipient authentication input received by the modular mobile autonomy control module comprises an access code provided by the delivery recipient through the user input panel disposed on the modular cargo storage system and operatively coupled to the modular mobile autonomy control module.

53. The method of embodiment 1, wherein the delivery recipient authentication input received by the modular mobile autonomy control module comprises a biometric input provided by the delivery recipient through the user input panel disposed on the modular cargo storage system and operatively coupled to the modular mobile autonomy control module.

54. The method of embodiment 1, wherein the delivery recipient authentication input received by the modular mobile autonomy control module is provided by the delivery recipient through an external wireless node disposed external to the modular autonomous bot apparatus assembly.

55. The method of embodiment 54, wherein the delivery recipient authentication input received by the modular mobile autonomy control module comprises an access code provided by the delivery recipient through the external wireless node disposed external to the modular autonomous bot apparatus assembly.

56. The method of embodiment 54, wherein the delivery recipient authentication input received by the modular mobile autonomy control module comprises a biometric input provided by the delivery recipient through the external wireless node disposed external to the modular autonomous bot apparatus assembly.

57. The method of embodiment 1, wherein the authentication information related to the dispatched logistics operation from the hold-at-location logistics facility includes an identifier of the authorized delivery recipient for the deliverable item for transport as part of the dispatched logistics operation from the hold-at-location logistics facility; and
   wherein the step of receiving the delivery recipient authentication input comprises:
      detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the destination location identified by the destination information; and
      authenticating, by the modular mobile autonomy control module, that the external wireless node is associated with the authorized delivery recipient for the item being shipped within the modular cargo storage system based upon the identifier of the authorized delivery recipient and identifier information within the detected advertising signal broadcast from the external wireless node.

58. The method of embodiment 1, wherein the authentication information related to the dispatched logistics operation from the hold-at-location logistics facility includes an identifier of the authorized delivery recipient for the deliverable item for transport as part of the dispatched logistics operation from the hold-at-location logistics facility; and
  wherein the step of receiving the delivery recipient authentication input comprises:
    detecting, by the modular mobile autonomy control module, an unprompted advertising signal from an external wireless node within a predetermined range of the modular autonomous bot apparatus assembly once the modular autonomous bot apparatus assembly has arrived at the destination location identified by the destination information; and
    establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched logistics operation from the hold-at-location logistics facility.

59. The method of embodiment 1, wherein the step of receiving the deliverable item comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

60. The method of embodiment 59, wherein actuating, by the modular mobile autonomy control module, the actuated cargo door comprises actuating an actuated joint on the actuated cargo door to cause the actuated cargo door to move from the closed position to the open position.

61. The method of embodiment 59, wherein actuating, by the modular mobile autonomy control module, the actuated cargo door further comprises actuating an electro-mechanical lock on the actuated cargo door to cause the actuated cargo door to unlock before moving from the closed position to the open position.

62. The method of embodiment 1, wherein the step of receiving the deliverable item comprises actuating, by the modular mobile autonomy control module, an actuated sliding arm disposed on the modular cargo storage system to move the deliverable item into a payload area within the modular cargo storage system.

63. The method of embodiment 1, wherein the step of receiving the deliverable item comprises actuating, by the modular mobile autonomy control module, an actuated grabbing arm disposed on the modular cargo storage system to grab and move the deliverable item into a payload area within the modular cargo storage system as part of receiving the deliverable item.

64. The method of embodiment 1, wherein the step of receiving the deliverable item comprises actuating, by the modular mobile autonomy control module, an actuated belt surface disposed on the modular auxiliary power module as a movable support surface exposed within a payload area inside the modular cargo storage system, the actuated belt surface being operative when actuated to cause the deliverable item as placed on the actuated belt surface to move within the payload area as part of receiving the deliverable item.

65. The method of embodiment 1, wherein the step of providing selective access to the deliverable item comprises actuating, by the modular mobile autonomy control module, an actuated cargo door disposed on the modular auxiliary power module to an open position once the delivery recipient authentication input correlates to a portion of the authentication information related to the dispatched logistics operation, wherein the actuated cargo door provides a seal to a payload area within the modular cargo storage system when the actuated cargo door is in a closed position and the actuated cargo door provides access to the payload area within the modular cargo storage system when the actuated cargo door is in the open position.

66. The method of embodiment 65, wherein actuating, by the modular mobile autonomy control module, the actuated cargo door comprises actuating an actuated joint on the actuated cargo door to cause the actuated cargo door to move from the closed position to the open position.

67. The method of embodiment 65, wherein actuating, by the modular mobile autonomy control module, the actuated cargo door further comprises actuating an electro-mechanical lock on the actuated cargo door to cause the actuated cargo door to unlock before moving from the closed position to the open position.

68. The method of embodiment 1, wherein the step of providing selective access to the deliverable item comprises actuating, by the modular mobile autonomy control module, an actuated sliding arm disposed on the modular cargo storage system to move the deliverable item out from a payload area within the modular cargo storage system.

69. The method of embodiment 1, wherein the step of providing selective access to the deliverable item comprises actuating, by the modular mobile autonomy control module, an actuated grabbing arm disposed on the modular cargo storage system to grab and move the deliverable item out from a payload area within the modular cargo storage system.

70. The method of embodiment 1, wherein the step of providing selective access to the deliverable item comprises actuating, by the modular mobile autonomy control module, an actuated belt surface disposed on the modular auxiliary power module as a movable support surface exposed within a payload area inside the modular cargo storage system, the actuated belt surface being operative when actuated to cause the deliverable item as placed on the actuated belt surface to move out from within the payload area.

71. A remotely-actuated logistics receptacle apparatus for wirelessly interfacing with a dispatched mobile autonomous delivery vehicle, comprising:
  a logistics receptacle for receiving and temporarily maintaining an object deposited for shipment, the logistics receptacle comprising
    a storage enclosure defining a temporary storage area within which the object is temporarily maintained,
    an entrance opening through which the object can pass when being retrieved from the storage enclosure, and an access door disposed on the storage enclosure next to the entrance opening, the access door selectively securing the entrance opening when in a closed position and allowing the object to be retrieved from the storage enclosure through the entrance opening when in an open position, a wireless node-based remote access control module disposed with the logistics receptacle, the wireless node-based remote access control module comprising
a controller,
a control module memory coupled to the controller, the control module memory maintaining remote storage access program code and pickup authentication information related to an authorized pickup logistics operation for the object by the dispatched mobile autonomous delivery vehicle as an authorized pickup entity for the object deposited for shipment, and
a wireless communication interface operatively coupled to the controller, the wireless communication interface providing a wireless communication path to the dispatched mobile autonomous delivery vehicle;

a door actuator coupled between the access door and the storage enclosure, the door actuator being operatively activated by the controller, the door actuator selectively causing the access door to open when activated to move from the closed position to the open position and selectively cause the access door close when activated to move the access door from the open position to closed position; and a parcel object actuator disposed within the temporary storage area, the parcel object actuator being operatively activated by the controller, the parcel object actuator selectively causing the object to move out of the temporary storage area and through the entrance opening;

wherein the controller, when executing the remote storage access program code, is operative to
receive a pickup authentication signal over the wireless communication interface from an external wireless node,
transmit a first remote control actuation signal to the door actuator only if the received pickup authentication signal is determined to be from the dispatched mobile autonomous delivery vehicle as the authorized pickup entity according to the pickup authentication information in the control module memory, the first remote control actuation signal activating the door actuator to cause the access door to open,
transmit a second remote control actuation signal to the parcel object actuator once the access door is open and only if the received pickup authentication signal is determined to be from the dispatched mobile autonomous delivery vehicle as the authorized pickup entity according to the pickup authentication information in the control module memory, the second remote control actuation signal activating the parcel object actuator to cause the object to move from where it is maintained in the temporary storage area and through the entrance opening.

72. The apparatus of embodiment 71, wherein the controller, when executing the remote storage access program code, is further operative to receive a ready confirmation signal over the wireless communication interface from the dispatched mobile autonomous deliver vehicle as the authorized pickup entity; and wherein the controller is operative to transmit the second remote control actuation signal to the parcel object actuator causing the object to move through the entrance opening only after the controller received the ready confirmation signal from the dispatched mobile autonomous deliver vehicle as the authorized pickup entity.

73. The apparatus of embodiment 71, wherein the controller is operative to determine if the received pickup authentication signal from the dispatched mobile autonomous delivery vehicle is from the authorized pickup entity according to the pickup authentication information in the control module memory by being operative to:

generate association data indicating a secure association between the external node and the controller after detecting the pickup authentication signal from the external wireless node, the secure association between the external node and the controller allowing secure sharing of information between the external node and the controller and being pre-authorized by the dispatch server as indicated by the pickup authentication information related to the authorized pickup logistics operation.

74. The apparatus of embodiment 71, wherein the controller, when executing the remote storage access program code, is further operative to receive the pickup authentication information related to the authorized pickup logistics operation from a dispatch server over the wireless communication interface.

75. The apparatus of embodiment 71, further comprising a sensor disposed within the storage enclosure for detecting deposit of the object deposited for shipment, the sensor being operatively coupled to the controller of the wireless node-based remote access control module, the sensor being operative to generate sensor data reflecting the detected deposit of the object deposited for shipment within the storage enclosure; and wherein the controller, when executing the remote storage access program code, is further operative to receive the sensor data from the sensor and responsively transmit a dispatch request message over the wireless communication interface to the dispatch server, the dispatch request initiating dispatch of the dispatched mobile autonomous delivery vehicle for the authorized pickup logistics operation.

76. The apparatus of embodiment 71, wherein the parcel object actuator is operative when activated to cause the object being shipped to be removed from the temporary storage area and placed into custody of the dispatched mobile autonomous delivery vehicle.

77. The apparatus of embodiment 71, wherein the parcel object actuator comprises an actuated support base that temporarily maintains the object deposited for shipment, wherein the actuated support base is operative when actuated to tilt towards the entrance opening causing the object being shipped to at least slide towards the entrance opening.

78. The apparatus of embodiment 71, wherein the parcel object actuator comprises an actuated pushing arm that is operative when actuated to contact the object being shipped and at least push the object being shipped towards the entrance opening.

79. The apparatus of embodiment 71, wherein the parcel object actuator comprises an actuated sliding arm that is operative when actuated to contact the object being shipped and at least slide the object being shipped towards the entrance opening.

80. The apparatus of embodiment 71, wherein the parcel object actuator comprises an actuated grabbing arm operative when actuated to engage the object being shipped, move the object being shipped towards and through the entrance opening, and place the object being shipped with the dispatched mobile autonomous delivery vehicle.

81. The apparatus of embodiment 71, wherein the parcel object actuator comprises an actuated moving surface that temporarily maintains the object deposited for shipment, wherein the actuated moving surface is operative when actuated to move while supporting the object being shipped to cause the object being shipped to move towards the entrance opening.

82. The apparatus of embodiment 71, wherein the logistics receptacle comprises a drop box receptacle.

83. The apparatus of embodiment 71, wherein the logistics receptacle comprises a locker receptacle having a plurality of secure storage enclosures, wherein the storage enclosure defining the temporary storage area within which the object is temporarily maintained is one of the secure storage enclosures.

84. The apparatus of embodiment 71, wherein the logistics receptacle further comprising a docking interface disposed on the exterior of the logistics receptacle and extending from the storage enclosure as a contact registration point for engaging the dispatched mobile autonomous delivery vehicle when the dispatched mobile autonomous delivery vehicle approaches the remotely-actuated logistics receptacle apparatus as part of the authorized pickup logistics operation.

85. The apparatus of embodiment 84, wherein the contact registration point comprises a mated alignment interface configured to fit with a corresponding mated alignment interface on the dispatched mobile autonomous delivery vehicle when the dispatched mobile autonomous delivery vehicle approaches and engages the remotely-actuated logistics receptacle apparatus as part of the authorized pickup logistics operation.

86. The apparatus of embodiment 84, wherein docking interface comprises an extended engagement barrier disposed on the exterior of the logistics receptacle and below the entrance opening.

87. The apparatus of embodiment 86, wherein docking interface comprises a set of latches disposed on an outward peripheral edge of the extended engagement barrier, the set of latches configured to mate with a set of complementary latches on the dispatched mobile autonomous delivery vehicle.

88. The apparatus of embodiment 86, wherein the set of latches comprises a set of recessed latches.

89. The apparatus of embodiment 86, wherein the set of latches comprises a set of actuated latches activated by the controller to move and engage a mated set of latches on the dispatched mobile autonomous delivery vehicle to secure the dispatched mobile autonomous delivery vehicle to the extended engagement barrier of the logistics receptacle.

90. A method of performing a dispatched logistics operation for a deliverable item maintained within a remotely-actuated logistics receptacle and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least temporarily maintain the deliverable item within the modular autonomous bot apparatus assembly, and a modular mobile autonomy control module that autonomously controls operation of the modular autonomous bot apparatus assembly during the dispatched logistics operation, the method comprising the steps of:

detecting, by the remotely-actuated logistics receptacle, deposit of the deliverable item based upon sensor data generated by a sensor within the remotely-actuated logistics receptacle;

transmitting, by the remotely-actuated logistics receptacle, a dispatch request message to the dispatch server in response to the detected deposit of the deliverable item, the dispatch request message including shipping information on the deliverable item and identifier information on the remotely-actuated logistics receptacle;

receiving, by the modular mobile autonomy control module, a dispatch command from the dispatch server, the dispatch command comprising at least
        identifier information on the deliverable item based upon the shipping information,
        transport parameters on the deliverable item based upon the shipping information,
        destination delivery information related to pickup of the deliverable item, and
        pickup authentication information related to the modular autonomous bot assembly as an authorized pickup entity for the deliverable item;

verifying, by the modular mobile autonomy control module, that each of the modular mobile autonomy control module, the modular mobility base, the modular auxiliary power module, and the modular cargo storage system are compatible with transporting the deliverable item as part of the dispatched logistics operation for the deliverable item based upon the dispatch command;

autonomously causing, by the modular mobile autonomy control module, the modular mobility base to move from a bot storage location to a location of the remotely-actuated logistics receptacle as identified by the destination delivery information in the dispatch command;

broadcasting, by the modular mobile autonomy control module, a pickup authentication signal when the modular autonomous bot apparatus assembly is within a threshold notification range of the location of the remotely-actuated logistics receptacle;

autonomously causing, by the modular mobile autonomy control module, the modular mobility base to move to a receiving position proximate an access door on the remotely-actuated logistics receptacle upon arrival at the location of the remotely-actuated logistics receptacle;

detecting, by the remotely-actuated logistics receptacle, the pickup authentication signal from the modular mobile autonomy control module;

authenticating, by the remotely-actuated logistics receptacle, that the modular autonomous bot apparatus assembly is the authorized pickup entity for the deliverable item when authentication information in the pickup authentication signal correlates to the pickup authentication information from the dispatch command;

activating, by the remotely-actuated logistics receptacle, a door actuator on the remotely actuated logistics receptacle after authenticating that the modular autonomous bot apparatus assembly is the authorized pickup entity based upon the pickup authentication signal, wherein activating the door actuator causing the access door on the remotely-actuated logistics receptacle to move from a secure closed position to an open position;

broadcasting, by the modular mobile autonomy control module, a ready confirmation signal once the modular mobility base is located at the receiving position proximate the access door on the remotely-actuated logistics receptacle;

activating, by the remotely-actuated logistics receptacle, a parcel object actuator on the remotely-actuated logistics receptacle in response to the ready confirmation signal from the modular mobile autonomy control module and only if the authentication information in the pickup authentication signal correlates to the pickup authentication information from the dispatch command, wherein activating the parcel object actuator moves the deliverable item from where it is maintained in the remotely-actuated logistics receptacle and into the custody of the modular cargo storage system; and autonomously causing, by the modular mobile autonomy control module, the modular mobility base to move from the remotely-actuated logistics receptacle to a destination location for delivery of the deliverable item, the destination location being identified as part of the destination delivery information from the dispatch command.

91. The method of embodiment 90, wherein the step of detecting the pickup authentication signal comprises:

detecting, by the remotely-actuated logistics receptacle, an advertising signal from the modular mobile autonomy control module;

establishing a secure association between the remotely-actuated logistics receptacle and the modular mobile autonomy control module after detecting the advertising signal and by generating association data stored on the remotely-actuated logistics receptacle indicating the secure association and allowing secure sharing of information between the remotely-actuated logistics receptacle and the modular mobile autonomy control module, wherein the secure association being pre-authorized by the dispatch server as it relates to the dispatched logistics operation for the deliverable item;

securely transmitting, by the modular mobile autonomy control module, the pickup authentication signal to the remotely-actuated logistics receptacle once the secure association is established and the association data is generated; and securely receiving, by the remotely-actuated logistics receptacle, the pickup authentication signal from the modular mobile autonomy control module.

92. The method of embodiment 90, wherein the step of activating the parcel object actuator further comprises causing the parcel object actuator to remove the deliverable item from the remotely-actuated logistics receptacle and transfer the deliverable item to an articulating object receiver on the modular cargo storage system being controlled by the modular mobile autonomy control module.

93. The method of embodiment 92, further comprising the steps of:

receiving, by the articulating object receiver on the modular cargo storage system under control of the modular mobile autonomy control module, the deliverable item from the parcel object actuator on the remotely-actuated logistics receptacle; and placing, by the articulating object receiver on the modular cargo storage system under control of the modular mobile autonomy control module, the deliverable item within the modular cargo storage system.

94. The method of embodiment 93, wherein the articulating object receiver comprises one from the group consisting of an actuated sliding arm, an actuated grabbing arm, and an actuated belt surface.

95. The method of embodiment 90, wherein the step of activating the parcel object actuator comprises activating, by the remotely-actuated logistics receptacle, an actuated support base within a storage compartment of the remotely-actuated logistics receptacle in response to the ready confirmation signal, wherein activating the actuated support base causes the actuated support base to tilt towards an entrance opening to the storage compartment at the access door and causing the deliverable item to at least slide towards the entrance opening.

96. The method of embodiment 90, wherein the step of activating the parcel object actuator comprises activating, by the remotely-actuated logistics receptacle, an actuated pushing arm within a storage compartment of the remotely-actuated logistics receptacle in response to the ready confirmation signal, wherein activating the actuated pushing arm causes the actuated pushing arm to contact the deliverable item and at least push the deliverable item towards an entrance opening to the storage compartment at the access door.

97. The method of embodiment 90, wherein the step of activating the parcel object actuator comprises activating, by the remotely-actuated logistics receptacle, an actuated sliding arm within a storage compartment of the remotely-actuated logistics receptacle in response to the ready confirmation signal, wherein activating the actuated sliding arm causes the actuated sliding arm to contact the deliverable item and at least slide the deliverable item towards an entrance opening to the storage compartment at the access door.

98. The method of embodiment 90, wherein the step of activating the parcel object actuator comprises activating, by the remotely-actuated logistics receptacle, an actuated grabbing arm within a storage compartment of the remotely-actuated logistics receptacle in response to the ready confirmation signal, wherein activating the actuated grabbing arm causes the actuated grabbing arm to engage the deliverable item, move the deliverable item towards and through an entrance opening to the storage compartment at the access door, and place the deliverable item into the modular cargo storage system.

99. The method of embodiment 90, wherein the step of activating the parcel object actuator comprises activating, by the remotely-actuated logistics receptacle, an actuated belt surface in response to the ready confirmation signal, the actuated belt surface temporarily supporting the deliverable item within a storage compartment of the remotely-actuated logistics receptacle, wherein activating the actuated belt surface causes the actuated moving surface to move the deliverable item towards and through an entrance opening to the storage compartment at the access door.

100. The method of embodiment 90, wherein the destination delivery information related to pickup of the deliverable item comprises an identifier of one of a plurality of secure storage enclosures within the remotely-actuated logistics receptacle that temporarily maintains the deliverable item.

101. The method of embodiment 90, wherein the step of activating the door actuator comprises activating, by the remotely-actuated logistics receptacle, the door actuator on the remotely actuated logistics receptacle (a) after authenticating that the modular autonomous bot apparatus assembly is the authorized pickup entity based upon the pickup authentication signal and (b) after receiving a door activation request signal from the modular mobile autonomy control module.

102. The method of embodiment 90, wherein the step of verifying that each of the modular mobile autonomy control module, the modular mobility base, the modular auxiliary power module, and the modular cargo storage system are compatible with transporting the deliverable item as part of the dispatched logistics operation for the deliverable item based upon the dispatch command comprises verifying that at least the modular cargo storage system is compatible with a size of the deliverable item according to the transport parameters identified on the deliverable item in the dispatch command.

103. The method of embodiment 90, wherein the step of verifying that each of the modular mobile autonomy control module, the modular mobility base, the modular auxiliary power module, and the modular cargo storage system are compatible with transporting the deliverable item as part of the dispatched logistics operation for the deliverable item based upon the dispatch command comprises verifying that at least the modular cargo storage system is compatible with a weight of the deliverable item according to the transport parameters on the deliverable item identified in the dispatch command.

104. The method of embodiment 90, wherein the step of verifying that each of the modular mobile autonomy control module, the modular mobility base, the modular auxiliary power module, and the modular cargo storage system are compatible with transporting the deliverable item as part of the dispatched logistics operation for the deliverable item based upon the dispatch command comprises:
   verifying, by the modular mobile autonomy control module, that at least the modular cargo storage system is compatible with the transport parameters on the deliverable item identified in the dispatch command; and
   transmitting, by the modular mobile autonomy control module, a configuration change request to the dispatch server if the at least modular cargo storage system is verified to be incompatible with the transport parameters on the deliverable item, the configuration change request identifying that the at least modular cargo storage system are incompatible with the transport parameters on the deliverable item.

105. The method of embodiment 104, wherein the step of transmitting the configuration change request to the dispatch server comprises transmitting, by the modular mobile autonomy control module, the configuration change request to the dispatch server if the at least modular cargo storage system is verified to be incompatible with the transport parameters on the deliverable item prior to when the modular mobile autonomy control module causes the modular mobility base to move from the bot storage location.

106. The method of embodiment 90, further comprising the step of initiating, by the dispatch server, a configuration change operation on the modular autonomous bot apparatus assembly to change at least one of the modular mobile autonomy control module, the modular mobility base, the modular auxiliary power module, and the modular cargo storage system that are verified to be incompatible with transporting the deliverable item as part of the dispatched logistics operation for the deliverable item based upon the dispatch command prior to when the modular mobile autonomy control module causes the modular mobility base to move from the bot storage location.

107. A method of performing a dispatched hold-at-location logistics operation for a deliverable item from an origin location using a modular autonomous bot apparatus assembly operating as a temporary hold-at-location logistics receptacle and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least temporarily maintain the deliverable item within the modular autonomous bot apparatus assembly, and a modular mobile autonomy control module that autonomously controls operation of the modular autonomous bot apparatus assembly during the dispatched logistics operation from the hold-at-location logistics facility, the method comprising the steps of:
   (a) receiving, by the modular mobile autonomy control module, a delivery dispatch command for the dispatched hold-at-location logistics operation from the dispatch server, the delivery dispatch command comprising at least
      identifier information on the deliverable item,
      transport parameters on the deliverable item,
      hold-at-location information related to an intermediate hold location for the deliverable item as maintained within the modular autonomous bot apparatus assembly, and
      delivery authentication information related to an authorized delivery recipient of the deliverable item;
   (b) verifying, by the modular mobile autonomy control module, that each of the modular mobile autonomy control module, the modular mobility base, the modular auxiliary power module, and the modular cargo storage system are compatible with the dispatched hold-at-location logistics operation for the deliverable item based upon the delivery dispatch command;
   (c) receiving, by the modular cargo storage system, the deliverable item into a payload area within the modular cargo storage system at the origin location;
   (d) autonomously causing, by the modular mobile autonomy control module, the modular mobility base to move from the original on a route to the intermediate hold location identified by the hold-at-location information;
   (e) notifying, by the modular mobile autonomy control module, the authorized delivery recipient of the deliverable item of an approaching arrival at the intermediate hold location when the modular autonomous bot apparatus assembly is within a threshold notification range of the intermediate hold location identified by the hold-at-location information;
   (f) receiving delivery recipient authentication input by the modular mobile autonomy control module from a delivery recipient disposed external to the modular autonomous bot apparatus assembly at the intermediate hold location;
   (g) providing, by the modular cargo storage system, selective access to the deliverable item within the modular cargo storage system only when the delivery recipient authentication input correlates to the delivery authentication information indicating that the delivery recipient providing the delivery recipient authentication input is the authorized delivery recipient;
   (h) monitoring, by the modular mobile autonomy control module, unloading of the deliverable item from within the modular cargo storage system using one or more sensors on at least one of the modular mobile autonomy control module and the modular cargo storage system; and (i) autonomously causing, by the modular mobile autonomy control module, the modular mobility base to move from the intermediate hold location on a return route to the origin location after the deliverable item is no longer detected within the modular cargo storage system.

108. The method of embodiment 107, wherein the intermediate hold location comprises a hold-at-location logistics facility.

109. The method of embodiment 107, wherein the intermediate hold location comprises a location of a mobile external wireless node designated as part of the hold-at-location information.

110. The method of embodiment 109, wherein the mobile external wireless node comprises a delivery vehicle master node disposed with a delivery vehicle.

111. The method of embodiment 109, wherein the mobile external wireless node comprises a delivery courier master node operated by delivery personnel.

112. The method of embodiment 109, wherein the mobile external wireless node comprises a user access device operated by the authorized delivery recipient.

113. The method of embodiment 109, wherein the mobile external wireless node comprises a mobile master node operated by a designated alternative recipient identified by the authorized delivery recipient according to the hold-at-location information and the delivery authentication information.

114. The method of embodiment 108, wherein the steps of (f) receiving delivery recipient authentication input and (g) providing selective access to the deliverable item comprises:
autonomously causing, by the modular mobile autonomy control module, the modular mobility base to wait at the intermediate hold location for at least until a pre-determined closing time of the hold-at-location facility; and
providing, by the modular cargo storage system at the direction of the modular mobile autonomy control module, selective access to the deliverable item when the modular mobile autonomy control module detects the delivery recipient authentication input and determines the detected delivery authentication input indicates the delivery recipient providing the delivery recipient authentication input is the authorized delivery recipient and the pre-determined deadline for closing of the hold-at-location facility has not expired.

115. The method of embodiment 114, wherein the steps of (f)-(i) comprises:
autonomously causing, by the modular mobile autonomy control module, the modular mobility base to wait at the intermediate hold location for at least until a pre-determined closing time of the hold-at-location facility;
monitoring, by the modular mobile autonomy control module, for receipt of delivery recipient authentication input from the authorized delivery recipient according to the delivery authentication information;
autonomously causing, by the modular mobile autonomy control module, the modular mobility base to move from the intermediate hold location to the origin location when the pre-determined deadline for closing of the hold-at-location facility has expired and the monitoring has not indicated receipt of the delivery recipient authentication input from the authorized delivery recipient; and
repeating steps (d)-(i) after a subsequent pre-determined opening time of the hold-at-location facility.

Further Embodiment N—Methods and Systems for Navigating to a Designated Shipping Location as Part of a Multi-Leg Logistics Operation Using a Wireless Node Network and Multiple Node-Enabled Autonomous Transport Vehicles in the Network 1. A method for navigating to a designated shipping location as part of a multi-leg logistics operation using a plurality of nodes in a wireless node network, a server in the network, and a plurality of node-enabled autonomous transport vehicles in the network, comprising:
detecting, by a first mobile master node of the plurality of nodes, a signal broadcast from a second mobile master node of the plurality of nodes, wherein the first mobile master node is associated with a first of the node-enabled autonomous transport vehicles and the second mobile master node is associated with a second of the node-enabled autonomous transport vehicles;
instructing, by the first mobile master node, the second mobile master node to alter a power level of the signal broadcast from the second mobile master node;
identifying, by the first mobile master node, the signal broadcast from the second mobile master node with the altered power level;
determining, by the first mobile master node, a direction of the second mobile master node relative to the first mobile master node based upon the detected signal from the second mobile master node with the altered power level;
navigating, by the first mobile master node, to the second mobile master node associated with the second of the node-enabled autonomous transport vehicles based upon the determined direction of the second mobile master node relative to the first mobile master node;
transferring at least one item as payload from the first of the node-enabled autonomous transport vehicles to the second of the node-enabled autonomous transport vehicles at a waypoint location of the second of the node-enabled autonomous transport vehicles;
detecting, by the second mobile master node, a signal broadcast from another of the plurality of nodes, the another node being associated with the designated shipping location for the payload;
instructing, by the second mobile master node, the another node to alter a power level of the signal broadcast from the another node;
identifying, by the second mobile master node, the signal broadcast from the another node with the altered power level;
determining, by the second mobile master node, a direction of the another node relative to the second mobile master node based upon the detected signal from the another node with the altered power level; and
navigating, by the second mobile master node, to the another node based upon the determined direction of the another node relative to the second mobile master node.

2. The method of embodiment 1, wherein the step of transferring the at least one item as payload comprises transferring a payload container as the payload from the first of the node-enabled autonomous transport vehicles to the second of the node-enabled autonomous transport vehicles at a waypoint location of the second of the node-enabled autonomous transport vehicles, the payload container maintaining the at least one item.

3. The method of embodiment 1 further comprising the step of initiating, by the second mobile master node, an offload operation of the at least one item as the payload at the designated shipping location using an object manipulating system on the second of the node-enabled autonomous transport vehicles.

4. The method of embodiment 3, wherein the designated shipping location is in the courier transport vehicle.

5. The method of embodiment 3, wherein the designated shipping location is at a delivery address for the at least one item.

6. The method of embodiment 3, wherein the offload operation of the at least one item as the payload at the designated shipping location comprises initiating, by the second mobile master node, the offload operation of a payload container maintaining the at least one item as the payload at the designated shipping location using an object manipulating system on the second of the node-enabled autonomous transport vehicles to obtain and move the payload container.

7. The method of embodiment 1 further comprising the step of initiating, by the first mobile master node, a loading operation of the at least one item as the payload at a pickup location using an object manipulating system on the first of the node-enabled autonomous transport vehicles.

8. The method of embodiment 7, wherein the pickup location is in the courier transport vehicle.

9. The method of embodiment 7, wherein the pickup location is at a pickup address for the at least one item.

10. The method of embodiment 7, wherein the loading operation of the at least one item as the payload at the pickup location comprises initiating, by the first mobile master node, a loading operation of a payload container maintaining the at least one item as the payload at the pickup location using an object manipulating system on the first of the node-enabled autonomous transport vehicles to obtain and move the payload container.

11. The method of embodiment 1, wherein the step of transferring comprises:
    detecting the second of the node-enabled autonomous transport vehicles by a proximity sensor on the first of the node-enabled autonomous transport vehicles, as the first of the node-enabled autonomous transport vehicles navigates towards and approaches the second of the node-enabled autonomous transport vehicles;
    causing, by the first mobile master node, a transfer alignment configuration of the first of the node-enabled autonomous transport vehicle and the second of the node-enabled autonomous transport vehicles as the first mobile master node controls movement of the first of the node-enabled autonomous transport vehicles; and
    initiating, by the first mobile master node, transfer of the at least one item from the first of the node-enabled autonomous transport vehicles to the second of the node-enabled autonomous transport vehicles while the first of the node-enabled autonomous transport vehicles and the second of the node-enabled autonomous transport vehicles are in the transfer alignment configuration.

12. The method of embodiment 11, wherein the step of causing the transfer alignment configuration of the first of the node-enabled autonomous transport vehicle and the second of the node-enabled autonomous transport vehicles comprises the first mobile master node aligning a first docking interface disposed on the first of the node-enabled autonomous transport vehicles with a second docking interface disposed on the second of the node-enabled autonomous transport vehicles as the first mobile master node controls movement of the first of the node-enabled autonomous transport vehicles.

13. The method of embodiment 11, wherein the step of causing the transfer alignment configuration of the first of the node-enabled autonomous transport vehicle and the second of the node-enabled autonomous transport vehicles comprises:
    aligning, by the first mobile master node, a first docking interface disposed on the first of the node-enabled autonomous transport vehicles with a second docking interface disposed on the second of the node-enabled autonomous transport vehicles as the first mobile master node controls movement of the first of the node-enabled autonomous transport vehicles; and
    securing the first docking interface to the second docking interface to create the transfer alignment orientation.

14. The method of embodiment 11, wherein the initiating step comprises:
    deploying, by the first mobile master node, an object manipulation system on the first of the node-enabled autonomous transport vehicles to initiate control of the at least one item while on the first of the node-enabled autonomous transport vehicles; and
    moving, by the first mobile master node, the at least one item from the first of the node-enabled autonomous transport vehicles to the second of the node-enabled autonomous transport vehicles using the object manipulation system on the first of the node-enabled autonomous transport vehicles.

15. The method of embodiment 1, wherein the step of transferring comprises:
    detecting the first of the node-enabled autonomous transport vehicles by a proximity sensor on the second of the node-enabled autonomous transport vehicles, as the first of the node-enabled autonomous transport vehicles navigates towards and approaches the second of the node-enabled autonomous transport vehicles;
    causing, by the second mobile master node, a transfer alignment configuration of the first of the node-enabled autonomous transport vehicle and the second of the node-enabled autonomous transport vehicles as the second mobile master node controls movement of the second of the node-enabled autonomous transport vehicles relative to the first of the node-enabled autonomous transport vehicles; and
    initiating, by the second mobile master node, transfer of the at least one item from the first of the node-enabled autonomous transport vehicles to the second of the node-enabled autonomous transport vehicles while the first of the node-enabled autonomous transport vehicle and the second of the node-enabled autonomous transport vehicles are in the transfer alignment configuration.

16. The method of embodiment 15, wherein the step of causing the transfer alignment configuration of the first of the node-enabled autonomous transport vehicle and the second of the node-enabled autonomous transport vehicles comprises the second mobile master node aligning a second docking interface disposed on the second of the node-enabled autonomous transport vehicles with a first docking interface disposed on the first of the node-enabled autonomous transport vehicles as the second mobile master node controls movement of the second of the node-enabled autonomous transport vehicles relative to the first of the node-enabled autonomous transport vehicles.

17. The method of embodiment 15, wherein the step of causing the transfer alignment configuration of the first of the node-enabled autonomous transport vehicle and the second of the node-enabled autonomous transport vehicles comprises:
  aligning, by the second mobile master node, a second docking interface disposed on the second of the node-enabled autonomous transport vehicles with a first docking interface disposed on the first of the node-enabled autonomous transport vehicles as the second mobile master node controls movement of the second of the node-enabled autonomous transport vehicles relative to the first of the node-enabled autonomous transport vehicles; and
  securing the second docking interface to the first docking interface to create the transfer alignment orientation.

18. The method of embodiment 15, wherein the initiating step comprises:
  deploying, by the second mobile master node, an object manipulation system on the second of the node-enabled autonomous transport vehicles to initiate control of the at least one item while on the first of the node-enabled autonomous transport vehicles; and
  moving, by the second mobile master node, the at least one item from the first of the node-enabled autonomous transport vehicles to the second of the node-enabled autonomous transport vehicles using the object manipulation system on the second of the node-enabled autonomous transport vehicles.

19. The method of embodiment 1, wherein the step of transferring comprises:
  navigating, by the first mobile master node, to the waypoint location of the second of the node-enabled autonomous transport vehicles;
  detecting the first of the node-enabled autonomous transport vehicles by a proximity sensor on the second of the node-enabled autonomous transport vehicles, as the first of the node-enabled autonomous transport vehicles navigates towards and approaches the second of the node-enabled autonomous transport vehicles;
  detecting the second of the node-enabled autonomous transport vehicles by a proximity sensor on the first of the node-enabled autonomous transport vehicles, as the first of the node-enabled autonomous transport vehicles navigates towards and approaches the second of the node-enabled autonomous transport vehicles;
  controlling, by the first mobile master node, a position of the first of the node-enabled autonomous transport vehicles by moving the first of the node-enabled autonomous transport vehicles into a first transfer position;
  controlling, by the second mobile master node, a position of the second of the node-enabled autonomous transport vehicles by moving the second of the node-enabled autonomous transport vehicles into a second transfer position;
  refining the relative alignment of the first transfer position and the second transfer position to cause the first of the node-enabled autonomous transport vehicles and the second of the node-enabled autonomous transport vehicles to be in a transfer alignment orientation; and
  moving the at least one item from the first of the node-enabled autonomous transport vehicles to the second of the node-enabled autonomous transport vehicles using a first object manipulation system on the first of the node-enabled autonomous transport vehicles and a second object manipulation system on the second of the node-enabled autonomous transport vehicles.

20. The method of embodiment 1, wherein the step of navigating to the second mobile master node further comprises navigating, by the first mobile master node, to the second mobile master node as the power level of the signal broadcast from the second mobile master node is incrementally decreased over time as the first mobile master node approaches the second mobile master node; and
  wherein the step of navigating to the another node further comprises navigating, by the second mobile master node, to the another node as the power level of the signal broadcast from the another node is incrementally decreased over time and as the second mobile master node approaches the another node.

21. The method of embodiment 1, wherein the first mobile master node is associated with a control system of the first of the autonomous transport vehicles and the second mobile master node is associated with a control system of the second of the autonomous transport vehicles;
  wherein the step of navigating by the first mobile master node further comprises providing, by the first mobile master node, the determined direction of the second mobile master node relative to the first mobile master node to an input of the control system of the first of the autonomous transport vehicles; and
  wherein the step of navigating by the second mobile master node further comprises providing, by the second mobile master node, the determined direction of the another node relative to the second mobile master node to an input of the control system of the second of the autonomous transport vehicles.

22. The method of embodiment 21 further comprising the steps of:
  causing, by the first mobile master node, the first of the autonomous transport vehicles to stop moving when a current location of the first mobile master node is within a predetermined range of the second mobile master node; and
  causing, by the second mobile master node, the second of the autonomous transport vehicles to stop moving when a current location of the second mobile master node is within a predetermined range of the another node.

23. The method of embodiment 1, wherein the step of navigating by the first mobile master node further comprises:
  accessing first context data that relates to an operating environment of the second mobile master node; and
  navigating, by the first mobile master node, to the second mobile master node with reference to the accessed first context data as the power level of the signal broadcast from the second mobile master node is incrementally decreased over time and as the first mobile master node approaches the second mobile master node; and
  wherein the step of navigating by the second mobile master node further comprises
    accessing second context data that relates to an operating environment of the another node; and
    navigating, by the second mobile master node, to the another node with reference to the accessed second context data as the power level of the signal broadcast from the another node is incrementally decreased over time and as the second mobile master node approaches the another node.

24. The method of embodiment 1 further comprising:
transmitting, by the first mobile master node to the server, an updated location of the first mobile master node as the first mobile master node approaches the second mobile master node; and
transmitting, by the second mobile master node to the server, an updated location of the second mobile master node as the second mobile master node approaches the another node.

25. The method of embodiment 24, wherein the updated location of the first mobile master node is determined using location circuitry on the first mobile master node and the updated location of the second mobile master node is determined using location circuitry on the second mobile master node.

26. The method of embodiment 24, wherein the first mobile master node is associated with a control system of the first of the autonomous transport vehicles and the second mobile master node is associated with a control system of the second of the autonomous transport vehicles;
wherein the updated location of the first mobile master node is determined based at least in part upon a determined position from a first inertial navigation unit deployed on the first of the autonomous transport vehicles; and
wherein the updated location of the second mobile master node is determined based at least in part upon a determined position from a second inertial navigation unit deployed on the second of the autonomous transport vehicles.

27. The method of embodiment 1, wherein the first of the node-enabled autonomous transport vehicles comprises a modular autonomous bot apparatus assembly having a modular mobility base propelling the modular autonomous bot apparatus assembly, a modular auxiliary power module providing power for the modular autonomous bot apparatus assembly, a modular cargo storage system configured to at least temporarily maintain the at least one item within the modular autonomous bot apparatus assembly, and a modular mobile autonomy control module as the first mobile master node that autonomously controls operation of the modular autonomous bot apparatus assembly.

28. The method of embodiment 1, wherein the second of the node-enabled autonomous transport vehicles comprises a modular autonomous bot apparatus assembly having a modular mobility base propelling the modular autonomous bot apparatus assembly, a modular auxiliary power module providing power for the modular autonomous bot apparatus assembly, a modular cargo storage system configured to at least receive and temporarily maintain the at least one item within the modular autonomous bot apparatus assembly, and a modular mobile autonomy control module as the second mobile master node that autonomously controls operation of the modular autonomous bot apparatus assembly.

29. The method of embodiment 1, wherein the step of transferring comprises:
detecting the second of the node-enabled autonomous transport vehicles by a proximity sensor on the first of the node-enabled autonomous transport vehicles, as the first of the node-enabled autonomous transport vehicles navigates towards and approaches the second of the node-enabled autonomous transport vehicles;
causing, by the first mobile master node, a transfer alignment configuration of the first of the node-enabled autonomous transport vehicle and the second of the node-enabled autonomous transport vehicles as the first mobile master node controls movement of the first of the node-enabled autonomous transport vehicles and remotely controls movement of the second of the node-enabled autonomous transport vehicles through interaction with the second mobile master node; and
initiating, by the first mobile master node, transfer of the at least one item from the first of the node-enabled autonomous transport vehicles to the second of the node-enabled autonomous transport vehicles while the first of the node-enabled autonomous transport vehicles and the second of the node-enabled autonomous transport vehicles are in the transfer alignment configuration.

30. The method of embodiment 29, wherein the step of causing the transfer alignment configuration of the first of the node-enabled autonomous transport vehicle and the second of the node-enabled autonomous transport vehicles comprises the first mobile master node aligning a first docking interface disposed on the first of the node-enabled autonomous transport vehicles with a second docking interface disposed on the second of the node-enabled autonomous transport vehicles as the first mobile master node controls movement of the first of the node-enabled autonomous transport vehicles and remotely controls movement of the second of the node-enabled autonomous transport vehicles through wireless interaction with the second mobile master node.

31. The method of embodiment 29, wherein the step of causing the transfer alignment configuration of the first of the node-enabled autonomous transport vehicle and the second of the node-enabled autonomous transport vehicles comprises:
aligning, by the first mobile master node, a first docking interface disposed on the first of the node-enabled autonomous transport vehicles with a second docking interface disposed on the second of the node-enabled autonomous transport vehicles as the first mobile master node controls movement of the first of the node-enabled autonomous transport vehicles and remotely controls movement of the second of the node-enabled autonomous transport vehicles through wireless interaction with the second mobile master node; and
securing the first docking interface to the second docking interface to create the transfer alignment orientation.

32. The method of embodiment 29, wherein the initiating step comprises:
deploying, by the first mobile master node, an object manipulation system on the first of the node-enabled autonomous transport vehicles to initiate control of the at least one item while on the first of the node-enabled autonomous transport vehicles; and
moving, by the first mobile master node, the at least one item from the first of the node-enabled autonomous transport vehicles to the second of the node-enabled autonomous transport vehicles using the object manipulation system on the first of the node-enabled autonomous transport vehicles.

33. The method of embodiment 1, wherein the step of transferring comprises:
detecting the first of the node-enabled autonomous transport vehicles by a proximity sensor on the second of the node-enabled autonomous transport vehicles, as the second of the node-enabled autonomous transport vehicles navigates towards and approaches the first of the node-enabled autonomous transport vehicles;

causing, by the second mobile master node, a transfer alignment configuration of the first of the node-enabled autonomous transport vehicle and the second of the node-enabled autonomous transport vehicles as the second mobile master node controls movement of the second of the node-enabled autonomous transport vehicles and remotely controls movement of the first of the node-enabled autonomous transport vehicles through interaction with the first mobile master node; and initiating, by the second mobile master node, transfer of the at least one item from the first of the node-enabled autonomous transport vehicles to the second of the node-enabled autonomous transport vehicles while the first of the node-enabled autonomous transport vehicles and the second of the node-enabled autonomous transport vehicles are in the transfer alignment configuration.

34. The method of embodiment 33, wherein the step of causing the transfer alignment configuration of the first of the node-enabled autonomous transport vehicle and the second of the node-enabled autonomous transport vehicles comprises the seconding mobile master node aligning a second docking interface disposed on the second of the node-enabled autonomous transport vehicles with a first docking interface disposed on the first of the node-enabled autonomous transport vehicles as the second mobile master node controls movement of the second of the node-enabled autonomous transport vehicles and remotely controls movement of the first of the node-enabled autonomous transport vehicles through wireless interaction with the first mobile master node.

35. The method of embodiment 33, wherein the step of causing the transfer alignment configuration of the first of the node-enabled autonomous transport vehicle and the second of the node-enabled autonomous transport vehicles comprises:

aligning, by the second mobile master node, a second docking interface disposed on the second of the node-enabled autonomous transport vehicles with a first docking interface disposed on the first of the node-enabled autonomous transport vehicles as the second mobile master node controls movement of the second of the node-enabled autonomous transport vehicles and remotely controls movement of the first of the node-enabled autonomous transport vehicles through wireless interaction with the first mobile master node; and securing the first docking interface to the second docking interface to create the transfer alignment orientation.

36. The method of embodiment 33, wherein the initiating step comprises:

deploying, by the second mobile master node, an object manipulation system on the first of the node-enabled autonomous transport vehicles to initiate control of the at least one item while on the first of the node-enabled autonomous transport vehicles; and moving, by the second mobile master node, the at least one item from the first of the node-enabled autonomous transport vehicles to the second of the node-enabled autonomous transport vehicles using the object manipulation system on the first of the node-enabled autonomous transport vehicles.

37. A system for navigating to a designated shipping location with an item being shipped as part of a multi-leg autonomous logistics operation for the item being shipped, comprising:

a primary node-enabled autonomous transport vehicle comprising at least a primary mobile transport vehicle base, a primary steering and propulsion system configured to control and move the primary mobile transport vehicle base in response to a first onboard control input, a primary payload storage disposed on the primary mobile transport vehicle base, the primary payload storage being configured to temporarily maintain at least one object, a first mobile master node as one of a plurality of nodes in a wireless node network, the first mobile master node being disposed on the primary mobile transport vehicle base and operative to provide the first onboard control input to the primary steering and propulsion system, a first master node memory coupled to the first mobile master node, the first master node memory for maintaining at least a first autonomous navigation program module operative to be executed by the first mobile master node, a primary wireless communication interface coupled to the first mobile master node, and a primary object manipulation system configured to manipulate contents of the payload area;

a secondary node-enabled autonomous transport vehicle comprising at least a secondary mobile transport vehicle base, a secondary steering and propulsion system configured to control and move the secondary mobile transport vehicle base in response to a second onboard control input, a secondary payload storage disposed on the secondary mobile transport vehicle base, the secondary payload storage being configured to temporarily maintain the at least one object, a second mobile master node as another of the plurality of nodes in a wireless node network, the second mobile master node being disposed on the secondary mobile transport vehicle base and operative to provide the second onboard control input to the secondary steering and propulsion system, a second master node memory coupled to the second mobile master node, the second master node memory for maintaining a second autonomous navigation program module operative to be executed by the second mobile master node, a secondary wireless communication interface coupled to the first mobile master node, and a secondary object manipulation system configured to manipulate contents of the secondary payload storage;

wherein the first mobile master node, when executing the first autonomous navigation program module, is further operative to detect a signal broadcast from the second mobile master node via the primary wireless communication interface, transmit an instruction over the primary wireless communication interface to the second mobile master node to alter a power level of the signal broadcast from the second mobile master node, identify the signal broadcast from the second mobile master node with the altered power level, determine a direction of the second mobile master node relative to the first mobile master node based upon the detected signal from the second mobile master node with the altered power level, generate a value of the first onboard control input to cause the primary node-enabled autonomous transport vehicle to navigate to the second mobile master node based upon the determined direction of the second mobile master node relative to the first mobile master node, cause the primary object manipulation system to transfer the item being shipped as payload from the primary payload storage disposed on the primary mobile transport vehicle base to the secondary payload storage disposed on the secondary mobile transport vehicle base once the primary node-enabled autonomous transport vehicle is at a waypoint location of the secondary node-enabled autonomous transport vehicle; and wherein the second mobile master node, when executing the second autonomous navigation program module, is further operative to detect a signal broadcast from another node associated with the designated shipping location for the payload, transmit an instruction over the secondary wireless communication interface to the another node to alter a power level of the signal broadcast from the another node, identify the signal broadcast from the another node with the altered power level, determine a direction of the another node relative to the second mobile master node based upon the detected signal from the another node with the altered power level, generate a value of the second onboard control input to cause the secondary node-enabled autonomous transport vehicle to navigate to the another node based upon the determined direction of the another node relative to the second mobile master node, and cause the secondary object manipulation system to transfer the item being shipped off the secondary mobile transport vehicle base to at the designated shipping location.

38. The system of embodiment 37, wherein the primary payload storage being configured to temporarily maintain a payload container that temporarily maintains the at least one object;

wherein the secondary payload storage being configured to temporarily maintain the payload container that temporarily maintains the at least one object;

wherein the first mobile master node, when executing the first autonomous navigation program module, is operative to cause the primary object manipulation system to transfer the item being shipped as the payload from the primary payload storage disposed on the primary mobile transport vehicle base to the secondary payload storage disposed on the secondary mobile transport vehicle base by being further operative to cause the primary object manipulation system to transfer the payload container with the item being shipped from the primary payload storage disposed on the primary mobile transport vehicle base to the secondary payload storage disposed on the secondary mobile transport vehicle base; and wherein the second mobile master node, when executing the second autonomous navigation program module, is operative to cause the secondary object manipulation system to transfer the item being shipped off the secondary mobile transport vehicle base to at the designated shipping location by being further operative to cause the secondary object manipulation system to transfer the payload container with the item being shipped off the secondary mobile transport vehicle base to at the designated shipping location.

39. The system of embodiment 37, wherein the second mobile master node, when executing the second autonomous navigation program module, is further operative to initiate an offload operation of the at least one object as the payload at the designated shipping location using the secondary object manipulating system on the secondary node-enabled autonomous transport vehicle.

40. The system of embodiment 39, wherein the designated shipping location is in the courier transport vehicle.

41. The system of embodiment 39, wherein the designated shipping location is at a delivery address for the at least one object.

42. The system of embodiment 38, wherein the second mobile master node, when executing the second autonomous navigation program module, is further operative to initiate an offload operation of the payload container the at least one object as the payload at the designated shipping location using the secondary object manipulating system on the secondary node-enabled autonomous transport vehicle to obtain the payload container and remove the payload container from the secondary node-enabled autonomous transport vehicle.

43. The system of embodiment 37, wherein the first mobile master node, when executing the first autonomous navigation program module, is further operative to initiate a loading operation of the at least one object as the payload at a pickup location using the primary object manipulating system on the primary node-enabled autonomous transport vehicle.

44. The system of embodiment 43, wherein the pickup location is in the courier transport vehicle.

45. The system of embodiment 43, wherein the pickup location is at a pickup address for the at least one object.

46. The system of embodiment 38, wherein the first mobile master node, when executing the first autonomous navigation program module, is further operative to initiate a loading operation of the payload container with at least one object as the payload at a pickup location using the primary object manipulating system on the primary node-enabled autonomous transport vehicle to obtain the payload container and load the payload container onto the primary node-enabled autonomous transport vehicle.

47. The method of embodiment 37, wherein the first mobile master node, when executing the first autonomous navigation program module, is operative to generate the value of the first onboard control input to cause the primary node-enabled autonomous transport vehicle to navigate to the second mobile master node by being further operative to generate the value of the first onboard control input to cause the primary node-enabled autonomous transport vehicle to navigate to a second docking interface disposed on the secondary node-enabled autonomous transport vehicle based upon the determined direction of the second mobile master node relative to the first mobile master node and engage a first docking interface disposed on the primary node-enabled autonomous transport vehicle at the waypoint location of the secondary node-enabled autonomous transport vehicle; and wherein the first mobile master node, when executing the first autonomous navigation program module, is operative to cause the primary object manipulation system to transfer the item being shipped once the first docking interface on the primary node-enabled autonomous transport vehicle is secured to the second docking interface on the secondary node-enabled autonomous transport vehicle at the waypoint location.

48. The system of embodiment 37, wherein the first mobile master node, when executing the first autonomous navigation program module, is further operative to transmit an updated location of the first mobile master node to a server over the primary wireless communication interface as the first mobile master node approaches the second mobile master node; and
wherein the second mobile master node, when executing the second autonomous navigation program module, is further operative to transmit an updated location of the second mobile master node to the server over the secondary wireless communication interface as the second mobile master node approaches the first mobile master node.

49. The system of embodiment 48, wherein the primary node-enabled autonomous transport vehicle further comprises a first location circuitry coupled to the first mobile master node;
wherein the secondary node-enabled autonomous transport vehicle further comprises a second location circuitry coupled to the second mobile master node; and
wherein the updated location of the first mobile master node is determined using first location circuitry and the updated location of the second mobile master node is determined using second location circuitry.

50. The system of embodiment 48, wherein the first location circuitry comprises a first inertial navigation unit deployed on the primary node-enabled autonomous transport vehicle;
wherein the second location circuitry comprises a second inertial navigation unit deployed on the secondary node-enabled autonomous transport vehicle;
wherein the updated location of the first mobile master node is determined based at least in part upon a determined position from the first inertial navigation unit; and
wherein the updated location of the second mobile master node is determined based at least in part upon a determined position from the second inertial navigation unit.

51. The system of embodiment 37, wherein the primary node-enabled autonomous transport vehicle comprises a modular autonomous bot apparatus assembly, wherein the modular autonomous bot apparatus assembly comprises:
a modular mobility base configured to propel the modular autonomous bot apparatus assembly, the modular mobility base comprising
the primary mobile transport vehicle base,
the primary steering and propulsion system, and
a first interface to a common modular component power and data transport bus;
a modular cargo storage system detachably connected to the modular mobility base and configured to at least temporarily maintain the at least one object, the modular cargo storage system comprising
the primary payload storage configured to temporarily maintain the at least one object, and
a second interface to the common modular component power and data transport bus; and
a modular mobile autonomy control module detachably connected to the modular cargo storage system, the modular mobile autonomy control module comprising
the first mobile master node,
the first master node memory,
the primary wireless communication interface, and
a third interface to the common modular component power and data transport bus;
wherein the common modular component power and data transport bus coupling the first mobile master node to the primary steering and propulsion system.

52. The system of embodiment 51, wherein the modular mobility base further comprises a primary modular auxiliary power module detachably connected to the primary mobile transport vehicle base, the primary modular auxiliary power module being coupled to the first interface and providing power for the modular autonomous bot apparatus assembly.

53. The system of embodiment 37, wherein the secondary node-enabled autonomous transport vehicle comprises a modular autonomous bot apparatus assembly, wherein the modular autonomous bot apparatus assembly comprises:
a modular mobility base configured to propel the modular autonomous bot apparatus assembly, the modular mobility base comprising
the secondary mobile transport vehicle base,
the secondary steering and propulsion system, and
a first interface to a common modular component power and data transport bus;
a modular cargo storage system detachably connected to the modular mobility base and configured to at least temporarily maintain the at least one object, the modular cargo storage system comprising
the secondary payload storage configured to temporarily maintain the at least one object, and
a second interface to the common modular component power and data transport bus; and
a modular mobile autonomy control module detachably connected to the modular cargo storage system, the modular mobile autonomy control module comprising
the second mobile master node,
the second master node memory,
the secondary wireless communication interface, and
a third interface to the common modular component power and data transport bus;
wherein the common modular component power and data transport bus coupling the second mobile master node to the secondary steering and propulsion system.

54. The system of embodiment 53, wherein the modular mobility base further comprises a secondary modular auxiliary power module detachably connected to the secondary mobile transport vehicle base, the secondary modular auxiliary power module being coupled to the first interface and providing power for the modular autonomous bot apparatus assembly.

55. A method for navigating to a designated shipping location as part of a multi-leg logistics operation for an item being shipped using a plurality of nodes in a wireless node network, a server in the network, and selective ones of a plurality of node-enabled autonomous transport vehicles in the network, comprising:
receiving, by a first mobile master node of the plurality of nodes, logistics information related to an item being shipped on a primary one of the node-enabled autonomous transport vehicles, wherein the first mobile master node is associated with the primary one of the node-enabled autonomous transport vehicles, wherein the primary one of the node-enabled autonomous transport vehicles being responsible for a first leg of the multi-leg logistics operation;

accessing, by the first mobile master node, the logistics information from a memory on the first mobile master node, the logistics information indicating a plurality of characteristic parameters about the item being shipped;

selecting, by the first mobile master node, a secondary one of the node-enabled autonomous transport vehicles to be deployed for a second leg of the multi-leg logistics operation based upon the logistics information about the item being shipped;

detecting, by the first mobile master node, a signal broadcast from a second mobile master node of the plurality of nodes, wherein the second mobile master node is associated with the selected secondary one of the node-enabled autonomous transport vehicles;

navigating, by the first mobile master node, to the selected secondary one of the node-enabled autonomous transport vehicles in a direction determined by the first mobile master node to be towards the second mobile master node relative to the first mobile master node based upon the detected signal broadcast from the second mobile master node;

autonomously transferring the item from the primary one of the node-enabled autonomous transport vehicles to the selected secondary one of the node-enabled autonomous transport vehicles at a waypoint location of the selected secondary one of the node-enabled autonomous transport vehicles;

detecting, by the second mobile master node, a signal broadcast from another of the plurality of nodes, the another node being associated with the designated shipping location; and navigating, by the second mobile master node, to the designated shipping location in a direction determined by the second mobile master node to be towards the another node relative to the second mobile master node based upon the detected signal broadcast from the another node.

56. The method of embodiment 55, wherein the step of autonomously transferring the item comprises transferring a payload container as payload the primary one of the node-enabled autonomous transport vehicles to the selected secondary one of the node-enabled autonomous transport vehicles at a waypoint location of the selected secondary one of the node-enabled autonomous transport vehicles, the payload container maintaining the item.

57. The method of embodiment 55 further comprising the step of initiating, by the second mobile master node, an offload operation of the item being shipped at the designated shipping location using an object manipulating system on the selected secondary one of the node-enabled autonomous transport vehicles that is operative to move the item being shipped off of the selected secondary one of the node-enabled autonomous transport vehicles.

58. The method of embodiment 57, wherein the designated shipping location is at a delivery address for the item being shipped.

59. The method of embodiment 55 further comprising the step of receiving, by the primary one of the node-enabled autonomous transport vehicles, the item being shipped.

60. The method of embodiment 59, wherein the step of receiving the item being shipped comprises receiving, by the primary one of the node-enabled transport vehicles the time being shipped into a removable payload container.

61. The method of embodiment 60 further comprising the step of initiating, by the second mobile master node, an offload operation of the removable payload container with the item being shipped at the designated shipping location using an object manipulating system on the selected secondary one of the node-enabled autonomous transport vehicles that is operative to move removable payload container with the item being shipped off of the selected secondary one of the node-enabled autonomous transport vehicles.

62. The method of embodiment 59, wherein the step of receiving the item being shipped further comprises initiating, by the first mobile master node, a load operation of the item being shipped using an object manipulating system on the primary one of the node-enabled autonomous transport vehicles that is operative to place the item being shipped onto the primary one of the node-enabled autonomous transport vehicles.

63. The method of embodiment 60, wherein the step of receiving the item being shipped further comprises initiating, by the first mobile master node, a load operation of the removable payload container with the item being shipped using an object manipulating system on the primary one of the node-enabled autonomous transport vehicles that is operative to place the removable payload container with the item being shipped onto the primary one of the node-enabled autonomous transport vehicles.

64. The method of embodiment 55, wherein the logistics information received by the first mobile master node comprises at least shipping information on where the item is being shipped and context information about the item being shipped.

65. The method of embodiment 64, wherein the context information comprises weight and size information on the item being shipped.

66. The method of embodiment 64, wherein the context information comprises environmental condition requirement information on the item being shipped.

67. The method of embodiment 64, wherein the context information comprises manipulation requirement information on the item being shipped.

68. The method of embodiment 64, wherein the context information comprises delivery address automation information related to the item being shipped.

69. The method of embodiment 64, wherein the context information comprises regulatory/compliance information.

70. The method of embodiment 55, wherein the step of navigating to the selected secondary one of the node-enabled autonomous transport vehicles comprises:

instructing, by the first mobile master node, the second mobile master node to alter a power level of the signal broadcast from the second mobile master node;

identifying, by the first mobile master node, the signal broadcast from the second mobile master node with the altered power level;

determining, by the first mobile master node, the direction towards the second mobile master node relative to the first mobile master node based upon the detected signal from the second mobile master node with the altered power level; and navigating, by the first mobile master node, to the selected secondary one of the node-enabled autonomous transport vehicles in the determined direction towards the second mobile master node relative to the first mobile master node.

71. The method of embodiment 55, wherein the step of navigating to the designated shipping location comprises:

instructing, by the second mobile master node, the another node to alter a power level of the signal broadcast from the another node;

identifying, by the second mobile master node, the signal broadcast from the another node with the altered power level;

determining, by the second mobile master node, the direction towards the another node relative to the second mobile master node based upon the detected signal from the another node with the altered power level; and navigating, by the second mobile master node, to the designated shipping location in the determined direction towards the another node relative to the second mobile master node.

72. The method of embodiment 55, wherein the step of autonomously transferring comprises:

detecting the selected secondary one of the node-enabled autonomous transport vehicles by a proximity sensor on the primary one of the node-enabled autonomous transport vehicles, as the primary one of the node-enabled autonomous transport vehicles navigates towards and approaches the selected secondary one of the node-enabled autonomous transport vehicles;

causing, by the first mobile master node, a transfer alignment configuration of the primary one of the node-enabled autonomous transport vehicles and the selected secondary one of the node-enabled autonomous transport vehicles as the first mobile master node controls movement of the primary one of the node-enabled autonomous transport vehicles; and initiating, by the first mobile master node, transfer of the item being shipped from the primary one of the node-enabled autonomous transport vehicles to the selected secondary one of the node-enabled autonomous transport vehicles while the primary one of the node-enabled autonomous transport vehicle and the selected secondary one of the node-enabled autonomous transport vehicles are in the transfer alignment configuration.

73. The method of embodiment 72, wherein the step of causing the transfer alignment configuration of the primary one of the node-enabled autonomous transport vehicle and the selected secondary one of the node-enabled autonomous transport vehicles comprises the first mobile master node aligning a first docking interface disposed on the primary one of the node-enabled autonomous transport vehicles with a second docking interface disposed on the selected secondary one of the node-enabled autonomous transport vehicles as the first mobile master node controls movement of the primary one of the node-enabled autonomous transport vehicles.

74. The method of embodiment 72, wherein the initiating step comprises:

deploying, by the first mobile master node, an object manipulation system on the primary one of the node-enabled autonomous transport vehicles to initiate control of the item being shipped while on the primary one of the node-enabled autonomous transport vehicles; and moving, by the first mobile master node, the item being shipped from the primary one of the node-enabled autonomous transport vehicles to the selected secondary one of the node-enabled autonomous transport vehicles using the object manipulation system on the primary one of the node-enabled autonomous transport vehicles.

75. The method of embodiment 55, wherein the step of transferring comprises:

detecting the primary one of the node-enabled autonomous transport vehicles by a proximity sensor on the selected secondary one of the node-enabled autonomous transport vehicles, as the primary one of the node-enabled autonomous transport vehicles navigates towards and approaches the selected secondary one of the node-enabled autonomous transport vehicles;

causing, by the second mobile master node, a transfer alignment configuration of the primary one of the node-enabled autonomous transport vehicle and the selected secondary one of the node-enabled autonomous transport vehicles as the second mobile master node controls movement of the selected secondary one of the node-enabled autonomous transport vehicles relative to the primary one of the node-enabled autonomous transport vehicles; and initiating, by the second mobile master node, transfer of the item being shipped from the primary one of the node-enabled autonomous transport vehicles to the selected secondary one of the node-enabled autonomous transport vehicles while the primary one of the node-enabled autonomous transport vehicle and the selected secondary one of the node-enabled autonomous transport vehicles are in the transfer alignment configuration.

76. The method of embodiment 75, wherein the step of causing the transfer alignment configuration of the primary one of the node-enabled autonomous transport vehicle and the selected secondary one of the node-enabled autonomous transport vehicles comprises the first mobile master node aligning a first docking interface disposed on the primary one of the node-enabled autonomous transport vehicles with a second docking interface disposed on the selected secondary one of the node-enabled autonomous transport vehicles as the first mobile master node controls movement of the primary one of the node-enabled autonomous transport vehicles.

77. The method of embodiment 75, wherein the initiating step comprises:

deploying, by the second mobile master node, an object manipulation system on the selected secondary one of the node-enabled autonomous transport vehicles to initiate control of the item being shipped while on the primary one of the node-enabled autonomous transport vehicles; and moving, by the second mobile master node, the item being shipped from the primary one of the node-enabled autonomous transport vehicles to the selected secondary one of the node-enabled autonomous transport vehicles using the object manipulation system on the selected secondary one of the node-enabled autonomous transport vehicles.

78. The method of embodiment 55, wherein the step of transferring comprises:

navigating, by the first mobile master node, the primary one of the node-enabled autonomous transport vehicles to the waypoint location of the selected secondary one of the node-enabled autonomous transport vehicles;

detecting the selected secondary one of the node-enabled autonomous transport vehicles by a proximity sensor on the primary one of the node-enabled autonomous transport vehicles, as the primary one of the node-enabled autonomous transport vehicles navigates towards and approaches the selected secondary one of the node-enabled autonomous transport vehicles;

detecting the primary one of the node-enabled autonomous transport vehicles by a proximity sensor on the selected secondary one of the node-enabled autonomous transport vehicles, as the primary one of the node-enabled autonomous transport vehicles navigates towards and approaches the selected secondary one of the node-enabled autonomous transport vehicles;

controlling, by the first mobile master node, a position of the primary one of the node-enabled autonomous transport vehicles by moving the primary one of the node-enabled autonomous transport vehicles into a first transfer position;

controlling, by the second mobile master node, a position of the selected secondary one of the node-enabled autonomous transport vehicles by moving the selected secondary one of the node-enabled autonomous transport vehicles into a second transfer position;

refining the relative alignment of the first transfer position and the second transfer position to cause the primary one of the node-enabled autonomous transport vehicles and the selected secondary one of the node-enabled autonomous transport vehicles to be in a transfer alignment orientation; and moving the item being shipped from the primary one of the node-enabled autonomous transport vehicles to the selected secondary one of the node-enabled autonomous transport vehicles using a first object manipulation system on the primary one of the node-enabled autonomous transport vehicles and a second object manipulation system on the selected secondary one of the node-enabled autonomous transport vehicles.

79. The method of embodiment 78, wherein the step of refining the relative alignment of the first transfer position and the second transfer position to cause the primary one of the node-enabled autonomous transport vehicles and the selected secondary one of the node-enabled autonomous transport vehicles to be in the transfer alignment orientation comprises causing the first mobile master node to align a first docking interface disposed on the primary one of the node-enabled autonomous transport vehicles to a second docking interface disposed on the selected secondary one of the node-enabled autonomous transport vehicles.

80. The method of embodiment 78, wherein the step of refining the relative alignment of the first transfer position and the second transfer position to cause the primary one of the node-enabled autonomous transport vehicles and the selected secondary one of the node-enabled autonomous transport vehicles to be in the transfer alignment orientation comprises causing the second mobile master node to align a second docking interface disposed on the selected secondary one of the node-enabled autonomous transport vehicles to a first docking interface disposed on the primary one of the node-enabled autonomous transport vehicles.

81. The method of embodiment 78, wherein the step of controlling the position of the primary one of the node-enabled autonomous transport vehicles by moving the primary one of the node-enabled autonomous transport vehicles into the first transfer position comprises controlling, by the first mobile master node, the position of the primary one of the node-enabled autonomous transport vehicles by moving a first docking interface disposed on the primary one of the node-enabled autonomous transport vehicles proximate a second docking interface disposed on the selected secondary one of the node-enabled autonomous transport vehicles as the first transfer position; and wherein the step of controlling the position of the selected secondary one of the node-enabled autonomous transport vehicles by moving the selected secondary one of the node-enabled autonomous transport vehicles into the second transfer position comprises controlling, by the second mobile master node, the position of the selected secondary one of the node-enabled autonomous transport vehicles by moving the second docking interface proximate the first docking interface as the second transfer position.

82. The method of embodiment 78, wherein the step of refining the relative alignment of the first transfer position and the second transfer position to cause the primary one of the node-enabled autonomous transport vehicles and the selected secondary one of the node-enabled autonomous transport vehicles to be in the transfer alignment orientation comprises securing a first docking interface disposed on the primary one of the node-enabled autonomous transport vehicles to a second docking interface disposed on the selected secondary one of the node-enabled autonomous transport vehicles to create the transfer alignment orientation.

83. The method of embodiment 55, wherein the step of navigating to the selected secondary one of the node-enabled autonomous transport vehicles further comprises navigating, by the first mobile master node, to the second mobile master node as the power level of the signal broadcast from the second mobile master node is incrementally decreased over time and as the first mobile master node approaches the second mobile master node; and wherein the step of navigating to the designated shipping location further comprises navigating, by the second mobile master node, to the another node as the power level of the signal broadcast from the another node is incrementally decreased over time and as the second mobile master node approaches the another node.

84. The method of embodiment 55, wherein the first mobile master node is associated with a control system of the primary one of the autonomous transport vehicles and the second mobile master node is associated with a control system of the selected secondary one of the autonomous transport vehicles;

wherein the step of navigating by the first mobile master node further comprises providing, by the first mobile master node, the direction determined by the first mobile master node to be towards the second mobile master node relative to the first mobile master node to an input of the control system of the primary one of the autonomous transport vehicles; and wherein the step of navigating by the second mobile master node further comprises providing, by the second mobile master node, the direction determined by the second mobile master node to be towards the another node relative to the second mobile master node to an input of the control system of the selected secondary one of the autonomous transport vehicles.

85. The method of embodiment 84 further comprising the steps of:

causing, by the first mobile master node, the primary one of the autonomous transport vehicles to stop moving when a current location of the first mobile master node is within a predetermined range of the second mobile master node; and causing, by the second mobile master node, the selected secondary one of the autonomous transport vehicles to stop moving when a current location of the second mobile master node is within a predetermined range of the another node.

86. The method of embodiment 55, wherein the primary one of the node-enabled autonomous transport vehicles comprises a modular autonomous bot apparatus assembly having a modular mobility base propelling the modular autonomous bot apparatus assembly, a modular auxiliary power module providing power for the modular autonomous bot apparatus assembly, a modular cargo storage system configured to at least temporarily maintain the at least one item within the modular autonomous bot apparatus assembly, and a modular mobile autonomy control module as the first mobile master node that autonomously controls operation of the modular autonomous bot apparatus assembly.

87. The method of embodiment 55, wherein the selected secondary one of the node-enabled autonomous transport vehicles comprises a modular autonomous bot apparatus assembly having a modular mobility base propelling the modular autonomous bot apparatus assembly, a modular auxiliary power module providing power for the modular autonomous bot apparatus assembly, a modular cargo storage system configured to at least receive and temporarily maintain the at least one item within the modular autonomous bot apparatus assembly, and a modular mobile autonomy control module as the second mobile master node that autonomously controls operation of the modular autonomous bot apparatus assembly.

88. The method of embodiment 87, wherein the step of selecting the secondary one of the node-enabled autonomous transport vehicles to be deployed for the second leg of the multi-leg logistics operation is based upon compatibility of at least the modular cargo storage system and the item being shipped according to the logistics information.

89. The method of embodiment 87, wherein the step of selecting the secondary one of the node-enabled autonomous transport vehicles to be deployed for the second leg of the multi-leg logistics operation is based upon compatibility of at least the modular mobility base and the logistics information.

90. The method of embodiment 87, wherein the step of selecting the secondary one of the node-enabled autonomous transport vehicles to be deployed for the second leg of the multi-leg logistics operation is based upon compatibility of at least the modular auxiliary power module and the logistics information.

91. The method of embodiment 87, wherein the step of selecting the secondary one of the node-enabled autonomous transport vehicles to be deployed for the second leg of the multi-leg logistics operation is based upon compatibility of at least the modular mobile autonomy control module and the logistics information.

92. The method of embodiment 87, wherein the step of selecting the secondary one of the node-enabled autonomous transport vehicles to be deployed for the second leg of the multi-leg logistics operation is based upon compatibility of the logistics information as compared with the combination of the modular mobility base, the modular auxiliary power module, the modular cargo storage system, and the modular mobile autonomy control module as configured in the modular autonomous bot apparatus assembly.

93. A method for navigating to a designated shipping location as part of a multi-leg logistics operation using a plurality of nodes in a wireless node network, a server in the network, and a plurality of node-enabled autonomous transport vehicles in the network, comprising:
  detecting, by a first mobile master node of the plurality of nodes, a signal broadcast from a second mobile master node of the plurality of nodes, wherein the first mobile master node is associated with and disposed on a first of the node-enabled autonomous transport vehicles and the second mobile master node is associated with and disposed on a second of the node-enabled autonomous transport vehicles;
  instructing, by the first mobile master node, the second mobile master node to alter a power level of the signal broadcast from the second mobile master node;
  identifying, by the first mobile master node, the signal broadcast from the second mobile master node with the altered power level;
  determining, by the first mobile master node, a direction of the second mobile master node relative to the first mobile master node based upon the detected signal from the second mobile master node with the altered power level;
  navigating, by the first mobile master node, to the second mobile master node associated with the second of the node-enabled autonomous transport vehicles based upon the determined direction of the second mobile master node relative to the first mobile master node;
  causing, by the first mobile master node, a first docking interface on the first of the node-enabled autonomous transport vehicles to securely engage a second docking interface on the second of the node-enabled autonomous transport vehicles at a waypoint location of the second of the node-enable autonomous transport vehicles as the first mobile master node controls movement of the first of the node-enabled autonomous transport vehicles and remotely controls movement of the second of the node-enabled autonomous transport vehicles through interaction with the second mobile master node;
  initiating, by the first mobile master node, transfer of the at least one item from the first of the node-enabled autonomous transport vehicles to the second of the node-enabled autonomous transport vehicles while the first of the node-enabled autonomous transport vehicles and the second of the node-enabled autonomous transport vehicles are securely engaged; and
  causing, by the first mobile master node, the first docking interface to disengage from the second docking interface after the at least one item is no longer present on the first of the node-enabled autonomous transport vehicles based upon monitoring by one or more payload monitoring sensors on the first of the node-enabled autonomous transport vehicles.

94. The method of embodiment 93, wherein the first docking interface and the second docking interface comprise at least one mated set of latches that has at least one from the mated set of latches being disposed on the first of the node-enabled autonomous transport vehicles and a matching other from the mated set of latches being disposed on the second of the node-enabled autonomous transport vehicles.

95. The method of embodiment 94, wherein the at least one from the mated set of latches on the first of the node-enabled autonomous transport vehicles comprises an actuated set of latches activated by the first mobile master node to securely engage the first docking interface to the second docking interface.

96. The method of embodiment 94, wherein the matching other from the mated set of latches on the second of the node-enabled autonomous transport vehicles comprises an actuated set of latches activated by the second mobile master node to securely engage the first docking interface to the second docking interface.

In summary, it should be emphasized that the sequence of operations to perform any of the methods and variations of the methods described in the embodiments herein are merely exemplary, and that a variety of sequences of operations may be followed while still being true and in accordance with the principles of the present invention as understood by one skilled in the art.

At least some portions of exemplary embodiments outlined above may be used in association with portions of other exemplary embodiments to better pickup, transport, and deliver items/objects being moved, delivered, transported, or otherwise shipped using an autonomous transport vehicle, such as modular autonomous logistics vehicle transport (e.g., an exemplary MALVT bot apparatus assembly 1700 and its variations described herein). Moreover, at least some of the exemplary embodiments disclosed herein may be used independently from one another and/or in combination with one another and may have applications to devices, components, assemblies, systems, and methods not disclosed herein.

Further, those skilled in the art will appreciate that embodiments may provide one or more advantages, and not all embodiments described above necessarily provide all or more than one particular advantage as set forth here. Additionally, it will be apparent to those skilled in the art that various modifications and variations can be made to the structures and methodologies described herein. Thus, it should be understood that the invention is not limited to the subject matter discussed in the description. Rather, the present invention, as recited in the embodiments below, is intended to cover modifications and variations.

What is claimed is:

1. A method of performing a dispatched consumer-to-store return logistics operation related to an item being replaced and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system operative to at least temporarily maintain the item being replaced within the modular autonomous bot apparatus assembly, and a modular mobile autonomy control module that autonomously controls operation of the modular autonomous bot apparatus assembly during the dispatched consumer-to-store return logistics operation, the method comprising the steps of:

receiving, by the modular mobile autonomy control module, a return operation dispatch command from the dispatch server, the return operation dispatch command comprising at least
identifier information on the item being replaced,
transport parameters on the item being replaced,
designated pickup information related to pickup of the item being replaced, and
pickup authentication information related to an authorized supplier of the item being replaced;

verifying, by the modular mobile autonomy control module, that each of the modular mobile autonomy control module, the modular mobility base, the modular auxiliary power module, and the modular cargo storage system are compatible with the dispatched consumer-to-store return logistics operation based upon the dispatch command;

autonomously causing, by the modular mobile autonomy control module, the modular mobility base to move from an origin location on a route to a designated pickup location identified by the designated pickup information;

notifying, by the modular mobile autonomy control module, the authorized supplier of the item being replaced of an approaching pickup for the item being replaced once the modular autonomous bot apparatus assembly is within a threshold notification range of the designated pickup location identified by the designated pickup information;

receiving supplier authentication input by the modular mobile autonomy control module from a return entity disposed external to the modular autonomous bot apparatus assembly at the designated pickup location;

providing, by the modular cargo storage system, selective access to a payload area within the modular cargo storage system only when the supplier authentication input received correlates to the pickup authentication information indicating that the return entity providing the supplier authentication input is the authorized supplier of the item being replaced;

monitoring, by the modular mobile autonomy control module, loading of the item being replaced into the payload area of the modular cargo storage system using one or more sensors on at least one of the modular mobile autonomy control module and the modular cargo storage system;

receiving, by the modular cargo storage system, the item being replaced in the payload area within the modular cargo storage system;

receiving, by the modular cargo storage system, return documentation provided by the authorized supplier of the item being return, the return documentation indicating the item being replaced is authorized to be returned in accordance with a return transaction order received by the dispatch server; and autonomously causing, by the modular mobile autonomy control module, the modular mobility base to move from the designated pickup location on a return route to the origin location after the item being replaced is detected to be within the modular cargo storage system based upon monitoring the loading of the item being replaced and the return documentation is loaded within the modular cargo storage system with the item being replaced.

2. The method of claim 1, wherein the notifying step comprises generating a display alert for the authorized supplier of the item being replaced on a display on the modular mobile autonomy control module once the modular autonomous bot apparatus assembly is within the threshold notification range of the designated pickup location identified by the designated pickup information.

3. The method of claim 1, wherein the notifying step comprises generating an audio notification for the authorized supplier of the item being replaced on a speaker on the modular mobile autonomy control module once the modular autonomous bot apparatus assembly is within the threshold notification range of the pickup location identified by the designated pickup information.

4. The method of claim 1, wherein the notifying step comprises transmitting a pickup notification message to an external wireless node once the modular autonomous bot apparatus assembly is within the threshold notification range of the pickup location identified by the designated pickup information, the external wireless node being related to the authorized supplier of the item being replaced according to the designated pickup information.

5. The method of claim 1, wherein the notifying step comprises transmitting a pickup notification message to an external wireless node after the modular autonomous bot apparatus assembly moves from the origin location, the external wireless node being related to the authorized supplier of the item being replaced according to the designated pickup information.

6. The method of claim 5, wherein the pickup notification message comprises one from a group consisting of a text message, an electronic mail message, and a phone call.

7. The method of claim 5, wherein the notifying step further comprises transmitting an arrival estimate to the external wireless node, the arrival estimate indicating an estimated time to arrive at the pickup location.

8. The method of claim 1, wherein the notifying step further comprising the steps of:
transmitting, by the modular mobile autonomy control module, a verification request to confirm pickup of the item being replaced to the authorized supplier of the item being replaced, the verification request asking for a responsive confirmation that the item being replaced should be picked up by the modular autonomous bot apparatus assembly at the designated pickup location; and
autonomously causing, by the modular mobile autonomy control module, the modular mobility base to continue moving to the designated pickup location to complete the dispatched consumer-to-store return logistics operation unless the responsive confirmation from the authorized supplier indicated that the item being replaced should not be picked up at that designated pickup location.

9. The method of claim 1, wherein the step of receiving the return operation dispatch command from the dispatch server comprises receiving, by the modular mobile autonomy control module, a return order assignment message as the return operation dispatch command from a retail system that received the return transaction order for the item being replaced, wherein the retail system operating as the dispatch server.

10. The method of claim 9, wherein the designated pickup information related to the pickup of the item being replaced includes a pickup time and pickup date as selected in the return transaction order.

11. The method of claim 1, wherein the step of monitoring loading of the item being replaced comprises generating a log entry in a custodial inventory data structure when the item being replaced is detected to be within the modular cargo storage system, the log entry reflecting receipt of the item being replaced within the modular cargo storage system.

12. The method of claim 1, wherein the step of monitoring loading of the item being replaced comprises:
capturing sensor data from the one or more sensors on at least one of the modular mobile autonomy control module and the modular cargo storage system; and
detecting when the item being replaced is received within the modular cargo storage system based upon the captured sensor data.

13. The method of claim 12, wherein the captured sensor data comprises visual images of what is disposed within the modular cargo storage system.

14. The method of claim 1, wherein the step of monitoring loading of the item being replaced comprises:
generating barcode scan data related to item being replaced as the item being replaced is received within the modular cargo storage system using a barcode scanner as one of the one or more sensors; and
processing the generated barcode scan data to monitor the ordered item as the ordered item is placed within the modular cargo storage system.

15. The method of claim 1, wherein the step of monitoring loading of the item being replaced comprises:
generating image data related to item being replaced as the item being replaced is received within the modular cargo storage system using a camera as one of the one or more sensors;
processing the generated image data to monitor the ordered item as the ordered item is placed within the modular cargo storage system.

16. The method of claim 1, wherein the step of monitoring loading of the item being replaced comprises:
generating video data related to item being replaced as the item being replaced is received within the modular cargo storage system using a video camera as one of the one or more sensors; and
processing the generated video data to monitor the ordered item as the ordered item is placed within the modular cargo storage system.

17. The method of claim 1, wherein the step of monitoring loading of the item being replaced comprises:
capturing audio data using a microphone as one of the one or more sensors disposed to record sound within and proximate to the modular cargo storage system as the item being replaced is received within the modular cargo storage system; and
processing the captured audio data to monitor the ordered item as the ordered item is placed within the modular cargo storage system.

18. The method of claim 1, wherein the step of monitoring loading of the item being replaced comprises detecting movement of a wireless node associated with the item being replaced as the item being replaced is received within the modular cargo storage system based upon a plurality of signals broadcast from the wireless node associated with the item being replaced.

19. The method of claim 1, wherein the step of monitoring loading of the item being replaced comprises detecting a change in location of a wireless node associated with the item being replaced from outside the modular cargo storage system to inside the modular cargo storage system as the item being replaced is received within the modular cargo storage system as determined by the modular mobile autonomous control module.

20. The method of claim 1, further comprising the step of notifying, by the modular mobile autonomy control module, a retail entity at the origin location of an approaching delivery for the item being replaced once the modular autonomous bot apparatus assembly is within a threshold notification range of the origin location.

21. The method of claim 1, further comprising the step of notifying, by the modular mobile autonomy control module, a retail entity at the origin location about delivery of the item being replaced after the modular autonomous bot apparatus assembly arrives at the origin location.

22. The method of claim 1, further comprising the step of notifying, by the modular mobile autonomy control module, the authorized supplier about delivery of the item being replaced after the modular autonomous bot apparatus assembly arrives at the origin location.

23. The method of claim 1, wherein the step of autonomously causing the modular mobility base to move from the origin location to the designated pickup location comprises autonomously causing, by the modular mobile autonomy control module, the modular mobility base to move from the origin location to the designated pickup location while interacting with a wireless building facility node to actuate a pathway obstacle disposed in a path on the route to the designated pickup location.

24. The method of claim 23, wherein the pathway obstacle comprises an actuated door controlled by the wireless building facility node.

25. The method of claim 23, wherein the pathway obstacle comprises an actuated elevator controlled by the wireless building facility node.

26. The method of claim 23, wherein the pathway obstacle comprises an actuated lock controlled by the wireless building facility node.

27. The method of claim 23, wherein interacting with the wireless building facility node to actuate the pathway obstacle comprises:
    establishing an authorized association pairing between the modular mobile autonomy control module and the wireless building facility node based upon the authentication information related to the dispatched logistics operation; and
    causing the wireless building facility node to actuate the pathway obstacle after establishing the authorized association pairing between the modular mobile autonomy control module and the wireless building facility node.

28. The method of claim 1, wherein the step of autonomously causing the modular mobility base to move from the origin location to the designated pickup location comprises autonomously causing, by the modular mobile autonomy control module, the modular mobility base to move from the origin location to the designated pickup location while engaging a pathway obstacle disposed in a path on the route to the designated pickup location using an articulating arm disposed on the modular autonomous bot apparatus assembly and using a plurality of sensors disposed on at least one of the modular mobility base and the modular mobile autonomy control module.

29. The method of claim 28, wherein the pathway obstacle comprises a manually actuated door.

30. The method of claim 28, wherein the pathway obstacle comprises a manually actuated elevator.

31. The method of claim 28, wherein the pathway obstacle comprises a manually actuated lock.

32. The method of claim 28, wherein engaging the pathway obstacle using the articulating arm and sensors comprises:
    guiding, by the modular mobile autonomy control module, the articulating arm to a control element of the pathway obstacle using one or more of the sensors disposed on at least one of the modular mobility base and the modular mobile autonomy control module; and
    actuating the pathway obstacle, by the modular mobile autonomy control module, once the articulating arm engages the control element of the pathway obstacle.

33. The method of claim 32, wherein the control element of the pathway obstacle comprises one from the group consisting of a handle for the pathway obstacle, a button for the pathway obstacle, a switch for the pathway obstacle, and a portion of a control panel for the pathway obstacle.

34. The method of claim 1, wherein the providing step comprises actuating, by the modular mobile autonomy control module, an actuated cargo door disposed on the modular auxiliary power module to an open position, where the actuated cargo door provides a seal to a payload area within the modular cargo storage system when the actuated cargo door is in a closed position and the actuated cargo door provides access to the payload area within the modular cargo storage system when the actuated cargo door is in the open position.

35. The method of claim 34, wherein actuating, by the modular mobile autonomy control module, the actuated cargo door comprises actuating an actuated joint on the actuated cargo door to cause the actuated cargo door to move from the closed position to the open position.

36. The method of claim 34, wherein actuating, by the modular mobile autonomy control module, the actuated cargo door further comprises actuating an electro-mechanical lock on the actuated cargo door to cause the actuated cargo door to unlock before moving from the closed position to the open position.

37. The method of claim 1, wherein the providing step comprises actuating, by the modular mobile autonomy control module, an actuated sliding arm disposed on the modular cargo storage system to move the item being replaced into the payload area within the modular cargo storage system.

38. The method of claim 1, wherein the providing step comprises actuating, by the modular mobile autonomy control module, an actuated grabbing arm disposed on the modular cargo storage system to grab and move the item being replaced into the payload area within the modular cargo storage system as part of receiving the item being replaced.

39. The method of claim 1, wherein the providing step comprises actuating, by the modular mobile autonomy control module, an actuated belt surface disposed on the modular auxiliary power module as a movable support surface exposed within a payload area inside the modular cargo storage system, the actuated belt surface being operative when actuated to cause the item being replaced on the actuated belt surface to move within the payload area as part of receiving the item being replaced.

40. The method of claim 1, wherein the supplier authentication input received by the modular mobile autonomy control module is provided by the return entity through a user input panel disposed on the modular autonomous bot apparatus coupled to the modular mobile autonomy control module.

41. The method of claim 1, wherein the supplier authentication input received by the modular mobile autonomy control module comprises an access code provided by the return entity through the user input panel disposed on the modular cargo storage system and operatively coupled to the modular mobile autonomy control module.

42. The method of claim 1, wherein the supplier authentication input received by the modular mobile autonomy control module comprises a biometric input provided by the return entity through the user input panel disposed on the modular cargo storage system and operatively coupled to the modular mobile autonomy control module.

43. The method of claim 1, wherein the supplier authentication input received by the modular mobile autonomy control module is provided by the return entity through an external wireless node disposed external to the modular autonomous bot apparatus assembly.

44. The method of claim 43, wherein the supplier authentication input received by the modular mobile autonomy control module comprises an access code provided by the return entity through the external wireless node disposed external to the modular autonomous bot apparatus assembly.

45. The method of claim 43, wherein the supplier authentication input received by the modular mobile autonomy control module comprises a biometric input provided by the return entity through the external wireless node disposed external to the modular autonomous bot apparatus assembly.

46. The method of claim 1, wherein the pickup authentication information related to the dispatched consumer-to-store return logistics operation includes an identifier of the authorized supplier for the item being replaced as part of the dispatched consumer-to-store return logistics operation; and
wherein the step of receiving the supplier authentication input comprises:
detecting, by the modular mobile autonomy control module, an advertising signal as the supplier authentication input from an external wireless node within a predetermined range of the modular autonomous bot apparatus assembly once the modular autonomous bot apparatus assembly has arrived at the designated pickup location identified by the designated pickup information; and
authenticating, by the modular mobile autonomy control module, that the external wireless node is associated with the authorized supplier for the item being replaced within the modular cargo storage system based upon the identifier of the authorized supplier and identifier information within the detected advertising signal broadcast from the external wireless node.

47. The method of claim 1, wherein the pickup authentication information related to the dispatched consumer-to-store return logistics operation includes an identifier of the authorized supplier for the item being replaced as part of the dispatched consumer-to-store return logistics operation; and
wherein the step of receiving the supplier authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the designated pickup location identified by the designated pickup information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched consumer-to-store return logistics operation.

48. A method of performing a dispatched swap logistics operation related to an item being replaced being swapped for a replacement item and using a modular autonomous bot apparatus assembly and a dispatch server, the modular autonomous bot apparatus assembly having at least a modular mobility base propelling the modular autonomous bot apparatus assembly, a modular auxiliary power module providing power for the modular autonomous bot apparatus assembly, a modular cargo storage system configured to at least maintain the item being replaced within the modular autonomous bot apparatus assembly, and a modular mobile autonomy control module that autonomously controls operation of the modular autonomous bot apparatus assembly during the dispatched swap logistics operation, the method comprising the steps of:

receiving, by the modular mobile autonomy control module, a swap operation dispatch command from the dispatch server, the swap operation dispatch command comprising at least
identifier information on the item being replaced and identifier information on the replacement item,
transport parameters on the item being replaced and the replacement item,
designated pickup information related to swapping the item being replaced for the replacement item, and
pickup authentication information related to an authorized delivery recipient of replacement item;
verifying, by the modular mobile autonomy control module, that each of the modular mobile autonomy control module, the modular mobility base, the modular auxiliary power module, and the modular cargo storage system are compatible with the dispatched swap logistics operation based upon the swap operation dispatch command;
receiving, by the modular cargo storage system, the replacement item in a payload area within the modular cargo storage system;
autonomously causing, by the modular mobile autonomy control module, the modular mobility base to move from an origin location on a route to a designated swap location identified by the designated pickup information;
notifying, by the modular mobile autonomy control module, the authorized delivery recipient of the replacement item of an approaching pickup for the item being replaced and delivery of the replacement item once the modular autonomous bot apparatus assembly is within a threshold notification range of the designated swap location identified by the designated pickup information;
receiving delivery recipient authentication input by the modular mobile autonomy control module from a delivery recipient disposed external to the modular autonomous bot apparatus assembly at the designated swap location;
providing, by the modular cargo storage system, selective access to the payload area within the modular cargo storage system only when the delivery recipient authentication input received correlates to the pickup authentication information indicating that the delivery recipient providing the delivery recipient authentication input is the authorized delivery recipient of the replacement item;
monitoring, by the modular mobile autonomy control module, an exchange of the replacement item from the payload area of the modular cargo storage system with the item being replaced using one or more sensors on at least one of the modular mobile autonomy control module and the modular cargo storage system; and
autonomously causing, by the modular mobile autonomy control module, the modular mobility base to move from the designated swap location on a return route to the origin location after the item being replaced is detected to be within the modular cargo storage system based upon the monitored loading of the item being replaced.

49. The method of claim 48, wherein the item being replaced and the replacement items are consumable items.

50. The method of claim 48, wherein the notifying step comprises generating a display alert for the authorized delivery recipient of the replacement item on a display on the modular mobile autonomy control module once the modular autonomous bot apparatus assembly is within the threshold notification range of the designated swap location identified by the designated pickup information.

51. The method of claim 48, wherein the notifying step comprises generating an audio notification for the authorized delivery recipient of the replacement item on a speaker on the modular mobile autonomy control module once the modular autonomous bot apparatus assembly is within the threshold notification range of the designated swap location identified by the designated pickup information.

52. The method of claim 48, wherein the notifying step comprises transmitting a delivery notification message to an external wireless node once the modular autonomous bot apparatus assembly is within the threshold notification range of the designated swap location identified by the designated pickup information, the external wireless node being related to the authorized delivery recipient of the replacement item according to the designated pickup information.

53. The method of claim 48, wherein the notifying step comprises transmitting a delivery notification message to an external wireless node after the modular autonomous bot apparatus assembly moves from the origin location, the external wireless node being related to the authorized delivery recipient of the replacement item according to the designated pickup information.

54. The method of claim 53, wherein the delivery notification message comprises one from a group consisting of a text message, an electronic mail message, and a phone call.

55. The method of claim 53, wherein the notifying step further comprises transmitting an arrival estimate to the external wireless node, the arrival estimate indicating an estimated time to arrive at the designated swap location.

56. The method of claim 48, wherein the notifying step further comprising the steps of:
transmitting, by the modular mobile autonomy control module, a verification request to confirm pickup of the item being replaced to the authorized delivery recipient of the replacement item, the verification request asking for a responsive confirmation that the item being replaced should be picked up by the modular autonomous bot apparatus assembly at the designated swap location; and
autonomously causing, by the modular mobile autonomy control module, the modular mobility base to continue moving to the designated swap location to complete the dispatched swap logistics operation unless the responsive confirmation from the authorized delivery recipient indicates that the item being replaced should not be picked up at the designated swap location.

57. The method of claim 48, wherein the notifying step further comprising the steps of:
transmitting, by the modular mobile autonomy control module, a verification request to confirm pickup of the item being replaced to the authorized delivery recipient of the replacement item, the verification request asking for a responsive confirmation that the item being replaced should be picked up by the modular autonomous bot apparatus assembly at the designated swap location; and
autonomously causing, by the modular mobile autonomy control module, the modular mobility base to continue moving to the designated swap location to complete the dispatched swap logistics operation unless the responsive confirmation from the authorized delivery recipient indicates that the replacement item should not be delivered at the designated swap location.

58. The method of claim 48, wherein the step of receiving the swap operation dispatch command from the dispatch server comprises receiving, by the modular mobile autonomy control module, a replacement order message as the swap operation dispatch command from a retail system that received a swap transaction order for the replacement item, wherein the retail system operating as the dispatch server.

59. The method of claim 58, wherein designated pickup information related to swapping the item being replaced for the replacement item includes a delivery time and delivery date as selected in the swap transaction order.

60. The method of claim 48, wherein the step of monitoring the exchange of the replacement item from the payload area of the modular cargo storage system with the item being replaced comprises the steps of:
monitoring, by the modular mobile autonomy control module, unloading of the replacement item from the payload area of the modular cargo storage system using the one or more sensors on at least one of the modular mobile autonomy control module and the modular cargo storage system; and
monitoring, by the modular mobile autonomy control module, loading of the item being replaced into the modular cargo storage system using the one or more sensors as the item being replaced is received into the payload area of the modular cargo storage system.

61. The method of claim 48, wherein the step of monitoring the exchange of the replacement item from the payload area of the modular cargo storage system with the item being replaced comprises generating a log entry in a custodial inventory data structure when the replacement item is detected to be removed from the modular cargo storage system and the item being replaced is detected to be within the modular cargo storage system, the log entry reflecting the exchange of the replacement item for the item being replacement.

62. The method of claim 48, wherein the step of monitoring the exchange of the replacement item from the payload area of the modular cargo storage system with the item being replaced comprises:
capturing sensor data from the one or more sensors on at least one of the modular mobile autonomy control module and the modular cargo storage system; and
detecting when the replacement item is removed from the modular cargo storage system and when the item being replaced is received within the modular cargo storage system based upon the captured sensor data.

63. The method of claim 62, wherein the captured sensor data comprises visual images of what is disposed within the modular cargo storage system.

64. The method of claim 48, wherein the step of monitoring the exchange of the replacement item from the payload area of the modular cargo storage system with the item being replaced comprises:
generating barcode scan data related to the item being replaced and the replacement item as the item being replaced is swapped in for the replacement item that is removed from within the modular cargo storage system using a barcode scanner as one of the one or more sensors; and
processing the generated barcode scan data to monitor the item being replaced and the replacement item as the item being replaced is swapped in for the replacement item that is removed from within the modular cargo storage system.

65. The method of claim 48, wherein the step of monitoring the exchange of the replacement item from the payload area of the modular cargo storage system with the item being replaced comprises:
  generating image data related to item being replaced and the replacement item as the item being replaced is swapped in for the replacement item that is removed from within the modular cargo storage system using a camera as one of the one or more sensors; and
  processing the generated image data to monitor the item being replaced and the replacement item as the item being replaced is swapped in for the replacement item that is removed from within the modular cargo storage system.

66. The method of claim 48, wherein the step of monitoring the exchange of the replacement item from the payload area of the modular cargo storage system with the item being replaced comprises:
  generating video data related to item being replaced and the replacement item as the item being replaced is swapped in for the replacement item that is removed from within the modular cargo storage system using a video camera as one of the one or more sensors; and
  processing the generated video data to monitor the item being replaced and the replacement item as the item being replaced is swapped in for the replacement item that is removed from within the modular cargo storage system.

67. The method of claim 48, wherein the step of monitoring the exchange of the replacement item from the payload area of the modular cargo storage system with the item being replaced comprises:
  capturing audio data using a microphone as one of the one or more sensors disposed to record sound within and proximate to the modular cargo storage system as the item being replaced is swapped in for the replacement item that is removed from within the modular cargo storage system; and
  processing the captured audio data to monitor the item being replaced and the replacement item as the item being replaced is swapped in for the replacement item that is removed from within the modular cargo storage system.

68. The method of claim 48, wherein the step of monitoring the exchange of the replacement item from the payload area of the modular cargo storage system with the item being replaced comprises detecting movement of a wireless node associated with the item being replaced as the item being replaced is swapped in for the replacement item being removed from within the modular cargo storage system based upon a plurality of signals broadcast from the wireless node associated with the item being replaced.

69. The method of claim 48, wherein the step of monitoring the exchange of the replacement item from the payload area of the modular cargo storage system with the item being replaced comprises detecting movement of a wireless node associated with the replacement item as the replacement item is swapped out from within the modular cargo storage system for the item being replaced based upon a plurality of signals broadcast from the wireless node associated with replacement item.

70. The method of claim 48, wherein the step of monitoring the exchange of the replacement item from the payload area of the modular cargo storage system with the item being replaced comprises detecting a change in location of a wireless node associated with the item being replaced from a location outside the modular cargo storage system to the payload area inside the modular cargo storage system as the item being replaced is swapped for the replacement item that is removed from within the modular cargo storage system as determined by the modular mobile autonomous control module.

71. The method of claim 48, wherein the step of monitoring the exchange of the replacement item from the payload area of the modular cargo storage system with the item being replaced comprises detecting a change in location of a wireless node associated with the replacement item from inside the modular cargo storage system to outside the modular cargo storage system as the item being replaced is swapped in for the replacement item that is removed from within the modular cargo storage system as determined by the modular mobile autonomous control module.

72. The method of claim 48 further comprising the step of notifying, by the modular mobile autonomy control module, a retail entity at the origin location of an approaching return delivery of the item being replaced once the modular autonomous bot apparatus assembly is within a threshold notification range of the origin location.

73. The method of claim 48, further comprising the step of notifying, by the modular mobile autonomy control module, a retail entity at the origin location about delivery of the item being replaced after the modular autonomous bot apparatus assembly arrives at the origin location.

74. The method of claim 48, wherein the step of autonomously causing the modular mobility base to move from the origin location to the designated swap location comprises autonomously causing, by the modular mobile autonomy control module, the modular mobility base to move from the origin location to the designated swap location while interacting with a wireless building facility node to actuate a pathway obstacle disposed in a path on the route to the designated swap location.

75. The method of claim 74, wherein the pathway obstacle comprises an actuated door controlled by the wireless building facility node.

76. The method of claim 74, wherein the pathway obstacle comprises an actuated elevator controlled by the wireless building facility node.

77. The method of claim 74, wherein the pathway obstacle comprises an actuated lock controlled by the wireless building facility node.

78. The method of claim 74, wherein interacting with the wireless building facility node to actuate the pathway obstacle comprises:
  establishing an authorized association pairing between the modular mobile autonomy control module and the wireless building facility node based upon the authentication information related to the dispatched swap logistics operation; and
  causing the wireless building facility node to actuate the pathway obstacle after establishing the authorized association pairing between the modular mobile autonomy control module and the wireless building facility node.

79. The method of claim 48, wherein the step of autonomously causing the modular mobility base to move from the origin location to the designated swap location comprises autonomously causing, by the modular mobile autonomy control module, the modular mobility base to move from the origin location to the designated swap location while engaging a pathway obstacle disposed in a path on the route to the designated swap location using an articulating arm disposed on the modular autonomous bot apparatus assembly and using a plurality of sensors disposed on at least one of the modular mobility base and the modular mobile autonomy control module.

80. The method of claim 79, wherein the pathway obstacle comprises a manually actuated door.

81. The method of claim 79, wherein the pathway obstacle comprises a manually actuated elevator.

82. The method of claim 79, wherein the pathway obstacle comprises a manually actuated lock.

83. The method of claim 79, wherein engaging the pathway obstacle using the articulating arm and the sensors comprises:
   guiding, by the modular mobile autonomy control module, the articulating arm to a control element of the pathway obstacle using one or more of the sensors disposed on at least one of the modular mobility base and the modular mobile autonomy control module; and
   actuating the pathway obstacle, by the modular mobile autonomy control module, once the articulating arm engages the control element of the pathway obstacle.

84. The method of claim 83, wherein the control element of the pathway obstacle comprises one from the group consisting of a handle for the pathway obstacle, a button for the pathway obstacle, a switch for the pathway obstacle, and a portion of a control panel for the pathway obstacle.

85. The method of claim 48, wherein the receiving step comprises actuating, by the modular mobile autonomy control module, an actuated cargo door disposed on the modular auxiliary power module to an open position, where the actuated cargo door provides a seal to the payload area within the modular cargo storage system when the actuated cargo door is in a closed position and the actuated cargo door provides access to the payload area within the modular cargo storage system when the actuated cargo door is in the open position.

86. The method of claim 85, wherein actuating, by the modular mobile autonomy control module, the actuated cargo door comprises actuating an actuated joint on the actuated cargo door to cause the actuated cargo door to move from the closed position to the open position.

87. The method of claim 85, wherein actuating, by the modular mobile autonomy control module, the actuated cargo door further comprises actuating an electro-mechanical lock on the actuated cargo door to cause the actuated cargo door to unlock before moving from the closed position to the open position.

88. The method of claim 48, wherein the receiving step comprises actuating, by the modular mobile autonomy control module, an actuated sliding arm disposed on the modular cargo storage system to move the item being replaced into the payload area within the modular cargo storage system.

89. The method of claim 48, wherein the receiving step comprises actuating, by the modular mobile autonomy control module, an actuated grabbing arm disposed on the modular cargo storage system to grab and move the item being replaced into the payload area within the modular cargo storage system as part of receiving the item being replaced.

90. The method of claim 48, wherein the receiving step comprises actuating, by the modular mobile autonomy control module, an actuated belt surface disposed on the modular auxiliary power module as a movable support surface exposed within the payload area inside the modular cargo storage system, the actuated belt surface being operative when actuated to cause the item being replaced as placed on the actuated belt surface to move within the payload area as part of receiving the item being replaced.

91. The method of claim 48 further comprising, after the providing step, unloading, by the modular cargo storage system, the replacement item from within the payload area of the modular cargo storage system and loading the item being replaced into the payload area within the modular cargo storage system.

92. The method of claim 91, wherein each of the steps of unloading the replacement item and loading the item being replaced comprises actuating, by the modular mobile autonomy control module, an actuated cargo door disposed on the modular auxiliary power module to an open position once the delivery recipient authentication input correlates to a portion of the pickup authentication information related to the dispatched swap logistics operation, wherein the actuated cargo door provides a seal to the payload area within the modular cargo storage system when the actuated cargo door is in a closed position and the actuated cargo door provides access to the payload area within the modular cargo storage system when the actuated cargo door is in the open position.

93. The method of claim 92, wherein actuating, by the modular mobile autonomy control module, the actuated cargo door comprises actuating an actuated joint on the actuated cargo door to cause the actuated cargo door to move from the closed position to the open position.

94. The method of claim 92, wherein actuating, by the modular mobile autonomy control module, the actuated cargo door further comprises actuating an electro-mechanical lock on the actuated cargo door to cause the actuated cargo door to unlock before moving from the closed position to the open position.

95. The method of claim 91, wherein the step of unloading the replacement item comprises actuating, by the modular mobile autonomy control module, an actuated sliding arm disposed on the modular cargo storage system to move the replacement item out from the payload area within the modular cargo storage system.

96. The method of claim 91, wherein the step of loading the item being replaced comprises actuating, by the modular mobile autonomy control module, an actuated sliding arm disposed on the modular cargo storage system to move the item being replaced into the payload area within the modular cargo storage system.

97. The method of claim 91, wherein the step of unloading the replacement item comprises actuating, by the modular mobile autonomy control module, an actuated grabbing arm disposed on the modular cargo storage system to grab and move the replacement item out from the payload area within the modular cargo storage system.

98. The method of claim 91, wherein the step of loading the item being replaced comprises actuating, by the modular mobile autonomy control module, an actuated grabbing arm disposed on the modular cargo storage system to move the item being replaced into the payload area within the modular cargo storage system.

99. The method of claim 91, wherein the step of unloading the replacement item comprises actuating, by the modular mobile autonomy control module, an actuated belt surface disposed on the modular auxiliary power module as a movable support surface exposed within the payload area inside the modular cargo storage system, the actuated belt surface being operative when actuated to cause the replacement item as placed on the actuated belt surface to move out from within the payload area.

100. The method of claim 91, wherein the step of loading the item being replaced comprises actuating, by the modular mobile autonomy control module, an actuated belt surface disposed on the modular auxiliary power module as a movable support surface exposed within the payload area inside the modular cargo storage system, the actuated belt surface being operative when actuated to cause the item being replaced as placed on the actuated belt surface to move into the payload area.

101. The method of claim 48, wherein the delivery recipient authentication input received by the modular mobile autonomy control module is provided by the delivery recipient through a user input panel disposed on the modular autonomous bot apparatus coupled to the modular mobile autonomy control module.

102. The method of claim 48, wherein the delivery recipient authentication input received by the modular mobile autonomy control module comprises an access code provided by the delivery recipient through the user input panel disposed on the modular cargo storage system and operatively coupled to the modular mobile autonomy control module.

103. The method of claim 48, wherein the delivery recipient authentication input received by the modular mobile autonomy control module comprises a biometric input provided by the delivery recipient through the user input panel disposed on the modular cargo storage system and operatively coupled to the modular mobile autonomy control module.

104. The method of claim 48, wherein the delivery recipient authentication input received by the modular mobile autonomy control module is provided by the delivery recipient through an external wireless node disposed external to the modular autonomous bot apparatus assembly.

105. The method of claim 104, wherein the delivery recipient authentication input received by the modular mobile autonomy control module comprises an access code provided by the delivery recipient through the external wireless node disposed external to the modular autonomous bot apparatus assembly.

106. The method of claim 104, wherein the delivery recipient authentication input received by the modular mobile autonomy control module comprises a biometric input provided by the delivery recipient through the external wireless node disposed external to the modular autonomous bot apparatus assembly.

107. The method of claim 48, wherein the pickup authentication information related to the dispatched swap logistics operation includes an identifier of the authorized delivery recipient for the replacement item as part of the dispatched swap logistics operation; and
wherein the step of receiving the delivery recipient authentication input comprises:
detecting, by the modular mobile autonomy control module, an advertising signal as the delivery recipient authentication input from an external wireless node within a predetermined range of the modular autonomous bot apparatus assembly once the modular autonomous bot apparatus assembly has arrived at the designated swap location identified by the designated pickup information; and
authenticating, by the modular mobile autonomy control module, that the external wireless node is associated with the authorized delivery recipient for the item being replaced within the modular cargo storage system based upon the identifier of the authorized delivery recipient and identifier information within the detected advertising signal broadcast from the external wireless node.

108. The method of claim 48, wherein the pickup authentication information related to the dispatched swap logistics operation includes an identifier of the authorized delivery recipient for the replacement item as part of the dispatched swap logistics operation; and
wherein the step of receiving the delivery recipient authentication input comprises:
detecting, by the modular mobile autonomy control module, an unprompted advertising signal from an external wireless node within a predetermined range of the modular autonomous bot apparatus assembly once the modular autonomous bot apparatus assembly has arrived at the designated swap location identified by the designated pickup information; and
establishing a secure association between the external node and the modular mobile autonomy control module after detecting the unprompted advertising signal from the external wireless node, the secure association between the external node and the modular mobile autonomy control module allowing secure sharing of information between the external node and the modular mobile autonomy control module and being pre-authorized by the dispatch server as it relates to the dispatched swap logistics operation.

109. The method of claim 48, wherein the designated swap location comprises a fixed address where the authorized delivery recipient receives the replacement item and provides the item being replaced within the mobile cargo storage system as part of dispatched swap logistics operation.

110. The method of claim 48, wherein the designated swap location comprises a mobile location where the authorized delivery recipient receives the replacement item and provides the item being replaced within the mobile cargo storage system as part of dispatched swap logistics operation, wherein the mobile location being defined by the designated pickup information as a location of an external wireless mobile node being related to the authorized delivery recipient.

111. The method of claim 107, further comprising the step of transmitting, by the modular mobile autonomy control module, an unload assistance request to the retail entity once the modular autonomous bot apparatus assembly is within a threshold notification range of the origin location.

112. The method of claim 108, further comprising the step of transmitting, by the modular mobile autonomy control module, an unload assistance request to the retail entity after the modular autonomous bot apparatus assembly arrives at the origin location.

\* \* \* \* \*